(12) United States Patent
Blake et al.

(10) Patent No.: US 9,969,694 B2
(45) Date of Patent: May 15, 2018

(54) N-(ARYLALKYL)-N'-PYRAZOLYL-UREA, THIOUREA, GUANIDINE AND CYANOGUANIDINE COMPOUNDS AS TRKA KINASE INHIBITORS

(71) Applicant: Array BioPharma Inc., Boulder, CO (US)

(72) Inventors: James F. Blake, Boulder, CO (US); Barbara J. Brandhuber, Boulder, CO (US); Julia Haas, Boulder, CO (US); Brad Newhouse, Boulder, CO (US); Allen A. Thomas, Kearney, NE (US); Shannon L. Winski, Boulder, CO (US)

(73) Assignee: Array BioPharma Inc., Boulder, CO (US)

( * ) Notice: Subject to any disclaimer, the term of this patent is extended or adjusted under 35 U.S.C. 154(b) by 23 days.

(21) Appl. No.: 14/442,576

(22) PCT Filed: Nov. 12, 2013

(86) PCT No.: PCT/US2013/069750
§ 371 (c)(1),
(2) Date: May 13, 2015

(87) PCT Pub. No.: WO2014/078331
PCT Pub. Date: May 22, 2014

(65) Prior Publication Data
US 2016/0272592 A1 Sep. 22, 2016

Related U.S. Application Data

(60) Provisional application No. 61/725,933, filed on Nov. 13, 2012.

(51) Int. Cl.
| | | |
|---|---|---|
| *C07D 231/38* | (2006.01) | |
| *C07D 231/52* | (2006.01) | |
| *C07D 403/12* | (2006.01) | |
| *C07D 401/14* | (2006.01) | |
| *C07D 231/40* | (2006.01) | |
| *C07D 231/54* | (2006.01) | |
| *C07D 401/04* | (2006.01) | |
| *C07D 401/12* | (2006.01) | |
| *C07D 403/04* | (2006.01) | |
| *C07D 413/12* | (2006.01) | |
| *C07D 495/04* | (2006.01) | |
| *C07D 405/12* | (2006.01) | |
(Continued)

(52) U.S. Cl.
CPC ........ *C07D 231/52* (2013.01); *C07D 231/38* (2013.01); *C07D 231/40* (2013.01); *C07D 231/54* (2013.01); *C07D 401/04* (2013.01); *C07D 401/12* (2013.01); *C07D 401/14* (2013.01); *C07D 403/04* (2013.01); *C07D 403/12* (2013.01); *C07D 405/12* (2013.01); *C07D 405/14* (2013.01); *C07D 413/12* (2013.01); *C07D 453/02* (2013.01); *C07D 495/04* (2013.01)

(58) Field of Classification Search
CPC .................................................. C07D 231/52
See application file for complete search history.

(56) References Cited

U.S. PATENT DOCUMENTS

| 5,849,779 A | 12/1998 | Hirota et al. |
| 5,998,424 A | 12/1999 | Galemmo, Jr. et al. |
(Continued)

FOREIGN PATENT DOCUMENTS

| EP | 0761658 A1 | 12/1997 |
| EP | 1043995 B1 | 11/2006 |
(Continued)

OTHER PUBLICATIONS

Vicentini, 4994, Heterocycles, vol. 32, No. 4, p. 727-734.*
(Continued)

*Primary Examiner* — Rebecca L Anderson
*Assistant Examiner* — Karen Cheng
(74) *Attorney, Agent, or Firm* — Viksnins Harris Padys Malen LLP; Sarah S. Mastous

(57) ABSTRACT

Compounds of Formula I or stereoisomers, tautomers, or pharmaceutically acceptable salts, solvates or prodrugs thereof, wherein Ring A, Ring C, X, Ra, Rb, Rc, Rd and n are as defined herein, are inhibitors of TrkA kinase and are useful in the treatment of diseases which can be treated with a TrkA kinase inhibitor such as pain, cancer, inflammation/inflammatory diseases, neurodegenerative diseases, certain infectious diseases, Sjogren's syndrome, endometriosis, diabetic peripheral neuropathy, prostatitis or pelvic pain syndrome.

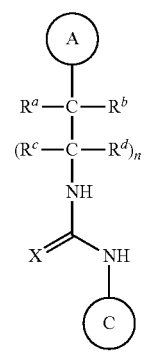

1 Claim, No Drawings

(51) Int. Cl.
 *C07D 405/14* (2006.01)
 *C07D 453/02* (2006.01)

(56) References Cited

U.S. PATENT DOCUMENTS

| | | |
|---|---|---|
| 6,197,798 B1 | 3/2001 | Fink et al. |
| 6,410,533 B1 | 6/2002 | Hirth et al. |
| 7,223,782 B2 | 5/2007 | Atkinson et al. |
| 7,625,915 B2 | 12/2009 | Dumas et al. |
| 8,592,454 B2 | 11/2013 | Shirai et al. |
| 9,163,017 B2 | 10/2015 | Degoey et al. |

FOREIGN PATENT DOCUMENTS

| | | |
|---|---|---|
| EP | 2033955 A1 | 3/2009 |
| EP | 1451160 B1 | 1/2010 |
| EP | 2336105 B9 | 9/2014 |
| JP | 2005206527 A | 8/2005 |
| WO | 9804521 A1 | 2/1998 |
| WO | 9923091 A1 | 5/1999 |
| WO | 9932110 A1 | 7/1999 |
| WO | 0039116 A1 | 7/2000 |
| WO | 0043384 A1 | 7/2000 |
| WO | 200112188 A1 | 2/2001 |
| WO | 200202525 A2 | 1/2002 |
| WO | 2002088101 A2 | 11/2002 |
| WO | 2002090326 A1 | 11/2002 |
| WO | 2003037274 A2 | 5/2003 |
| WO | 2003045920 A1 | 6/2003 |
| WO | 2003051275 A2 | 6/2003 |
| WO | 2004005262 A2 | 1/2004 |
| WO | 2004032870 A2 | 4/2004 |
| WO | 2004060305 A2 | 7/2004 |
| WO | 2004060306 A2 | 7/2004 |
| WO | 2004061084 A2 | 7/2004 |
| WO | 2004111009 A1 | 12/2004 |
| WO | 2005024755 A2 | 3/2005 |
| WO | 2005048948 A2 | 6/2005 |
| WO | 2005110994 A2 | 11/2005 |
| WO | 2006014290 A2 | 2/2006 |
| WO | 2006068591 A1 | 6/2006 |
| WO | 2006070198 A1 | 7/2006 |
| WO | 2006071940 A2 | 7/2006 |
| WO | 2006081034 A2 | 8/2006 |
| WO | 2006123257 A2 | 11/2006 |
| WO | 2007008917 A2 | 1/2007 |
| WO | 2007059202 A2 | 5/2007 |
| WO | 2007061882 A2 | 5/2007 |
| WO | 2007064872 A2 | 6/2007 |
| WO | 2008016811 A2 | 2/2008 |
| WO | 2008021859 A1 | 2/2008 |
| WO | 2008033999 A2 | 3/2008 |
| WO | 2008034008 A2 | 3/2008 |
| WO | 2008046003 A2 | 4/2008 |
| WO | 2008131276 A1 | 10/2008 |
| WO | 2008150899 A1 | 12/2008 |
| WO | 2009140128 A2 | 11/2009 |
| WO | 2010032856 A1 | 3/2010 |
| WO | 2010033941 A1 | 3/2010 |
| WO | 2010040663 A1 | 4/2010 |
| WO | 2010048314 A1 | 4/2010 |
| WO | 2010059719 A2 | 5/2010 |
| WO | 2010075376 A2 | 7/2010 |
| WO | 2010077680 A2 | 7/2010 |
| WO | 2010104488 A1 | 9/2010 |
| WO | 2010125799 A1 | 11/2010 |
| WO | 2011006074 A1 | 1/2011 |
| WO | 2011032291 A1 | 3/2011 |
| WO | 2011146336 A1 | 11/2011 |
| WO | 2012158413 A1 | 11/2012 |
| WO | 2013063214 A1 | 5/2013 |
| WO | 2013096226 A1 | 6/2013 |
| WO | 2013176970 A1 | 11/2013 |
| WO | 2014052563 A1 | 4/2014 |
| WO | 2014052566 A1 | 4/2014 |
| WO | 2014078322 A1 | 5/2014 |
| WO | 2014078323 A1 | 5/2014 |
| WO | 2014078325 A1 | 5/2014 |
| WO | 2014078328 A1 | 5/2014 |
| WO | 2014078331 A1 | 5/2014 |
| WO | 2014078372 A1 | 5/2014 |
| WO | 2014078378 A1 | 5/2014 |
| WO | 2014078408 A1 | 5/2014 |
| WO | 2014078417 A1 | 5/2014 |
| WO | 2014078454 A1 | 5/2014 |
| WO | 2015039333 A1 | 3/2015 |
| WO | 2015042085 A2 | 3/2015 |

OTHER PUBLICATIONS

CAS Reg No. 1388855-96-6, entered into STN Aug. 10, 2012.*
CAS Reg No. 1389166-72-6, entered into STN Aug. 10, 2012.*
CAS Reg No. 135510-57-5, entered into STN Aug. 16, 1991.*
Tsuzuki, Y., et al., Tetrahedron Asymmetry 12 (2001), 2989-2997.
Wadhwa, S., et al., Journal of Biosciences, 2003, 28(2), 181-188.
Wang, T., et al., Expert Opinion in Therapeutic Patents (2009) 19(3)305-319.
Woolf, C.J. et al. (1994) Neuroscience, 62, 327-331.
Yilmaz, T., et al., Cancer Biology and Therapy, 2010, 10(6), 644-653.
Zahn, P.K. et al. (2004) J. Pain, 5, 157-163.
Patent Cooperation Treaty, International Searching Authority, Search Report and Written Opinion for PCT/US2013/069750, dated May 28, 2015, 9 Pages.
Adriaenssens, E., et al. Cancer Res (2008) 68:(2) 346-351.
Asaumi, K., et al., Bone (2000) 26(6) 625-633.
Bardelli, A., Science 2003, 300, 949.
Bhattacharya, S. K., et al., Bioorganic & Medicinal Chemistry Letters (2012) 22(24) 7523-7526.
Bouhana, Karyn S., et al., "Comparison of Analgesic Effects of an Allosteric Inhibitor of TrkA to that of an ATP site inhibitor of the pan-Trk axis in a Rodent Model of Inflammatory Pain", Gordon Conference, Salve Regina University, Newport, RI, Jun. 7, 2011.
Brodeur, G. M., Nat. Rev. Cancer 2003, 3, 203-216.
Bruno, O., Bioorganic & Medicinal Chemistry (2009) 17, 3379-3387.
Burger, K., et al., Synthesis (1990) vol. 4, 360-365.
Chambers, L. J., et al., Bioorganic & Medicinal Chemistry Letters (2010) 20(10) 3161-3164.
Davidson. B., et al., Clin. Cancer Res. 2003, 9, 2248-2259.
Davies, Stephen G., et al., Asymmetric synthesis of 3,4-anti- and 3,4-syn-substituted aminopyrrolidines via lithium amide conjugate addition, Org. Biomol. Chem., 2007, 5, 1961-1969.
Delafoy, L. et al. (2003) Pain 105, 489-497.
Demelo-Jorge, M. et al., Cell Host & Microbe (2007) 1(4), 251-261.
Dimola, F. F, et. al., Gut (2000) 46(5), 670-678.
Dou, Y.-C., et. al. Archives of Dermatological Research (2006) 298(1), 31-37.
Du, et al., World Journal of Gastroenterology, 2003, 9(7), 1431-1434.
Eguchi, M., et al., Blood 1999, 93 (4), pp. 1355-1363.
El Haddad, M., et al., J. Heterocyclic Chem., (2000) 37, 1247-1252.
Eliav, E. et al., Pain 79, 255-264 (1999).
Euthus, D.M., et al., Cancer Cell 2002, 2 (5), pp. 347-348.
Freund-Michel, V; Frossard, N., Pharmacology & Therapeutics (2008) 117(1), 52-76.
Greco, A., et al., Molecular and Cellular Endocrinology 2010, 321 (1), pp. 44-49.
Gruber-Olipitz, M., et al., Journal of Proteome Research 2008, 7 (5), pp. 1932-1944.
Gwak, Y. S. et al. (2003) Neurosci. Lett. 336, 117-120.
Han, S., et al., J. Biological Chem., (2009), 284(19) 13199-13201.
Herzberg, U. et al., Neuroreport 1997; 8:1613-1618.
Hu, Vivian Y; et al., The Journal of Urology (2005), 173(3), 1016-1021.
Jaggar, S. I. et al., Br. J. Anaesth. (1999) 83, 442-448.
Jin, W., et al., Carcinogenesis (2010) 31 (11), pp. 1939-1947.

(56) References Cited

OTHER PUBLICATIONS

Kaymakcioglu, B.K., et al., European Journal of Pharmaceutical Sciences (2005) 26(1), 97-103.
Lamb, K. et al. (2003) Neurogastroenterol. Motil. 15, 355-361.
Li, L. et al. (2003) Mol. Cell. Neurosci. 23, 232-250.
Li, Y.-G., et al., Chinese Journal of Cancer Prevention and Treatment, 2009, 16 (6), pp. 428-430 (with English Abstract).
Ma, Q. P. and Woolf, C. J. NeuroReport (1997) 8, 807-810.
Mantyh, Patrick W., et al., Anesthesiology, vol. 115, No. 1, Jul. 2011, 189-204.
McCarthy, C. and Walker, E., Expert Opin. Ther. Patents (2014) 24(7):731-744.
McMahon, S.B. et al., (1995) Nat. Med. 1, 774-780.
Meyer, J. et al. (2007) Leukemia, 21(10):2171-2180.
Nakagawara, A. (2001) Cancer Letters 169:107-114.
Patapoutian, A. et al., Current Opinion in Neurobiology, 2001, 11, 272-280.
Pierottia, M.A. and Greco A., (2006) Cancer Letters 232:90-98.
Pinski, J. et al., Cancer Research, (2002) 62:986-989.
Ramer, M. S. and Bisby, M. A. (1999) Eur. J. Neurosci. 11, 837-846.
Raychaudhuri, S. P., et al., J. Investigative Dermatology (2004) 122(3), 812-819.
Ricci A., et al., American Journal of Respiratory Cell and Molecular Biology, 2001, 25(4), pp. 439-446.
Ro, L. S. et al., Pain, Feb. 1999; 79(2-3):265-274.
Shelton, D. L. et al. (2005) Pain, 116, 8-16.
Theodosiou, M. et al. (1999) Pain, 81, 245-255.
Truzzi, F., et al., Dermato-Endocrinology, 2011, 3(1), 32-36.

\* cited by examiner

N-(ARYLALKYL)-N'-PYRAZOLYL-UREA, THIOUREA, GUANIDINE AND CYANOGUANIDINE COMPOUNDS AS TRKA KINASE INHIBITORS

RELATED APPLICATIONS

This application is a 371 filing of PCT Application No. PCT/US2013/069750, filed Nov. 12, 2013, which claims priority to U.S. Provisional Application Ser. No. 61/725,933, filed Nov. 13, 2012.

BACKGROUND OF THE INVENTION

The present invention relates to novel compounds, to pharmaceutical compositions comprising the compounds, to processes for making the compounds and to the use of the compounds in therapy. More particularly, it relates to arylalkyl and heteroarylalkyl urea, thiourea, guanidine and cyanoguanidine compounds which exhibit TrkA kinase inhibition, and which are useful in the treatment of pain, cancer, inflammation/inflammatory diseases, neurodegenerative diseases, certain infectious diseases, Sjogren's syndrome, endometriosis, diabetic peripheral neuropathy, prostatitis or pelvic pain syndrome.

The current treatment regimens for pain conditions utilize several classes of compounds. The opioids (such as morphine) have several drawbacks including emetic, constipatory and negative respiratory effects, as well as the potential for addictions. Non-steroidal anti-inflammatory analgesics (NSAIDs, such as COX-1 or COX-2 types) also have drawbacks including insufficient efficacy in treating severe pain. In addition, COX-1 inhibitors can cause ulcers of the mucosa. Accordingly, there is a continuing need for new and more effective treatments for the relief of pain, especially chronic pain.

Trk's are the high affinity receptor tyrosine kinases activated by a group of soluble growth factors called neurotrophins (NT). The Trk receptor family has three members: TrkA, TrkB and TrkC. Among the neurotrophins are (i) nerve growth factor (NGF) which activates TrkA, (ii) brain-derived neurotrophic factor (BDNF) and NT-4/5 which activate TrkB and (iii) NT3 which activates TrkC. Trk's are widely expressed in neuronal tissue and are implicated in the maintenance, signaling and survival of neuronal cells (Patapoutian, A. et al., *Current Opinion in Neurobiology*, 2001, 11, 272-280).

Inhibitors of the Trk/neurotrophin pathway have been demonstrated to be effective in numerous pre-clinical animal models of pain. For example, antagonistic NGF and TrkA antibodies such as RN-624 have been shown to be efficacious in inflammatory and neuropathic pain animal models (Woolf, C. J. et al. (1994) *Neuroscience* 62, 327-331; Zahn, P. K. et al. (2004) *J. Pain* 5, 157-163; McMahon, S. B. et al., (1995) *Nat. Med.* 1, 774-780; Ma, Q. P. and Woolf, C. J. (1997) *NeuroReport* 8, 807-810; Shelton, D. L. et al. (2005) *Pain* 116, 8-16; Delafoy, L. et al. (2003) *Pain* 105, 489-497; Lamb, K. et al. (2003) *Neurogastroenterol. Motil.* 15, 355-361; Jaggar, S. I. et al. (1999) *Br. J. Anaesth.* 83, 442-448) and neuropathic pain animal models (Ramer, M. S. and Bisby, M. A. (1999) *Eur. J. Neurosci.* 11, 837-846; Ro, L. S. et al. (1999); Herzberg, U. et al., *Pain* 79, 265-274 (1997) *Neuroreport* 8, 1613-1618; Theodosiou, M. et al. (1999) *Pain* 81, 245-255; Li, L. et al. (2003) *Mol. Cell. Neurosci.* 23, 232-250; Gwak, Y. S. et al. (2003) *Neurosci. Lett.* 336, 117-120).

It has also been shown that NGF secreted by tumor cells and tumor invading macrophages directly stimulates TrkA located on peripheral pain fibers. Using various tumor models in both mice and rats, it was demonstrated that neutralizing NGF with a monoclonal antibody inhibits cancer related pain to a degree similar or superior to the highest tolerated dose of morphine. Because TrkA kinase may serve as a mediator of NGF driven biological responses, inhibitors of TrkA and/or other Trk kinases may provide an effective treatment for chronic pain states.

Recent literature has also shown that overexpression, activation, amplification and/or mutation of Trk kinases are associated with many cancers including neuroblastoma (Brodeur, G. M., *Nat. Rev. Cancer* 2003, 3, 203-216), ovarian (Davidson. B., et al., *Clin. Cancer Res.* 2003, 9, 2248-2259), colorectal cancer (Bardelli, A., *Science* 2003, 300, 949), melanoma (Truzzi, F., et al., *Dermato-Endocrinology* 2008, 3 (1), pp. 32-36), head and neck cancer (Yilmaz, T., et al., *Cancer Biology and Therapy* 2010, 10 (6), pp. 644-653), gastric carcinoma (Du, J. et al., *World Journal of Gastroenterology* 2003, 9 (7), pp. 1431-1434), lung carcinoma (Ricci A., et al., *American Journal of Respiratory Cell and Molecular Biology* 25 (4), pp. 439-446), breast cancer (Jin, W., et al., *Carcinogenesis* 2010, 31 (11), pp. 1939-1947), Glioblastoma (Wadhwa, S., et al., *Journal of Biosciences* 2003, 28 (2), pp. 181-188), medulloblastoma (Gruber-Olipitz, M., et al., *Journal of Proteome Research* 2008, 7 (5), pp. 1932-1944), secratory breast cancer (Euthus, D. M., et al., *Cancer Cell* 2002, 2 (5), pp. 347-348), salivary gland cancer (Li, Y.-G., et al., *Chinese Journal of Cancer Prevention and Treatment* 2009, 16 (6), pp. 428-430), papillary thyroid carcinoma (Greco, A., et al., *Molecular and Cellular Endocrinology* 2010, 321 (1), pp. 44-49) and adult myeloid leukemia (Eguchi, M., et al., *Blood* 1999, 93 (4), pp. 1355-1363). In preclinical models of cancer, non-selective small molecule inhibitors of TrkA, B and C were efficacious in both inhibiting tumor growth and stopping tumor metastasis (Nakagawara, A. (2001) *Cancer Letters* 169:107-114; Meyer, J. et al. (2007) *Leukemia*, 1-10; Pierottia, M. A. and Greco A., (2006) *Cancer Letters* 232:90-98; Eric Adriaenssens, E., et al. *Cancer Res* (2008) 68:(2) 346-351).

In addition, inhibition of the neurotrophin/Trk pathway has been shown to be effective in treatment of pre-clinical models of inflammatory diseases with NGF antibodies or non-selective small molecule inhibitors of TrkA. For example, inhibition of the neurotrophin/Trk pathway has been implicated in preclinical models of inflammatory lung diseases including asthma (Freund-Michel, V; Frossard, N., *Pharmacology & Therapeutics* (2008) 117(1), 52-76), interstitial cystitis (Hu Vivian Y; et. al. *The Journal of Urology* (2005), 173(3), 1016-21), bladder pain syndrome (Liu, H.-T., et al., (2010) *BJU International*, 106 (11), pp. 1681-1685), inflammatory bowel diseases including ulcerative colitis and Crohn's disease (Di Mola, F. F, et. al., *Gut* (2000) 46(5), 670-678) and inflammatory skin diseases such as atopic dermatitis (Dou, Y.-C., et. al. *Archives of Dermatological Research* (2006) 298(1), 31-37), eczema and psoriasis (Raychaudhuri, S. P., et al., *J Investigative Dermatology* (2004) 122(3), 812-819).

The TrkA receptor is also thought to be critical to the disease process of the parasitic infection of *Trypanosoma cruzi* (Chagas disease) in human hosts (de Melo-Jorge, M. et al., *Cell Host & Microbe* (2007) 1(4), 251-261).

Trk inhibitors may also find use in treating disease related to an imbalance of the regulation of bone remodeling, such as osteoporosis, rheumatoid arthritis, and bone metastases. Bone metastases are a frequent complication of cancer, occurring in up to 70 percent of patients with advanced breast or prostate cancer and in approximately 15 to 30 percent of patients with carcinoma of the lung, colon, stomach, bladder, uterus, rectum, thyroid, or kidney. Osteolytic metastases can cause severe pain, pathologic fractures, life-threatening hypercalcemia, spinal cord compression, and other nerve-compression syndromes. For these reasons, bone metastasis is a serious and costly complication of cancer. Therefore, agents that can induce apoptosis of proliferating osteoblasts would be highly advantageous. Expression of TrkA receptors has been observed in the bone-forming area in mouse models of bone fracture (K. Asaumi, et al., *Bone* (2000) 26(6) 625-633). In addition, localization of NGF was observed in almost all bone-forming cells (K. Asaumi, et al.). Recently, it was demonstrated that a Trk inhibitor inhibits the signaling activated by neurotrophins binding to all three of the Trk receptors in human hFOB osteoblasts (J. Pinski, et al., (2002) 62, 986-989). These data support the rationale for the use of Trk inhibitors for the treatment of bone remodeling diseases, such as bone metastases in cancer patients.

Trk inhibitors may also find use in treating diseases and disorders such as Sjogren's syndrome (Fauchais, A. L., et al., (2009) Scandinavian Journal of Rheumatology, 38(1), pp. 50-57), endometriosis (Barcena De Arellano, M. L., et al., (2011) Reproductive Sciences, 18(12), pp. 1202-1210; Barcena De Arellano, et al., (2011) Fertility and Sterility, 95(3), pp. 1123-1126; Cattaneo, A., (2010) Current Opinion in Molecular Therapeutics, 12(1), pp. 94-106), diabetic peripheral neuropathy (Kim, H. C., et al., (2009) Diabetic Medicine, 26 (12), pp. 1228-1234; Siniscalco, D., et al., (2011) Current Neuropharmacology, 9(4), pp. 523-529; Ossipov, M. H., (2011) Current Pain and Headache Reports, 15(3), pp. 185-192), and prostatitis and pelvic pain syndrome (Watanabe, T., et al., (2011) BJU International, 108 (2), pp. 248-251; and Miller, L. J., et al., (2002) Urology, 59(4), pp. 603-608).

Several classes of small molecule inhibitors of Trk kinases said to be useful for treating pain or cancer are known (*Expert Opin. Ther. Patents* (2009) 19(3), 305-319).

SUMMARY OF THE INVENTION

It has now been found that pyrrolidinyl urea, thiourea, guanidine and cyanoguanidine compounds are inhibitors of TrkA, and useful for treating disorders and diseases such as pain, including chronic and acute pain. Compounds of the invention useful in the treatment of multiple types of pain including inflammatory pain, neuropathic pain, and pain associated with cancer, surgery, or bone fracture. In addition, compounds of the invention are useful for treating cancer, inflammation or inflammatory diseases, neurodegenerative diseases, certain infectious diseases, Sjogren's syndrome, endometriosis, diabetic peripheral neuropathy, prostatitis or pelvic pain syndrome, and diseases related to an imbalance of the regulation of bone remodeling, such as osteoporosis, rheumatoid arthritis, and bone metastases.

More specifically, provided herein are compounds of Formula I:

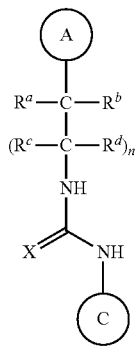

or stereoisomers, tautomers, or pharmaceutically acceptable salts, solvates or prodrugs thereof, wherein Ring A, Ring C, X, $R^a$, $R^b$, $R^c$, $R^d$ and n are as defined herein.

Another aspect of the present invention provides methods of treating a disease or disorder modulated by TrkA, comprising administering to a mammal in need of such treatment an effective amount of a compound of this invention or a stereoisomer, solvate or pharmaceutically acceptable salt thereof. In one embodiment, the disease and disorders include chronic and acute pain, including but not limited to inflammatory pain, neuropathic pain, and pain associated with cancer, surgery, or bone fracture. In another embodiment, the disease and disorders include, but are not limited to, cancer, inflammation or inflammatory diseases, neurodegenerative diseases, certain infectious diseases, Sjogren's syndrome, endometriosis, diabetic peripheral neuropathy, prostatitis or pelvic pain syndrome, and diseases related to an imbalance of the regulation of bone remodeling, such as osteoporosis, rheumatoid arthritis, and bone metastases. In one embodiment, the treatment includes treating the mammal with a compound of this invention in combination with an additional therapeutic agent.

Another aspect of the present invention provides a pharmaceutical composition comprising a compound of the present invention or a pharmaceutically acceptable salt thereof.

Another aspect of the present invention provides the compounds of the present invention for use in therapy.

Another aspect of the present invention provides the compounds of the present invention for use in the treatment of disease and disorders such as chronic and acute pain, including but not limited to inflammatory pain, neuropathic pain, and pain associated with cancer, surgery, or bone fracture. Another aspect of the present invention provides the compounds of the present invention for use in the treatment of disease and disorders selected from cancer, inflammation or inflammatory diseases, neurodegenerative diseases, certain infectious diseases, Sjogren's syndrome, endometriosis, diabetic peripheral neuropathy, prostatitis or pelvic pain syndrome, and diseases related to an imbalance of the regulation of bone remodeling, such as osteoporosis, rheumatoid arthritis, and bone metastases.

Another aspect of the present invention provides the use of a compound of this invention in the manufacture of a medicament for the treatment of disease and disorders such as chronic and acute pain including, but not limited to, inflammatory pain, neuropathic pain, and pain associated with cancer, surgery, or bone fracture.

Another aspect of the present invention provides the use of a compound of this invention in the manufacture of a medicament for the treatment of disease and disorders selected from cancer, inflammation or inflammatory diseases, neurodegenerative diseases, certain infectious diseases, Sjogren's syndrome, endometriosis, diabetic peripheral neuropathy, prostatitis or pelvic pain syndrome, and diseases related to an imbalance of the regulation of bone remodeling, such as osteoporosis, rheumatoid arthritis, and bone metastases.

Another aspect of the present invention provides intermediates for preparing compounds of Formula I.

Another aspect of the present invention includes methods of preparing, methods of separation, and methods of purification of the compounds of this invention.

DETAILED DESCRIPTION OF THE INVENTION

Provided herein are compounds, and pharmaceutical formulations thereof, that are useful in the treatment of diseases, conditions and/or disorders modulated by TrkA.

A representative compound of the invention (See Table B below), was found to be highly selective for TrkA over a panel of about 230 other kinases at 10 μM concentration. In addition, compounds of the invention such as those shown in Table A below, were found to be at least 1000 fold more selective for TrkA versus p38α.

One embodiment provides a compound of Formula I:

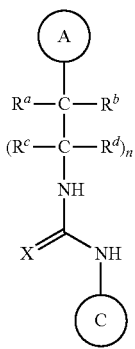

I or stereoisomers, tautomers, or pharmaceutically acceptable salts, solvates or prodrugs thereof, wherein:

X is O, S, NH or N—CN;

Ring A is formula A-1 or A-2

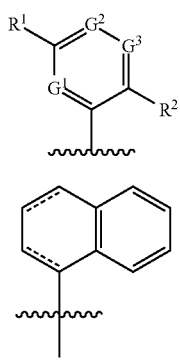

A-1

A-2 wherein the dashed lines are optional double bonds;
n is 0 or 1 when Ring A is formula A-1, and n is 0 when Ring A is formula A-2;

$G^1$, $G^2$ and $G^3$ are independently $CR^x$ or N, wherein no more than 2 of $G^1$, $G^2$ and $G^3$ can be N;

each $R^x$ is independently H, halogen, (1-4C)alkyl or (1-4C)alkoxy;

$R^1$ is H, halogen, (1-3C)alkoxy(1-3C)alkyl (optionally substituted with 1-5 fluoros), (1-3C alkyl)sulfanyl(1-3C)alkyl (optionally substituted with 1-5 fluoros), (1-3C)alkyl (optionally substituted with 1-5 fluoros), (1-3C)alkoxy (optionally substituted with 1-5 fluoros), (1-3C alkyl)sulfanyl (optionally substituted with 1-5 fluoros), cyano(1-3C)alkyl (optionally substituted with 1-5 fluoros), hydroxy(1-3C)alkyl (optionally substituted with 1-5 fluoros), (1-4C)alkyl (optionally substituted with 1-5 fluoros), $CH_3CH_2NR^y$, $CF_3CH_2NR^y$, $HCF_2CH_2NR^y$, $H_2CFCH_2NR^y$, $CH_3NR^yCH_2$, $R^yR^yNCH_2CH_2$, $R^yR^yNCH_2CFH$, or $R^yR^yNCH_2CF_2$;

each $R^y$ is independently H or methyl;

when n is 0, $R^2$ is selected from the group consisting of H, halogen, (1-6C)alkyl [optionally substituted with 1-5 fluoros], (1-6C)alkoxy [optionally substituted with 1-5 fluoros], (1-3C alkoxy)(1-4C)alkyl, (3-6C cycloalkyl)$CH_2O$—, amino(1-3C)alkyl, $CF_3CH_2NHCH_2$, $HCF_2CH_2NHCH_2$, a C5-C8 bridged cycloalkyl, hetCyc$^a$, hetCyc$^a$CH$_2$, Cyc$^a$, hetAr$^1$ and Ar$^1$, and when n is 1, $R^2$ is selected from the group consisting of H, halogen, $CF_3$, $F_2CH$, $FCH_2$, methyl and methoxy.

hetCyc$^a$ is a 4-6 membered heterocyclic ring having a ring heteroatom selected from N, O and S and optionally substituted with 1-3 groups independently selected from OH, F, (1-6C)alkoxy or (1-6C)alkyl [optionally substituted with 1-3 fluoros];

Cyc$^a$ is a (3-6C)cycloalkyl optionally substituted with (1-4C)alkoxy, (1-4C)alkyl, F or OH;

hetAr$^1$ is a 5-6 membered heteroaryl having 1-3 ring heteroatoms independently selected from N, S and O, and optionally substituted with 1-2 groups independently selected from (1-6C)alkyl, halogen, OH, $CF_3$, $NH_2$ and hydroxy(1-2C)alkyl;

Ar$^1$ is phenyl optionally substituted with one or more substituents independently selected from halogen, $CF_3$, $CF_3O$—, (1-4C)alkoxy, (1-4C)sulfanyl, hydroxy(1-4C)alkyl, (1-6C)alkyl and CN;

$R^a$ is H, (1-3C)alkyl, cyclopropyl, cyclobutyl, or $CF_3$, and $R^b$ is H, methyl or ethyl, or $R^a$ and $R^b$ together with the carbon atom to which they are attached form a 3-6 membered cycloalkyl ring;

$R^c$ is H, methyl or ethyl $R^d$ is $CF_3CH_2CH_2$, phenyl or phenylCH$_2$— wherein each phenyl ring is optionally substituted with one or more substituents independently selected from halogen, methoxy and methoxymethyl;

Ring C is formula C-1 or C-2

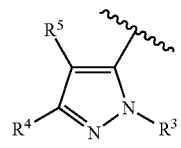

C-1

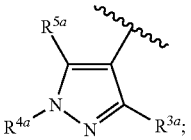

C-2

R³ is (1-6C)alkyl, hydroxy(1-6C)alkyl, Ar², hetCyc¹, (3-7C)cycloalkyl, a C5-C8 bridged cycloalkyl, or hetAr²;

Arᵉ is phenyl optionally substituted with one or more groups independently selected from halogen and (1-6C)alkyl;

hetCyc¹ is a 5-6-membered saturated or partially unsaturated heterocyclic ring having 1-2 ring heteroatoms independently selected from N and O;

hetAr² is a 5-6 membered heteroaryl ring having 1-3 ring heteroatoms independently selected from N, O and S and optionally substituted with one or more groups independently selected from (1-6C)alkyl and halogen;

R⁴ is OH, (1-6C)alkyl, monofluoro(1-6C)alkyl, difluoro(1-6C)alkyl, trifluoro(1-6C)alkyl, tetrafluro(2-6C)alkyl, pentafluro(2-6C)alkyl, cyano(1-6C)alkyl, hydroxy(1-6C)alkyl, dihydroxy(2-6C)alkyl, (1-3C alkoxy)(1-6C)alkyl, amino(1-6C)alkyl, aminocarbonyl(1-6C)alkyl, (1-3C)alkylsulfonamido(1-6C)alkyl, sulfamido(1-6C)alkyl, hydroxycarbonyl (1-6C)alkyl, hetAr³ (1-6C)alkyl, Ar³ (1-6C)alkyl, (1-6C)alkoxy, monofluoro(1-6C)alkoxy, difluoro(1-6C)alkoxy, trifluoro(1-6C)alkoxy, tetrafluoro(2-6C)alkoxy, pentafluoro(2-6C)alkoxy, cyano(1-6C)alkoxy, hydroxy(1-6C)alkoxy, dihydroxy(2-6C)alkoxy, amino(2-6C)alkoxy, hydroxyl-carbonyl(1-6C)alkoxy, hetCyc²(1-6C)alkoxy, hetAr³(1-6C)alkoxy, Ar³(1-6C)alkoxy, (1-4C alkoxy)(1-6C)alkoxy, (1-3C alkylsulfonyl)(1-6C)alkoxy, (3-6C)cycloalkyl [optionally substituted with F, OH, (1-6C alkyl), (1-6C)alkoxy, or (1-3C alkoxy)(1-6C)alkyl], hetAr⁴, hetAr⁴—O—, Ar⁴, hetCyc²(O)CH₂—, (1-4C alkoxycarbonyl)(1-6C)alkoxy, hydroxycarbonyl(1-6C)alkoxy, aminocarbonyl(1-6C)alkoxy, hetCyc²C(=O)(1-6C)alkoxy, hydroxy(1-3C alkoxy)(1-6C)alkoxy, hydroxytrifluoro(1-6C)alkoxy, (1-3C)alkyl sulfonamido(1-6C)alkoxy, (1-3C)alkylamido(1-6C)alkoxy, di(1-3C alkyl)amino-carboxy, hetCyc²C(=O)O—, hydroxydifluoro(1-6C)alkyl, (1-4C alkylcarboxy)(1-6C)alkyl, (1-6C)alkoxycarbonyl, hydroxylcarbonyl, aminocarbonyl, (1-3C alkoxy)aminocarbonyl, hetCyc³, halogen, CN, trifluoromethylsulfonyl, N-(1-3C alkyl)oxadiazolonyl, hetAr⁵, Ar⁴—O—, hetCyc⁴-O—, Cyc¹-O—, or aminohydroxy(1-6C)alkoxy;

hetCyc² is a 4-6 membered heterocyclic ring having 1-2 ring heteroatoms independently selected from N and O and optionally substituted with 1-2 groups independently selected from (1-6C)alkyl, 1-4C alkoxy)carbonyl, (1-6C)acyl, halogen and oxo;

hetCyc³ is a 4-7 membered heterocycle having 1-2 ring heteroatoms independently selected from N and O and optionally substituted with one or more substituents independently selected from F, CN, (1-6C)alkyl, trifluoro(1-6C)alkyl, hydroxy(1-6C)alkyl, (1-3C alkoxy)(1-6C)alkyl, (1-6C)acyl-, (1-6C)alkylsulfonyl, trifluoromethylsulfonyl and (1-4C alkoxy)carbonyl;

hetCyc⁴ is a 5-8 membered monocyclic, spirocyclic or bridged heterocycle having a ring nitrogen atom and optionally substituted with one or more groups independently selected from (1-6C)alkyl and halogen;

Cyc¹ is a 3-6 membered carbocycle optionally substituted with an amino group;

hetAr³ is a 5-membered heteroaryl ring having 1-3 ring atoms independently selected from N, O and S and optionally substituted with (1-6C)alkyl;

Ar³ is phenyl optionally substituted with (1-4C)alkoxy;

hetAr⁴ is a 5-6 membered heteroaryl ring having 1-3 ring heteroatoms independently selected from N, S and O and optionally substituted with one or more substituents independently selected from (1-6C)alkyl, halogen, CN, hydroxy(1-6C)alkyl, trifluoro(1-6C)alkyl, difluoro(1-6C)alkyl, fluoro(1-6C)alkyl, (3-6C)cycloalkyl, (3-6C cycloalkyl)CH₂— (3-6C cycloalkyl)C(=O)—, (1-3C alkoxy)(1-6C)alkyl, (1-6C)alkoxy, (1-6C)alkylsulfonyl, NH₂, (1-6C alkyl)amino, di(1-6C alkyl)amino, (1-3C trifluoroalkoxy), fluoro(1-6C alkyl)amino, difluoro(1-6C alkyl)amino, trifluoro(1-6C alkyl)amino, and (3-4C cycloalkyl)amino;

hetAr⁵ is a group selected from the structures:

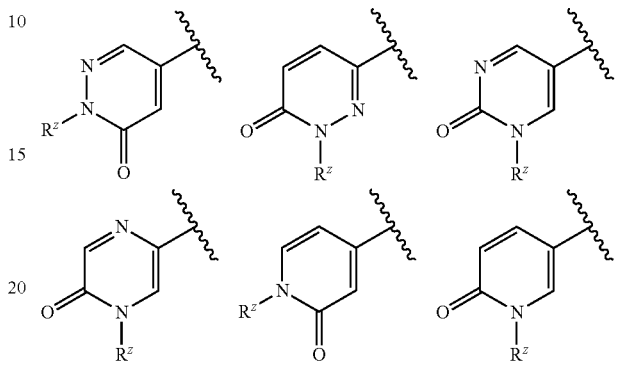

where R^z is (3-4C)cycloalkyl or (1-3C)alkyl (optionally substituted with 1-3 fluoros), wherein each of said hetAr⁵ groups is optionally further substituted with one or more groups independently selected from F and (1-3C)alkyl optionally substituted with 1-3 fluoros;

Ar⁴ is phenyl optionally substituted with one or more groups independently selected from (1-6C)alkyl, halogen, CN, CF₃, CF₃O—, (1-6C)alkoxy, (1-6Calkyl)OC(=O)—, aminocarbonyl, (1-6C)alkylthio, hydroxy(1-6C)alkyl, (1-6C alkyl)SO₂—, HOC(=O)— and (1-3C alkoxy)(1-3C alkyl)OC(=O)—;

R⁵ is (1-6C)alkyl, monofluoro(1-6C)alkyl, difluoro(1-6C)alkyl, trifluoro(1-6C)alkyl, tetrafluoro(2-6C)alkyl, pentafluoro(2-6C)alkyl, halogen, CN, (1-4C)alkoxy, hydroxy(1-4C)alkyl, (1-3C alkoxy)(1-4C)alkyl, (1-4C alkyl)OC(=O)—, (1-6C)alkylthio, (3-4C)cycloalkyl, amino, aminocarbonyl, trifluoro(1-3C alkyl)amido, or phenyl (optionally substituted with one or more groups independently selected from halogen, (1-6C)alkyl and (1-6C)alkoxy); or R⁴ and R⁵ together with the atoms to which they are attached form a 5-6 membered saturated, partially unsaturated or unsaturated carbocyclic ring optionally substituted with one or more substituents independently selected from (1-6C)alkyl, or R⁴ and R⁵ together with the atoms to which they are attached form 5-6 membered saturated, partially unsaturated or unsaturated heterocyclic ring having a ring heteroatom selected from N, O or S, wherein said heterocyclic ring is optionally substituted with one or two substituents independently selected from (1-6C alkyl)C(=O)O—, (1-6C)acyl, (1-6C)alkyl and oxo, and said sulfur ring atom is optionally oxidized to S(=O) or SO₂;

R^{3a} is hydrogen, halogen, (1-6C)alkyl, trifluoro(1-6C)alkyl, (3-6C)cycloalkyl, phenyl optionally substituted with one or more substituents independently selected from halogen and (1-6C)alkyl, or a 5-6 membered heteroaryl ring having 1-3 ring heteroatoms independently selected from N, O and S and optionally substituted with one or more groups independently selected from (1-6C)alkyl and halogen;

R^{4a} is hydrogen, (1-6C)alkyl, trifluoro(1-6C)alkyl, phenyl [optionally substituted with one or more groups independently selected from (1-6C)alkyl, halogen, CN, CF₃, CF₃O—, (1-6C)alkoxy, (1-6Calkyl)OC(=O)—, aminocarbonyl, (1-6C)alkylthio, hydroxy(1-6C)alkyl, (1-6C alkyl)SO$_2$—, HOC(=O)— and (1-3C alkoxy)(1-3C alkyl)OC(=O)—], or a 5-6 membered heteroaryl ring having 1-3 ring heteroatoms independently selected from N, S and O and optionally substituted with 1-2 substituents independently selected from (1-6C)alkyl, hydroxy(1-6C)alkyl, trifluoro(1-6C)alkyl, (3-6C)cycloalkyl, (3-6C cycloalkyl)CH$_2$-(3-6C cycloalkyl)C(=O)—, (1-3C alkoxy)(1-6C)alkyl, (1-6C)alkoxy, (1-6C)alkylsulfonyl, (1-6C alkyl)amino, di(1-6C alkyl)amino and (1-3C trifluoroalkoxy)(1-3C)trifluoroalkyl; and $R^{5a}$ is hydrogen, halogen, (1-6C)alkyl, trifluoro(1-6C)alkyl, (3-6C)cycloalkyl, phenyl optionally substituted with one or more substituents independently selected from halogen and (1-6C)alkyl, or a 5-6 membered heteroaryl ring having 1-3 ring heteroatoms independently selected from N, O and S and optionally substituted with one or more groups independently selected from (1-6C)alkyl and halogen.

In one embodiment, compounds of Formula I include compounds of Formula I-A

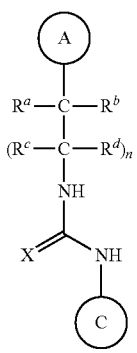

I-A or stereoisomers, tautomers, or pharmaceutically acceptable salts, solvates or prodrugs thereof, wherein:
X is O, S, NH or N—CN;
Ring A is formula A-1 or A-2

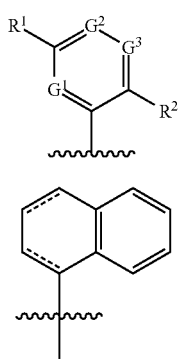

A-1

A-2 wherein the dashed lines are optional double bonds;
n is 0 or 1 when Ring A is formula A-1, and n is 0 when Ring A is formula A-2;
$G^1$, $G^2$ and $G^3$ are independently $CR^x$ or N, wherein no more than 2 of $G^1$, $G^2$ and $G^3$ can be N;
each $R^x$ is independently H, halogen, (1-4C)alkyl or (1-4C)alkoxy;

$R^1$ is H, halogen, (1-3C)alkoxy(1-3C)alkyl (optionally substituted with 1-5 fluoros), (1-3C alkyl)sulfanyl(1-3C)alkyl (optionally substituted with 1-5 fluoros), (1-3C)alkyl (optionally substituted with 1-5 fluoros), (1-3C)alkoxy (optionally substituted with 1-5 fluoros), (1-3C alkyl)sulfanyl (optionally substituted with 1-5 fluoros), cyano(1-3C)alkyl (optionally substituted with 1-5 fluoros), hydroxy(1-3C)alkyl (optionally substituted with 1-5 fluoros), (1-4C)alkyl (optionally substituted with 1-5 fluoros), CH$_3$CH$_2$NR$^y$, CF$_3$CH$_2$NR$^y$, HCF$_2$CH$_2$NR$^y$, H$_2$CFCH$_2$NR$^y$, CH$_3$NR$^y$CH$_2$, R$^y$R$^y$NCH$_2$CH$_2$, R$^y$R$^y$NCH$_2$CFH, or R$^y$R$^y$NCH$_2$CF$_2$;
each $R^y$ is independently H or methyl;
when n is 0, $R^2$ is selected from the group consisting of H, halogen, (1-6C)alkyl [optionally substituted with 1-5 fluoros], (1-6C)alkoxy [optionally substituted with 1-5 fluoros], (1-3C alkoxy)(1-4C)alkyl, (3-6C cycloalkyl)CH$_2$O—, amino(1-3C)alkyl, CF$_3$CH$_2$NHCH$_2$, HCF$_2$CH$_2$NHCH$_2$, a C5-C8 bridged cycloalkyl, hetCyc$^a$, hetCyc$^a$CH$_2$, Cyc$^a$, hetAr$^1$ and Ar$^1$, and
when n is 1, $R^2$ is selected from the group consisting of H, halogen, CF$_3$, F$_2$CH, FCH$_2$, methyl and methoxy.

hetCyc$^a$ is a 4-6 membered heterocyclic ring having a ring heteroatom selected from N, O and S and optionally substituted with 1-3 groups independently selected from OH, F, (1-6C)alkoxy or (1-6C)alkyl [optionally substituted with 1-3 fluoros];
Cyc$^a$ is a (3-6C)cycloalkyl optionally substituted with (1-4C)alkoxy, (1-4C)alkyl, F or OH;
hetAr$^1$ is a 5-6 membered heteroaryl having 1-3 ring heteroatoms independently selected from N, S and O, and optionally substituted with 1-2 groups independently selected from (1-6C)alkyl, halogen, OH, CF$_3$, NH$_2$ and hydroxy(1-2C)alkyl;
Ar$^1$ is phenyl optionally substituted with one or more substituents independently selected from halogen, CF$_3$, CF$_3$O—, (1-4C)alkoxy, (1-4C)sulfanyl, hydroxy(1-4C)alkyl, (1-6C)alkyl and CN;
$R^a$ is H, (1-3C)alkyl, cyclopropyl or cyclobutyl, and
$R^b$ is H, methyl or ethyl,
or $R^a$ and $R^b$ together with the carbon atom to which they are attached form a 3-6 membered cycloalkyl ring;
$R^c$ is H, methyl or ethyl
$R^d$ is CF$_3$CH$_2$CH$_2$, phenyl or phenylCH$_2$— wherein each phenyl ring is optionally substituted with one or more substituents independently selected from halogen and methoxy;
Ring C is formula C-1 or C-2

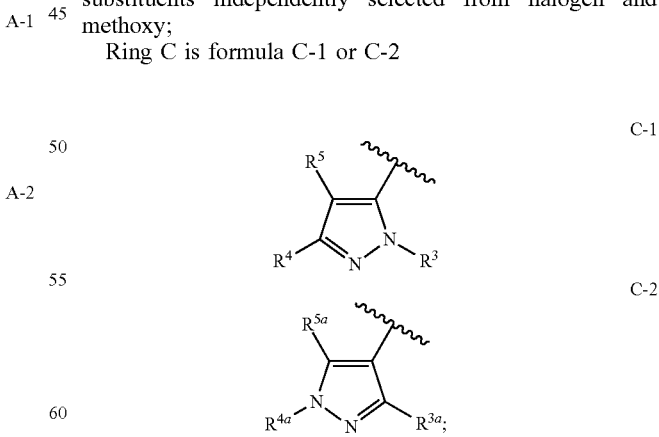

C-1

C-2

$R^3$ is (1-6C)alkyl, hydroxy(1-6C)alkyl, Ar$^2$, hetCyc$^1$, (3-7C)cycloalkyl, a C5-C8 bridged cycloalkyl, or hetAr$^2$;
Ar$^2$ is phenyl optionally substituted with one or more groups independently selected from halogen and (1-6C)alkyl;

hetCyc¹ is a 5-6-membered saturated or partially unsaturated heterocyclic ring having 1-2 ring heteroatoms independently selected from N and O;

hetAr² is a 5-6 membered heteroaryl ring having 1-3 ring heteroatoms independently selected from N, O and S and optionally substituted with one or more groups independently selected from (1-6C)alkyl and halogen;

R⁴ is OH, (1-6C)alkyl, monofluoro(1-6C)alkyl, difluoro (1-6C)alkyl, trifluoro(1-6C)alkyl, tetrafluro(2-6C)alkyl, pentafluro(2-6C)alkyl, cyano(1-6C)alkyl, hydroxy(1-6C)alkyl, dihydroxy(2-6C)alkyl, (1-3C alkoxy)(1-6C)alkyl, amino(1-6C)alkyl, aminocarbonyl(1-6C)alkyl, (1-3C)alkylsulfonamido(1-6C)alkyl, sulfamido(1-6C)alkyl, hydroxycarbonyl(1-6C)alkyl, hetAr³ (1-6C)alkyl, Ar³ (1-6C)alkyl, (1-6C)alkoxy, monofluoro(1-6C)alkoxy, difluoro(1-6C)alkoxy, trifluoro(1-6C)alkoxy, tetrafluoro(2-6C)alkoxy, pentafluoro(2-6C)alkoxy, cyano(1-6C)alkoxy, hydroxy(1-6C)alkoxy, dihydroxy(2-6C)alkoxy, amino(2-6C)alkoxy, hydroxyl-carbonyl(1-6C)alkoxy, hetCyc²(1-6C)alkoxy, hetAr³(1-6C)alkoxy, Ar³(1-6C)alkoxy, (1-4C alkoxy)(1-6C)alkoxy, (1-3C alkylsulfonyl)(1-6C)alkoxy, (3-6C)cycloalkyl [optionally substituted with F, OH, (1-6C alkyl), (1-6C) alkoxy, or (1-3C alkoxy)(1-6C)alkyl], hetAr⁴, hetAr⁴—O—, Ar⁴, hetCyc²(O)CH₂—, (1-4C alkoxycarbonyl)(1-6C)alkoxy, hydroxycarbonyl(1-6C)alkoxy, aminocarbonyl(1-6C)alkoxy, hetCyc²C(=O)(1-6C)alkoxy, hydroxy(1-3C alkoxy)(1-6C)alkoxy, hydroxytrifluoro(1-6C)alkoxy, (1-3C) alkyl sulfonamido(1-6C)alkoxy, (1-3C)alkylamido(1-6C)alkoxy, di(1-3C alkyl)amino-carboxy, hetCyc²C(=O)O—, hydroxydifluoro(1-6C)alkyl, (1-4C alkylcarboxy)(1-6C) alkyl, (1-6C)alkoxycarbonyl, hydroxylcarbonyl, aminocarbonyl, (1-3C alkoxy)aminocarbonyl, hetCyc³, halogen, CN, trifluoromethylsulfonyl, N-(1-3C alkyl)oxadiazolonyl, or hetAr⁵;

hetCyc² is a 4-6 membered heterocyclic ring having 1-2 ring heteroatoms independently selected from N and O and optionally substituted with 1-2 groups independently selected from (1-6C)alkyl, (1-4C alkylcarboxy)(1-6C)alkyl, and (1-6C)acyl;

hetCyc³ is a 4-7 membered heterocycle having 1-2 ring heteroatoms independently selected from N and O and optionally substituted with one or more substituents independently selected from F, CN, (1-6C)alkyl, trifluoro(1-6C)alkyl, hydroxy(1-6C)alkyl, (1-3C alkoxy)(1-6C)alkyl, (1-6C)acyl-, (1-6C)alkylsulfonyl, trifluoromethylsulfonyl and (1-4C alkoxy)carbonyl;

hetAr³ is a 5-membered heteroaryl ring having 1-3 ring atoms independently selected from N, O and S and optionally substituted with (1-6C)alkyl;

Ar³ is phenyl optionally substituted with (1-4C)alkoxy;

hetAr⁴ is a 5-6 membered heteroaryl ring having 1-3 ring heteroatoms independently selected from N, S and O and optionally substituted with one or more substituents independently selected from (1-6C)alkyl, halogen, CN, hydroxy (1-6C)alkyl, trifluoro(1-6C)alkyl, difluoro(1-6C)alkyl, fluoro(1-6C)alkyl, (3-6C)cycloalkyl, (3-6C cycloalkyl)CH₂— (3-6C cycloalkyl)C(=O)—, (1-3C alkoxy)(1-6C)alkyl, (1-6C)alkoxy, (1-6C)alkylsulfonyl, NH₂, (1-6C alkyl)amino, di(1-6C alkyl)amino, (1-3C trifluoroalkoxy), fluoro(1-6C alkyl)amino, difluoro(1-6C alkyl)amino, trifluoro(1-6C alkyl)amino, and (3-4C cycloalkyl)amino;

hetAr⁵ is a group selected from the structures:

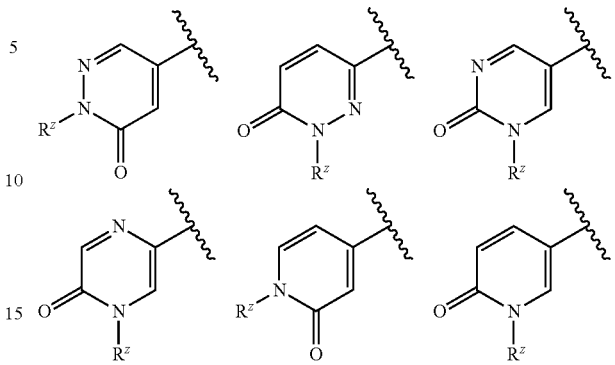

where R^z is (3-4C)cycloalkyl or (1-3C)alkyl (optionally substituted with 1-3 fluoros), wherein each of said hetAr⁵ groups is optionally further substituted with one or more groups independently selected from F and (1-3C)alkyl optionally substituted with 1-3 fluoros;

Ar⁴ is phenyl optionally substituted with one or more groups independently selected from (1-6C)alkyl, halogen, CN, CF₃, CF₃O—, (1-6C)alkoxy, (1-6Calkyl)OC(=O)—, aminocarbonyl, (1-6C)alkylthio, hydroxy(1-6C)alkyl, (1-6C alkyl)SO₂—, HOC(=O)— and (1-3C alkoxy)(1-3C alkyl)OC(=O)—;

R⁵ is (1-6C)alkyl, monofluoro(1-6C)alkyl, difluoro(1-6C) alkyl, trifluoro(1-6C)alkyl, tetrafluoro(2-6C)alkyl, pentafluoro(2-6C)alkyl, halogen, CN, (1-4C)alkoxy, hydroxy(1-4C)alkyl, (1-3C alkoxy)(1-4C)alkyl, (1-4C alkyl)OC(=O)—, (1-6C)alkylthio, (3-4C)cycloalkyl, amino, aminocarbonyl, trifluoro(1-3C alkyl)amido, or phenyl (optionally substituted with one or more groups independently selected from halogen, (1-6C)alkyl and (1-6C)alkoxy; or R⁴ and R⁵ together with the atoms to which they are attached form a 5-6 membered saturated, partially unsaturated or unsaturated carbocyclic ring optionally substituted with one or more substituents independently selected from (1-6C)alkyl, or R⁴ and R⁵ together with the atoms to which they are attached form 5-6 membered saturated, partially unsaturated or unsaturated heterocyclic ring having a ring heteroatom selected from N, O or S, wherein said heterocyclic ring is optionally substituted with one or two substituents independently selected from (1-6C alkyl)C(=O)O—, (1-6C)acyl, (1-6C)alkyl and oxo, and said sulfur ring atom is optionally oxidized to S(=O) or SO₂;

R^{3a} is hydrogen, halogen, (1-6C)alkyl, trifluoro(1-6C) alkyl, (3-6C)cycloalkyl, phenyl optionally substituted with one or more substituents independently selected from halogen and (1-6C)alkyl, or a 5-6 membered heteroaryl ring having 1-3 ring heteroatoms independently selected from N, O and S and optionally substituted with one or more groups independently selected from (1-6C)alkyl and halogen;

R^{4a} is hydrogen, (1-6C)alkyl, trifluoro(1-6C)alkyl, phenyl [optionally substituted with one or more groups independently selected from (1-6C)alkyl, halogen, CN, CF₃, CF₃O—, (1-6C)alkoxy, (1-6Calkyl)OC(=O)—, aminocarbonyl, (1-6C)alkylthio, hydroxy(1-6C)alkyl, (1-6C alkyl)SO₂—, HOC(=O)— and (1-3C alkoxy)(1-3C alkyl)OC(=O)—], or a 5-6 membered heteroaryl ring having 1-3 ring heteroatoms independently selected from N, S and O and optionally substituted with 1-2 substituents independently selected from (1-6C)alkyl, hydroxy(1-6C)alkyl, trifluoro(1-6C)alkyl, (3-6C)cycloalkyl, (3-6C cycloalkyl)CH₂-(3-6C cycloalkyl)C(=O)—, (1-3C alkoxy)(1-6C)alkyl, (1-6C)alkoxy, (1-6C)alkylsulfonyl, NH₂, (1-6C alkyl)amino, di(1-6C alkyl)amino and (1-3C trifluoroalkoxy)(1-3C)trifluoroalkyl; and $R^{5a}$ is hydrogen, halogen, (1-6C)alkyl, trifluoro(1-6C)alkyl, (3-6C)cycloalkyl, phenyl optionally substituted with one or more substituents independently selected from halogen and (1-6C)alkyl, or a 5-6 membered heteroaryl ring having 1-3 ring heteroatoms independently selected from N, O and S and optionally substituted with one or more groups independently selected from (1-6C)alkyl and halogen.

In one embodiment, compounds of Formula I include compounds of Formula I-B

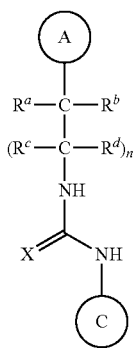

I-B or stereoisomers, tautomers, or pharmaceutically acceptable salts, solvates or prodrugs thereof, wherein:

X is O, S, NH or N—CN;

Ring A is formula A-1 or A-2

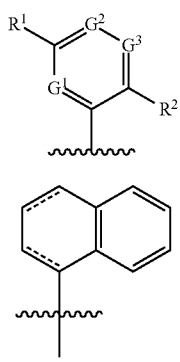

A-1

A-2 wherein the dashed lines are optional double bonds;

n is 0 or 1 when Ring A is formula A-1, and n is 0 when Ring A is formula A-2;

$G^1$, $G^2$ and $G^3$ are independently $CR^x$ or N, wherein no more than 2 of $G^1$, $G^2$ and $G^3$ can be N;

each $R^x$ is independently H, halogen, (1-4C)alkyl or (1-4C)alkoxy;

$R^1$ is H, halogen, (1-3C)alkoxy(1-3C)alkyl (optionally substituted with 1-5 fluoros), (1-3C alkyl)sulfanyl(1-3C)alkyl (optionally substituted with 1-5 fluoros), (1-3C)alkyl (optionally substituted with 1-5 fluoros), (1-3C)alkoxy (optionally substituted with 1-5 fluoros), (1-3C alkyl)sulfanyl (optionally substituted with 1-5 fluoros), cyano(1-3C)alkyl (optionally substituted with 1-5 fluoros), hydroxy(1-3C)alkyl (optionally substituted with 1-5 fluoros), (1-4C)alkyl (optionally substituted with 1-5 fluoros), $CH_3CH_2NR^y$, $CF_3CH_2NR^y$, $HCF_2CH_2NR^y$, $H_2CFCH_2NR^y$, $CH_3NR^yCH_2$, $R^yR^yNCH_2CH_2$, $R^yR^yNCH_2CFH$, or $R^yR^yNCH_2CF_2$;

each $R^y$ is independently H or methyl;

when n is 0, $R^2$ is selected from the group consisting of H, halogen, (1-6C)alkyl [optionally substituted with 1-5 fluoros], (1-6C)alkoxy [optionally substituted with 1-5 fluoros], (1-3C alkoxy)(1-4C)alkyl, (3-6C cycloalkyl)CH₂O—, amino(1-3C)alkyl, $CF_3CH_2NHCH_2$, $HCF_2CH_2NHCH_2$, a C5-C8 bridged cycloalkyl, $hetCyc^a$, $hetCyc^aCH_2$, $Cyc^a$, $hetAr^1$ and $Ar^1$, and when n is 1, $R^2$ is selected from the group consisting of H, halogen, $CF_3$, $F_2CH$, $FCH_2$, methyl and methoxy.

$hetCyc^a$ is a 4-6 membered heterocyclic ring having a ring heteroatom selected from N, O and S and optionally substituted with 1-3 groups independently selected from OH, F, (1-6C)alkoxy or (1-6C)alkyl [optionally substituted with 1-3 fluoros];

$Cyc^a$ is a (3-6C)cycloalkyl optionally substituted with (1-4C)alkoxy, (1-4C)alkyl, F or OH;

$hetAr^1$ is a 5-6 membered heteroaryl having 1-3 ring heteroatoms independently selected from N, S and O, and optionally substituted with 1-2 groups independently selected from (1-6C)alkyl, halogen, OH, $CF_3$, $NH_2$ and hydroxy(1-2C)alkyl;

$Ar^1$ is phenyl optionally substituted with one or more substituents independently selected from halogen, $CF_3$, (1-4C)alkoxy, (1-4C)sulfanyl, hydroxy(1-4C)alkyl, (1-6C)alkyl and CN;

$R^a$ is H, (1-3C)alkyl, cyclopropyl or cyclobutyl, and $R^b$ is H, methyl or ethyl, or $R^a$ and $R^b$ together with the carbon atom to which they are attached form a 3-6 membered cycloalkyl ring;

$R^c$ is H, methyl or ethyl $R^d$ is $CF_3CH_2CH_2$, phenyl or phenylCH₂— wherein each phenyl ring is optionally substituted with one or more substituents independently selected from halogen and methoxy;

Ring C is formula C-1 or C-2

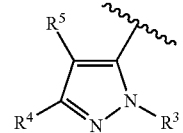

C-1

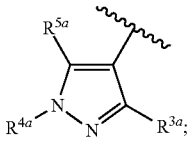

C-2

$R^3$ is (1-6C)alkyl, hydroxy(1-6C)alkyl, $Ar^2$, $hetCyc^1$, (3-7C)cycloalkyl, a C5-C8 bridged cycloalkyl, or $hetAr^2$;

$Ar^2$ is phenyl optionally substituted with one or more groups independently selected from halogen and (1-6C)alkyl;

$hetCyc^1$ is a 5-6-membered saturated or partially unsaturated heterocyclic ring having 1-2 ring heteroatoms independently selected from N and O;

$hetAr^2$ is a 5-6 membered heteroaryl ring having 1-3 ring heteroatoms independently selected from N, O and S and optionally substituted with one or more groups independently selected from (1-6C)alkyl and halogen;

R⁴ is OH, (1-6C)alkyl, monofluoro(1-6C)alkyl, difluoro (1-6C)alkyl, trifluoro(1-6C)alkyl, tetrafluro(2-6C)alkyl, pentafluro(2-6C)alkyl, cyano(1-6C)alkyl, hydroxy(1-6C)alkyl, dihydroxy(2-6C)alkyl, (1-3C alkoxy)(1-6C)alkyl, amino(1-6C)alkyl, aminocarbonyl(1-6C)alkyl, (1-3C)alkylsulfonamido(1-6C)alkyl, sulfamido(1-6C)alkyl, hydroxycarbonyl(1-6C)alkyl, hetAr³(1-6C)alkyl, Ar³(1-6C)alkyl, (1-6C)alkoxy, monofluoro(1-6C)alkoxy, difluoro(1-6C)alkoxy, trifluoro(1-6C)alkoxy, tetrafluoro(2-6C)alkoxy, pentafluoro(2-6C)alkoxy, cyano(1-6C)alkoxy, hydroxy(1-6C)alkoxy, dihydroxy(2-6C)alkoxy, amino(2-6C)alkoxy, hydroxyl-carbonyl(1-6C)alkoxy, hetCyc²(1-6C)alkoxy, hetAr³(1-6C)alkoxy, Ar³(1-6C)alkoxy, (1-4C alkoxy)(1-6C)alkoxy, (1-3C alkylsulfonyl)(1-6C)alkoxy, (3-6C)cycloalkyl [optionally substituted with F, OH, (1-6C alkyl), (1-6C) alkoxy, or (1-3C alkoxy)(1-6C)alkyl], hetAr⁴, hetAr⁴—O—, Ar⁴, hetCyc²(O)CH₂—, (1-4C alkoxycarbonyl)(1-6C)alkoxy, hydroxycarbonyl(1-6C)alkoxy, aminocarbonyl(1-6C)alkoxy, hetCyc²C(=O)(1-6C)alkoxy, hydroxy(1-3C alkoxy)(1-6C)alkoxy, hydroxytrifluoro(1-6C)alkoxy, (1-3C)alkylsulfonamido(1-6C)alkoxy, (1-3C)alkylamido(1-6C)alkoxy, di(1-3C alkyl)amino-carboxy, hetCyc²C(=O)O—, hydroxydifluoro(1-6C)alkyl, (1-4C alkylcarboxy)(1-6C)alkyl, (1-6C)alkoxycarbonyl, hydroxylcarbonyl, aminocarbonyl, (1-3C alkoxy)aminocarbonyl, hetCyc³, halogen, CN, trifluoromethylsulfonyl, N-(1-3C alkyl)oxadiazolonyl, or hetAr⁵;

hetCyc² is a 4-6 membered heterocyclic ring having 1-2 ring heteroatoms independently selected from N and O and optionally substituted with 1-2 groups independently selected from (1-6C)alkyl, (1-4C alkylcarboxy)(1-6C)alkyl, and (1-6C)acyl;

hetCyc³ is a 4-7 membered heterocycle having 1-2 ring heteroatoms independently selected from N and O and optionally substituted with one or more substituents independently selected from F, CN, (1-6C)alkyl, trifluoro(1-6C)alkyl, hydroxy(1-6C)alkyl, (1-3C alkoxy)(1-6C)alkyl, (1-6C)acyl-, (1-6C)alkylsulfonyl, trifluoromethylsulfonyl and (1-4C alkoxy)carbonyl;

hetAr³ is a 5-membered heteroaryl ring having 1-3 ring atoms independently selected from N, O and S and optionally substituted with (1-6C)alkyl;

Ar^a is phenyl optionally substituted with (1-4C)alkoxy;

hetAr⁴ is a 5-6 membered heteroaryl ring having 1-3 ring heteroatoms independently selected from N, S and O and optionally substituted with one or more substituents independently selected from (1-6C)alkyl, halogen, CN, hydroxy(1-6C)alkyl, trifluoro(1-6C)alkyl, difluoro(1-6C)alkyl, fluoro(1-6C)alkyl, (3-6C)cycloalkyl, (3-6C cycloalkyl)CH₂— (3-6C cycloalkyl)C(=O)—, (1-3C alkoxy)(1-6C)alkyl, (1-6C)alkoxy, (1-6C)alkylsulfonyl, NH₂, (1-6C alkyl)amino, di(1-6C alkyl)amino, (1-3C trifluoroalkoxy), fluoro(1-6C alkyl)amino, difluoro(1-6C alkyl)amino, trifluoro(1-6C alkyl)amino, and (3-4C cycloalkyl)amino;

hetAr⁵ is a group selected from the structures:

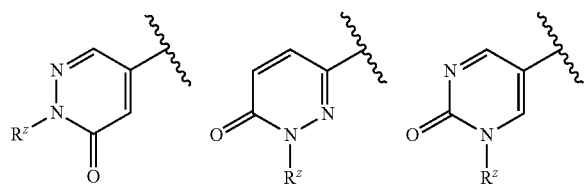

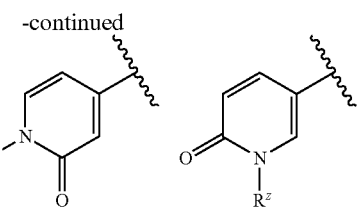

where R^z is (3-4C)cycloalkyl or (1-3C)alkyl (optionally substituted with 1-3 fluoros), wherein each of said hetAr⁵ groups is optionally further substituted with one or more groups independently selected from F and (1-3C)alkyl optionally substituted with 1-3 fluoros;

Ar⁴ is phenyl optionally substituted with one or more groups independently selected from (1-6C)alkyl, halogen, CN, CF₃, CF₃O—, (1-6C)alkoxy, (1-6Calkyl)OC(=O)—, aminocarbonyl, (1-6C)alkylthio, hydroxy(1-6C)alkyl, (1-6C alkyl)SO₂—, HOC(=O)— and (1-3C alkoxy)(1-3C alkyl)OC(=O)—;

R⁵ is (1-6C)alkyl, monofluoro(1-6C)alkyl, difluoro(1-6C)alkyl, trifluoro(1-6C)alkyl, tetrafluoro(2-6C)alkyl, pentafluoro(2-6C)alkyl, halogen, CN, (1-4C)alkoxy, hydroxy(1-4C)alkyl, (1-3C alkoxy)(1-4C)alkyl, (1-4C alkyl)OC(=O)—, (1-6C)alkylthio, (3-4C)cycloalkyl, amino, aminocarbonyl, trifluoro(1-3C alkyl)amido, or phenyl (optionally substituted with one or more groups independently selected from halogen, (1-6C)alkyl and (1-6C)alkoxy); or R⁴ and R⁵ together with the atoms to which they are attached form a 5-6 membered saturated, partially unsaturated or unsaturated carbocyclic ring optionally substituted with one or more substituents independently selected from (1-6C)alkyl, or R⁴ and R⁵ together with the atoms to which they are attached form 5-6 membered saturated, partially unsaturated or unsaturated heterocyclic ring having a ring heteroatom selected from N, O or S, wherein said heterocyclic ring is optionally substituted with one or two substituents independently selected from (1-6C alkyl)C(=O)O—, (1-6C)acyl, (1-6C)alkyl and oxo, and said sulfur ring atom is optionally oxidized to S(=O) or SO₂;

R^{3a} is halogen, (1-6C)alkyl, trifluoro(1-6C)alkyl, (3-6C)cycloalkyl, phenyl optionally substituted with one or more substituents independently selected from halogen and (1-6C)alkyl, or a 5-6 membered heteroaryl ring having 1-3 ring heteroatoms independently selected from N, O and S and optionally substituted with one or more groups independently selected from (1-6C)alkyl and halogen;

R^{4a} is hydrogen, (1-6C)alkyl, trifluoro(1-6C)alkyl, phenyl [optionally substituted with one or more groups independently selected from (1-6C)alkyl, halogen, CN, CF₃, CF₃O—, (1-6C)alkoxy, (1-6 Calkyl)OC(=O)—, aminocarbonyl, (1-6C)alkylthio, hydroxy(1-6C)alkyl, (1-6C alkyl)SO₂—, HOC(=O)— and (1-3C alkoxy)(1-3C alkyl)OC(=O)—], or a 5-6 membered heteroaryl ring having 1-3 ring heteroatoms independently selected from N, S and O and optionally substituted with 1-2 substituents independently selected from (1-6C)alkyl, hydroxy(1-6C)alkyl, trifluoro(1-6C)alkyl, (3-6C)cycloalkyl, (3-6C cycloalkyl)CH₂-(3-6C cycloalkyl)C(=O)—, (1-3C alkoxy)(1-6C)alkyl, (1-6C)alkoxy, (1-6C)alkylsulfonyl, NH₂, (1-6C alkyl)amino, di(1-6C alkyl)amino and (1-3C trifluoroalkoxy)(1-3C)trifluoroalkyl; and R^{5a} is halogen, (1-6C)alkyl, trifluoro(1-6C)alkyl, (3-6C)cycloalkyl, phenyl optionally substituted with one or more substituents independently selected from halogen and (1-6C)alkyl, or a 5-6 membered heteroaryl ring having 1-3 ring heteroatoms independently selected from N, O and S and optionally substituted with one or more groups independently selected from (1-6C)alkyl and halogen.

In one embodiment, compounds of Formula I include compounds of Formula I-C

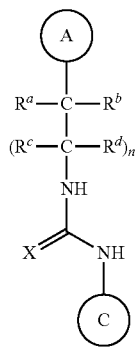

I-C or stereoisomers, tautomers, or pharmaceutically acceptable salts, solvates or prodrugs thereof, wherein:

X is O, S, NH or N—CN;
Ring A is formula A-1 or A-2

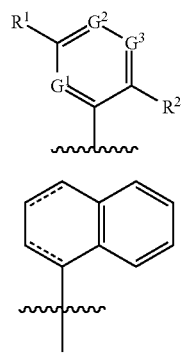

A-1

A-2 wherein the dashed lines are optional double bonds;
n is 0 or 1 when Ring A is formula A-1, and n is 0 when Ring A is formula A-2;
$G^1$, $G^2$ and $G^3$ are independently $CR^x$ or N, wherein no more than 2 of $G^1$, $G^2$ and $G^3$ can be N;
each $R^x$ is independently H, halogen, (1-4C)alkyl or (1-4C)alkoxy;
$R^1$ is H, halogen, (1-3C)alkoxy(1-3C)alkyl (optionally substituted with 1-5 fluoros), (1-3C alkyl)sulfanyl(1-3C)alkyl (optionally substituted with 1-5 fluoros), (1-3C)alkyl (optionally substituted with 1-5 fluoros), (1-3C)alkoxy (optionally substituted with 1-5 fluoros), (1-3C alkyl)sulfanyl (optionally substituted with 1-5 fluoros), cyano(1-3C)alkyl (optionally substituted with 1-5 fluoros), hydroxy(1-3C) alkyl (optionally substituted with 1-5 fluoros), (1-4C)alkyl (optionally substituted with 1-5 fluoros), $CH_3CH_2NR^y$, $CF_3CH_2NR^y$, $HCF_2CH_2NR^y$, $H_2CFCH_2NR^y$, $CH_3NR^yCH_2$, $R^yR^yNCH_2CH_2$, $R^yR^yNCH_2CFH$, or $R^yR^yNCH_2CF_2$;
each $R^y$ is independently H or methyl;
when n is 0, $R^2$ is selected from the group consisting of H, halogen, (1-6C)alkyl [optionally substituted with 1-5 fluoros], (1-6C)alkoxy [optionally substituted with 1-5 fluoros], (1-3C alkoxy)(1-4C)alkyl, (3-6C cycloalkyl)$CH_2O$—, amino(1-3C)alkyl, $CF_3CH_2NHCH_2$, $HCF_2CH_2NHCH_2$, a C5-C8 bridged cycloalkyl, $hetCyc^a$, $hetCyc^aCH_2$, $Cyc^a$, $hetAr^1$ and $Ar^1$, and
when n is 1, $R^2$ is selected from the group consisting of 1-1, halogen, $CF_3$, $F_2CH$, $FCH_2$, methyl and methoxy.
$hetCyc^a$ is a 4-6 membered heterocyclic ring having a ring heteroatom selected from N, O and S and optionally substituted with 1-3 groups independently selected from OH, F, (1-6C)alkoxy or (1-6C)alkyl [optionally substituted with 1-3 fluoros];
$Cyc^a$ is a (3-6C)cycloalkyl optionally substituted with (1-4C)alkoxy, (1-4C)alkyl, F or OH;
$hetAr^1$ is a 5-6 membered heteroaryl having 1-3 ring heteroatoms independently selected from N, S and O, and optionally substituted with 1-2 groups independently selected from (1-6C)alkyl, halogen, OH, $CF_3$, $NH_2$ and hydroxy(1-2C)alkyl;
$Ar^1$ is phenyl optionally substituted with one or more substituents independently selected from halogen, $CF_3$, $CF_3O$—, (1-4C)alkoxy, (1-4C)sulfanyl, hydroxy(1-4C)alkyl, (1-6C)alkyl and CN;
$R^a$ is H, (1-3C)alkyl, cyclopropyl, cyclobutyl, or $CF_3$, and $R^b$ is H, methyl or ethyl,
or $R^a$ and $R^b$ together with the carbon atom to which they are attached form a 3-6 membered cycloalkyl ring;
$R^c$ is H, methyl or ethyl
$R^d$ is $CF_3CH_2CH_2$, phenyl or phenyl$CH_2$— wherein each phenyl ring is optionally substituted with one or more substituents independently selected from halogen, methoxy and methoxymethyl;
Ring C is formula C-1 or C-2

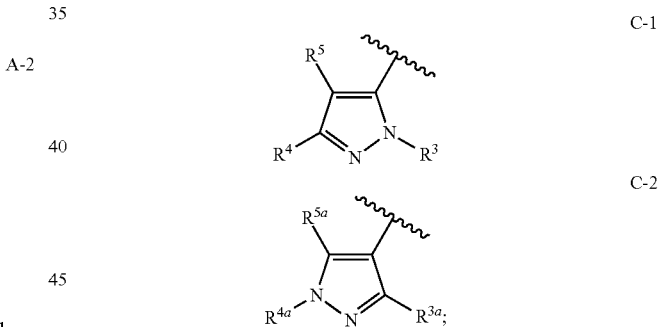

C-1

C-2

$R^3$ is (1-6C)alkyl, hydroxy(1-6C)alkyl, $Ar^2$, $hetCyc^1$, (3-7C)cycloalkyl, a C5-C8 bridged cycloalkyl, or $hetAr^2$;
$Ar^2$ is phenyl optionally substituted with one or more groups independently selected from halogen and (1-6C)alkyl;
$hetCyc^1$ is a 5-6-membered saturated or partially unsaturated heterocyclic ring having 1-2 ring heteroatoms independently selected from N and O;
$hetAr^2$ is a 5-6 membered heteroaryl ring having 1-3 ring heteroatoms independently selected from N, O and S and optionally substituted with one or more groups independently selected from (1-6C)alkyl and halogen;
$R^4$ is OH, (1-6C)alkyl, monofluoro(1-6C)alkyl, difluoro(1-6C)alkyl, trifluoro(1-6C)alkyl, tetrafluro(2-6C)alkyl, pentafluro(2-6C)alkyl, cyano(1-6C)alkyl, hydroxy(1-6C)alkyl, dihydroxy(2-6C)alkyl, (1-3C alkoxy)(1-6C)alkyl, amino(1-6C)alkyl, aminocarbonyl(1-6C)alkyl, (1-3C)alkylsulfonamido(1-6C)alkyl, sulfamido(1-6C)alkyl, hydroxycarbonyl(1-6C)alkyl, $hetAr^3$(1-6C)alkyl, $Ar^3$(1-6C)alkyl, (1-6C)alkoxy, monofluoro(1-6C)alkoxy, difluoro(1-6C)alkoxy, trifluoro(1-6C)alkoxy, tetrafluoro(2-6C)alkoxy, pentafluoro(2-6C)alkoxy, cyano(1-6C)alkoxy, hydroxy(1-6C)alkoxy, dihydroxy(2-6C)alkoxy, amino(2-6C)alkoxy, hydroxyl-carbonyl(1-6C)alkoxy, hetCyc²(1-6C)alkoxy, hetAr³(1-6C)alkoxy, Ar³(1-6C)alkoxy, (1-4C alkoxy)(1-6C)alkoxy, (1-3C alkylsulfonyl)(1-6C)alkoxy, (3-6C)cycloalkyl [optionally substituted with F, OH, (1-6C alkyl), (1-6C)alkoxy, or (1-3C alkoxy)(1-6C)alkyl], hetAr⁴, hetAr⁴—O—, Ar⁴, hetCyc²(O)CH₂—, (1-4C alkoxycarbonyl)(1-6C)alkyl, hydroxycarbonyl(1-6C)alkoxy, aminocarbonyl(1-6C)alkoxy, hetCyc²C(=O)(1-6C)alkoxy, hydroxy(1-3C alkoxy)(1-6C)alkoxy, hydroxytrifluoro(1-6C)alkoxy, (1-3C)alkylsulfonamido(1-6C)alkoxy, (1-3C)alkylamido(1-6C)alkoxy, di(1-3C alkyl)amino-carboxy, hetCyc²C(=O)O—, hydroxydifluoro(1-6C)alkyl, (1-4C alkylcarboxy)(1-6C)alkyl, (1-6C)alkoxycarbonyl, hydroxylcarbonyl, aminocarbonyl, (1-3C alkoxy)aminocarbonyl, hetCyc³, halogen, CN, trifluoromethylsulfonyl, N-(1-3C alkyl)oxadiazolonyl, hetAr⁵, Ar⁴—O—, hetCyc⁴-O—, Cyc¹-O—, or aminohydroxy(1-6C)alkoxy;

hetCyc² is a 4-6 membered heterocyclic ring having 1-2 ring heteroatoms independently selected from N and O and optionally substituted with 1-2 groups independently selected from (1-6C)alkyl, 1-4C alkoxy)carbonyl, (1-6C) acyl, halogen and oxo;

hetCyc³ is a 4-7 membered heterocycle having 1-2 ring heteroatoms independently selected from N and O and optionally substituted with one or more substituents independently selected from F, CN, (1-6C)alkyl, trifluoro(1-6C)alkyl, hydroxy(1-6C)alkyl, (1-3C alkoxy)(1-6C)alkyl, (1-6C)acyl-, (1-6C)alkylsulfonyl, trifluoromethylsulfonyl and (1-4C alkoxy)carbonyl;

hetCyc⁴ is a 5-8 membered monocyclic, spirocyclic or bridged heterocycle having a ring nitrogen atom and optionally substituted with one or more groups independently selected from (1-6C)alkyl and halogen;

Cyc¹ is a 3-6 membered carbocycle optionally substituted with an amino group;

hetAr³ is a 5-membered heteroaryl ring having 1-3 ring atoms independently selected from N, O and S and optionally substituted with (1-6C)alkyl;

Ar³ is phenyl optionally substituted with (1-4C)alkoxy;

hetAr⁴ is a 5-6 membered heteroaryl ring having 1-3 ring heteroatoms independently selected from N, S and O and optionally substituted with one or more substituents independently selected from (1-6C)alkyl, halogen, CN, hydroxy(1-6C)alkyl, trifluoro(1-6C)alkyl, difluoro(1-6C)alkyl, fluoro(1-6C)alkyl, (3-6C)cycloalkyl, (3-6C cycloalkyl)CH₂— (3-6C cycloalkyl)C(=O)—, (1-3C alkoxy)(1-6C) alkyl, (1-6C)alkoxy, (1-6C)alkylsulfonyl, NH₂, (1-6C alkyl)amino, di(1-6C alkyl)amino, (1-3C trifluoroalkoxy), fluoro(1-6C alkyl)amino, difluoro(1-6C alkyl)amino, trifluoro(1-6C alkyl)amino, and (3-4C cycloalkyl)amino;

hetAr⁵ is a group selected from the structures:

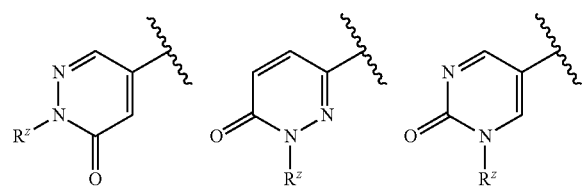

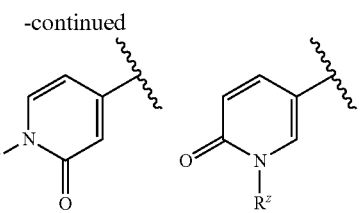

where $R^z$ is (3-4C)cycloalkyl or (1-3C)alkyl (optionally substituted with 1-3 fluoros), wherein each of said hetAr⁵ groups is optionally further substituted with one or more groups independently selected from F and (1-3C)alkyl optionally substituted with 1-3 fluoros;

Ar⁴ is phenyl optionally substituted with one or more groups independently selected from (1-6C)alkyl, halogen, CN, CF₃, CF₃O—, (1-6C)alkoxy, (1-6Calkyl)OC(=O)—, aminocarbonyl, (1-6C)alkylthio, hydroxy(1-6C)alkyl, (1-6C alkyl)SO₂—, HOC(=O)— and (1-3C alkoxy)(1-3C alkyl)OC(=O)—;

R⁵ is (1-6C)alkyl, monofluoro(1-6C)alkyl, difluoro(1-6C)alkyl, trifluoro(1-6C)alkyl, tetrafluoro(2-6C)alkyl, pentafluoro(2-6C)alkyl, halogen, CN, (1-4C)alkoxy, hydroxy(1-4C)alkyl, (1-3C alkoxy)(1-4C)alkyl, (1-4C alkyl)OC(=O)—, (1-6C)alkylthio, (3-4C)cycloalkyl, amino, aminocarbonyl, trifluoro(1-3C alkyl)amido, or phenyl (optionally substituted with one or more groups independently selected from halogen, (1-6C)alkyl and (1-6C)alkoxy); or R⁴ and R⁵ together with the atoms to which they are attached form a 5-6 membered saturated, partially unsaturated or unsaturated carbocyclic ring optionally substituted with one or more substituents independently selected from (1-6C)alkyl, or R⁴ and R⁵ together with the atoms to which they are attached form 5-6 membered saturated, partially unsaturated or unsaturated heterocyclic ring having a ring heteroatom selected from N, O or S, wherein said heterocyclic ring is optionally substituted with one or two substituents independently selected from (1-6C alkyl)C(=O)O—, (1-6C)acyl, (1-6C)alkyl and oxo, and said sulfur ring atom is optionally oxidized to S(=O) or SO₂;

R³ᵃ is halogen, (1-6C)alkyl, trifluoro(1-6C)alkyl, (3-6C)cycloalkyl, phenyl optionally substituted with one or more substituents independently selected from halogen and (1-6C)alkyl, or a 5-6 membered heteroaryl ring having 1-3 ring heteroatoms independently selected from N, O and S and optionally substituted with one or more groups independently selected from (1-6C)alkyl and halogen;

R⁴ᵃ is hydrogen, (1-6C)alkyl, trifluoro(1-6C)alkyl, phenyl [optionally substituted with one or more groups independently selected from (1-6C)alkyl, halogen, CN, CF₃, CF₃O—, (1-6C)alkoxy, (1-6Calkyl)OC(=O)—, aminocarbonyl, (1-6C)alkylthio, hydroxy(1-6C)alkyl, (1-6C alkyl)SO₂—, HOC(=O)— and (1-3C alkoxy)(1-3C alkyl)OC(=O)—], or a 5-6 membered heteroaryl ring having 1-3 ring heteroatoms independently selected from N, S and O and optionally substituted with 1-2 substituents independently selected from (1-6C)alkyl, hydroxy(1-6C)alkyl, trifluoro(1-6C)alkyl, (3-6C)cycloalkyl, (3-6C cycloalkyl)CH₂-(3-6C cycloalkyl)C(=O)—, (1-3C alkoxy)(1-6C)alkyl, (1-6C)alkoxy, (1-6C)alkylsulfonyl, NH₂, (1-6C alkyl)amino, di(1-6C alkyl)amino and (1-3C trifluoroalkoxy)(1-3C)trifluoroalkyl; and R⁵ᵃ is halogen, (1-6C)alkyl, trifluoro(1-6C)alkyl, (3-6C)cycloalkyl, phenyl optionally substituted with one or more substituents independently selected from halogen and (1-6C)alkyl, or a 5-6 membered heteroaryl ring having 1-3 ring heteroatoms independently selected from N, O and S and optionally substituted with one or more groups independently selected from (1-6C)alkyl and halogen.

It is to be understood that in instances where two or more radicals are used in succession to define a substituent attached to a structure, the first named radical is considered to be terminal and the last named radical is considered to be attached to the structure in question. Thus, for example, the radical "alkoxyalkyl" is attached to the structure in question by the alkyl group.

The terms "(1-6C)alkyl", "(1-4C)alkyl" and "(1-3C) alkyl" as used herein refer to saturated linear monovalent hydrocarbon radicals of one to six carbon atoms, one to four carbon atoms, and one to three carbon atoms, respectively, or a branched saturated monovalent hydrocarbon radical of three to six carbon atoms, three to four carbon atoms, or three carbon atoms, respectively. Examples include, but are not limited to, methyl, ethyl, 1-propyl, 2-propyl, 1-butyl, 2-methyl-1-propyl, 2-butyl, 2-methyl-2-propyl, 2,2-dimethylpropyl, 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, and 3,3-dimethyl-2-butyl.

"(1-4C)Alkoxy", "(1-3C)alkoxy", "(1-6C)alkoxy" and "(2-6C)alkoxy" refer to an —OR radical where R is (1-4C) alkyl, (1-3C)alkyl, (1-6C)alkyl, or (2-6C)alkyl, respectively, as defined above. Examples include methoxy, ethoxy, and the like.

"(1-6)Acyl" means a RC(=O)— radical where R is a linear saturated monovalent hydrocarbon radical of one to five carbon atoms or a branched saturated monovalent hydrocarbon radical of three to five carbon atoms, e.g., methylcarbonyl, and the like.

"(1-3C Alkoxy)(1-6C)alkyl" and "(1-3C alkoxy)(1-4C) alkyl" mean a linear saturated monovalent hydrocarbon radical of one to six carbon atoms or one to four carbon atoms, or a branched saturated monovalent hydrocarbon radical of three to six carbon atoms or three to four carbon atoms, respectively, wherein one of the carbon atoms is substituted with one (1-3C)alkoxy group as defined herein.

"(1-3C Alkoxy)(1-6C)alkoxy" means a (1-6C)alkoxy group as defined herein, wherein one of the carbon atoms is substituted with a (1-3C)alkoxy group as defined herein. Examples include methoxymethoxy, methoxyethoxy, and the like.

"(1-3C Alkoxy)aminocarbonyl" means a (1-3C alkyl)-O—NH—C(=O)— group.

"(1-6C)Alkoxycarbonyl" and "(1-4C)alkoxycarbonyl" mean a (1-6C)—O—C(=O)— and (1-4C)—O—C(=O)— group, respectively.

"(1-4C Alkoxycarbonyl)(1-6C alkoxy)" means a (1-6C) alkoxy group as defined herein wherein one of the carbon atoms is substituted with one (1-4C alkoxycarbonyl group, i.e., an alkyl-O—C(=O)— group.

"(1-3C Alkoxy)hydroxycarbonylalkyl" means a hydroxycarbonylalkyl group as defined herein wherein one of the carbon atoms is substituted with one (1-3C alkoxy) group.

"Amino" means a —NRR' group where R and R' are independently selected from hydrogen or (1-3C)alkyl as defined herein. Examples include H$_2$N—, CH$_3$NH—, (CH$_3$)$_2$N, and the like. "Amino(1-6C)alkyl" means a linear saturated monovalent hydrocarbon radical of one to six carbon atoms or a branched saturated monovalent hydrocarbon radical of three to six carbon atoms, wherein one of the carbon atoms is substituted with one —NRR' group where R and R' are independently selected from hydrogen or (1-3C)alkyl as defined herein. Examples include aminomethyl, methylaminoethyl, 2-ethylamino-2-methylethyl, and the like.

"Amino(2-6C)alkoxy" means a (2-6C)alkoxy group as defined herein, wherein one of the carbon atoms is substituted with one —NRR' group where R and R' are independently selected from hydrogen or (1-3C)alkyl as defined herein.

"Aminocarbonyl" means a RR'NCO— radical where R and R' are independently hydrogen or (1-6C)alkyl as defined herein. Examples include H$_2$NCO—, dimethylaminocarbonyl, and the like.

"Aminocarbonyl(1-6C)alkyl" means a linear saturated hydrocarbon radical of one to six carbon atoms or a branched saturated monovalent hydrocarbon radical of three to six carbons wherein one of the carbon atoms is substituted with one aminocarbonyl group as defined herein, e.g., 2-aminocarbonylethyl, 1-, 2-, or 3-dimethylaminocarbonylpropyl, and the like.

"Aminocarbonyl(1-6C)alkoxy" means a (1-6C)alkoxy as defined herein, wherein one of the carbon atoms is substituted with one aminocarbonyl group as defined herein.

"Aminohydroxy(1-6C)alkoxy" means a (1-6C)alkoxy as defined herein, wherein one of the carbon atoms is substituted with one amino group as defined herein, and one of the carbon atoms (other than the carbon atom substituted with the amino group) is substituted with one OH group.

"(1-3C)Alkylamido(1-6C)alkoxy" means a (1-6C)alkoxy as defined herein, wherein one of the carbon atoms is substituted with one alkylamido group, i.e., substituted with a (1-3C)C(=O)NH— group.

"(1-4C alkyl)carboxy" means a R'—C(=O)O— group where R' is (1-4C)alkyl.

"(1-4C alkylsiloxy)(1-6C)alkoxy" means a (1-6C)alkoxy group as defined herein wherein one of the carbon atoms is substituted with one (1-4C alkyl)siloxy group, e.g., a (1-4C alkyl)Si—O— group such as a tert-butylsiloxy group.

"(1-3C)Alkylsulfonamido" means a (1-3C) alkylSO$_2$NH— radical where (1-3C)alkyl is as defined herein "(1-3C Alkylsulfonamido)(1-6C)alkyl" means a linear saturated hydrocarbon radical of one to six carbon atoms or a branched saturated monovalent hydrocarbon radical of three to six carbons substituted with one (1-3C)alkylsulfonamido group as defined herein.

"(1-3C)Alkylsulfonamido(1-6C)alkoxy" means a (1-6C) alkoxy group as defined herein wherein one of the carbon atoms is substituted with one (1-3C)alkylsulfonamido group as defined herein.

"(1-3C)Alkylsulfonyl" means a —SO$_2$R radical where R is (1-3C)alkyl as defined above, e.g., methylsulfonyl, and the like.

"(1-3C Alkylsulfonyl)(1-6C)alkoxy" means a (1-6C) alkoxy group as defined herein, wherein one of the carbon atoms is substituted with a (1-3C)alkylsulfonyl group.

"Hydroxycarbonyl" means HOC(=O)—.

"(1-4C alkyl)carboxy(1-6C)alkyl" means a (1-6C)alkyl group as defined herein wherein one of the carbon atoms is substituted with a (1-4C alkyl)carboxy group as defined herein.

"Cyano(1-6C)alkyl" means a linear saturated hydrocarbon radical of one to six carbon atoms or a branched saturated monovalent hydrocarbon radical of three to six carbons substituted with a cyano (CN) group.

"(3-6C)Cycloalkyl" means a cyclic saturated monovalent hydrocarbon radical of three to six carbon atoms, e.g., cyclopropyl, cyclobutyl, cyclopentyl, or cyclohexyl.

"Dihydroxy(2-6C)alkyl" means a linear saturated hydrocarbon radical of two to six carbon atoms or a branched saturated monovalent hydrocarbon radical of three to six carbons substituted with two hydroxy (OH) groups, provided that two hydroxy groups are not both on the same carbon atom.

"Dihydroxy(2-6C)alkoxy" means a (2-6C)alkoxy group as defined herein, wherein two of the carbon atoms are substituted with a hydroxy group.

"Halogen" as used herein means F, Cl, Br or I.

"Heterocycle" refers to a saturated or partially unsaturated ring system having one or more ring heteroatoms as recited for the specific heterocyclic group, wherein the heterocycle is optionally substituted with substituents as defined for that particular heterocyclic group.

"Heteroaryl" refers to a 5-6 membered unsaturated ring system having one or more ring heteroatoms as recited for the specific heteroaryl group, wherein the heteroaryl is optionally substituted with substituents as defined for that particular heteroaryl group.

"hetCyc$^2$C(=O)(1-6C)alkoxy" means a (1-6C)alkoxy as defined herein, wherein one of the carbon atoms is substituted with a hetCyc$^2$C(=O) group, wherein hetCyc$^2$ is as defined herein.

"Hydroxy(1-6C)alkyl" and "hydroxy(1-4C)alkyl" means a linear saturated hydrocarbon radical of one to six carbon atoms or one to four carbon atoms, respectively, or a branched saturated monovalent hydrocarbon radical of three to six carbon atoms or three to four carbon atoms, respectively, wherein one of the carbon atoms is substituted with a hydroxy (OH) group.

"Hydroxy(1-6C)alkoxy" means a (1-6C)alkoxy group as defined herein, wherein one of the carbon atoms is substituted with a hydroxy group.

"Hydroxy(1-3C alkoxy)(1-6C)alkoxy" means a (1-3C alkoxy)(1-6C)alkoxy as defined herein, wherein one of the carbon atoms is substituted with a hydroxy group.

"Hydroxydifluoro(1-6C)alkyl" means a difluoro(1-6C)alkyl group as defined herein, wherein one of the carbon atoms is substituted with a hydroxy group.

"Hydroxytrifluoro(1-6C)alkoxy" means a trifluoro(1-6C)alkoxy group as defined herein, wherein one of the carbon atoms is substituted with a hydroxy group.

"Hydroxycarbonylalkyl" means a linear saturated hydrocarbon radical of one to six carbon atoms or a branched saturated monovalent hydrocarbon radical of three to six carbons substituted with one —COOH group. Examples include 2-hydroxycarbonylethyl, 1-, 2-, or 3-hydroxycarbonylpropyl, and the like.

"Isoindoline-1,3-dionyl(1-6C)alkoxy" means a (1-6C) alkoxy group as defined herein, wherein one of the carbon atoms is substituted with an isoindoline-1,3-dionyl group.

"Monofluoro(1-6C)alkyl", "difluoro(1-6C)alkyl" and "trifluoro(1-6C)alkyl" refer to a (1-6C)alkyl group as defined herein wherein one to three hydrogen atoms, respectively, is replaced by a fluoro group.

"Tetrafluoro(2-6C)alkyl" and "pentafluoro(2-6C)alkyl" refer to a linear saturated monovalent hydrocarbon radical of two to six carbon atoms or a branched saturated monovalent hydrocarbon radical of three to six carbon atoms wherein four to five hydrogen atoms, respectively, is replaced by a fluoro group.

"Trifluoro(1-3C alkyl)amido" means a (1-3C alkyl)C(=O)NH— group wherein one of the carbons is substituted with three fluoros.

"Trifluoro(1-6C)alkoxy" means a (1-6C)alkoxy group as defined herein, wherein one of the carbon atoms is substituted with three fluoros.

"Sulfamido(1-6C)alkyl" means a linear saturated hydrocarbon radical of one to six carbon atoms or a branched saturated monovalent hydrocarbon radical of three to six carbons substituted with one sulfamido (H$_2$NSO$_2$NH—) group.

It should be noted that compounds of the invention may contain groups that may exist in tautomeric forms, such as heteroatom substituted heteroaryl or heterocyclic groups and the like, which are illustrated in the following general and specific examples:

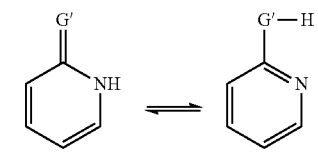

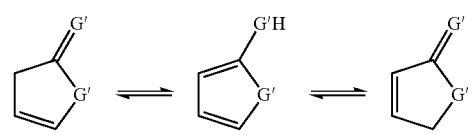

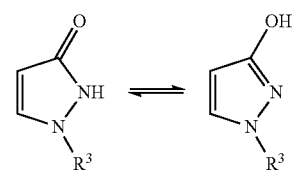

where G'=O, S, or NR, and though one form is named, described, displayed and/or claimed herein, all the tautomeric forms are intended to be inherently included in such name, description, display and/or claim.

In one embodiment of Formula I, X is O.

In one embodiment of Formula I, X is S.

In one embodiment of Formula I, X is NH.

In one embodiment of Formula I, X is N—CN.

In one embodiment of Formula I, Ring A is Formula A-1:

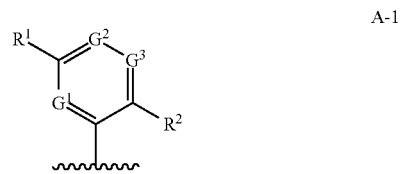

where G$^1$, G$^2$ and G$^3$ are independently CR$^x$ or N, wherein no more than 2 of G$^1$, G$^2$ and G$^3$ can be N; and R$^1$ and R$^2$ are as defined for Formula I.

In one embodiment of Formula I, G$^1$, G$^2$ and G$^3$ are CR$^x$ and Formula A-1 has the structure:

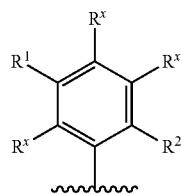

where $R^x$, $R^1$ and $R^2$ are as defined for Formula I. In one embodiment, each $R^x$ is independently H or F. In one embodiment, each $R^x$ is hydrogen.

In one embodiment of Formula I, $G^1$ is N and $G^2$ and $G^3$ are $CR^x$, and Formula A-1 has the structure:

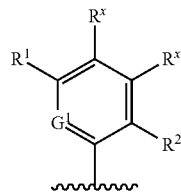

where $R^x$, $R^1$ and $R^2$ are as defined for Formula I. In one embodiment, each $R^x$ is independently H or F. In one embodiment, each $R^x$ is hydrogen.

In one embodiment of Formula I, $G^2$ is N and $G^1$ and $G^3$ are $CR^x$, and Formula A-1 has the structure:

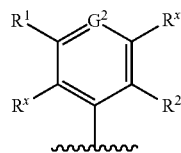

where $R^x$, $R^1$ and $R^2$ are as defined for Formula I. In one embodiment, each $R^x$ is independently H or F. In one embodiment, each $R^x$ is hydrogen.

In one embodiment of Formula I, $G^3$ is N and $G^1$ and $G^2$ are $CR^x$, and Formula A-1 has the structure:

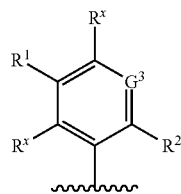

where $R^x$, $R^1$ and $R^2$ are as defined for Formula I. In one embodiment, each $R^x$ is independently H or F. In one embodiment, each $R^x$ is hydrogen.

In one embodiment of Formula I, $G^1$ and $G^2$ are N and $G^3$ is $CR^x$, and Formula A-1 has the structure:

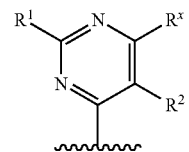

where $R^x$, $R^1$ and $R^2$ are as defined for Formula I. In one embodiment, each $R^x$ is independently H or F. In one embodiment, $R^x$ is hydrogen.

In one embodiment of Formula I, $G^1$ and $G^3$ are N and $G^2$ is $CR^x$, and Formula A-1 has the structure:

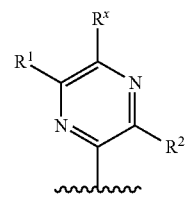

where $R^x$, $R^1$ and $R^2$ are as defined for Formula I. In one embodiment, each $R^x$ is independently H or F. In one embodiment, $R^x$ is hydrogen.

In one embodiment of Formula I, $G^1$ is $CR^x$ and $G^2$ and $G^3$ are N, and Formula A-1 has the structure:

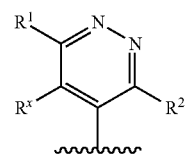

where $R^x$, $R^1$ and $R^2$ are as defined for Formula I. In one embodiment, each $R^x$ is independently H or F. In one embodiment, $R^x$ is hydrogen.

In one embodiment of Formula I, Ring A is Formula A-2:

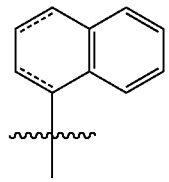

A-2 wherein the dashed lines are optional double bonds.

In one embodiment of Formula I, Formula A-2 has the structure:

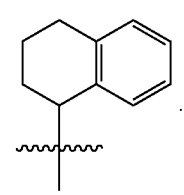 [SMILES: *C1CCCc2ccccc21]

In one embodiment of Formula I, Formula A-2 has the structure:

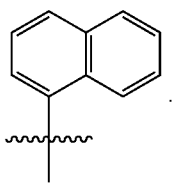 [SMILES: *c1cccc2ccccc12]

In one embodiment of Formula I, $R^1$ is H.

In one embodiment of Formula I, $R^1$ is halogen. In one embodiment of Formula I, $R^1$ is Br.

In one embodiment of Formula I, $R^1$ is (1-3C)alkoxy(1-3C)alkyl optionally substituted with 1-5 fluoros. In one embodiment, $R^1$ is (1-3C)alkoxy(1-3C)alkyl. In one embodiment, $R^1$ is (1-3C)alkoxy(1-3C)alkyl which is substituted with 1-5 fluoros. In one embodiment, $R^1$ is $CH_3OCH_2$—, $CF_3OCH_2$—, or $CH_3OCF_2$—. In one embodiment, $R^1$ is $CH_3OCH_2$—.

In one embodiment of Formula I, $R^1$ is (1-3C alkyl)sulfanyl(1-3C)alkyl optionally substituted with 1-5 fluoros. In one embodiment, $R^1$ is (1-3C alkyl)sulfanyl(1-3C)alkyl. In one embodiment, $R^1$ is (1-3C alkyl)sulfanyl(1-3C)alkyl substituted with 1-5 fluoros. In one embodiment, $R^1$ is $CH_3SCH_2$ or $CF_3SCH_2$.

In one embodiment of Formula I, $R^1$ is (1-3C)alkyl optionally substituted with 1-5 fluoros. In one embodiment of Formula I, $R^1$ is (1-3C)alkyl. In one embodiment, $R^1$ is (1-3C)alkyl substituted with 1-3 fluoros. In one embodiment, $R^1$ is methyl, ethyl, n-propyl, isopropyl, trifluoromethyl or 2,2,2-trifluoroethyl.

In one embodiment of Formula I, $R^1$ is (1-3C)alkoxy optionally substituted with 1-5 fluoros. In one embodiment, $R^1$ is (1-3C)alkoxy. In one embodiment, $R^1$ is (1-3C)alkoxy substituted with 1-5 fluoros. In one embodiment, $R^1$ is $CH_3O$—, $CH_3CH_2O$—, or $CF_3O$—.

In one embodiment of Formula I, $R^1$ is (1-3C alkyl)sulfanyl optionally substituted with 1-5 fluoros. In one embodiment $R^1$ is (1-3C alkyl)sulfanyl. In one embodiment, $R^1$ is (1-3C alkyl)sulfanyl substituted with 1-5 fluoros. In one embodiment, $R^1$ is $CH_3S$, $CF_3S$ or $CH_3CH_2S$.

In one embodiment of Formula I, $R^1$ is cyano(1-3C)alkyl optionally substituted with 1-5 fluoros. In one embodiment, $R^1$ is $CNCH_2CH_2CH_2$.

In one embodiment of Formula I, $R^1$ is hydroxy(1-3C)alkyl optionally substituted with 1-5 fluoros. In one embodiment, $R^1$ is $HOCH_2CH_2CH_2$.

In one embodiment of Formula I, $R^1$ is (1-4C)alkyl optionally substituted with 1-5 fluoros. In one embodiment of Formula I, $R^1$ is $CF_3CH_2CH_2CH_2$.

In one embodiment of Formula I, $R^1$ is $CH_3CH_2NR^y$, $CF_3CH_2NR^y$, $HCF_2CH_2NR^y$, $H_2FCH_2NR^y$, $CH_3NR^yCH_2$, $R^yR^yNCH_2CH_2$ or $R^yR^yNCH_2CF_2$, where each $R^y$ is independently H or methyl.

In one embodiment of Formula I, n is 0; $R^2$ is selected from the group consisting of H, halogen, (1-6C)alkyl [optionally substituted with 1-5 fluoros], (1-6C)alkoxy [optionally substituted with 1-5 fluoros], (1-3C alkoxy)(1-4C)alkyl, (3-6C cycloalkyl)O—, (3-6C cycloalkyl)$CH_2$O—, amino(1-3C)alkyl, $CF_3CH_2NHCH_2$, $HCF_2CH_2NHCH_2$, a C5-C8 bridged cycloalkyl, hetCyc$^a$, hetCyc$^a$$CH_2$, Cyc$^a$, hetAr$^1$ and Ar$^1$; and $R^1$, X, Ring C, $R^a$ and $R^b$ are as defined for Formula I. In one embodiment, $R^a$ is H, (1-3C)alkyl, cyclopropyl, cyclobutyl or $CF_3$, and $R^b$ is H, methyl or ethyl. In one embodiment, $R^a$ and $R^b$ are both H. In one embodiment, $R^a$ is cyclopropyl and $R^b$ is H. In one embodiment, $R^a$ is methyl and $R^b$ is H. In one embodiment, $R^a$ is $CF_3$ and $R^b$ is H.

In one embodiment of Formula I, n is 0; $R^2$ is H; and R', X, Ring C, $R^a$ and $R^b$ are as defined for Formula I. In one embodiment, $R^a$ is H, (1-3C)alkyl, cyclopropyl, cyclobutyl or $CF_3$, and $R^b$ is H, methyl or ethyl. In one embodiment, $R^a$ and $R^b$ are both H. In one embodiment, $R^a$ is cyclopropyl and $R^b$ is H. In one embodiment, $R^a$ is methyl and $R^b$ is H. In one embodiment, $R^a$ is $CF_3$ and $R^b$ is H.

In one embodiment of Formula I, n is 0; $R^2$ is halogen; and $R^1$, X, Ring C, $R^a$ and $R^b$ are as defined for Formula I. In one embodiment, $R^a$ is H, (1-3C)alkyl, cyclopropyl, cyclobutyl or $CF_3$, and $R^b$ is H, methyl or ethyl. In one embodiment, $R^a$ and $R^b$ are both H. In one embodiment, $R^a$ is cyclopropyl and $R^b$ is H. In one embodiment, $R^a$ is methyl and $R^b$ is H. In one embodiment, $R^a$ is $CF_3$ and $R^b$ is H. In one embodiment, $R^2$ is F or Cl.

In one embodiment of Formula I, n is 0; $R^2$ is (1-6C)alkyl [optionally substituted with 1-5 fluoros]; and $R^1$, X, Ring C, $R^a$ and $R^b$ are as defined for Formula I. In one embodiment, $R^a$ is H, (1-3C)alkyl, cyclopropyl, cyclobutyl or $CF_3$, and $R^b$ is H, methyl or ethyl. In one embodiment, $R^a$ and $R^b$ are both H. In one embodiment, $R^a$ is cyclopropyl and $R^b$ is H. In one embodiment, $R^a$ is methyl and $R^b$ is H. In one embodiment, $R^a$ is $CF_3$ and $R^b$ is H. In one embodiment of Formula I, $R^2$ is methyl, ethyl, isopropyl, tert-butyl or trifluoromethyl.

In one embodiment of Formula I, n is 0; $R^2$ is (1-6C)alkoxy [optionally substituted with 1-5 fluoros]; and R', X, Ring C, $R^a$ and $R^b$ are as defined for Formula I. In one embodiment, $R^a$ is H, (1-3C)alkyl, cyclopropyl, cyclobutyl or $CF_3$, and $R^b$ is H, methyl or ethyl. In one embodiment, $R^a$ and $R^b$ are both H. In one embodiment, $R^a$ is cyclopropyl and $R^b$ is H. In one embodiment, $R^a$ is methyl and $R^b$ is H. In one embodiment, $R^a$ is $CF_3$ and $R^b$ is H. In one embodiment of Formula I, $R^2$ is methoxy, ethoxy, fluoromethoxy, trifluoromethoxy, difluoromethoxy, or 2,2,2-trifluoroethoxy; and $R^a$ and $R^b$ are as defined for Formula I.

In one embodiment of Formula I, n is 0; $R^2$ is (1-3C alkoxy)(1-4C)alkyl; and $R^1$, X, Ring C, $R^a$ and $R^b$ are as defined for Formula I. In one embodiment, $R^a$ is H, (1-3C)alkyl, cyclopropyl, cyclobutyl or $CF_3$, and $R^b$ is H, methyl or ethyl. In one embodiment, $R^a$ and $R^b$ are both H. In one embodiment, $R^a$ is cyclopropyl and $R^b$ is H. In one embodiment, $R^a$ is methyl and $R^b$ is H. In one embodiment, $R^a$ is $CF_3$ and $R^b$ is H. In one embodiment, $R^2$ is $CH_3OCH_2$—.

In one embodiment of Formula I, n is 0; $R^2$ is (3-6C cycloalkyl)O—; and $R^1$, X, Ring C, $R^a$ and $R^b$ are as defined for Formula I. In one embodiment, $R^a$ is H, (1-3C)alkyl, cyclopropyl, cyclobutyl or $CF_3$, and $R^b$ is H, methyl or ethyl. In one embodiment, $R^a$ and $R^b$ are both H. In one embodiment, $R^a$ is cyclopropyl and $R^b$ is H. In one embodiment, $R^a$ is methyl and $R^b$ is H. In one embodiment, $R^a$ is $CF_3$ and $R^b$ is H. In one embodiment, $R^2$ has the structure:

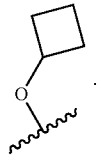

In one embodiment of Formula I, n is 0; $R^2$ is (3-6C cycloalkyl)$CH_2$O—; and $R^1$, X, Ring C, $R^a$ and $R^b$ are as defined for Formula I. In one embodiment, $R^a$ is H, (1-3C)alkyl, cyclopropyl, cyclobutyl or $CF_3$, and $R^b$ is H, methyl or ethyl. In one embodiment, R$^a$ and R$^b$ are both H. In one embodiment, R$^a$ is cyclopropyl and R$^b$ is H. In one embodiment, R$^a$ is methyl and R$^b$ is H. In one embodiment, R$^a$ is CF$_3$ and R$^b$ is H. In one embodiment, R$^2$ is cyclopropylmethoxy.

In one embodiment of Formula I, n is 0; R$^2$ is amino(1-3C)alkyl; and R$^1$, X, Ring C, R$^a$ and R$^b$ are as defined for Formula I. In one embodiment, R$^2$ is NH$_2$CH$_2$—. In one embodiment, R$^a$ is H, (1-3C)alkyl, cyclopropyl, cyclobutyl or CF$_3$, and R$^b$ is H, methyl or ethyl. In one embodiment, R$^a$ and R$^b$ are both H. In one embodiment, R$^a$ is cyclopropyl and R$^b$ is H. In one embodiment, R$^a$ is methyl and R$^b$ is H. In one embodiment, R$^a$ is CF$_3$ and R$^b$ is H.

In one embodiment of Formula I, n is 0; R$^2$ is CF$_3$CH$_2$NHCH$_2$; and R$^1$, X, Ring C, R$^a$ and R$^b$ are as defined for Formula I. In one embodiment, R$^a$ is H, (1-3C)alkyl, cyclopropyl, cyclobutyl or CF$_3$, and R$^b$ is H, methyl or ethyl. In one embodiment, R$^a$ and R$^b$ are both H. In one embodiment, R$^a$ is cyclopropyl and R$^b$ is H. In one embodiment, R$^a$ is methyl and R$^b$ is H. In one embodiment, R$^a$ is CF$_3$ and R$^b$ is H.

In one embodiment of Formula I, n is 0; R$^2$ is HCF$_2$CH$_2$NHCH$_2$; and R$^1$, X, Ring C, R$^a$ and R$^b$ are as defined for Formula I. In one embodiment, R$^a$ is H, (1-3C)alkyl, cyclopropyl, cyclobutyl or CF$_3$, and R$^b$ is H, methyl or ethyl. In one embodiment, R$^a$ and R$^b$ are both H. In one embodiment, R$^a$ is cyclopropyl and R$^b$ is H. In one embodiment, R$^a$ is methyl; R$^b$ is H; and R$^a$ and R$^b$ are as defined for Formula I. In one embodiment, R$^a$ and R$^b$ are both H. In one embodiment, R$^a$ is cyclopropyl and R$^b$ is H. In one embodiment, R$^a$ is methyl and R$^b$ is H. In one embodiment, R$^a$ is CF$_3$ and R$^b$ is H.

In one embodiment of Formula I, n is 0; R$^2$ is HCF$_2$CH$_2$NHCH$_2$; and R$^1$, X, Ring C, R$^a$ and R$^b$ are as defined for Formula I. In one embodiment, R$^a$ is H, (1-3C)alkyl, cyclopropyl, cyclobutyl or CF$_3$, and R$^b$ is H, methyl or ethyl. In one embodiment, R$^a$ and R$^b$ are both H. In one embodiment, R$^a$ is cyclopropyl and R$^b$ is H. In one embodiment, R$^a$ is methyl and R$^b$ is H. In one embodiment, R$^a$ is CF$_3$ and R$^b$ is H.

In one embodiment of Formula I, n is 0; R$^2$ is a C5-C8 bridged cycloalkyl; and R$^1$, X, Ring C, R$^a$ and R$^b$ are as defined for Formula I. In one embodiment, R$^a$ is H, (1-3C)alkyl, cyclopropyl, cyclobutyl or CF$_3$, and R$^b$ is H, methyl or ethyl. In one embodiment, R$^a$ and R$^b$ are both H. In one embodiment, R$^a$ is cyclopropyl and R$^b$ is H. In one embodiment, R$^a$ is methyl and R$^b$ is H. In one embodiment, R$^2$ has the structure:

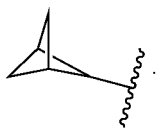 [SMILES: *C1C2CC1C2]

In one embodiment of Formula I, n is 0; R$^2$ is hetCyc$^a$, where hetCyc$^a$ is a 4-6 membered heterocyclic ring having a ring heteroatom selected from N, O and S and optionally substituted with 1-3 groups independently selected from OH, F, (1-6C)alkoxy and (1-6C)alkyl [optionally substituted with 1-3 fluoros]; and R$^1$, X, Ring C, R$^a$ and R$^b$ are as defined for Formula I. In one embodiment, R$^a$ is H, (1-3C)alkyl, cyclopropyl, cyclobutyl or CF$_3$, and R$^b$ is H, methyl or ethyl. In one embodiment, R$^a$ and R$^b$ are both H. In one embodiment, R$^a$ is cyclopropyl and R$^b$ is H. In one embodiment, R$^a$ is methyl and R$^b$ is H. In one embodiment, R$^a$ is CF$_3$ and R$^b$ is H. In one embodiment, R$^2$ is hetCyc$^a$, where hetCyc$^a$ is a 4-6 membered heterocyclic ring having a ring oxygen atom and optionally substituted with OH, F, (1-6C)alkoxy or (1-6C)alkyl [optionally substituted with 1-3 fluoros]. In one embodiment of Formula I, n is 0 and R$^2$ has the structure:

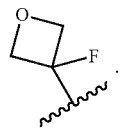

In one embodiment of Formula I, n is 0; R$^2$ is hetCyc$^a$CH$_2$; and R$^1$, X, Ring C, R$^a$ and R$^b$ are as defined for Formula I. In one embodiment, R$^a$ is H, (1-3C)alkyl, cyclopropyl, cyclobutyl or CF$_3$, and R$^b$ is H, methyl or ethyl. In one embodiment, R$^a$ and R$^b$ are both H. In one embodiment, R$^a$ is cyclopropyl and R$^b$ is H. In one embodiment, R$^a$ is methyl and R$^b$ is H. In one embodiment, R$^a$ is CF$_3$ and R$^b$ is H.

In one embodiment of Formula I, n is 0; R$^2$ is Cyc$^a$, where Cyc$^a$ is a (3-6C)cycloalkyl optionally substituted with (1-4C)alkoxy, (1-4C)alkyl, F or OH; and R$^1$, X, Ring C, R$^a$ and R$^b$ are as defined for Formula I. In one embodiment, R$^a$ is H, (1-3C)alkyl, cyclopropyl, cyclobutyl or CF$_3$, and R$^b$ is H, methyl or ethyl. In one embodiment, R$^a$ and R$^b$ are both H. In one embodiment, R$^a$ is cyclopropyl and R$^b$ is H. In one embodiment, R$^a$ is methyl and R$^b$ is H. In one embodiment, R$^a$ is CF$_3$ and R$^b$ is H. In one embodiment, R$^2$ is cyclopropyl, cyclobutyl, cyclopentyl, 2,2-difluorocyclopropyl, 3,3-difluorocyclobutyl, or 1-methoxycyclobutyl.

In one embodiment of Formula I, n is 0; R$^2$ is hetAr$^1$, where hetAr$^1$ is a 5-6 membered heteroaryl having 1-3 ring heteroatoms independently selected from N, S and O, and optionally substituted with 1-2 groups independently selected from (1-6C)alkyl, halogen, OH, CF$_3$, NH$_2$ and hydroxy(1-2C)alkyl; and R$^1$, X, Ring C, R$^a$ and R$^b$ are as defined for Formula I. In one embodiment, R$^a$ is H, (1-3C)alkyl, cyclopropyl, cyclobutyl or CF$_3$, and R$^b$ is H, methyl or ethyl. In one embodiment, R$^a$ and R$^b$ are both H. In one embodiment, R$^a$ is cyclopropyl and R$^b$ is H. In one embodiment, R$^a$ is methyl and R$^b$ is H. In one embodiment, R$^a$ is CF$_3$ and R$^b$ is H.

In one embodiment of Formula I, n is 0; R$^2$ is Ar$^1$, where Ar$^1$ is phenyl optionally substituted with one or more substituents independently selected from halogen, CF$_3$, CF$_3$O—, (1-4C)alkoxy, (1-4C)sulfanyl, hydroxy(1-4C)alkyl, (1-6C)alkyl and CN; and R$^1$, X, Ring C, R$^a$ and R$^b$ are as defined for Formula I. In one embodiment, Ar$^1$ is phenyl. In one embodiment, R$^a$ is H, (1-3C)alkyl, cyclopropyl, cyclobutyl or CF$_3$, and R$^b$ is H, methyl or ethyl. In one embodiment, R$^a$ and R$^b$ are both H. In one embodiment, R$^a$ is cyclopropyl and R$^b$ is H. In one embodiment, R$^a$ is methyl and R$^b$ is H. In one embodiment, R$^a$ is CF$_3$ and R$^b$ is H.

In one embodiment, the portion of Formula I which has the structure

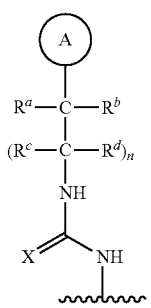
when n is 0 is selected from the structures:
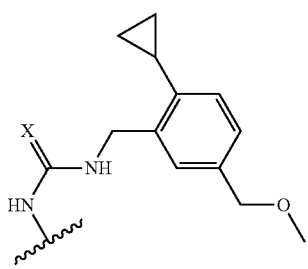
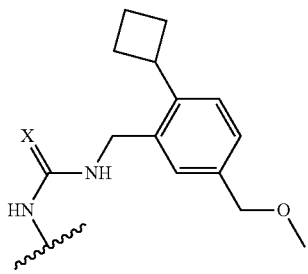
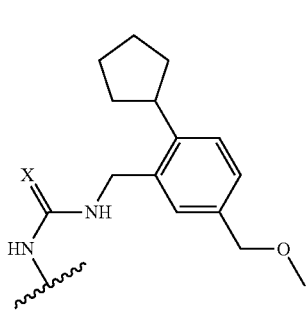
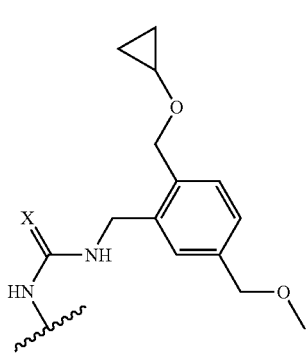
-continued
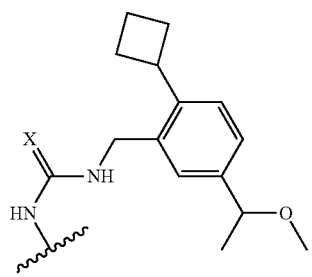
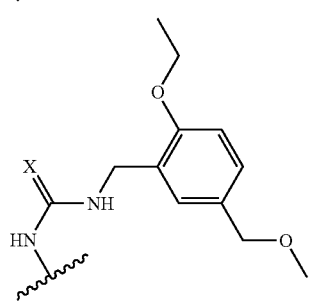
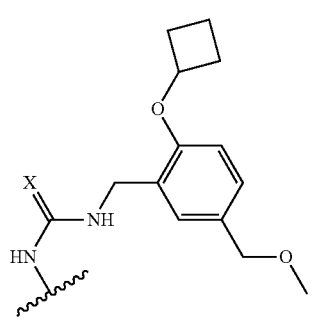
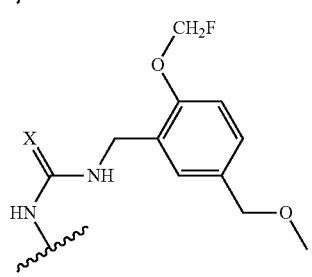
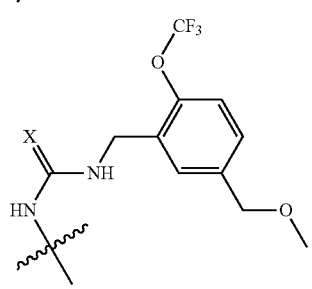
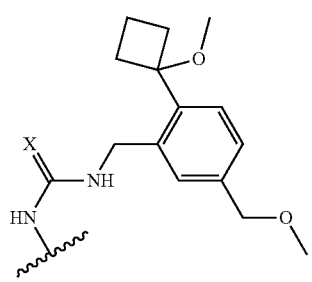

-continued
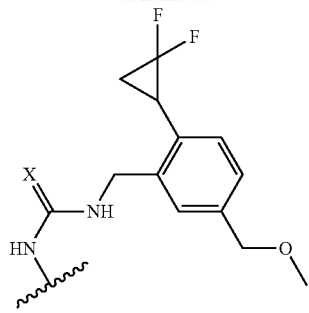
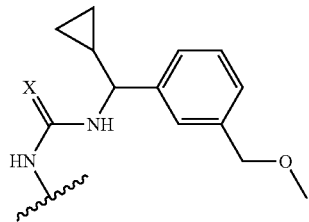
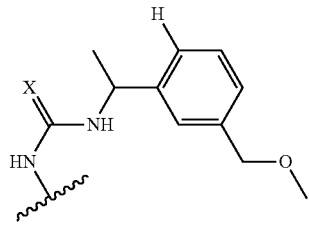
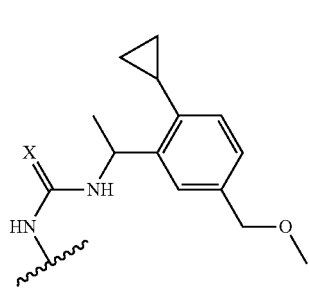
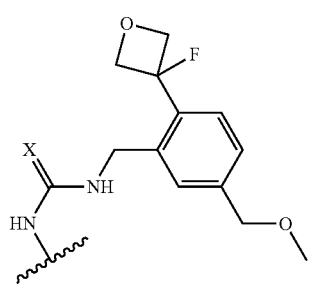
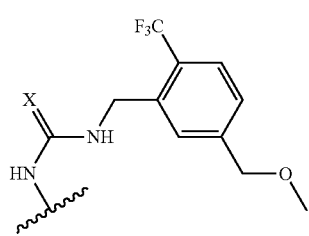
-continued
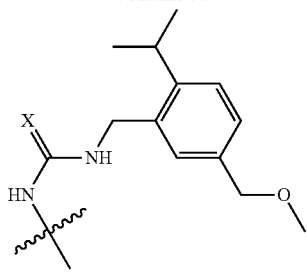
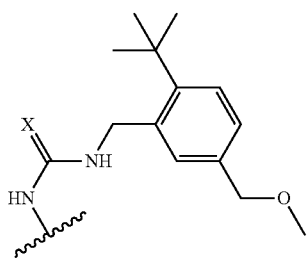
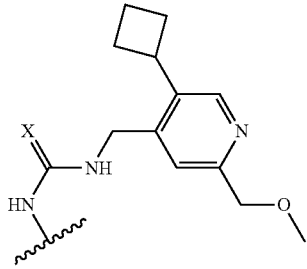
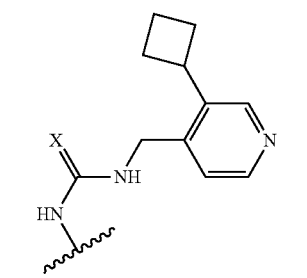
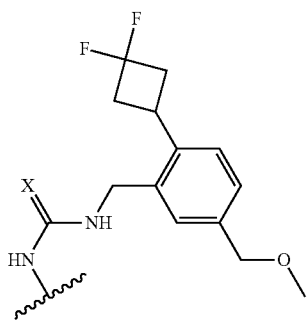
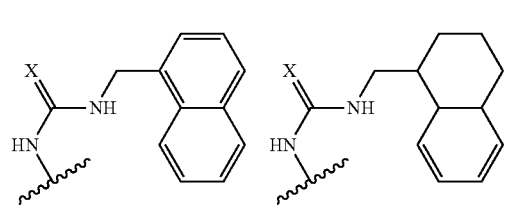

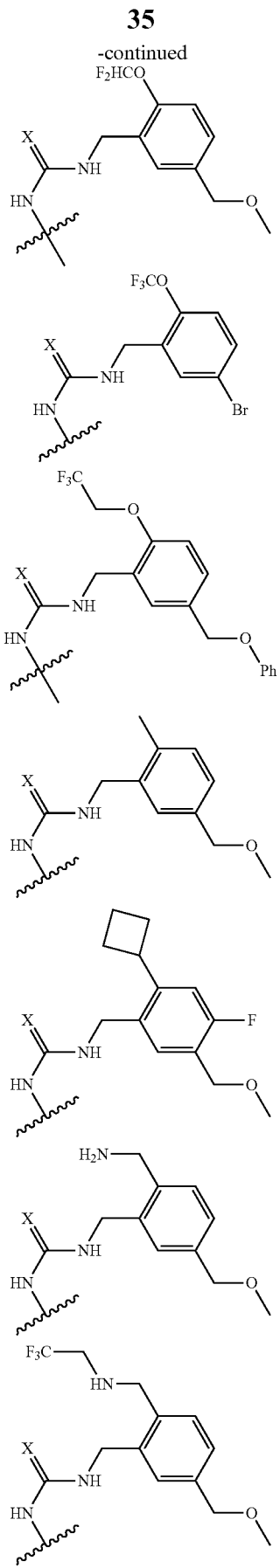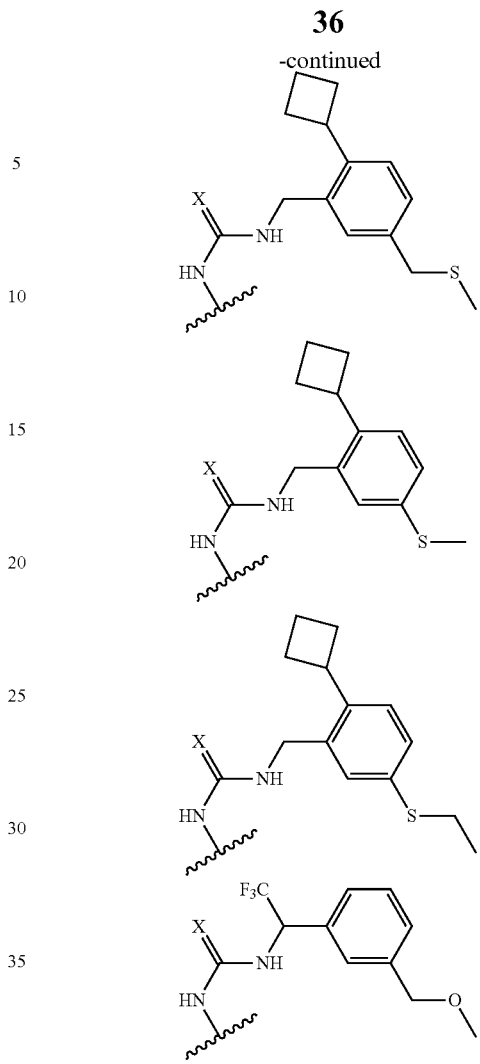

where X and Ring C are as defined for Formula I. In one embodiment of the above structures, X is O and Ring C is as defined for Formula I. In one embodiment of the above structures, X is O and Ring C is formula C-1.

In one embodiment of Formula I, n is 1; Ring A is A-1; $R^2$ is selected from the group consisting of H, halogen, $CF_3$, $F_2CH$, $FCH_2$, MeO and methyl; and $R^a$, $R^b$, $R^c$, $R^d$, X, $R^1$ and Ring C are as defined for Formula I. In one embodiment of Formula I, n is 1; Ring A is A-1; $R^2$ is selected from the group consisting of H, halogen, $CF_3$, $F_2CH$, $FCH_2$, MeO and methyl; $R^a$ and $R^b$ are hydrogen; and $R^c$, $R^d$, X, $R^1$ and Ring C are as defined for Formula I.

In one embodiment of Formula I, n is 1; Ring A is A-1; $R^2$ is H; and $R^a$, $R^b$, $R^c$, $R^d$, X, $R^1$, and Ring C are as defined for Formula I. In one embodiment of Formula I, n is 1; Ring A is A-1; $R^2$ is H; $R^a$ and $R^b$ are hydrogen; and $R^c$, $R^d$, X, $R^1$, and Ring C are as defined for Formula I.

In one embodiment of Formula I, n is 1; Ring A is A-1; $R^2$ is halogen; and $R^a$, $R^b$, $R^c$, $R^d$, X, $R^1$, and Ring C are as defined for Formula I. In one embodiment of Formula I, n is 1; Ring A is A-1; $R^2$ is halogen; $R^a$ and $R^b$ are hydrogen; and $R^c$, $R^d$, X, $R^1$, and Ring C are as defined for Formula I.

In one embodiment of Formula I, n is 1; Ring A is A-1; $R^2$ is $CF_3$, $F_2CH$, $FCH_2$ or methyl; and $R^a$, $R^b$, $R^c$, $R^d$, X, $R^1$, and Ring C are as defined for Formula I. In one embodiment of Formula I, n is 1; Ring A is A-1; $R^2$ is $CF_3$, $F_2CH$, $FCH_2$ or methyl; $R^a$ and $R^b$ are hydrogen; and $R^c$, $R^d$, X, $R^1$, and Ring C are as defined for Formula I.

In one embodiment of Formula I, n is 1; Ring A is A-1; $R^2$ is methoxy; and $R^a$, $R^b$, $R^c$, $R^d$, X, $R^1$, and Ring C are as defined for Formula I. In one embodiment of Formula I, n is 1; Ring A is A-1; $R^2$ is methoxy; $R^a$ and $R^b$ are hydrogen; and $R^c$, $R^d$, X, $R^1$, and Ring C are as defined for Formula I.

In one embodiment, the portion of Formula I which has the structure

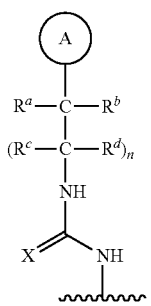

when n is 1 is selected from the structures:

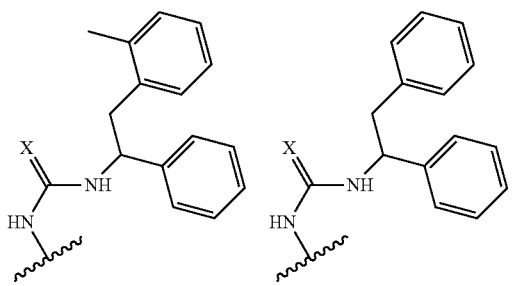

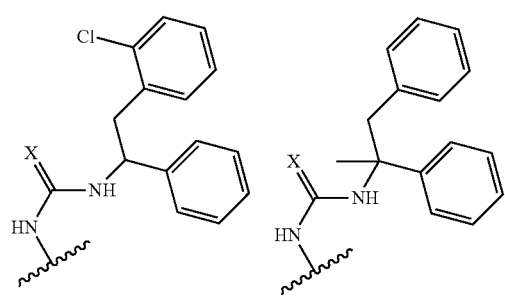

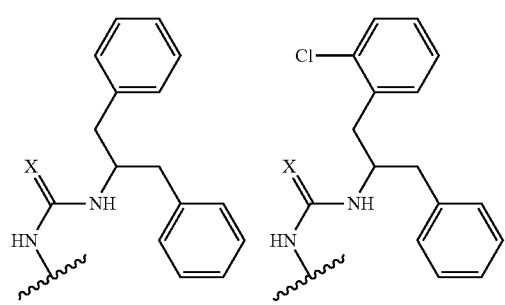

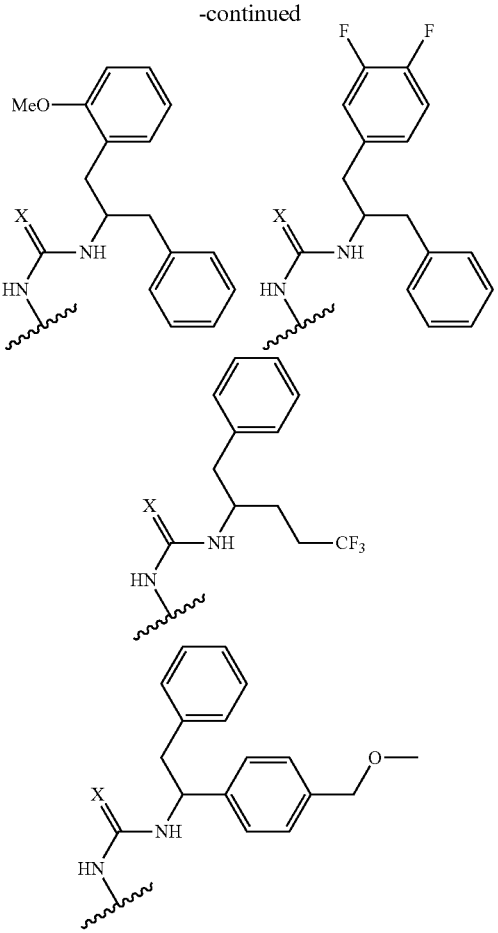

where X and Ring C are as defined for Formula I. In one embodiment, X is O and Ring C is as defined for Formula I. In one embodiment, X is O and Ring C is formula C-1.

Reference will now be made to Ring C.

In one embodiment, Ring C is formula C-1:

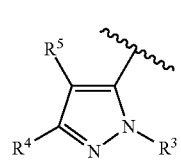

where $R^3$, $R^4$ and $R^5$ are as defined for Formula I.

In one embodiment, $R^3$ is (1-6C)alkyl. In one embodiment, $R^3$ is methyl or ethyl.

In one embodiment, $R^3$ is hydroxy(1-6C)alkyl. An example of $R^3$ is 2-hydroxyethyl.

In one embodiment, $R^3$ is $Ar^2$, where $Ar^2$ is phenyl optionally substituted with one or more groups independently selected from halogen and (1-6C)alkyl.

In one embodiment, $R^3$ when represented by $Ar^2$ is phenyl, 2-fluorophenyl, 3-fluorophenyl, 4-fluorophenyl, 2-methylphenyl, 3-methylphenyl, 4-methylphenyl, 3-chlorophenyl, 3-chloro-4-fluorophenyl or 3-chloro-2-fluorophenyl. In one embodiment, $R^3$ when represented by $Ar^2$ is phenyl, 2-fluorophenyl, 3-fluorophenyl, 4-fluorophenyl, 2-methylphenyl, 3-methylphenyl or 4-methylphenyl. In one embodiment, $R^3$ is phenyl.

In one embodiment, R³ is hetCyc¹, where hetCyc¹ is a 5-6-membered saturated or partially unsaturated heterocyclic ring having 1-2 ring heteroatoms independently selected from N and O. In one embodiment, R³ is a pyrrolidinyl, tetrahydrofuranyl, imidazolidinyl, piperidinyl, piperazinyl, tetrahydropyranyl, or morpholinyl ring. In one embodiment, R³ is tetrahydro-2H-pyran-4-yl.

In one embodiment, R³ is (3-7C)cycloalkyl. In one embodiment R³ is cyclohexyl.

In one embodiment, R³ is hetAr², where hetAr² is 5-6 membered heteroaryl ring having 1-3 ring heteroatoms independently selected from N, O and S and optionally substituted with one or more substituents independently selected from (1-6C)alkyl and halogen. In one embodiment, R³ is thienyl, furyl, imidazolyl, pyrazolyl, thiazolyl, isothiazolyl, oxazolyl, isoxazolyl, triazolyl, thiadiazolyl, oxadiazolyl, pyridyl, pyrimidyl, pyrazinyl, or pyridazinyl optionally substituted with one or more substituents independently selected from (1-6C)alkyl and halogen. In one embodiment, R³ is pyrazolyl, pyridyl or pyridazinyl optionally substituted with one or more groups independently selected from (1-6C) alkyl and halogen. In one embodiment, R³ is pyrazolyl, pyridyl or pyridazinyl optionally substituted with (1-6C) alkyl or halogen. In one embodiment, R³ when represented by hetAr² is 1-methyl-1H-pyrazol-4-yl, pyrid-2-yl, pyrid-3-yl, pyrid-4-yl, pyridazinyl or 3-chloropyrid-5-yl.

In one embodiment, R³ is selected from Ar² and hetAr².

In one embodiment, R³ is Ar². In one embodiment, R³ is phenyl.

In one embodiment, R⁴ is OH, (1-6C)alkyl, monofluoro (1-6C)alkyl, difluoro(1-6C)alkyl, trifluoro(1-6C)alkyl, tetrafluro(2-6C)alkyl, pentafluro(2-6C)alkyl, cyano(1-6C)alkyl, hydroxy(1-6C)alkyl, dihydroxy(2-6C)alkyl, (1-3C alkoxy) (1-6C)alkyl, amino(1-6C)alkyl, aminocarbonyl(1-6C)alkyl, (1-3C)alkylsulfonamido(1-6C)alkyl, sulfamido(1-6C)alkyl, hydroxycarbonyl(1-6C)alkyl, hetAr³(1-6C)alkyl, Ar³(1-6C) alkyl, (1-6C)alkoxy, monofluoro(1-6C)alkoxy, difluoro(1-6C)alkoxy, trifluoro(1-6C)alkoxy, tetrafluoro(2-6C)alkoxy, pentafluoro(2-6C)alkoxy, cyano(1-6C)alkoxy, hydroxy(1-6C)alkoxy, dihydroxy(2-6C)alkoxy, amino(2-6C)alkoxy, hydroxyl-carbonyl(1-6C)alkoxy, hetCyc²(1-6C)alkoxy, hetAr³(1-6C)alkoxy, Ar³(1-6C)alkoxy, (1-4C alkoxy)(1-6C) alkoxy, (1-3C alkylsulfonyl)(1-6C)alkoxy, (3-6C)cycloalkyl [optionally substituted with F, OH, (1-6C alkyl), (1-6C) alkoxy, or (1-3C alkoxy)(1-6C)alkyl], hetAr⁴, hetAr⁴—O—, Ar⁴, hetCyc²(O)CH₂—, (1-4C alkoxycarbonyl)(1-6C) alkoxy, hydroxycarbonyl(1-6C)alkoxy, aminocarbonyl(1-6C)alkoxy, hetCyc²C(=O)(1-6C)alkoxy, hydroxy(1-3C alkoxy)(1-6C)alkoxy, hydroxytrifluoro(1-6C)alkoxy, (1-3C) alkylsulfonamido(1-6C)alkoxy, (1-3C)alkylamido(1-6C) alkoxy, di(1-3C alkyl)amino-carboxy, hetCyc²C(=O)O—, hydroxydifluoro(1-6C)alkyl, (1-4C alkylcarboxy)(1-6C) alkyl, (1-6C)alkoxycarbonyl, hydroxylcarbonyl, aminocarbonyl, (1-3C alkoxy)aminocarbonyl, hetCyc³, halogen, CN, trifluoromethylsulfonyl, N-(1-3C alkyl)oxadiazolonyl, hetAr⁵, Ar⁴—O—, hetCyc⁴-O—, Cyc¹-O—, or aminohydroxy(1-6C)alkoxy; and R⁵ is (1-6C)alkyl, monofluoro(1-6C)alkyl, difluoro(1-6C) alkyl, trifluoro(1-6C)alkyl, tetrafluoro(2-6C)alkyl, pentafluoro(2-6C)alkyl, halogen, CN, (1-4C)alkoxy, hydroxy(1-4C)alkyl, (1-3C alkoxy)(1-4C)alkyl, (1-4C alkyl)OC (=O)—, (1-6C)alkylthio, (3-4C)cycloalkyl, amino, aminocarbonyl, trifluoro(1-3C alkyl)amido, or phenyl (optionally substituted with one or more groups independently selected from halogen, (1-6C)alkyl and (1-6C)alkoxy).

In one embodiment, R⁴ is OH. In one embodiment, R⁴ is OH and R³ is H. Examples of C-1 rings when R⁴ is OH and R³ is H include the following tautomeric structures:

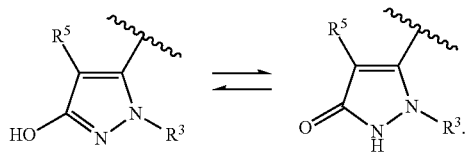

In one embodiment, R⁴ is (1-6C)alkyl. In one embodiment, R⁴ is methyl, ethyl, isopropyl or tert-butyl.

In one embodiment, R⁴ is monofluoro(1-6C)alkyl, difluoro(1-6C)alkyl, trifluoro(1-6C)alkyl, tetrafluoro(2-6C) alkyl or pentafluoro(2-6C)alkyl. In one embodiment, R⁴ is fluoromethyl, 2-fluoroethyl, difluoromethyl and 2,2-difluoroethyl, trifluoromethyl, 2,2,2-trifluoroethyl, 3,3,3-trifluoropropyl, 2,2,3,3-tetrafluoropropyl or 2,2,3,3,3-pentafluoropropyl In one embodiment, R⁴ is trifluoro(1-6C)alkyl. In one embodiment, R⁴ is CF₃.

In one embodiment, R⁴ is cyano(1-6C)alkyl. In one embodiment, R⁴ is cyanomethyl or 2-cyanopropan-2-yl.

In one embodiment, R⁴ is hydroxy(1-6C)alkyl. In one embodiment, R⁴ is hydroxymethyl, 2-hydroxyethyl, 2-hydroxypropyl, 2-hydroxy-2-methylpropyl or 1-hydroxy-2-methylpropan-2-yl.

In one embodiment, R⁴ is dihydroxy(2-6C)alkyl. In one embodiment, R⁴ is 2,3-dihydroxypropyl.

In one embodiment, R⁴ is (1-3C alkoxy)(1-6C)alkyl. In one embodiment, R⁴ is methoxymethyl, 2-methoxyethyl or 3-methoxypropyl.

In one embodiment, R⁴ is amino(1-6C)alkyl. In one embodiment, R⁴ is aminomethyl, 2-aminoethyl or 3-aminopropyl.

In one embodiment, R⁴ is aminocarbonyl(1-6C)alkyl. In one embodiment, R⁴ is aminocarbonylmethyl and 2-(aminocarbonyl)ethyl.

In one embodiment, R⁴ is (1-3C)alkylsulfonamido(1-6C) alkyl. In one embodiment, R⁴ is CH₃SO₂NHCH₂— or CH₃SO₂NHCH₂CH₂—.

In one embodiment, R⁴ is hydroxycarbonyl(1-6C)alkyl. In one embodiment, R⁴ is HOC(=O)CH₂— and HOC(=O) CH₂CH₂—.

In one embodiment, R⁴ is hetAr³(1-6C)alkyl, where hetAr³ is a 5-membered heteroaryl ring having 1-3 ring atoms independently selected from N, S and O and optionally substituted with (1-6C)alkyl. In one embodiment, hetAr³ is a thienyl, furyl, imidazolyl, pyrazolyl, thiazolyl, isothiazolyl, oxazolyl, isoxazolyl, triazolyl, thiadiazolyl or oxadiazolyl ring optionally substituted with (1-6C)alkyl. In one embodiment, R⁴ when represented by hetAr³(1-6C) alkyl is (1-methyl-1H-1,2,4-triazol-3-yl)methyl or (5-methyl-1,3,4-oxadiazol-2-yl)methyl.

In one embodiment, R⁴ is Ar³(1-6C)alkyl, where phenyl optionally substituted with (1-4C)alkoxy or hydroxy(1-4C) alkyl. In one embodiment, Ar³(1-6C)alkyl is benzyl.

In one embodiment, R⁴ is (1-6C)alkoxy. Examples include methoxy and ethoxy.

In one embodiment, R⁴ is monofluoro(1-6C)alkoxy, difluoro(1-6C)alkoxy, trifluoro(1-6C)alkoxy, tetrafluoro(2-6C) alkoxy or pentafluoro(2-6C)alkoxy. In one embodiment, R⁴ is fluoromethoxy, 2-fluoroethoxy, 2,2-difluoromethoxy, trifluoromethoxy, 2,2,2-trifluoroethoxy or 2,2-difluoroethoxy. In one embodiment, $R^4$ is 2-fluoroethoxy.

In one embodiment, $R^4$ is cyano(1-6C)alkoxy. In one embodiment, $R^4$ is cyanomethoxy or 2-cyanoethoxy.

In one embodiment, $R^4$ is hydroxy(1-6C)alkoxy. In one embodiment, $R^4$ is 2-hydroxy-2-methylpropoxy, 2-hydroxyethoxy, 2-hydroxypropoxy, 2-hydroxy-2-methylpropoxy or 2-hydroxybutoxy.

In one embodiment, $R^4$ is dihydroxy(2-6C)alkoxy. In one embodiment, $R^4$ is 2,3-dihydroxypropoxy or 3-hydroxy-2-(hydroxymethyl)propoxy.

In one embodiment, $R^4$ is amino(2-6C)alkoxy. In one embodiment, $R^4$ is $H_2NCH_2CH_2O-$ or $H_2NCH(CH_3)CH_2O-$.

In one embodiment, $R^4$ is hetCyc²(1-6C)alkoxy, where hetCyc² is a 4-6 membered heterocyclic ring having 1-2 ring heteroatoms independently selected from N and O, wherein hetCyc² is optionally substituted with 1-2 groups independently selected from (1-6C)alkyl, (1-4C alkoxy)carbonyl, (1-6C)acyl, halogen and oxo. In one embodiment, hetCyc² is oxetaynyl, tetrahydrofuranyl, tetrahydropyranyl, azetidinyl, pyrrolidinyl, piperidinyl, piperazinyl, morpholinyl, or and 1,3-dioxolanyl optionally substituted with 1-2 groups independently selected from (1-6C)alkyl, 1-4C alkoxy)carbonyl, (1-6C)acyl, halogen and oxo.

In one embodiment, $R^4$ is hetCyc²(1-6C)alkoxy, where hetCyc² is a 4-6 membered heterocyclic ring having 1-2 ring heteroatoms independently selected from N and O, wherein hetCyc² is optionally substituted with 1-2 groups independently selected from (1-6C)alkyl, (1-4C alkoxy)carbonyl, and (1-6C)acyl. In one embodiment, hetCyc² is oxetaynyl, tetrahydrofuranyl, tetrahydropyranyl, azetidinyl, pyrrolidinyl, piperidinyl, piperazinyl, morpholinyl, or and 1,3-dioxolanyl optionally substituted with 1-2 groups independently selected from (1-6C)alkyl, (1-4C alkoxy)carbonyl and (1-6C)acyl. In one embodiment, $R^4$ when represented by hetCyc²(1-6C)alkoxy is oxetan-2-ylmethoxy, 2-(oxetan-2-yl)propoxy, 2-morpholinoethoxy, piperazinylethyoxy or piperidinylethoxy optionally substituted with 1-2 groups independently selected from (1-6C)alkyl, (1-4C alkoxy)carbonyl and (1-6C)acyl.

In one embodiment, $R^4$ is represented by the structures:

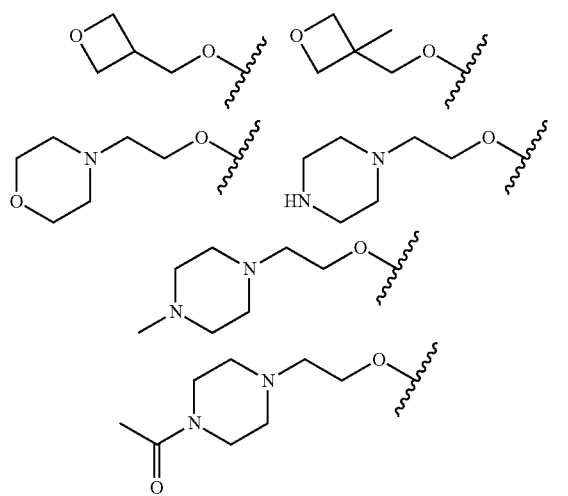

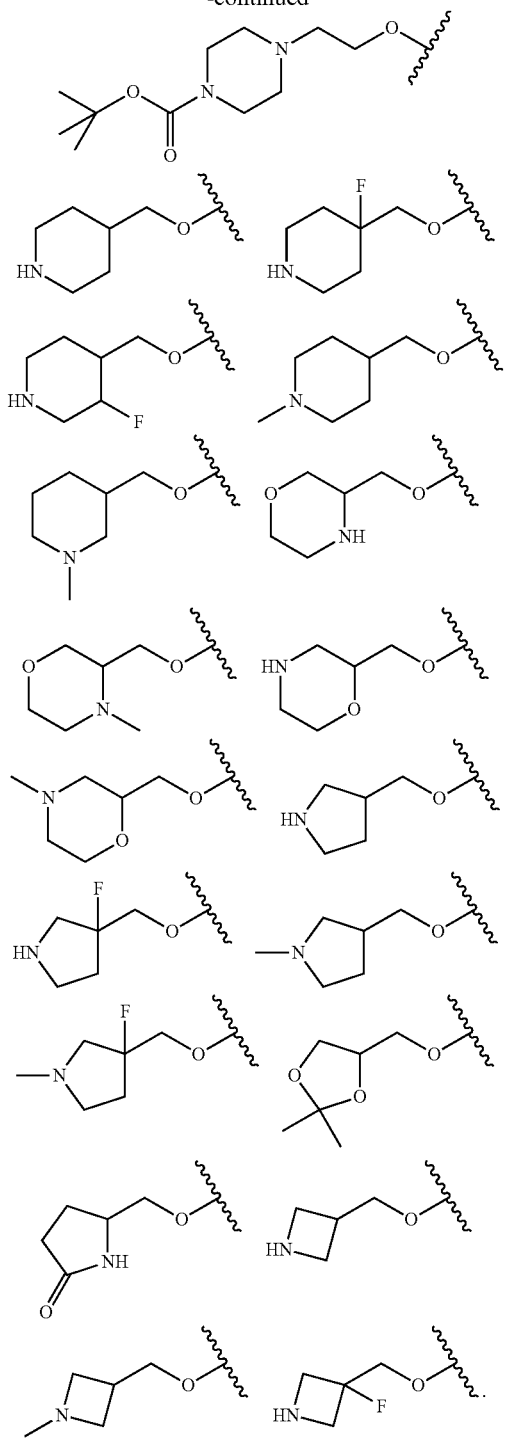

In one embodiment, $R^4$ is hetAr³(1-6C)alkoxy, where hetAr³ is a 5-membered heteroaryl ring having 1-3 ring atoms independently selected from N, S and O and optionally substituted with (1-6C)alkyl. In one embodiment, hetAr³ is a thienyl, furyl, imidazolyl, pyrazolyl, thiazolyl, isothiazolyl, oxazolyl, isoxazolyl, triazolyl, thiadiazolyl or oxadiazolyl ring optionally substituted with (1-6C)alkyl. In one embodiment, hetAr³ is triazolyl or oxadiazolyl ring optionally substituted with a (1-6C)alkyl group such as a methyl group. In one embodiment, $R^4$ when represented by hetAr³(1-6C)alkoxy is (1-methyl-1H-1,2,4-triazol-3-yl)

methoxy or (5-methyl-1,3,4-oxadiazol-2-yl)methoxy, which can be represented by the structures:

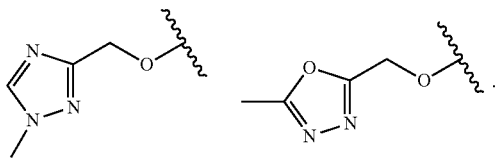

In one embodiment, R⁴ is Ar³(1-6C)alkoxy, where Ar$^a$ is phenyl optionally substituted with (1-4C)alkoxy. In one embodiment, R⁴ is phenylmethoxy or (4-methoxyphenyl) methoxy having the structures:

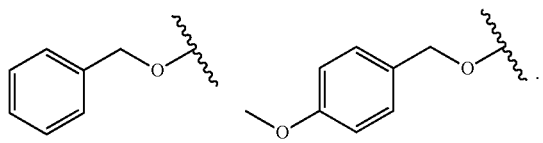 [SMILES: *OCc1ccccc1 ; *OCc1ccc(OC)cc1]

In one embodiment, R⁴ is (1-4C alkoxy)(1-6C)alkoxy. In one embodiment, R⁴ is (2-methoxy)ethoxy having the structure:

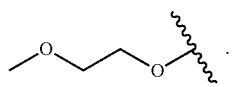 [SMILES: *OCCOC]

In one embodiment, R⁴ is (1-3Calkylsulfonyl)(1-6C) alkoxy. In one embodiment, R⁴ is (2-methylsulfonyl)ethoxy having the structure:

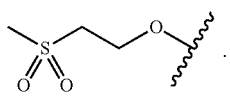

In one embodiment, R⁴ is (3-6C)cycloalkyl optionally substituted with F, OH, (1-6C alkyl), (1-6C)alkoxy or (1-3C alkoxy)(1-6C)alkyl. Examples include cyclopropyl, cyclobutyl, cyclopentyl, cyclohexyl, 2-hydroxycyclobutyl. In one embodiment, R⁴ is cyclopropyl or 2-hydroxycyclobutyl. In one embodiment, R⁴ is cyclopropyl.

In one embodiment, R⁴ is hetAr⁴, where hetAr⁴ is a 5-6 membered heteroaryl ring having 1-3 ring heteroatoms independently selected from N, S and O and optionally substituted with one or more substituents independently selected from (1-6C)alkyl, halogen, CN, hydroxy(1-6C) alkyl, trifluoro(1-6C)alkyl, difluoro(1-6C)alkyl, fluoro(1-6C)alkyl, (3-6C)cycloalkyl, (3-6C cycloalkyl)CH₂— (3-6C cycloalkyl)C(=O)—, (1-3C alkoxy)(1-6C)alkyl, (1-6C) alkoxy, (1-6C)alkylsulfonyl, NH₂, (1-6C alkyl)amino, di(1-6C alkyl)amino, (1-3C trifluoroalkoxy), fluoro(1-6C alkyl) amino, difluoro(1-6C alkyl)amino, trifluoro(1-6C alkyl) amino, and (3-4C cycloalkyl)amino.

In one embodiment, R⁴ is hetAr⁴ where hetAr⁴ is pyridyl, pyrimidinyl pyridazinyl, pyrazolyl, imidazolyl, thienyl, 1,2, 3-triazolyl, thiazolyl, oxazolyl, 1,3,4-oxadiazolyl, or 1,2,4-oxadiazolyl optionally substituted with one or more substituents independently selected from (1-6C)alkyl, halogen, CN, hydroxy(1-6C)alkyl, trifluoro(1-6C)alkyl, difluoro(1-6C)alkyl, fluoro(1-6C)alkyl, (3-6C)cycloalkyl, (3-6C cycloalkyl)CH₂-(3-6C cycloalkyl)C(=O)—, (1-3C alkoxy) (1-6C)alkyl, (1-6C)alkoxy, (1-6C)alkylsulfonyl, NH₂, (1-6C alkyl)amino, di(1-6C alkyl)amino, (1-3C trifluoroalkoxy), fluoro(1-6C alkyl)amino, difluoro(1-6C alkyl)amino, trifluoro(1-6C alkyl)amino, and (3-4C cycloalkyl)amino.

In one embodiment, R⁴ is hetAr⁴ where hetAr⁴ is pyridyl, pyrimidinyl pyridazinyl, pyrazolyl, imidazolyl, thienyl, 1,2, 3-triazolyl, thiazolyl, oxazolyl, 1,3,4-oxadiazolyl, or 1,2,4-oxadiazolyl optionally substituted with one or more substituents independently selected from (1-6C)alkyl, hydroxy (1-6C)alkyl, trifluoro(1-6C)alkyl, (3-6C)cycloalkyl, (3-6C cycloalkyl)CH₂— (3-6C cycloalkyl)C(=O)—, (1-3C alkoxy)(1-6C)alkyl, (1-6C)alkoxy, (1-6C)alkylsulfonyl, NH₂, (1-6C alkyl)amino, di(1-6C alkyl)amino, (1-3C trifluoroalkoxy)(1-3C)trifluoroalkyl and cyclopropylNH—.

In one embodiment, R⁴ is hetAr⁴, where hetAr⁴ is pyridyl, pyrimidinyl pyridazinyl, pyrazolyl, imidazolyl, thionyl, 1,2, 3-triazolyl, thiazolyl, oxazolyl, 1,3,4-oxadiazolyl, or 1,2,4-oxadiazolyl optionally substituted with 1-3 substituents independently selected from fluoro, methyl, ethyl, isopropyl, cyclopropylmethyl, cyclopropyl, trifluoromethyl, 2,2,2-trifluoroethyl, methoxy, ethoxy, CN, H₂N—, (CH₃)₂N—, 2-hydroxyethyl, 2-methoxyethyl, 1-(2,2,2-trifluoroethoxy)-2,2, 2-trifluoroethyl, cyclopropylcarbonyl, methylsulfonyl and cyclopropylNH—.

In one embodiment, R⁴ is hetAr⁴, where hetAr⁴ is pyridyl, pyrimidinyl or pyridazinyl optionally substituted with 1-3 substituents independently selected from fluoro, methyl, ethyl, isopropyl, cyclopropylmethyl, cyclopropyl, trifluoromethyl, 2,2,2-trifluoroethyl, methoxy, ethoxy, CN, H₂N—, CH₃NH—, (CH₃)₂N—, and cyclopropylNH—.

In one embodiment, R⁴ when represented by hetAr⁴ is selected from the structures:

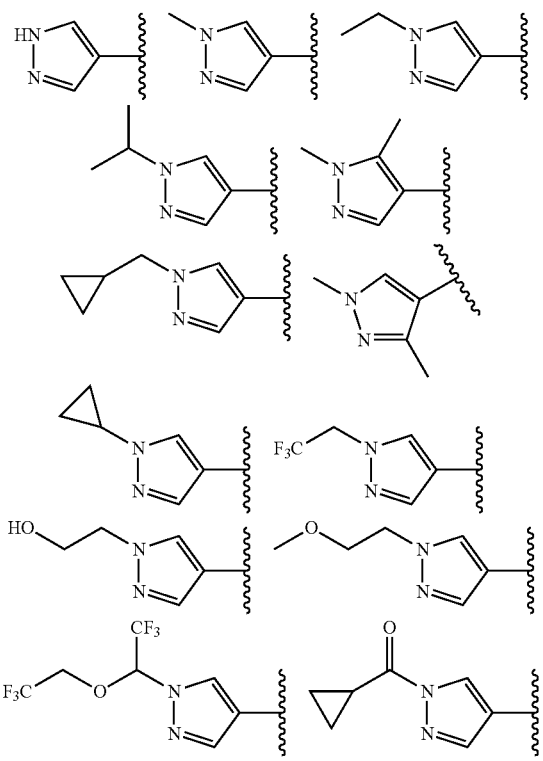

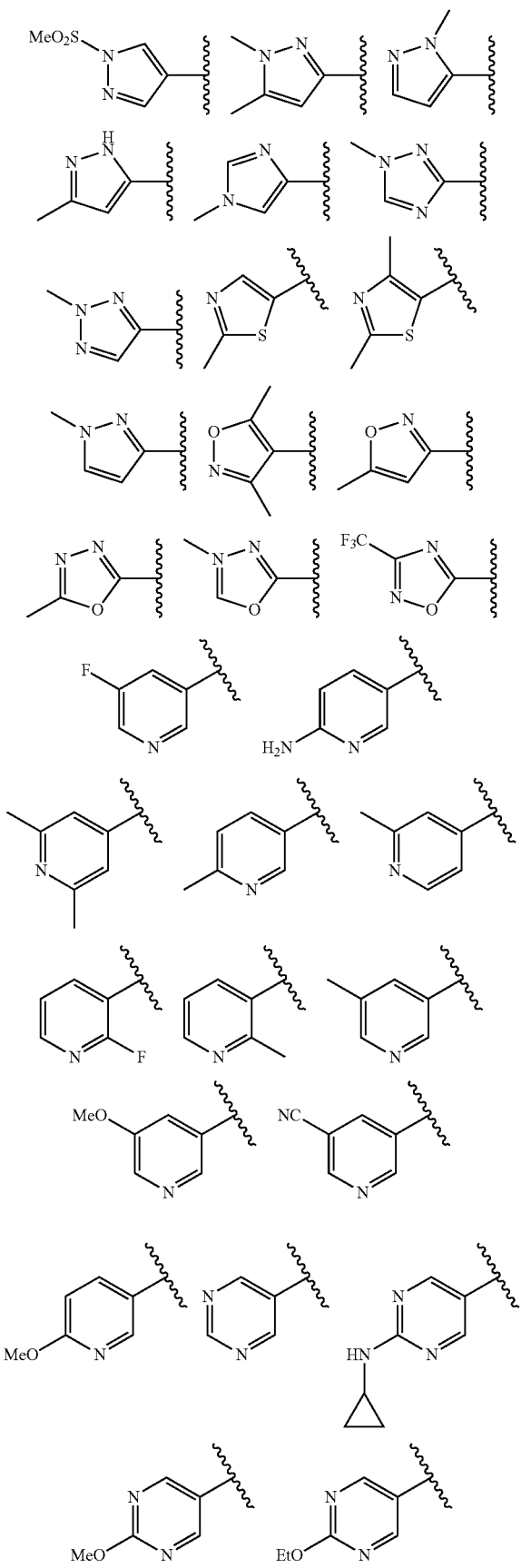
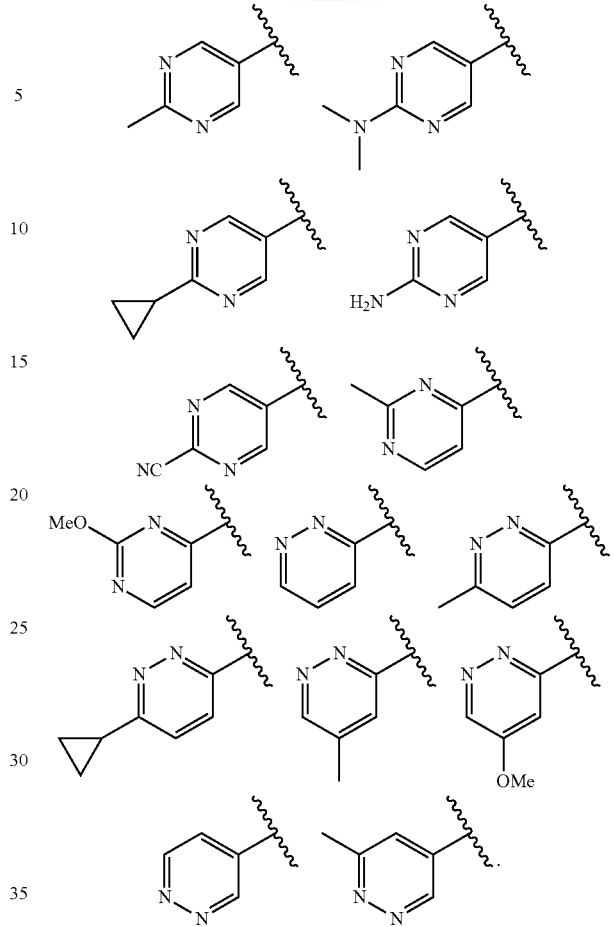

In one embodiment, R⁴ is hetAr⁴—O—. In one embodiment, R⁴ is hetAr⁴—O—, where hetAr⁴ is pyridyl, pyrimidinyl pyridazinyl, pyrazolyl, imidazolyl, thienyl, 1,2,4-triazolyl, 1,2,3-triazolyl, thiazolyl, oxazolyl, 1,3,4-oxadiazolyl, or 1,2,4-oxadiazolyl optionally substituted with one or more substituents independently selected from (1-6C) alkyl, hydroxy(1-6C)alkyl, trifluoro(1-6C)alkyl, (3-6C)cycloalkyl, (3-6C cycloalkyl)CH₂— (3-6C cycloalkyl)C(=O)—, (1-3C alkoxy)(1-6C)alkyl, (1-6C)alkoxy, (1-6C) alkylsulfonyl, NH₂, (1-6C alkyl)amino, di(1-6C alkyl) amino, (1-3C trifluoroalkoxy)(1-3C)trifluoroalkyl and cyclopropylNH—.

In one embodiment, R⁴ is hetAr⁴—O—, where hetAr⁴ is pyridyl, pyrimidinyl pyridazinyl, pyrazolyl, imidazolyl, thionyl, 1,2,4-triazolyl, 1,2,3-triazolyl, thiazolyl, oxazolyl, 1,3,4-oxadiazolyl, or 1,2,4-oxadiazolyl optionally substituted with 1-3 substituents independently selected from fluoro, methyl, ethyl, isopropyl, cyclopropylmethyl, cyclopropyl, trifluoromethyl, 2,2,2-trifluoroethyl, methoxy, ethoxy, CN, H₂N—, (CH₃)₂N—, 2-hydroxyethyl, 2-methoxyethyl, 1-(2,2,2-trifluoroethoxy)-2,2,2-trifluoroethyl, cyclopropylcarbonyl, methylsulfonyl and cyclopropylNH—.

In one embodiment, R⁴ is hetAr⁴—O—, where hetAr⁴ is pyridyl, pyrimidinyl or pyridazinyl optionally substituted with 1-3 substituents independently selected from fluoro, methyl, ethyl, isopropyl, cyclopropylmethyl, cyclopropyl, trifluoromethyl, 2,2,2-trifluoroethyl, methoxy, ethoxy, CN, H₂N—, CH₃NH—, (CH₃)₂N—, and cyclopropylNH—.

In one embodiment, $R^4$ when represented by hetAr$^4$—O— is a group having the structure:

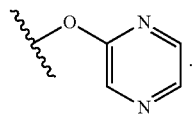 [SMILES: *Oc1cnccn1]

In one embodiment, $R^4$ is Ar$^4$, where Ar$^4$ is phenyl optionally substituted with one or more groups independently selected from (1-6C)alkyl, halogen, CN, CF$_3$, CF$_3$O—, (1-6C)alkoxy, (1-6Calkyl)OC(=O)—, aminocarbonyl, (1-6C)alkylthio, hydroxy(1-6C)alkyl, (1-6C alkyl)SO$_2$—, HOC(=O)— and (1-3C alkoxy)(1-3C alkyl)OC(=O)—. In one embodiment, Ar$^4$ is phenyl optionally substituted with one or more groups independently selected from methyl, F, Cl, CN, methoxy, CH$_3$OC(=O)—, aminocarbonyl, methylaminocarbonyl, dimethylaminocarbonyl, methylthio, CH$_3$SO$_2$—, HOC(=O)— and CH$_3$OCH$_2$CH$_2$OC(=O)—. In one embodiment, Ar$^4$ is phenyl optionally substituted with one or two of said substituents. In one embodiment, Ar$^4$ is selected from the structures:

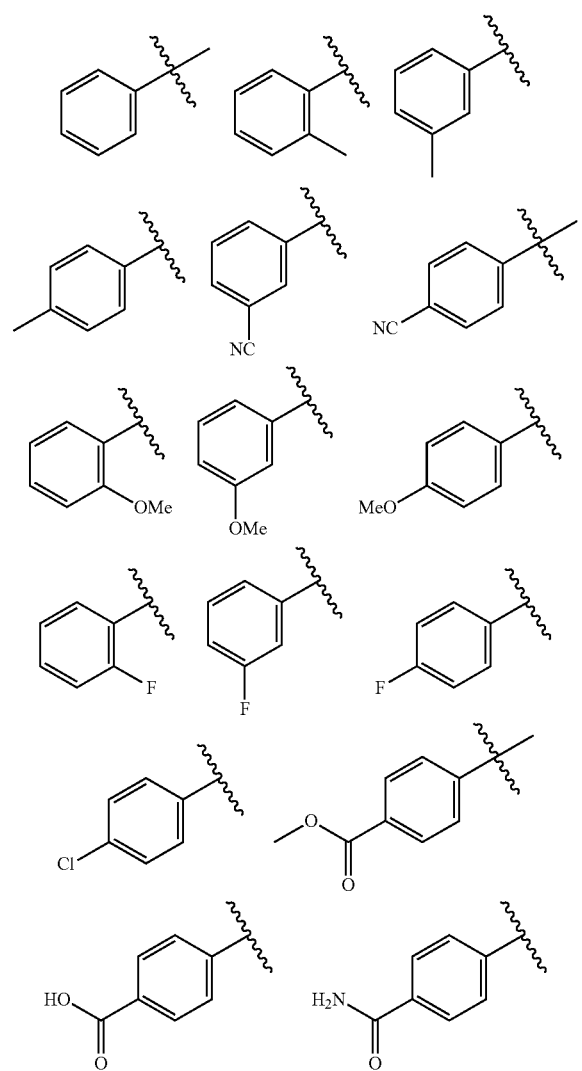

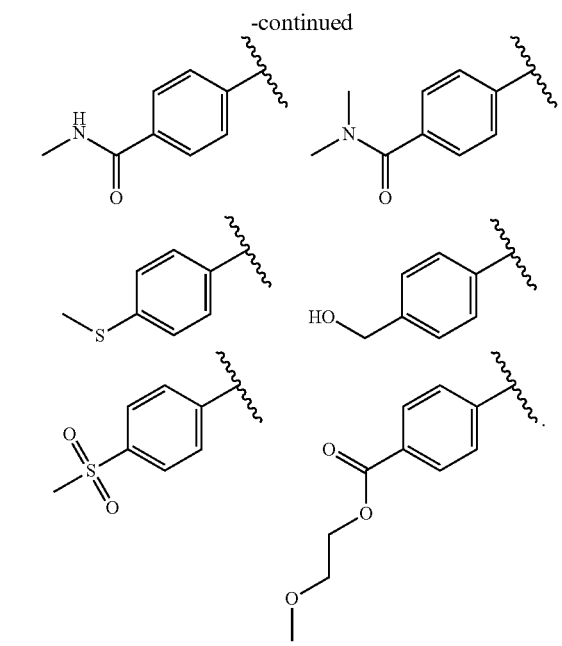

In one embodiment, $R^4$ is hetCyc$^2$(O)CH$_2$, where hetCyc$^2$ is a 4-6 membered heterocyclic ring having 1-2 ring heteroatoms independently selected from N and O, wherein hetCyc$^2$ is optionally substituted with 1-2 groups independently selected from (1-6C)alkyl, (1-4C alkoxy)carbonyl, and (1-6C)acyl. Examples of hetCyc$^2$ include oxetaynyl, tetrahydrofuranyl, tetrahydropyranyl, azetidinyl, pyrrolidinyl, piperidinyl, piperazinyl, morpholinyl, and 1,3-dioxolanyl rings optionally substituted with 1-2 groups independently selected from (1-6C)alkyl, (1-4C alkoxy)carbonyl and (1-6C)acyl. In one embodiment, $R^4$ when represented by hetCyc$^2$(O)CH$_2$, is selected from the structures:

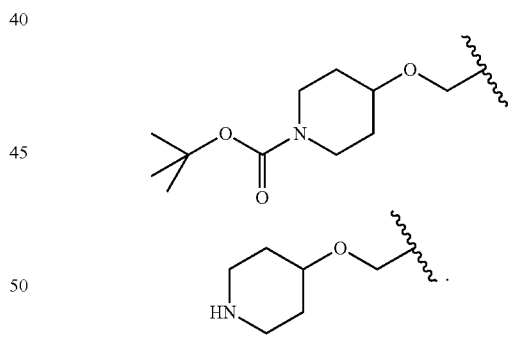

In one embodiment, $R^4$ is (1-4C alkoxycarbonyl)(1-6C)alkoxy. In one embodiment, $R^4$ is methoxycarbonyl(1-6C)alkoxy or ethylcarbonyl(1-6C)alkoxy. A particular example is ethoxycarbonylmethoxy.

In one embodiment, $R^4$ is hydroxycarbonyl(1-6C)alkoxy. In one embodiment, $R^4$ is hydroxycarbonylmethoxy.

In one embodiment, $R^4$ is aminocarbonyl(1-6C)alkoxy. In one embodiment, $R^4$ is H$_2$NC(=O)(1-6C)alkoxy, (1-6C alkyl)NHC(=O)(1-6C)alkoxy, or di(1-6Calkyl)NC(=O)(1-6C)alkoxy. In one embodiment, $R^4$ is H$_2$NC(=O)CH$_2$O—, H$_2$NC(=O)CH$_2$CH$_2$O— or CH$_3$CH$_2$NC(=O)CH$_2$O—.

In one embodiment, $R^4$ is hetCyc$^2$C(=O)(1-6C)alkoxy, where hetCyc$^2$ is a 4-6 membered heterocyclic ring having 1-2 ring heteroatoms independently selected from N and O and optionally substituted with 1-2 groups independently selected from (1-6C)alkyl, (1-4C alkoxy)carbonyl, and (1-6C)acyl. In one embodiment, hetCyc² is oxetaynyl, tetrahydrofuranyl, tetrahydropyranyl, azetidinyl, pyrrolidinyl, piperidinyl, piperazinyl, morpholinyl, or 1,3-dioxolanyl optionally substituted with 1-2 groups independently selected from (1-6C)alkyl, (1-4C alkoxy)carbonyl and (1-6C)acyl. In one embodiment, hetCyc² is morpholinyl. In one embodiment, R⁴ when represented by hetCyc²C(=O) (1-6C)alkoxy is the structure:

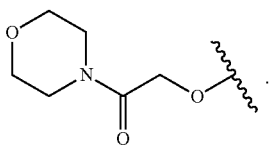 [SMILES: *OCC(=O)N1CCOCC1]

In one embodiment, R⁴ is hydroxy(1-3C alkoxy)(1-6C) alkoxy. In one embodiment, R⁴ is 2-hydroxy-3-methoxypropoxy, having the structure:

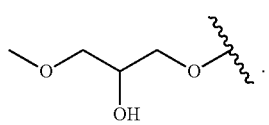 [SMILES: *OCC(O)COC]

In one embodiment, R⁴ is hydroxytrifluoro(1-6C)alkoxy. In one embodiment, R⁴ is 3,3,3-difluoro-2-hydroxypropoxy having the structure:

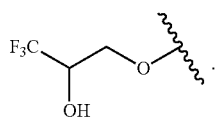

In one embodiment, R⁴ is (1-3C)alkylsulfonamido(1-6C)alkoxy. In one embodiment, R⁴ is methanesulfonamido(1-6C)alkoxy. In one embodiment, R⁴ is 2-methanesulfonamidoethoxy having the structure:

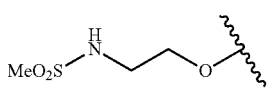

In one embodiment, R⁴ is (1-3C)alkylamido(1-6C)alkoxy. In one embodiment, R⁴ is 2-(methylamido)ethoxy having the structure:

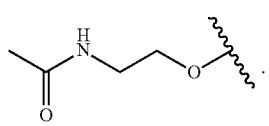 [SMILES: *OCCNC(C)=O]

In one embodiment, R⁴ is di(1-3C alkyl)aminocarboxy. In one embodiment, R⁴ is dimethylaminocarboxy having the structure:

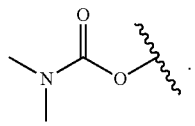 [SMILES: *OC(=O)N(C)C]

In one embodiment, R⁴ is hetCyc²C(=O)O—, where hetCyc² is a 4-6 membered heterocyclic ring having 1-2 ring heteroatoms independently selected from N and O and optionally substituted with 1-2 groups independently selected from (1-6C)alkyl, (1-4C alkoxy)carbonyl and (1-6C)acyl. In one embodiment, hetCyc² is oxetaynyl, tetrahydrofuranyl, tetrahydropyranyl, azetidinyl, pyrrolidinyl, piperidinyl, piperazinyl, morpholinyl, or 1,3-dioxolanyl optionally substituted with 1-2 groups independently selected from (1-6C)alkyl, (1-4C alkoxy)carbonyl and (1-6C)acyl. In one embodiment, hetCyc² is morpholinyl. In one embodiment, R⁴ when represented by hetCyc²C(=O)O— is the structure:

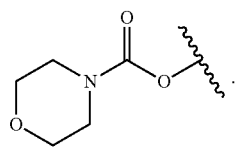 [SMILES: *OC(=O)N1CCOCC1]

In one embodiment, R⁴ is hydroxydifluoro(1-6C)alkyl. In one embodiment, R⁴ is 2,2-difluoro-2-hydroxyethyl.

In one embodiment, R⁴ is (1-4C alkylcarboxy)(1-6C)alkyl. In one embodiment, R⁴ is methylcarboxy(1-6C)alkyl. In one embodiment, R⁴ is 2-(methylcarboxy)ethyl.

In one embodiment, R⁴ is (1-6C)alkoxycarbonyl. In one embodiment, R⁴ is methoxycarbonyl or ethoxycarbonyl.

In one embodiment, R⁴ is hydroxycarbonyl.

In one embodiment, R⁴ is aminocarbonyl, that is, a RR'NCO— radical where R and R' are independently hydrogen or (1-6C)alkyl as defined herein. In one embodiment, R⁴ is aminocarbonyl, methylaminocarbonyl, dimethylaminocarbonyl, ethylcarbonyl or isopropylaminocarbonyl.

In one embodiment, R⁴ is (1-3C alkoxy)aminocarbonyl. In one embodiment, R⁴ is methoxyaminocarbonyl.

In one embodiment, R⁴ is hetCyc³, where is a 4-7 membered heterocycle having 1-2 ring heteroatoms independently selected from N and O and optionally substituted with one or more substituents independently selected from F, CN, CF₃, (1-6C)alkyl, hydroxy(1-6C)alkyl, (1-3C alkoxy)(1-6C)alkyl, (1-6C)acyl-, (1-6C)alkylsulfonyl, trifluoromethylsulfonyl and (1-4C alkoxy)carbonyl. In one embodiment, hetCyc³ is tetrahydropyranyl, piperidinyl, pyrrolidinyl or azetidinyl optionally substituted with one or more substituents independently selected from F, CN, (1-6C)alkyl, trifluoro(1-6C)alkyl, hydroxy(1-6C)alkyl, (1-3C alkoxy)(1-6C)alkyl, (1-6C)acyl-, (1-6C)alkylsulfonyl, trifluoromethylsulfonyl and (1-4C alkoxy)carbonyl. In one embodiment, hetCyc³ is optionally substituted with one or two of said substituents. In one embodiment, hetCyc³ is tetrahydropyranyl, piperidinyl, pyrrolidinyl or azetidinyl optionally substituted with CN, Me, CH₃C(=O)—, MeSO₂—, or CF₃SO₂—. In one embodiment, R⁴ when represented by hetCyc³ is selected from the structures:

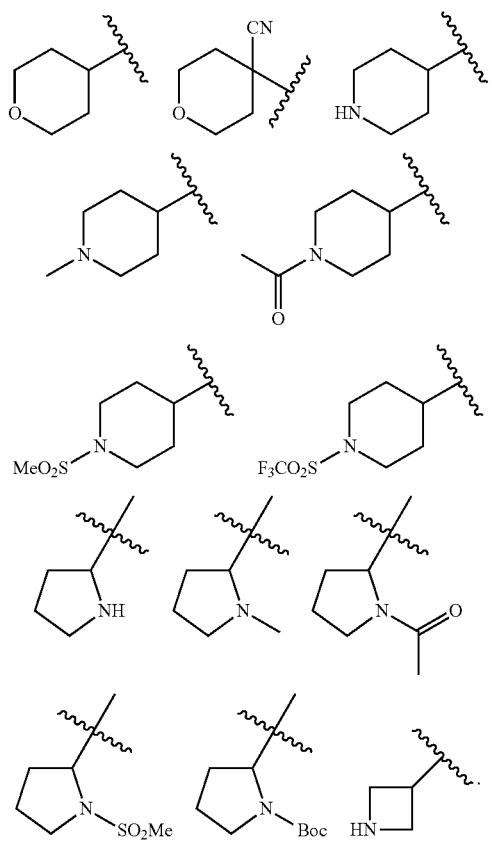
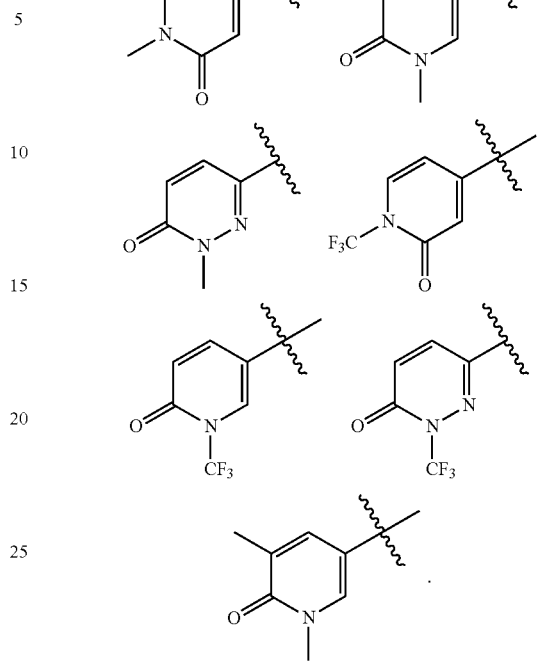

In one embodiment, $R^4$ is halogen. In one embodiment, $R^4$ is Br.

In one embodiment, $R^4$ is CN.

In one embodiment, $R^4$ is trifluoromethylsulfonyl.

In one embodiment, $R^4$ is $hetAr^5$, where $hetAr^5$ is a group selected from the structures:

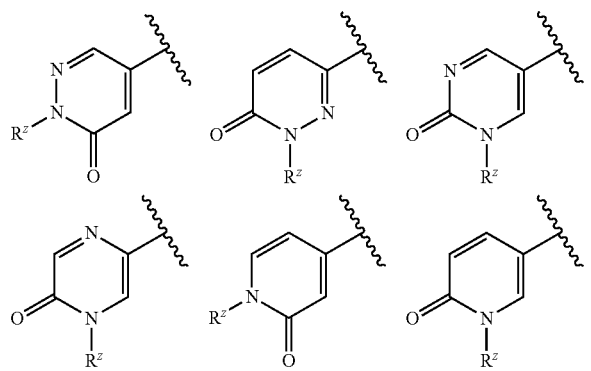

where $R^z$ is (3-4C)cycloalkyl or (1-3C)alkyl (optionally substituted with 1-3 fluoros), wherein each of said $hetAr^5$ groups is optionally further substituted with one or more groups independently selected from F and (1-3C)alkyl optionally substituted with 1-3 fluoros.

In one embodiment, $R^4$ when represented by $hetAr^5$ is selected from the structures:

In one embodiment, $R^4$ is N-(1-3C alkyl)oxadiazolonyl. In one embodiment, $R^4$ is represented by the structures:

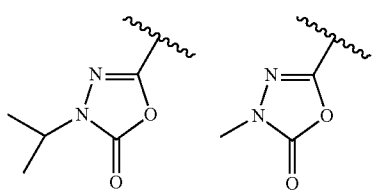

In one embodiment, $R^4$ is $Ar^4$—O—, where $Ar^4$ is phenyl optionally substituted with one or more groups independently selected from (1-6C)alkyl, halogen, CN, $CF_3$, $CF_3O$—, (1-6C)alkoxy, (1-6Calkyl)OC(=O)—, aminocarbonyl, (1-6C)alkylthio, hydroxy(1-6C)alkyl, (1-6C alkyl)$SO_2$—, HOC(=O)— and (1-3C alkoxy)(1-3C alkyl)OC(=O)—. In one embodiment, $R^4$ is phenoxy.

In one embodiment, $R^4$ is $hetCyc^4$-O—, where $hetCyc^4$ is a 5-8 membered monocyclic, spirocyclic or bridged heterocycle having a ring nitrogen atom and optionally substituted with one or more groups independently selected from (1-6C) alkyl and halogen.

In one embodiment, $R^4$ is $hetCyc^4$-O—, where $hetCyc^4$ is pyrrolidinyl, piperidinyl, 2-azaspiro[3.3]heptanyl, 1-azaspiro[3.3]heptane or quinuclidinyl, optionally substituted with one or more groups independently selected from (1-6C)alkyl and halogen.

In one embodiment, $R^4$ when represented by $hetCyc^4$-O— is selected from the structures:

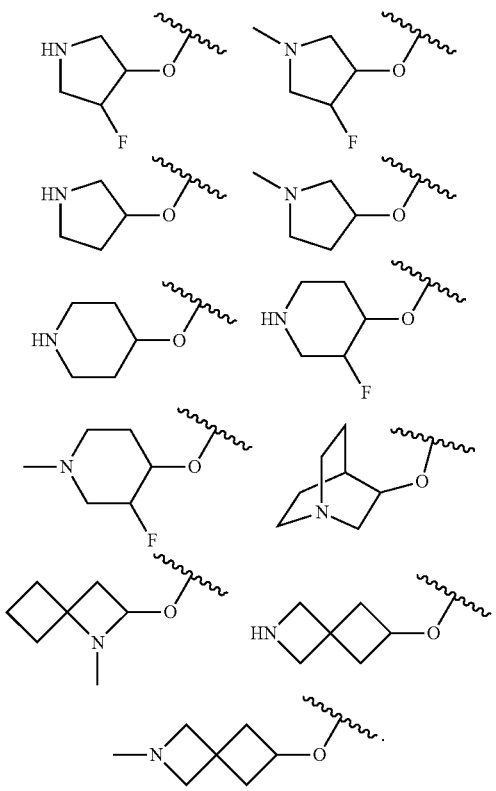

In one embodiment, R⁴ is Cyc¹-O—, where Cyc¹ is a 3-6 membered carbocycle optionally substituted with an amino group. In one embodiment, R⁴ is Cyc¹-O—, where Cyc¹ is cyclopropyl, cyclobutyl, cyclopentyl or cyclohexyl optionally substituted with NH₂, NHCH₃ or N(CH₃)₂. In one embodiment, R⁴ is cyclobutyl optionally substituted with an amino group. In one embodiment, R⁴ is cyclobutyl optionally substituted with NH₂, NHCH₃ or N(CH₃)₂. In one embodiment, R⁴ when represented by Cyc¹-O— is selected from the structures:

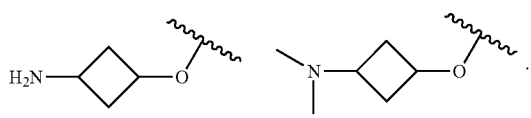

In one embodiment, R⁴ is aminohydroxy(1-6C)alkoxy. In one embodiment, R⁴ is 2-amino-3-hydroxypropoxy.

In one embodiment, R⁴ is selected from H, (1-6C)alkyl, trifluoro(1-6C)alkyl, hydroxy(1-6C)alkyl, cyano(1-6C)alkyl, (1-3C alkoxy)(1-6C)alkyl, (1-6C)alkoxy, monofluoro(1-6C)alkoxy, cyano(1-6C)alkoxy, hydroxy(1-6C)alkoxy, dihydroxy(2-6C)alkoxy, hetCyc²(1-6C)alkoxy, Ar³(1-6C)alkoxy, (1-4C alkoxy)(1-6C)alkoxy, (1-3C alkylsulfonyl)(1-6C)alkoxy, (3-6C)cycloalkyl, hetAr⁴, hetAr⁴—O—, Ar⁴, and hetAr⁵.

In one embodiment, R⁴ is hetAr⁴, Ar⁴, or hetAr⁵.

In one embodiment, R⁴ is hetAr⁴ or hetAr⁵.

In one embodiment, R⁴ is pyrazolyl optionally substituted with one or more groups independently selected from (1-6C)alkyl, or a hetAr⁵ group having the structure:

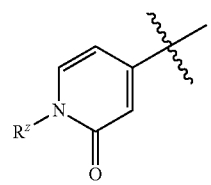

where R$^z$ is (3-4C)cycloalkyl or (1-3C)alkyl (optionally substituted with 1-3 fluoros), wherein said hetAr⁵ group is optionally further substituted with one or more groups independently selected from F and (1-3C)alkyl optionally substituted with 1-3 fluoros.

In one embodiment, R⁵ is (1-6C)alkyl. In one embodiment, R⁵ is methyl, ethyl, propyl, isopropyl or butyl.

In one embodiment, R⁵ is monofluoro(1-6C)alkyl, difluoro(1-6C)alkyl, trifluoro(1-6C)alkyl, tetrafluoro(2-6C)alkyl or pentafluoro(2-6C)alkyl. In one embodiment, R⁵ is fluoromethyl, 2-fluoroethyl, difluoromethyl, 2,2-difluoroethyl, 1,3-difluoroprop-2-yl, trifluoromethyl, 2,2,2-trifluoroethyl, 3,3,3-trifluoropropyl, 1,1,2,2-tetrafluoropropane or 2,2,3,3,3-pentafluoropropyl.

In one embodiment, R⁵ is halogen. In one embodiment, R⁵ is F. In one embodiment, R⁵ is Cl. In one embodiment, R⁵ is Br.

In one embodiment, R⁵ is CN.

In one embodiment, R⁵ is (1-4C)alkoxy. In one embodiment, R⁵ is methoxy or ethoxy.

In one embodiment, R⁵ is hydroxy(1-4C)alkyl. In one embodiment, R⁵ is hydroxymethyl or 3-hydroxypropyl.

In one embodiment, R⁵ is (1-4C alkyl)OC(=O)—. In one embodiment, R⁵ is CH₃CH₂OC(=O)—.

In one embodiment, R⁵ is (1-6C)alkylthio. In one embodiment, R⁵ is methylthio (MeS—).

In one embodiment, R⁵ is phenyl optionally substituted with one or more groups independently selected from halogen, (1-6C)alkyl and (1-6C)alkoxy. In one embodiment, R⁵ is phenyl optionally substituted with one or more groups independently selected from F, Cl, methyl, ethyl, methoxy and ethoxy. In one embodiment, R⁵ is phenyl.

In one embodiment, R⁵ is (3-4C)cycloalkyl. In one embodiment, R⁵ is cyclopropyl. In one embodiment, R⁵ is cyclobutyl.

In one embodiment, R⁵ is amino. In one embodiment, R⁵ is NH₂.

In one embodiment, R⁵ is aminocarbonyl. In one embodiment, R⁵ is H₂NC(=O)—.

In one embodiment, R⁵ is trifluoro(1-3C alkyl)amido. In one embodiment, R⁵ is CF₃C(=O)NH—.

In one embodiment, R⁵ is halogen, CN, (1-6C)alkyl, (1-4C)alkoxy, hydroxy(1-4C)alkyl, or phenyl optionally substituted with one or more groups independently selected from halogen, (1-6C)alkyl and (1-6C)alkoxy.

In one embodiment, R⁵ is selected from halogen, and (1-6C)alkyl.

In one embodiment, R⁵ is selected from methyl, Cl and Br.

In one embodiment of Formula I, R⁴ is selected from H, (1-6C)alkyl, trifluoro(1-6C)alkyl, cyano(1-6C)alkyl, (1-3C alkoxy)(1-6C)alkyl, (1-6C)alkoxy, cyano(1-6C)alkoxy, hydroxy(1-6C)alkoxy, (1-4C alkoxy)(1-6C)alkoxy, (3-6C)cycloalkyl, hetAr⁴, Ar⁴, and hetAr⁵; and R⁵ is selected from halogen, CN, (1-6C)alkyl, (1-4C)alkoxy, hydroxy(1-4C)alkyl, (1-6C)alkylthio, and phenyl optionally substituted with one or more groups independently selected from halogen, (1-6C)alkyl and (1-6C)alkoxy.

In one embodiment, $R^4$ is selected from (1-6C)alkoxy, cyano(1-6C)alkoxy, hydroxy(1-6C)alkoxy, (1-4C alkoxy)(1-6C)alkoxy, hetAr$^4$, hetAr$^5$, Ar$^4$—O—, hetCyc$^4$-O—, Cyc$^1$-O—, or aminohydroxy(1-6C)alkoxy.

In one embodiment, $R^4$ is selected from (1-6C)alkoxy, cyano(1-6C)alkoxy, hydroxy(1-6C)alkoxy, (1-4C alkoxy)(1-6C)alkoxy, hetAr$^4$ and hetAr$^5$.

In one embodiment of Formula I, $R^4$ is selected from hetAr$^4$, Ar$^4$, and hetAr$^5$; and $R^5$ is selected from (1-6C)alkyl.

In one embodiment of Formula I, $R^4$ is selected from hetAr$^4$ and hetAr$^5$; and $R^5$ is selected from (1-6C)alkyl.

In one embodiment of Formula I, $R^4$ is hetAr$^4$ and $R^5$ is selected from (1-6C)alkyl.

In one embodiment of Formula I, $R^4$ is pyrazolyl optionally substituted with one or more substituents independently selected from (1-6C)alkyl; and $R^5$ is selected from (1-6C) alkyl.

In one embodiment of Formula I, $R^4$ is hetAr$^5$; and $R^5$ is selected from (1-6C)alkyl.

In one embodiment of Formula I, $R^4$ is a hetAr$^5$ group having the structure:

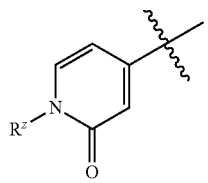

where $R^z$ is (3-4C)cycloalkyl or (1-3C)alkyl (optionally substituted with 1-3 fluoros), wherein said hetAr$^5$ group is optionally further substituted with one or more groups independently selected from F and (1-3C)alkyl optionally substituted with 1-3 fluoros; and $R^5$ is selected from (1-6C) alkyl.

In one embodiment, $R^4$ and $R^5$ together with the atoms to which they are attached form a 5-6 membered saturated, partially unsaturated or unsaturated carbocyclic ring optionally substituted with one or more substituents independently selected from (1-6C)alkyl; or $R^4$ and $R^5$ together with the atoms to which they are attached form a 5-6 membered saturated, partially unsaturated or unsaturated heterocyclic ring having a ring heteroatom selected from N, O or S, wherein said heterocyclic ring is optionally substituted with one or two substituents independently selected from (1-6C alkyl)C(=O)O—, (1-6C)acyl, (1-6C)alkyl and oxo, and said sulfur ring atom is optionally oxidized to S(=O) or SO$_2$.

In one embodiment, $R^4$ and $R^5$ together with the atoms to which they are attached form a 5-6 membered saturated, partially unsaturated or unsaturated carbocyclic ring optionally substituted with one or more substituents independently selected from (1-6C)alkyl. In one embodiment, Ring C when $R^4$ and $R^5$ together with the atoms to which they are attached form a 5-6 membered saturated or unsaturated carbocyclic ring is selected from the structures:

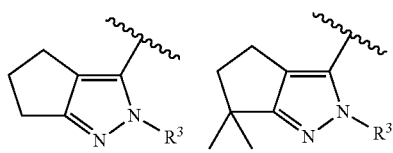

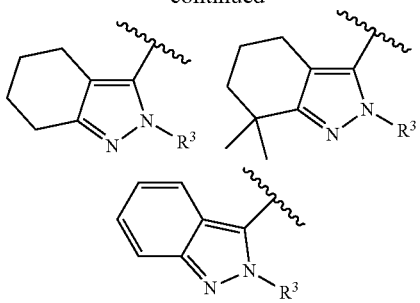

where $R^3$ is as defined for Formula I. In one embodiment of the above structures, $R^3$ is phenyl.

In one embodiment, $R^4$ and $R^5$ together with the atoms to which they are attached form a 5-6 membered saturated carbocyclic ring optionally substituted with one or more substituents independently selected from (1-6C)alkyl, or $R^4$ and $R^5$ together with the atoms to which they are attached form a 5-6 membered saturated heterocyclic ring having a ring heteroatom selected from N, O or S, wherein said ring nitrogen atom is optionally substituted with (1-6C alkyl)C(=O)O— or (1-6C)acyl, and said sulfur ring atom is optionally oxidized to S(=O) or SO$_2$.

In one embodiment, $R^4$ and $R^5$ together with the atoms to which they are attached form a 5-6 membered saturated carbocyclic ring optionally substituted with one or more substituents independently selected from (1-6C)alkyl. In one embodiment, Ring C when $R^4$ and $R^5$ together with the atoms to which they are attached form a 5-6 membered saturated carbocyclic ring is selected from the structures:

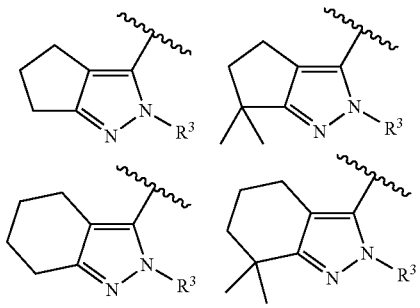

where $R^3$ is as defined for Formula I. In one embodiment of the above structures, $R^3$ is phenyl.

In one embodiment, $R^4$ and $R^5$ together with the atoms to which they are attached form a 5-6 membered saturated, partially unsaturated or unsaturated heterocyclic ring having a ring heteroatom selected from N, O or S, wherein said ring N atom is optionally substituted with (1-6C alkyl)C(=O)O—, (1-6C alkyl)C(=O)—, (1-6C)alkyl or oxo, and said S ring atom is optionally oxidized to S(=O) or SO$_2$. In one embodiment, Ring C when $R^4$ and $R^5$ together with the atoms to which they are attached form a 5-6 membered saturated heterocyclic ring is selected from the structures:

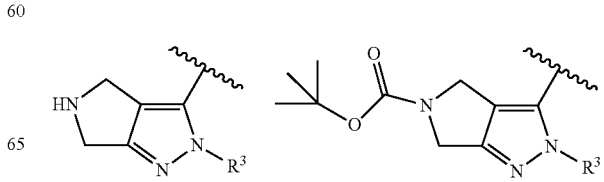

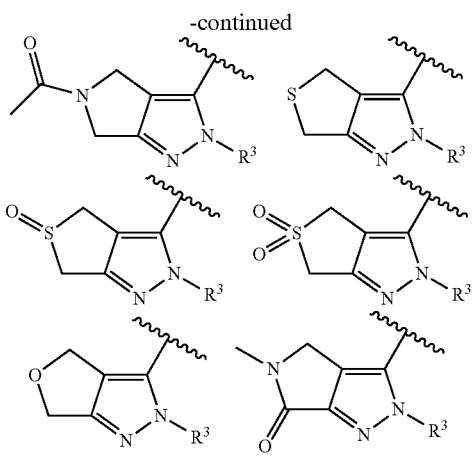

where R³ is as defined for Formula I. In one embodiment of the above structures, R³ is phenyl.

In one embodiment, R⁴ and R⁵ together with the atoms to which they are attached form a 5-6 membered saturated heterocyclic ring having a ring heteroatom selected from N, O or S, wherein said ring N atom is optionally substituted with (1-6C alkyl)C(=O)O— or (1-6C alkyl)C(=O)—, and said S ring atom is optionally oxidized to S(=O) or SO₂. In one embodiment, Ring C when R⁴ and R⁵ together with the atoms to which they are attached form a 5-6 membered saturated heterocyclic ring is selected from the structures:

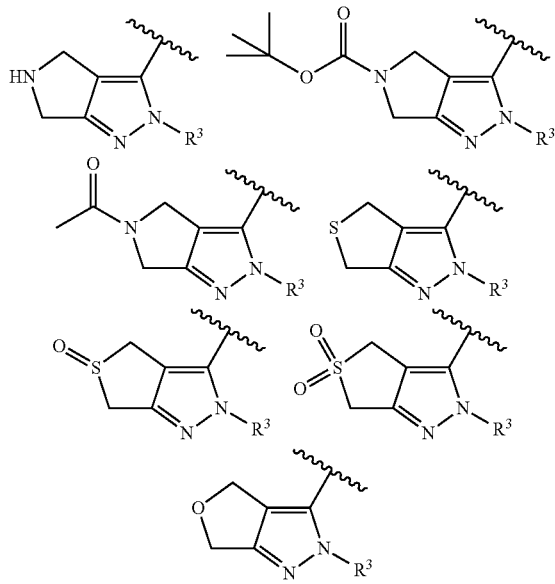

where R³ is as defined for Formula I. In one embodiment of the above structures, R³ is phenyl.

In one embodiment, Ring C is formula C-2

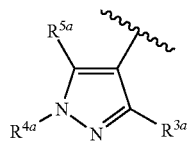

where R³ᵃ, R⁴ᵃ and R⁵ᵃ are as defined for Formula I.

In one embodiment, R³ᵃ is hydrogen.
In one embodiment, R³ᵃ is halogen.
In one embodiment, R³ᵃ is (1-6C)alkyl. In one embodiment, R³ᵃ is methyl.
In one embodiment, R³ᵃ is trifluoro(1-6C)alkyl. In one embodiment, R³ᵃ is CF₃.
In one embodiment, R³ᵃ is (3-6C)cycloalkyl. In one embodiment, R³ᵃ is cyclopropyl.
In one embodiment, R³ᵃ is phenyl optionally substituted with one or more substituents independently selected from halogen and (1-6C)alkyl. In one embodiment, R³ᵃ is phenyl, fluorophenyl or methylphenyl, for example include phenyl, 2-fluorophenyl, 3-fluorophenyl, 4-fluorophenyl, 2-methylphenyl, 3-methylphenyl, 4-methylphenyl, 3-chlorophenyl, 3-chloro-4-fluorophenyl or 3-chloro-2-fluorophenyl. In one embodiment, R³ᵃ is phenyl.
In one embodiment, R³ᵃ is a 5-6 membered heteroaryl ring having 1-3 ring heteroatoms independently selected from N, O and S and optionally substituted with one or more groups independently selected from (1-6C)alkyl and halogen. In one embodiment, R³ᵃ is a thienyl, furyl, imidazolyl, pyrazolyl, thiazolyl, isothiazolyl, oxazolyl, isoxazolyl, triazolyl, thiadiazolyl, oxadiazolyl, pyridyl, pyrimidyl, pyrazinyl, or pyridazinyl ring optionally substituted with (1-6C) alkyl or halogen. In one embodiment, R³ᵃ is pyrazolyl, pyridyl or pyridazinyl optionally substituted with one or more groups independently selected from (1-6C)alkyl and halogen. In one embodiment, R³ᵃ is pyrazolyl, pyridyl or pyridazinyl optionally substituted with (1-6C)alkyl or halogen.
In one embodiment, R⁴ᵃ is hydrogen.
In one embodiment, R⁴ᵃ is (1-6C)alkyl. In one embodiment, R⁴ᵃ is methyl, ethyl or isopropyl.
In one embodiment, R⁴ᵃ is trifluoro(1-6C)alkyl. In one embodiment, R⁴ᵃ is 2,2,2-trifluoroethyl.
In one embodiment, R⁴ᵃ is phenyl optionally substituted with one or more groups independently selected from (1-6C) alkyl, halogen, CN, CF₃, CF₃O—, (1-6C)alkoxy, (1-6Calkyl)OC(=O)—, aminocarbonyl, (1-6C)alkylthio, hydroxy(1-6C)alkyl, (1-6C alkyl)SO₂—, HOC(=O)— and (1-3C alkoxy)(1-3C alkyl)OC(=O)—. In one embodiment, R⁴ᵃ is phenyl optionally substituted with one or more groups independently selected from methyl, F, Cl, CN, methoxy, CH₃OC(=O)—, aminocarbonyl, methylaminocarbonyl, dimethylaminocarbonyl, methylthio, CH₃SO₂—, HOC(=O)— or CH₃OCH₂CH₂OC(=O)—. In certain embodiments, R⁴ᵃ is phenyl optionally substituted with one or two of said substituents. In one embodiment, R⁴ᵃ is phenyl.
In one embodiment, R⁴ᵃ is a 5-6 membered heteroaryl ring having 1-3 ring heteroatoms independently selected from N, S and O and optionally substituted with 1-2 substituents independently selected from (1-6C)alkyl, hydroxy (1-6C)alkyl, trifluoro(1-6C)alkyl, (3-6C)cycloalkyl, (3-6C cycloalkyl)CH₂— (3-6C cycloalkyl)C(=O)—, (1-3C alkoxy)(1-6C)alkyl, (1-6C)alkoxy, (1-6C)alkylsulfonyl, NH₂, (1-6C alkyl)amino, di(1-6C alkyl)amino, and (1-3C trifluoroalkoxy)(1-3C)trifluoroalkyl. In one embodiment, R⁴ᵃ is pyridyl, pyrimidinyl pyridazinyl, pyrazolyl, imidazolyl, thionyl, 1,2,4-triazolyl, 1,2,3-triazolyl, thiazolyl, oxazolyl, 1,3,4-oxadiazolyl, 1,2,4-oxadiazolyl or imidazo[1,2-a]pyridinyl optionally substituted with 1-2 substituents independently selected from (1-6C)alkyl, hydroxy(1-6C) alkyl, trifluoro(1-6C)alkyl, (3-6C)cycloalkyl, (3-6C cycloalkyl)CH₂— (3-6C cycloalkyl)C(=O)—, (1-3C alkoxy)(1-6C)alkyl, (1-6C)alkoxy, (1-6C)alkylsulfonyl, NH$_2$, (1-6C alkyl)amino, di(1-6C alkyl)amino, and (1-3C trifluoroalkoxy)(1-3C)trifluoroalkyl. In one embodiment, R$^{4a}$ is pyrazinyl.

In one embodiment, R$^{5a}$ is as defined for Formula I.

In one embodiment, R$^{5a}$ is selected from hydrogen, halogen, (1-6C)alkyl and phenyl.

In one embodiment, R$^{5a}$ is hydrogen.

In one embodiment, R$^{5a}$ is halogen.

In one embodiment, R$^{5a}$ is (1-6C)alkyl. In one embodiment, R$^{5a}$ is methyl.

In one embodiment, R$^{5a}$ is phenyl.

In one embodiment, Ring C is formula C-2, in which R$^{3a}$ is (1-6C)alkyl, trifluoro(1-6C)alkyl or phenyl; R$^{4a}$ is (1-6C)alkyl, trifluoro(1-6C)alkyl, phenyl or pyrazinyl; and R$^{5a}$ is hydrogen, (1-6C)alkyl or phenyl.

In one embodiment of Formula I, Ring A is A-1, and R$^1$, R$^2$, R$^a$, R$^b$, n, R$^c$, R$^d$, G$^1$, G$^2$, G$^3$, X, Ring C, R$^3$, R$^4$, R$^5$, R$^{3a}$, R$^{4a}$ and R$^{5a}$ are as defined for Formula I.

In one embodiment of Formula I, Ring A is A-1; n is 0; and G$^1$, G$^2$, G$^3$, R$^1$, R$^2$, R$^a$, R$^b$, X, Ring C, R$^3$, R$^4$, R$^5$, R$^{3a}$, R$^{4a}$ and R$^{5a}$ are as defined for Formula I.

In one embodiment of Formula I, Ring A is A-1; n is 0; X is O; and G$^1$, G$^2$, G$^3$, R$^1$, R$^2$, R$^a$, R$^b$, Ring C, R$^3$, R$^4$ and R$^5$ are as defined for Formula I.

In one embodiment of Formula I, Ring A is A-1; n is 0; X is O; Ring C is C-1; and G$^1$, G$^2$, G$^3$, R$^1$, R$^2$, R$^a$, R$^b$, R$^3$, R$^4$ and R$^5$ are as defined for Formula I.

In one embodiment of Formula I, Ring A is A-1; n is 0; X is O; Ring C is C-1; R$^4$ is hetAr$^4$ or hetAr$^5$; and G$^1$, G$^2$, G$^3$, R$^1$, R$^2$, R$^a$, R$^b$, R$^3$, and R$^5$ are as defined for Formula I.

In one embodiment of Formula I, Ring A is A-1; n is 0; X is O; Ring C is C-1; R$^4$ is hetAr$^4$ or hetAr$^5$; R$^3$ is Ar$^2$; and G$^1$, G$^2$, G$^3$, R$^1$, R$^2$, R$^a$, R$^b$, and R$^5$ are as defined for Formula I.

In one embodiment of Formula I, Ring A is A-1; n is 0; Ring C is C-1; R$^4$ is hetAr$^4$ or hetAr$^5$; R$^3$ is Ar$^2$; R$^5$ is (1-6C)alkyl; and G$^1$, G$^2$, G$^3$, R$^1$, R$^2$, R$^a$, and R$^b$ are as defined for Formula I.

In one embodiment of Formula I, Ring A is A-1; n is 0; X is O; Ring C is C-1; R$^4$ is hetAr$^4$ or hetAr$^5$; R$^3$ is Ar$^2$; R$^5$ is (1-6C)alkyl; R$^b$ is H; and G$^1$, G$^2$, G$^3$, R$^1$, R$^2$, and R$^a$ are as defined for Formula I.

In one embodiment of Formula I, Ring A is A-1; n is 0; X is O; Ring C is C-1; R$^4$ is hetAr$^4$ or hetAr$^5$; R$^3$ is Ar$^2$; R$^5$ is (1-6C)alkyl; R$^b$ is H; R$^a$ is H; and G$^1$, G$^2$, G$^3$, R$^1$, and R$^2$ are as defined for Formula I.

In one embodiment of Formula I, Ring A is A-1; n is 0; X is O; Ring C is C-1; R$^4$ is hetAr$^4$ or hetAr$^5$; R$^3$ is Ar$^2$; R$^5$ is (1-6C)alkyl; R$^b$ is H; R$^a$ is H; R$^1$ is (1-3C)alkoxy(1-3C)alkyl; and G$^1$, G$^2$, G$^3$, and R$^2$ are as defined for Formula I.

In one embodiment of Formula I, Ring A is A-1; n is 0; X is O; Ring C is C-1; R$^4$ is hetAr$^4$ or hetAr$^5$; R$^3$ is Ar$^2$; R$^5$ is (1-6C)alkyl; R$^b$ is H; R$^a$ is H; R$^1$ is (1-3C)alkoxy(1-3C)alkyl; R$^2$ is H, halogen, CF$_3$, F$_2$CH, FCH$_2$ or methoxy; and G$^1$, G$^2$, and G$^3$ are as defined for Formula I.

In one embodiment of Formula I, Ring A is A-1; n is 0; X is O; Ring C is C-1; R$^4$ is hetAr$^4$ or hetAr$^5$; R$^3$ is Ar$^2$; R$^5$ is (1-6C)alkyl; R$^b$ is H; R$^a$ is H; R$^1$ is (1-3C)alkoxy(1-3C)alkyl; R$^2$ is H, halogen, CF$_3$, F$_2$CH, FCH$_2$ or methoxy; G$^1$, G$^2$ and G$^3$ are CR$^x$.

In one embodiment of Formula I, Ring A is A-1; n is 0; X is O; Ring C is C-1; R$^4$ is hetAr$^4$ or hetAr$^5$; R$^3$ is Ar$^2$; R$^5$ is (1-6C)alkyl; R$^b$ is H; R$^a$ is H; R$^1$ is (1-3C)alkoxy(1-3C)alkyl; R$^2$ is H, halogen, CF$_3$, F$_2$CH, FCH$_2$ or methoxy; G$^1$ and G$^2$ are CR$^x$; and G$^3$ is N.

In one embodiment of Formula I, Ring A is A-1; n is 0; X is O; Ring C is C-1; R$^4$ is hetAr$^4$ or hetAr$^5$; R$^3$ is Ar$^2$; R$^5$ is (1-6C)alkyl; R$^b$ is H; R$^a$ is H; R$^1$ is (1-3C)alkoxy(1-3C)alkyl; R$^2$ is H, halogen, CF$_3$, F$_2$CH, FCH$_2$ or methoxy; G$^1$ and G$^2$ are N; and G$^3$ is CR$^x$.

In one embodiment of Formula I, Ring A is A-1; n is 0; X is O; Ring C is C-1; R$^4$ is hetAr$^4$ or hetAr$^5$; R$^3$ is Ar$^2$; R$^5$ is (1-6C)alkyl; R$^b$ is H; R$^a$ is H; R$^1$ is (1-3C)alkoxy(1-3C)alkyl; R$^2$ is H, halogen, CF$_3$, F$_2$CH, FCH$_2$ or methoxy; G$^2$ and G$^3$ are N; and G$^1$ is CR$^x$.

In one embodiment of Formula I, Ring A is A-1; n is 0; X is O; Ring C is C-1; R$^4$ is hetAr$^4$ or hetAr$^5$; R$^3$ is Ar$^2$; R$^5$ is (1-6C)alkyl; R$^b$ is H; R$^a$ is H; R$^1$ is (1-3C)alkoxy(1-3C)alkyl; R$^2$ is H, halogen, CF$_3$, F$_2$CH, FCH$_2$ or methoxy; G$^1$ and G$^3$ are N; and G$^2$ is CR$^x$.

In one embodiment of Formula I, n is 1; Ring A is A-1; R$^2$ is selected from the group consisting of H, halogen, CF$_3$, F$_2$CH, FCH$_2$, MeO and methyl; and G$^1$, G$^2$, G$^3$, R$^a$, R$^b$, R$^c$, R$^d$, X, R$^1$, Ring C, R$^3$, R$^4$, R$^5$, R$^{3a}$, R$^{4a}$ and R$^{5a}$ are as defined for Formula I.

In one embodiment of Formula I, n is 1; Ring A is A-1; R$^2$ is selected from the group consisting of H, halogen, CF$_3$, F$_2$CH, FCH$_2$, MeO and methyl; X is O; and G$^1$, G$^2$, G$^3$, R$^a$, R$^b$, R$^c$, R$^d$, R$^1$, Ring C, R$^3$, R$^4$, R$^5$, R$^{3a}$, R$^{4a}$ and R$^{5a}$ are as defined for Formula I.

In one embodiment of Formula I, n is 1; Ring A is A-1; R$^2$ is selected from the group consisting of H, halogen, CF$_3$, F$_2$CH, FCH$_2$, MeO and methyl; X is O; Ring C is C-1; and G$^1$, G$^2$, G$^3$, R$^a$, R$^b$, R$^c$, R$^d$, X, R$^1$, R$^3$, R$^4$, and R$^5$ are as defined for Formula I. In one embodiment, G$^1$, G$^2$, G$^3$, R$^a$, R$^b$, R$^c$, R$^d$, X, R$^1$, R$^3$, R$^4$, and R$^5$ are as defined for Formula I-C.

In one embodiment of Formula I, n is 1; Ring A is A-1; R$^2$ is selected from the group consisting of H, halogen, CF$_3$, F$_2$CH, FCH$_2$, MeO and methyl; X is O; Ring C is C-1; R$^4$ is hetAr$^4$ or hetAr$^5$; and G$^1$, G$^2$, G$^3$, R$^a$, R$^b$, R$^c$, R$^d$, X, R$^1$, R$^3$, and R$^5$ are as defined for Formula I.

In one embodiment of Formula I, n is 1; Ring A is A-1; R$^2$ is selected from the group consisting of H, halogen, CF$_3$, F$_2$CH, FCH$_2$, MeO and methyl; X is O; Ring C is C-1; R$^4$ is hetAr$^4$ or hetAr$^5$; R$^3$ is Ar$^2$; and G$^1$, G$^2$, G$^3$, R$^a$, R$^b$, R$^c$, R$^d$, X, R$^1$, and R$^5$ are as defined for Formula I. In one embodiment, G$^1$, G$^2$, G$^3$, R$^a$, R$^b$, R$^c$, R$^d$, X, R$^1$, and R$^5$ are as defined for Formula I-C.

In one embodiment of Formula I, n is 1; Ring A is A-1; R$^2$ is selected from the group consisting of H, halogen, CF$_3$, F$_2$CH, FCH$_2$, MeO and methyl; X is O; Ring C is C-1; R$^4$ is hetAr$^4$ or hetAr$^5$; R$^3$ is Ar$^2$; R$^5$ is (1-6C)alkyl; and G$^1$, G$^2$, G$^3$, R$^a$, R$^b$, R$^c$, R$^d$, and R$^1$ are as defined for Formula I. In one embodiment, G$^1$, G$^2$, G$^3$, R$^a$, R$^b$, R$^c$, R$^d$, and R$^1$ are as defined for Formula I-C.

In one embodiment of Formula I, n is 1; Ring A is A-1; R$^2$ is selected from the group consisting of H, halogen, CF$_3$, F$_2$CH, FCH$_2$, MeO and methyl; X is O; Ring C is C-1; R$^4$ is hetAr$^4$ or hetAr$^5$; R$^3$ is Ar$^2$; R$^5$ is (1-6C)alkyl; R$^a$ and R$^b$ are H; and G$^1$, G$^2$, G$^3$, R$^c$, R$^d$, and R$^1$ are as defined for Formula I. In one embodiment, G$^1$, G$^2$, G$^3$, R$^c$, R$^d$, and R$^1$ are as defined for Formula I-C.

In one embodiment of Formula I, n is 1; Ring A is A-1; R$^2$ is selected from the group consisting of H, halogen, CF$_3$, F$_2$CH, FCH$_2$, MeO and methyl; X is O; Ring C is C-1; R$^4$ is hetAr$^4$ or hetAr$^5$; R$^3$ is Ar$^2$; R$^5$ is (1-6C)alkyl; R$^a$ and R$^b$ are H; $R^c$ is H; and $G^1$, $G^2$, $G^3$, $R^d$, and $R^1$ are as defined for Formula I. In one embodiment, $G^1$, $G^2$, $G^3$, $R^d$, and $R^1$ are as defined for Formula I-C.

In one embodiment of Formula I, n is 1; Ring A is A-1; $R^2$ is selected from the group consisting of H, halogen, $CF_3$, $F_2CH$, $FCH_2$, MeO and methyl; X is O; Ring C is C-1; $R^4$ is $hetAr^4$ or $hetAr^5$; $R^3$ is $Ar^2$; $R^5$ is (1-6C)alkyl; $R^a$ and $R^b$ are H; $R^c$ is H; $R^1$ is (1-3C)alkoxy(1-3C)alkyl; and $G^1$, $G^2$, $G^3$, and $R^d$ are as defined for Formula I. In one embodiment, $G^1$, $G^2$, $G^3$, and $R^d$ are as defined for Formula I-C.

In one embodiment of Formula I, n is 1; Ring A is A-1; $R^2$ is selected from the group consisting of H, halogen, $CF_3$, $F_2CH$, $FCH_2$, MeO and methyl; X is O; Ring C is C-1; $R^4$ is $hetAr^4$ or $hetAr^5$; $R^3$ is $Ar^2$; $R^5$ is (1-6C)alkyl; $R^a$ and $R^b$ are H; $R^c$ is H; $R^1$ is (1-3C)alkoxy(1-3C)alkyl; $G^1$, $G^2$ and $G^3$ are $CR^x$; and $R^d$ is as defined for Formula I. In one embodiment, $R^d$ is as defined for Formula I-C.

In one embodiment of Formula I, n is 1; Ring A is A-1; $R^2$ is selected from the group consisting of H, halogen, $CF_3$, $F_2CH$, $FCH_2$, MeO and methyl; X is O; Ring C is C-1; $R^4$ is $hetAr^4$ or $hetAr^5$; $R^3$ is $Ar^2$; $R^5$ is (1-6C)alkyl; $R^a$ and $R^b$ are H; $R^c$ is H; $R^1$ is (1-3C)alkoxy(1-3C)alkyl; $G^1$ and $G^3$ are $CR^x$; $G^2$ is N; and $R^d$ is as defined for Formula I. In one embodiment, $R^d$ is as defined for Formula I-C.

In one embodiment of Formula I, n is 1; Ring A is A-1; $R^2$ is selected from the group consisting of H, halogen, $CF_3$, $F_2CH$, $FCH_2$, MeO and methyl; X is O; Ring C is C-1; $R^4$ is $hetAr^4$ or $hetAr^5$; $R^3$ is $Ar^2$; $R^5$ is (1-6C)alkyl; $R^a$ and $R^b$ are H; $R^c$ is H; $R^1$ is (1-3C)alkoxy(1-3C)alkyl; $G^1$ and $G^2$ are $CR^x$; $G^3$ is N; and $R^d$ is as defined for Formula I. In one embodiment, $R^d$ is as defined for Formula I-C.

In one embodiment of Formula I, n is 1; Ring A is A-1; $R^2$ is selected from the group consisting of H, halogen, $CF_3$, $F_2CH$, $FCH_2$, MeO and methyl; X is O; Ring C is C-1; $R^4$ is $hetAr^4$ or $hetAr^5$; $R^3$ is $Ar^2$; $R^5$ is (1-6C)alkyl; $R^a$ and $R^b$ are H; $R^c$ is H; $R^1$ is (1-3C)alkoxy(1-3C)alkyl; $G^1$ and $G^2$ are N; $G^3$ is $CR^x$; and $R^d$ is as defined for Formula I. In one embodiment, $R^d$ is as defined for Formula I-C.

In one embodiment of Formula I, n is 1; Ring A is A-1; $R^2$ is selected from the group consisting of H, halogen, $CF_3$, $F_2CH$, $FCH_2$, MeO and methyl; X is O; Ring C is C-1; $R^4$ is $hetAr^4$ or $hetAr^5$; $R^3$ is $Ar^2$; $R^5$ is (1-6C)alkyl; $R^a$ and $R^b$ are H; $R^c$ is H; $R^1$ is (1-3C)alkoxy(1-3C)alkyl; $G^2$ and $G^3$ are N; $G^1$ is $CR^x$; and $R^d$ is as defined for Formula I. In one embodiment, $R^d$ is as defined for Formula I-C.

In one embodiment of Formula I, n is 1; Ring A is A-1; $R^2$ is selected from the group consisting of H, halogen, $CF_3$, $F_2CH$, $FCH_2$, MeO and methyl; X is O; Ring C is C-1; $R^4$ is $hetAr^4$ or $hetAr^5$; $R^3$ is $Ar^2$; $R^5$ is (1-6C)alkyl; $R^a$ and $R^b$ are H; $R^c$ is H; $R^1$ is (1-3C)alkoxy(1-3C)alkyl; $G^1$ and $G^3$ are N; $G^2$ is $CR^x$; and $R^d$ is as defined for Formula I. In one embodiment, $R^d$ is as defined for Formula I-C.

In one embodiment of Formula I, Ring A is A-2, and $R^a$, $R^b$, X, Ring C, $R^3$, $R^4$, $R^5$, $R^{3a}$, $R^{4a}$ and $R^{5a}$ are as defined for Formula I. In one embodiment, $R^a$, $R^b$, X, Ring C, $R^3$, $R^4$, $R^5$, $R^{3a}$, $R^{4a}$ and $R^{5a}$ are as defined for Formula I-C.

In one embodiment of Formula I, Ring A is A-2; X is O; and $R^a$, $R^b$, Ring C, $R^3$, $R^4$, $R^5$, $R^{3a}$, $R^{4a}$ and $R^{5a}$ are as defined for Formula I. In one embodiment, $R^a$, $R^b$, Ring C, $R^3$, $R^4$, $R^5$, $R^{3a}$, $R^{4a}$ and $R^{5a}$ are as defined for Formula I-C.

In one embodiment of Formula I, Ring A is A-2; X is O; Ring C is C-1; and $R^a$, $R^b$, $R^3$, $R^4$, and $R^5$ are as defined for Formula I. In one embodiment, $R^a$, $R^b$, $R^3$, $R^4$, and $R^5$ are as defined for Formula I-C.

In one embodiment of Formula I, Ring A is A-2; X is O; Ring C is C-1; $R^4$ is $hetAr^4$ or $hetAr^5$; and $R^a$, $R^b$, $R^3$ and $R^5$ are as defined for Formula I. In one embodiment, $R^a$, $R^b$, $R^3$ and $R^5$ are as defined for Formula I-C.

In one embodiment of Formula I, Ring A is A-2; X is O; Ring C is C-1; $R^4$ is $hetAr^4$ or $hetAr^5$; $R^3$ is $Ar^2$; and $R^a$, $R^b$ and $R^5$ are as defined for Formula I. In one embodiment, $R^a$, $R^b$ and $R^5$ are as defined for Formula I-C.

In one embodiment of Formula I, Ring A is A-2; X is O; Ring C is C-1; $R^4$ is $hetAr^4$ or $hetAr^5$; $R^3$ is $Ar^2$; $R^5$ is (1-6C)alkyl; and $R^a$ and $R^b$ are as defined for Formula I. In one embodiment, $R^a$ and $R^b$ are as defined for Formula I-C.

In one embodiment of Formula I, Ring A is A-2; X is O; Ring C is C-1; $R^4$ is $hetAr^4$ or $hetAr^5$; $R^3$ is $Ar^2$; $R^5$ is (1-6C)alkyl; and $R^a$ and $R^b$ are H.

It will be appreciated that certain compounds according to the invention may contain one or more centers of asymmetry and may therefore be prepared and isolated in a mixture of isomers such as a racemic mixture, or in an enantiomerically pure form.

It will further be appreciated that the compounds of Formula I or their salts may be isolated in the form of solvates, and accordingly that any such solvate is included within the scope of the present invention. For example, compounds of Formula I can exist in unsolvated as well as solvated forms with pharmaceutically acceptable solvents such as water, ethanol, and the like.

The compounds of Formula I include pharmaceutically acceptable salts thereof. In addition, the compounds of Formula I also include other salts of such compounds which are not necessarily pharmaceutically acceptable salts, and which are useful as intermediates for preparing and/or purifying compounds of Formula I and/or for separating enantiomers of compounds of Formula I. Particular examples of salts include hydrochloride salts and trifluoroacetate salts.

In one embodiment, the compounds of Formula I include the free base form of compounds of Examples 1-132, or pharmaceutically acceptable salts thereof In one embodiment, the compounds of Formula I include the hydrochloride salts of compounds of Examples 1-132.

In one embodiment, the compounds of Formula I include the trifluoroacetate salts of compounds of Examples 1-132.

The term "pharmaceutically acceptable" indicates that the substance or composition is compatible chemically and/or toxicologically, with the other ingredients comprising a formulation, and/or the mammal being treated therewith.

The present invention also provides a process for the preparation of a compound of Formula I or a salt thereof as defined herein, which comprises:

(a) for a compound of Formula I where X is O, coupling a corresponding compound having the formula II

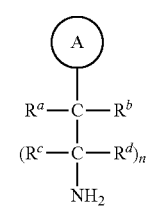

II with a corresponding compound having the formula III

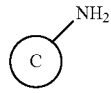
III in the presence carbonyldiimidazole or triphosgene and a base; or (b) for a compound of Formula I where X is S, coupling a corresponding compound having the formula II

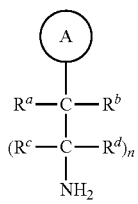
II with a corresponding compound having the formula III

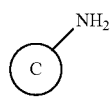
III in the presence di(1H-imidazol-2-yl)methanethione and a base; or (c) for a compound of Formula I where X is O, coupling a corresponding compound having the formula II

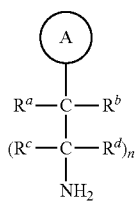
II with a corresponding compound having the formula IV

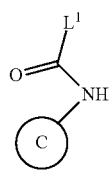
IV where $L^1$ is a leaving group, in the presence of a base; or (d) for a compound of Formula I where X is O, coupling a corresponding compound having the formula V

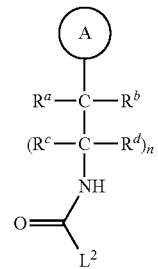
V where $L^2$ is a leaving group, with a corresponding compound having the formula III

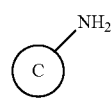
III in the presence of a base; or (e) for a compound of Formula I where X is O, activating a corresponding compound having the formula VI

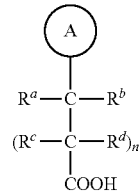
VI with diphenylphosphoryl azide followed by coupling the activated intermediate with a corresponding compound having the formula III

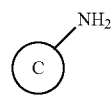
III in the presence a base; or (f) for a compound of Formula I where X is O, coupling a corresponding compound having the formula II

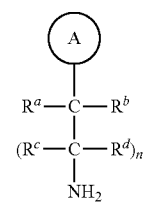
II with a corresponding compound having the formula VII

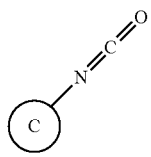

in the presence of a base; or (g) for a compound of Formula I where X is O, coupling a corresponding compound having the formula VIII

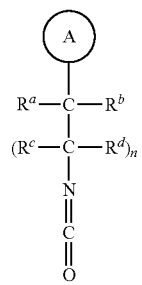

with a corresponding compound having the formula III

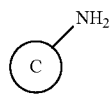

in the presence of a base; and optionally removing protecting groups and optionally preparing a pharmaceutically acceptable salt thereof.

In the above methods, the term "corresponding" means that the definitions for the "corresponding compound" are as defined for Formula I unless stated otherwise.

Referring to method (a), the base may be an amine base, such as triethylamine or diisopropylethylamine. Suitable solvents include dichloromethane, dichloroethane, THF, DMA and DMF. The reaction is conveniently performed at ambient temperature.

Referring to method (b), the base may be an amine base, such as triethylamine or diisopropylethylamine. Suitable solvents include dichloromethane, dichloroethane, THF, DMA and DMF. The reaction is conveniently performed at ambient temperature.

Referring to method (c), the leaving group may be, for example, phenoxy or 4-nitrophenoxy. The base may be an amine base, such as triethylamine or diisopropylethylamine. Suitable solvents include DMA, DMF and DCE. The reaction is conveniently performed at ambient temperature.

Referring to method (d), the leaving group may be, for example, phenoxy or 4-nitrophenoxy. The base may be an amine base, such as triethylamine or diisopropylethylamine. Suitable solvents include DCE, DMA and DMF. The reaction is conveniently performed at ambient temperature.

Referring to method (e), the base may be an amine base, such as triethylamine or diisopropylethylamine. Suitable solvents include toluene and DMF. The reaction is conveniently performed at elevated temperatures, for example the reflux temperature of the solvent.

Referring to methods (f) and (g), the base may be an amine base, such as triethylamine or diisopropylethylamine. Suitable solvents include DCM, DCE, DMF and THF. The reaction is conveniently performed at temperatures between about 0° C. and ambient temperature.

Amine groups in compounds described in any of the above methods may be protected with any convenient amine protecting group, for example as described in Greene & Wuts, eds., "Protecting Groups in Organic Synthesis", $2^{nd}$ ed. New York; John Wiley & Sons, Inc., 1991. Examples of amine protecting groups include acyl and alkoxycarbonyl groups, such as t-butoxycarbonyl (BOC) and [2-(trimethylsilyl)ethoxy]methyl (SEM). Likewise, carboxyl groups may be protected with any convenient carboxyl protecting group, for example as described in Greene & Wuts, eds., "Protecting Groups in Organic Synthesis", $2^{nd}$ ed. New York; John Wiley & Sons, Inc., 1991. Examples of carboxyl protecting groups include (1-6C)alkyl groups, such as methyl, ethyl and t-butyl. Alcohol groups may be protected with any convenient alcohol protecting group, for example as described in Greene & Wuts, eds., "Protecting Groups in Organic Synthesis", $2^{nd}$ ed. New York; John Wiley & Sons, Inc., 1991. Examples of alcohol protecting groups include benzyl, trityl, silyl ethers, and the like.

The compounds of the formulas II, IV, V, VI, VII and VIII are also provided as further aspects of the invention. In one embodiment, the compounds of the formulas II, IV, V, VI, VII and VIII are useful as intermediates for the preparation of compounds of Formula I.

Compounds of Formula I are useful in the treatment of pain, cancer, inflammation/inflammatory diseases, neurodegenerative diseases, certain infectious diseases, Sjogren's syndrome, endometriosis, diabetic peripheral neuropathy, prostatitis or pelvic pain syndrome.

In one embodiment, compounds of Formula I are useful for treating pain, including chronic and acute pain. For example, compounds of Formula I are useful in the treatment of multiple types of pain including inflammatory pain, neuropathic pain, and pain associated with cancer, surgery or bone fracture.

In one embodiment, compounds of Formula I are useful for treating acute pain. Acute pain, as defined by the International Association for the Study of Pain, results from disease, inflammation, or injury to tissues. This type of pain generally comes on suddenly, for example, after trauma or surgery, and may be accompanied by anxiety or stress, and is confined to a given period of time and severity. In some instances, it can become chronic.

In one embodiment, compounds of Formula I are useful for treating chronic pain. Chronic pain, as defined by the International Association for the Study of Pain, is widely believed to represent a disease in itself. It can be made much worse by environmental and psychological factors. Chronic pain persists over a longer period than acute pain and is resistant to most medical treatments, generally over 3 months or more. It can and often does cause severe problems for patients.

Compounds of Formula I are also useful for treating cancer. Particular examples include neuroblastoma, ovarian, pancreatic, colorectal and prostate cancer.

Compounds of Formula I are also useful for treating inflammation and certain infectious diseases. For example, compounds of Formula I may be used to treat interstitial cystitis (IC), painful bladder syndrome (PBS), urinary incontinence, asthma, atopic dermatitis, and psoriasis.

Compounds of Formula I are also useful for treating a neurodegenerative disease in a mammal, comprising administering to said mammal one or more compounds of Formula I or a pharmaceutically acceptable salt thereof in an amount effective to treat said neurodegenerative disease. In one embodiment, compounds of Formula I may also be used to treat demyelination and dysmyelination by promoting myelination, neuronal survival, and oligodendrocyte differentiation via blocking Sp35-TrkA interaction. In one embodiment, the neurodegenerative disease is multiple sclerosis. In one embodiment, the neurodegenerative disease is Parkinson's disease. In one embodiment, the neurodegenerative disease is Alzheimer's disease.

Compounds of Formula I are also useful for treating certain infectious diseases such as *Trypanosoma cruzi* infection in a mammal.

Compounds of Formula I are also useful for treating Sjogren's syndrome in a mammal.

Compounds of Formula I are also useful for treating endometriosis in a mammal.

Compounds of Formula I are also useful for treating diabetic peripheral neuropathy in a mammal.

Compounds of Formula I are also useful for treating prostatitis in a mammal.

Compounds of Formula I are also useful for treating pelvic pain syndrome in a mammal.

Compounds of Formula I are also useful in treating diseases related to an imbalance of the regulation of bone remodeling, such as osteoporosis, rheumatoid arthritis, and bone metastases.

As used herein, terms "treat" or "treatment" refer to therapeutic or palliative measures. Beneficial or desired clinical results include, but are not limited to, alleviation, in whole or in part, of symptoms associated with a disorder or condition, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

In certain embodiments, compounds of Formula I are useful for preventing diseases and disorders as defined herein. The term "preventing" as used herein means the prevention of the onset, recurrence or spread, in whole or in part, of the disease or condition as described herein, or a symptom thereof, and includes to the administration of a compound of Formula I prior to the onset of symptoms.

Accordingly, one embodiment of this invention provides a method of treating pain in a mammal, comprising administering to said mammal in need thereof one or more compounds of Formula I or a pharmaceutically acceptable salt thereof in an amount effective to treat said pain. In one embodiment, the pain is chronic pain. In one embodiment, the pain is acute pain. In one embodiment, the pain is inflammatory pain, neuropathic pain, or pain associated with cancer, surgery, or bone fracture.

Another embodiment of this invention provides a method of preventing pain in a mammal, comprising administering to said mammal in need thereof one or more compounds of Formula I or a pharmaceutically acceptable salt thereof in an amount effective to prevent said pain. In one embodiment, the pain is chronic pain. In one embodiment, the pain is acute pain. In one embodiment, the pain is inflammatory pain, neuropathic pain, or pain associated with cancer, surgery, or bone fracture.

Another embodiment of this invention provides a method of treating cancer in a mammal, comprising administering to said mammal in need thereof one or more compounds of Formula I or a pharmaceutically acceptable salt thereof in an amount effective to treat said cancer.

In one embodiment, provided herein is a method for treating a patient diagnosed with a cancer having a dysregulation of TrkA, comprising administering to the patient a therapeutically effective amount of a compound of the invention or a pharmaceutically acceptable salt thereof.

In one embodiment, the dysregulation of TrkA comprises overexpression of wild-type TrkA (autocrine activation).

In one embodiment, the dysregulation of TrkA comprises one or more chromosome translocations or inversions resulting in TrkA gene fusions. In one embodiment, the dysregulation is a result of genetic translocations in which the expressed protein is a fusion protein containing residues from non-TrkA and TrkA proteins, and at a minimum the TrkA kinase domain. In one embodiment, the TrkA fusion protein is LMNA-TrkA, TFG-TrkA, TPM3-TrkA, CD74-TrkA, NFASC-TrkA, MPRIP-TrkA, BCAN-TrkA, or TPR-TrkA, where:

LMNA=Prelamin-A/C;
TFG=TRK-fused gene protein;
TPM3=Tropomyosin alpha-3;
CD74=HLA class II histocompatibility antigen gamma chain;
NFASC=Neurofascin;
MPRIP=MPRIP protein;
BCAN=Brevican core protein; and
TPR=Nucleoprotein TPR In one embodiment, the dysregulation of TrkA comprises one or more deletions, insertions or mutations in the TrkA protein. In one embodiment, the dysregulation comprises a deletion of one or more residues from the TrkA protein, resulting in constitutive activity of TrkA kinase. In one embodiment the deletion includes deletion of residues 303-377 in TrkA Isoform 2.

In one embodiment, the dysregulation of TrkA comprises a splice variation in which the expressed protein is an alternatively spliced variant of TrkA having one or more residues deleted resulting in constitutive activity of TrkA kinase. In one embodiment, an alternatively spliced form of TrkA with constitutive activity has deletions of exons 8, 9, and 11 resulting in an expressed protein missing residues 192-284 and 393-398 relative to TrkA Isoform 2.

Cancers identified as having dysregulation of TrkA (see literature references below; also see www.cancer.gov and www.nccn.org) include:

(A) Cancers wherein the dysregulation of TrkA comprises one or more chromosome translocations or inversions resulting in TrkA gene fusions, including:

| Cancer | Literature reference(s) | Standard of Care |
|---|---|---|
| Non-Small Cell Lung Cancer | Vaishnavi et al. 2013: Nature Medicine 19, 1469-1472 | radiotherapy (e.g. radioiodide therapy, external-beam radiation, radium 223 therapy), chemotherapeutics as single agents (e.g. afatinib dimaleate, bevacizumab, carboplatin, cetuximab, cisplatin, crizotinib, erlotinib, gefitinib, |

-continued

| Cancer | Literature reference(s) | Standard of Care |
|---|---|---|
| | | gemcitabine, methotrexate, paclitaxel, pemetrexed) or combinations (e.g. carboplatin-paclitaxel, gemcitabine-paclitaxel, chemoradiation) |
| Papillary Thyroid Carcinoma | Caria et al. 2010: Cancer Genetics and Cytogenetics 203: 21-29 | Radiotherapies (e.g. radioiodide therapy, external-beam radiation) and chemotherapeutics (e.g. sorafenib, sunitinib, pazopanib) |
| Glioblastoma Multiforme | Frattini et al. 2013: Nature Genet. 45(10): 1141-9 | Chemotherapeutics (e.g. bevacizumab, everolimus, lomustine, temozolomide) |
| Colorectal Carcinoma | Martin-Zanca et al. 1986: Nature 319: 743 | Chemotherapeutics as single agents (aflibercept, bevacizumab, capecitabine, cetuximab, fluorouracil, irinotecan, leucovorin, oxaliplatin, panitumumab, regorafenib) or combinations (e.g. folfox, folfiri, capox, folfiri-bevacizumab, folfiri-cetuximab, xelox) |
| Melanoma | WO 2013/059740 A1 | Chemotherapeutics (e.g. aldesleukin, dabrafenib, dacarbazine, interferon alfa-2b, ipilimumab, peginterferon alfa-2b, trametinib, vemurafenib) |

(B) Cancers wherein the dysregulation of TrkA comprises one or more deletions, insertions or mutations in the TrkA protein, including:

| Cancer | Literature reference(s) | Standard of care |
|---|---|---|
| Acute Myeloid leukemia | Meyer 2007: Leukemia 21: 2171-2180 Reuther et al. 2000: Mol Cell Biol 20: 8655-8666 | Chemotherapeutics as single agents (e.g. arsenic trioxide, cyclophosphamide, cytarabine, daunorubicin, doxorubicin, vincristine) or combinations (e.g. ADE) |
| Large Cell Neuroendocrine Carcinoma | Marchetti et al 2008: Human Mutation 29(5): 609-616 | Radiotherapy (e.g. radioiodide therapy, external-beam radiation, radium 223 therapy) and/or chemotherapeutics (e.g. cisplatin, carboplatin, etoposide) |
| Neuroblastoma | Tacconelli et al 2004: Cancer Cell 6: 347 | Chemotherapeutics (e.g. cyclophosphamide, doxorubicin, vincristine) |

(C) Cancers driven by overexpression of wild-type TrkA (autocrine activation), including:

| Cancer | Literature Reference(s) | Standard of care |
|---|---|---|
| Prostate Carcinoma | Walch et al: Clinical & Experimental Metastasis 17: 307-314 Papatsoris et al 2007: Expert Opinion on Investigational Drugs 16(3): 303-309 | Radiotherapy (e.g. radium 223 therapy) or chemotherapeutics (e.g. abiraterone, cabazitaxel, degarelix, denosumab, docetaxel, enzalutamide, leuprolide, prednisone, sipuleucel-T) |
| Neuroblastoma | Van Noesel et al 2004: Gene 325: 1-15 | Chemotherapeutics (e.g. cyclophosphamide, doxorubicin, vincristine) |
| Pancreatic Carcinoma | Zhang et al 2005: Oncology Reports 14: 161-171 | Chemotherapeutics as single agents (e.g. erlotinib, fluorouracil, gemcitabine, mitomycin C) or combinations (e.g. gemcitabine-oxaliplatin) |
| Melanoma | Truzzi et al 2008: Journal of Investigative Dermatology 128(8): 2031 | Chemotherapeutics (e.g. aldesleukin, dabrafenib, dacarbazine, interferon alfa-2b, ipilimumab, peginterferon alfa-2b, trametinib, vemurafenib) |

-continued

| Cancer | Literature Reference(s) | Standard of care |
|---|---|---|
| Head and Neck Squamous Cell Carcinoma | Kolokythas et al 2010: Journal of Oral and Maxillofacial Surgery 68(6): 1290-1295 | Radiotherapy and/or chemotherapeutics (e.g. bleomycin, cetuximab, cisplatin, docetaxel, fluorouracil, methotrexate) |
| Gastric Carcinoma | Ni et al 2012: Asian Pacific Journal of Cancer Prevention 13: 1511 | Chemotherapeutics (e.g. docetaxel, doxorubicin, fluorouracil, mitomycin C, trastuzumab) |

In one embodiment, provided herein is a method for treating a patient diagnosed with a cancer having a dysregulation of TrkA, comprising administering to the patient a therapeutically effective amount of a compound of the invention, or a pharmaceutically acceptable salt thereof, wherein the cancer is selected from non-small cell lung cancer, papillary thyroid carcinoma, glioblastoma multiforme, acute myeloid leukemia, colorectal carcinoma, large cell neuroendocrine carcinoma, prostate cancer, neuroblastoma, pancreatic carcinoma, melanoma, head and neck squamous cell carcinoma and gastric carcinoma.

In one embodiment, the compounds of the present invention are useful for treating cancer in combination with one or more additional therapeutic agents or therapies that work by the same or a different mechanism of action.

In one embodiment, the additional therapeutic agent(s) is selected from receptor tyrosine kinase-targeted therapeutic agents, including cabozantinib, crizotinib, erlotinib, gefitinib, imatinib, lapatinib, nilotinib, pazopanib, pertuzumab, regorafenib, sunitinib, and trastuzumab.

In one embodiment, the additional therapeutic agent(s) is selected from signal transduction pathway inhibitors, including Ras-Raf-MEK-ERK pathway inhibitors (e.g. sorafenib, trametinib, vemurafenib), PI3K-Akt-mTOR-S6K pathway inhibitors (e.g. everolimus, rapamycin, perifosine, temsirolimus) and modulators of the apoptosis pathway (e.g. obataclax).

In one embodiment, the additional therapeutic agent(s) is selected from cytotoxic chemotherapeutics, including arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, and vincristine.

In one embodiment, the additional therapeutic agent(s) is selected from angiogenesis-targeted therapies, including aflibercept and bevacizumab.

In one embodiment, the additional therapeutic agent(s) is selected from immune-targeted agents, including aldesleukin, ipilimumab, lambrolizumab, nivolumab, sipuleucel-T.

In one embodiment, the additional therapeutic agent(s) is selected from agents active against the TrkA pathway, including NGF-targeted biopharmaceuticals such as NGF antibodies, and panTrk inhibitors.

In one embodiment, the additional therapeutic agent or therapy is radiotherapy, including radioiodide therapy, external-beam radiation and radium 223 therapy.

In one embodiment, the additional therapeutic agent(s) includes any one of the above listed therapies or therapeutic agents which are standards of care in cancers wherein the cancer has a dysregulation of TrkA.

In one embodiment, provided herein is a method of treating cancer in a patient, comprising administering to said patient a compound of the invention or a pharmaceutically acceptable salt thereof, in combination with at least one additional therapy or therapeutic agent selected from radiotherapy (e.g. radioiodide therapy, external-beam radiation, radium 223 therapy), cytotoxic chemotherapeutics (e.g. arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, vincristine), tyrosine kinase targeted-therapeutics (e.g. afatinib, cabozantinib, cetuximab, crizotinib, dabrafenib, erlotinib, gefitinib, imatinib, lapatinib, nilotinib, pazopanib, panitumumab, pertuzumab, regorafenib, sunitinib, trastuzumab), apoptosis modulators and signal transduction inhibitors (e.g. everolimus, perifosine, rapamycin, sorafenib, temsirolimus, trametinib, vemurafenib), immune-targeted therapies (e.g. aldesleukin, interferon alfa-2b, ipilimumab, lambrolizumab, nivolumab, prednisone, sipuleucel-T) and angiogenesis-targeted therapies (e.g. aflibercept, bevacizumab), wherein the amount of the compound of the invention or a pharmaceutically acceptable salt thereof is, in combination with the additional therapy or therapeutic agent, is effective in treating said cancer. These additional therapeutic agents may be administered with one or more compounds of the invention as part of the same or separate dosage forms, via the same or different routes of administration, and on the same or different administration schedules according to standard pharmaceutical practice known to one skilled in the art.

Also provided herein is (i) a pharmaceutical combination for treating cancer in a patient in need thereof, which comprises (a) a compound of the invention or a pharmaceutically acceptable salt thereof, (b) an additional therapeutic agent and (c) optionally at least one pharmaceutically acceptable carrier for simultaneous, separate or sequential use for the treatment of a tumor disease, wherein the amounts of the compound or salt thereof and of the additional therapeutic agent are together effective in treating said cancer; (ii) a pharmaceutical composition comprising such a combination; (iii) the use of such a combination for the preparation of a medicament for the treatment of cancer; and (iv) a commercial package or product comprising such a combination as a combined preparation for simultaneous, separate or sequential use; and to a method of treatment of cancer a patient in need thereof.

In one embodiment, the combination therapy is for treating a cancer is selected from non-small cell lung cancer, papillary thyroid carcinoma, glioblastoma multiforme, acute myeloid leukemia, colorectal carcinoma, large cell neuroendocrine carcinoma, prostate cancer, neuroblastoma, pancreatic carcinoma, melanoma, head and neck squamous cell carcinoma and gastric carcinoma.

Another embodiment of this invention provides a method of treating inflammation or an inflammatory disease or disorder in a mammal, comprising administering to said mammal in need thereof one or more compounds of Formula I or a pharmaceutically acceptable salt thereof in an amount effective to treat said inflammation. In one embodiment, the inflammatory disease is inflammatory lung diseases (such as asthma), interstitial cystitis, bladder pain syndrome, inflammatory bowel diseases (including ulcerative colitis and Crohn's disease), and inflammatory skin diseases such as atopic dermatitis.

In one embodiment, the method of treating inflammation or an inflammatory disease or disorder comprises administering a compound of the invention in combination with one or more additional agents. Examples of additional agents include anti-TNF treatments (for example monoclonal antibody such as infliximab (Remicade), adalimumab (Humira), certolizumab pegol (Cimzia), and golimumab (Simponi), or a circulating receptor fusion protein such as etanercept (Enbrel)), antimetabolite and antifolate drug (for example Methotrexate), or targeted kinase inhibitors (for example JAK family inhibitors Ruxolitinib, Tofacitinib, CYT387, Lestaurtinib, Pacritinib and TG101348).

Another embodiment of this invention provides a method of treating *Trypanosoma cruzi* infection in a mammal, comprising administering to said mammal in need thereof one or more compounds of Formula I or a pharmaceutically acceptable salt thereof in an amount effective to treat said *Trypanosoma cruzi* infection.

Another embodiment of this invention provides a method of treating Sjogren's syndrome in a mammal, comprising administering to said mammal in need thereof one or more compounds of Formula I or a pharmaceutically acceptable salt thereof in an amount effective to treat said syndrome.

Another embodiment of this invention provides a method of treating endometriosis in a mammal, comprising administering to said mammal in need thereof one or more compounds of Formula I or a pharmaceutically acceptable salt thereof in an amount effective to treat said endometriosis.

Another embodiment of this invention provides a method of treating diabetic peripheral neuropathy in a mammal, comprising administering to said mammal in need thereof one or more compounds of Formula I or a pharmaceutically acceptable salt thereof in an amount effective to treat said diabetic peripheral neuropathy.

Another embodiment of this invention provides a method of treating prostatitis in a mammal, comprising administering to said mammal in need thereof one or more compounds of Formula I or a pharmaceutically acceptable salt thereof in an amount effective to treat said prostatitis.

Another embodiment of this invention provides a method of treating pelvic pain syndrome in a mammal, comprising administering to said mammal in need thereof one or more compounds of Formula I or a pharmaceutically acceptable salt thereof in an amount effective to treat said pelvic pain syndrome.

Another embodiment of this invention provides a method of treating a neurodegenerative disease in a mammal, comprising administering to said mammal in need thereof one or more compounds of Formula I or a pharmaceutically acceptable salt thereof in an amount effective to treat said neurodegenerative disease.

Another embodiment of this invention provides a method of treating diseases related to an imbalance of the regulation of bone remodeling in a mammal, comprising administering to said mammal in need thereof one or more compounds of Formula I or a pharmaceutically acceptable salt thereof in an amount effective to treat said disease. In one embodiment, the disease is osteoporosis, rheumatoid arthritis, and bone metastases.

In one embodiment, the method for treating diseases related to an imbalance of the regulation of bone remodeling in a mammal comprises administering a TrkA inhibitor of the invention in combination with one or more additional therapeutic agents or therapies. Examples of additional therapeutic agents or therapies include anti-TNF treatments (for example monoclonal antibody such as infliximab (Remicade), adalimumab (Humira), certolizumab pegol (Cimzia), and golimumab (Simponi), or with a circulating receptor fusion protein such as etanercept (Enbrel)), antimetabolite and antifolate drug (for example Methotrexate), or targeted kinase inhibitors (for example JAK family inhibitors Ruxolitinib, Tofacitinib, CYT387, Lestaurtinib, Pacritinib and TG101348).

As used herein, an "effective amount" means an amount of compound that, when administered to a mammal in need of such treatment, is sufficient to (i) treat a particular disease, condition, or disorder which can be treated with a compound of Formula I, or (ii) attenuate, ameliorate, or eliminate one or more symptoms of the particular disease, condition, or disorder described herein.

The amount of a compound of Formula I that will correspond to such an amount will vary depending upon factors such as the particular compound, disease condition and its severity, the identity (e.g., weight) of the mammal in need of treatment, but can nevertheless be routinely determined by one skilled in the art.

As used herein, the term "mammal" refers to a warm-blooded animal that has or is at risk of developing a disease described herein and includes, but is not limited to, guinea pigs, dogs, cats, rats, mice, hamsters, and primates, including humans.

The compounds of the present invention can be used in combination with one or more additional therapeutic agents that work by the same or a different mechanism of action. Examples of additional therapeutic agents include anti-inflammatory compounds, steroids (e.g., dexamethasone, cortisone and fluticasone), analgesics such as NSAIDs (e.g., aspirin, ibuprofen, indomethacin, and ketoprofen), and opioids (such as morphine), and chemotherapeutic agents.

Also provided herein is a pharmaceutical combination comprising an effective amount of: (a) at least one compound of Formula I; and (b) at least one additional therapeutic agent selected from anti-inflammatory compounds, steroids (e.g., dexamethasone, cortisone and fluticasone), analgesics such as NSAIDs (e.g., aspirin, ibuprofen, indomethacin, and ketoprofen), and opioids (such as morphine), for use in the treatment of pain in a mammal, wherein (a) and (b) can be in separate dosage forms or in the same dosage form.

The term "pharmaceutical combination" as used herein refers to a pharmaceutical therapy resulting from the mixing or combining of more than one active ingredient and includes both fixed and non-fixed combinations of the active ingredients. The term "fixed combination" means that at least one of the compounds of Formula I, and at least one additional therapeutic agent are both administered to a patient simultaneously in the form of a single entity or dosage. The term "non-fixed combination" means that at least one of the compounds of Formula I, and at least one additional therapeutic agent, are administered to a patient as separate entities either simultaneously or sequentially with variable intervening time limits, wherein such administration provides effective levels of the two or more compounds in the body of the patient. These also apply to cocktail therapies, e.g. the administration of three or more active ingredients.

Also provided herein is a method of treating pain in a mammal, comprising co-administering to a mammal in need thereof an effective amount of: (a) at least one compound of Formula I; and (b) at least one additional therapeutic agent selected from anti-inflammatory compounds, steroids (e.g., dexamethasone, cortisone and fluticasone), analgesics such as NSAIDs (e.g., aspirin, ibuprofen, indomethacin, and ketoprofen), opioids (such as morphine), calcitonin gene-related peptide receptor antagonists, subtype-selective ion channel modulators, anticonvulsants (for example Pregabalin and gabapentin), dual serotonin-norepinephrin reuptake inhibitors (for example duloxetine, venlafaxine and milnacipran), and tricyclic antidepressants (such as amitriptyline, nortriptyline and desipramine).

The term "co-administering" is meant to encompass administration of the selected therapeutic agents to a single patient, and is intended to include treatment regimens in which the agents are administered by the same or different route of administration or at the same or different times. This term encompasses administration of two or more agents to a mammal so that both agents and/or their metabolites are present in the mammal at the same time. It includes simultaneous administration in separate compositions, administration at different times in separate compositions, and/or administration in a composition in which both agents are present. In some embodiments, the compound(s) of the invention and the other therapeutic agent(s) are administered in a single composition. In some embodiments, compound(s) of the invention and the other agent(s) are admixed in the composition.

Also provided herein is a medicament containing a compound of Formula I for treatment of pain in a mammal in combination with an additional therapeutic agent selected from anti-inflammatory compounds, steroids (e.g., dexamethasone, cortisone and fluticasone), analgesics such as NSAIDs (e.g., aspirin, ibuprofen, indomethacin, and ketoprofen), and opioids (such as morphine).

Also provided herein is a medicament containing a therapeutic agent selected from anti-inflammatory compounds, steroids (e.g., dexamethasone, cortisone and fluticasone), analgesics such as NSAIDs (e.g., aspirin, ibuprofen, indomethacin, and ketoprofen), and opioids (such as morphine) for treatment of pain in a mammal in combination with a compound of Formula I.

Compounds of the invention may be administered by any convenient route, e.g. into the gastrointestinal tract (e.g. rectally or orally), the nose, lungs, musculature or vasculature, or transdermally or dermally. Compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. If parenteral administration is desired, the compositions will be sterile and in a solution or suspension form suitable for injection or infusion. Such compositions form a further aspect of the invention.

Another formulation may be prepared by mixing a compound described herein and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound described herein or pharmaceutical composition thereof) or aid in the manufacturing of the pharmaceutical product (i.e., medicament).

Accordingly, another aspect of the present invention provides a pharmaceutical composition, which comprises a compound of Formula I or a pharmaceutically acceptable salt thereof, as defined hereinabove, together with a pharmaceutically acceptable diluent or carrier.

According to another embodiment, the present invention provides a compound of Formula I or a pharmaceutically acceptable salt thereof, for use in the treatment of pain in a mammal. In one embodiment, the pain is chronic pain. In one embodiment the pain is acute pain. In one embodiment, the pain is inflammatory pain, neuropathic pain, or pain associated with cancer, surgery, or bone fracture.

According to another embodiment, the present invention provides a compound of Formula I or a pharmaceutically acceptable salt thereof, for use in the treatment of cancer in a mammal.

In another embodiment, the present invention provides a compound of Formula I or a pharmaceutically acceptable salt thereof, for use in the treatment of inflammation or an inflammatory disease or disorder in a mammal. In one embodiment, the inflammatory disease is inflammatory lung diseases (such as asthma), interstitial cystitis, bladder pain syndrome, inflammatory bowel diseases (including ulcerative colitis and Crohn's disease), and inflammatory skin diseases such as atopic dermatitis.

In another embodiment, the present invention provides a compound of Formula I or a pharmaceutically acceptable salt thereof, for use in the treatment of infectious diseases, for example *Trypanosoma cruzi* infection, in a mammal.

In another embodiment, the present invention provides a compound of Formula I or a pharmaceutically acceptable salt thereof, for use in the treatment of Sjogren's syndrome in a mammal.

In another embodiment, the present invention provides a compound of Formula I or a pharmaceutically acceptable salt thereof, for use in the treatment of endometriosis in a mammal.

In another embodiment, the present invention provides a compound of Formula I or a pharmaceutically acceptable salt thereof, for use in the treatment of diabetic peripheral neuropathy in a mammal, In another embodiment, the present invention provides a compound of Formula I or a pharmaceutically acceptable salt thereof, for use in the treatment of prostatitis in a mammal, In another embodiment, the present invention provides a compound of Formula I or a pharmaceutically acceptable salt thereof, for use in the treatment of pelvic pain syndrome in a mammal, In another embodiment, the present invention provides a compound of Formula I or a pharmaceutically acceptable salt thereof, for use in the treatment of a neurodegenerative disease in a mammal.

According to a further aspect, the present invention provides the use of a compound of Formula I or a pharmaceutically acceptable salt thereof, in the manufacture of a medicament for the treatment of a condition selected from pain, cancer, inflammation, neurodegenerative disease or *Trypanosoma cruzi* infection. In one embodiment, the condition is chronic pain. In one embodiment, the condition is acute pain. In one embodiment, the pain is inflammatory pain, neuropathic pain, or pain associated with cancer, surgery, or bone fracture. In one embodiment, the condition is cancer. In one embodiment, the condition is inflammation. In one embodiment, the condition is a neurodegenerative disease. In one embodiment, the condition is *Trypanosoma cruzi* infection. In one embodiment, the condition is Sjogren's syndrome. In one embodiment, the condition is endometriosis. In one embodiment, the condition is diabetic peripheral neuropathy. In one embodiment, the condition is prostatitis. In one embodiment, the condition is pelvic pain syndrome.

EXAMPLES

The following examples illustrate the invention. In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel or C-18 reverse phase column, or on a silica SepPak cartridge (Waters).

Biological Assays

Example A-1

TrkA Kinase Binding Assay

TrkA binding activity was determined in a TrkA LanthaScreen™ Eu Kinase Binding Assay. 5 nM His-tagged recombinant human TrkA (6HIS tagged cytoplasmic domain from Invitrogen, Catalog No. PV3144) was incubated with 4 nM Alexa-Fluor® Tracer 236 (Invitrogen Cat. No. PV5592), 2 nM biotinylated anti-His (Invitrogen Cat. No. PV6090), and 2 nM europium-labeled Streptavidin (Invitrogen Cat. No. PV5899), in buffer (25 mM MOPS, pH 7.5, 5 mM $MgCl_2$, 0.005% Triton X-100). Three fold serial dilutions of compounds of the invention in DMSO were added to a final percentage of 2% DMSO. After 60-minute incubation at 22° C., the reaction was measured using the EnVision mutlimode plate reader (PerkinElmer) via TR-FRET dual wavelength detection at 615 nM and 665 nM. The percent of control was calculated using a ratiometric emission factor. The $IC_{50}$ values were determined by fitting a four parameter model to the percent of control data.

Table A provides averaged $IC_{50}$ values for compounds of the invention when tested in the assay of Example A, where A represents an averaged $IC_{50}$ value <100 nM; B represents an averaged $IC_{50}$ value from 100 to 1,000 nM; and C represents an average 1050 value above 1000 nM.

TABLE A

| Example # | TrkA Enzyme $IC_{50}$ (nM) |
| --- | --- |
| 1 | A |
| 2 | A |
| 3 | A |
| 4 | A |
| 5 | A |
| 6 | A |
| 7 | A |
| 8 | A |
| 9 | A |
| 10 | A |
| 11 | A |
| 12 | A |
| 13 | A |
| 14 | A |
| 15 | A |
| 16 | B |
| 17 | A |
| 18 | B |
| 19 | A |
| 20 | A |
| 21 | A |
| 22 | B |
| 23 | A |
| 24 | B |
| 25 | A |
| 26 | B |
| 27 | B |
| 28 | B |
| 29 | B |
| 30 | B |
| 31 | A |
| 32 | B |
| 33 | A |
| 34 | A |
| 35 | A |
| 36 | A |
| 37 | B |
| 38 | A |
| 39 | B |
| 40 | B |
| 41 | B |
| 42 | A |
| 43 | B |
| 44 | A |
| 45 | B |
| 46 | A |
| 47 | A |
| 48 | B |
| 49 | B |
| 50 | B |
| 51 | A |
| 52 | A |
| 53 | A |
| 54 | A |
| 55 | A |
| 56 | A |
| 57 | A |
| 58 | A |
| 59 | A |
| 60 | A |
| 61 | A |
| 62 | A |
| 63 | A |
| 64 | A |
| 65 | A |
| 66 | A |
| 67 | A |
| 68 | B |
| 69 | A |
| 70 | A |

TABLE A-continued

| Example # | TrkA Enzyme IC$_{50}$ (nM) |
|---|---|
| 71 | A |
| 72 | A |
| 73 | A |
| 74 | A |
| 75 | A |
| 76 | A |
| 77 | B |
| 78 | A |
| 79 | A |
| 80 | A |
| 81 | A |
| 82 | A |
| 83 | A |
| 84 | A |
| 85 | A |
| 86 | A |
| 87 | A |
| 88 | A |
| 89 | A |
| 90 | A |
| 91 | A |
| 92 | A |
| 93 | A |
| 94 | A |
| 95 | A |
| 96 | A |
| 97 | A |
| 98 | A |
| 99 | A |
| 100 | A |
| 101 | A |
| 102 | A |
| 103 | A |
| 104 | A |
| 105 | A |
| 106 | A |
| 107 | A |
| 108 | A |
| 109 | A |
| 110 | A |
| 111 | A |
| 112 | A |
| 113 | A |
| 114 | A |
| 115 | A |
| 116 | A |
| 117 | A |
| 118 | B |
| 119 | B |
| 120 | A |
| 121 | A |
| 122 | A |
| 123 | A |
| 124 | A |
| 125 | A |
| 126 | A |
| 127 | B |
| 128 | B |
| 129 | A |
| 130 | A |
| 131 | A |
| 132 | C |

Example A-2 p38 Kinase Binding Assay p38α binding activity was determined in a p38α LanthaScreen™ Eu Kinase Binding Assay. 5 nM of inactive, GST-tagged recombinant human p38α (GST-tagged cytoplasmic domain from Invitrogen, Catalog No. PV3305) was incubated with 5 nM Alexa-Fluor® Tracer 199 (Invitrogen Cat. No. PV5830), and 2 nM europium labeled anti-GST antibody (Invitrogen Cat. No. PV5594), in buffer (25 mM [Na] HEPES pH 7.3, 10 mM MgCl$_2$, 100 µM NaVO$_4$). Three fold serial dilutions of compounds of the invention in DMSO were added to a final percentage of 2% DMSO. After 60-minute incubation at 22° C., the reaction was measured using the EnVision multimode plate reader (PerkinElmer) via TR-FRET dual wavelength detection at 615 nM and 665 nM. The percent of control was calculated using a ratiometric emission factor. The IC$_{50}$ values were determined by fitting a four parameter model to the percent of control data. The compounds of Examples 1-132 were tested in this assay, and all compounds were found to be 1000 fold more potent against TrkA than p38α.

Example B

Off-Target Kinase Profiling

Representative compounds of the invention (Examples 33 and 10) were tested for off-target kinase activity at a concentration of 10 µM by Millipore, Inc. in their KinaseProfiler™ service against all the kinases available in their full kinase panel. Compounds were run in duplicate at a concentration of ATP near the Km for each individual kinase according to Millipore's specifications. The results are shown in Table B. Data are reported as percent of control (POC) and are the average of the two replicates.

In the KinaseProfiler™ the representative compounds showed remarkable and unexpected selectivity for inhibiting TrkA and TrkB versus other kinases in the panel. In fact, the compounds were largely inactive against off-target kinases at a concentration of 10 µM, and thus would not be expected to inhibit off-target kinases at therapeutic doses in mammals. The ability of compounds of the invention to selectively inhibit the Trk pathway without inhibiting other off-target kinases could translate into drug profiles that are essentially free of side-effects related to inhibition of off-target kinases. Such a drug profile would represent a safer approach to treating pain, inflammation, cancer and certain skin diseases than has been previously reported.

TABLE B

| Kinase | Example 33 Avg POC | Example 10 Avg POC |
|---|---|---|
| Abl2 | 139.5 | 95 |
| Abl-P | 170.5 | 97 |
| AKT1 | 132 | 105 |
| AKT2 | 199 | 142 |
| AKT3 | 124 | 102.5 |
| ALK | 116 | 102.5 |
| ALK4 | 106 | 111.5 |
| AMPK(A1/B1/G1) | 147.5 | 111.5 |
| ARK5 | 85.5 | 87 |
| AURKA | 112 | 90 |
| Axl | 117 | 104.5 |
| BLK_m | 119 | 97.5 |
| Bmx | 127.5 | 100 |
| BrSK1 | 119 | 86.5 |
| BrSK2 | 145.5 | 95 |
| BTK | 125 | 117.5 |
| CAMK1 | 111.5 | 92 |
| CAMK1d | 111.5 | 81 |
| CAMK2b | 96 | 94 |
| CAMK2d | 118 | 126.5 |
| CAMK2g | 112 | 101 |
| CAMK4 | 149 | 144.5 |
| CDK1/cyclinB | 99 | 92 |
| CDK2/cyclinA | 103.5 | 98.5 |
| CDK2/cyclinE | 115.5 | 93 |
| CDK3/cyclinE | 98.5 | 90.5 |
| CDK5/p25 | 100.5 | 107.5 |

TABLE B-continued

| Kinase | Example 33 Avg POC | Example 10 Avg POC |
|---|---|---|
| CDK5/p35 | 108.5 | 97 |
| CDK6/cyclinD3 | 108 | 102 |
| CDK7/cyclinH/MAT1 | 113.5 | 96.5 |
| CDK9/cyclinT1 | 108 | 98 |
| CHK1 | 97 | 102.5 |
| CHK2 | 138 | 93 |
| CK1_y | 97.5 | 97 |
| CK1delta | 127.5 | 85.5 |
| CK1gamma1 | 105.5 | 79 |
| CK1gamma2 | 113.5 | 69.5 |
| CK1gamma3 | 119.5 | 39 |
| CK2 | 94.5 | 94.5 |
| CK2alpha2 | 99.5 | 109 |
| CLK2 | 131.5 | 97.5 |
| CLK3 | 102 | 104.5 |
| c-RAF | 94.5 | 90 |
| CSK | 127.5 | 132 |
| DAPK1 | 141.5 | 98 |
| DAPK2 | 109.5 | 105 |
| DAPK3 | 113 | 93.5 |
| DCAMKL2 | 254.5 | 96.5 |
| DDR2 | 111 | 105.5 |
| DMPK | 104 | 101.5 |
| DRAK1 | 141.5 | 92.5 |
| DYRK2 | 91.5 | 92.5 |
| eEF-2K | 169.5 | 109.5 |
| EGFR | 116.5 | 107.5 |
| EphA1 | 90 | 98 |
| EphA2 | 126.5 | 103 |
| EphA3 | 116.5 | 119 |
| EphA4 | 120 | 105.5 |
| EphA5 | 123 | 114 |
| EphA7 | 94.5 | 92.5 |
| EphA8 | 123 | 97.5 |
| EphB1 | 133 | 131 |
| EphB2 | 112.5 | 103 |
| EphB3 | 69 | 100 |
| EphB4 | 128 | 140.5 |
| ErbB4 | 130.5 | 108.5 |
| ERK1 | 95.5 | 89.5 |
| ERK2 | 117 | 104 |
| FAK | 99 | 96.5 |
| FAK2 | 108 | 96 |
| Fer | 90.5 | 96.5 |
| Fes | 109 | 90 |
| FGFR1 | 96 | 68 |
| FGFR2 | 109.5 | 103.5 |
| FGFR3 | 116 | 104 |
| FGFR4 | 201.5 | 118 |
| Fgr | 121 | 97 |
| Flt1 | 91 | 88 |
| Flt3 | 78.5 | 54 |
| Flt4 | 94 | 88 |
| Fms | 88.5 | 83.5 |
| Fyn | 113 | 103 |
| GRK5 | 82 | 81.5 |
| GRK6 | 99 | 97.5 |
| GRK7 | 103 | 105 |
| GSK3alpha | 161 | 105 |
| GSK3beta | 136.5 | 115 |
| Haspin | 109 | 80.5 |
| Hck | 140 | 67 |
| HIPK1 | 115.5 | 100.5 |
| HIPK2 | 95 | 102.5 |
| HIPK3 | 102 | 95.5 |
| IGF-1R | 44 | 82 |
| IGF-1R Activated | 86.5 | 93.5 |
| IKKalpha | 137.5 | 112.5 |
| IKKbeta | 120.5 | 104.5 |
| IR | 68 | 90 |
| IR Activated | 103.5 | 99 |
| IRAK1 | 113 | 101 |
| IRAK4 | 109.5 | 122.5 |
| IRR | 96.5 | 96 |
| ITK | 124 | 112 |
| JAK2 | 130 | 106.5 |
| JAK3 | 114 | 94.5 |
| JNK1alpha1 | 103 | 98 |
| JNK2alpha2 | 89.5 | 81.5 |
| JNK3 | 135 | 74 |
| KDR | 139.5 | 97.5 |
| KIT | 94 | 102 |
| Lck | 93 | 75.5 |
| LIMK1 | 91.5 | 92 |
| LKB1 | 90 | 89.5 |
| LOK | 93.5 | 101 |
| Lyn | 104.5 | 86 |
| MAP3K5 | 100 | 99 |
| MAP4K2 | 115.5 | 95.5 |
| MAPKAP-K2 | 146 | 106 |
| MAPKAP-K3 | 119.5 | 98.5 |
| MAPKAP-K5 | 97.5 | 92 |
| MARK1 | 109.5 | 97 |
| MARK2 | 103.5 | 98.5 |
| MEK1 | 117 | 121 |
| MELK | 114 | 83.5 |
| Mer | 96.5 | 87.5 |
| Met | 122.5 | 117 |
| MINK | 100 | 139.5 |
| MKK4_m | 137 | 125.5 |
| MKK6 | 143 | 131.5 |
| MKK7beta | 159 | 132.5 |
| MKNK2 | 101.5 | 98 |
| MLK1 | 105.5 | 100.5 |
| MRCKalpha | 147 | 122 |
| MRCKbeta | 116.5 | 108.5 |
| MSK1 | 147 | 88.5 |
| MSK2 | 207.5 | 110.5 |
| MSSK1 | 138.5 | 112 |
| MST1 | 87.5 | 87.5 |
| MST2 | 98 | 97.5 |
| MST3 | 126.5 | 99 |
| mTOR | 99 | 75 |
| mTOR/FKBP12 | 109.5 | 97.5 |
| MuSK | 94.5 | 95 |
| MYLK | 100.5 | 88 |
| NEK11 | 108 | 102 |
| NEK2 | 96 | 98 |
| NEK3 | 115.5 | 97.5 |
| NEK6 | 115.5 | 92.5 |
| NEK7 | 116.5 | 110 |
| NLK | 121 | 107 |
| p38alpha | 88.5 | 91.5 |
| p38beta | 111.5 | 101.5 |
| p38delta | 85 | 81 |
| p38gamma | 107.5 | 102.5 |
| p70S6K | 377 | 111 |
| PAK2 | 89.5 | 88 |
| PAK4 | 108.5 | 102.5 |
| PAK5 | 144.5 | 96.5 |
| PAK6 | 147.5 | 95.5 |
| PASK | 205 | 70 |
| PDGFRalpha | 126.5 | 102 |
| PDGFRbeta | 166.5 | 106 |
| PDK1 | 126.5 | 120.5 |
| PhKgamma2 | 116 | 118 |
| Pim-1 | 138 | 101.5 |
| Pim-2 | 146 | 118 |
| Pim-3 | 103 | 105.5 |
| PKAC-alpha | 139.5 | 132 |
| PKCalpha | 104.5 | 100.5 |
| PKCbetaI | 111.5 | 104.5 |
| PKCbetaII | 96 | 94 |
| PKCdelta | 93 | 91.5 |
| PKCepsilon | 92 | 83.5 |
| PKCeta | 98 | 86.5 |
| PKCgamma | 98 | 101 |
| PKCiota | 64 | 65.5 |
| PKCtheta | 112.5 | 94 |
| PKCzeta | 99 | 92.5 |
| PKD1 | 94 | 94.5 |
| PKD2 | 106 | 106 |
| Plk1 | 93 | 84 |
| Plk2 | 102 | 101 |

TABLE B-continued

| Kinase | Example 33 Avg POC | Example 10 Avg POC |
|---|---|---|
| Plk3 | 109.5 | 111 |
| PRK2 | 106 | 88.5 |
| PRKG1alpha | 122.5 | 113 |
| PRKG1beta | 121 | 107.5 |
| PrKX | 146.5 | 73.5 |
| PTK5 | 92.5 | 87.5 |
| PTK6 | 118.5 | 106.5 |
| Ret | 91 | 89.5 |
| RIPK2 | 98.5 | 99 |
| ROCK-I | 120.5 | 114 |
| ROCK-II | 107.5 | 98 |
| Ron | 95.5 | 100.5 |
| Ros | 100.5 | 97.5 |
| Rse | 110 | 103 |
| Rsk1 | 119.5 | 96.5 |
| Rsk2 | 146 | 129.5 |
| Rsk3 | 103 | 101 |
| Rsk4 | 95 | 87 |
| SGK1 | 279 | 96 |
| SGK2 | 208 | 80.5 |
| SGK3 | 150 | 92.5 |
| SIK | 139 | 104 |
| SRC | 101 | 96 |
| SRPK1 | 113.5 | 116 |
| SRPK2 | 112 | 114 |
| STK33 | 104.5 | 98 |
| Syk | 123.5 | 79.5 |
| TAK1 | 88.5 | 86 |
| TAO1 | 118.5 | 111 |
| TAO2 | 92.5 | 97.5 |
| TAO3 | 89.5 | 88.5 |
| TBK1 | 105.5 | 104.5 |
| TEC Activated | 138.5 | 88.5 |
| Tie2 | 137.5 | 81.5 |
| TLK2 | 109 | 97.5 |
| TNK2 | 119.5 | 114.5 |
| TrkA | −1 | −1 |
| TrkB | 0 | 0.5 |
| TSSK1 | 80 | 60 |
| TSSK2 | 131 | 90 |
| Txk | 156.5 | 104.5 |
| ULK2 | 98.5 | 89 |
| ULK3 | 99.5 | 93.5 |
| VRK2 | 90.5 | 90 |
| WNK2 | 140.5 | 109 |
| WNK3 | 111 | 101.5 |
| Yes | 113 | 88.5 |
| ZAP-70 | 149 | 120.5 |

Preparation of Intermediates

Preparation A

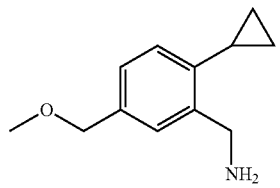

(2-cyclopropyl-5-(methoxymethyl)phenyl)methanamine

Step A: Preparation of
2-bromo-5-formylbenzonitrile

To a 1 liter, 3-neck round bottom flask equipped with a condenser, and temperature probe was added 2-fluoro-5-formylbenzonitrile (20 g, 134 mmol) and 535 mL of NMP, and lithium bromide (116.5 g, 1341 mmol). A modest exotherm was observed. This mixture was warmed to 150° C. under a nitrogen atmosphere for 3.5 days. After cooling to ambient temperature, the mixture was diluted with 2 liters of ice water, and extracted two times with MTBE. The combined extracts were washed two times with brine, dried over magnesium sulfate, and concentrated under reduced pressure. The resulting crude material was purified by flash chromatography, eluting with 100% DCM, to give 2-bromo-5-formylbenzonitrile as a white solid (5 g, 18% yield).

Step B: Preparation of
2-cyclopropyl-5-formylbenzonitrile

A heavy walled pressure tube was charged with 2-bromo-5-formylbenzonitrile (500 mg, 2.38 mmol) and 8 mL of toluene. To this mixture was added potassium cyclopropyltrifluoroborate (1.41 g, 9.52 mmol), palladium acetate (80 mg, 0.36 mmol), dicyclohexyl(2',6'-diisopropoxy-[1,1'-biphenyl]-2-yl)phosphine (333 mg, 0.71 mmol), $K_3PO_4$ (1.52 g, 7.14 mmol), and 2 mL of water. The mixture was purged with nitrogen for 5 minutes, tube sealed, and heated to 110° C. for 16 hours, then allowed to cool to ambient temperature. The mixture was then diluted with EtOAc/brine and filtered through GF/F filter paper. The organics were isolated from the filtrate, dried over sodium sulfate and concentrated under reduced pressure. The resulting crude material was purified by flash chromatography, eluting with 15% ethyl acetate/hexane to 25% ethyl acetate/Hex, to give 2-cyclopropyl-5-formylbenzonitrile (260 mg, 64% yield).

Step C: Preparation of
2-cyclopropyl-5-(hydroxymethyl)benzonitrile

To a round bottom flask containing 2-cyclopropyl-5-formylbenzonitrile (260 mg, 1.52 mmol) was added dry methanol (5 mL). A solution formed and was chilled to 0° C. Sodium borohydride (115 mg, 3.04 mmol) was then added in one portion and the mixture was then allowed to warm to ambient temperature. After about one hour, the mixture was then concentrated under reduced pressure and the crude was taken up in saturated ammonium chloride solution, diluted with water, extracted with EtOAc, extracts dried over sodium sulfate and concentrated under reduced pressure to give 2-cyclopropyl-5-(hydroxymethyl)benzonitrile (228 mg, 87%) as a white solid.

Step D: Preparation of
2-cyclopropyl-5-(methoxymethyl)benzonitrile

A round bottom flask and nitrogen inlet was charged with 2-cyclopropyl-5-(hydroxymethyl)benzonitrile (228 mg, 1.32 mmol) and dry DMF (13 mL). This solution was chilled to 0° C. and sodium hydride (105 mg, 2.63 mmol, 60% dispersion in mineral oil) was added in one portion. The cooling bath was removed and the mixture stirred for 45 minutes. To this was then added methyl iodide (247 µL, 3.95 mmol) and the mixture was stirred at ambient temperature for 16 hours. The reaction mixture was then quenched with brine and extracted with EtOAc. The extracts were washed with brine, dried over sodium sulfate and concentrated under reduced pressure to give 2-cyclopropyl-5-(methoxymethyl)benzonitrile (248 mg, 100%) as an oil.

Step E: Preparation of
(2-cyclopropyl-5-(methoxymethyl)phenyl)methanamine

To a round bottom flask containing 2-cyclopropyl-5-(methoxymethyl)benzonitrile (245 mg, 1.31 mmol) was added dry THF (13 mL) and LAH (3.93 mL, 3.93 mmol, 1M in THF). This was refluxed for 5 hours, then allowed to cool to ambient temperature. The mixture was chilled to 0° C. and quenched (Fieser) with 0.149 mL of water, 0.149 mL of 15% NaOH, and 0.447 mL of water. The mixture was vigorously stirred for 15 minutes, diluted with MTBE and sodium sulfate added. The mixture was then filtered through GF/F paper and the filtrate was concentrated under reduced pressure to give (2-cyclopropyl-5-(methoxymethyl)phenyl)methanamine (230 mg, 92%) as an oil.

Preparation B

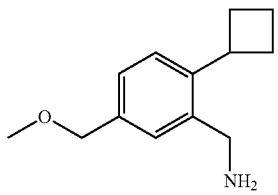

(2-cyclobutyl-5-(methoxymethyl)phenyl)methanamine

Step A: Preparation of 2-cyclobutyl-5-formylbenzonitrile

To a heavy walled pressure tube was added 2-bromo-5-formylbenzonitrile (250 mg, 1.19 mmol) and 5 mL of dry THF. To this was added palladium acetate (26.7 mg, 0.119 mmol), S-Phos (73.3 mg, 0.179 mmol), and cyclobutylzinc bromide 5.95 mL, 2.98 mmol, 0.5 M in THF), the tube was sealed and stirred under a nitrogen atmosphere for one hour. The mixture was then diluted with EtOAc/water and filtered through GF/F filter paper. The organics were isolated from the filtrate, dried over sodium sulfate and concentrated under reduced pressure. The crude material was purified by flash chromatography to give 2-cyclobutyl-5-formylbenzonitrile (110 mg, 50% yield) as an oil.

Step B: Preparation of 2-cyclobutyl-5-(methoxymethyl)phenyl)methanamine

Prepared by the methods described in Preparation A, Steps C through E, replacing 2-cyclopropyl-5-formylbenzonitrile with 2-cyclobutyl-5-formylbenzonitrile, to give the title compound.

Preparation C

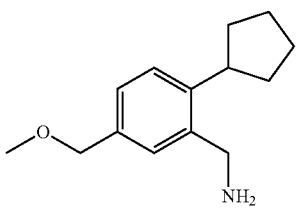 [SMILES: COCc1ccc(C2CCCC2)c(CN)c1]

(2-cyclopentyl-5-(methoxymethyl)phenyl)methanamine

Prepared by the methods described in Preparation B, Steps A through B, replacing cyclobutylzinc bromide with cyclopentylzinc bromide, to give the title compound.

Preparation D

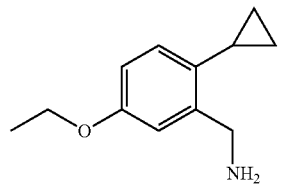

(2-cyclopropyl-5-ethoxyphenyl)methanamine

Step A: Preparation of 2-bromo-5-ethoxybenzonitrile

A round bottom flask and nitrogen inlet was charged with 2-bromo-5-hydroxybenzonitrile (1.50 g, 7.58 mmol) and dry DMF (30 mL). To this was added cesium carbonate (4.94 g, 15.2 mmol) followed by ethyl iodide (1.77 g, 11.4 mmol) and the mixture was stirred at ambient temperature for 16 hours. The mixture was then diluted with water and extracted two times with diethyl ether. The extracts were washed two times with brine, dried over magnesium sulfate and concentrated under reduced pressure to give 2-bromo-5-ethoxybenzonitrile (1.72 g, 100%) as a white solid.

Step B: Preparation of 2-cyclopropyl-5-ethoxybenzonitrile

A heavy walled pressure tube was charged with 2-bromo-5-ethoxybenzonitrile (0.750 g, 3.32 mmol) and 8 mL of toluene. To this was added potassium cyclopropyltrifluoroborate (1.96 g, 13.3 mmol), palladium acetate (0.111 g, 0.498 mmol), dicyclohexyl(2',6'-diisopropoxy-[1,1'-biphenyl]-2-yl)phosphine (0.464 g, 0.995 mmol), followed by potassium phosphate (2.11 g, 9.95 mmol) and 2 mL of water. The mixture was purged with nitrogen for 5 minutes, tube sealed and heated to 110° C. for 3 hours. The reaction mixture was allowed to cool to ambient temperature and diluted with EtOAc and water. This was filtered through GF/F filter paper and the organics were isolated from the filtrate, dried over sodium sulfate and concentrated under reduced pressure. The crude was purified by flash chromatography to give 2-cyclopropyl-5-ethoxybenzonitrile (0.446 g, 72% yield) as a light yellow oil.

Step C: Preparation of (2-cyclopropyl-5-ethoxyphenyl)methanamine

Prepared by the methods described in Preparation A, Step E, replacing 2-cyclopropyl-5-(methoxymethyl)benzonitrile with 2-cyclopropyl-5-ethoxybenzonitrile, to give the title compound (0.424 g, 94% yield).

Preparation E

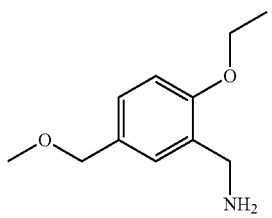

(2-ethoxy-5-(methoxymethyl)phenyl)methanamine

Step A: Preparation of 5-bromo-2-ethoxybenzonitrile

To a round bottom flask and nitrogen inlet was added 5-bromo-2-hydroxybenzonitrile (2.00 g, 10.1 mmol) and 40 mL of dry DMF. To this mixture was added powdered potassium carbonate (2.79 g, 20.2 mmol) and ethyl iodide (4.73 g, 30.3 mmol), which was stirred at ambient temperature for 2 hours under a nitrogen atmosphere. The mixture was then diluted with water and extracted two times with MTBE. The extracts were washed two times with brine, dried over magnesium sulfate and concentrated under reduced pressure to give 5-bromo-2-ethoxybenzonitrile (2.06 g, 90% yield).

Step B: Preparation of 2-ethoxy-5-(methoxymethyl)benzonitrile

A heavy walled pressure tube was charged with 5-bromo-2-ethoxybenzonitrile (0.500 g, 2.21 mmol), 8 mls of dioxane and 2 mls of water. Potassium methoxymethyltrifluoroborate (0.672 g, 4.42 mmol), $PdCl_2(dppf)$ dichloromethane adduct (0.361 g, 0.442 mmol), and cesium carbonate (2.16 g, 6.64 mmol) were then added to the reaction mixture under a nitrogen atmosphere, the tube was sealed and heated to 100° C. for 16 hours. After allowing to cool to ambient temperature, the mixture was diluted with EtOAc/water and filtered through GF/F filter paper. The organic layer was isolated from the filtrate, dried over sodium sulfate and concentrated under reduced pressure. The resulting crude material was purified by flash chromatography to give 2-ethoxy-5-(methoxymethyl)benzonitrile (0.100 g, 24% yield).

Step C: Preparation of (2-ethoxy-5-(methoxymethyl)phenyl)methanamine

Prepared by the methods described in Preparation A, Step E, replacing 2-cyclopropyl-5-(methoxymethyl)benzonitrile with 2-ethoxy-5-(methoxymethyl)benzonitrile to give the title compound (66 mg, 65% yield).

Preparation F

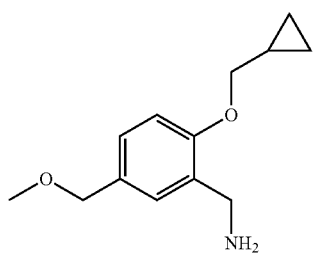 [SMILES: COCc1ccc(OCC2CC2)c(CN)c1]

(2-(cyclopropylmethoxy)-5-(methoxymethyl)phenyl)methanamine

Prepared by the methods described in Preparation E, Steps A through C, replacing ethyl iodide with (bromomethyl)cyclopropane in step A, to give the title compound (0.576 g, 27% overall yield).

Preparation G

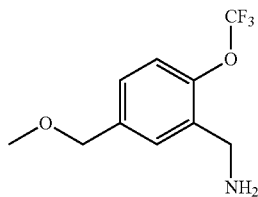 [SMILES: COCc1ccc(OC(F)(F)F)c(CN)c1]

(5-(methoxymethyl)-2-(trifluoromethoxy)phenyl)methanamine

Step A: Preparation of 5-(methoxymethyl)-2-(trifluoromethoxy)benzaldehyde

A heavy walled pressure tube was charged with 5-bromo-2-(trifluoromethoxy)benzaldehyde (1.00 g, 3.72 mmol), 37 mL of dioxane and 4 mL of water. Potassium methoxymethyltrifluoroborate (1.13 g, 7.43 mmol), palladium acetate (0.083 g, 0.372 mmol) S-Phos (0.305 g, 0.743 mmol), and cesium carbonate (4.84 g, 14.9 mmol) were then added, the tube was sealed and the mixture heated to 100° C. for 16 hours. After allowing to cool to ambient temperature, the mixture was diluted with EtOAc/water and filtered through GF/F filter paper. The organic layer was isolated from the filtrate, dried over sodium sulfate and concentrated under reduced pressure. The resulting crude material was purified by flash chromatography to give 5-(methoxymethyl)-2-(trifluoromethoxy)benzaldehyde as an oil (0.240 g, 28%).

Step B: Preparation of 5-(methoxymethyl)-2-(trifluoromethoxy)benzaldehyde oxime To a round bottom flask equipped a stir bar was added 5-(methoxymethyl)-2-(trifluoromethoxy)benzaldehyde (0.230 g, 0.982 mmol), ethanol (10 mL) and water (1 ml). Hydroxylamine hydrochloride (0.102 g, 1.47 mmol) was then added and the mixture was stirred at ambient temperature for 2 hrs. The mixture was then concentrated under reduced pressure and the crude was taken up in 10% aqueous potassium carbonate/EtOAc, organics isolated, dried over sodium sulfate and concentrated under reduced pressure to give 5-(methoxymethyl)-2-(trifluoromethoxy)benzaldehyde oxime (0.185 g, 76% yield) as an oil.

Step C: Preparation of 5-(methoxymethyl)-2-(trifluoromethoxy)phenyl)methanamine To a round bottom flask containing 5-(methoxymethyl)-2-(trifluoromethoxy)benzaldehyde oxime (0.180 g, 0.722 mmol) was added acetic acid (7 mL) and zinc powder 0.189 g, 2.89 mmol). This was warmed to 70° C. for 16 hours. The mixture was filtered and the filtrate concentrated under Preparation H

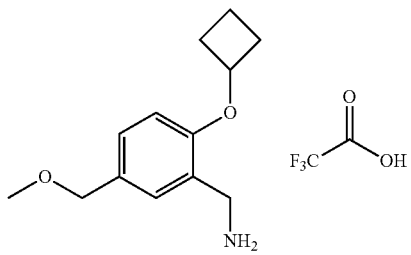 [SMILES: COCc1ccc(OC2CCC2)c(CN)c1 ; O=C(O)C(F)(F)F]

(2-cyclobutoxy-5-(methoxymethyl)phenyl)methanamine 2,2,2-trifluoroacetate

Step A: Preparation of 5-bromo-2-cyclobutoxybenzonitrile

A heavy walled pressure tube was charged with 5-bromo-2-hydroxybenzonitrile (1.00 g, 5.05 mmol), dry DMF (20 mL), powdered potassium carbonate (1.40 g, 10.1 mmol), and bromocyclobutane (2.05 g, 15.2 mmol). The tube was sealed and warmed to 80° C. for 16 hours, then allowed to cool to ambient temperature. The mixture was then diluted with water and extracted 2 times with MTBE. The extracts were washed 2 times with brine, dried over sodium sulfate, and concentrated under reduced pressure to give 5-bromo-2-cyclobutoxybenzonitrile (0.983 g, 77% yield) as an orange oil.

Step B: Preparation of (2-cyclobutoxy-5-(methoxymethyl)phenyl)methanamine 2,2,2-trifluoroacetate Prepared by the methods described in Preparation E, Steps B and C, replacing 5-bromo-2-ethoxybenzonitrile with 5-bromo-2-cyclobutoxybenzonitrile. The crude product in the reduction step was purified by reverse phase prep HPLC, to give the title compound (61 mg, 26% yield).

Preparation I

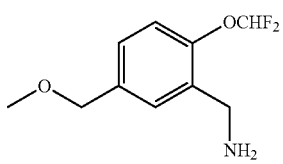

(2-(difluoromethoxy)-5-(methoxymethyl)phenyl)methanamine

Step A: Preparation of 5-bromo-2-(difluoromethoxy)benzonitrile

To a heavy walled pressure tube was added 5-bromohydroxybenzonitrile (5 g, 25.3 mmol), acetonitrile (250 mL) and 30% (w/w) of aqueous KOH (100 mL). This mixture was chilled to −78° C. and 2-chloro-2,2-difluoro-1-phenylethanone (9.62 g, 50.5 mmol) was then added. The tube was sealed, allowed to warm to ambient temperature, and heated to 80° C. for 4 hours. After cooling to ambient temperature, water was added and the mixture extracted 2 times with EtOAc, extracts dried over sodium sulfate, and concentrated under reduced pressure. The resulting crude material was taken up in DCM and filtered. The filtrate was purified by flash chromatography to give 5-bromo-2-(difluoromethoxy)benzonitrile (1.84 g, 29% yield) as a white solid.

Step B: Preparation of (2-(difluoromethoxy)-5-(methoxymethyl)phenyl)methanamine

Prepared by the methods described in Preparation E, Steps B and C, replacing 5-bromo-2-ethoxybenzonitrile with 5-bromo-2-(difluoromethoxy)benzonitrile, to give the title compound (70 mg, 11% yield).

Preparation J

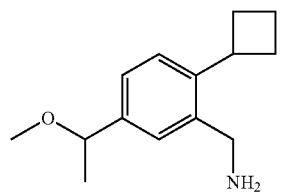 [SMILES: COC(C)c1ccc(C2CCC2)c(CN)c1]

(2-cyclobutyl-5-(1-methoxyethyl)phenyl)methanamine

Step A: Preparation of 2-bromo-5-(1-hydroxyethyl)benzonitrile

A round bottom flask and nitrogen inlet was charged with 2-bromo-5-formylbenzonitrile (0.300 g, 1.43 mmol) and dry THF (14 mL). This solution was chilled to 0° C. and MeMgI (0.952 mL, 2.86 mmol, 3M in ether) was then added by syringe, resulting in a cloudy mixture. This mixture was stirred at 0° C. for 30 minutes, then quenched with saturated ammonium chloride solution. Water was added and the mixture was extracted 2 times with EtOAc, extracts dried over sodium sulfate and concentrated under reduced pressure to give 2-bromo-5-(1-hydroxyethyl)benzonitrile (0.295 mg, 91%) as an orange oil.

Step B: Preparation of 2-bromo-5-(1-methoxyethyl)benzonitrile

Prepared by the method described in Preparation A, Step D, replacing 2-cyclopropyl-5-(hydroxymethyl)benzonitrile with 2-bromo-5-(1-hydroxyethyl)benzonitrile and DMF with THF, to give 2-bromo-5-(1-methoxyethyl)benzonitrile (86 mg, 54%) as a solid.

Step C: Preparation of 2-cyclobutyl-5-(1-methoxyethyl)benzonitrile

Prepared by the method described in Preparation B, Step A, replacing 2-bromo-5-formylbenzonitrile with 2-bromo-5-(1-methoxyethyl)benzonitrile to give 2-cyclobutyl-5-(1-methoxyethyl)benzonitrile (39 mg, 51% yield) as an oil.

Step D: Preparation of (2-cyclobutyl-5-(1-methoxyethyl)phenyl)methanamine

Prepared by the method described in Preparation A, Step E, replacing 2-cyclopropyl-5-(methoxymethyl)benzonitrile with 2-cyclobutyl-5-(1-methoxyethyl)benzonitrile to give the title compound (30 mg, 76% yield) as an oil.

Preparation K

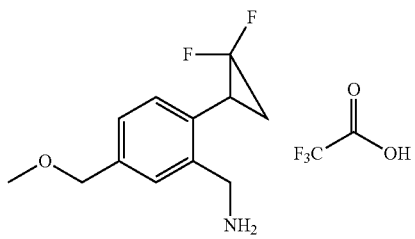 [SMILES: COCc1ccc(C2CC2(F)F)c(CN)c1 ; O=C(O)C(F)(F)F]

(2-(2,2-difluorocyclopropyl)-5-(methoxymethyl)phenyl)methanamine 2,2,2-trifluoroacetate

Step A: Preparation of (4-bromo-3-chlorophenyl)methanol

A round bottom flask equipped with a stirbar and nitrogen inlet was charged with dry THF (72 mL), and sodium borohydride (1.09 g, 28.9 mmol). This suspension was chilled to 0° C. and boron trifluoride etherate (8.20 g, 57.8 mmol) was then added and the mixture stirred at 0° C. for 15 minutes. To this was added 4-bromo-3-chlorobenzoic acid (3.40 g, 14.4 mmol) in one portion (gas evolution observed). The reaction mixture was allowed to warm to ambient temperature and stirred for 16 hours. The reaction mixture was then carefully quenched with methanol until gas evolution had ceased. The mixture was concentrated under reduced pressure and the resulting crude material was taken up in 100 mL of 20% aqueous NaOH and stirred at ambient temperature for 1 hour. The mixture was extracted 2 times with DCM, extracts dried over sodium sulfate and concentrated under reduced pressure to give (4-bromo-3-chlorophenyl)methanol (2.59 g, 81%) as an oil.

Step B: Preparation of 1-bromo-2-chloro-4-(methoxymethyl)benzene

Prepared by the method described in Preparation J, Step B, replacing 2-bromo-5-(1-hydroxyethyl)benzonitrile with (4-bromo-3-chlorophenyl)methanol to give 1-bromo-2-chloro-4-(methoxymethyl)benzene (1.72 g, 65% yield) as an oil.

Step C: Preparation of 2-chloro-4-(methoxymethyl)-1-vinylbenzene

To a heavy walled pressure tube was added 1-bromo-2-chloro-4-(methoxymethyl)benzene (1.72 g, 7.30 mmol), 35 mL of dioxane, and 4 mL of water. To this was added potassium vinyltrifluoroborate (1.96 g, 14.6 mmol), palladium chloride (0.0259 g, 0.146 mmol), triphenylphosphine (0.115 g, 0.438 mmol), and cesium carbonate (7.14 g, 21.9 mmol). The tube was sealed and warmed to 90° C. for 16 hours, then allowed to cool to ambient temperature. Ethyl acetate and water were added and the mixture filtered through GF/F filter paper. The organics were isolated from the filtrate, dried over sodium sulfate and concentrated under reduced pressure. The resulting crude material was purified by flash chromatography to afford 2-chloro-4-(methoxymethyl)-1-vinylbenzene (790 mg, 59% yield) as an oil.

Step D: Preparation of 2-chloro-1-(2,2-difluorocyclopropyl)-4-(methoxymethyl)benzene To a microwave reaction tube was added the 2-chloro-4-(methoxymethyl)-1-vinylbenzene (0.732 g, 4.01 mmol), dry toluene (2.5 mL) and NaF (0.0168 g, 0.401 mmol). The tube was capped and warmed to 100° C. under a nitrogen atmosphere. Trimethylsilyl 2,2-difluoro-2-(fluorosulfonyl)acetate (2.01 g, 8.02 mmol) was added by syringe, very slowly, over a 4 hour period, as vigorous gas evolution is observed. After the addition was complete, the mixture was stirred at 100° C. overnight, then allowed to cool to ambient temperature. The mixture was diluted with EtOAc, washed with 10% aqueous potassium carbonate, dried over sodium sulfate and concentrated under reduced pressure to an oil. This oil was purified by flash chromatography to give 2-chloro-1-(2,2-difluorocyclopropyl)-4-(methoxymethyl)benzene (0.419 g, 45% yield) as an oil.

Step E: Preparation of tert-butyl 2-(2,2-difluorocyclopropyl)-5-(methoxymethyl)benzylcarbamate To a microwave reaction tube was added 2-chloro-1-(2,2-difluorocyclopropyl)-4-(methoxymethyl)benzene (0.200 g, 0.860 mmol), potassium (((tert-butoxycarbonyl)amino)methyl)trifluoroborate (0.224 g, 0.946 mmol, *Org. Lett.*, 2012, 14 (12), pp 3138-3141) toluene (6.5 mL) and water (1.5 mL). To this was added palladium acetate (0.00965 g, 0.0430 mmol), S-Phos (0.0353 g, 0.0860 mmol), and potassium carbonate (0.356 g, 2.58 mmol). The tube was sealed and heated to 90° C. for 24 hours, then allowed to cool to ambient temperature. EtOAc and water were added and the mixture filtered through GF/F filter paper. The organic layer was isolated from the filtrate, dried over sodium sulfate and concentrated under reduced pressure. Prep plate purification afforded tert-butyl 2-(2,2-difluorocyclopropyl)-5-(methoxymethyl)benzylcarbamate (15 mg, 5% yield) as a film.

Step F: Preparation of (2-(2,2-difluorocyclopropyl)-5-(methoxymethyl)phenyl)methanamine 2,2,2-trifluoroacetate To a flask containing tert-butyl 2-(2,2-difluorocyclopropyl)-5-(methoxymethyl)benzylcarbamate (15 mg, 0.046 mmol) was added TFA (1 mL) and the mixture stirred at ambient temperature for one hour and then concentrated under reduced pressure to give (2-(2,2-difluorocyclopropyl)-5-(methoxymethyl)phenyl)methanamine 2,2,2-trifluoroacetate (0.016 mg, 100% yield).

Preparation L

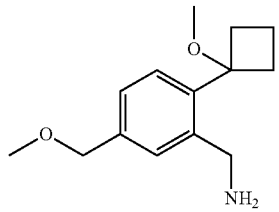 [SMILES: COCc1ccc(C2(OC)CCC2)c(CN)c1]

(2-(1-methoxycyclobutyl)-5-(methoxymethyl)phenyl)methanamine

Step A: Preparation of 2-bromo-5-(hydroxymethyl)benzonitrile

Prepared by the method described in Preparation A, Step C, replacing 2-cyclopropyl-5-formylbenzonitrile with 2-bromo-5-formylbenzonitrile, to give 2-bromo-5-(hydroxymethyl)benzonitrile (2.02 g, 100% yield) as a white solid.

Step B: Preparation of 2-bromo-5-(methoxymethyl)benzonitrile

Prepared by the method described in Preparation J, Step B, replacing 2-cyclopropyl-5-(hydroxymethyl)benzonitrile with 2-bromo-5-(hydroxymethyl)benzonitrile to give the title compound (1.35 g, 63%) as a waxy solid.

Step C: Preparation of 2-(1-hydroxycyclobutyl)-5-(methoxymethyl)benzonitrile

A flame dried round bottom flask and nitrogen inlet was charged with 2-bromo-5-(methoxymethyl)benzonitrile (0.205 g, 0.907 mmol) and dry THF (9 mL). This solution was chilled to −78° C. and n-BuLi (0.399 mL, 0.997 mmol, 2.5 M in hexanes) was then added dropwise by syringe. Once the addition was complete, the mixture was stirred at −78° C. for 10 minutes, and cyclobutanone (0.127 g, 1.81 mmol) was added by syringe, and the mixture was allowed to warm to ambient temperature. The reaction mixture was quenched with saturated ammonium chloride solution. Water was added and the mixture was extracted with EtOAc, extracts dried over sodium sulfate and concentrated under reduced pressure. The crude material was purified by flash chromatography to give 2-(1-hydroxycyclobutyl)-5-(methoxymethyl)benzonitrile (100 mg, 50% yield).

Step D: Preparation of 2-(1-methoxycyclobutyl)-5-(methoxymethyl)benzonitrile

Prepared by the method described in Preparation J, Step B, replacing 2-cyclopropyl-5-(hydroxymethyl)benzonitrile with 2-(1-hydroxycyclobutyl)-5-(methoxymethyl)benzonitrile, to give the title compound (60 mg, 56% yield) as an oil.

Step E: Preparation of (2-(1-methoxycyclobutyl)-5-(methoxymethyl)phenyl)methanamine Prepared by the method described in Preparation A, Step E, replacing 2-cyclopropyl-5-(methoxymethyl)benzonitrile with 2-(1-methoxycyclobutyl)-5-(methoxymethyl)benzonitrile, to give the title compound (44 mg, 79%) as an oil.

Preparation M

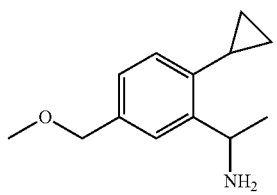

1-(2-cyclopropyl-5-(methoxymethyl)phenyl)ethanamine

To a round bottom flask and nitrogen inlet was added 2-cyclopropyl-5-(methoxymethyl)benzonitrile (0.082 g, 0.438 mmol) and dry THF (4 mL). The mixture was chilled to 0° C. and MeMgI (0.292 mL, 0.876 mmol, 3M in ether) was added by syringe, resulting in a white mixture. The mixture was allowed to warm to and stir at ambient temperature for one hour, then warmed to 60° C. for one hour. Them mixture was chilled to 0° C. and LAH (0.876 mL, 0.876 mmol, 1M in THF) was then added. The mixture was allowed to warm to ambient temperature and then refluxed for one hour. After stirring at ambient temperature for 16 hours, the mixture chilled to 0° C. and was quenched with 33 pt of water, 33 µL of 15% aqueous NaOH, and 100 µL of water, and vigorously stirred for 30 minutes. This was then diluted with MTBE and filtered. The filtrate was concentrated under reduced pressure to give a mixture of the title compound and (2-cyclopropyl-5-(methoxymethyl)phenyl)methanamine, which was used as is (90 mg, 100% yield).

Preparation N

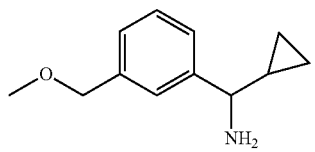

Cyclopropyl(3-(methoxymethyl)phenyl)methanamine

Step A: Preparation of 3-(methoxymethyl)benzonitrile

Prepared by the method described in Preparation A, Step D, replacing 2-cyclopropyl-5-(hydroxymethyl)benzonitrile with 3-(hydroxymethyl)benzonitrile to give 3-(methoxymethyl)benzonitrile (2.21 g, 100%) as an oil.

Step B: Preparation of cyclopropyl(3-(methoxymethyl)phenyl)methanamine

Prepared by the method described in Preparation M, Step A, replacing 2-cyclopropyl-5-(methoxymethyl)benzonitrile with 3-(methoxymethyl)benzonitrile and methylmagnesium iodide with cyclopropylmagnesium bromide, to give the title compound (0.39 g, 100%) as an oil.

Preparation O

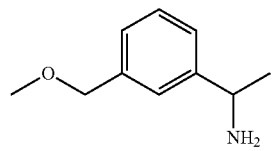

1-(3-(methoxymethyl)phenyl)ethanamine

Prepared by the method described in Preparation M, Step A, replacing 2-cyclopropyl-5-(methoxymethyl)benzonitrile with 3-(methoxymethyl)benzonitrile to give the title compound (0.236 g, 84%) as an orange/brown oil.

Preparation P

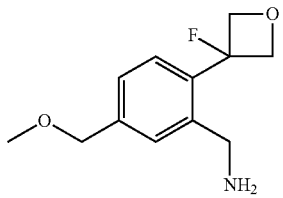

(2-(3-fluorooxetan-3-yl)-5-(methoxymethyl)phenyl)methanamine

Step A: Preparation of 3-(2-chloro-4-(methoxymethyl)phenyl)oxetan-3-ol

A round bottom flask was charged with 1-bromo-2-chloro-4-(methoxymethyl)benzene (1.00 g, 4.25 mmol) and dry THF (42 mL). This solution was chilled to −78° C. and n-BuLi (2.04 mL, 5.10 mmol, 2.5 M in hexanes) was added by syringe over a 5 minute period. This mixture was stirred at −78° C. for 1 hour and a THF solution (10 mL) of oxetan-3-one (0.306 g, 4.25 mmol) was then added by syringe. After 15 minutes, the cooling bath was removed. After about 20 minutes, the mixture was quenched with saturated ammonium chloride solution, diluted with water and extracted with EtOAc. The extracts were dried over sodium sulfate and concentrated under reduced pressure. The resulting crude material was purified by flash chromatography to give 3-(2-chloro-4-(methoxymethyl)phenyl)oxetan-3-ol (0.310 g, 32% yield) as an oil.

Step B: Preparation of 3-(2-chloro-4-(methoxymethyl)phenyl)-3-fluorooxetane

A round bottom flask was charged with 3-(2-chloro-4-(methoxymethyl)phenyl)oxetan-3-ol (0.305 g, 1.33 mmol) and dry DCM (13 mL). This solution was chilled to 0° C. and Deoxofluor (0.384 g, 1.30 mmol) was added. This mixture was stirred at 0° C. for 1 hour, then quenched with 10% aqueous potassium carbonate. This was extracted with EtOAc, extracts dried over sodium sulfate and concentrated under reduced pressure. The resulting crude material was purified by preparative TLC to give 3-(2-chloro-4-(methoxymethyl)phenyl)-3-fluorooxetane (0.165 g, 54%) as an oil.

Step C: Preparation tert-butyl 2-(3-fluorooxetan-3-yl)-5-(methoxymethyl)benzylcarbamate Prepared as described in Preparation K, Step E, replacing 2-chloro-1-(2,2-difluorocyclopropyl)-4-(methoxymethyl)benzene with 3-(2-chloro-4-(methoxymethyl)phenyl)-3-fluorooxetane to give tert-butyl 2-(3-fluorooxetan-3-yl)-5-(methoxymethyl)benzylcarbamate (0.100 g, 44%) as a white solid.

Step D: Preparation of (2-(3-fluorooxetan-3-yl)-5-(methoxymethyl)phenyl)methanamine A round bottom flask was charged with tert-butyl 2-(3-fluorooxetan-3-yl)-5-(methoxymethyl)benzylcarbamate (0.095 g, 0.292 mmol), dry DCM (3 mL) and TFA (0.322 g, 2.92 mmol). The mixture was stirred at ambient temperature for 3 hours, then diluted with EtOAc, washed with 10% aqueous potassium carbonate, dried over sodium sulfate and concentrated under reduced pressure to give the title compound (0.047 g, 72% yield) as an oil.

Intermediate 1

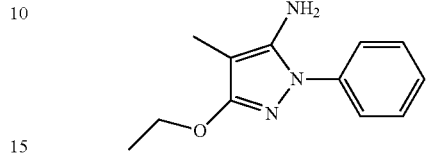

3-ethoxy-4-methyl-1-phenyl-1H-pyrazol-5-amine

Step A: Preparation of 5-amino-4-methyl-1-phenyl-1H-pyrazol-3(2H)-one

A mixture of ethyl 2-cyanopropanoate (5.0 g, 46 mmol) and phenylhydrazine (5.9 g, 46 mmol) in dioxane (10 mL) was heated at 110° C. for 17 hours. The crude material was cooled to ambient temperature, concentrated, and triturated with cold EtOH and Et₂O. The resultant solid was filtered, washed with Et₂O, and dried under vacuum to give the product as a white solid (3.4 g, 39% yield). MS (apci) m/z=190.0 (M−H).

Step B: Preparation of 3-ethoxy-4-methyl-1-phenyl-1H-pyrazol-5-amine

To a suspension of 5-amino-4-methyl-1-phenyl-1H-pyrazol-3(2H)-one (10.0 g, 52.9 mmol) in DMF (100 mL) was added K₂CO₃ (14.6 g, 106 mmol) and bromoethane (4.34 mL, 58.1) at ambient temperature. After stirring for 17 hours, the reaction mixture was treated with EtOAc and washed with water (to obtain the N-alkylation product) and brine, dried with MgSO₄, filtered, and concentrated to give the product (5.35 g, 47% yield). MS (apci) m/z=218.1 (M+H).

Intermediate 2

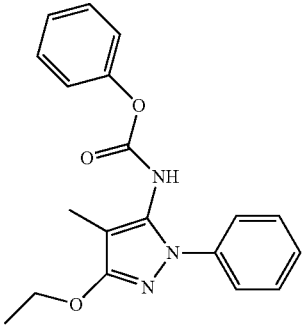

phenyl (3-ethoxy-4-methyl-1-phenyl-1H-pyrazol-5-yl)carbamate

To a suspension of 3-ethoxy-4-methyl-1-phenyl-1H-pyrazol-5-amine [Intermediate 1] (138 mg, 0.57 mmol) in EtOAc (7 mL) at 0° C. was added NaOH (0.57 mL, 2M, 1.14 mmol)

followed by phenyl chloroformate (0.12 mL, 0.97 mmol). The reaction was stirred at ambient temperature for 17 hours then treated with EtOAc, washed with water and brine, dried over MgSO$_4$, filtered and concentrated in vacuo. The residue was purified by silica column chromatography eluting with 6:1 hexanes/EtOAc to afford the title compound (139 mg, 72% yield). MS (apci) m/z=338.0 (M+).

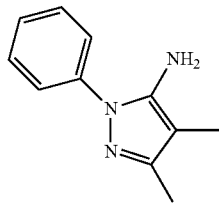

Intermediate 2

3,4-dimethyl-1-phenyl-1H-pyrazol-5-amine

To a solution of 2-methyl-3-oxobutanenitrile (295 mg, 3.038 mmol) in EtOH (40 mL) were added HCl (5-6M in iPrOH, 0.6 mL) and phenylhydrazine (0.299 mL, 3.038 mmol). The reaction mixture was heated to reflux for 17 hours, then cooled to ambient temperature. The reaction mixture was diluted with saturated NaHCO$_3$ (20 mL), extracted with DCM (2×25 mL), and the combined organic phases were dried over MgSO$_4$, filtered and concentrated in vacuo. The residue was purified by silica column chromatography, eluting with 0-3% MeOH/DCM to yield the title compound (555 mg, 97% yield) as a tan solid. MS (apci) m/z=188.2 (M+H).

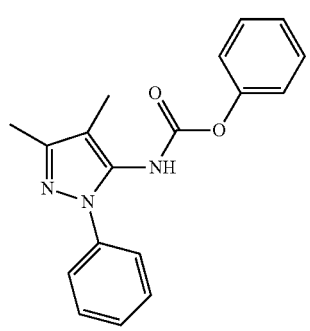

Intermediate 3 phenyl (3,4-dimethyl-1-phenyl-1H-pyrazol-5-yl)carbamate

To a solution of 3,4-dimethyl-1-phenyl-1H-pyrazol-5-amine (1.80 g, 9.6 mmol) in EtOAc (20 mL) was added 2N NaOH (9.6 mL, 19.2 mmol) followed by phenyl chloroformate (1.7 mL, 13.5 mmol). The mixture was stirred at ambient temperature for 16 hours then treated with phenyl chloroformate (500 µL) and stirred a further 4 hours. The mixture was diluted with water (100 mL) and extracted with EtOAc (3×50 mL). The combined organic phases were washed with saturated NaHCO$_3$ (50 mL) and brine (50 mL) then dried over Na$_2$SO$_4$, filtered and concentrated in vacuo. The residue was purified by silica column chromatography eluting with 4:1 hexanes/EtOAc to afford the title compound (1.83 g, 62% yield) as a white powder.

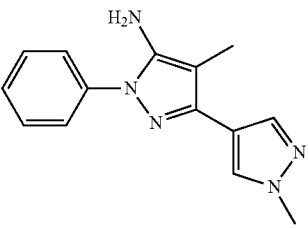

Intermediate 4

1',4-dimethyl-1-phenyl-1H,1'H-3,4'-bipyrazol-5-amine

Step A: ethyl 1-methyl-1H-pyrazole-4-carboxylate

To a 3000-mL three-necked flask was added ethyl 2-formyl-3-oxopropanoate (100 g, 694 mmol), followed by anhydrous 200-proof EtOH (694 mL). The reaction was cooled in an ice bath to 5° C., and then methylhydrazine (35.8 mL, 680 mmol) was added dropwise. A vigorous exotherm was observed during hydrazine addition and the temperature was kept below 12° C. by controlling the addition rate. After the hydrazine addition was complete, the ice bath was removed, and the reaction was allowed to stir at ambient temperature for 16 hours. The reaction was concentrated in vacuo and the residue dissolved in DCM and re-concentrated, then dried for 2 days to yield ethyl 1-methyl-1H-pyrazole-4-carboxylate (106 g, 99% yield) as a tan orange oil. MS (apci) m/z=155.1 (M+H).

Step B: 2-methyl-3-(1-methyl-1H-pyrazol-4-yl)-3-oxopropanenitrile

To a four-necked 5-liter round bottomed flask fitted with an overhead stirrer and addition funnel was charged LHMDS (1444 mL, 1444 mmol) (1.0M in THF). The solution was cooled in an acetone/dry ice bath first (internal temperature of −79° C.) under nitrogen, followed by slow addition of propiononitrile (103 mL, 1444 mmol) via dropping funnel. The mixture was stirred at −80° C. for 90 minutes. A solution of ethyl 1-methyl-1H-pyrazole-4-carboxylate (106 g, 688 mmol) in anhydrous THF (500 mL) was then introduced dropwise via an addition funnel (addition time: about 45 minutes; internal temperature during addition remained below −76° C.). After the addition was complete, the reaction was allowed to slowly warm to ambient temperature and stirred overnight. An orange glass deposited on the bottom of the flask. The organics were decanted and the glass was dissolved in warm water. The mixture was washed with ether (3×1000 mL). The aqueous phase was then pH-adjusted to 5 (pH paper) using concentrated HCl and saturated bicarbarbonate solution. The aqueous layer was extracted with DCM (3×1000 mL). The combined organic extracts were dried over MgSO4 filtered and concentrated to yield 2-methyl-3-(1-methyl-1H-pyrazol-4-yl)-3-oxopropanenitrile as an amber oil (92 g, 82% yield). MS (apci) m/z=162.1 (M−H).

Step C: 1',4-dimethyl-1-phenyl-1H,1'H-3,4'-bipyrazol-5-amine

A 3 L, 3 necked round bottomed flask was charged with 2-methyl-3-(1-methyl-1H-pyrazol-4-yl)-3-oxopropanenitrile (60 g, 368 mmol) absolute anhydrous ethanol (1000 mL) and phenylhydrazine hydrochloride (58 g, 404 mmol) at ambient temperature to form a yellowish suspension. The reaction vessel was equipped with a water condenser and refluxed (using a heating mantle) overnight. The reaction was concentrated and 1M NaOH (1 L) was added and the solid was broken up and collected. The solid was washed with water and hexanes. A second crop crashed out in the filtrate and was collected. The combined solids were crushed and triturated with ether (500 mL). The solid was collected by filtration, washed with hexanes and dried in vacuo to provide the title compound (93 g, 100% yield) as a yellow solid. MS (apci) m/z=254.1 (M+H).

Intermediate 5

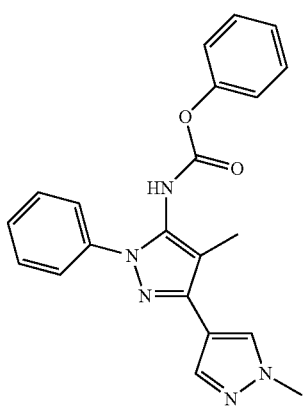

phenyl 1',4-dimethyl-1-phenyl-1H,1'H-3,4'-bipyrazol-5-ylcarbamate

A 3 L, round bottomed flask was charged with 1',4-dimethyl-1-phenyl-1H,1'H-3,4'-bipyrazol-5-amine (50 g, 197.4 mmol) and EtOAc (1000 mL) to obtain a clear brownish solution. To this was added NaOH (2M aq) (500 mL) in one portion to obtain a turbid mixture (the aqueous and organic layers were clear, but a precipitate was observed in between the two layers). After 3 minutes, phenyl carbonochloridate (74.29 mL, 592.2 mmol) was added slowly at ambient temperature (the temperature of the reaction mixture increased to 33° C. during the addition). The reaction stirred at ambient temperature for 2 hours. Additional phenyl carbonochloridate (10 mL) was added. After 30 minutes the organics layers were separated, washed with brine and concentrated in vacuo. The residue was purified by silica column chromatography eluting with 75% EtOAc/hexanes to provide the title compound (60 g, 81% yield) as a cream foam. MS (apci) m/z=374.1 (M+H).

Intermediate 6

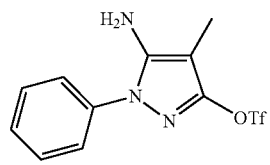

5-amino-4-methyl-1-phenyl-1H-pyrazol-3-yl trifluoromethanesulfonate

Step A: Preparation of 5-amino-4-methyl-1-phenyl-1H-pyrazol-3(2H)-one

A mixture of ethyl 2-cyanopropanoate (50.5 g, 397.2 mmol) and phenylhydrazine (39 mL, 397.2 mmol) in dioxane (100 mL) was heated at 110° C. for 5 days. The cooled mixture was concentrated to ½ volume then cooled in ice and triturated with cold Et2O. Solids were filtered, washed extensively with Et2O and dried in vacuo to afford 5-amino-4-methyl-1-phenyl-1H-pyrazol-3(2H)-one (34.69 g, 46% yield) as a fluffy white powder. MS (apci) m/z=190.1 (M+H).

Step B: Preparation of 5-amino-4-methyl-1-phenyl-1H-pyrazol-3-yl trifluoromethane sulfonate A suspension of 5-amino-4-methyl-1-phenyl-1H-pyrazol-3(2H)-one (13.72 g, 72.5 mmol) and N-phenylbis(trifluoromethylsulfonamide) (27.2 g, 76.1 mmol) in DMF (100 mL) was treated with DIEA (37.9 mL, 217.5 mmol) and the mixture stirred at ambient temperature for 16 hours. The mixture was partitioned between saturated NaHCO3 (400 mL) and EtOAc (200 mL) and the aqueous layer was extracted with EtOAc (2×200 mL). The combined organic phases were washed with water (5×50 mL) and brine (50 mL) then dried over Na2SO4, filtered and concentrated in vacuo. The residue was purified by silica column chromatography eluting with 4:1 hexanes/EtOAc, to afford the title compound (23.1 g, 99% yield) as a pale yellow solid. MS (apci) m/z=322.0 (M+H).

Intermediate 7

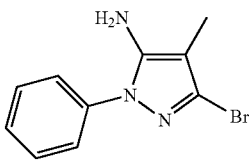

3-bromo-4-methyl-1-phenyl-1H-pyrazol-5-amine

To a suspension of 5-amino-4-methyl-1-phenyl-1H-pyrazol-3(2H)-one [Intermediate 6, step A] (1.60 g, 8.46 mmol) in acetonitrile (30 mL) was added phosphorus oxybromide (3.64 g, 12.7 mmol) in one portion. The mixture was stirred at reflux for 3 hours then cooled and concentrated in vacuo. The residue was treated with DCM (50 mL) then saturated NaHCO3 (50 mL) was slowly added. The mixture was stirred for 30 minutes, and then the layers were separated and the aqueous layer was extracted with DCM (2×50 mL). The combined organic phases were washed with brine (20 mL), dried over Na2SO4, filtered and concentrated in vacuo. The residue was purified by silica column chromatography eluting with 2:1 hexanes/EtOAc, to afford the title compound (273 mg, 13% yield) as a white solid. MS (apci) m/z=254.0 (M+H).

Intermediate 8

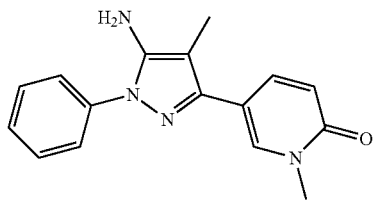

5-(5-amino-4-methyl-1-phenyl-1H-pyrazol-3-yl)-1-methylpyridin-2(1H)-one

3-Bromo-4-methyl-1-phenyl-1H-pyrazol-5-amine [Intermediate 7] (763 mg, 3.03 mmol), 1-methyl-5-(4,4,5,5-tetramethyl-1,3,2-dioxaborolan-2-yl)pyridin-2(1H)one (1.42 g, 6.05 mmol), K2CO3 (1.67 g, 12.1 mmol) and Pd(PPh3)4 (350 mg, 0.30 mmol) were combined in toluene (10 mL), water (5 mL) and EtOH (2.5 mL) and warmed to 95° C. in a sealed tube for 16 hours. The cooled mixture was filtered and the filtrate partitioned between water (30 mL) and EtOAc (30 mL). The aqueous layer was extracted with EtOAc (2×20 mL) and the combined organic phases were washed with brine (20 mL), dried over Na2SO4, filtered and concentrated in vacuo. The residue was purified by silica column chromatography eluting with 2% MeOH/DCM to afford the title compound (504 mg, 59% yield) as a yellow foam. MS (apci) m/z=281.2 (M+H).

Intermediate 9

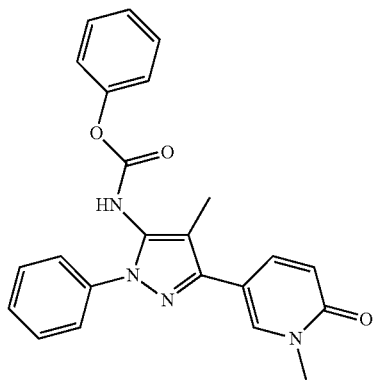

phenyl (4-methyl-3-(1-methyl-6-oxo-1,6-dihydropyridin-3-yl)-1-phenyl-1H-pyrazol-5-yl)carbamate To a suspension of 5-(5-amino-4-methyl-1-phenyl-1H-pyrazol-3-yl)-1-methylpyridin-2(1H)-one [Intermediate 8] (2.80 g, 9.99 mmol) in EtOAc (120 mL) was added 2N NaOH (14.98 mL, 29.97 mmol) followed by phenyl chloroformate (2.5 mL, 19.98 mmol). The mixture was stirred at ambient temperature for 16 hours then partitioned between water (100 mL) and EtOAc (100 mL) and the aqueous layer extracted with EtOAc (2×50 mL). The combined organic phases were washed with saturated NaHCO$_3$ (50 mL) and brine (50 mL) then dried over Na$_2$SO$_4$, filtered and concentrated to afford the title compound as a pale yellow syrup which was used directly without purification, assuming 100% yield. MS (apci) m/z=401.2 (M+H).

Intermediate 10

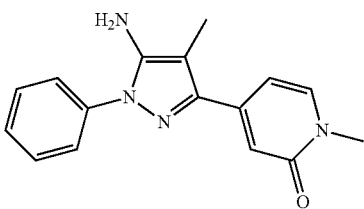

4-(5-amino-4-methyl-1-phenyl-1H-pyrazol-3-yl)-1-methylpyridin-2(1H)-one

Prepared according to the procedure of Intermediate 8, substituting 3-bromo-4-methyl-1-phenyl-1H-pyrazol-5-amine with 5-amino-4-methyl-1-phenyl-1H-pyrazol-3-yl trifluoromethanesulfonate and 1-methyl-5-(4,4,5,5-tetramethyl-1,3,2-dioxaborolan-2-yl)pyridin-2(1H)one with 1-methyl-4-(4,4,5,5-tetramethyl-1,3,2-dioxaborolan-2-yl)pyridin-2(1H)-one. Material was purified by silica column chromatography eluting with 2% MeOH/DCM to afford the title compound (160 mg, 37% yield) as a pink solid. MS (apci) m/z=281.1 (M+H).

Intermediate 11

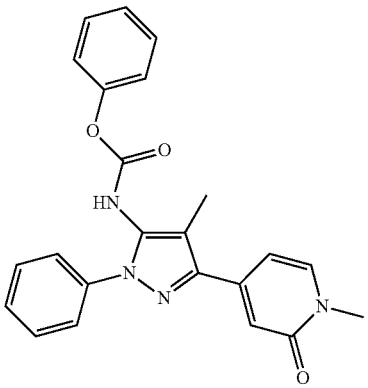

phenyl (4-methyl-3-(1-methyl-2-oxo-1,2-dihydropyridin-4-yl)-1-phenyl-1H-pyrazol-5-yl)carbamate Prepared according to the procedure of Intermediate 9, substituting 5-(5-amino-4-methyl-1-phenyl-1H-pyrazol-3-yl)-1-methylpyridin-2(1H)-one with 4-(5-amino-4-methyl-1-phenyl-1H-pyrazol-3-yl)-1-methylpyridin-2(1H)-one. MS (apci) m/z=401.1 (M+H).

Intermediate 12

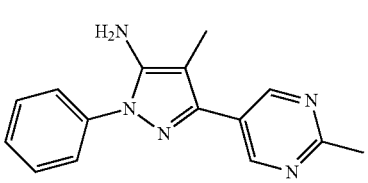

4-methyl-3-(2-methylpyrimidin-5-yl)-1-phenyl-1H-pyrazol-5-amine

5-Amino-4-methyl-1-phenyl-1H-pyrazol-3-yl trifluoromethanesulfonate (900 mg, 2.8 mmol), 2-methyl-5-(4,4, 5,5-tetramethyl-1,3,2-dioxaborolan-2-yl)pyrimidine (925 mg, 4.2 mmol), K₂CO₃ (1.55 g, 11.2 mmol) and Pd(PPh₃)₄ (324 mg, 0.28 mmol) were combined in toluene (10 mL), water (5 mL) and EtOH (2.5 mL) and warmed to 95° C. in a sealed tube for 16 hours. The cooled mixture was filtered and the filtrate partitioned between water (50 mL) and EtOAc (50 mL). The aqueous layer was extracted with EtOAc (2×30 mL) and the combined organic phases were washed with brine (30 mL), dried over Na₂SO₄, filtered and concentrated in vacuo. The residue was purified by silica column chromatography eluting with 2% MeOH/DCM to afford the title compound (533 mg, 72% yield) as a pink solid. MS (apci) m/z=266.1 (M+H).

Intermediate 13

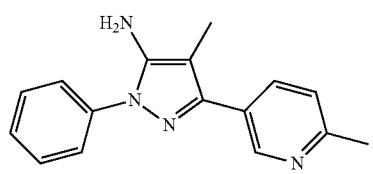

4-methyl-3-(6-methylpyridin-3-yl)-1-phenyl-1H-pyrazol-5-amine

Prepared according to the procedure for Intermediate 12, replacing 2-methyl-5-(4,4,5,5-tetramethyl-1,3,2-dioxaborolan-2-yl)pyrimidine with (6-methylpyridin-3-yl)boronic acid, to afford the title compound (529 mg, 64% yield) as a red solid. MS (apci) m/z=265.1 (M+H).

Intermediate 14

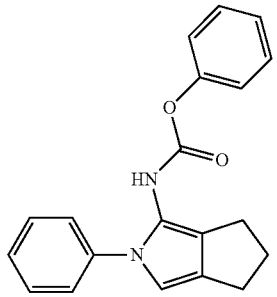

phenyl (2-phenyl-2,4,5,6-tetrahydrocyclopenta[c]pyrazol-3-yl)carbamate

A suspension of 2-phenyl-2,4,5,6-tetrahydrocyclopenta[c]pyrazol-3-amine (Ryan Scientific, Inc., catalog # EN300-14400) (6.0 g, 30.11 mmol) in EtOAc (250 mL) was cooled in ice bath and NaOH (2 N aq, 30.11 mL, 60.23 mmol) added in one portion. PhOCOCl (6.800 mL, 54.20 mmol) was added drop-wise and the reaction was allowed to warm to ambient temperature and stirred for 18 hours. The reaction mixture was diluted with EtOAc (100 mL) and phase-separated. The organic layer was washed with water (2×150 mL) and brine (150 mL), dried (MgSO₄), filtered and concentrated. The crude product was taken up in DCM and concentrated to dryness. The crude solid was triturated with ether/hexanes (2:1, 2×100 mL), filtered and dried, giving the product as an off-white solid (7.4 g, 77%). MS (apci) m/z=320.1 (M+H).

Table 1 provides a list of commercially available pyrazole intermediates can be used in the synthesis of compounds described in the Examples.

TABLE 1

| Pyrazole | Vendor/Catalog# | CAS# |
|---|---|---|
| 5-amino-3-tert-butyl-1-phenyl-1H-pyrazole | Oakwood, 021512 | 126208-61-5 |
| 5-amino-3-tert-butyl-1-(4-methylphenyl)-1H-pyrazole | Array BioPharma, A1075-0 | N/A |
| 5-amino-1-methyl-1H-pyrazole | Maybridge, GK03066 | 1192-21-8 |
| 2-phenyl-2,4,5,6-tetrahydrocyclopenta[c]pyrazol-3-amine | Ryan Scientific, EN300-14400 | 89399-92-8 |
| 5-amino-3-isopropyl-1-phenyl-1H-pyrazole | Oakwood, 021516 | N/A |
| 5-amino-3-tert-butyl-1-methyl-1H-pyrazole | Alfa Aesar, AAB20095-06 | 118430-73-2 |
| 5-amino-1,3-dimethyl-1H-pyrazole | Aldrich, 532223 | 3524-32-1 |
| 5-amino-3-tert-butyl-1-(pyridin-3-yl)-1H-pyrazole | Accela ChemBio Chem Co, SY003755 | 876299-97-7 |

TABLE 1-continued

| Pyrazole | Vendor/Catalog# | CAS# |
|---|---|---|
| (5-tert-butyl-2-(4-fluorophenyl)pyrazol-3-amine) | ChemImpex, 18122 | 778611-16-8 |
| (5-cyclopropyl-2-phenylpyrazol-3-amine) | Oakwood, 017105 | 175137-45-8 |
| (2,5-diphenylpyrazol-3-amine) | Alfa Aesar, AAB20464-06 | 5356-71-8 |
| (5-methyl-2-phenylpyrazol-3-amine) | Aldrich, 541001 | 1131-18-6 |
| (2-methyl-5-phenylpyrazol-3-amine) | Alfa Aesar, AAA15754-06 | 10199-50-5 |
| (1-phenylpyrazol-5-amine) | TCI America, A0174 | 826-85-7 |
| (5-tert-butyl-2-(2-fluorophenyl)pyrazol-3-amine) | Oakwood, 023890 | N/A |
| (5-tert-butyl-2-(3-fluorophenyl)pyrazol-3-amine) | J&W Pharmalab, 68-0035S | 1187931-80-1 |
| (5-cyclopentyl-2-phenylpyrazol-3-amine) | VWR, EN300-09508 | N/A |

TABLE 1-continued

| Pyrazole | Vendor/Catalog# | CAS# |
|---|---|---|
| (1-methyl-cyclopentapyrazol-3-amine) | ChemBridge, 4019184 | 885529-68-0 |
| (2,5-dimethyl-4-phenylpyrazol-3-amine) | ChemBridge, 4001950 | N/A |
| (5-tert-butyl-2-(2-methylphenyl)pyrazol-3-amine) | ChemImpex, 19156 | 337533-96-7 |
| (5-tert-butyl-2-(3-methylphenyl)pyrazol-3-amine) | ChemImpex, 19155 | 898537-77-4 |
| (2-methyl-4-phenylpyrazol-3-amine) | ChemBridge, 4006072 | N/A |
| (5-amino-3-methyl-1-phenylpyrazole-4-carbonitrile) | Oakwood, 005982 | 5346-56-5 |
| (2-phenyl-5-(trifluoromethyl)pyrazol-3-amine) | ChemImpex, 18771 | 182923-55-3 |
| (5-cyclopropyl-2-methylpyrazol-3-amine) | Maybridge, KM00278 | 118430-74-3 |
| (2-methyl-5-(thiophen-2-yl)pyrazol-3-amine) | Maybridge, KM00835 | 118430-78-7 |
| (2-methyl-5-(pyridin-2-yl)pyrazol-3-amine) | ChemBridge, 4015288 | N/A |

TABLE 1-continued

| Pyrazole | Vendor/Catalog# | CAS# |
|---|---|---|
| (H₂N-pyrazole-pyridine, N-methyl) | ChemBridge, 4015289 | N/A |
| (4-F-phenyl pyrazole, N-methyl, NH₂) | Matrix, 020274 | N/A |
| (4-MeO-phenyl pyrazole, N-methyl, NH₂) | Matrix, 019183 | N/A |
| (4-Cl-phenyl pyrazole, N-methyl, NH₂) | Maybridge, KM 04038 | 126417-82-1 |
| (phenyl-dimethyl pyrazole, NH₂) | ChemBridge, 4001950 | N/A |
| (5-amino-4-cyano-3-cyanomethyl-1-phenyl pyrazole) | Lancaster, AAA17470-06 | 7152-40-1 |
| (methyl-ethyl-phenyl pyrazole, NH₂) | ChemBridge, 4010196 | 91642-97-6 |
| (5-amino-1-phenyl-pyrazole-4-carboxylate OEt) | VWR, AAA13296-14 | 16078-71-0 |

N/A = Not available

Intermediate P1

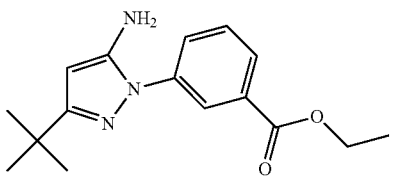

Ethyl 3-(5-amino-3-tert-butyl-1H-pyrazol-1-yl)benzoate

To a suspension of ethyl 3-hydrazinylbenzoate hydrochloride (500 mg, 2.31 mmol) in EtOH (20 mL) was added 4,4-dimethyl-3-oxopentanenitrile (318 mg, 2.54 mmol). The reaction mixture was heated to reflux for 18 hours, then cooled to ambient temperature and concentrated in vacuo. The crude product was purified by silica column chromatography, eluting with 0-5% MeOH/DCM to yield the product as a yellow oil (154 mg, 23% yield). MS (apci) m/z=288.2 (M+H).

The compounds in Table 2 were prepared by the method as described for Intermediate P1, substituting 4,4-dimethyl-3-oxopentanenitrile with the appropriate cyanoketone and ethyl 3-hydrazinylbenzoate hydrochloride with the appropriate hydrazine.

TABLE 2

| Intermediate # | Structure | Data |
|---|---|---|
| P2 | (1-phenyl-3,4-dimethyl-5-amino pyrazole) | MS (apci) m/z = 188.2 (M + H) |
| P3 | (cyclopenta-fused pyrazole with 3-F-phenyl, NH₂) | MS (apci) m/z = 218.1 (M + H) |
| P4 | (cyclopenta-fused pyrazole with 4-F-phenyl, NH₂) | MS (apci) m/z = 218.2 (M + H) |
| P5 | (3-phenyl-1-ethyl-5-amino pyrazole) | MS (apci) m/z = 188.2 (M + H) |
| P6 | (tetrahydroindazole with 2-phenyl, 3-NH₂) | MS (apci) m/z = 214.2 (M + H) |

TABLE 2-continued

| Intermediate # | Structure | Data |
|---|---|---|
| P7 | 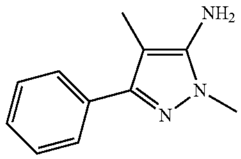 | MS (apci) m/z = 188.2 (M + H) |
| P8 | 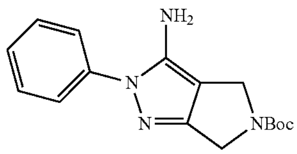 [SMILES: CC(C)(C)OC(=O)N1Cc2nn(-c3ccccc3)c(N)c2C1] | MS (apci) m/z = 301.0 (M + H) |
| P9 | 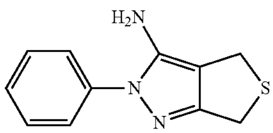 [SMILES: Nc1c2c(nn1-c1ccccc1)CSC2] | MS (apci) m/z = 218.1 (M + H) |
| P10 | 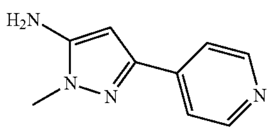 | MS (apci) m/z = 175.2 (M + H) |
| P11 | 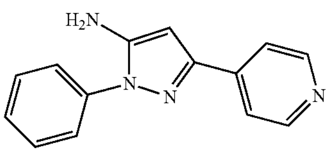 [SMILES: Nc1cc(-c2ccncc2)nn1-c1ccccc1] | MS (apci) m/z = 237.3 (M + H) |
| P12 | 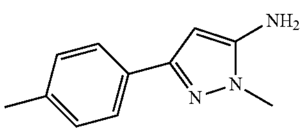 | MS (apci) m/z = 188.2 (M + H) |
| P13 | 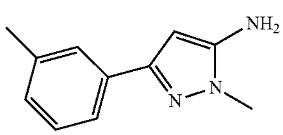 | MS (apci) m/z = 188.2 (M + H) |
| P14 | 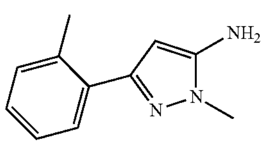 | MS (apci) m/z = 188.2 (M + H) |
| P15 | 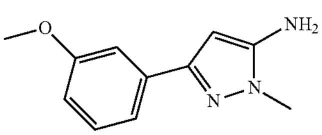 | MS (apci) m/z = 204.2 (M + H) |
| P16 | 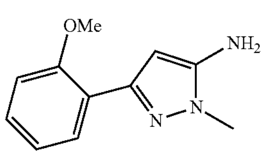 | MS (apci) m/z = 204.2 (M + H) |
| P17 | | MS (apci) m/z = 199.0 (M + H) |
| P18 | | MS (apci) m/z = 199.1 (M + H) |
| P19 | | MS (apci) m/z = 192.2 (M + H) |
| P20 | | MS (apci) m/z = 192.2 (M + H) |
| P21 | | MS (apci) m/z = 232.2 (M + H) |
| P22 | | MS (apci) m/z = 204.2 (M + H) |
| P23 | | MS (apci) m/z = 206.1 (M + H) |

Intermediate P101

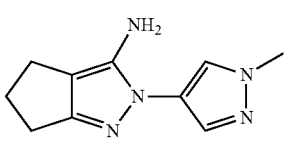

2-(1-methyl-1H-pyrazol-4-yl)-2,4,5,6-tetrahydrocyclopenta-[c]pyrazol-3-amine

Step A: Preparation of di-tert-butyl 1-(1-methyl-1H-pyrazol-4-yl)hydrazine-1,2-dicarboxylate To a solution of 4-bromo-1-methyl-1H-pyrazole (1.93 mL, 18.6 mmol) in ether (37.3 mL) cooled to −78° C. was added nBuLi (23.3 mL, 37.3 mmol). After stirring at −78° C. for 30 minutes, a solution of di-t-butyl azodicarboxylate (4.29 g, 18.6 mmol) in Et$_2$O (37.3 mL, 18.6 mmol) was added dropwise. After 1 hour, the reaction mixture was warmed up to −20° C. and quenched with ice. After warming to ambient temperature, the mixture was filtered and rinsed with Et$_2$O. The resulting solid was taken up in a mixture of DCM and water, and the mixture was phase separated. The organic layer was dried with MgSO$_4$, filtered and concentrated in vacuo to afford the first batch of product as a white solid (1.64 g, 28% yield). A second batch of product was recovered from the filtrate by silica column chromatography, eluting with 40-60% hexanes/EtOAc (0.51 g, 8.8% yield). MS (apci) m/z=313.0 (M+H).

Step B: Preparation of 2-(1-methyl-1H-pyrazol-4-yl)-2,4,5,6-tetrahydrocyclopenta-[c]pyrazol-3-amine To a solution of di-tert-butyl 1-(1-methyl-1H-pyrazol-4-yl)hydrazine-1,2-dicarboxylate (103 mg, 0.330 mmol) in EtOH (1.65 mL, 0.330 mmol) was added concentrated HCl (137 μL, 1.65 mmol). The mixture was stirred at ambient temperature for 5 minutes, then cooled in an ice bath followed by addition of 2-oxocyclopentanecarbonitrile (36.0 mg, 0.330 mmol). After stirring for 5 minutes, the reaction mixture was warmed to ambient temperature overnight. The reaction mixture was concentrated and partitioned in water and DCM. After phase-separation, the aqueous layer was basified (pH 10) and then extracted with DCM (3×10 mL). The combined organic extracts were dried with MgSO$_4$, filtered and concentrated in vacuo. The crude material was purified by reverse-phase column chromatography, eluting with 0-100% acetonitrile/water to afford the product as a yellow solid (4.5 mg, 6.7% yield). MS (apci) m/z=204.1 (M+H).

Intermediate P102

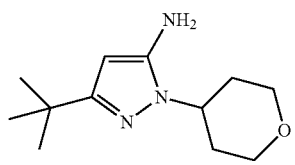

3-tert-butyl-1-(tetrahydro-2H-pyran-4-yl)-1H-pyrazol-5-amine

Step A: Preparation of (tetrahydro-2H-pyran-4-yl)hydrazine hydrochloride

A suspension of dihydro-2H-pyran-4(3H)-one (2.00 g, 20.0 mmol) and tert-butyl hydrazinecarboxylate (2.64 g, 20.0 mmol) in hexanes (20.0 mL) was refluxed for 2 hours. After cooling, BH$_3$-THF complex (20.0 mL, 20.0 mmol) was added and the reaction mixture was stirred for 1 hour. The mixture was then treated with 4 N HCl in dioxane (20.0 mL, 79.9 mmol), followed by 3 drops of water. After stirring at ambient temperature for 1 hour, the reaction mixture was filtered and rinsed with EtOAc to afford the product as a solid (2.39 g, 78.4% yield). MS (apci) m/z=117.0 (M+H).

Step B: Preparation of 3-tert-butyl-1-(tetrahydro-2H-pyran-4-yl)-1H-pyrazol-5-amine Prepared by the method as described in for the preparation of Intermediate P1, substituting (tetrahydro-2H-pyran-4-yl)hydrazine dihydrochloride for ethyl 3-hydrazinylbenzoate hydrochloride to yield the product as a yellow oil (0.472 g, 99.9% yield). MS (apci) m/z=224.1 (M+H).

Intermediate P103

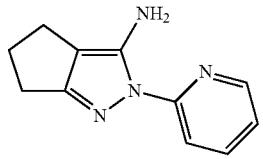

2-(pyridin-2-yl)-2,4,5,6-tetrahydrocyclopenta[c]pyrazol-3-amine

Step A: Preparation of 2-(2-(pyridin-2-yl)hydrazono)cyclopentanecarbonitrile

A solution of 2-hydrazinylpyridine (0.200 g, 1.83 mmol) and 2-oxocyclopentanecarbonitrile (0.200 g, 1.83 mmol) in MeOH (9.16 mL) was treated with concentrated HCl (0.764 mL, 9.16 mmol) and refluxed for 16 hours. The reaction mixture was concentrated in vacuo, and then partitioned in water and DCM. After phase-separation, the aqueous layer was washed with DCM, basified (saturated NaHCO$_3$, pH 10), and extracted with DCM. The combined organic layers were dried with MgSO$_4$, filtered and concentrated. The crude material was purified by silica column chromatography, eluting with 100% EtOAc to afford the product (0.289 g, 78.6% yield). MS (apci) m/z=201.2 (M+H).

Step B: Preparation of 2-(pyridin-2-yl)-2,4,5,6-tetrahydrocyclopenta[c]pyrazol-3-amine A solution of 2-(2-(pyridin-2-yl)hydrazono)cyclopentanecarbonitrile (0.243 g, 1.21 mmol) in EtOH (6.06 mL, 1.21 mmol) was treated with 6 M HCl (0.202 mL, 1.21 mmol) and refluxed for 3 days. After removal of the solvent, the crude residue was diluted in water, basified (saturated NaHCO$_3$, pH 10) and extracted with DCM. The combined organic layers were dried with MgSO$_4$, filtered and concentrated. The crude material was purified by silica column chromatography, eluting with 50% EtOAc/hexanes to afford the product (0.198 g, 81.6% yield). MS (apci) m/z=201.2 (M+H).

Intermediate P104

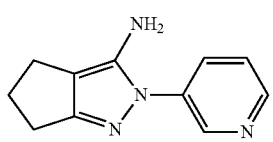

2-(pyridin-3-yl)-2,4,5,6-tetrahydrocyclopenta[c]pyrazol-3-amine

Prepared by the method described above for Intermediate P103, substituting 3-hydrazinylpyridine for 2-hydrazinylpyridine to afford the title product. MS (apci) m/z=201.1 (M+H).

Intermediate P105

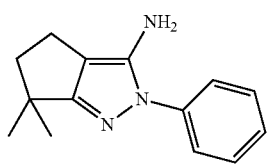

6,6-dimethyl-2-phenyl-2,4,5,6-tetrahydrocyclopenta[c]pyrazol-3-amine

Step A: Preparation of 5-chloro-2,2-dimethylpentanenitrile

Isobutyronitrile (1.38 g, 20.0 mmol) and 1-bromo-3-chloropropane (3.46 g, 22.0 mmol) were sequentially added to a 1 M solution of lithium bis(trimethylsilyl)amide (20.0 mL, 20.0 mmol) while stirring. After stirring at 70° C. for 16 hours, the reaction mixture was quenched with water then extracted with DCM. The combined organic layers were dried with $MgSO_4$, filtered and concentrated in vacuo to afford 5-chloro-2,2-dimethylpentanenitrile (2.91 g, 100% yield). NMR ($CDCl_3$) δ 3.57-3.61 (m, 2H), 1.94-2.02 (m, 2H), 1.67-1.72 (m, 2H), 1.37 (s, 6H).

Step B: Preparation of 2,2-dimethylhexanedinitrile

A suspension of 5-chloro-2,2-dimethylpentanenitrile (2.91 g, 20.0 mmol) and NaCN (1.57 g, 32.0 mmol) in DMF (20.0 mL) and water (1 mL) was heated at 100° C. for 16 hours. After cooling, the reaction mixture was diluted with water and refluxed for 30 minutes, then cooled, poured into water and stirred for 3 hours. The solution was then extracted with $Et_2O$. The combined $Et_2O$ extracts were washed with $H_2O$, dried with $MgSO_4$, filtered and concentrated in vacuo to afford the product (2.20 g, 80.7% yield). $^1H$ NMR ($CDCl_3$) δ 2.42-2.47 (m, 2H), 1.83-1.92 (m, 2H), 1.67-1.72 (m, 2H), 1.39 (s, 6H).

Step C: Preparation of 3,3-dimethyl-2-oxocyclopentanecarbonitrile

A suspension of KOtBu (0.511 g, 4.55 mmol) in toluene (18.4 mL) was treated a toluene (2.0 mL) solution of 2,2-dimethylhexanedinitrile (1.00 g, 7.34 mmol) and heated at 80° C. for 2 hours. The reaction mixture was then cooled to ambient temperature and quenched with water. The mixture was separated and the organic layer was stirred in 2 N HCl (20 mL) for 16 hours. The mixture was separated and the organic layer dried with $MgSO_4$, filtered and concentrated in vacuo to a yellow-white solid. The crude solid was purified by silica column chromatography, eluting with 10-40% EtOAc/hexanes, to afford the product (0.250 g, 24.8% yield). $^1H$ NMR ($CDCl_3$) δ 3.20-3.26 (m, 1H), 2.38-2.47 (m, 1H), 2.14-2.25 (m, 1H), 1.97-2.05 (m, 1H), 1.74-1.83 (m, 1H), 1.14 (s, 6H).

Step D: Preparation of 6,6-dimethyl-2-phenyl-2,4,5,6-tetrahydrocyclopenta[c]pyrazol-3-amine Prepared by the method as described for Intermediate P1, substituting phenylhydrazine for ethyl 3-hydrazinylbenzoate hydrochloride and 3,3-dimethyl-2-oxocyclopentanecarbonitrile for 4,4-dimethyl-3-oxopentanenitrile to afford the product (0.192 g, 46.2% yield) as a yellow solid. MS (apci) m/z=228.2 (M+H).

Intermediate P106

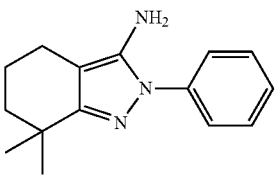

7,7-dimethyl-2-phenyl-4,5,6,7-tetrahydro-2H-indazol-3-amine

Step A: Preparation of 2,2-dimethylheptanedinitrile

Prepared by the method as described for Intermediate P105, Steps A and B, substituting 1-bromo-4-chlorobutane for 1-bromo-3-chloropropane to yield the product (2.21 g, 73.7% yield). $^1H$ NMR ($CDCl_3$) δ 2.37-2.42 (m, 2H), 1.53-1.77 (m, 6H), 1.36 (s, 6H).

Step B: Preparation of 3,3-dimethyl-2-oxocyclohexanecarbonitrile

A suspension of KOtBu (0.463 g, 4.13 mmol) in toluene (16.6 mL) was treated with a solution of 2,2-dimethylheptanedinitrile (1.00 g, 6.66 mmol) in toluene (2.0 mL) and heated at 80° C. for 48 hours. After cooling to ambient temperature, the reaction mixture was quenched with water and phase-separated, and the organic layer was stirred with 2 N HCl (20 mL) for 16 hours. After phase-separation, the organic layer was dried with $MgSO_4$, filtered and concentrated in vacuo. The crude material was purified by silica column chromatography, eluting with 10-20% EtOAc/hexanes to afford the product (0.374 g, 37.2% yield). $^1H$ NMR ($CDCl_3$) δ 3.72-3.78 (m, 1H), 2.42-2.50 (m, 1H), 1.78-2.04 (m, 4H), 1.60-1.70 (m, 1H), 1.21 (s, 3H), 1.16 (s, 3H).

Step C: Preparation of 7,7-dimethyl-2-phenyl-4,5,6,7-tetrahydro-2H-indazol-3-amine Prepared by the method as described for Intermediate P1, substituting phenylhydrazine for ethyl 3-hydrazinylbenzoate hydrochloride and 3,3-dimethyl-2-oxocyclohexanecarbonitrile for 4,4-dimethyl-3-oxopentanenitrile to yield the product as an off-white solid (0.490 g, 54.2% yield, 66% purity). MS (apci) m/z=242.2 (M+H).

Intermediate P107

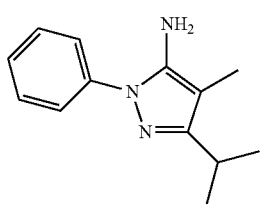

3-isopropyl-4-methyl-1-phenyl-1H-pyrazol-5-amine

Step A: Preparation of
2,4-dimethyl-3-oxopentanenitrile

To a solution of propiononitrile (518 mg, 9.40 mmol) in THF (50 mL, 7.83 mmol) at −78° C. under $N_2$ was slowly added lithium bis(trimethylsilyl)amide (1M in THF) (7.83 mL, 7.83 mmol). After 30 minutes, methyl isobutyrate (0.898 mL, 7.83 mmol) was added dropwise, and the reaction mixture was warmed to 0° C. A yellow precipitate formed, the reaction mixture was stirred for 1 hour, then diluted with $H_2O$ (50 mL) to dissolve the solids. The mixture was extracted with $Et_2O$ (25 mL), and the basic aqueous phase was acidified with 2M HCl (5 mL) and extracted with $Et_2O$ (2×50 mL). The combined organic phases were washed with brine (50 mL), dried with $MgSO_4$, filtered, and concentrated to afford the product (421 mg, 42.9% yield)

Step B: Preparation of
3-isopropyl-4-methyl-1-phenyl-1H-pyrazol-5-amine

Prepared by the method as described for Intermediate P1, substituting phenyl hydrazine for ethyl 3-hydrazinylbenzoate hydrochloride and 4,4-dimethyl-3-oxopentanenitrile with 2,4-dimethyl-3-oxopentanenitrile to yield the product as a yellow syrup (0.587 g, 81.1% yield). MS (apci) m/z=216.2 (M+H).

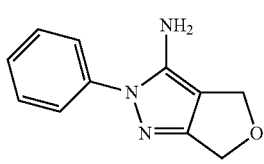

Intermediate P108

2-phenyl-4,6-dihydro-2H-furo[3,4-c]pyrazol-3-amine

Step A: Preparation of
4-oxotetrahydrofuran-3-carbonitrile

To a suspension of KOtBu (996.6 mg, 8.881 mmol) in THF (640.4 mg, 8.881 mmol) cooled to 0° C. was added dropwise methyl 2-hydroxyacetate (675.7 µL, 8.881 mmol) and stirred for 10 minutes. The acrylonitrile (589.1 µL, 8.881 mmol) was then added and the reaction stirred at ambient temperature. After 3 hours, the reaction was diluted with $H_2O$ (50 mL), then extracted with $Et_2O$ (25 mL) to remove any starting ester. The basic aqueous phase was acidified with 2M HCl (5 mL), then extracted with $Et_2O$ (2×50 mL). The combined organic phases were dried with $MgSO_4$, filtered, and concentrated to afford a light brown oil (446 mg, 45.2% yield). $^1$H NMR (CDCl$_3$) δ 4.63 (t, 1H), 4.24 (t, 1H), 4.14 (d, 1H), 4.02 (d, 1H), 3.57 (t, 1H).

Step B: Preparation of 2-phenyl-4,6-dihydro-2H-furo[3,4-c]pyrazol-3-amine

Prepared by the method as described for Intermediate P1, substituting phenyl hydrazine for ethyl 3-hydrazinylbenzoate hydrochloride and 4,4-dimethyl-3-oxopentanenitrile with 4-oxotetrahydrofuran-3-carbonitrile to yield the product as a reddish-brown syrup (182 mg, 22.5% yield). MS (apci) m/z=202.1 (M+H).

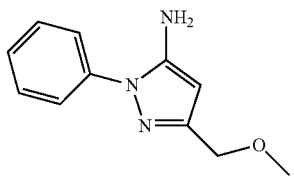

Intermediate P109

3-(methoxymethyl)-1-phenyl-1H-pyrazol-5-amine

Step A: Preparation of
4-methoxy-3-oxobutanenitrile

To a solution of methyl 2-methoxyacetate (0.4753 mL, 4.803 mmol) in THF (20 mL, 4.803 mmol) at −78° C. under $N_2$ was added acetonitrile (0.3033 mL, 5.763 mmol), followed by lithium bis(trimethylsilyl)amide (1M in THF) (4.803 mL, 4.803 mmol). After stirring 1 hour, the reaction mixture was warmed to 0° C. and stirred for 1 hour. The reaction mixture was then diluted with $H_2O$ (25 mL), washed with $Et_2O$ (25 mL), then neutralized with 2 M HCl (1.5 mL). This was extracted with $Et_2O$ (2×25 mL) and the combined organic phases were washed with brine (25 mL), dried with $MgSO_4$, filtered, and concentrated to afford the product (169 mg, 31.1% yield). $^1$H NMR (CDCl$_3$) δ 4.09 (s, 2H), 3.66 (s, 2H), 3.46 (s, 3H)

Step B: Preparation of
3-(methoxymethyl)-1-phenyl-1H-pyrazol-5-amine

Prepared by the method as described for Intermediate P1, substituting phenyl hydrazine for ethyl 3-hydrazinylbenzoate hydrochloride and 4,4-dimethyl-3-oxopentanenitrile with 4-methoxy-3-oxobutanenitrile to yield the product as a pale yellow residue (6.0 mg, 2.0% yield). MS (apci) m/z=204.0 (M+H).

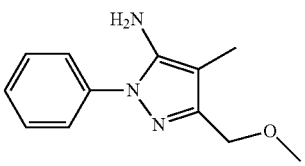

Intermediate P110

3-(methoxymethyl)-4-methyl-1-phenyl-1H-pyrazol-5-amine

Prepared according to the method as described for Intermediate P109, replacing acetonitrile with propionitrile to afford the product as an orange residue. MS (apci) m/z=218.0 (M+H).

Intermediate P111

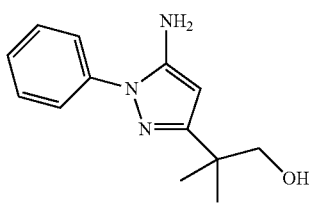

2-(5-amino-1-phenyl-1H-pyrazol-3-yl)-2-methylpropan-1-ol

Step A: Preparation of methyl 3-(tert-butyldimethylsilyloxy)-2,2-dimethylpropanoate Methyl 3-hydroxy-2,2-dimethylpropanoate (1.000 g, 7.567 mmol), TBDMS-Cl (1.140 g, 7.567 mmol) and imidazole (0.5666 g, 8.323 mmol) were dissolved in DMF (5 mL, 7.567 mmol) and stirred at ambient temperature overnight. The reaction mixture was diluted with H$_2$O (25 mL) and extracted with EtOAc (2×25 mL). The combined organic phases were washed with brine (25 mL), dried with MgSO$_4$, filtered and concentrated to afford the product (1.92 g, 103% yield). $^1$H NMR (CDCl$_3$) δ 3.66 (s, 3H), 3.57 (s, 2H), 1.15 (s, 6H), 0.87 (s, 9H), 0.02 (s, 6H).

Step B: Preparation of 5-(tert-butyldimethylsilyloxy)-4,4-dimethyl-3-oxopentanenitrile Prepared according to the method described for Intermediate P109, replacing methyl 2-methoxyacetate with methyl 3-(tert-butyldimethylsilyloxy)-2,2-dimethylpropanoate to afford the product as a pale yellow residue. $^1$H NMR (CDCl$_3$) δ 3.70 (s, 2H), 3.55 (s, 2H), 1.15 (s, 6H), 0.89 (s, 9H), 0.06 (s, 6H).

Step C: Preparation of 2-(5-amino-1-phenyl-1H-pyrazol-3-yl)-2-methylpropan-1-ol

Prepared by the method as described for Intermediate P1, substituting phenyl hydrazine for ethyl 3-hydrazinylbenzoate hydrochloride and 4,4-dimethyl-3-oxopentanenitrile with methyl 3-(tert-butyldimethylsilyloxy)-2,2-dimethylpropanoate to yield the product as yellow syrup (74 mg, 66% yield). MS (apci) m/z=232.2 (M+H).

Intermediate P112

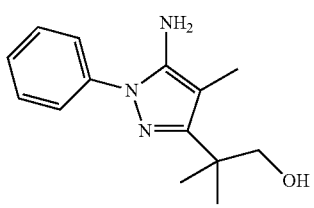

2-(5-amino-4-methyl-1-phenyl-1H-pyrazol-3-yl)-2-methylpropan-1-ol

Prepared according to the method described for Intermediate P111, replacing acetonitrile with propionitrile to afford the product as a yellow residue. MS (apci) m/z 246.2 (M+H).

Intermediate P113

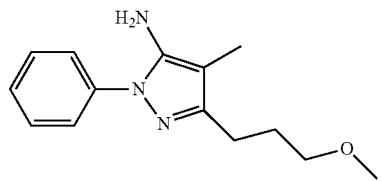

3-(3-methoxypropyl)-4-methyl-1-phenyl-1H-pyrazol-5-amine

Prepared according to the method described for Intermediate P109, replacing methyl 2-methoxyacetate with methyl 4-methoxybutanoate and replacing acetonitrile with propionitrile in Step A to afford the product as an orange-brown syrup. MS (apci) m/z=246.1 (M+H).

Intermediate P114

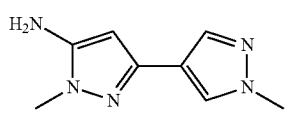

1,1'-dimethyl-1H,1'H-3,4'-bipyrazol-5-amine

Step A: Preparation of 3-(1-methyl-1H-pyrazol-4-yl)-3-oxopropanenitrile

A solution of ethyl 1-methyl-1H-pyrazole-4-carboxylate (500 mg, 3.24 mmol), toluene (7.50 mL, 70.4 mmol), and acetonitrile (346 μL, 6.49 mmol) was treated in one portion with KOtBu (1092 mg, 9.73 mmol) to give a hazy solution. The reaction was allowed to stir at ambient temperature for one hour, and was determined to be complete by HPLC analysis. The mixture was treated with water (7.5 mL) and stirred for 1 minute, then acidified with 3M HCl (3027 μL, 9.08 mmol) to pH 5.5-6. The aqueous layer was extracted with ethyl acetate (3×5 mL) and the combined organic extracts were concentrated in vacuo to give a yellow viscous oil, which completely solidified upon placing under high vacuum to afford the product (102 mg, 21.1% yield). $^1$H NMR (CDCl$_3$) δ 8.02 (s, 1H), 7.94 (s, 1H), 3.98 (s, 3H), 3.82 (s, 2H)

Step B: Preparation of 1,1'-dimethyl-1H,1'H-3,4'-bipyrazol-5-amine

Prepared by the method as described for Intermediate P1, substituting methyl hydrazine for ethyl 3-hydrazinylbenzoate hydrochloride and replacing 4,4-dimethyl-3-oxopentanenitrile with 3-(1-methyl-1H-pyrazol-4-yl)-3-oxopropanenitrile to yield the product as an ivory white solid (45 mg, 44.6% yield). MS (apci) m/z=178.1 (M+H).

Intermediate P115

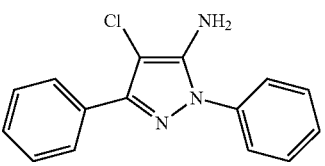

4-chloro-1,3-diphenyl-1H-pyrazol-5-amine

To a solution of 1,3-diphenyl-1H-pyrazol-5-amine (Table 1; 0.100 g, 0.425 mmol) in acetonitrile (2 mL) was added N-chlorosuccinimide (0.0568 g, 0.425 mmol). The pale yellow solution was stirred at ambient temperature for 3 hours, then concentrated in vacuo and purified by silica column chromatography eluting with 20% EtOAc/Hexanes to afford the product as a light brown oil (0.10 g, 87% yield). MS (apci) m/z=270.0 (M+H).

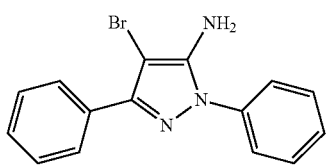

Intermediate P116

4-bromo-1,3-diphenyl-1H-pyrazol-5-amine

Prepared according to the procedure described for Intermediate P115, substituting N-chloro succinimide with N-bromo-succinimide. MS (apci) m/z=313.9 (M+H).

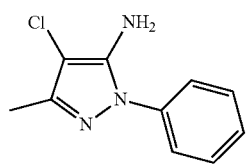

Intermediate P117

4-chloro-3-methyl-1-phenyl-1H-pyrazol-5-amine

Prepared according to the procedure described for Intermediate P115, substituting 1,3-diphenyl-1H-pyrazol-5-amine with 3-methyl-1-phenyl-1H-pyrazol-5-amine. MS (apci) m/z=207.9 (M+H).

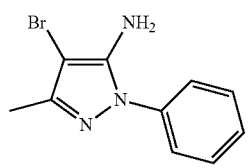

Intermediate P118

4-bromo-3-methyl-1-phenyl-1H-pyrazol-5-amine

Prepared according to the procedure described for Intermediate P117, substituting N-chloro succinimide with N-bromo-succinimide. MS (apci) m/z=251.9 (M+H).

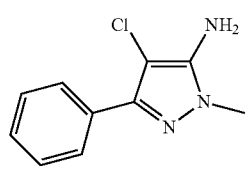

Intermediate P119

4-chloro-1-methyl-3-phenyl-1H-pyrazol-5-amine

Prepared according to the procedure described for Intermediate P115, substituting 1,3-diphenyl-1H-pyrazol-5-amine with 1-methyl-3-phenyl-1H-pyrazol-5-amine (Table 1). MS (apci) m/z=208.0 (M+H).

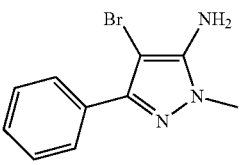

Intermediate P120

4-bromo-1-methyl-3-phenyl-1H-pyrazol-5-amine

Prepared according to the procedure described for Intermediate P119, substituting N-chloro succinimide with N-bromo-succinimide. MS (apci) m/z=251.9 (M+H).

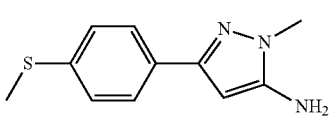

Intermediate P121

1-methyl-3-(4-(methylthio)phenyl)-1H-pyrazol-5-amine

Step A: Preparation of 3-(4-(methylthio)phenyl)-3-oxopropanenitrile

To a suspension of NaH (60% in mineral oil) (154 mg, 3.84 mmol) in dioxane (25.0 mL, 2.74 mmol) was added acetonitrile (0.217 mL, 4.12 mmol). The reaction mixture was stirred at ambient temperature for 30 minutes, then treated with methyl 4-(methylthio)benzoate (500 mg, 2.74 mmol) and heated to reflux for 15 hours. The suspension was cooled, then diluted with water (25 mL) and washed with $Et_2O$ (25 mL). The aqueous layer was neutralized with 2M HCl (1.8 mL) and extracted with $Et_2O$ (2×25 mL). The combined organic phases were washed with brine (25 mL), dried with $MgSO_4$, filtered and concentrated in vacuo. The resultant residue was purified by silica column chromatography eluting with 0-5% MeOH/DCM to afford the product (317 mg, 60.4% yield). $^1H$ NMR ($CDCl_3$) δ 7.82 (d, 2H), 7.30 (d, 2H), 4.02 (s, 2H), 2.54 (s, 3H).

Step B: Preparation of 1-methyl-3-(4-(methylthio)phenyl)-1H-pyrazol-5-amine Prepared by the method as described in Intermediate P1, substituting methylhydrazine for ethyl 3-hydrazinylbenzoate hydrochloride and substituting 3-(4-(methylthio)phenyl)-3-oxopropanenitrile for 4,4-dimethyl-3-oxopentanenitrile to yield the product as a yellow solid (0.307 g, 96.7% yield). MS (apci) m/z=220.0 (M+H).

Intermediate P122

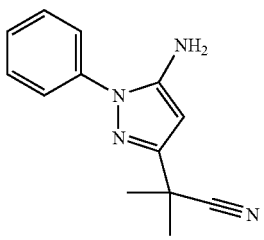

2-(5-amino-1-phenyl-1H-pyrazol-3-yl)-2-methylpropanenitrile

Prepared according to the procedure for Intermediate P121, substituting methyl 4-(methylthio)benzoate with ethyl 2-cyano-2-methylpropanoate in Step A and phenyl hydrazine hydrochloride for methyl hydrazine in Step B. MS (apci) m/z=227.1 (M+H).

Intermediate P123

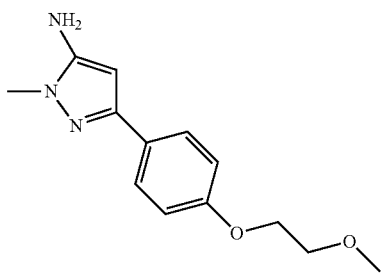

3-(4-(2-methoxyethoxy)phenyl)-1-methyl-1H-pyrazol-5-amine

Step A: Preparation of 3-(4-(benzyloxy)phenyl)-3-oxopropanenitrile

Prepared according to the procedure described for Intermediate P121, substituting methyl 4-(methylthio)benzoate with methyl 4-(benzyloxy)benzoate in Step A. $^1$H NMR (CDCl$_3$) δ 7.90 (d, 2H), 7.42 (m, 4H), 7.37 (m, 1H), 7.05 (d, 2H), 5.16 (s, 2H), 4.00 (s, 2H).

Step B: Preparation of 3-(4-(benzyloxy)phenyl)-1-methyl-1H-pyrazol-5-amine

Prepared by the method as described for Intermediate P1, substituting methylhydrazine for ethyl 3-hydrazinylbenzoate hydrochloride and 3-(4-(benzyloxy)phenyl)-3-oxopropanenitrile for 4,4-dimethyl-3-oxopentanenitrile to yield the product as a yellow solid. MS (apci) m/z=280.1 (M+H).

Step C: Preparation of 4-(5-amino-1-methyl-1H-pyrazol-3-yl)phenol

To a solution of 3-(4-(benzyloxy)phenyl)-1-methyl-1H-pyrazol-5-amine (47 mg, 0.17 mmol) in EtOH (5.0 mL) was added 5% Pd/C (9.0 mg, 0.0084 mmol) and stirred under a H$_2$ balloon for 17 hours. The reaction mixture was filtered through Celite®, rinsed with EtOH and concentrated in vacuo to afford the product (28 mg, 88% yield). MS (apci) m/z=190.1 (M+H).

Step D: Preparation of 3-(4-(2-methoxyethoxy)phenyl)-1-methyl-1H-pyrazol-5-amine To a solution of 4-(5-amino-1-methyl-1H-pyrazol-3-yl)phenol (14 mg, 0.074 mmol) in DMSO (0.50 mL, 7.0 mmol) was added Cs$_2$CO$_3$ (48 mg, 0.15 mmol) and 1-bromo-2-methoxyethane (9.7 µL, 0.10 mmol). The reaction mixture was stirred for 16 hours, then diluted with water (10 mL) and extracted with DCM (3×10 mL). The combined organic extracts were washed with brine (10 mL), dried with MgSO$_4$, filtered and concentrated to afford the crude product (22 mg, 120% yield). The crude product was used without purification in subsequent steps. MS (apci) m/z=248.0 (M+H).

Intermediate P124

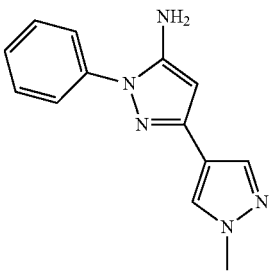

1'-methyl-1-phenyl-1H,1'H-3,4'-bipyrazol-5-amine

Prepared according to the procedure described for Intermediate P114, substituting methylhydrazine with phenylhydrazine in Step B. MS (apci) m/z=240.0 (M+H).

Intermediate P125

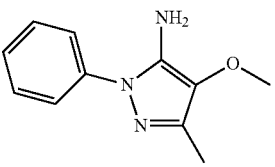

4-methoxy-3-methyl-1-phenyl-1H-pyrazol-5-amine

Prepared according to the procedure for Intermediate P121, substituting methyl 4-(methylthio)benzoate with ethyl acetate and substituting acetonitrile with 2-methoxyacetonitrile in Step A and phenyl hydrazine hydrochloride for methyl hydrazine in Step B. MS (apci) m/z=204.0 (M+H).

Intermediate P126

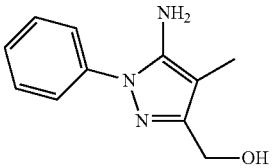

(5-amino-4-methyl-1-phenyl-1H-pyrazol-3-yl)methanol

Prepared according to the procedure for Intermediate P112, substituting methyl 3-hydroxy-2,2-dimethylpropanoate with ethyl 2-hydroxyacetate in Step A. MS (apci) m/z=204.1 (M+H).

Intermediate P127

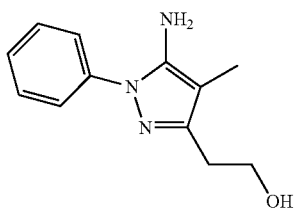

2-(5-amino-4-methyl-1-phenyl-1H-pyrazol-3-yl)ethanol

Prepared according to the procedure for Intermediate P112, substituting methyl 3-hydroxy-2,2-dimethylpropanoate with methyl 3-hydroxypropanoate in Step A. MS (apci) m/z=218.0 (M+H).

Intermediate P128

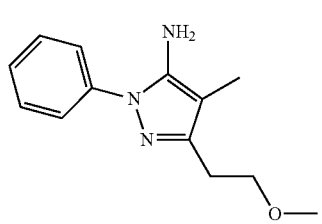

3-(2-methoxyethyl)-4-methyl-1-phenyl-1H-pyrazol-5-amine

Step A: Preparation of 5-methoxy-2-methyl-3-oxopentanenitrile

To a suspension of NaNH$_2$ (50 wt % suspension in toluene) (330 mg, 4.23 mmol) in THF (25 mL, 4.23 mmol) under N$_2$ at −78° C. was added propiononitrile (0.448 mL, 6.35 mmol), and the reaction mixture was stirred for 30 minutes. Methyl 3-methoxypropanoate (0.495 mL, 4.23 mmol) was added and the reaction mixture was stirred at −78° C. for 1 hour, then at 0° C. for 2.5 hours. The reaction mixture was diluted with H$_2$O (25 mL) and washed with Et$_2$O (25 mL). The basic aqueous phase was neutralized with 2M HCl (1.6 mL), then extracted with Et$_2$O (3×25 mL). The combined organic phases were washed with brine (25 mL), dried with MgSO$_4$, filtered, and concentrated to afford the crude product as a pale greenish oil (171 mg). The crude mixture was taken directly to the next step.

Step B: Preparation of 3-(2-methoxyethyl)-4-methyl-1-phenyl-1H-pyrazol-5-amine

Prepared by the method as described for Intermediate P1, substituting 5-methoxy-2-methyl-3-oxopentanenitrile for 4,4-dimethyl-3-oxopentanenitrile and substituting phenylhydrazine hydrochloride for ethyl 3-hydrazinylbenzoate hydrochloride to yield the product as a yellow solid (56 mg, 20% yield). MS (apci) m/z=232.0 (M+H).

Intermediate P129

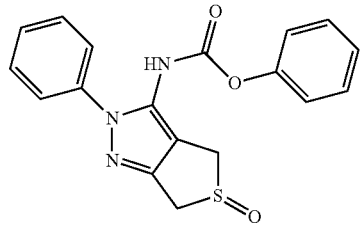

Phenyl (5-oxido-2-phenyl-4,6-dihydro-2H-thieno[3,4-c]pyrazol-3-yl)carbamate

A THF (4 mL) solution of phenyl 2-phenyl-4,6-dihydro-2H-thieno[3,4-c]pyrazol-3-ylcarbamate (Intermediate P130, Step B; 50 mg, 0.15 mmol) was cooled to −50° C. with an external dry-ice/MeCN bath and treated with a THF (2 mL) solution of 3-chlorobenzoperoxoic acid (33 mg, 0.13 mmol). After stirring for 1 hour, the mixture was quenched with Na$_2$S$_2$O$_3$ and water, extracted with EtOAc, washed with NaHCO$_3$ and brine, dried with MgSO$_4$, filtered, and concentrated to give the product which was directly used in next step without further purification. MS (apci) m/z=354.1 (M+H).

Intermediate P130

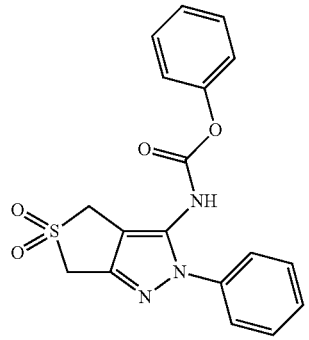

Phenyl (5,5-dioxido-2-phenyl-4,6-dihydro-2H-thieno[3,4-c]pyrazol-3-yl)carbamate

Step A: Preparation of 2-phenyl-4,6-dihydro-2H-thieno[3,4-c]pyrazol-3-amine

A suspension of 4-oxotetrahydrothiophene-3-carbonitrile (1.00 g, 7.86 mmol) and phenylhydrazine hydrochloride (1.25 g, 8.65 mmol) in absolute EtOH (40 mL) was refluxed for 2 hours. After removal of solvent under reduced pressure, the white solid residue was triturated with 1 N NaOH (40 mL). The solid was collected by filtration, washed with 0.1 N NaOH, water, and hexanes (approx. 10 mL each) then dried on high vacuum to yield the product as white solid (1.6 g, 95% yield). MS (apci pos) m/z=218.1 (M+H).

Step B: Preparation of phenyl 2-phenyl-4,6-dihydro-2H-thieno[3,4-c]pyrazol-3-ylcarbamate To a suspension of 2-phenyl-4,6-dihydro-2H-thieno[3,4-c]pyrazol-3-amine (500 mg, 2.30 mmol) in EtOAc (10 mL)

was added NaOH (2M aq, 2.3 mL, 4.60 mmol), followed by dropwise addition of phenyl carbonochloridate (0.400 mL, 3.22 mmol). After stirring at ambient temperature for 2 hours, another portion of phenyl carbonochloridate (0.16 mL, 1.3 mmol) was added dropwise, and the reaction was stirred at ambient temperature for 15 hours. The reaction mixture was diluted with EtOAc (20 mL) and phase-separated. The organic phase was washed with H$_2$O, brine (25 mL each), then dried with Na$_2$SO$_4$, filtered and concentrated. The crude material was purified by reverse-phase column chromatography, eluting with 5-70% acetonitrile/water to yield the product as white solid (0.5 g, 64% yield). MS (apci pos) m/z=338.1 (M+H).

Step C: Preparation of phenyl (5,5-dioxido-2-phenyl-4,6-dihydro-2H-thieno[3,4-c]pyrazol-3-yl)carbamate To a turbid solution of phenyl 2-phenyl-4,6-dihydro-2H-thieno[3,4-c]pyrazol-3-ylcarbamate (50 mg, 0.15 mmol) in DCM (1.5 mL) at 0° C. was added MCPBA (91 mg, 0.37 mmol, 70-75% water complex), and the mixture was stirred at ambient temperature for 10 min. The mixture was then diluted with DCM (3 mL) and washed with saturated aqueous NaHCO$_3$ (3×2 mL) and saturated aqueous Na$_2$S$_2$O$_3$ (3×2 mL). The organic layer was dried with MgSO$_4$, filtered and concentrated under reduced pressure to yield the title product as light yellowish foamy solid (31 mg, 57% yield, 95% pure). MS (apci pos) m/z=371.0 (M+H).

Intermediate P132

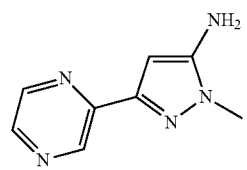

1-methyl-3-(pyrazin-2-yl)-1H-pyrazol-5-amine

Step A: Preparation of 3-oxo-3-(pyrazin-2-yl)propanenitrile

To a suspension of NaH (60% in mineral oil, 81.1 mg, 2.03 mmol) in dioxane (15 mL) was added acetonitrile (0.114 mL, 2.17 mmol), followed by methyl pyrazine-2-carboxylate (200 mg, 1.45 mmol) and the reaction heated to reflux for 2.5 hours. The reaction mixture was cooled to ambient temperature and diluted with H$_2$O (25 mL) and extracted with Et$_2$O (25 mL). The aqueous phase was neutralized with 2M aqueous HCl (0.7 mL), then extracted with 10% MeOH/DCM (3×25 mL). The combined organic phases were washed with brine (25 mL), dried with MgSO$_4$, filtered, and concentrated to yield the crude product as an orange syrup (134 mg, 62.9% yield). $^1$H NMR (CDCl$_3$) δ 9.32 (d, 1H), 8.87 (d, 1H), 8.68 (dd, 1H), 4.34 (s, 2H).

Step B: Preparation of 1-methyl-3-(pyrazin-2-yl)-1H-pyrazol-5-amine

To a suspension of 3-oxo-3-(pyrazin-2-yl)propanenitrile (67.0 mg, 0.455 mmol) in EtOH (5 mL) was added methylhydrazine (0.024 mL, 0.455 mmol). The reaction mixture was refluxed for 15 hours, then concentrated in vacuo. The crude product was purified by silica column chromatography, eluting with 0-5% MeOH/DCM to yield the product as a brown residue (33 mg, 41% yield). MS (apci) m/z=176.2 (M+H).

Intermediate P133

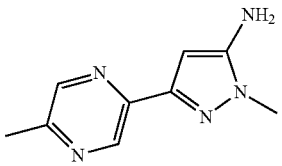

1-methyl-3-(5-methylpyrazin-2-yl)-1H-pyrazol-5-amine

Prepared by the method as described for Intermediate P107, substituting methyl isobutyrate in Step A with methyl 5-methylpyrazine-2-carboxylate and propionitrile with acetonitrile to afford 3-(5-methylpyrazin-2-yl)-3-oxopropanenitrile. In Step B, phenylhydrazine was replaced by methylhydrazine to afford the title pyrazole. MS (apci) m/z=190.2 (M+H).

Intermediate P134

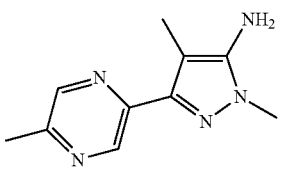

1,4-dimethyl-3-(5-methylpyrazin-2-yl)-1H-pyrazol-5-amine

Prepared by the method as described for Intermediate P107, substituting methyl isobutyrate in Step A with methyl 5-methylpyrazine-2-carboxylate to afford 2-methyl-3-(5-methylpyrazin-2-yl)-3-oxopropanenitrile. In Step B, phenylhydrazine was replaced by methylhydrazine to afford the title compound. MS (apci) m/z=204.1 (M+H).

Intermediate P135

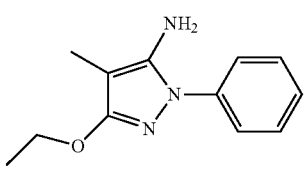

3-ethoxy-4-methyl-1-phenyl-1H-pyrazol-5-amine

Step A: Preparation of 5-amino-4-methyl-1-phenyl-1H-pyrazol-3(2H)-one

A mixture of ethyl 2-cyanopropanoate (5.0 g, 46 mmol) and phenylhydrazine (5.9 g, 46 mmol) in dioxane (10 mL) was heated at 110° C. for 17 hours. The crude material was cooled to ambient temperature, concentrated, and triturated with cold EtOH and Et$_2$O. The resultant solid was filtered, washed with Et₂O, and dried under vacuum to give the product as a white solid (3.4 g, 39% yield). MS (apci) m/z=190.0 (M−H).

Step B: Preparation of
3-ethoxy-4-methyl-1-phenyl-1H-pyrazol-5-amine

To a suspension of 5-amino-4-methyl-1-phenyl-1H-pyrazol-3(2H)-one (10.0 g, 52.9 mmol) in DMF (100 mL) was added K₂CO₃ (14.6 g, 106 mmol) and bromoethane (4.34 mL, 58.1) at ambient temperature. After stirring for 17 hours, the reaction mixture was treated with EtOAc and washed with water (3×, to obtain the N-alkylation product) and brine, dried with MgSO₄, filtered, and concentrated to give the product (5.35 g, 47% yield). MS (apci) m/z=218.1 (M+H).

The compounds in Table 3 were prepared by the method as described for Intermediate P135, substituting bromoethane with the appropriate alkyl halide or alkyl methanesulfonate.

TABLE 3

| Intermediate # | Structure | Data |
|---|---|---|
| P200 | | MS (apci) m/z = 248.1 (M + H) |
| P201 | | MS (apci) m/z = 204.1 (M + H) |
| P202 | | MS (apci) m/z = 229.0 (M + H) |
| P203 | | MS (apci) m/z = 348.1 (M + H) |
| P204 | | MS (apci) m/z = 310.0 (M + H) |
| P205 | | MS (apci) m/z = 236.1 (M + H) |

TABLE 3-continued

| Intermediate # | Structure | Data |
|---|---|---|
| P206 | 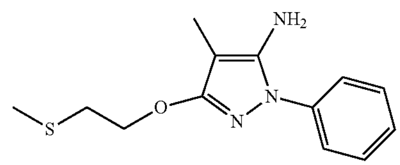 | MS (apci) m/z = 264.0 (M + H) |
| P207 | 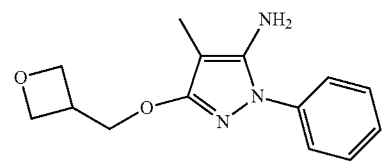 [SMILES: Cc1c(OCC2COC2)nn(-c2ccccc2)c1N] | MS (apci) m/z = 260.1 (M + H) |
| P208 | 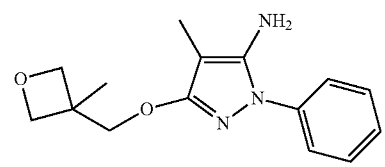 [SMILES: Cc1c(OCC2(C)COC2)nn(-c2ccccc2)c1N] | MS (apci) m/z = 274.1 (M + H) |
| P209 | 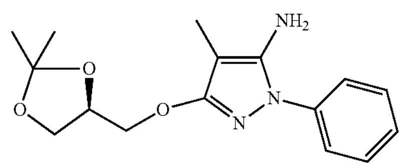 [SMILES: Cc1c(OC[C@H]2COC(C)(C)O2)nn(-c2ccccc2)c1N] | MS (apci) m/z = 304.1 (M + H) |
| P210 | 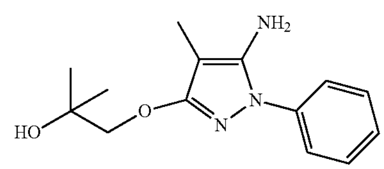 [SMILES: Cc1c(OCC(C)(C)O)nn(-c2ccccc2)c1N] | MS (apci) m/z = 262.1 (M + H) |
| P211 | 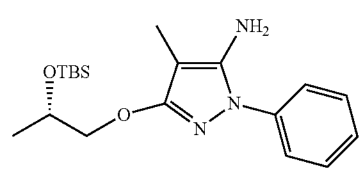 [SMILES: Cc1c(OC[C@H](C)O[Si](C)(C)C(C)(C)C)nn(-c2ccccc2)c1N] | MS (apci) m/z = 362.0 (M + H) |
| P212 | 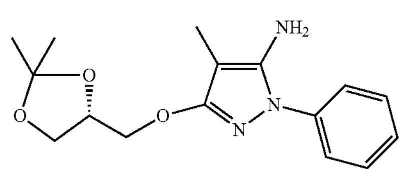 [SMILES: Cc1c(OC[C@@H]2COC(C)(C)O2)nn(-c2ccccc2)c1N] | MS (apci) m/z = 304.1 (M + H) |

Intermediate P136

3-(benzyloxy)-1-methyl-1H-pyrazol-5-amine

Step A: Preparation of 5-amino-1-methyl-4-phenyl-1H-pyrazol-3(2H)-one

To a suspension of ethyl 2-cyano-2-phenylacetate (2.56 g, 13.3 mmol) in EtOH (10 mL) was added dropwise methylhydrazine (1.09 mL, 19.9 mmol). The reaction was heated at 85° C. for 15 hours. The reaction mixture was cooled to 0° C. and filtered. The resultant solid was washed with cold EtOH (20 mL) and Et$_2$O (20 mL) to give the desired product (2.10 g, 83.7% yield). MS (apci) m/z=190.2 (M+H).

Step B: Preparation of 3-(benzyloxy)-1-methyl-1H-pyrazol-5-amine

A suspension of 5-amino-1-methyl-1H-pyrazol-3(2H)-one (0.35 g, 3.1 mmol), Benzyl chloride (0.43 g, 3.4 mmol), and K$_2$CO$_3$ (1.3 g, 9.3 mmol) in DMF (4 mL) was heated at 70° C. for 17 hours. After cooling, the reaction mixture was treated with EtOAc, washed with water and brine, dried with MgSO$_4$, and concentrated in vacuo. The crude product was purified by silica column chromatography eluting with 2-6% MeOH/DCM to afford the title compound (0.16 g, 25% yield). MS (apci) m/z=204.0 (M+H).

Intermediate P137

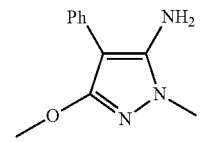

3-methoxy-1-methyl-4-phenyl-1H-pyrazol-5-amine

To a suspension of 5-amino-1-methyl-4-phenyl-1H-pyrazol-3(2H)-one (Step A of the preparation of Intermediate P136; 208 mg, 1.10 mmol) and K$_2$CO$_3$ (456 mg, 3.30 mmol) in DMF (5 mL) was added dropwise iodomethane (172 mg, 1.21 mmol). The reaction mixture was stirred for 15 hours. The solvent was removed under reduced pressure and the residue was purified by silica column chromatography eluting with 33% EtOAc/Hexanes to give the title pyrazole (66.0 mg, 30.4% yield). MS (apci) m/z=204.1 (M+H).

Intermediate P138

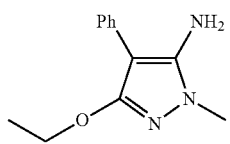

3-ethoxy-1-methyl-4-phenyl-1H-pyrazol-5-amine

Prepared as described in Intermediate P137, replacing iodomethane with iodoethane in Step B to afford the title compound. MS (apci) m/z=218.2 (M+H).

Intermediate P139

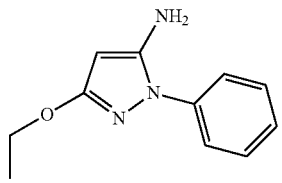

3-ethoxy-1-phenyl-1H-pyrazol-5-amine

Prepared according to the procedure described for Intermediate 135, substituting ethyl-2-cyanopropanoate with ethyl-2-cyanoacetate in Step A. MS (apci) m/z=204.0 (M+H).

The compounds in the following Table were prepared by the method as described for Intermediate P135, substituting bromoethane with the appropriate alkyl halide, alkyl methanesulfonate or epoxide.

| Intermediate # | Structure | MS (apci) m/z |
| --- | --- | --- |
| P140 | 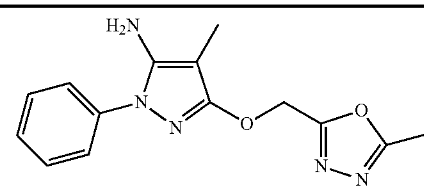 | 286.1 (M + H) |
| P141 | 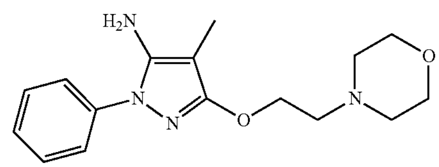 [SMILES: Cc1c(OCCN2CCOCC2)nn(-c2ccccc2)c1N] | 303.1 (M + H) |
| P142 | 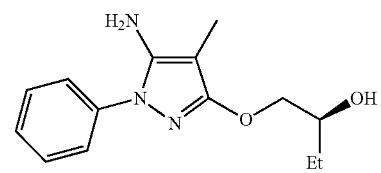 [SMILES: CC[C@H](O)COc1nn(-c2ccccc2)c(N)c1C] | 262.1 (M + H) |
| P143 | 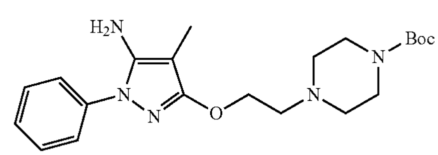 [SMILES: Cc1c(OCCN2CCN(C(=O)OC(C)(C)C)CC2)nn(-c2ccccc2)c1N] | 402.2 (M + H) |
| P144 | 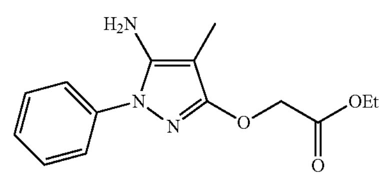 [SMILES: CCOC(=O)COc1nn(-c2ccccc2)c(N)c1C] | 276.1 (M + H) |
| P145 | 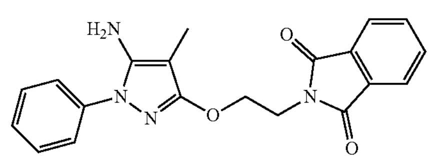 [SMILES: Cc1c(OCCN2C(=O)c3ccccc3C2=O)nn(-c2ccccc2)c1N] | 363.1 (M + H) |

| Intermediate # | Structure | MS (apci) m/z |
|---|---|---|
| P146 | 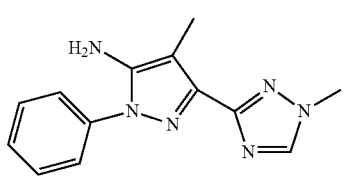 | 248.1 (M + H) |
| P147 | 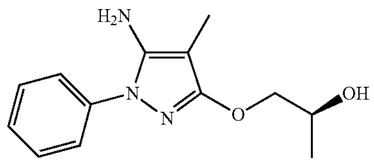 [SMILES: Cc1c(OC[C@H](C)O)nn(-c2ccccc2)c1N] | 248.1 (M + H) |
| P148 | 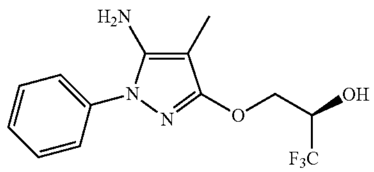 [SMILES: Cc1c(OC[C@@H](O)C(F)(F)F)nn(-c2ccccc2)c1N] | 302.1 (M + H) |
| P149 | 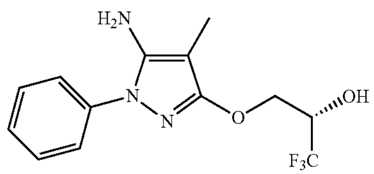 [SMILES: Cc1c(OC[C@H](O)C(F)(F)F)nn(-c2ccccc2)c1N] | 302.1 (M + H) |
| P150 | 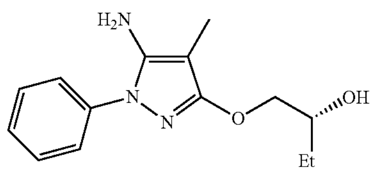 [SMILES: CC[C@@H](O)COc1nn(-c2ccccc2)c(N)c1C] | 262.1 (M + H) |

Intermediate 151

1'-(2-methoxyethyl)-1-phenyl-1H,1'H-[3,4'-bipyrazol]-5-amine

Step A: Preparation of methyl 1-methyl-1H-1,2,4-triazole-3-carboxylate

To a stirred suspension of NaH (60% oil dispersion, 0.346 g, 8.66 mmol) in DMF (20 mL) was added dropwise a solution of methyl 1H-1,2,4-triazole-3-carboxylate (1.00 g, 7.87 mmol) in DMF (20 mL) at 0° C. under nitrogen. The reaction mixture was stirred at 0° C. for 1 hour. MeI (0.982 mL, 15.7 mmol) was added dropwise. The reaction mixture was stirred at ambient temperature overnight. The reaction was poured into cold water and extracted with EtOAc. The combined organic layers were washed with brine, dried and concentrated. The residue was purified by column chromatography (3:1 hexanes/EtOAc) to give the title compound (0.380 g, 34% yield) as a white solid. MS (apci) m/z=142.1 (M+H).

Step B: Preparation of 1'-(2-methoxyethyl)-1-phenyl-1H,1'H-[3,4'-bipyrazol]-5-amine Prepared according to the method described for Intermediate P109, using methyl 1-methyl-1H-1,2,4-triazole-3-carboxylate as a replacement for methyl 2-methoxyacetate, and substituting propionitrile for acetonitrile in Step A. MS (apci) m/z=255.1 (M+H).

Intermediate 152

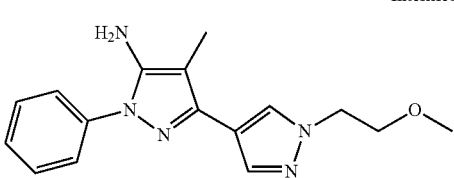

1'-(2-methoxyethyl)-4-methyl-1-phenyl-1H,1'H-[3,4'-bipyrazol]-5-amine

Prepared according to the method described for Intermediate P109, using ethyl 1-(2-methoxyethyl)-1H-pyrazole-4-carboxylate as a replacement for methyl 2-methoxyacetate, and substituting propionitrile for acetonitrile in Step A.

Intermediate 153

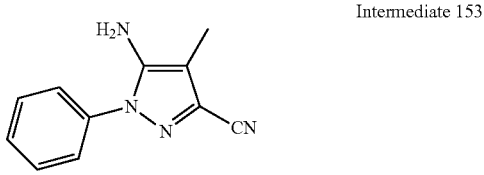

5-amino-4-methyl-1-phenyl-1H-pyrazole-3-carbonitrile

To a stirred solution of aniline (2.02 g, 21.7 mmol) in 6 N HCl (22 mL) was added dropwise a solution of NaNO₂ (1.50 g, 21.7 mmol) in water (20 mL) at 0-5° C. The reaction mixture was stirred at 0° C. for 15 minutes. Acetic acid (10 mL) was added. This solution was added dropwise to a stirred solution of ethyl 2,3-dicyanobutanoate (Prepared according to the procedure described in *Bioorganic & Medicinal Chemistry*, 2004, 12, 3345-3356, 3.60 g, 21.7 mmol) in acetic acid (12 mL) and water (18 mL) at 0° C. After stirring for 1 hour, concentrated ammonium hydroxide (50 mL) was added dropwise followed by THF (50 mL). The reaction was stirred at ambient temperature overnight. The organic layer was separated. The aqueous layer was extracted with EtOAc. The combined organic layers were washed with brine, dried and concentrated. The residue was purified by flash chromatography on silica gel (3:1 hexanes/EtOAc) to give the title compound (2.95 g, 69% yield). MS (apci) m/z=198.9 (M+H).

Intermediate 155

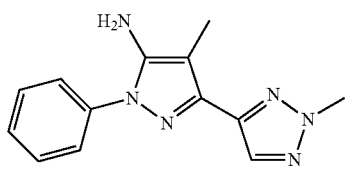

4-methyl-3-(2-methyl-2H-1,2,3-triazol-4-yl)-1-phenyl-1H-pyrazol-5-amine

Step A: Preparation of ethyl 2-methyl-2H-1,2,3-triazole-4-carboxylate

A mixture of ethyl 2H-1,2,3-triazole-4-carboxylate (2.00 g, 14.2 mmol), $K_2CO_3$ (3.53 g, 25.5 mmol) and methyl iodide (3.54 mL, 56.7 mmol) in acetonitrile (40 mL) was stirred at 50° C. under nitrogen overnight. After cooling to ambient temperature, the mixture was filtered through Celite®. The filtrate was concentrated in vacuo. The residue was purified by flash chromatography on silica gel (4:1 hexane/EtOAc) to give the title compound (0.780 g, 35% yield). MS (apci) m/z=156.0 (M+H).

Step B: Preparation of 4-methyl-3-(2-methyl-2H-1,2,3-triazol-4-yl)-1-phenyl-1H-pyrazol-5-amine Prepared according to the method described for Intermediate P109 using ethyl 2-methyl-2H-1,2,3-triazole-4-carboxylate as a replacement for methyl 2-methoxyacetate, and substituting propionitrile for acetonitrile in Step A. MS (apci) m/z=254.9 (M+H).

Intermediate 156

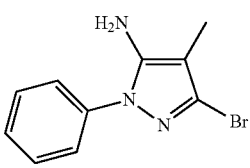

3-bromo-4-methyl-1-phenyl-1H-pyrazol-5-amine

To a stirred solution of 5-amino-4-methyl-1-phenyl-1H-pyrazol-3(2H)-one (Intermediate P135, Step A, 1.00 g, 5.29 mmol) in MeCN (20 mL) was added $POBr_3$ (2.27 g, 7.93 mmol). The reaction mixture was heated at reflux for 3 hours. The reaction was concentrate in vacuo. The residue was taken up in DCM. Saturated aqueous $NaHCO_3$ solution was carefully added. The aqueous layer was extracted with DCM. The combined organic layers were washed with brine, dried and concentrated. The residue was purified by flash chromatography on silica gel (1:2 hexane/EtOAc to give the title compound (0.23 g, 17% yield). MS (apci) m/z=251.8 (M+H).

Intermediate 157

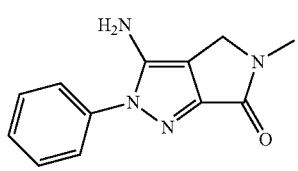

3-amino-5-methyl-2-phenyl-4,5-dihydropyrrolo[3,4-c]pyrazol-6(2H)-one

Step A: Preparation of ethyl 5-amino-4-((methylamino)methyl)-1-phenyl-1H-pyrazole-3-carboxylate To a stirred solution of ethyl 5-amino-4-formyl-1-phenyl-1H-pyrazole-3-carboxylate (Prepared according to the procedure described in *J. Heterocyclic Chemistry*, 2010, 47, p. 287-291, 142 mg, 0.548 mmol) in DCM (3 mL) was added 2.0 M $MeNH_2$ in THF (0.822 mL, 1.64 mmol). Two drops of acetic acid was added. The reaction mixture was stirred at ambient temperature overnight. MeOH (0.4 mL) was added followed by $NaBH_4$ (31 mg, 0.82 mmol) portionwise. The reaction was quenched by the slow addition of water. The mixture was extracted with DCM. The combined organic layers were washed with brine, dried and concentrated. The crude was used in the next step without further purification. MS (apci) m/z=275.0 (M+H).

Step B: Preparation of 3-amino-5-methyl-2-phenyl-4,5-dihydropyrrolo[3,4-c]pyrazol-6(2H)-one To a stirred solution of ethyl 5-amino-4-((methylamino)methyl)-1-phenyl-1H-pyrazole-3-carboxylate (crude, 65 mg, 0.24 mmol) in MeOH (0.5 mL) and THF (0.5 mL) was added 2 N NaOH (0.24 mL, 0.47 mmol). The reaction mixture was stirred at ambient temperature for 4 hours and then concentrated in vacuo. To the residue was added water. The pH was adjusted to 4-5 using 1 N HCl. Water was evaporated under reduced pressure. The crude acid (58 mg) was dissolved in DMF (3 mL). $Et_3N$ (66 μL, 0.47 mmol) was added followed by EDCI (90 mg, 0.47 mmol) and HOBt (32 mg, 0.24 mmol). The reaction mixture was stirred at ambient temperature overnight and then partitioned between EtOAc and water. The aqueous layer was extracted with EtOAc. The combined organic layers were washed with water and brine, dried and concentrated. The residue was purified by flash chromatography on silica gel (2% MeOH in DCM) to give the title compound (15 mg, 28%) as a white solid. MS (apci) m/z=228.9 (M+H).

Intermediate 158

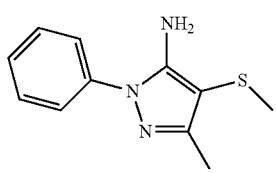

3-methyl-4-(methylthio)-1-phenyl-1H-pyrazol-5-amine

Prepared according to the method described for Intermediate P109, replacing methyl 2-methoxyacetate with ethyl acetate and replacing acetonitrile with 2-(methylthio)acetonitrile in Step A to afford the product as a brown oil. MS (apci) m/z=220.1 (M+H).

Intermediate 159

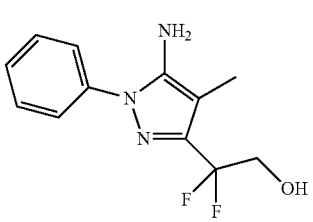

2-(5-amino-4-methyl-1-phenyl-1H-pyrazol-3-yl)-2,2-difluoroethanol

Prepared according to the method described for Intermediate P111, replacing acetonitrile with propionitrile and replacing methyl 3-hydroxy-2,2-dimethylpropanoate with ethyl 2,2-difluoro-3-hydroxypropanoate to afford the product as a pale yellow solid. MS (apci) m/z=254.1 (M+H).

Intermediate 160

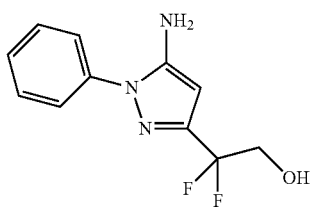

2-(5-amino-1-phenyl-1H-pyrazol-3-yl)-2,2-difluoroethanol

Prepared according to the method described for Intermediate P111, replacing methyl 3-hydroxy-2,2-dimethylpropanoate with ethyl 2,2-difluoro-3-hydroxypropanoate to afford the product as a pale yellow solid. MS (apci) m/z=240.0 (M+H).

Intermediate 161

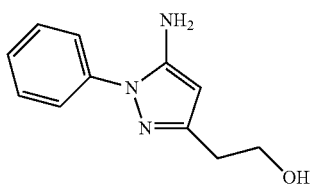

2-(5-amino-1-phenyl-1H-pyrazol-3-yl)ethanol

Prepared according to the method described in Intermediate P111, replacing methyl 3-hydroxy-2,2-dimethylpropanoate with methyl 3-hydroxypropanoate in Step A. MS (apci) m/z=204.1 (M+H).

Intermediate 162

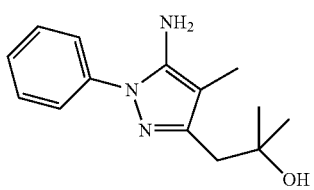

1-(5-amino-4-methyl-1-phenyl-1H-pyrazol-3-yl)-2-methylpropan-2-ol

Step A: Preparation of ethyl 3-hydroxy-3-methylbutanoate

To a solution of lithium bis(trimethylsilyl)amide (1M in THF) (100 mL, 100 mmol) in THF (100 mL) under $N_2$ and cooled to −78° C. was added ethyl acetate (9.74 mL, 100 mmol). The reaction mixture was stirred for 30 minutes, and then acetone (8.81 mL, 120 mmol) was added. The reaction mixture was stirred for 10 minutes, and then quenched with HCl (2M aqueous, 70 mL, 140 mmol) and allowed to warm to ambient temperature. The reaction mixture was extracted with EtOAc (2×150 mL). The organic phases were combined and washed with saturated aqueous $NaHCO_3$ (2×50 mL), dried ($MgSO_4$), filtered and concentrated to afford the product as a yellow oil (12.8 g, 88% yield). $^1$H NMR ($CDCl_3$) δ 4.18 (q, 3H), 2.49 (s, 2H), 1.29 (m, 9H).

Step B: Preparation of 5-hydroxy-5-methyl-3-oxohexanenitrile

To a solution of propionitrile (1.77 mL, 30.5 mmol) in THF (100 mL) under $N_2$ at −78° C. was added lithium bis(trimethylsilyl)amide (1M in THF) (27.9 mL, 27.9 mmol). Stirred 1 hour, then ethyl 3-hydroxy-3-methylbutanoate (1.86 g, 12.7 mmol) was added. The reaction mixture was stirred at −78° C. for 1 hour, then stirred at 0° C. for 1.5 hours, then diluted with $H_2O$ (100 mL) and extracted with $Et_2O$ (50 mL). The phases were separated and the basic aqueous phase was neutralized with HCl (6M aqueous, 4.5 mL), then extracted with $Et_2O$ (3×75 mL). The combined organic phases were washed with brine (75 mL), dried ($MgSO_4$), filtered, and concentrated to afford the product as a pale yellow oil (1.24 g, 63% yield). $^1$H NMR ($CDCl_3$) δ 3.54 (m, 1H), 2.89 (s, 2H), 1.50 (d, 3H), 1.32 (s, 3H), 1.31 (s, 3H).

Step C: Preparation of 1-(5-amino-4-methyl-1-phenyl-1H-pyrazol-3-yl)-2-methylpropan-2-ol To a suspension of phenylhydrazine (0.793 mL, 7.99 mmol) and HCl (5-6M in iPrOH, 1.60 mL, 7.99 mmol) in EtOH (25 mL) was added a solution of 5-hydroxy-2,5-dimethyl-3-oxohexanenitrile (1.24 g, 7.99 mmol) in EtOH (25 mL). The reaction mixture was refluxed for 17 hours, then cooled to ambient temperature, diluted with saturated aqueous $NaHCO_3$ (10 mL), extracted 10:90 MeOH/DCM (3×25 mL), and the combined organic phases were dried ($MgSO_4$), filtered and concentrated. Purified by silica column chromatography eluting with 0-75% acetone/hexanes to afford the title compound as an orange oil (1.13 g, 58% yield). MS (apci) m/z=246.1 (M+H).

The following pyrazole intermediates were prepared according to the method used for the preparation of Intermediate 162, Steps B and C, using the appropriate starting material. For the preparation of Intermediates 168 and 169, the starting material (purchased from Oakwood) was a mixture of cis and trans diastereomers.

| Intermediate # | Structure | Name | MS (apci) m/z |
|---|---|---|---|
| 163 | 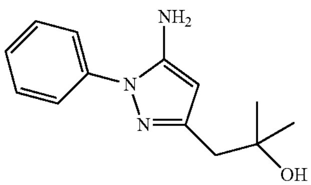 [SMILES: CC(C)(O)Cc1cc(N)n(-c2ccccc2)n1] | 1-(5-amino-1-phenyl-1H-pyrazol-3-yl)-2-methylpropan-2-ol | 232.1 (M + H) |
| 164 | 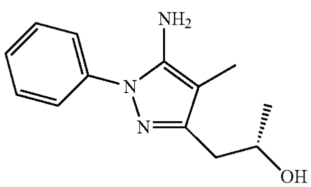 [SMILES: Cc1c(C[C@H](C)O)nn(-c2ccccc2)c1N] | (S)-1-(5-amino-4-methyl-1-phenyl-1H-pyrazol-3-yl)propan-2-ol | 232.1 (M + H) |
| 165 | 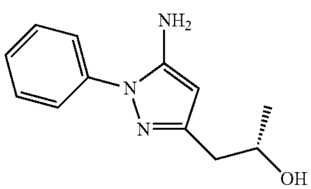 [SMILES: C[C@H](O)Cc1cc(N)n(-c2ccccc2)n1] | (S)-1-(5-amino-1-phenyl-1H-pyrazol-3-yl)propan-2-ol | 218.1 (M + H) |
| 166 | 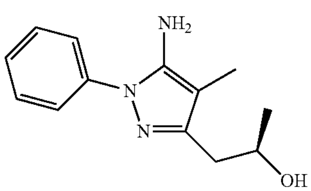 [SMILES: Cc1c(C[C@@H](C)O)nn(-c2ccccc2)c1N] | (R)-1-(5-amino-4-methyl-1-phenyl-1H-pyrazol-3-yl)propan-2-ol | 232.1 (M + H) |
| 167 | 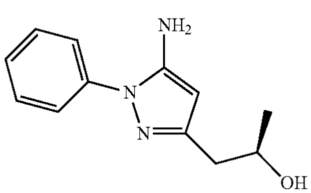 [SMILES: C[C@@H](O)Cc1cc(N)n(-c2ccccc2)n1] | (R)-1-(5-amino-1-phenyl-1H-pyrazol-3-yl)propan-2-ol | 218.1 (M + H) |
| 168 | 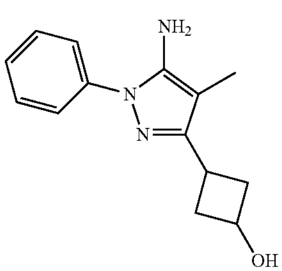 [SMILES: Cc1c(C2CC(O)C2)nn(-c2ccccc2)c1N] | 3-(5-amino-4-methyl-1-phenyl-1H-pyrazol-3-yl)cyclobutanol | 244.1 (M + H) |
| 169 | 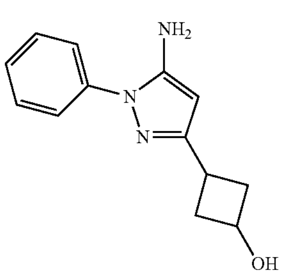 [SMILES: Nc1cc(C2CC(O)C2)nn1-c1ccccc1] | 3-(5-amino-1-phenyl-1H-pyrazol-3-yl)cyclobutanol | 230.1 (M + H) |

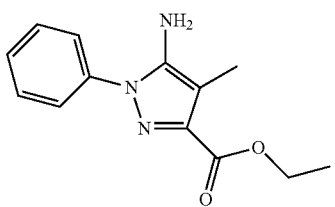

Intermediate 170 ethyl 5-amino-4-methyl-1-phenyl-1H-pyrazole-3-carboxylate

Prepared according to the method described for Intermediate P109, replacing methyl 2-methoxyacetate with diethyl oxalate and replacing acetonitrile with propionitrile in Step A to afford the product as a yellow solid. MS (apci) m/z=246.1 (M+H).

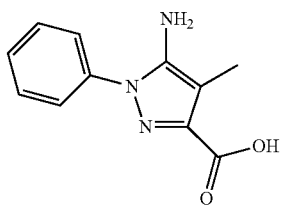

Intermediate 171

5-amino-4-methyl-1-phenyl-1H-pyrazole-3-carboxylic acid

To a solution of ethyl 5-amino-4-methyl-1-phenyl-1H-pyrazole-3-carboxylate (Intermediate 170, 1.52 mg, 6.21 mmol) in THF (12 mL) and MeOH (6 mL) was added LiOH (2M aq, 9.31 mL, 18.6 mmol). The reaction mixture was stirred at ambient temperature for 19 hours, then partially concentrated under reduced pressure, then neutralized with 6M HCl (3.2 mL), extracted with 10:90 MeOH/DCM (3×25 mL), and the combined organic extracts were washed with brine (50 mL), dried (MgSO$_4$), filtered and concentrated to give the title compound as a yellow solid (1.3 g, 96% yield) MS (apci) m/z=218.1 (M+H).

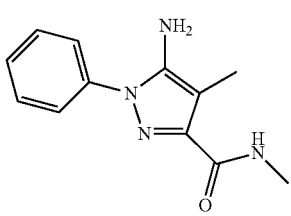

Intermediate 172

5-amino-N,4-dimethyl-1-phenyl-1H-pyrazole-3-carboxamide

To a solution of 5-amino-4-methyl-1-phenyl-1H-pyrazole-3-carboxylic acid (Intermediate 171, 223 mg, 1.02 mmol) in acetonitrile (10 mL) were added DIEA (0.71 mL, 4.10 mmol), methanamine hydrochloride (138 mg, 2.05 mmol), DMF (2 mL), and then HATU (428 mg, 1.13 mmol). The reaction mixture was stirred at ambient temperature for 19 hours and then partially concentrated under reduced pressure. The mixture was purified by reverse-phase column chromatography, eluting with 5-60% acetonitrile/water to afford the title compound as a pale yellow solid (182 mg, 77% yield). MS (apci) m/z=231.1 (M+H).

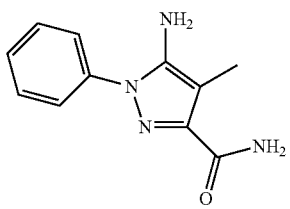

Intermediate 173

5-amino-4-methyl-1-phenyl-1H-pyrazole-3-carboxamide

A solution of 5-amino-4-methyl-1-phenyl-1H-pyrazole-3-carbonitrile (150 mg, 0.757 mmol) in concentrated H$_2$SO$_4$ (0.5 mL) was stirred at ambient temperature for 17 hours. The reaction mixture was cooled and neutralized by the addition of aqueous NaOH (2M, 11 mL), then extracted 10% MeOH/DCM (5×10 mL), and the combined organic extracts were washed with brine, dried (MgSO$_4$), filtered and concentrated under reduced pressure to afford the title compound as a white solid (151 mg, 95% yield). MS (apci) m/z=239.1 (M+Na).

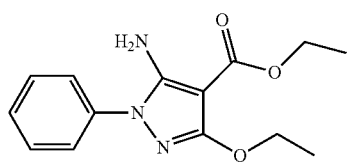

Intermediate 174 ethyl 5-amino-3-ethoxy-1-phenyl-1H-pyrazole-4-carboxylate

Step A: Preparation of diethyl 2-cyanomalonate

To a suspension of NaH (60 wt % in mineral oil, 499 mg, 12.49 mmol) in THF (100 mL) under N$_2$ at 0° C. was added diethyl malonate (1.90 mL, 12.49 mmol). The ice bath was removed and the reaction mixture was stirred at ambient temperature for 30 minutes, then cooled to 0° C. and cyanic bromide (5M in MeCN, 2.5 mL, 12.49 mmol) was added. The reaction mixture was stirred at ambient temperature for 19 hours, then diluted with H$_2$O (50 mL), extracted with Et$_2$O (50 mL). The aqueous phase was neutralized with HCl (2M aq, 3 mL) then extracted with DCM (2×50 mL). The combined DCM extracts were dried (MgSO$_4$), filtered, and concentrated to afford the product as a yellow oil (837 mg, 36% yield). 1H NMR (CDCl$_3$) δ 4.46 (s, 1H), 4.35 (q, 4H), 1.35 (t, 6H).

Step B: Preparation of ethyl 5-amino-3-ethoxy-1-phenyl-1H-pyrazole-4-carboxylate Prepared according to the method described for Intermediate P135, replacing ethyl 2-cyanopropanoate with diethyl 2-cyanomalonate in Step A to afford the product as a brown syrup (400 mg, 32% yield). MS (apci) m/z=276.1 (M+H).

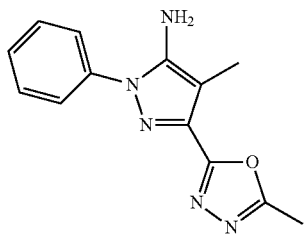

Intermediate 175

4-methyl-3-(5-methyl-1,3,4-oxadiazol-2-yl)-1-phenyl-1H-pyrazol-5-amine

Step A: Preparation of N'-acetyl-5-amino-4-methyl-1-phenyl-1H-pyrazole-3-carbohydrazide To a solution of 5-amino-4-methyl-1-phenyl-1H-pyrazole-3-carboxylic acid (Intermediate 171, 93 mg, 0.428 mmol) in DCM (5 mL) and DIEA (0.149 mL, 0.856 mmol) was added isobutyl carbonochloridate (0.061 mL, 0.471 mmol). The reaction mixture was stirred at ambient temperature for 1 hour, then acetohydrazide (48 mg, 0.642 mmol) was added. The reaction mixture was stirred at ambient temperature for 18 hours, then diluted with H$_2$O (10 mL), extracted DCM (2×10 mL), dried (MgSO$_4$), filtered and concentrated under reduced pressure to afford the product as a pale yellow solid (119 mg, 101% yield). MS (apci) m/z=274.1 (M+H).

Step B: Preparation of 4-methyl-3-(5-methyl-1,3,4-oxadiazol-2-yl)-1-phenyl-1H-pyrazol-5-amine A mixture of N'-acetyl-5-amino-4-methyl-1-phenyl-1H-pyrazole-3-carbohydrazide (117 mg, 0.428 mmol) and POCl$_3$ (0.5 mL) was heated in a pressure tube to 90° C. for 1 hour. The reaction mixture was transferred to a separatory funnel with EtOAc (5 mL), then diluted with saturated aqueous NaHCO$_3$ (20 mL), extracted with EtOAc (2×15 mL), dried (MgSO$_4$), filtered and concentrated. The residue was purified by silica column chromatography eluting with 0-75% acetone/hexanes to afford the title compound as a yellow solid (19.6 mg, 18% yield). MS (apci) m/z=256.1 (M+H).

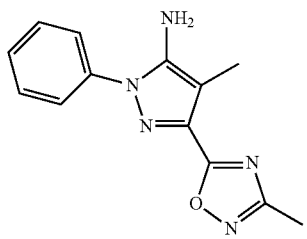

Intermediate 176

4-methyl-3-(3-methyl-1,2,4-oxadiazol-5-yl)-1-phenyl-1H-pyrazol-5-amine

To a suspension of NaH (60% in mineral oil, 36 mg, 0.897 mmol) in THF (5 mL) under N$_2$ was added N-hydroxyacetimidamide (66 mg, 0.897 mmol). The reaction mixture was heated to reflux for 1 hour, then cooled to ambient temperature and ethyl 5-amino-4-methyl-1-phenyl-1H-pyrazole-3-carboxylate (Intermediate 170, 200 mg, 0.815 mmol) was added. The reaction mixture was heated to reflux for 18 hours, then cooled to ambient temperature and additional NaH (60% in mineral oil, 18 mg, 0.449 mmol) was added. The reaction mixture was heated to reflux for 4 hours, then diluted with H$_2$O (10 mL), extracted DCM (2×15 mL), and the combined organic extracts were dried (MgSO$_4$), filtered and concentrated under reduced pressure. The residue was purified by silica column chromatography eluting with 0-50% acetone/hexanes to afford the title compound as an orange solid (84 mg, 40% yield). MS (apci) m/z=256.1 (M+H).

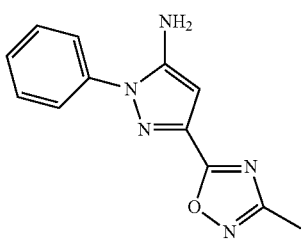

Intermediate 177

3-(3-methyl-1,2,4-oxadiazol-5-yl)-1-phenyl-1H-pyrazol-5-amine

Prepared according to the method described in Intermediate 176, replacing ethyl 5-amino-4-methyl-1-phenyl-1H-pyrazole-3-carboxylate with ethyl 5-amino-1-phenyl-1H-pyrazole-3-carboxylate (Nanjing Chemlin Chemical Co.) to afford the product as a tan solid (83 mg, 53% yield). MS (apci) m/z=242.1 (M+H).

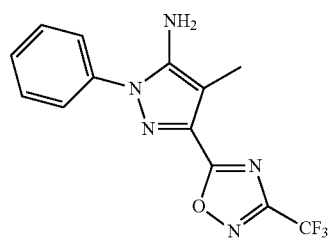

Intermediate 178

4-methyl-1-phenyl-3-(3-(trifluoromethyl)-1,2,4-oxadiazol-5-yl)-1H-pyrazol-5-amine Step A: Preparation of 2,2,2-trifluoro-N'-hydroxyacetimidamide To a suspension of hydroxylamine hydrochloride (5.45 g, 78.4 mmol) in MeOH (100 mL) was added NaOMe (25 wt % solution in MeOH, 17.9 mL, 78.4 mmol) and the mixture stirred at ambient temperature for 10 minutes, then filtered and the solid was washed with MeOH. The filtrate was cooled to 0° C. and then 2,2,2-trifluoroacetonitrile (7.45 g, 78.4 mmol) gas was bubbled into the solution over 30 minutes. The reaction mixture was then allowed to warm to ambient temperature for 19 hours. The solution was concentrated under reduced pressure to 50 mL and the solids were filtered. The filtrate was concentrated, re-suspended in cold MeOH, and filtered. The filtrate was concentrated, again re-suspended in cold MeOH, and filtered. The filtrate was concentrated to give the product as a waxy white solid (6.7 g, 67% yield). $^1$H NMR (CD$_3$CN) δ 8.32 (s, 1H), 5.25 (br s, 2H). $^{19}$F NMR (CD$_3$CN) δ −71.8 (s).

Step B: Preparation of 4-methyl-1-phenyl-3-(3-(trifluoromethyl)-1,2,4-oxadiazol-5-yl)-1H-pyrazol-5-amine To a suspension of NaH (60% in mineral oil, 356 mg, 0.897 mmol) in THF (5 mL, 0.815 mmol) under N$_2$ was added 2,2,2-trifluoro-N'-hydroxyacetimidamide (115 mg, 0.897 mmol). The reaction mixture was heated to reflux for 1 hour, then cooled to ambient temperature and powdered 4 A molecular sieves (200 mg) and ethyl 5-amino-4-methyl-1-phenyl-1H-pyrazole-3-carboxylate (Intermediate 170; 200 mg, 0.815 mmol) were added and heated to reflux. The reaction mixture was heated to reflux for 18 hours, then filtered, diluted with H$_2$O (15 mL), extracted DCM (2×25 mL), and the combined organic extracts were washed with brine (25 mL), dried (MgSO$_4$), filtered and concentrated under reduced pressure. The residue was purified by silica column chromatography eluting with 0-50% acetone/hexanes to afford the title compound as a white solid (44 mg, 17% yield). MS (apci) m/z=310.1 (M+H).

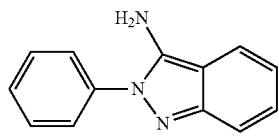

Intermediate 179

2-phenyl-2H-indazol-3-amine

Step A: Preparation of 1-(2-iodophenyl)-2-phenyldiazene

To a solution of 2-iodoaniline (1.00 g, 4.57 mmol) in acetic acid (46 mL) was added nitrosobenzene (0.880 g, 8.22 mmol) and the mixture was heated at 85° C. for 16 hours. The mixture was cooled to ambient temperature, poured into water and slowly treated with saturated NaHCO$_3$ until basic. The mixture was extracted with EtOAc (3×) and the combined extracts were washed with water, saturated NaCl and dried over MgSO$_4$. The solution was filtered, concentrated and the residue purified by reverse phase chromatography to provide the title compound as a red solid (0.880 g, 63% yield). $^1$H NMR (CDCl$_3$) δ 7.23-7.39 (m, 3H), 7.64 (d, 1H), 7.56-7.51 (m, 3H), 7.45 (t, 1H), 7.1 (t, 1H).

Step B: 2-(phenyldiazenyl)benzonitrile

To a solution of 1-(2-iodophenyl)-2-phenyldiazene (0.44 g, 1.4 mmol) in 1-propanol (14 mL) was added CuCN (0.900 g, 10.0 mmol) and the reaction was heated at reflux for 16 hours. The mixture was cooled to ambient temperature, filtered and the collected solid washed with CH$_2$Cl$_2$. The combined filtrate and washes were concentrated to provide the title compound as red-orange solid that was dried in vacuum (0.280 g, 95% yield). $^1$H NMR (CDCl$_3$) δ 8.03-8.06 (m, 2H), 7.88 (dd, 2H), 7.71 (t, 1H), 7.54-7.58 (m, 4H).

Step C: 2-phenyl-2H-indazol-3-amine

A mixture of 2-(phenyldiazenyl)benzonitrile (0.28 g, 1.35 mmol) and SnCl$_2$ dihydrate (0.562 mL, 6.76 mmol) in EtOH (14 mL) was heated at reflux for 16 hours. The mixture was cooled to ambient temperature and concentrated. The residue was diluted with EtOAc and water and filtered. The aqueous layer was removed and the EtOAc layer was washed with water. The combined aqueous fractions were basified with saturated NaHCO$_3$ and extracted with CH$_2$Cl$_2$ (2×). The combined organic layers were dried over MgSO$_4$, filtered and concentrated to provide the title compound as a light purple solid that was dried in vacuum (0.241 g, 85% yield). $^1$H NMR (CDCl$_3$) δ 7.69 (d, 2H), 7.52-7.58 (m, 3H), 7.47 (d, 2H), 7.26 (t, 1H), 6.90 (t, 1H), 4.28 (br s, 2H).

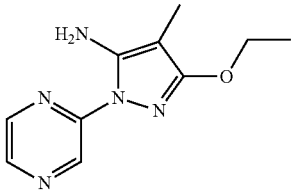

Intermediate 180

3-ethoxy-4-methyl-1-(pyrazin-2-yl)-1H-pyrazol-5-amine

Step A: 5-amino-4-methyl-1-(pyrazin-2-yl)-1H-pyrazol-3(2H)-one

To a mixture of 2-hydrazinylpyrazine (0.551 g, 5.00 mmol) and ethyl 2-cyanopropanoate (0.669 g, 5.00 mmol) in abs. EtOH (10 mL) was added 3M NaOEt in EtOH (0.167 mL, 0.501 mmol) and the mixture was heated at reflux for 64 hours. The mixture was concentrated and the residual yellow-brown solid was treated with EtOAc (30 mL) and sonicated. The resulting tan suspension was stirred vigorously for 8 hours. The solid was collected via vacuum filtration, washed with EtOAc and dried in vacuum to afford the title compound as a light tan powder (682 mg, 71%). $^1$H NMR (DMSO d$_6$) δ 10.3 (br s, 1H), 8.82 (s, 1H), 8.30 (d, 2H), 6.55 (s, 2H), 1.71 (s, 3H).

Step B: 3-ethoxy-4-methyl-1-(pyrazin-2-yl)-1H-pyrazol-5-amine

A mixture of 5-amino-4-methyl-1-(pyrazin-2-yl)-1H-pyrazol-3(2H)-one (382 mg, 2.00 mmol) and powdered K$_2$CO$_3$ (552 mg, 4.00 mmol) in dry DMF (3.0 mL) was stirred at ambient temperature for 10 minutes. The mixture was cooled to 0° C. and bromoethane (229 mg, 2.10 mmol) was added. The mixture was allowed to reach ambient temperature and was stirred 24 hours. The reaction mixture poured into cold H$_2$O (12 mL), allowed to reach ambient temperature and was extracted with EtOAc (3×). The combined extracts were washed with saturated NaCl (2×), dried over MgSO$_4$ and activated carbon. The dried solution was diluted with and equal volume of hexanes and filtered through a SiO$_2$ plug capped with a MgSO$_4$ layer eluting with 50% EtOAc-hexanes. The filtrate was concentrated and the residual yellow solid was washed with hexanes (3×) and dried in vacuum to afford the title compound as a light yellow crystalline solid (195 mg, 45%). $^1$H NMR (CDCl$_3$) δ 9.10 (s, 1H), 8.23 (s, 1H), 8.14 (s, 1H), 5.50 (br s, 2H), 4.33 (q, 2H), 1.80 (s, 3H), 1.42 (t, 3H).

Intermediate 181

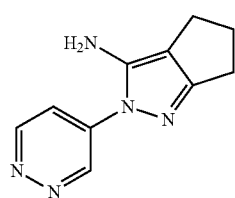

2-(pyridazin-4-yl)-2,4,5,6-tetrahydrocyclopenta[c]pyrazol-3-amine

A suspension of 4-hydrazinylpyridazine hydrobromide (0.368 g, 1.93 mmol) in absolute EtOH (5 mL) was treated with 2-oxocyclopentanecarbonitrile (0.191 g, 1.75 mmol) and the mixture was heated at reflux for 22 hours. The mixture was cooled to ambient temperature and was concentrated to an orange solid. The solid was suspended in 1M NaOH and stirred for 10 minutes. The solid was collected, washed thoroughly with H$_2$O and Et$_2$O and dried in vacuum to furnish title compound as a tan powder (0.323 g, 92%). MS (apci) m/z=202.1 (M+H).

Intermediate 182

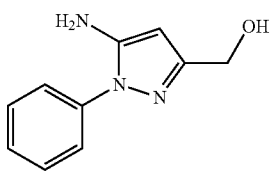

(5-amino-1-phenyl-1H-pyrazol-3-yl)methanol

Step A: Ethyl 2-(tert-butyldimethylsilyloxy)acetate

A mixture of ethyl 2-hydroxyacetate (3.00 g, 28.8 mmol), TBDMS-Cl (5.21 g, 34.6 mmol) and imidazole (2.55 g, 37.5 mmol) was stirred at ambient temperature for 60 hours. The mixture was concentrated and the residue was purified by SiO$_2$ chromatography eluting with 10% EtOAc-hexanes to provide the title compound as a colorless oil (4.12 g, 65%). $^1$H NMR (CDCl$_3$) δ 4.12 (s, 2H), 4.09 (q, 2H), 1.17 (t, 3H), 0.18 (s, 9H), 0.00 (s, 6H).

Step B: (5-amino-1-phenyl-1H-pyrazol-3-yl)methanol

A solution of acetonitrile (0.526 mL, 10.1 mmol) in dry THF (20.4 mL, 9.16 mmol) was cooled to −78° C. and 2.5M nBuLi in hexanes (4.21 mL, 10.5 mmol) was added dropwise. The reaction mixture was stirred for 15 minutes and ethyl 2-(tert-butyldimethylsilyloxy)acetate (2.00 g, 9.16 mmol) was added. The reaction mixture was allowed to warm to ambient temperature and was stirred for 2 hours. The reaction mixture was diluted with ice water and was concentrated. The residual aqueous mixture was acidified to pH=5 and extracted with EtOAc (3×). The combined organics were washed with brine, dried over MgSO$_4$, filtered and concentrated. The residual brown oil was dissolved in MeOH (23 mL) and phenyl hydrazine (0.907 mL, 9.14 mmol) was added. The mixture was treated with concentrated HCl (3.81 mL, 45.7 mmol) and heated at reflux for 18 hours. Upon cooling, the mixture was concentrated and the residue was partitioned into in H$_2$O and CH$_2$Cl$_2$. The mixture was filtered and the organic layer was removed from the filtrate. The aqueous portion was washed with CH$_2$Cl$_2$ and was treated with saturated NaHCO$_3$ until basic. The aqueous mixture was extracted with CH$_2$Cl$_2$ (3×) and the combined organic fractions were dried over MgSO$_4$, filtered and concentrated. The residue was purified by silica column chromatography using 70-100% EtOAc/hexanes gradient elution followed by 0-5% MeOH/EtOAc. The product pools were combined and concentrated to give the title compound as a yellow foam (0.760 g, 44% yield). MS (apci) m/z=190.1 (M+H).

Intermediate 183

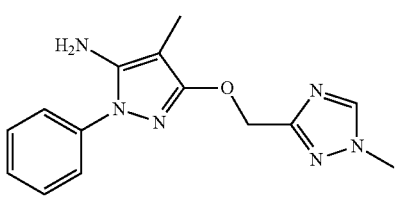

4-methyl-3-((1-methyl-1H-1,2,4-triazol-3-yl)methoxy)-1-phenyl-1H-pyrazol-5-amine The title compound was prepared by the method as described for Intermediate P135, substituting bromoethane with 3-(chloromethyl)-1-methyl-1H-1,2,4-triazole hydrochloride. The product was isolated as a gold syrup (110 mg, 27%). MS (apci) m/z=285.1 (M+H).

Intermediate 184

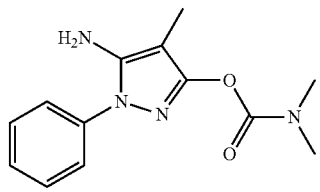

5-amino-4-methyl-1-phenyl-1H-pyrazol-3-yl dimethylcarbamate

A mixture of 5-amino-4-methyl-1-phenyl-1H-pyrazol-3(2H)-one (Intermediate P135 Step A, 0.378 g, 2.00 mmol) and powdered K$_2$CO$_3$ (0.553 g, 4.00 mmol) in dry DMF (4 mL) was stirred at ambient temperature for 5 minutes. Dimethylcarbamoyl chloride (0.206 mL, 2.20 mmol) was added and the mixture was stirred for 6 hours. The mixture was poured into chilled H$_2$O (40 mL) and was extracted with EtOAc (3×). The combined extracts were washed with saturated NaCl (2×), dried over MgSO$_4$ and filtered through a SiO$_2$ plug capped with a MgSO$_4$ layer (EtOAc elution). The filtrate was concentrated and the residue dried in Intermediate 185

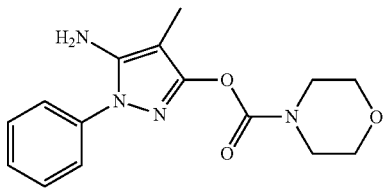

5-amino-4-methyl-1-phenyl-1H-pyrazol-3-yl morpholine-4-carboxylate

The title compound was prepared using morpholine-4-carbonyl chloride in the procedure outlined for 5-amino-4-methyl-1-phenyl-1H-pyrazol-3-yl dimethylcarbamate (Intermediate 184). The compound was isolated as a light yellow wax (0.285 g, 47%). $^1$H NMR (CDCl$_3$) δ 7.54 (d, 2H), 7.43 (t, 2H), 7.31 (t, 1H), 3.66-3.78 (m, 8H), 3.57 (br s, 2H), 1.85 (s, 3H).

Intermediate 186

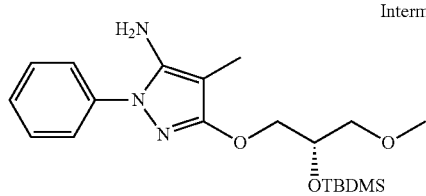

(S)-3-(2-((tert-butyldimethylsilyl)oxy)-3-methoxypropoxy)-4-methyl-1-phenyl-1H-pyrazol-5-amine Step A: (S)-1-(5-amino-4-methyl-1-phenyl-1H-pyrazol-3-yloxy)-3-methoxypropan-2-ol A mixture of 5-amino-4-methyl-1-phenyl-1H-pyrazol-3(2H)-one (P135 Step A, 1.21 g, 6.40 mmol) and powdered K$_2$CO$_3$ (1.77 g, 12.8 mmol) in dry DMF (12 mL) was stirred at ambient temperature for 10 minutes. (S)-2-(methoxymethyl)oxirane (0.622 mL, 6.72 mmol) was added and the mixture was stirred at 80° C. for 6 hours. The mixture was cooled to ambient temperature, poured into chilled H$_2$O (25 mL) and extracted with EtOAc (3×). The combined extracts were washed with saturated NaCl (2×), dried over MgSO$_4$ and filtered through a SiO$_2$ plug capped with a layer of MgSO$_4$ eluting with EtOAc. The filtrate was concentrated to give the title compound as a colorless, viscous oil (701 mg, 40%). MS (apci) m/z=278.1 (M+H).

Step B: (S)-3-(2-((tert-butyldimethylsilyl)oxy)-3-methoxypropoxy)-4-methyl-1-phenyl-1H-pyrazol-5-amine To a solution of TBDMS-Cl (725 mg, 4.81 mmol) and imidazole (390 mg, 5.72 mmol) in dry DMF (7.0 mL) was added (S)-1-(5-amino-4-methyl-1-phenyl-1H-pyrazol-3-yloxy)-3-methoxypropan-2-ol (635 mg, 2.29 mmol) in dry DMF (2 mL). The mixture stirred at ambient temperature for 2.5 hours. The mixture added to H$_2$O (70 mL), mixed for 5 minutes and extracted with Et$_2$O (3×). The combined extracts were washed with saturated NaCl (2×) and dried over MgSO$_4$. The dried solution was filtered through a SiO$_2$ plug capped with a layer of MgSO$_4$ (Et$_2$O elution). The filtrate was concentrated to give the title compound as a colorless oil that was dried in vacuum (940 mg, 105%). MS (apci) m/z=392.2 (M+H). $^1$H NMR (CDCl$_3$) δ 7.50 (d, 2H), 7.40 (t, 2H), 7.23 (t, 1H), 4.09-4.30 (m, 3H), 3.57 (br s, 2H), 3.38-3.44 (m, 2H), 3.32 (s, 3H), 1.83 (s, 3H), 0.88 (s, 9H), 0.11 (s, 6H).

Intermediate 187

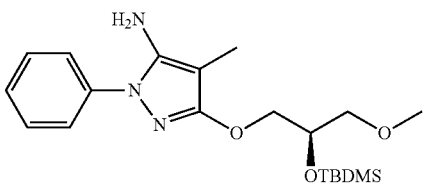

(R)-3-(2-((tert-butyldimethylsily)oxy)-3-methoxypropoxy)-4-methyl-1-phenyl-1H-pyrazol-5-amine The title compound was prepared using the procedure described for (S)-3-(2-((tert-butyldimethylsilyl)oxy)-3-methoxypropoxy)-4-methyl-1-phenyl-1H-pyrazol-5-amine (Intermediate 186) substituting (S)-2-(methoxymethyl)oxirane with (R)-2-(methoxymethyl)oxirane in Step A. The product was obtained as a colorless syrup (921 mg, 38% over 2 steps). MS (apci) m/z=392.2 (M+H). $^1$H NMR (CDCl$_3$) δ 7.50 (d, 2H), 7.40 (t, 2H), 7.23 (t, 1H), 4.09-4.30 (m, 3H), 3.57 (br s, 2H), 3.38-3.44 (m, 2H), 3.32 (s, 3H), 1.83 (s, 3H), 0.88 (s, 9H), 0.11 (s, 6H).

Intermediate 188

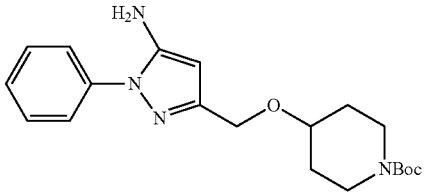

tert-butyl 4-((5-amino-1-phenyl-1H-pyrazol-3-yl)methoxy)piperidine-1-carboxylate Step A: tert-butyl 4-(2-ethoxy-2-oxoethoxy)piperidine-1-carboxylate A solution of tert-butyl 4-hydroxypiperidine-1-carboxylate (2.00 g, 9.94 mmol) in dry THF (25 mL) was cooled to 0° C. and KOtBu (1.12 g, 9.94 mmol) was added. The mixture was allowed to reach ambient temperature and was stirred for 10 minutes. The mixture was cooled to 0° C. and ethyl 2-bromoacetate (1.65 mL, 14.9 mmol) was added dropwise. The reaction was allowed to reach ambient temperature and was stirred for 17 hours. The mixture was partitioned into in H$_2$O and EtOAc, mixed and the organic layer was removed. The organic layer was dried over MgSO$_4$, filtered and concentrated. The residual thick yellow oil was purified by silica chromatography using a 10-25%

EtOAc/hexanes gradient elution to afford the title compound as a colorless oil (0.967 g, 34% yield). $^1$H NMR (CDCl$_3$) δ 4.22 (q, 2H), 4.12 (s, 2H), 3.67-3.84 (m, 2H), 3.52-3.63 (m, 1H), 3.05-3.11 (m, 2H), 1.81-1.90 (m, 2H), 1.53-1.62 (m, 2H), 1.45 (s, 9H), 1.29 (t, 3H).

Step B: tert-butyl 4-((5-amino-1-phenyl-1H-pyrazol-3-yl)methoxy)piperidine-1-carboxylate A solution of diisopropylamine (1.08 mL, 7.74 mmol) in dry THF (5 mL) was cooled to 0° C. and 2.5M nBuLi in hexanes (2.96 mL, 7.41 mmol) was slowly added. The mixture was stirred at 0° C. for 10 minutes and was cooled to −78° C. Acetonitrile (0.404 mL, 7.74 mmol) was added and the mixture was stirred for 15 minutes. A solution of tert-butyl 4-(2-ethoxy-2-oxoethoxy)piperidine-1-carboxylate (0.967 g, 3.37 mmol) in THF (2.5 mL) was added and the mixture was stirred at −78° C. for 1 hour. The mixture was allowed to reach ambient temperature, was quenched with ice water and concentrated. The residual aqueous mixture was neutralized with 2M HCl and was extracted with CH$_2$Cl$_2$ (3×). The combined organic fractions were dried over MgSO$_4$, filtered and concentrated to provide the crude cyano-ketone as a yellow oil that was used immediately in the next step.

Step C: tert-butyl 4-((5-amino-1-phenyl-1H-pyrazol-3-yl)methoxy)piperidine-1-carboxylate The crude oil obtained in Step B was dissolved in EtOH (17 mL) and phenylhydrazine (0.396 mL, 3.99 mmol) was added. The mixture was heated at 60° C. for 60 hours, was cooled to ambient temperature and was concentrated. The residue was partitioned into EtOAc and water, mixed and the organic layer removed. The aqueous layer was extracted with EtOAc (2×) and the combined EtOAc portions were dried over MgSO$_4$, filtered and concentrated. The residual orange oil was purified by silica chromatography using a 10-100% EtOAc/hexanes gradient elution. The pooled product fractions were concentrated and the residual yellow-orange oil was re-purified by reverse phase HPLC using a 0-100% acetonitrile/water gradient to provide the title compound as an orange foam (0.264 g, 21% yield). MS (apci) m/z=373.2 (M+H).

Intermediate 189

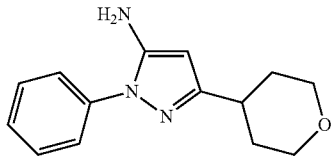

1-phenyl-3-(tetrahydro-2H-pyran-4-yl)-1H-pyrazol-5-amine

Step A:
3-oxo-3-(tetrahydro-2H-pyran-4-yl)propanenitrile

A 1M solution of LHMDS in dry THF (26.3 mL, 26.3 mmol) was cooled to −78° C. and acetonitrile (1.43 mL, 27.5 mmol) was added dropwise over 2 minutes. The mixture was stirred at −78° C. for 1 hour and a solution of methyl tetrahydro-2H-pyran-4-carboxylate (3.41 mL, 25.0 mmol) in dry THF (12 mL) was added. The mixture was stirred for 1 hour, the dry ice bath was removed and the mixture allowed to reach ambient temperature. The mixture was poured into chilled H$_2$O (250 mL) and was extracted with Et$_2$O (3×). The aqueous portion was cooled to 0° C. and 6M HCl was added dropwise to pH=3 (starting pH=12). The mixture was extracted with EtOAc (3×) and the combined extracts were dried over MgSO$_4$. The solution eluted through a SiO$_2$ plug eluting with EtOAc. The filtrate was concentrated to give the title compound as a colorless oil (2.52 g, 66%). $^1$H NMR (CDCl$_3$) δ 3.99-4.06 (m, 2H), 3.54 (s, 2H), 3.46 (t, 2H), 2.76-2.86 (m, 1H), 1.70-1.86 (m, 4H).

Step B: 1-phenyl-3-(tetrahydro-2H-pyran-4-yl)-1H-pyrazol-5-amine

To a solution of 3-oxo-3-(tetrahydro-2H-pyran-4-yl)propanenitrile (2.30 g, 12.8 mmol) in absolute EtOH (35 mL) was added phenylhydrazine hydrochloride (2.21 g, 15.3 mmol) and the mixture was heated at reflux until complete by TLC (5 hours). The mixture was cooled to ambient temperature and was concentrated. The residue was partitioned in H$_2$O (75 mL) and EtOAc (40 mL). 2M NaOH was added to pH=5 with vigorous mixing, the organic layer was removed and the aqueous was extracted with EtOAc (2×). The combined EtOAc fractions were washed with H$_2$O and saturated NaCl. The solution was diluted with an equal volume of hexanes, dried over MgSO$_4$/activated carbon and eluted through a SiO$_2$ plug eluting with 50% EtOAc-hexanes. The filtrate was concentrated to give a gold syrup. The syrup was treated with Et$_2$O and stirred until a fine, granular suspension formed. The solid was collected, washed with Et$_2$O and dried in vacuum to furnish the title compound as a white solid (2.01 g, 65%). $^1$H NMR (CDCl$_3$) δ 7.55 (d, 2H), 7.46 (t, 2H), 7.32 (t, 1H), 5.49 (s, 1H), 4.00-4.08 (m, 2H), 3.97 (br s, 2H), 3.52 (dt, 2H), 2.86 (m, 1H) 1.73-1.93 (m, 4H).

The following compounds were prepared according to the method used for the preparation of 1-phenyl-3-(tetrahydro-2H-pyran-4-yl)-1H-pyrazol-5-amine (Intermediate 189) using either acetonitrile or propiononitrile in Step A in conjunction with the appropriate ester.

| Intermediate # | Structure | Data |
|---|---|---|
| 190 | ![structure] | MS (apci) m/z = 343.1 (M + H) |

| Intermediate # | Structure | Data |
|---|---|---|
| 191 | 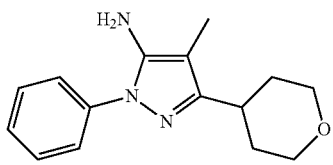 [SMILES: Cc1c(C2CCOCC2)nn(-c2ccccc2)c1N] | MS (apci) m/z = 258.0 (M + H) |
| 192 | 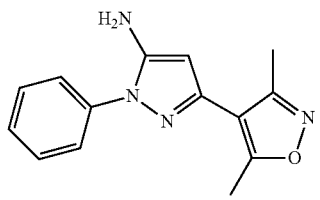 [SMILES: Cc1noc(C)c1-c1cc(N)n(-c2ccccc2)n1] | $^1$H NMR (CDCl$_3$) δ 7.62 (d, 2H), 7.50 (t, 2H), 7.37 (t, 1H), 5.72 (s, 1H), 3.91 (br s, 2H), 2.58 (s, 3H), 2.44 (s, 3H). |
| 193 | 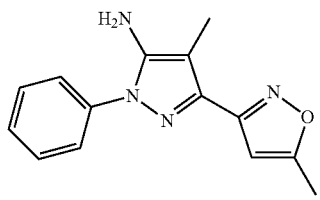 [SMILES: Cc1cc(-c2nn(-c3ccccc3)c(N)c2C)no1] | $^1$H NMR (CDCl$_3$) δ 7.60 (d, 2H), 7.49 (t, 2H), 7.37 (t, 1H), 6.45 (s, 1H), 3.67 (br s, 2H), 2.45 (s, 3H), 2.24 (s, 3H). |
| 194 | 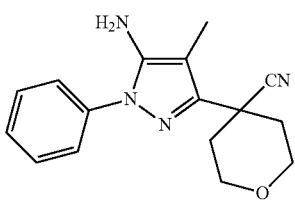 [SMILES: Cc1c(C2(C#N)CCOCC2)nn(-c2ccccc2)c1N] | $^1$H NMR (CDCl$_3$) δ 7.45-7.56 (m, 4H), 7.35 (t, 1H), 4.00-4.06 (m, 2H), 3.88 (dt, 2H), 3.62 (br s, 2H), 2.18-2.34 (m, 4H), 2.11 (s, 3H). |
| 195 | 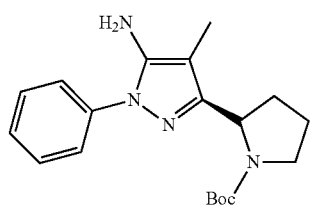 | MS (apci) m/z = 343.2 (M + H) |
| 196 | 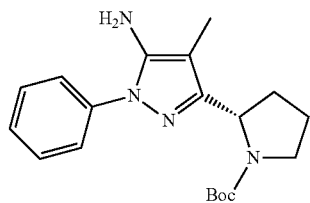 [SMILES: Cc1c([C@@H]2CCCN2C(=O)OC(C)(C)C)nn(-c2ccccc2)c1N] | MS (apci) m/z = 343.2 (M + H) |
| 197 | 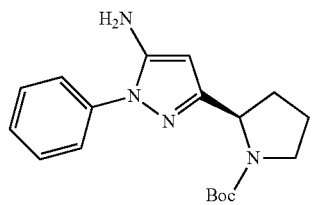 [SMILES: CC(C)(C)OC(=O)N1CCC[C@@H]1c1cc(N)n(-c2ccccc2)n1] | MS (apci) m/z = 329.2 (M + H) |

| Intermediate # | Structure | Data |
|---|---|---|
| 198 | ![structure] | MS (apci) m/z = 329.2 (M + H) |

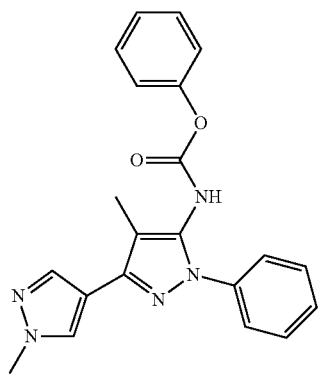

Intermediate 199

Phenyl 1',4-dimethyl-1-phenyl-1H,1'H-3,4'-bipyrazol-5-ylcarbamate

Step A: ethyl 1-methyl-1H-pyrazole-4-carboxylate

To a 3000-mL three-necked flask was added ethyl 2-formyl-3-oxopropanoate (100 g, 694 mmol), followed by anhydrous 200-proof EtOH (694 mL) to obtain a clear yellowish solution. The reaction was cooled in an ice bath to 5° C., and then methylhydrazine (35.8 mL, 680 mmol) was added dropwise. A vigorous exotherm was observed during hydrazine addition and the temperature was kept below 12° C. by controlling the addition rate. After the hydrazine addition was complete, the ice bath was removed, and the reaction was allowed to stir at ambient temperature overnight. The reaction was concentrated on a rotary evaporator to a crude orange oil. The crude was taken up in DCM and re-concentrated, then on high vacuum for 2 days to yield tan orange oil. LC/MS and $^1$H NMR showed essentially pure ethyl 1-methyl-1H-pyrazole-4-carboxylate (106 g, 99.1%).

Step B: 2-methyl-3-(1-methyl-1H-pyrazol-4-yl)-3-oxopropanenitrile

To a four-necked 5-liter round bottomed flask fitted with an overhead stirrer and addition funnel was charged LHMDS (1444 mL, 1444 mmol) (1.0M in THF). The solution was cooled in an acetone/dry ice bath first (internal temperature of −79° C.) under nitrogen, followed by slow addition of propiononitrile (103 mL, 1444 mmol) via dropping funnel. The mixture was stirred at −80° C. for 90 minutes. A solution of ethyl 1-methyl-1H-pyrazole-4-carboxylate (106 g, 688 mmol) in anhydrous THF (500 mL) was then introduced dropwise via an addition funnel (addition time: about 45 minutes; internal temperature during addition remained below −76° C.). After the addition was complete, the reaction was allowed to slowly warm to ambient temperature and stirred overnight. An orange glass deposited on the bottom of the flask. The organics were decanted and the glass was dissolved in warm water. The mixture was washed with ether (3×1000 mL). The aqueous phase was then pH-adjusted to 5 (pH paper) using concentrated HCl and saturated bicarbarbonate solution. The aqueous layer was extracted with DCM (3×1000 mL). The combined organic extracts were dried over MgSO$_4$ filtered and concentrated to yield the 2-methyl-3-(1-methyl-1H-pyrazol-4-yl)-3-oxopropanenitrile as an amber oil (92 g, 82%). MS (apci) m/z=162.1 (M−H).

Step C: 1',4-dimethyl-1-phenyl-1H,1'H-3,4'-bipyrazol-5-amine

A 3 L, 3 necked round bottomed flask was charged with 2-methyl-3-(1-methyl-1H-pyrazol-4-yl)-3-oxopropanenitrile (60 g, 368 mmol) absolute anhydrous ethanol (1000 mL) and phenylhydrazine hydrochloride (58 g, 404 mmol) at ambient temperature to form a yellowish suspension. The reaction vessel was equipped with a water condenser and refluxed (using a heating mantle) overnight. The reaction was concentrated and 1M NaOH (1 L) was added and the solid was broken up and collected. The solid was washed with water and hexanes. A second crop crashed out in the filtrate and was collected. The combined solids were crushed and triturated with ether (500 mL). The solid was collected filtration, washed with hexanes and air dried under vacuum to provide 1',4-dimethyl-1-phenyl-1H,1'H-3,4'-bipyrazol-5-amine (93 g, 100%).

Step D: phenyl 1',4-dimethyl-1-phenyl-1H,1'H-3,4'-bipyrazol-5-ylcarbamate

In a 3 L, round bottomed flask was charged with 1',4-dimethyl-1-phenyl-1H,1'H-3,4'-bipyrazol-5-amine (50 g, 197.4 mmol) and EtOAc (1000 mL) to obtain a clear brownish solution. To this was added NaOH (2M aq) (500 mL) in one portion to obtain a turbid mixture (both the aqueous and organic layers were clear but a precipitate was observed in between the two layers). After 3 minutes, phenyl carbonochloridate (74.29 mL, 592.2 mmol) was added slowly at ambient temperature exotherm to 33° C. The reaction stirred at ambient temperature for 2 hours. Additional phenyl carbonochloridate (10 mL) was added. After 30 minutes the organics were separated, washed with brine and concentrated in vacuo. The product was purified by silica gel chromatography (eluting with 75% ethyl acetate in hexanes) to provide phenyl 1',4-dimethyl-1-phenyl-1H,1'H-3,4'-bipyrazol-5-ylcarbamate (60 g, 81.4%).

Intermediate 200

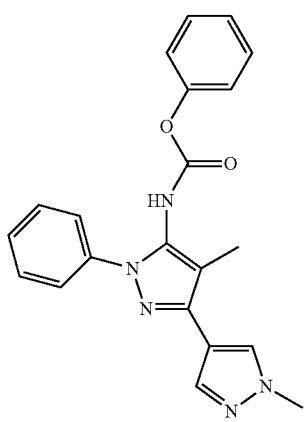

phenyl 1',4-dimethyl-1-phenyl-1H,1'H-3,4'-bipyrazol-5-ylcarbamate

A 3 L, round bottomed flask was charged with 1',4-dimethyl-1-phenyl-1H,1'H-3,4'-bipyrazol-5-amine (50 g, 197.4 mmol) and EtOAc (1000 mL) to obtain a clear brownish solution. To this was added NaOH (2M aq) (500 mL) in one portion to obtain a turbid mixture (the aqueous and organic layers were clear, but a precipitate was observed in between the two layers). After 3 minutes, phenyl carbonochloridate (74.29 mL, 592.2 mmol) was added slowly at ambient temperature (the temperature of the reaction mixture increased to 33° C. during the addition). The reaction stirred at ambient temperature for 2 hours. Additional phenyl carbonochloridate (10 mL) was added. After 30 minutes the organics layers were separated, washed with brine and concentrated in vacuo. The residue was purified by silica gel chromatography (eluting with 75% ethyl acetate in hexanes) to provide phenyl 1',4-dimethyl-1-phenyl-1H,1'H-3,4'-bipyrazol-5-ylcarbamate (60 g, 81.4%).

Intermediate 201

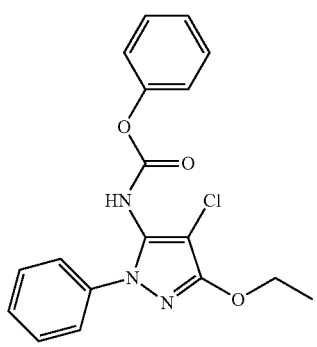

phenyl (4-chloro-3-ethoxy-1-phenyl-1H-pyrazol-5-yl)carbamate

Step A: Preparation of phenyl (3-ethoxy-1-phenyl-1H-pyrazol-5-yl)carbamate

To a suspension of 3-ethoxy-1-phenyl-1H-pyrazol-5-amine (Intermediate P139, 169 mg, 0.832 mmol) in EtOAc (5 mL) at 0° C. was added 2.0 M aqueous NaOH solution (1.25 mL, 2.50 mmol), followed by dropwise addition of phenyl carbonochloridate (0.178 mL, 1.41 mmol). The reaction was stirred at ambient temperature for 15 hours. The reaction mixture was diluted with EtOAc and phase-separated. The organic layer was washed with water and brine, dried over $MgSO_4$, and concentrated. The residue was purified by flash chromatography on silica gel (6:1 hexanes:EtOAc) to give the title compound (219 mg, 81% yield). MS (apci) m/z=324.1 (M+H).

Step B: Preparation of phenyl (4-chloro-3-ethoxy-1-phenyl-1H-pyrazol-5-yl)carbamate To a solution of phenyl 3-ethoxy-1-phenyl-1H-pyrazol-5-ylcarbamate (92 mg, 0.28 mmol) and pyridinium 4-methylbenzenesulfonate (7.2 mg, 0.028 mmol) in DCM (2 mL) was added N-chlorosuccinimide (42 mg, 0.31 mmol) at ambient temperature. The mixture was stirred at ambient temperature for 2 days and then concentrated under reduced pressure. The residue was purified by flash chromatography on silica gel (9:1, hexanes/EtOAc) to give the title compound (76 mg, 75% yield). MS (apci) m/z=358.1 (M+H).

Intermediate 203

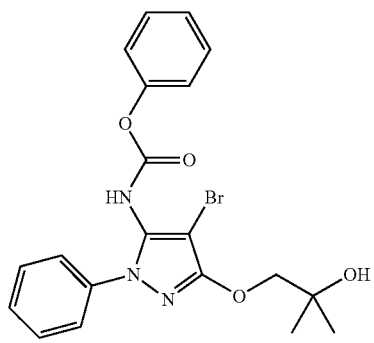

Phenyl (4-bromo-3-(2-hydroxy-2-methylpropoxy)-1-phenyl-1H-pyrazol-5-yl)carbamate Step A: Preparation of 5-amino-1-phenyl-1H-pyrazol-3(2H)-one Prepared according to the method described for Intermediate P1, replacing 4,4-dimethyl-3-oxopentanenitrile with ethyl 2-cyanoacetate, and substituting phenylhydrazine for ethyl 3-hydrazinylbenzoate hydrochloride. MS (apci) m/z=176.0 (M+H).

Step B: Preparation of 1-((5-amino-1-phenyl-1H-pyrazol-3-yl)oxy)-2-methylpropan-2-ol A mixture of 5-amino-1-phenyl-1H-pyrazol-3(2H)-one (0.330 g, 1.88 mmol), 2,2-dimethyloxirane (0.143 g, 1.98 mmol) and $K_2CO_3$ (0.521 g, 3.77 mmol) in DMA (5 mL) was heated at 80° C. for 3 days. After cooling, the reaction mixture was diluted with EtOAc, washed with water and brine and dried over $MgSO_4$. The mixture was filtered through a pad of $SiO_2$ eluting with EtOAc to yield the title compound. MS (apci) m/z=248.1 (M+H).

Step C: Preparation of phenyl (3-(2-hydroxy-2-methylpropoxy)-1-phenyl-1H-pyrazol-5-yl)carbamate Prepared according to the method described for Intermediate 201. Step A using 1-((5-amino-1-phenyl-1H-pyrazol-3-yl)oxy)-2-methylpropan-2-ol as a replacement for 3-ethoxy-1-phenyl-1H-pyrazol-5-amine. MS (apci) m/z=368.1 (M+H).

Step D: Preparation of phenyl (4-bromo-3-(2-hydroxy-2-methylpropoxy)-1-phenyl-1H-pyrazol-5-yl) carbamate Prepared according to the method described for Intermediate 201, Step B using N-bromosuccinimide as a replacement for N-chlorosuccinimide, and substituting phenyl (3-(2-hydroxy-2-methylpropoxy)-1-phenyl-1H-pyrazol-5-yl) carbamate for phenyl 3-ethoxy-1-phenyl-1H-pyrazol-5-ylcarbamate. MS (apci) m/z=446.1 (M+H).

The following compounds prepared according to the method describe for the preparation of Intermediate 200, using the appropriate amino pyrazole intermediate:

| Intermediate # | Structure | Name | Data |
| --- | --- | --- | --- |
| 204 | 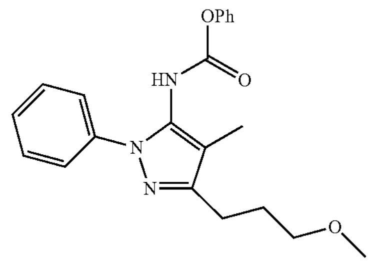 [SMILES: COCCCc1nn(-c2ccccc2)c(NC(=O)Oc2ccccc2)c1C] | phenyl 3-(3-methoxypropyl)-4-methyl-1-phenyl-1H-pyrazol-5-ylcarbamate | MS (apci) m/z = 366.1 (M + H). |
| 205 | 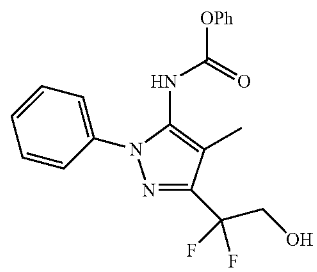 [SMILES: Cc1c(C(F)(F)CO)nn(-c2ccccc2)c1NC(=O)Oc1ccccc1] | phenyl 3-(1,1-difluoro-2-hydroxyethyl)-4-methyl-1-phenyl-1H-pyrazol-5-ylcarbamate | MS (apci) m/z = 374.1 (M + H). |
| 206 | 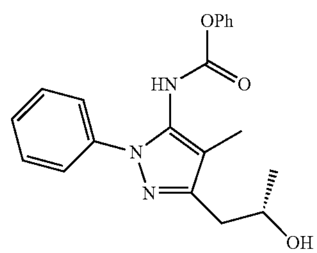 [SMILES: Cc1c(C[C@H](C)O)nn(-c2ccccc2)c1NC(=O)Oc1ccccc1] | (S)-phenyl 3-(2-hydroxypropyl)-4-methyl-1-phenyl-1H-pyrazol-5-ylcarbamate | MS (apci) m/z = 352.1 (M + H). |
| 207 | 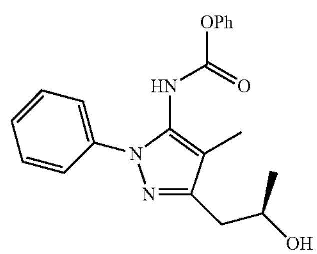 [SMILES: Cc1c(C[C@@H](C)O)nn(-c2ccccc2)c1NC(=O)Oc1ccccc1] | (R)-phenyl 3-(2-hydroxypropyl)-4-methyl-1-phenyl-1H-pyrazol-5-ylcarbamate | MS (apci) m/z = 352.1 (M + H). |
| 208 | 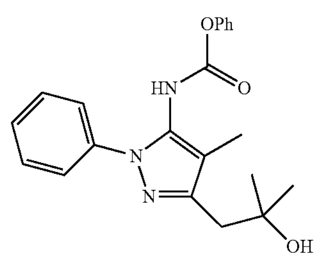 [SMILES: Cc1c(CC(C)(C)O)nn(-c2ccccc2)c1NC(=O)Oc1ccccc1] | phenyl 3-(2-hydroxy-2-methylpropyl)-4-methyl-1-phenyl-1H-pyrazol-5-ylcarbamate | MS (apci) m/z = 366.2 (M + H). |

| Intermediate # | Structure | Name | Data |
|---|---|---|---|
| 209 | 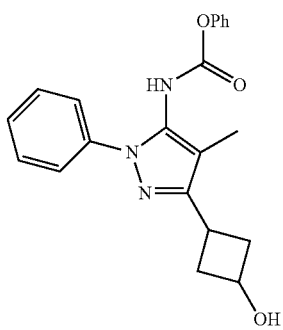 [SMILES: Cc1c(C2CC(O)C2)nn(-c2ccccc2)c1NC(=O)Oc1ccccc1] | phenyl 3-(3-hydroxycyclobutyl)-4-methyl-1-phenyl-1H-pyrazol-5-ylcarbamate | MS (apci) m/z = 364.2 (M + H). |
| 210 | 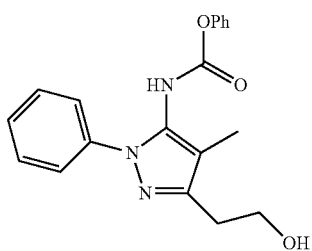 [SMILES: Cc1c(CCO)nn(-c2ccccc2)c1NC(=O)Oc1ccccc1] | phenyl 3-(2-hydroxyethyl)-4-methyl-1-phenyl-1H-pyrazol-5-ylcarbamate | MS (apci) m/z = 338.1 (M + H). |
| 211 | 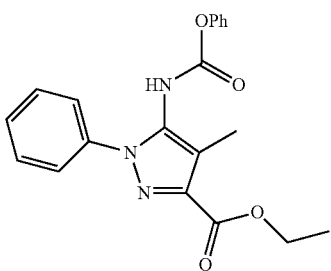 [SMILES: CCOC(=O)c1nn(-c2ccccc2)c(NC(=O)Oc2ccccc2)c1C] | ethyl 4-methyl-5-(phenoxycarbonyl-amino)-1-phenyl-1H-pyrazole-3-carboxylate | MS (apci) m/z = 366.1 (M + H). |
| 212 | 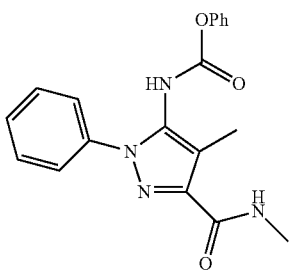 [SMILES: CNC(=O)c1nn(-c2ccccc2)c(NC(=O)Oc2ccccc2)c1C] | phenyl 4-methyl-3-(methylcarbamoyl)-1-phenyl-1H-pyrazol-5-ylcarbamate | MS (apci) m/z = 351.1 (M + H). |
| 213 | 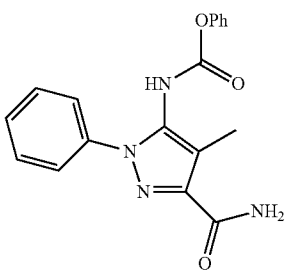 [SMILES: Cc1c(C(N)=O)nn(-c2ccccc2)c1NC(=O)Oc1ccccc1] | phenyl 3-carbamoyl-4-methyl-1-phenyl-1H-pyrazol-5-ylcarbamate | MS (apci) m/z = 337.1 (M + H). |

-continued

| Intermediate # | Structure | Name | Data |
|---|---|---|---|
| 214 | 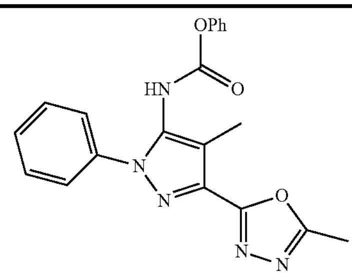 | phenyl (4-methyl-3-(5-methyl-1,3,4-oxadiazol-2-yl)-1-phenyl-1H-pyrazol-5-yl)carbamate | MS (apci) m/z = 376.1 (M + H). |
| 215 | 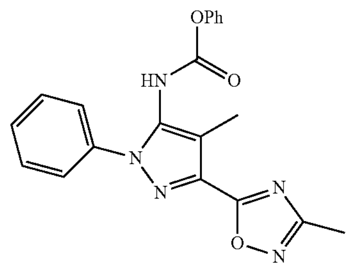 | phenyl 4-methyl-3-(3-methyl-1,2,4-oxadiazol-5-yl)-1-phenyl-1H-pyrazol-5-ylcarbamate | MS (apci) m/z = 376.1 (M + H). |
| 216 | 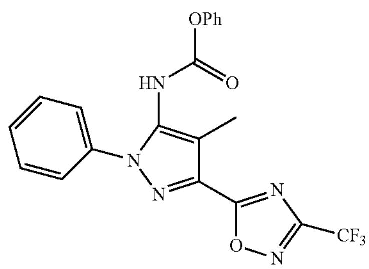 [SMILES: Cc1c(-c2nc(C(F)(F)F)no2)nn(-c2ccccc2)c1NC(=O)Oc1ccccc1] | phenyl 4-methyl-1-phenyl-3-(3-(trifluoromethyl)-1,2,4-oxadiazol-5-yl)-1H-pyrazol-5-ylcarbamate | MS (apci) m/z = 430.1 (M + H). |
| 217 | 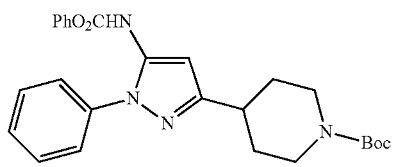 | tert-butyl 4-(5-((phenoxycarbonyl)amino)-1-phenyl-1H-pyrazol-3-yl)piperidine-1-carboxylate | MS (apci) m/z = 463.3 (M + H) |
| 218 | 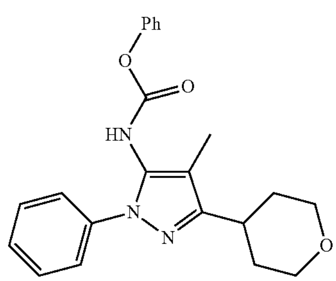 [SMILES: Cc1c(C2CCOCC2)nn(-c2ccccc2)c1NC(=O)Oc1ccccc1] | phenyl (4-methyl-1-phenyl-3-(tetrahydro-2H-pyran-4-yl)-1H-pyrazol-5-yl)carbamate | MS (apci) m/z = 378.2 (M + H) |
| 219 | 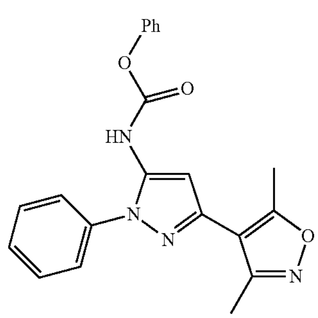 [SMILES: Cc1noc(C)c1-c1cc(NC(=O)Oc2ccccc2)n(-c2ccccc2)n1] | phenyl (3-(3,5-dimethylisoxazol-4-yl)-1-phenyl-1H-pyrazol-5-yl)carbamate | $^1$H NMR (CDCl$_3$) δ 7.56-7.64 (m, 4H), 7.48-7.52 (m, 1H), 7.40 (t, 2H), 7.26 (t, 2H), 7.16 (br s, 2H), 6.71 (br s, 1H), 2.60 (s, 3H) 2.46 (s, 3H) |

| Intermediate # | Structure | Name | Data |
|---|---|---|---|
| 220 | 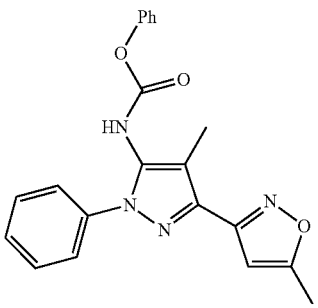 [SMILES: Cc1cc(-c2nn(-c3ccccc3)c(NC(=O)Oc3ccccc3)c2C)no1] | phenyl (4-methyl-3-(5-methylisoxazol-3-yl)-1-phenyl-1H-pyrazol-5-yl)carbamate | $^1$H NMR (CDCl$_3$) δ 7.54 (d, 2H), 7.49 (t, 2H), 7.41 (t, 1H), 7.33 (br s, 2H), 7.20 (br s, 1H), 7.08 (br s, 1H), 6.74 (br s, 1H), 6.66 (br s, 1H), 6.48 (s, 1H), 2.45 (s, 3H) 2.34 (s, 3H) |
| 221 | 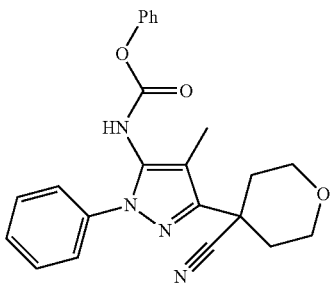 [SMILES: Cc1c(C2(C#N)CCOCC2)nn(-c2ccccc2)c1NC(=O)Oc1ccccc1] | phenyl (3-(4-cyanotetrahydro-2H-pyran-4-yl)-4-methyl-1-phenyl-1H-pyrazol-5-yl)carbamate | $^1$H NMR (CDCl$_3$) δ 7.06-7.56 (m, 9H), 6.75 (br s, 1H), 6.51 (s, 1H), 4.04 (d, 2H) 3.89 (t, 2H), 2.20-2.39 (m, 4H), 2.28 (s, 3H) |
| 222 | 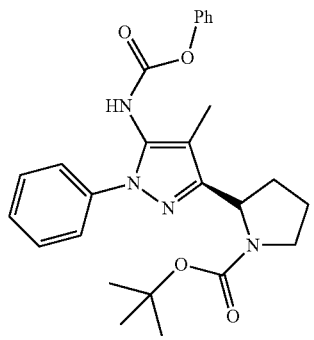 | (R)-tert-butyl 2-(4-methyl-5-((phenoxycarbonyl)amino)-1-phenyl-1H-pyrazol-3-yl)pyrrolidine-1-carboxylate | MS (apci) m/z = 463.2 (M + H) |
| 223 | 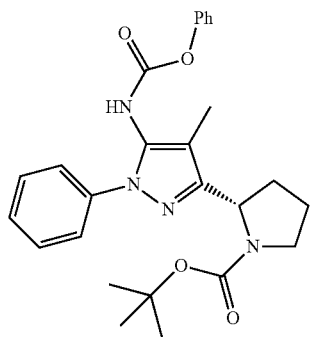 [SMILES: Cc1c([C@@H]2CCCN2C(=O)OC(C)(C)C)nn(-c2ccccc2)c1NC(=O)Oc1ccccc1] | (S)-tert-butyl 2-(4-methyl-5-((phenoxycarbonyl)amino)-1-phenyl-1H-pyrazol-3-yl)pyrrolidine-1-carboxylate | MS (apci) m/z = 463.2 (M + H) |

| Intermediate # | Structure | Name | Data |
|---|---|---|---|
| 224 | 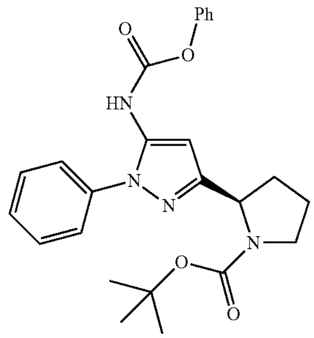 [SMILES: CC(C)(C)OC(=O)N1CCC[C@@H]1c1cc(NC(=O)Oc2ccccc2)n(-c2ccccc2)n1] | (R)-tert-butyl 2-(5-((phenoxycarbonyl)amino)-1-phenyl-1H-pyrazol-3-yl)pyrrolidine-1-carboxylate | MS (apci) m/z = 449.2 (M + H) |
| 225 | 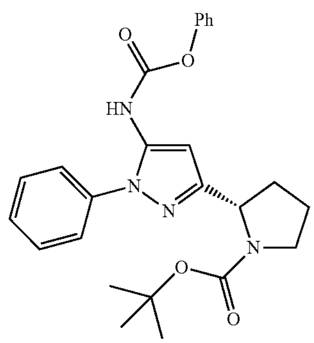 [SMILES: CC(C)(C)OC(=O)N1CCC[C@H]1c1cc(NC(=O)Oc2ccccc2)n(-c2ccccc2)n1] | (S)-tert-butyl 2-(5-((phenoxycarbonyl)amino)-1-phenyl-1H-pyrazol-3-yl)pyrrolidine-1-carboxylate | MS (apci) m/z = 449.2 (M + H) |
| 226 | 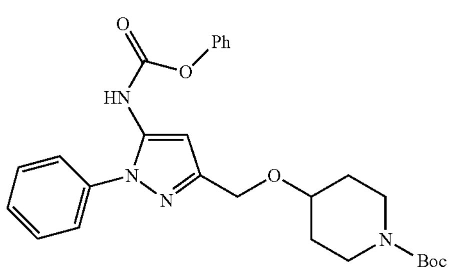 [SMILES: CC(C)(C)OC(=O)N1CCC(OCc2cc(NC(=O)Oc3ccccc3)n(-c3ccccc3)n2)CC1] | tert-butyl 4-((5-((phenoxycarbonyl)amino)-1-phenyl-1H-pyrazol-3-yl)methoxy)piperidine-1-carboxylate | MS (apci) m/z = 493.2 (M + H) |
| 227 | 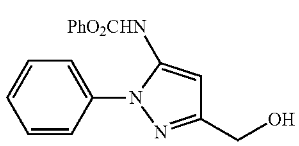 | phenyl (3-(hydroxymethyl)-1-phenyl-1H-pyrazol-5-yl)carbamate | MS (apci) m/z = 310.1 (M + H) |

Intermediate 228

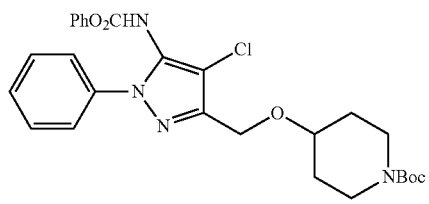

tert-butyl 4-((4-chloro-5-((phenoxycarbonyl)amino)-1-phenyl-1H-pyrazol-3-yl)methoxy)piperidine-1-carboxylate To a suspension of tert-butyl 4-((5-(phenoxycarbonylamino)-1-phenyl-1H-pyrazol-3-yl)methoxy)piperidine-1-carboxylate (Intermediate 226), 98.5 mg, 0.200 mmol) in DCM (2.0 mL) was added pyridinium 4-methylbenzenesulfonate (PPTS) (5.03 mg, 0.020 mmol) and N-chlorosuccinimide (40.1 mg, 0.300 mmol). The resulting solution was stirred at ambient temperature for 8 days. The mixture was diluted with water and CH$_2$Cl$_2$, the organic layer was separated and the aqueous was extracted with CH$_2$Cl$_2$ (2×). The combined organic fractions were dried over MgSO$_4$, filtered and concentrated. The residue was purified by silica chromatography using 30-40% EtOAc/hexanes gradient elution to afford the title compound as an orange oil (73.5 mg, 70% yield). MS (apci) m/z=527.2 (M+H).

Intermediate 229

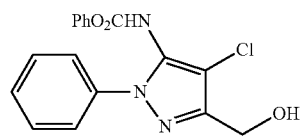

Phenyl (4-chloro-3-(hydroxymethyl)-1-phenyl-1H-pyrazol-5-yl)carbamate

Prepared from phenyl 3-(hydroxymethyl)-1-phenyl-1H-pyrazol-5-ylcarbamate (Intermediate 227) using the procedure outlined for the preparation of tert-butyl 4-((4-chloro-5-((phenoxycarbonyl)amino)-1-phenyl-1H-pyrazol-3-yl)methoxy)piperidine-1-carboxylate (Intermediate 228). In this instance, the compound was isolated a white solid (108 mg, 28%). MS (apci) m/z=344.0 (M+H).

Intermediate 230

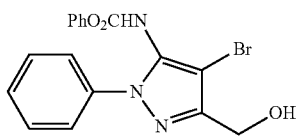

Phenyl (4-bromo-3-(hydroxymethyl)-1-phenyl-1H-pyrazol-5-yl)carbamate

To a suspension of phenyl 3-(hydroxymethyl)-1-phenyl-1H-pyrazol-5-ylcarbamate (Intermediate 227, 100 mg, 0.323 mmol) in CH$_2$Cl$_2$ (1.6 mL) was added pyridinium 4-methylbenzenesulfonate (PPTS) (8.12 mg, 0.0323 mmol) and N-bromosuccinimide (86.3 mg, 0.485 mmol). The reaction mixture was stirred for 16 hours at ambient temperature. The resulting suspension was filtered and the collected solid washed briefly with CH$_2$Cl$_2$ and dried in vacuum to afford the title compound a white solid (48.5 mg, 39%). MS (apci) m/z=388.0 (M+H).

The following pyrazole intermediates were made according to the methods described for the preparation of Intermediate 228, 229 or 230.

| Intermediate | Structure | Name | MS (apci) m/z |
|---|---|---|---|
| 231 | 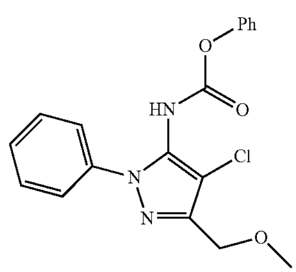 [SMILES: COCc1nn(-c2ccccc2)c(NC(=O)Oc2ccccc2)c1Cl] | phenyl (4-chloro-3-(methoxymethyl)-1-phenyl-1H-pyrazol-5-yl)carbamate | 358.1 (M + H) |
| 232 | 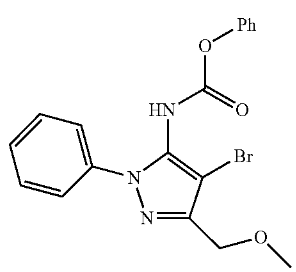 [SMILES: COCc1nn(-c2ccccc2)c(NC(=O)Oc2ccccc2)c1Br] | phenyl (4-bromo-3-(methoxymethyl)-1-phenyl-1H-pyrazol-5-yl)carbamate | 402.2 (M + H) |

| Intermediate | Structure | Name | MS (apci) m/z |
|---|---|---|---|
| 233 | 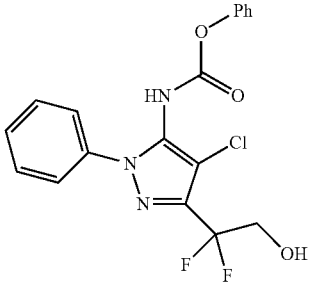 [SMILES: O=C(Nc1c(Cl)c(C(F)(F)CO)nn1-c1ccccc1)Oc1ccccc1] | phenyl (4-chloro-3-(1,1-difluoro-2-hydroxyethyl)-1-phenyl-1H-pyrazol-5-yl)carbamate | 394.1 (M + H) |
| 234 | 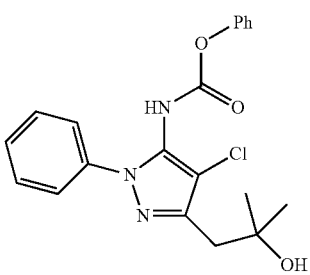 [SMILES: CC(C)(O)Cc1nn(-c2ccccc2)c(NC(=O)Oc2ccccc2)c1Cl] | phenyl (4-chloro-3-(2-hydroxy-2-methylpropyl)-1-phenyl-1H-pyrazol-5-yl)carbamate | 386.1 (M + H) |
| 235 | 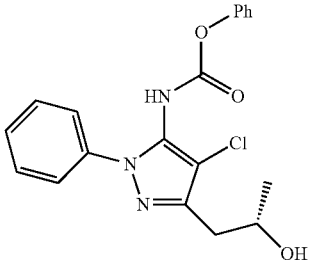 [SMILES: C[C@H](O)Cc1nn(-c2ccccc2)c(NC(=O)Oc2ccccc2)c1Cl] | (S)-phenyl (4-chloro-3-(2-hydroxypropyl)-1-phenyl-1H-pyrazol-5-yl)carbamate | 372.1 (M + H) |
| 236 | 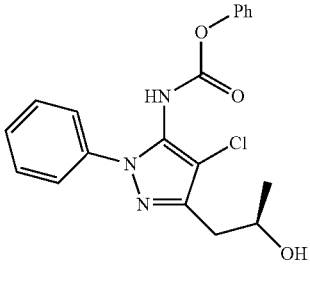 [SMILES: C[C@@H](O)Cc1nn(-c2ccccc2)c(NC(=O)Oc2ccccc2)c1Cl] | (R)-phenyl (4-chloro-3-(2-hydroxypropyl)-1-phenyl-1H-pyrazol-5-yl)carbamate | 372.1 (M + H) |
| 237 | 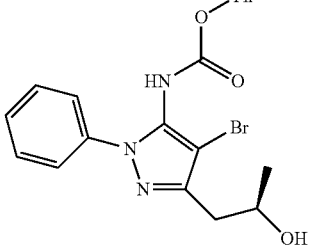 | (R)-phenyl (4-bromo-3-(2-hydroxypropyl)-1-phenyl-1H-pyrazol-5-yl)carbamate | 416.0 (M + H) |

-continued

| Intermediate | Structure | Name | MS (apci) m/z |
|---|---|---|---|
| 238 | 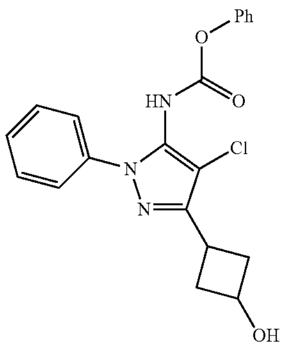 [SMILES: O=C(Nc1c(Cl)c(C2CC(O)C2)nn1-c1ccccc1)Oc1ccccc1] | phenyl (4-chloro-3-(3-hydroxycyclobutyl)-1-phenyl-1H-pyrazol-5-yl)carbamate | 384.1 (M + H) |
| 239 | 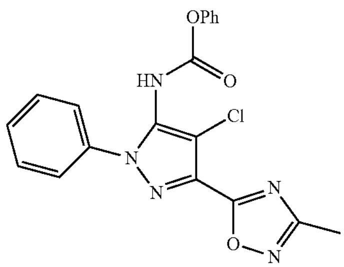 [SMILES: Cc1noc(-c2nn(-c3ccccc3)c(NC(=O)Oc3ccccc3)c2Cl)n1] | phenyl 4-chloro-3-(3-methyl-1,2,4-oxadiazol-5-yl)-1-phenyl-1H-pyrazol-5-ylcarbamate | 396.0 (M + H) |
| 240 | 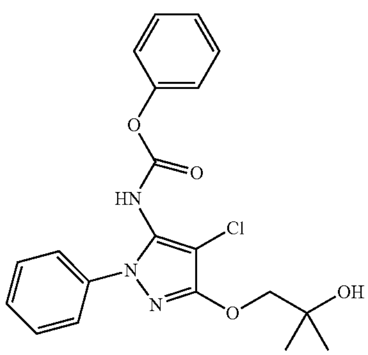 | phenyl (4-chloro-3-(2-hydroxy-2-methylpropoxy)-1-phenyl-1H-pyrazol-5-yl)carbamate | 446.1 (M + H) |
| 241 | 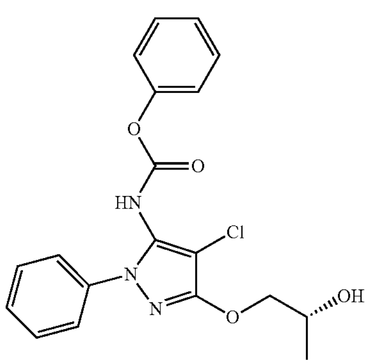 [SMILES: C[C@@H](O)COc1nn(-c2ccccc2)c(NC(=O)Oc2ccccc2)c1Cl] | phenyl (4-chloro-3-(2-hydroxy-2-methylpropoxy)-1-phenyl-1H-pyrazol-5-yl)carbamate | 388.1 (M + H) |

-continued

| Intermediate | Structure | Name | MS (apci) m/z |
|---|---|---|---|
| 242 | 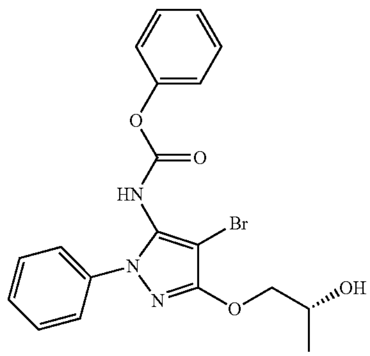 [SMILES: C[C@@H](O)COc1nn(-c2ccccc2)c(NC(=O)Oc2ccccc2)c1Br] | phenyl (4-bromo-3-(2-hydroxy-2-methylpropoxy)-1-phenyl-1H-pyrazol-5-yl)carbamate | 433.0 (M + H) |
| 243 | 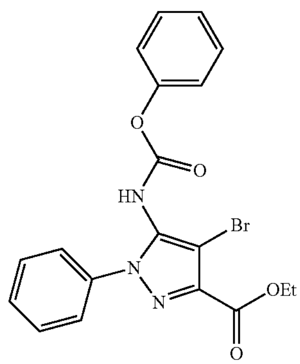 [SMILES: CCOC(=O)c1nn(-c2ccccc2)c(NC(=O)Oc2ccccc2)c1Br] | ethyl 4-bromo-5-((phenoxycarbonyl)amino)-1-phenyl-1H-pyrazole-3-carboxylate | 430.0 (M + H) |

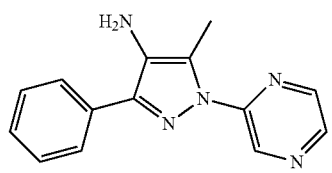

Intermediate 245

5-methyl-3-phenyl-1-(pyrazin-2-yl)-1H-pyrazol-4-amine

Step A: 2-(5-methyl-4-nitroso-3-phenyl-1H-pyrazol-1-yl)pyrazine

To a solution of 2-hydrazinylpyrazine (0.485 g, 4.40 mmol) in HOAc (6 mL) was added (2-(hydroxyimino)-1-phenylbutane-1,3-dione (0.765 g, 4.00 mmol) in small portions over 2 minutes. The mixture was stirred for 5 minutes and the resulting light orange suspension was stirred at 60° C. for 6 hours. EtOH (1 mL) was added and the mixture was heated at 60° C. for an additional 6 hours. The resulting dark green suspension was cooled to ambient temperature and the mixture was diluted with H$_2$O (30 mL). The green suspension was stirred for 1 hour and the solid was collected via vacuum filtration. The collected solid was washed with H$_2$O and dried in vacuum. The solid was suspended in EtOH (25 mL) and concentrated HCl (500 µL) was added. The mixture was heated at reflux for 20 hours, cooled to ambient temperature and diluted with chilled H$_2$O (75 mL). The mixture was treated with 1M NaOH to pH=7 and was extracted with Et$_2$O (3×). The combined extracts were washed with saturated NaCl and dried over MgSO$_4$. The dried solution was filtered through packed Celite® and concentrated. The residual green-yellow solid was purified on a SiO$_2$ column using step gradient elution (25% CH$_2$Cl$_2$, 50% EtOAc/hexanes) to furnish the title compound as a turquoise solid (325 mg, 31%). MS (apci) m/z=266.1 (M+H).

Step B: 5-methyl-3-phenyl-1-(pyrazin-2-yl)-1H-pyrazol-4-amine

To a mixture of 2-(5-methyl-4-nitroso-3-phenyl-1H-pyrazol-1-yl)pyrazine (325 mg, 1.04 mmol) and Zn dust (340 mg, 5.21 mmol) in EtOH (10 mL) was added concentrated HCl (95.5 µL, 1.15 mmol). The mixture was stirred at ambient temperature for 17 hours, then at 65° C. for 3 hours. The mixture was cooled to ambient temperature and was filtered through packed Celite® eluting with MeOH. The eluent was concentrated, and the residue was treated with H$_2$O and mixed. The resulting orange suspension treated with 2M HCl to pH=1 and the mixture was extracted with Et$_2$O (3×). The aqueous portion was treated with 2M NaOH to pH=8 and extracted with EtOAc (3×). The combined EtOAc extracts were washed with saturated NaCl and dried over MgSO$_4$/activated carbon. The solution was eluted through a SiO$_2$ plug eluting with EtOAc. The eluent was concentrated to give the title compound as a light yellow wax (33 mg, 13%). MS (esi) m/z=252.2 (M+H).

Intermediate 246

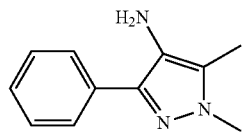

1,5-dimethyl-3-phenyl-1H-pyrazol-4-amine

Step A: 1,5-dimethyl-4-nitroso-3-phenyl-1H-pyrazole

To a solution of methylhydrazine (0.484 g, 10.5 mmol) in HOAc (10 mL) was added 2-(hydroxyimino)-1-phenylbutane-1,3-dione (2.01 g, 10.5 mmol) in small portions over 5 minutes. The reaction mixture was heated at 60° C. for 1 hour and was cooled to ambient temperature. $Et_2O$ (50 mL) and $H_2O$ (10 mL) were added to the mixture followed by slow addition of saturated $Na_2CO_3$ until pH=8 was obtained. The organic layer was removed and the aqueous layer was extracted with $Et_2O$ (2×). The combined organic fractions were dried over $Na_2SO_4$, filtered and concentrated. The residue was purified by silica gel chromatography (1:5 EtOAc/hexanes) to give the title compound as a green solid (1.32 g, 63%). MS (apci) m/z=202.1 (M+H).

Step B: 1,5-dimethyl-3-phenyl-1H-pyrazol-4-amine

To a solution of 1,5-dimethyl-4-nitroso-3-phenyl-1H-pyrazole (1.32 g, 6.60 mmol) in MeOH (50 mL) was added Pd(OH)$_2$ on carbon (200 mg, 20 wt %, 0.286 mmol) and the reaction mixture was shaken under 50 psi of $H_2$ for 3 hours at ambient temperature. The reaction mixture was evacuated, purged with $N_2$ filtered through a pad of Celite® with MeOH elution. The eluent was concentrated and the residue dried in vacuum to provide the title compound as a tan solid (1.23 g, 100%). MS (apci) m/z=188.1 (M+H).

Intermediate 247

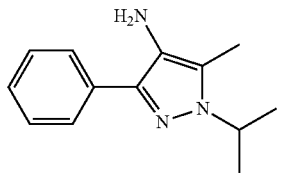

1-isopropyl-5-methyl-3-phenyl-1H-pyrazol-4-amine

The title compound was prepared according to the method described for Intermediate 246, using isopropylhydrazine hydrochloride in place of methylhydrazine in Step A to provide 620 mg (57%) of the title compound over 2 steps. MS (apci) m/z=216.1 (M+H).

Intermediate 248

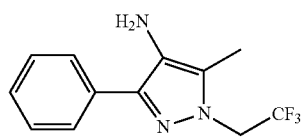

5-methyl-3-phenyl-1-(2,2,2-trifluoroethyl)-1H-pyrazol-4-amine

Step A: 5-methyl-4-nitroso-3-phenyl-1-(2,2,2-trifluoroethyl)-1H-pyrazole

The title compound was prepared using (2,2,2-trifluoroethyl)hydrazine in place of methylhydrazine in Step A of the procedure described for the preparation of 1,5-dimethyl-3-phenyl-1H-pyrazol-4-amine (Intermediate 246). The compound was isolated as a green solid (999 mg, 71%). $^1$H NMR (CDCl$_3$) δ 7.60-7.73 (m, 5H), 4.70 (q, 2H), 2.27 (t, 3H).

Step B: 5-methyl-3-phenyl-1-(2,2,2-trifluoroethyl)-1H-pyrazol-4-amine

To a mixture of 5-methyl-4-nitroso-3-phenyl-1-(2,2,2-trifluoroethyl)-1H-pyrazole (50 mg, 0.186 mmol) and Zn dust (60.7 mg, 0.929 mmol) in EtOH (0.4 mL) was added concentrated HCl (17.0 μL, 0.204 mmol) and the mixture was heated at reflux for 3 hours. The mixture was cooled to ambient temperature and was diluted with MeOH and filtered. The filtrate was concentrated and the residue was diluted in water. The aqueous mixture was treated with saturated NaHCO$_3$ until pH=10 was achieved. The mixture was extracted with DCM (3×) and the combined extracts were dried over Na$_2$SO$_4$, filtered and concentrated afford the title compound as a yellow oil (47.1 mg, 99.4% yield). MS (apci) m/z=256.1 (M+H).

Intermediate 249

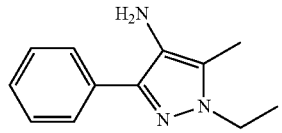

1-ethyl-5-methyl-3-phenyl-1H-pyrazol-4-amine

Step A: 1-ethyl-5-methyl-4-nitroso-3-phenyl-1H-pyrazole

The title compound was prepared according to the procedure described for the preparation of Intermediate 246, using ethylhydrazine oxalate in place of methylhydrazine in Step A. 1-Ethyl-5-methyl-4-nitroso-3-phenyl-1H-pyrazole was isolated as a green oil (288 mg, 26%). $^1$H NMR (CDCl$_3$) δ 8.19 (d, 2H), 7.46-7.50 (m, 3H), 4.15 (q, 2H), 2.43 (s, 3H), 1.50 (t, 3H). The minor regioisomer, 1-ethyl-3-methyl-4-nitroso-5-phenyl-1H-pyrazole, was also obtained as a blue-green solid (165 mg, 15%). $^1$H NMR (CDCl$_3$) δ 7.71 (dd, 2H), 7.59 (m, 3H), 4.17 (q, 2H), 2.28 (s, 3H), 1.51 (t, 3H).

Step B: 1-ethyl-5-methyl-3-phenyl-1H-pyrazol-4-amine

Prepared according to the procedure described for the preparation of Intermediate 248, using 1-ethyl-5-methyl-4-nitroso-3-phenyl-1H-pyrazole in Step B. The title compound was isolated as a light purple solid (281 mg, 104%). MS (apci) m/z=202.1 (M+H).

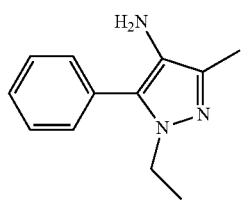

Intermediate 250

1-ethyl-3-methyl-5-phenyl-1H-pyrazol-4-amine

Prepared according to the procedure described for the preparation of Intermediate 249, using 1-ethyl-3-methyl-4-nitroso-5-phenyl-1H-pyrazole in Step A. The title compound was prepared according to Step B. The compound was isolated as a colorless oil (82.4 mg, 52.5%) after purification by reverse-phase chromatography. MS (apci) m/z=202.1 (M+H).

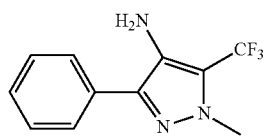

Intermediate 251

1-methyl-5-phenyl-3-(trifluoromethyl)-1H-pyrazol-4-amine

Step A: 4,4,4-trifluoro-2-(hydroxyimino)-1-phenylbutane-1,3-dione

A solution of 4,4,4-trifluoro-1-phenylbutane-1,3-dione (5.00 g, 23.1 mmol) in HOAc (46.3 mL) was chilled to 10° C. and sodium nitrite (1.84 g, 26.6 mmol) in water (6.0 mL) was added. The mixture was stirred at ambient temperature for 90 minutes and was diluted with H₂O (150 mL). The mixture was extracted with Et₂O (3×) and the combined organic fractions were carefully washed with saturated NaHCO₃ until pH=9. The Et₂O solution was washed with H₂O and saturated NaCl and was dried over MgSO₄. The dried solution was filtered and concentrated to afford the title compound as a yellow foam (4.21 g, 74.2% yield). MS (apci) m/z=244.1 (M−H).

Step B: 4-nitroso-3-phenyl-5-(trifluoromethyl)-1H-pyrazole

A solution of hydrazine monohydrate (0.204 g, 4.08 mmol) in EtOH (5 mL) was cooled to 0° C. and 4,4,4-trifluoro-2-(hydroxyimino)-1-phenylbutane-1,3-dione (1.00 g, 4.08 mmol) in EtOH (15 mL) was added. The reaction mixture was stirred at ambient temperature for 3 hours, excess powdered MgSO₄ was added and the mixture was heated at 60° C. for 16 hours. The mixture was cooled to ambient temperature, filtered and concentrated to afford the crude title compound as a green solid (78.7 mg, 8.0%) that was taken directly to the next step. MS (apci) m/z=240.0 (M−H).

Step C: 1-methyl-5-phenyl-3-(trifluoromethyl)-1H-pyrazol-4-amine

To a solution of 4-nitroso-3-phenyl-5-(trifluoromethyl)-1H-pyrazole (78.7 mg, 0.326 mmol) in DMF (1.6 mL) was added NaH (14.4 mg, 0.359 mmol) and the mixture was stirred at ambient temperature for 30 minutes. The mixture was treated with methyl iodide (40.6 µL, 0.653 mmol) and stirred for 17 hours. The reaction mixture was directly purified by reverse phase HPLC using 20-100% acetonitrile/water gradient elution to provide a light blue solid (40.2 mg). The solid was dissolved in EtOH (0.35 mL) and was subjected to the reduction procedure described in Step B of the preparation of 5-methyl-3-phenyl-1-(2,2,2-trifluoroethyl)-1H-pyrazol-4-amine (Intermediate 248). The title compound was obtained as white solid (25.1 mg, 66.1%).

Intermediate 252

1-methyl-3-phenyl-5-(trifluoromethyl)-1H-pyrazol-4-amine

Step A: 1-methyl-4-nitroso-3-phenyl-5-(trifluoromethyl)-1H-pyrazole

To a solution of methylhydrazine (0.214 mL, 4.08 mmol) in EtOH (20 mL) was added 4,4,4-trifluoro-2-(hydroxyimino)-1-phenylbutane-1,3-dione (Intermediate 251, Step A; 1.00 g, 4.079 mmol). The reaction mixture was stirred at ambient temperature for 1 hour and excess MgSO₄ was added. The mixture was stirred at 60° C. for 48 hours and was cooled to ambient temperature. The mixture was filtered and the filtrate concentrated to a green residue. The residue was purified by silica gel chromatography using a 10-30% EtOAc/hexanes gradient for elution to provide the title compound as a green solid (482 mg, 46%). ¹H NMR (CDCl₃) δ 7.89 (d, 2H), 7.45-7.52 (m, 3H), 4.15 (s, 3H).

Step B: 1-methyl-3-phenyl-5-(trifluoromethyl)-1H-pyrazol-4-amine

Prepared from 1-methyl-4-nitroso-3-phenyl-5-(trifluoromethyl)-1H-pyrazole according to the method described for the preparation of Intermediate 248, Step B. The title compound was obtained as white solid (309 mg, 68%). ¹H NMR (CDCl₃) δ 7.65 (d, 2H), 7.45 (t, 2H), 7.35 (t, 1H), 3.93 (s, 3H), 3.52 (br s, 2H).

Example 1

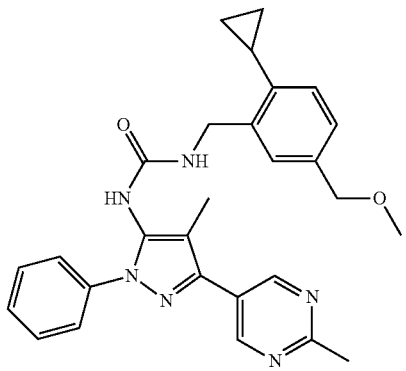 [SMILES: COCc1ccc(C2CC2)c(CNC(=O)Nc2c(C)c(-c3cnc(C)nc3)nn2-c2ccccc2)c1]

1-(2-cyclopropyl-5-(methoxymethyl)benzyl)-3-(4-methyl-3-(2-methylpyrimidin-5-yl)-1-phenyl-1H-pyrazol-5-yl)urea To a reaction tube containing 4-methyl-3-(2-methylpyrimidin-5-yl)-1-phenyl-1H-pyrazol-5-amine (50 mg, 0.19 mmol), dry dichloromethane (2 mL), was added triphosgene (28 mg, 0.094 mmol). A yellow precipitate formed, but immediately went into solution upon the addition of di-isopropylethylamine (98 µL, 0.56 mmol). The reaction mixture was allowed to stir at ambient temperature for 30 minutes, then a dichloromethane solution (1 mL) of (2-cyclopropyl-5-(methoxymethyl)phenyl)methanamine (36 mg, 0.19 mmol) was added and the mixture was stirred at ambient temperature for 16 hours, then concentrated under reduced pressure. The resulting crude material was triturated with acetonitrile and the solids collected to give 1-(2-cyclopropyl-5-(methoxymethyl)benzyl)-3-(4-methyl-3-(2-methylpyrimidin-5-yl)-1-phenyl-1H-pyrazol-5-yl)urea (42 mg, 46%). MS (APCI) m/z=483.3 (M+H).

Example 2

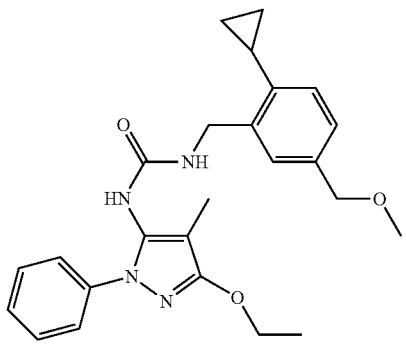 [SMILES: CCOc1nn(-c2ccccc2)c(NC(=O)NCc2cc(COC)ccc2C2CC2)c1C]

1-(2-cyclopropyl-5-(methoxymethyl)benzyl)-3-(3-ethoxy-4-methyl-1-phenyl-1H-pyrazol-5-yl)urea To a reaction tube containing phenyl (3-ethoxy-4-methyl-1-phenyl-1H-pyrazol-5-yl)carbamate (50 mg, 0.15 mmol) was added dry 1,2-DCE (2 mL) and (2-cyclopropyl-5-(methoxymethyl)phenyl)methanamine (28 mg, 0.15 mmol). DIEA (77 µL, 0.44 mmol) was then added, tube sealed and the mixture was stirred at ambient temperature overnight. The mixture was concentrated under reduced pressure and purified by reverse phase HPLC. The fractions containing the product were combined, neutralized with 10% aqueous potassium carbonate, extracted with EtOAc, the extracts dried over sodium sulfate and concentrated under reduced pressure to give 1-(2-cyclopropyl-5-(methoxymethyl)benzyl)-3-(3-ethoxy-4-methyl-1-phenyl-1H-pyrazol-5-yl)urea (21 mg, 33% yield) as a white solid. MS (APCI) m/z=435.2 (M+H).

Example 3

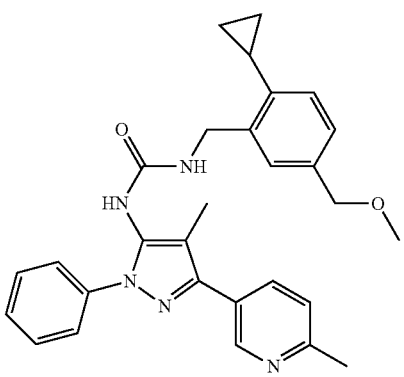 [SMILES: COCc1ccc(C2CC2)c(CNC(=O)Nc2c(C)c(-c3ccc(C)nc3)nn2-c2ccccc2)c1]

1-(2-cyclopropyl-5-(methoxymethyl)benzyl)-3-(4-methyl-3-(6-methylpyridin-3-yl)-1-phenyl-1H-pyrazol-5-yl)urea Prepared by the method as described in Example 1, Step A, replacing 4-methyl-3-(2-methylpyrimidin-5-yl)-1-phenyl-1H-pyrazol-5-amine with 4-methyl-3-(6-methylpyridin-3-yl)-1-phenyl-1H-pyrazol-5-amine. The crude material was purified by reverse phase prep HPLC and neutralization with 10% aqueous potassium carbonate to give the title compound (35 mg, 38% yield) as a white solid. MS (APCI) m/z=482.2 (M+H).

Example 4

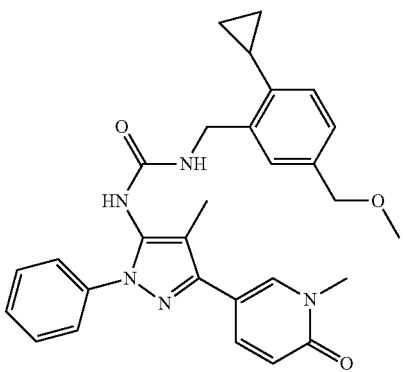 [SMILES: COCc1ccc(C2CC2)c(CNC(=O)Nc2c(C)c(-c3ccc(=O)n(C)c3)nn2-c2ccccc2)c1]

1-(2-cyclopropyl-5-(methoxymethyl)benzyl)-3-(4-methyl-3-(1-methyl-6-oxo-1,6-dihydropyridin-3-yl)-1-phenyl-1H-pyrazol-5-yl)urea Prepared by the method described in Example 2, Step A, replacing phenyl (3-ethoxy-4-methyl-1-phenyl-1H-pyrazol-5-yl)carbamate with phenyl (4-methyl-3-(1-methyl-6-oxo-1,6-dihydropyridin-3-yl)-1-phenyl-1H-pyrazol-5-yl)carbamate to give the title compound (27 mg, 43% yield). MS (APCI) m/z=498.2 (M+H).

Example 5

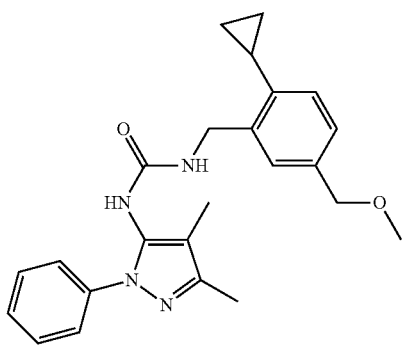 [SMILES: COCc1ccc(C2CC2)c(CNC(=O)Nc2c(C)c(C)nn2-c2ccccc2)c1]

1-(2-cyclopropyl-5-(methoxymethyl)benzyl)-3-(3,4-dimethyl-1-phenyl-1H-pyrazol-5-yl)urea Prepared by the method described in Example 2, Step A, replacing phenyl (3-ethoxy-4-methyl-1-phenyl-1H-pyrazol-5-yl)carbamate with phenyl (3,4-dimethyl-1-phenyl-1H-pyrazol-5-yl)carbamate to give the title compound (35 mg, 53% yield). MS (APCI) m/z=405.2 (M+H).

Example 6

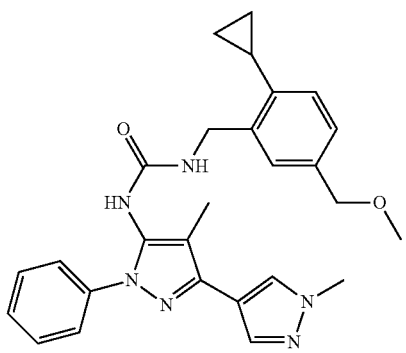 [SMILES: COCc1ccc(C2CC2)c(CNC(=O)Nc2c(C)c(-c3cnn(C)c3)nn2-c2ccccc2)c1]

1-(2-cyclopropyl-5-(methoxymethyl)benzyl)-3-(1',4-dimethyl-1-phenyl-1H,1'H-[3,4'-bipyrazol]-5-yl)urea Prepared by the method described in Example 2, Step A, replacing phenyl (3-ethoxy-4-methyl-1-phenyl-1H-pyrazol-5-yl)carbamate with phenyl (1',4-dimethyl-1-phenyl-1H,1'H-[3,4'-bipyrazol]-5-yl)carbamate to give the title compound (9 mg, 5% yield). MS (APCI) m/z=471.3 (M+H).

Example 7

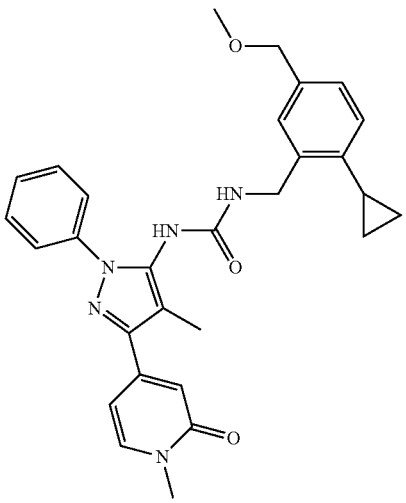 [SMILES: COCc1ccc(C2CC2)c(CNC(=O)Nc2c(C)c(-c3ccn(C)c(=O)c3)nn2-c2ccccc2)c1]

1-(2-cyclopropyl-5-(methoxymethyl)benzyl)-3-(4-methyl-3-(1-methyl-2-oxo-1,2-dihydropyridin-4-yl)-1-phenyl-1H-pyrazol-5-yl)urea Prepared by the method described in Example 2, Step A, replacing phenyl (3-ethoxy-4-methyl-1-phenyl-1H-pyrazol-5-yl)carbamate with phenyl (4-methyl-3-(1-methyl-2-oxo-1,2-dihydropyridin-4-yl)-1-phenyl-1H-pyrazol-5-yl)carbamate to give the title compound (30 mg, 48% yield). MS (APCI) m/z=496.1 (M−H).

Example 8

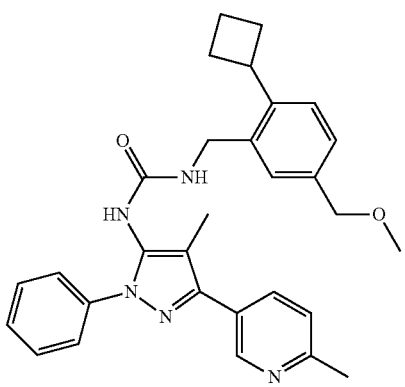 [SMILES: COCc1ccc(C2CCC2)c(CNC(=O)Nc2c(C)c(-c3ccc(C)nc3)nn2-c2ccccc2)c1]

1-(2-cyclobutyl-5-(methoxymethyl)benzyl)-3-(4-methyl-3-(6-methylpyridin-3-yl)-1-phenyl-1H-pyrazol-5-yl)urea Prepared by the method as described in Example 1, Step A, replacing 4-methyl-3-(2-methylpyrimidin-5-yl)-1-phenyl-1H-pyrazol-5-amine with 4-methyl-3-(6-methylpyridin-3-yl)-1-phenyl-1H-pyrazol-5-amine and (2-cyclopropyl-5-(methoxymethyl)phenyl)methanamine with (2-cyclobutyl-5-(methoxymethyl)phenyl)methanamine. The crude material was purified by reverse phase prep HPLC and neutralization with 10% aqueous potassium carbonate to give the title compound (20 mg, 21% yield) as a tan solid. MS (APCI) m/z=496.3 (M+H).

Example 9

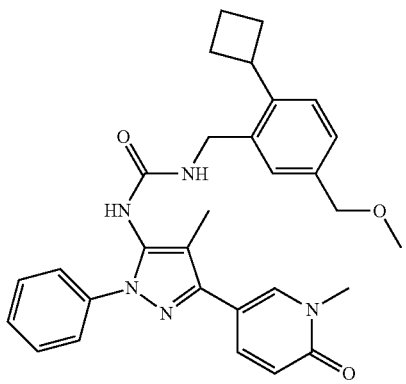 [SMILES: COCc1ccc(C2CCC2)c(CNC(=O)Nc2c(C)c(-c3ccc(=O)n(C)c3)nn2-c2ccccc2)c1]

1-(2-cyclobutyl-5-(methoxymethyl)benzyl)-3-(4-methyl-3-(1-methyl-6-oxo-1,6-dihydropyridin-3-yl)-1-phenyl-1H-pyrazol-5-yl)urea Prepared by the method described in Example 2, Step A, replacing phenyl (3-ethoxy-4-methyl-1-phenyl-1H-pyrazol-5-yl)carbamate with phenyl (4-methyl-3-(1-methyl-6-oxo-1,6-dihydropyridin-3-yl)-1-phenyl-1H-pyrazol-5-yl)carbamate and (2-cyclopropyl-5-(methoxymethyl)phenyl)methanamine with (2-cyclobutyl-5-(methoxymethyl)phenyl)methanamine. The crude was purified by trituration with acetonitrile to give the title compound (18 mg, 16% yield). MS (APCI) m/z=510.2 (M−H).

Example 10

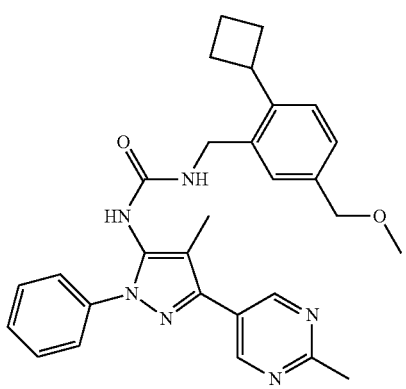 [SMILES: COCc1ccc(C2CCC2)c(CNC(=O)Nc2c(C)c(-c3cnc(C)nc3)nn2-c2ccccc2)c1]

1-(2-cyclobutyl-5-(methoxymethyl)benzyl)-3-(4-methyl-3-(2-methylpyrimidin-5-yl)-1-phenyl-1H-pyrazol-5-yl)urea Prepared by the method described in Example 1, Step A, replacing (2-cyclopropyl-5-(methoxymethyl)phenyl)methanamine with (2-cyclobutyl-5-(methoxymethyl)phenyl) methanamine to give the title compound (37 mg, 44% yield) as a white solid. MS (APCI) m/z=495.2 (M−H).

Example 11

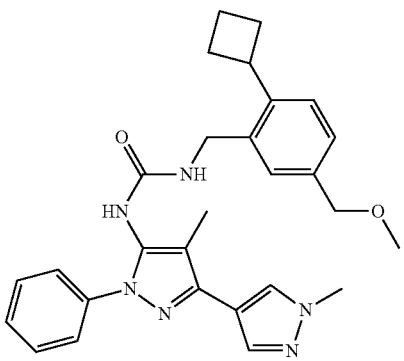 [SMILES: COCc1ccc(C2CCC2)c(CNC(=O)Nc2c(C)c(-c3cnn(C)c3)nn2-c2ccccc2)c1]

1-(2-cyclobutyl-5-(methoxymethyl)benzyl)-3-(1',4-dimethyl-1-phenyl-1H,1'H-[3,4'-bipyrazol]-5-yl)urea Prepared by the method described in Example 2, Step A, replacing phenyl (3-ethoxy-4-methyl-1-phenyl-1H-pyrazol-5-yl)carbamate with phenyl (1',4-dimethyl-1-phenyl-1H,1'H-[3,4'-bipyrazol]-5-yl)carbamate and (2-cyclopropyl-5-(methoxymethyl)phenyl)methanamine with (2-cyclobutyl-5-(methoxymethyl)phenyl)methanamine to give the title compound (45 mg, 50% yield). MS (APCI) m/z=485.2 (M+H).

Example 12

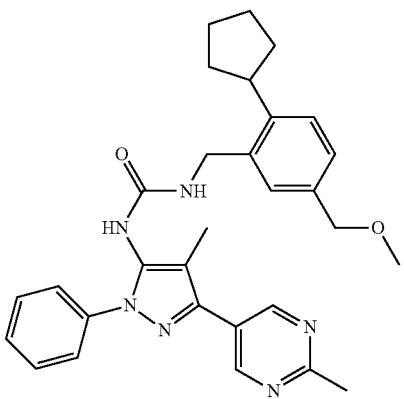 [SMILES: COCc1ccc(C2CCCC2)c(CNC(=O)Nc2c(C)c(-c3cnc(C)nc3)nn2-c2ccccc2)c1]

1-(2-cyclopentyl-5-(methoxymethyl)benzyl)-3-(4-methyl-3-(2-methylpyrimidin-5-yl)-1-phenyl-1H-pyrazol-5-yl)urea Prepared by the method as described in Example 1, Step A, replacing (2-cyclopropyl-5-(methoxymethyl)phenyl) methanamine with (2-cyclopentyl-5-(methoxymethyl)phenyl)methanamine. The crude material was purified by reverse phase prep HPLC and neutralization with 10% aqueous potassium carbonate to give the title compound (17 mg, 25% yield) as a white solid. MS (APCI) m/z=511.3 (M+H).

Example 13

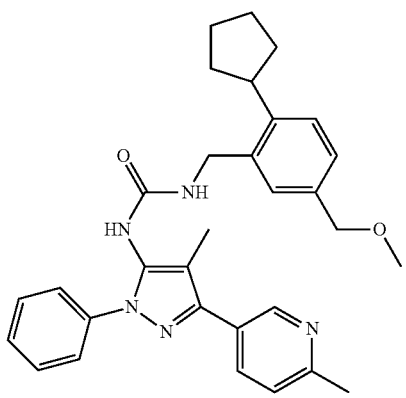 [SMILES: COCc1ccc(C2CCCC2)c(CNC(=O)Nc2c(C)c(-c3ccc(C)nc3)nn2-c2ccccc2)c1]

1-(2-cyclopentyl-5-(methoxymethyl)benzyl)-3-(4-methyl-3-(6-methylpyridin-3-yl)-1-phenyl-1H-pyrazol-5-yl)urea Prepared by the method as described in Example 1, Step A, replacing 4-methyl-3-(2-methylpyrimidin-5-yl)-1-phenyl-1H-pyrazol-5-amine with 4-methyl-3-(6-methylpyridin-3-yl)-1-phenyl-1H-pyrazol-5-amine and (2-cyclopropyl-5-(methoxymethyl)phenyl)methanamine with (2-cyclopentyl-5-(methoxymethyl)phenyl)methanamine. The crude material was purified by reverse phase prep HPLC and neutralization with 10% aqueous potassium carbonate to give the title compound (28 mg, 41% yield). MS (APCI) m/z=510.3 (M+H).

Example 14

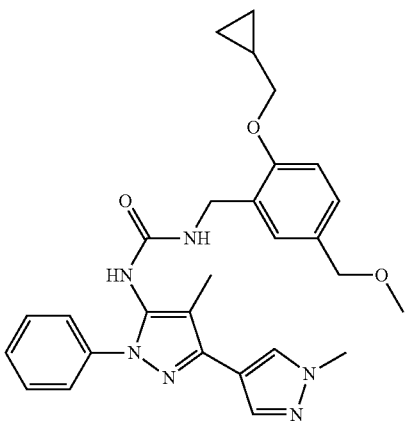 [SMILES: COCc1ccc(OCC2CC2)c(CNC(=O)Nc2c(C)c(-c3cnn(C)c3)nn2-c2ccccc2)c1]

1-(2-(cyclopropylmethoxy)-5-(methoxymethyl)benzyl)-3-(1',4-dimethyl-1-phenyl-1H,1'H-[3,4'-bipyrazol]-5-yl)urea Prepared by the method described in Example 2, Step A, replacing phenyl (3-ethoxy-4-methyl-1-phenyl-1H-pyrazol-5-yl)carbamate with phenyl (1',4-dimethyl-1-phenyl-1H,1'H-[3,4'-bipyrazol]-5-yl)carbamate and (2-cyclopropyl-5-(methoxymethyl)phenyl)methanamine with (2-(cyclopropylmethoxy)-5-(methoxymethyl)phenyl)methanamine (material from HPLC purification was triturated with methanol) to give the title compound (11 mg, 16% yield). MS (APCI) m/z=501.2 (M+H).

Example 15

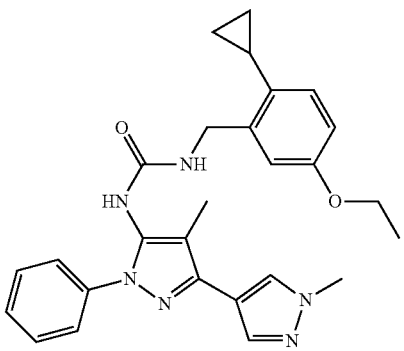 [SMILES: CCOc1ccc(C2CC2)c(CNC(=O)Nc2c(C)c(-c3cnn(C)c3)nn2-c2ccccc2)c1]

1-(2-cyclopropyl-5-ethoxybenzyl)-3-(1',4-dimethyl-1-phenyl-1H,1'H-[3,4'-bipyrazol]-5-yl)urea Prepared by the method described in Example 2, Step A, replacing phenyl (3-ethoxy-4-methyl-1-phenyl-1H-pyrazol-5-yl)carbamate with phenyl (1',4-dimethyl-1-phenyl-1H,1'H-[3,4'-bipyrazol]-5-yl)carbamate and (2-cyclopropyl-5-(methoxymethyl)phenyl)methanamine with (2-cyclopropyl-5-ethoxyphenyl)methanamine) to give the title compound (55 mg, 58% yield). MS (APCI) m/z=471.2 (M+H).

Example 16

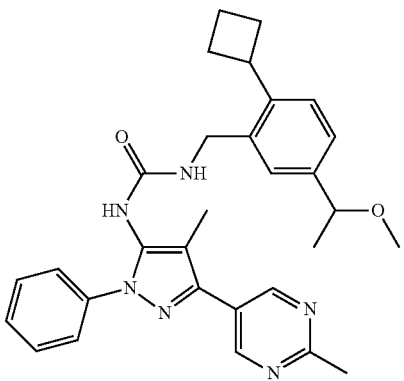 [SMILES: COC(C)c1ccc(C2CCC2)c(CNC(=O)Nc2c(C)c(-c3cnc(C)nc3)nn2-c2ccccc2)c1]

1-(2-cyclobutyl-5-(1-methoxyethyl)benzyl)-3-(4-methyl-3-(2-methylpyrimidin-5-yl)-1-phenyl-1H-pyrazol-5-yl)urea Prepared by the method as described in Example 1, Step A, replacing (2-cyclopropyl-5-(methoxymethyl)phenyl)methanamine with (2-cyclobutyl-5-(1-methoxyethyl)phenyl)methanamine. The crude material was purified by reverse phase prep HPLC and neutralization with 10% aqueous potassium carbonate to give the title compound (12 mg, 17% yield) as a white solid. MS (APCI) m/z=509.3 (M−H).

Example 17

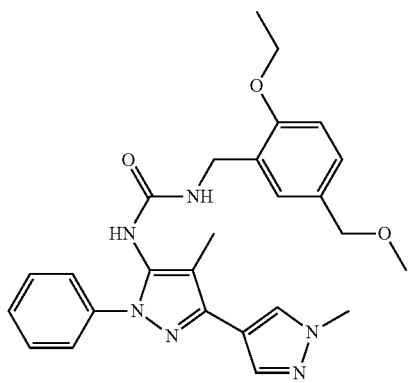 [SMILES: CCOc1ccc(COC)cc1CNC(=O)Nc1c(C)c(-c2cnn(C)c2)nn1-c1ccccc1]

1-(1',4-dimethyl-1-phenyl-1H,1'H-[3,4'-bipyrazol]-5-yl)-3-(2-ethoxy-5-(methoxymethyl)benzyl)urea Prepared by the method described in Example 2, Step A, replacing phenyl (3-ethoxy-4-methyl-1-phenyl-1H-pyrazol-5-yl)carbamate with phenyl (1',4-dimethyl-1-phenyl-1H,1'H-[3,4'-bipyrazol]-5-yl)carbamate and (2-cyclopropyl-5-(methoxymethyl)phenyl)methanamine with (2-ethoxy-5-(methoxymethyl)phenyl)methanamine to give the title compound (3 mg, 9% yield). MS (APCI) m/z=475.2 (M+H).

Example 18

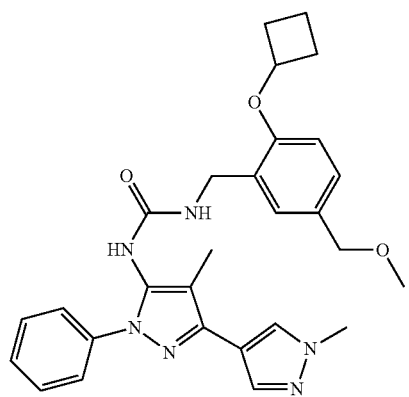 [SMILES: COCc1ccc(OC2CCC2)c(CNC(=O)Nc2c(C)c(-c3cnn(C)c3)nn2-c2ccccc2)c1]

1-(2-cyclobutoxy-5-(methoxymethyl)benzyl)-3-(1',4-dimethyl-1-phenyl-1H,1'H-[3,4'-bipyrazol]-5-yl)urea Prepared by the method described in Example 2, Step A, replacing phenyl (3-ethoxy-4-methyl-1-phenyl-1H-pyrazol-5-yl)carbamate with phenyl (1',4-dimethyl-1-phenyl-1H,1'H-[3,4'-bipyrazol]-5-yl)carbamate and (2-cyclopropyl-5-(methoxymethyl)phenyl)methanamine with (2-cyclobutoxy-5-(methoxymethyl)phenyl)methanamine to give the title compound (12 mg, 45% yield). MS (APCI) m/z=501.2 (M+H).

Example 19

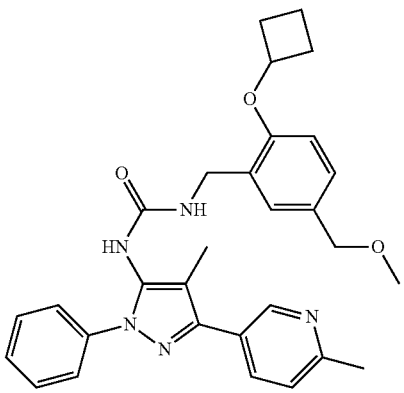 [SMILES: COCc1ccc(OC2CCC2)c(CNC(=O)Nc2c(C)c(-c3ccc(C)nc3)nn2-c2ccccc2)c1]

1-(2-cyclobutoxy-5-(methoxymethyl)benzyl)-3-(4-methyl-3-(6-methylpyridin-3-yl)-1-phenyl-1H-pyrazol-5-yl)urea Prepared by the method as described in Example 1, Step A, replacing 4-methyl-3-(2-methylpyrimidin-5-yl)-1-phenyl-1H-pyrazol-5-amine with 4-methyl-3-(6-methylpyridin-3-yl)-1-phenyl-1H-pyrazol-5-amine and (2-cyclopropyl-5-(methoxymethyl)phenyl)methanamine with (2-cyclobutoxy-5-(methoxymethyl)phenyl)methanamine. The crude material was purified by reverse phase prep HPLC and neutralization with 10% aqueous potassium carbonate to give the title compound (34 mg, 50% yield). MS (APCI) m/z=512.3 (M+H).

Example 20

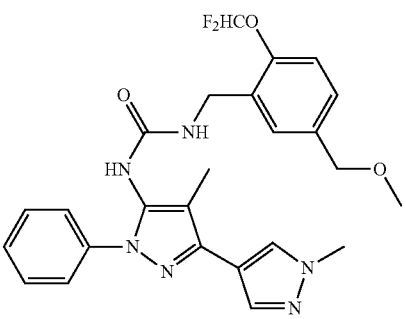 [SMILES: COCc1ccc(OC(F)F)c(CNC(=O)Nc2c(C)c(-c3cnn(C)c3)nn2-c2ccccc2)c1]

1-(2-(difluoromethoxy)-5-(methoxymethyl)benzyl)-3-(1',4-dimethyl-1-phenyl-1H,1'H-[3,4'-bipyrazol]-5-yl)urea Prepared by the method described in Example 2, Step A, replacing phenyl (3-ethoxy-4-methyl-1-phenyl-1H-pyrazol-5-yl)carbamate with phenyl (1',4-dimethyl-1-phenyl-1H,1'H-[3,4'-bipyrazol]-5-yl)carbamate and (2-cyclopropyl-5-(methoxymethyl)phenyl)methanamine with (2-

(difluoromethoxy)-5-(methoxymethyl)phenyl)methanamine to give the title compound (15 mg, 23% yield). MS (APCI) m/z=497.2 (M+H).

Example 21

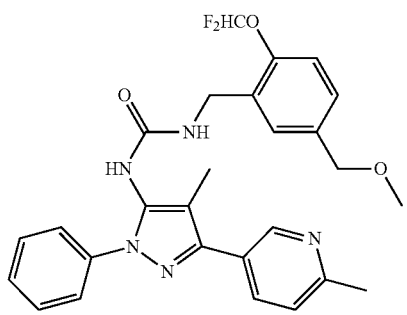 [SMILES: COCc1ccc(OC(F)F)c(CNC(=O)Nc2c(C)c(-c3ccc(C)nc3)nn2-c2ccccc2)c1]

1-(2-(difluoromethoxy)-5-(methoxymethyl)benzyl)-3-(4-methyl-3-(6-methylpyridin-3-yl)-1-phenyl-1H-pyrazol-5-yl)urea Prepared by the method as described in Example 1, Step A, replacing 4-methyl-3-(2-methylpyrimidin-5-yl)-1-phenyl-1H-pyrazol-5-amine with 4-methyl-3-(6-methylpyridin-3-yl)-1-phenyl-1H-pyrazol-5-amine and (2-cyclopropyl-5-(methoxymethyl)phenyl)methanamine with (2-(difluoromethoxy)-5-(methoxymethyl)phenyl) methanamine. The crude material was purified by reverse phase prep HPLC and neutralization with 10% aqueous potassium carbonate to give the title compound (23 mg, 24% yield). MS (APCI) m/z=508.2 (M+H).

Example 22

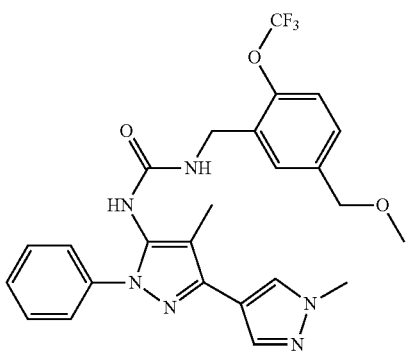 [SMILES: COCc1ccc(OC(F)(F)F)c(CNC(=O)Nc2c(C)c(-c3cnn(C)c3)nn2-c2ccccc2)c1]

1-(1',4-dimethyl-1-phenyl-1H,1'H-[3,4'-bipyrazol]-5-yl)-3-(5-(methoxymethyl)-2-(trifluoromethoxy)benzyl)urea Prepared by the method described in Example 2, Step A, replacing phenyl (3-ethoxy-4-methyl-1-phenyl-1H-pyrazol-5-yl)carbamate with phenyl (1',4-dimethyl-1-phenyl-1H,1'H-[3,4'-bipyrazol]-5-yl)carbamate and (2-cyclopropyl-5-(methoxymethyl)phenyl)methanamine with (5-(methoxymethyl)-2-(trifluoromethoxy)phenyl)methanamine to give the title compound (20 mg, 29% yield). MS (APCI) m/z=515.2 (M+H).

Example 23

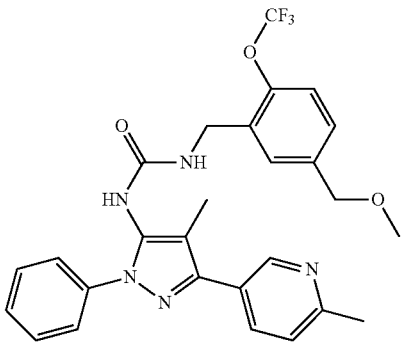 [SMILES: COCc1ccc(OC(F)(F)F)c(CNC(=O)Nc2c(C)c(-c3ccc(C)nc3)nn2-c2ccccc2)c1]

1-(5-(methoxymethyl)-2-(trifluoromethoxy)benzyl)-3-(4-methyl-3-(6-methylpyridin-3-yl)-1-phenyl-1H-pyrazol-5-yl)urea Prepared by the method as described in Example 1, Step A, replacing 4-methyl-3-(2-methylpyrimidin-5-yl)-1-phenyl-1H-pyrazol-5-amine with 4-methyl-3-(6-methylpyridin-3-yl)-1-phenyl-1H-pyrazol-5-amine and (2-cyclopropyl-5-(methoxymethyl)phenyl)methanamine with (5-(methoxymethyl)-2-(trifluoromethoxy)phenyl) methanamine. The crude material was purified by reverse phase prep HPLC and neutralization with 10% aqueous potassium carbonate to give the title compound (26 mg, 26% yield). MS (APCI) m/z=524.2 (M−H).

Example 24

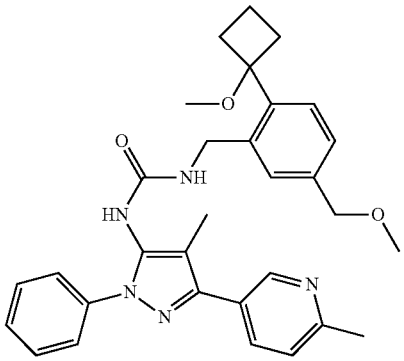 [SMILES: COCc1ccc(C2(OC)CCC2)c(CNC(=O)Nc2c(C)c(-c3ccc(C)nc3)nn2-c2ccccc2)c1]

1-(2-(1-methoxycyclobutyl)-5-(methoxymethyl)benzyl)-3-(4-methyl-3-(6-methylpyridin-3-yl)-1-phenyl-1H-pyrazol-5-yl)urea Prepared by the method as described in Example 1, Step A, replacing 4-methyl-3-(2-methylpyrimidin-5-yl)-1-phenyl-1H-pyrazol-5-amine with 4-methyl-3-(6-methylpyridin-3-yl)-1-phenyl-1H-pyrazol-5-amine and (2-cyclopropyl-5-(methoxymethyl)phenyl)methanamine with (2-(1- methoxycyclobutyl)-5-(methoxymethyl)phenyl)methanamine. The crude material was purified by reverse phase prep HPLC and neutralization with 10% aqueous potassium carbonate to give the title compound (26 mg, 52% yield). MS (APCI) m/z=526.3 (M+H).

Example 25

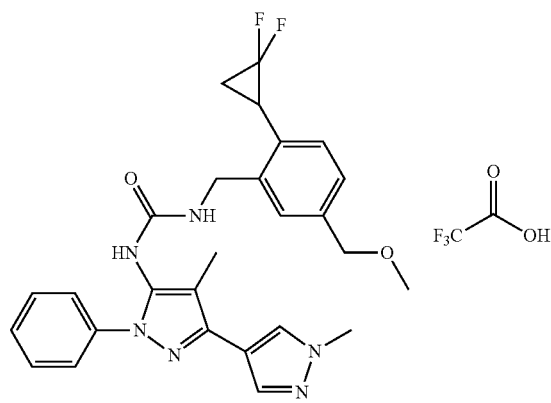 [SMILES: COCc1ccc(C2CC2(F)F)c(CNC(=O)Nc2c(C)c(-c3cnn(C)c3)nn2-c2ccccc2)c1 ; O=C(O)C(F)(F)F]

1-(2-(2,2-difluorocyclopropyl)-5-(methoxymethyl)benzyl)-3-(1',4-dimethyl-1-phenyl-1H,1'H-[3,4'-bipyrazol]-5-yl)urea 2,2,2-trifluoroacetate Prepared by the method described in Example 2, Step A, replacing phenyl (3-ethoxy-4-methyl-1-phenyl-1H-pyrazol-5-yl)carbamate with phenyl (1',4-dimethyl-1-phenyl-1H,1'H-[3,4'-bipyrazol]-5-yl)carbamate and (2-cyclopropyl-5-(methoxymethyl)phenyl)methanamine with (2-(2,2-difluorocyclopropyl)-5-(methoxymethyl)phenyl)methanamine 2,2,2-trifluoroacetate (no neutralization performed) to give the title compound (20 mg, 29% yield) as a TFA salt. MS (APCI) m/z=507.2 (M+H).

Example 26

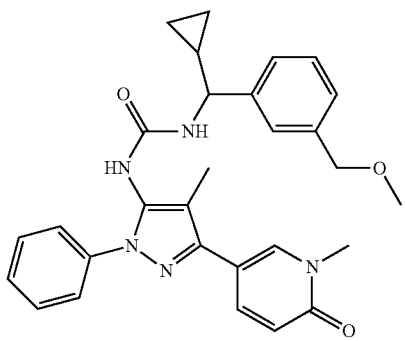 [SMILES: COCc1cccc(C(NC(=O)Nc2c(C)c(-c3ccc(=O)n(C)c3)nn2-c2ccccc2)C2CC2)c1]

1-(cyclopropyl(3-(methoxymethyl)phenyl)methyl)-3-(4-methyl-3-(1-methyl-6-oxo-1,6-dihydropyridin-3-yl)-1-phenyl-1H-pyrazol-5-yl)urea Prepared by the method described in Example 2, Step A, replacing phenyl (3-ethoxy-4-methyl-1-phenyl-1H-pyrazol-5-yl)carbamate with phenyl (4-methyl-3-(1-methyl-6-oxo-1,6-dihydropyridin-3-yl)-1-phenyl-1H-pyrazol-5-yl)carbamate and (2-cyclopropyl-5-(methoxymethyl)phenyl)methanamine with cyclopropyl(3-(methoxymethyl)phenyl)methanamine. The crude material was purified by reverse phase prep HPLC and neutralization with 10% aqueous potassium carbonate to give the title compound (12 mg, 39% yield). MS (APCI) m/z=496.2 (M−H).

Example 27

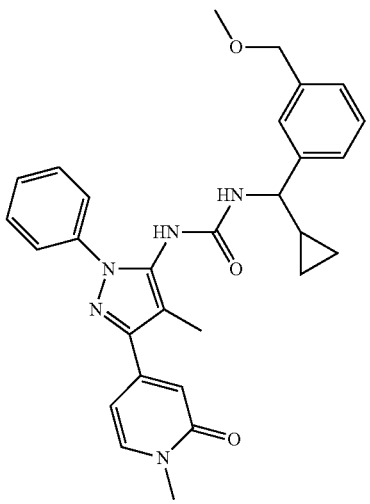 [SMILES: COCc1cccc(C(NC(=O)Nc2c(C)c(-c3ccn(C)c(=O)c3)nn2-c2ccccc2)C2CC2)c1]

1-(cyclopropyl(3-(methoxymethyl)phenyl)methyl)-3-(4-methyl-3-(1-methyl-2-oxo-1,2-dihydropyridin-4-yl)-1-phenyl-1H-pyrazol-5-yl)urea Prepared by the method described in Example 2, Step A, replacing phenyl (3-ethoxy-4-methyl-1-phenyl-1H-pyrazol-5-yl)carbamate with phenyl (4-methyl-3-(1-methyl-2-oxo-1,2-dihydropyridin-4-yl)-1-phenyl-1H-pyrazol-5-yl)carbamate and (2-cyclopropyl-5-(methoxymethyl)phenyl)methanamine with cyclopropyl(3-(methoxymethyl)phenyl)methanamine. The crude material was purified by reverse phase prep HPLC and neutralization with 10% aqueous potassium carbonate to give the title compound (7 mg, 43% yield). MS (APCI) m/z=496.3 (M−H).

Example 28

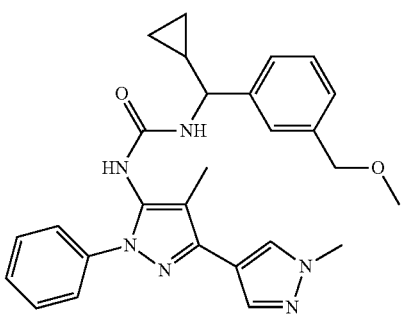 [SMILES: COCc1cccc(C(NC(=O)Nc2c(C)c(-c3cnn(C)c3)nn2-c2ccccc2)C2CC2)c1]

1-(cyclopropyl(3-(methoxymethyl)phenyl)methyl)-3-(1',4-dimethyl-1-phenyl-1H,1'H-[3,4'-bipyrazol]-5-yl)urea Prepared by the method described in Example 2, Step A, replacing phenyl (3-ethoxy-4-methyl-1-phenyl-1H-pyrazol-5-yl)carbamate with phenyl (1',4-dimethyl-1-phenyl-1H,1'H-[3,4'-bipyrazol]-5-yl)carbamate and (2-cyclopropyl-5-(methoxymethyl)phenyl)methanamine with (cyclopropyl(3-(methoxymethyl)phenyl)methanamine to give the title compound (26 mg, 41% yield). MS (APCI) m/z=471.2 (M+H).

1-(1-(2-cyclopropyl-5-(methoxymethyl)phenyl)ethyl)-3-(1',4-dimethyl-1-phenyl-1H,1'H-[3,4'-bipyrazol]-5-yl)urea Prepared by the method described in Example 2, Step A, replacing phenyl (3-ethoxy-4-methyl-1-phenyl-1H-pyrazol-5-yl)carbamate with phenyl (1',4-dimethyl-1-phenyl-1H,1'H-[3,4'-bipyrazol]-5-yl)carbamate and (2-cyclopropyl-5-(methoxymethyl)phenyl)methanamine with 1-(2-cyclopropyl-5-(methoxymethyl)phenyl)ethanamine to give the title compound (3 mg, 2% yield). MS (APCI) m/z=485.3 (M+H).

Example 29

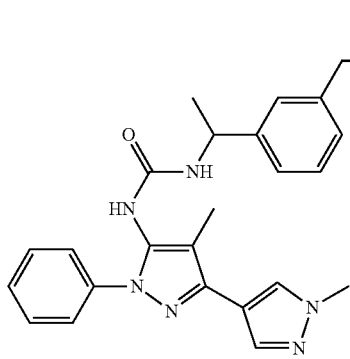
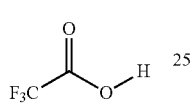

Example 31

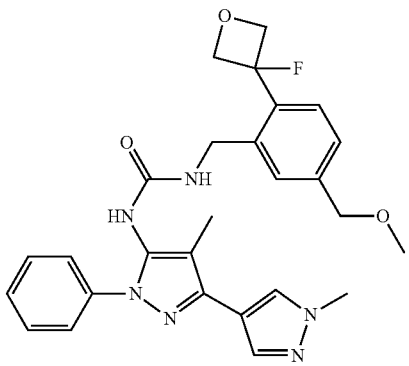

1-(1',4-dimethyl-1-phenyl-1H,1'H-[3,4'-bipyrazol]-5-yl)-3-(1-(3-(methoxymethyl)phenyl)ethyl)urea 2,2,2-trifluoroacetate Prepared by the method described in Example 2, Step A, replacing phenyl (3-ethoxy-4-methyl-1-phenyl-1H-pyrazol-5-yl)carbamate with phenyl (1',4-dimethyl-1-phenyl-1H,1'H-[3,4'-bipyrazol]-5-yl)carbamate and (2-cyclopropyl-5-(methoxymethyl)phenyl)methanamine with 1-(3-(methoxymethyl)phenyl)ethanamine (no neutralization performed) to give the title compound (1.5 mg, 2.5% yield) as a TFA salt. MS (APCI) m/z=445.2 (M+H).

1-(1',4-dimethyl-1-phenyl-1H,1'H-[3,4'-bipyrazol]-5-yl)-3-(2-(3-fluorooxetan-3-yl)-5-(methoxymethyl)benzyl)urea Prepared by the method described in Example 2, Step A, replacing phenyl (3-ethoxy-4-methyl-1-phenyl-1H-pyrazol-5-yl)carbamate with phenyl (1',4-dimethyl-1-phenyl-1H,1'H-[3,4'-bipyrazol]-5-yl)carbamate and (2-cyclopropyl-5-(methoxymethyl)phenyl)methanamine with (2-(3-fluorooxetan-3-yl)-5-(methoxymethyl)phenyl)methanamine to give the title compound (7 mg, 21% yield). MS (APCI) m/z=505.2 (M+H).

Example 30

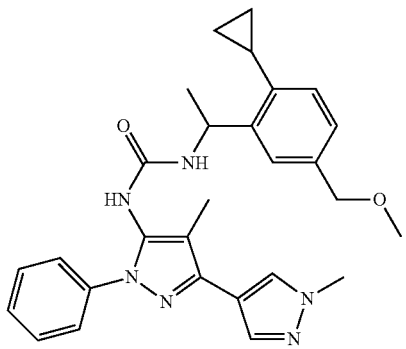 [SMILES: COCc1ccc(C2CC2)c(C(C)NC(=O)Nc2c(C)c(-c3cnn(C)c3)nn2-c2ccccc2)c1]

Example 32

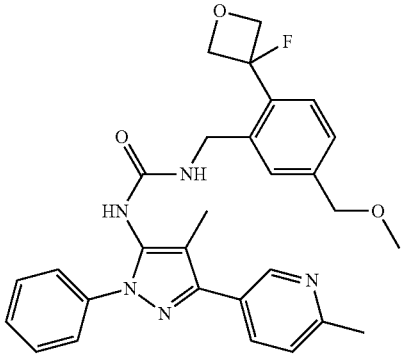 [SMILES: COCc1ccc(C2(F)COC2)c(CNC(=O)Nc2c(C)c(-c3ccc(C)nc3)nn2-c2ccccc2)c1]

1-(2-(3-fluorooxetan-3-yl)-5-(methoxymethyl)benzyl)-3-(4-methyl-3-(6-methylpyridin-3-yl)-1-phenyl-1H-pyrazol-5-yl)urea Prepared by the method as described in Example 1, Step A, replacing 4-methyl-3-(2-methylpyrimidin-5-yl)-1-phenyl-1H-pyrazol-5-amine with 4-methyl-3-(6-methylpyridin-3-yl)-1-phenyl-1H-pyrazol-5-amine and (2-cyclopropyl-5-(methoxymethyl)phenyl)methanamine with ((2-(3-fluorooxetan-3-yl)-5-(methoxymethyl)phenyl) methanamine. The crude material was purified by reverse phase prep HPLC and neutralization with 10% aqueous potassium carbonate to give the title compound (21 mg, 26% yield). MS (APCI) m/z=516.3 (M+H).

Example 33

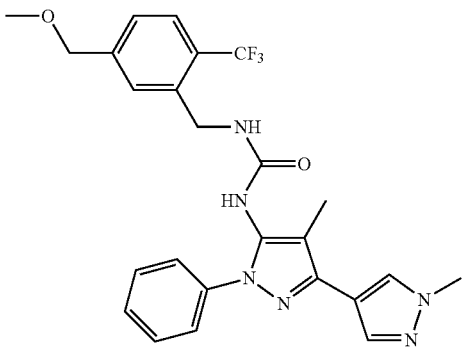

1-(1',4-dimethyl-1-phenyl-1H,1'H-[3,4'-bipyrazol]-5-yl)-3-(5-(methoxymethyl)-2-(trifluoromethyl)benzyl) urea Step A: Preparation of (3-fluoro-4-(trifluoromethyl)phenyl)methanol Charged a round bottomed flask plus stir bar with 3-fluoro-4-(trifluoromethyl)benzaldehyde (2.0 g, 10 mmol) and anhydrous MeOH (20 mL). The flask was chilled in an ice bath and sodium borohydride (0.47 g, 12 mmol) was added in portions. Removed ice bath and allowed reaction to warm to ambient temperature. Added saturated NH₄Cl (2 mL) and concentrated mixture in vacuo. The residue was diluted with additional saturated NH₄Cl (30 mL) and extracted with EtOAc (3×30 mL). The combined organic phases were dried (MgSO₄), filtered, and concentrated. Yield: 1.8 g (80%). Product carried forward without purification.

Step B: Preparation of 2-fluoro-4-(methoxymethyl)-1-(trifluoromethyl)benzene

Charged a dry round bottomed flask plus stir bar with (3-fluoro-4-(trifluoromethyl)phenyl)methanol (1.6 g, 8.24 mmol) and anhydrous DMF (25 mL). Cooled in an ice bath under N₂, and added sodium hydride (0.659 g, 16.5 mmol; 60% wt. in mineral oil) in portions over a 20 min period. Removed ice bath and stirred at ambient temperature for 20 minutes. The reaction mixture was again cooled in an ice bath and iodomethane was added (1.55 mL, 24.7 mmol) dropwise. Removed from ice bath and stirred for 30 min.

Quenched reaction by careful addition of saturated aqueous NH₄Cl (50 mL). Then extracted product with EtOAc (50 mL, then 30 mL). Washed combined organics with water (50 mL), brine (30 mL), dried (MgSO₄), filtered, and concentrated. Yield: 1.8 g (84%). The product carried forward without purification.

Step C: Preparation of 5-(methoxymethyl)-2-(trifluoromethyl)benzonitrile

Charged a thick walled glass pressure vessel with 2-fluoro-4-(methoxymethyl)-1-(trifluoromethyl)benzene (1.9 g, 9.1 mmol), anhydrous DMSO (25 mL) and KCN (0.71 g, 11.0 mmol). Heated to 120° C. overnight with stirring. Charged the reaction mixture with more KCN (0.71 g, 11.0 mmol) and continued heating at 120° C. for another day. After cooling to ambient temperature, the mixture was partitioned between EtOAc (75 mL) and water (75 mL). The phases were separated and the aqueous layer was extracted with EtOAc (50 mL). The combined organic phases were washed with water (2×50 mL), brine (50 mL), dried (MgSO₄), filtered, and concentrated. The crude material was purified by Biotage Flash 40 silica gel column, eluting with a gradient of 5%-20% EtOAc/hexanes. Yield: 537 mg (26%).

Step D: Preparation of (5-(methoxymethyl)-2-(trifluoromethyl)phenyl)methanamine

Charged a dry round bottomed flask bar with 5-(methoxymethyl)-2-(trifluoromethyl)benzonitrile (50 mg, 0.23 mmol), anhydrous THF (1 mL), and lastly lithium aluminum hydride (232 μL, 0.232 mmol; 1M in diethyl ether). Heated to reflux under N₂ for 2 hours. After cooling to ambient temperature, quenched excess hydride reagent by addition of water (30 μL), then stirring for 2-3 minutes. Added 2N NaOH (30 μL), again stirring 2-3 minutes, and then more water (100 μL), followed by stirring for 15 min at ambient temperature. Diluted with MTBE, and filtered suspension through Celite®, rinsing with MTBE. Concentrated filtrate, azeotroping with toluene to remove residual water (3×5 mL), to obtain 32 mg (50% yield) of desired product. Product carried forward without purification.

Step E: Preparation of 1-(1',4-dimethyl-1-phenyl-1H,1'H-[3,4'-bipyrazol]-5-yl)-3-(5-(methoxymethyl)-2-(trifluoromethyl)benzyl)urea Charged a vial plus stir bar with phenyl (1',4-dimethyl-1-phenyl-1H,1'H-[3,4'-bipyrazol]-5-yl)carbamate (Intermediate 5, 45 mg, 0.12 mmol), anhydrous 1,2-dichloroethane (0.5 mL), (5-(methoxymethyl)-2-(trifluoromethyl)phenyl) methanamine (32 mg, 0.14 mmol), and DIEA (63 μL, 0.36 mmol). Stirred overnight at ambient temperature. Diluted reaction with DCM (20 mL) and washed with 0.5 M aqueous HCl (2×10 mL). Organic phase was dried (MgSO₄), filtered, and concentrated. Purified crude product by preparative TLC (1 mm thickness, $R_f$=0.31) eluting with 7.5% MeOH/DCM. Yield: 13 mg (19%). MS m/z (APCI-pos) M+1=499.

Example 34

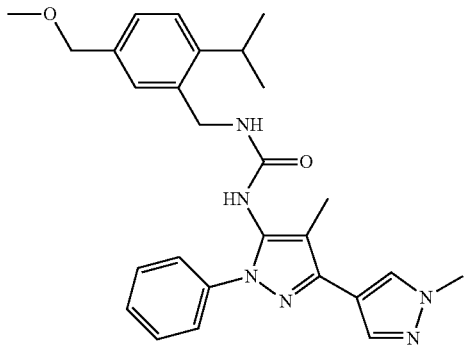

1-(1',4-dimethyl-1-phenyl-1H,1'H-[3,4'-bipyrazol]-5-yl)-3-(2-isopropyl-5-(methoxymethyl)benzyl)urea

Step A: Preparation of 5-formyl-2-(prop-1-en-2-yl)benzonitrile

Charged a thick walled glass pressure vessel with 2-bromo-5-formylbenzonitrile (Preparation A, Step A, 1.0 g, 4.8 mmol) and anhydrous toluene (20 mL). To this was added potassium isopropenyl-trifluoroborate (2.82 g, 19.0 mmol), Pd(OAc)$_2$ (0.053 g, 0.29 mmol), and dicyclohexyl (2',6'-diisopropoxy-[1,1'-biphenyl]-2-yl)phosphine (0.22 g, 0.48 mmol), followed by K$_3$PO$_4$ (3.0 g, 14 mmol), and water (5 mL). Sparged with Ar gas for 5-10 minutes. Heated to 110° C. overnight. After cooling to ambient temperature, the mixture was transferred to a separatory funnel with EtOAc (30 mL) and water (30 mL). Separated phases. Washed organic phase with brine (30 mL), dried (MgSO$_4$), filtered, and concentrated. The crude material was purified by Biotage Flash 40 silica gel chromatography, eluting with a gradient of 10%-20% EtOAc/hexanes. Yield: 756 mg (91%).

Step B: Preparation of 5-(hydroxymethyl)-2-isopropylbenzonitrile

Charged a round bottomed flask plus stir bar with 5-formyl-2-(prop-1-en-2-yl)benzonitrile (750 mg, 4.38 mmol), EtOAc (20 mL), and lastly Pd(OH)$_2$ (308 mg, 0.438 mmol; 20% wt/wt. Degussa type). Purged with N$_2$, and then stirred overnight under a balloon of H$_2$. Filtered reaction mixture through Celite®, rinsing with DCM. Concentrated filtrate to obtain an oil. Yield: 735 mg (91%). Product carried forward without purification.

Step C: Preparation of 2-isopropyl-5-(methoxymethyl)benzonitrile

The title compound was prepared from 5-(hydroxymethyl)-2-isopropylbenzonitrile (730 mg, 4.17 mmol) according to the procedure provided for Example 33, Step B. Yield: 860 mg (93%).

Step D: Preparation of (2-isopropyl-5-(methoxymethyl)phenyl)methanamine

The title compound was prepared from 2-isopropyl-5-(methoxymethyl)benzonitrile (200 mg, 1.06 mmol) according to the procedure provided for Example 33, Step D. Yield: 195 mg (81%).

Step E: Preparation of 1-(1',4-dimethyl-1-phenyl-1H,1'H-[3,4'-bipyrazol]-5-yl)-3-(2-isopropyl-5-(methoxymethyl)benzyl)urea The title compound was prepared from (2-isopropyl-5-(methoxymethyl)phenyl)methanamine (23 mg, 0.12 mmol) and phenyl (1',4-dimethyl-1-phenyl-1H,1'H-[3,4'-bipyrazol]-5-yl)carbamate (Intermediate 5, 30 mg, 0.080 mmol) according to the procedure provided for Example 33, Step E. Purified crude product by preparative TLC (1 mm thickness, R$_f$=0.42) eluting with 10% MeOH/DCM. Yield: 29 mg (69%). MS m/z (APCI-pos) M+1=473.

Example 35

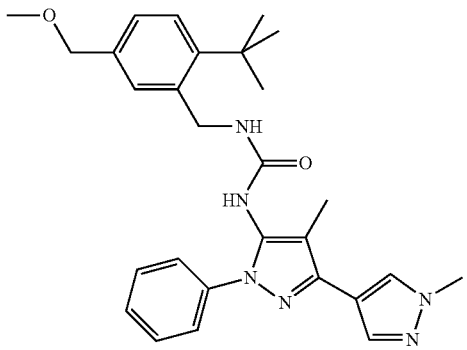

1-(2-(tert-butyl)-5-(methoxymethyl)benzyl)-3-(1',4-dimethyl-1-phenyl-1H,1'H-[3,4'-bipyrazol]-5-yl)urea

Step A: Preparation of 2-bromo-1-(tert-butyl)-4-nitrobenzene

Charged a round bottomed flask plus stir bar with 1-(tert-butyl)-4-nitrobenzene (9.0 g, 50 mmol), 90% sulfuric acid (50 mL), and Ag$_2$SO$_4$ (10 g, 32 mmol). To this stirred mixture was added bromine (2.6 mL, 50 mmol) dropwise. Stirred at ambient temperature overnight. The reaction mixture was then slowly poured into an ice cold 10% aqueous solution of sodium bisulfate (200 mL) with mixing by spatula, and the product then extracted into EtOAc (3×75 mL). The combined organic phases were dried (MgSO$_4$), filtered, and concentrated to a beige solid. Yield: 12.8 g (84%). Product carried forward without purification.

Step B: Preparation of 2-(tert-butyl)-5-nitrobenzonitrile

Charged a stainless steel bomb with 2-bromo-1-(tert-butyl)-4-nitrobenzene (9.7 g, 38 mmol), anhydrous dimethylacetamide (60 mL), and lastly copper(I) cyanide (3.7 g, 41 mmol). Heated to 150° C. for 3 days. After cooling to ambient temperature, the mixture was transferred to a separatory funnel with diethyl ether (100 mL) and water (100 mL). Added diethyl amine (10 mL) to the mixture, which resulted in formation of a precipitate. Separated phases, and re-extracted aqueous phase with diethyl ether (3×50 mL). The combined organic phases were washed with 10% aqueous KCN (50 mL), then with water (100 mL). The combined organic phases were dried (MgSO$_4$), filtered, and concentrated. The crude material was purified by Biotage Flash 65 silica gel chromatography, eluting with a gradient of 5%-15% EtOAc/hexanes. Yield: 4.6 g (59%).

Step C: Preparation of
5-amino-2-(tert-butyl)benzonitrile

Charged a round bottomed flask with 2-(tert-butyl)-5-nitrobenzonitrile (4.8 g, 24 mmol) and EtOH (100 mL). Heated mixture to reflux under $N_2$. Added ammonium formate (4.4 g, 71 mmol), followed by palladium on carbon (2.5 g, 2.4 mmol; 10% wt/wt). Continued heating for 2 hours at reflux. Cooled to ambient temperature. Filtered through Celite®, rinsing with DCM. Concentrated in vacuo. Took residue back up in DCM (30 mL) and washed with water (30 mL). Re-extracted aqueous with DCM (30 mL). The combined organic phases were dried ($MgSO_4$), filtered, and concentrated to an oil. Yield: 4.1 g (80%). Product carried forward without purification.

Step D: Preparation of
5-bromo-2-(tert-butyl)benzonitrile

Charged a round bottomed flask plus stir bar with 5-amino-2-(tert-butyl)benzonitrile (2.0 g, 12 mmol), acetonitrile (20 mL) and hydrogen bromide (1.43 mL, 12.6 mmol; 48% wt/wt in water). Cooled in an ice bath and added sodium nitrite (0.950 g, 13.8 mmol) dissolved in water (2 mL) dropwise with stirring, maintaining internal temperature below 5° C. Stirred for 15 min. Copper(II) bromide (5.13 g, 23.0 mmol) and copper(I) bromide (0.329 g, 2.30 mmol) were added. Continued stirring overnight at ambient temperature, allowing reaction to warm slowly. Partioned mixture between EtOAc (50 mL) and aqueous saturated $NaHCO_3$ (50 mL). Stirred mixture for 15 min until gas evolution ceased. Filtered through Celite®. Separated phases. Re-extracted aqueous phase with EtOAc (30 mL). The combined organic phases were washed with brine (50 mL), dried ($MgSO_4$), filtered, and concentrated. Partially purified crude by Biotage Flash 40 silica gel column, eluting with a gradient of 5%-10% EtOAc/hexanes. Purified isolated material by a second Biotage Flash 40 silica gel column, eluting with a gradient of neat hexanes to 2.5%-10% EtOAc/hexanes. Yield: 415 mg (12%).

Step E: Preparation of
2-(tert-butyl)-5-(methoxymethyl)benzonitrile

Charged a thick walled glass pressure vessel with 5-bromo-2-(tert-butyl)benzonitrile (520 mg, 2.18 mmol), dicyclohexyl(2',6'-dimethoxy-[1,1'-biphenyl]-2-yl)phosphine ("S-Phos") (179 mg, 0.437 mmol), Pd(OAc)$_2$ (49.0 mg, 0.218 mmol), potassium (methoxymethyl)trifluoroborate (664 mg, 4.37 mmol), $Cs_2CO_3$ (2.8 g, 8.7 mmol), and 1:1 dioxane/water (10 mL). Sparged with $N_2$ for several minutes, then heated to 100° C. overnight with stirring. After cooling to ambient temperature, partioned mixture between EtOAc (20 mL) and water (20 mL). Separated phases, re-extracting aqueous with EtOAc (10 mL). Combined organics were washed with brine (20 mL), dried ($MgSO_4$), filtered, and concentrated. The crude material was purified by Biotage Flash 40 silica gel column, eluting with a gradient of 5%-10% EtOAc/hexanes. Yield: 187 mg (36%).

Step F: Preparation of (2-(tert-butyl)-5-(methoxymethyl)phenyl)methanamine

The title compound was prepared from 2-(tert-butyl)-5-(methoxymethyl)benzonitrile (187 mg, 0.920 mmol) according to the procedure provided for Example 33, Step D. Yield: 169 mg (53%).

Step G: Preparation of 1-(2-(tert-butyl)-5-(methoxymethyl)benzyl)-3-(1',4-dimethyl-1-phenyl-1H,1'H-[3,4'-bipyrazol]-5-yl)urea The title compound was prepared from (2-(tert-butyl)-5-(methoxymethyl)phenyl)methanamine (50 mg, 0.24 mmol) and phenyl (1',4-dimethyl-1-phenyl-1H,1'H-[3,4'-bipyrazol]-5-yl)carbamate (Intermediate 5, 90 mg, 0.24 mmol) according to the procedure provided for Example 33, Step E. Purified crude product by preparative TLC (2 mm thickness, $R_f$=0.39) eluting with 7.5% MeOH/DCM. Yield: 52 mg (36%). MS m/z (APCI-pos) M+1=487.

Example 36

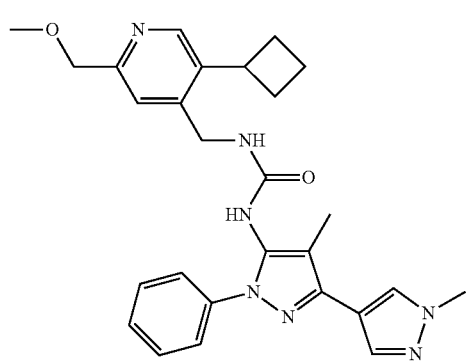

1-((5-cyclobutyl-2-(methoxymethyl)pyridin-4-yl)methyl)-3-(1',4-dimethyl-1-phenyl-1H,1'H-[3,4'-bipyrazol]-5-yl)urea Step A: Preparation of 3-bromoisonicotinaldehyde oxime Charged a round bottomed flask (equipped with a water condenser) with 3-bromoisonicotinaldehyde (25.0 g, 134 mmol), sodium acetate (13.8 g, 168 mmol), and water (1 L). Heated to reflux with stirring. Hydroxylamine hydrochloride (14.0 g, 202 mmol) was added, resulting in immediate precipitate formation. Cooled the suspension to ambient temperature, then in an ice bath. Filtered solids, washing with ice cold water, then dried solids by toluene azeotrope on a rotary evaporator (3×100 mL). Yield: 24.4 g (89%). Carried product forward without purification.

Step B: Preparation of 3-bromoisonicotinonitrile

Charged a round bottomed flask plus stir bar with 3-bromoisonicotinaldehyde oxime (24.4 g, 121 mmol), anhydrous THF (200 mL), and $Et_3N$ (68 mL, 486 mmol). Cooled in an ice bath under $N_2$, and then added $POCl_3$ (11.7 mL, 127 mmol) dropwise. Continued stirring in the ice bath for 3 hours. The mixture was partitioned between EtOAc (400 mL) and saturated aqueous $NaHCO_3$ (400 mL). Separated phases. Re-extracted aqueous with EtOAc (2×150 mL). The combined organic phases were dried (Na₂SO₄), filtered, and concentrated. Triturated crude with pentane (100-150 mL), and filtered pink solids. Concentrated the mother liquor. Triturated the resulting solids with more pentane (50-75 mL) to obtain a second crop. Pooled the first and second crops (which contained some triethyl amine hydrochloride by NMR) and partitioned the combined crops between 10% EtOAc in Et₂O (150 mL) and water (50 mL). Neutralized the aqueous layer with saturated aqueous NaHCO₃ (50-100 mL). Separated phases, and re-extracted aqueous phase with more 10% EtOAc in Et₂O (2×50 mL). The combined organic phases were dried (MgSO₄), filtered, and concentrated to provide desired product as a solid. Yield: 19.7 g (87%).

Step C: Preparation of 3-cyclobutylisonicotinonitrile

Charged a dry round bottomed flask plus stir bar with 3-bromoisonicotinonitrile (6.1 g, 33 mmol), anhydrous THF (150 mL), dicyclohexyl(2',6'-dimethoxy-[1,1'-biphenyl]-2-yl)phosphine "S-Phos" (1.0 g, 2.5 mmol), and Pd(OAc)₂ (0.37 g, 1.7 mmol). Purged the reaction mixture with N₂. Added cyclobutylzinc(II) bromide (100 mL, 50 mmol; 0.5 M in THF) over 15 minutes via cannula. Stirred the reaction mixture for 2 hours at ambient temperature. Partioned mixture between EtOAc (200 mL) and water (200 mL), and filtered through Celite® to remove insoluble solids, rinsing with EtOAc. Separated phases, and re-extracted aqueous phase with EtOAc (100 mL). The combined organic phases were washed with brine (150 mL), dried (MgSO₄), filtered, and concentrated. The crude material was purified by Biotage Flash 65 silica gel column, eluting with a gradient of 10% EtOAc/hexanes to 1:1 EtOAc/hexanes. Yield: 2.3 g (43%).

Step D: Preparation of 5-cyclobutyl-2-(methoxymethyl)isonicotinonitrile

Charged a thick walled glass vessel plus stir bar with 3-cyclobutylisonicotinonitrile (1.0 g, 6.3 mmol), 1:1 acetic acid/water (20 mL), trifluoroacetic acid (0.48 mL, 6.3 mmol), and potassium (methoxymethyl)trifluoroborate (1.92 g, 12.6 mmol). Stirred to dissolve, then added triacetoxymanganese dihydrate (4.24 g, 15.8 mmol). Heated to 60° C. with stirring. After 1 hour, added more triacetoxymanganese dihydrate (4.24 g, 15.8 mmol), and continued heating for 2 hours. After cooling to ambient temperature, the reaction mixture was filtered through Celite®, rinsing with EtOAc. Concentrated filtrate in vacuo. Performed a toluene azeotrope (2×20 mL) to remove excess acid and water. Partially purified crude mixture on a Redi-Sep 220 g silica gel column eluting with a gradient of neat DCM to 3% MeOH in DCM. Product containing fractions were re-purified by preparative TLC eluting with 5% MeOH in DCM. A second preparative TLC purification was performed to further enrich the concentration of the title compound in the mixture, eluting with 5% acetone in DCM. The title compound (260 mg) also contained 3-cyclobutylisonicotinonitrile (unreacted starting material) and 3-cyclobutyl-2,6-bis(methoxymethyl)isonicotinonitrile by-product, and it was carried forward to the next step as a mixture.

Step E: Preparation of (5-cyclobutyl-2-(methoxymethyl)pyridin-4-yl)methanamine

The title compound was prepared from 5-cyclobutyl-2-(methoxymethyl)isonicotinonitrile (130 mg, 0.64 mmol) according to the procedure provided for Example 33, Step D. Crude product was obtained as mixture with (3-cyclobutylpyridin-4-yl)methanamine and (3-cyclobutyl-2,6-bis(methoxymethyl)pyridin-4-yl)methanamine that were formed from reduction of 3-cyclobutylisonicotinonitrile and 3-cyclobutyl-2,6-bis(methoxymethyl)isonicotinonitrile, respectively, that were present in the starting material. The crude mixture (115 mg) was carried forward to the next step without separation of products.

Step F: Preparation of 1-((5-cyclobutyl-2-(methoxymethyl)pyridin-4-yl)methyl)-3-(1',4-dimethyl-1-phenyl-1H,1'H-[3,4'-bipyrazol]-5-yl)urea The title compound was prepared from (5-cyclobutyl-2-(methoxymethyl)pyridin-4-yl)methanamine (115 mg, 0.56 mmol) and phenyl (1',4-dimethyl-1-phenyl-1H-1,1'H-[3,4'-bipyrazol]-5-yl)carbamate from (Intermediate 5, 208 mg, 0.56 mmol) according to the procedure provided for Example 33, Step E. Partially purified crude product mixture by preparative TLC (2 mm thickness, R_f=0.13-0.23) eluting with 5% MeOH (containing 7N NH₃) in DCM. The product containing bands were pooled and an aliquot from these were re-purified by reverse phase HPLC (YMC ODS-AQ, 250×20 mm column) to obtain analytically pure title compound. MS m/z (APCI-pos) M+1=486.

Example 37

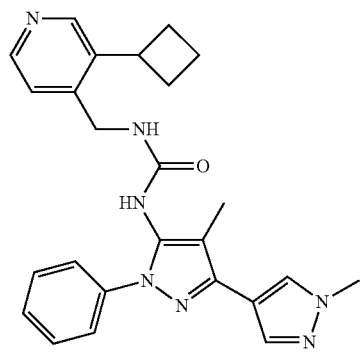 [SMILES: Cc1c(-c2cnn(C)c2)nn(-c2ccccc2)c1NC(=O)NCc1ccncc1C1CCC1]

1-((3-cyclobutylpyridin-4-yl)methyl)-3-(1',4-dimethyl-1-phenyl-1H,1'H-[3,4'-bipyrazol]-5-yl)ureaea The title compound was obtained from the purification of the crude reaction mixture described for Example 36, Step F, by reverse phase HPLC (YMC ODS-AQ, 250×20 mm column). MS m/z (APCI-pos) M+1=442.

Example 38

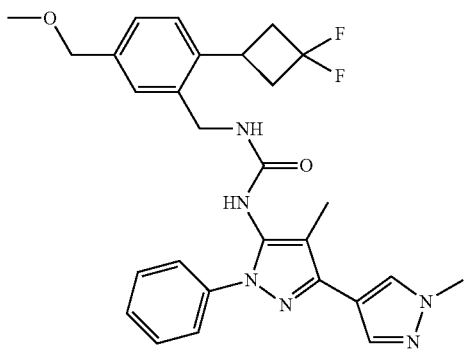

1-(2-(3,3-difluorocyclobutyl)-5-(methoxymethyl)
benzyl)-3-(1',4-dimethyl-1-phenyl-1H,1'H-[3,4'-
bipyrazol]-5-yl)urea

Step A: Preparation of 2-bromo-4-(methoxycarbonyl)benzenediazonium tetrafluoroborate To a stirred solution of $BF_3$-etherate (2.9 mL, 23 mmol) in DCM (10 mL) cooled in an ice/NaCl bath under $N_2$ was added methyl 4-amino-3-bromobenzoate (3.5 g, 15 mmol) dissolved in DCM (20 mL) dropwise. Next added a solution of tert-butyl nitrite (2.2 mL, 18 mmol) dissolved in DCM (5 mL) dropwise over a 10 min period. Following complete addition, left stirring in the ice/NaCl bath for 10 minutes. The reaction vessel was removed and placed in a regular ice water bath, stirring for 20 min more. Diluted the suspension with pentane, and filtered solids. Washed solids with pentanes then diethyl ether multiple times. Dried under high vacuum and stored in a −10° C. freezer. Yield: 4.9 g (97%).

Step B: Preparation of methyl 3-bromo-4-vinylbenzoate

Charged a round bottomed flask plus stir bar with dioxane (50 mL), potassium vinyltrifluoroborate (2.40 g, 17.9 mmol), and Pd(OAc)$_2$ (0.167 g, 0.745 mmol). Sparged mixture with $N_2$ for several minutes. Added 2-bromo-4-(methoxycarbonyl)benzenediazonium tetrafluoroborate (4.9 g, 15 mmol) over a 5-10 minute period in portions as a solid while stirring at ambient temperature. Reaction was somewhat exothermic, so placed in an ice bath for a few minutes when the flask became warm to the touch. Wrapped flask in Al foil to minimize light exposure and continued stirring under $N_2$ for 1 hour. Partioned mixture between EtOAc (50 mL) and aqueous saturated NaHCO$_3$ (50 mL). Separated phases, and re-extracted aqueous with EtOAc (30 mL). The combined organic phases were shaken with brine (50 mL), and the biphase was filtered through GF/F paper to remove insoluble solids, then the phases were separated. Organic phase was dried (MgSO$_4$), filtered, and concentrated. The crude material was purified by Red-Sep 120 silica gel column, eluting with 5% EtOAc/hexanes. Yield: 1.53 g (41%). Stored product in −10° C. freezer.

Step C: Preparation of (3-bromo-4-vinylphenyl)methanol

Charged a round bottomed flask plus stir bar with methyl 3-bromo-4-vinylbenzoate (1.8 g, 7.47 mmol) and anhydrous DCM (15 mL). Cooled to −78° C. under $N_2$, and added DIBAL-H (14.9 mL, 22.4 mmol; 1.5 M in toluene) dropwise. Stirred for 30 min at −78° C. Carefully quenched with dropwise MeOH addition (1-2 mL) at −78° C. (gas evolution), and then warmed to 0° C. before adding reaction mixture to 30% Rochelle's salt (75 mL). Much gas evolution—vent adequately. Diluted mixture with more DCM (75 mL) and stirred for 2-3 hours with Rochelle's salt. Filtered through GF/F paper and separated the phases, re-extracting aqueous with DCM (30 mL). The combined organic phases were washed with brine (30 mL), dried (MgSO4), filtered, and concentrated. Yield: 1.68 g (95%).

Step C: Preparation of 2-bromo-4-(methoxymethyl)-1-vinylbenzene

Charged a round bottomed flask plus stir bar with (3-bromo-4-vinylphenyl)methanol (1.68 g, 7.88 mmol) and anhydrous THF (20 mL). Cooled in an ice bath under $N_2$, and added sodium hydride (0.473 g, 11.8 mmol; 60% in mineral oil). Left stirring in the ice bath for 1 hour. Then added iodomethane (0.98 mL, 16 mmol) dropwise. Removed bath and warmed to ambient temperature, stirring for 1 hour. Carefully quenched with aqueous saturated NH$_4$Cl solution (5 mL) venting adequately until gas evolution ceased. Partioned mixture between water (20 mL) and EtOAc (20 mL). Separated phases, then re-extracted aqueous with EtOAc (20 mL). The combined organic phases were washed with 10% sodium thiosulfate (20 mL), brine (20 mL), dried (MgSO$_4$), filtered, and concentrated. This crude product was then purified by Redi-Sep 120 silica gel column, eluting with a gradient of neat hexanes to 10% EtOAc/hexanes. Yield: 1.15 g (61%).

Step D: Preparation of 3-(2-bromo-4-(methoxymethyl)phenyl)-2,2-dichlorocyclobutanone Charged a dry round bottomed flask plus stir bar with 2-bromo-4-(methoxymethyl)-1-vinylbenzene (1.1 g, 4.8 mmol), diethyl ether (20 mL), and activated zinc (0.950 g, 14.5 mmol; prepared as described in *J. Org. Chem.* 1978, 43, 2879-2882). Heated to reflux, then added a solution of POCl$_3$ (0.486 mL, 5.33 mmol) and 2,2,2-trichloroacetyl chloride (1.09 mL, 9.69 mmol) dissolved in diethyl ether (5 mL) over a 30 min period. Continued heating at reflux for 1 hour. Stirred at ambient temperature, overnight. As mostly unreacted starting material remained, added more activated zinc reagent (0.950 g, 14.5 mmol) as well as additional 2,2,2-trichloroacetyl chloride (0.55 mL, 4.8 mmol) and POCl$_3$ (0.24 mL, 2.7 mmol) dissolved in diethyl ether (3 mL) to the reaction mixture. Heated reaction to reflux, and continued heating at reflux overnight. Cooled reaction to ambient temperature, then filtered mixture through GF/F paper, rinsing multiple times with diethyl ether. Diluted the filtrate with EtOAc (15 mL) and ether (15 mL) and washed organic phase with water (20 mL), aqueous saturated NaHCO$_3$ (20 mL), then brine (20 mL). The organic phase was dried (MgSO4), filtered, and concentrated. Yield: 1.39 g (68%). Carried crude product forward to the next step without purification.

Step E: Preparation of 3-(2-bromo-4-(methoxymethyl)phenyl)cyclobutanone

Added 3-(2-bromo-4-(methoxymethyl)phenyl)-2,2-dichlorocyclobutanone (1.39 g, 4.11 mmol) dissolved in acetic acid (5 mL) to a stirred suspension of zinc dust (1.08 g, 16.4 mmol) in acetic acid (10 mL) that was cooled in an ice bath. Heated the mixture to 70° C. for 2 hours. After cooling to ambient temperature, concentrated the mixture in vacuo. Partitioned residue between Et₂O (30 mL) and washed organic phase with water (20 mL), aqueous saturated NaHCO₃ (20 mL), and brine (20 mL). The organic phase was dried (MgSO₄), filtered, and concentrated. Yield: 1.09 g (84%). Carried product forward to the next step without purification.

Step F: Preparation of 2-bromo-1-(3,3-difluorocyclobutyl)-4-(methoxymethyl)benzene Charged a round bottomed flask plus stir bar with 3-(2-bromo-4-(methoxymethyl)phenyl)cyclobutanone (1.09 g, 4.05 mmol), anhydrous DCM (10 mL), and cooled in an ice bath under N₂. Next added diethylaminosulfur trifluoride (DAST) (1.07 mL, 8.10 mmol) dropwise. Removed ice bath after addition was complete and stirred overnight at ambient temperature. Poured reaction mixture into aqueous saturated NaHCO₃ (150 mL) stirred with ice chunks, then diluted mixture with more DCM (50 mL). Stirred for 2 hours, then separated phases. Re-extracted the aqueous layer with more DCM (50 mL). The combined organic phases were dried (MgSO₄), filtered, and concentrated. Purified crude by RediSep 80 silica gel column, eluting with a gradient of neat hexanes to 10% EtOAc/hexanes. Yield: 720 mg (52%).

Step G: Preparation of 2-(3,3-difluorocyclobutyl)-5-(methoxymethyl)benzonitrile

Charged a stainless steel bomb containing a teflon insert plus stir bar with 2-bromo-1-(3,3-difluorocyclobutyl)-4-(methoxymethyl)benzene (670 mg, 2.30 mmol), DMA (5 mL), Pd(PPh₃)₄ (266 mg, 0.230 mmol), and Zn(CN)₂ (270 mg, 2.30 mmol). Sparged with N₂ for several minutes, then sealed up bomb and heated to 130° C. for 2 days. After cooling to ambient temperature, the reaction mixture was partitioned between EtOAc (20 mL) and aqueous saturated NaHCO₃ (20 mL). Separated phases, then re-extracted aqueous with EtOAc (10 mL). Washed organic phase with water (3×20 mL), brine (20 mL), dried (MgSO₄), filtered, and concentrated. The crude material was purified by Redi-Sep 40 silica gel column, eluting with a gradient of 10%-20% EtOAc/hexanes. Yield: 337 mg (59%).

Step H: Preparation of (2-(3,3-difluorocyclobutyl)-5-(methoxymethyl)phenyl)methanamine The title compound was prepared from 2-(3,3-difluorocyclobutyl)-5-(methoxymethyl)benzonitrile (200 mg, 0.84 mmol) according to the procedure provided for Example 33, Step D. Yield: 195 mg (91%).

Step I: Preparation of 1-(2-(3,3-difluorocyclobutyl)-5-(methoxymethyl)benzyl)-3-(1',4-dimethyl-1-phenyl-1H,1'H-[3,4'-bipyrazol]-5-yl)urea The title compound was prepared from (2-(3,3-difluorocyclobutyl)-5-(methoxymethyl)phenyl)methanamine (25 mg, 0.10 mmol) and phenyl (1',4-dimethyl-1-phenyl-1H,1'H-[3,4'-bipyrazol]-5-yl)carbamate from (Intermediate 5, 39 mg, 0.10 mmol) according to the procedure provided for Example 33, Step E. Purified crude product by preparative TLC (0.5 mm thickness, R$_f$=0.44) eluting with 10% MeOH/DCM. Yield: 34 mg (60%). MS m/z (APCI-pos) M+1=521.

Example 39

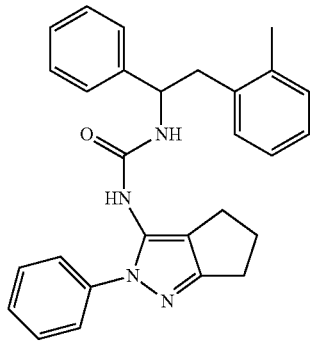 [SMILES: Cc1ccccc1CC(NC(=O)Nc1c2c(nn1-c1ccccc1)CCC2)c1ccccc1]

1-(2-phenyl-2,4,5,6-tetrahydrocyclopenta[c]pyrazol-3-yl)-3-(1-phenyl-2-o-tolylethyl)urea Step A: Preparation of 1-phenyl-2-o-tolylethanamine Phenylmagnesium chloride (3M in ether, 766 µL, 2.29 mmol) was added dropwise to a solution of 2-o-tolylacetonitrile (100 mg, 0.762 mmol) in ether (1 mL) at ambient temperature. The reaction was stirred for 2 hours and MeOH (2 mL) added slowly (very exothermic!). NaBH₄ (115 mg, 3.05 mmol) was added in small portions and the reaction was stirred overnight and poured into a mixture of 1N NaOH (13 mL) and Brine (15 mL). The mixture was extracted with EtOAc (suspension that separated after a few minutes) and the organic extract was washed with brine, dried (MgSO₄) and concentrated to provide the title compound (155 mg, 0.734 mmol, 96.2% yield). MS (apci) m/z=212.1 (M+H).

Step B: Preparation of 1-(2-phenyl-2,4,5,6-tetrahydrocyclopenta[c]pyrazol-3-yl)-3-(1-phenyl-2-o-tolylethyl)urea 1-phenyl-2-o-tolylethanamine (8 mg, 0.038 mmol), phenyl 2-phenyl-2,4,5,6-tetrahydrocyclopenta[c]pyrazol-3-ylcarbamate (10 mg, 0.032 mmol) and DIEA (4.1 mg, 0.032 mmol) were combined in 0.2 mL of DMF and stirred at ambient temperature for 1 hour. The reaction was loaded onto a samplet and purified by reverse-phase column chromatography, eluting with 0-80% acetonitrile/water, to afford the title compound (4.4 mg, 0.010 mmol, 32% yield). MS (apci) m/z=437.2 (M+H).

Table 1 provides a list of commercially available amines that were used in the synthesis of the compounds described in Table 2.

TABLE 1

| Structure | Vendor/Catalog# | CAS# |
|---|---|---|
| ![NH2 structure] | Aldrich/13,702-2 | 25611-78-3 |

TABLE 1-continued

| Structure | Vendor/Catalog# | CAS# |
|---|---|---|
| 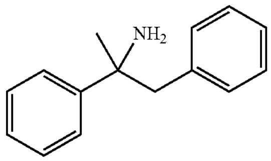 [SMILES: CC(N)(Cc1ccccc1)c1ccccc1] | Aurora Fine Chemicals/A00.752.681 | 118910-28-4 |
| 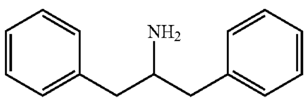 [SMILES: NC(Cc1ccccc1)Cc1ccccc1] | RCLSALOR/T151,076 | 4275-43-8 |
| | Aldrich/127,035 | 118-31-0 |
| | Ryan Scientific/EN300-30476 | 91245-72-6 |

The compounds in Table 2 were prepared by reacting the appropriate amine from Table 1 with the appropriate intermediate phenylcarbamate using the method as described for Example 39, Step 2.

TABLE 2

| Example # | Structure | Name | MS (apci) m/z |
|---|---|---|---|
| 40 | 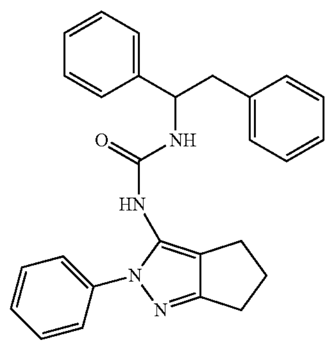 [SMILES: O=C(Nc1c2c(nn1-c1ccccc1)CCC2)NC(Cc1ccccc1)c1ccccc1] | 1-(1,2-diphenylethyl)-3-(2-phenyl-2,4,5,6-tetrahydrocyclopenta[c]pyrazol-3-yl)urea | 423.2 (M + H) |
| 41 | 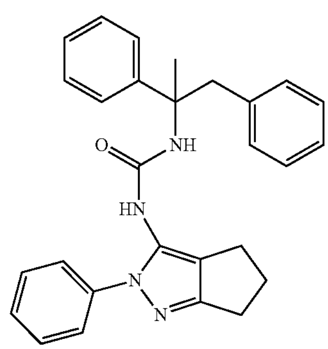 [SMILES: CC(Cc1ccccc1)(NC(=O)Nc1c2c(nn1-c1ccccc1)CCC2)c1ccccc1] | 1-(1,2-diphenylpropan-2-yl)-3-(2-phenyl-2,4,5,6-tetrahydrocyclopenta[c]pyrazol-3-yl)urea | 437.2 (M + H) |

TABLE 2-continued

| Example # | Structure | Name | MS (apci) m/z |
|---|---|---|---|
| 42 | 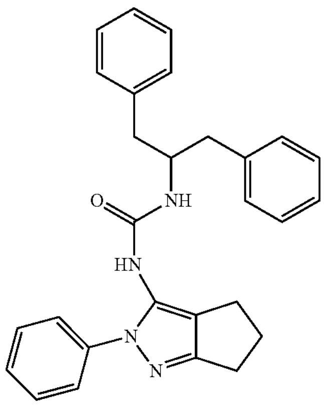 [SMILES: O=C(Nc1c2c(nn1-c1ccccc1)CCC2)NC(Cc1ccccc1)Cc1ccccc1] | 1-(1,3-diphenylpropan-2-yl)-3-(2-phenyl-2,4,5,6-tetrahydrocyclopenta[c]pyrazol-3-yl)urea | 437.2 (M + H) |
| 43 | 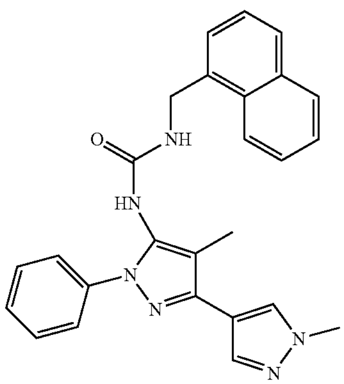 [SMILES: Cc1c(-c2cnn(C)c2)nn(-c2ccccc2)c1NC(=O)NCc1cccc2ccccc12] | 1-(1',4-dimethyl-1-phenyl-1H,1'H-3,4'-bipyrazol-5-yl)-3-(naphthalen-1-ylmethyl)urea | 437.2 (M + H) |
| 44 | 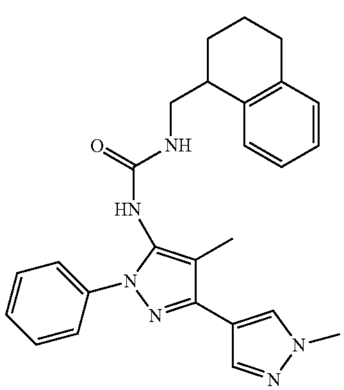 [SMILES: Cc1c(-c2cnn(C)c2)nn(-c2ccccc2)c1NC(=O)NCC1CCCc2ccccc21] | 1-(1',4-dimethyl-1-phenyl-1H,1'H-3,4'-bipyrazol-5-yl)-3-((1,2,3,4-tetrahydronaphthalen-1-yl)methyl)urea | 441.2 (M + H) |

Table 3 provides a list of commercially available nitriles that were used in the synthesis of the compounds described in Table 4.

TABLE 3

| Structure | Vendor/Catalog# | CAS# |
|---|---|---|
| 2-chlorobenzyl cyanide | Aldrich/188,492 | 2856-63-5 |
| 3,4-difluorobenzyl cyanide | Aldrich/26,452-0 | 658-99-1 |
| 2-methoxybenzyl cyanide | Aldrich/180,645 | 7035-03-2 |
| 4,4,4-trifluorobutyronitrile | Matrix Scientific/7160 | 690-95-9 |

The compounds in Table 4 were prepared by reacting the appropriate nitrile from Table 3 with either phenylmagnesium chloride or benzylmagnesium chloride and then elaborating using the method as described for Example 39.

TABLE 4

| Example # | Structure | Name | MS (apci) m/z |
|---|---|---|---|
| 45 | 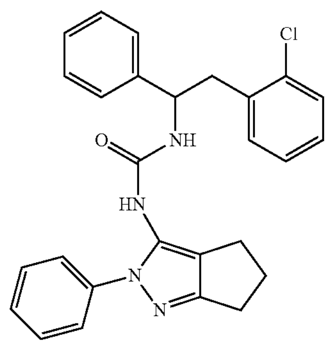 [SMILES: O=C(Nc1c2c(nn1-c1ccccc1)CCC2)NC(Cc1ccccc1Cl)c1ccccc1] | 1-(2-(2-chlorophenyl)-1-phenylethyl)-3-(2-phenyl-2,4,5,6-tetrahydro-cyclopenta[c]pyrazol-3-yl)urea | 457.2 (M + H) |
| 46 | 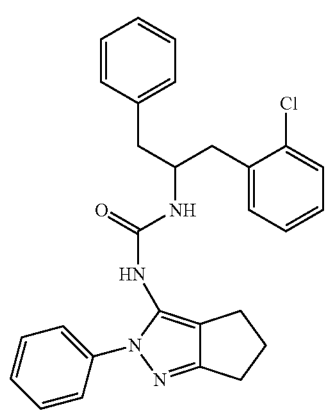 [SMILES: O=C(Nc1c2c(nn1-c1ccccc1)CCC2)NC(Cc1ccccc1)Cc1ccccc1Cl] | 1-(1-(2-chlorophenyl)-3-phenylpropan-2-yl)-3-(2-phenyl-2,4,5,6-tetrahydro-cyclopenta[c]pyrazol-3-yl)urea | 471.2 (M + H) |

TABLE 4-continued

| Example # | Name | MS (apci) m/z |
|---|---|---|
| 47 | 1-(1-(3,4-difluorophenyl)-3-phenylpropan-2-yl)-3-(2-phenyl-2,4,5,6-tetrahydrocyclopenta[c]pyrazol-3-yl)urea | 473.2 (M + H). |
| 48 | 1-(1-(2-methoxyphenyl)-3-phenylpropan-2-yl)-3-(2-phenyl-2,4,5,6-tetrahydrocyclopenta[c]pyrazol-3-yl)urea | 467.2 (M + H). |
| 49 | 1-(2-phenyl-2,4,5,6-tetrahydrocyclopenta[c]pyrazol-3-yl)-3-(5,5,5-trifluoro-1-phenylpentan-2-yl)urea | 443.2 (M + H). |

Example 50

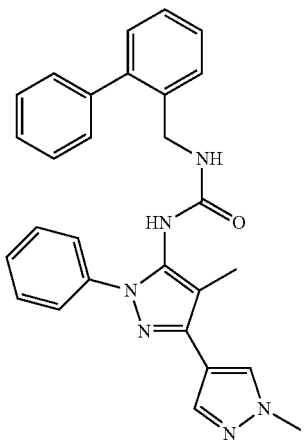 [SMILES: Cc1c(-c2cnn(C)c2)nn(-c2ccccc2)c1NC(=O)NCc1ccccc1-c1ccccc1]

1-([1,1'-biphenyl]-2-ylmethyl)-3-(1',4-dimethyl-1-phenyl-1H,1'H-[3,4'-bipyrazol]-5-yl)urea To a solution of [1,1'-biphenyl]-2-ylmethanamine (12 mg, 0.065 mmol) in DCM (1 mL) were added phenyl (1',4-dimethyl-1-phenyl-1H,1'H-[3,4'-bipyrazol]-5-yl)carbamate (Intermediate 5, 24.5 mg, 0.065 mmol) then DIEA (0.023 mL, 0.131 mmol). The reaction mixture was stirred at ambient temperature for 1 hour, then purified by reverse-phase column chromatography, eluting with 0-85% acetonitrile/water, to afford the title compound as a white solid (10 mg, 0.022 mmol, 34% yield). MS (apci) m/z=463.2 (M+H).

Example 51

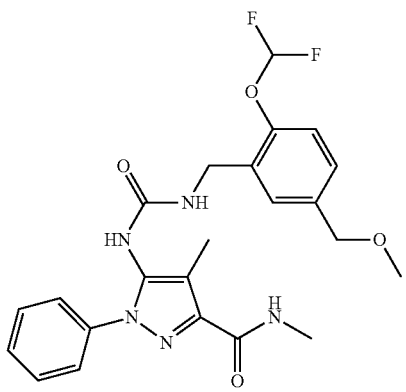 [SMILES: CNC(=O)c1nn(-c2ccccc2)c(NC(=O)NCc2cc(COC)ccc2OC(F)F)c1C]

5-(3-(2-(difluoromethoxy)-5-(methoxymethyl)benzyl)ureido)-N,4-dimethyl-1-phenyl-1H-pyrazole-3-carboxamide Prepared according to the procedure of Example 1, substituting 4-methyl-3-(2-methylpyrimidin-5-yl)-1-phenyl-1H-pyrazol-5-amine with 3-(6-methoxypyridin-3-yl)-4-methyl-1-phenyl-1H-pyrazol-5-amine and (2-cyclopropyl-5-(methoxymethyl)phenyl)methanamine with (2-(difluoromethoxy)-5-(methoxymethyl)phenyl)methanamine to give the title compound (21%). MS (APCI) m/z=524.2 (M+H).

Example 52

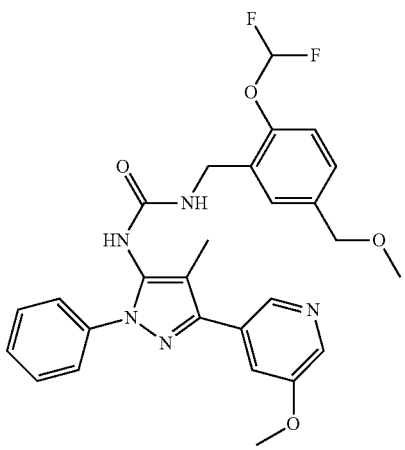 [SMILES: COCc1ccc(OC(F)F)c(CNC(=O)Nc2c(C)c(-c3cncc(OC)c3)nn2-c2ccccc2)c1]

1-(2-(difluoromethoxy)-5-(methoxymethyl)benzyl)-3-(3-(5-methoxypyridin-3-yl)-4-methyl-1-phenyl-1H-pyrazol-5-yl)urea Prepared according to the procedure of Example 1, substituting 4-methyl-3-(2-methylpyrimidin-5-yl)-1-phenyl-1H-pyrazol-5-amine with 3-(5-methoxypyridin-3-yl)-4-methyl-1-phenyl-1H-pyrazol-5-amine and (2-cyclopropyl-5-(methoxymethyl)phenyl)methanamine with (2-(difluoromethoxy)-5-(methoxymethyl)phenyl)methanamine to give the title compound (27%). MS (APCI) m/z=524.2 (M+H).

Example 53

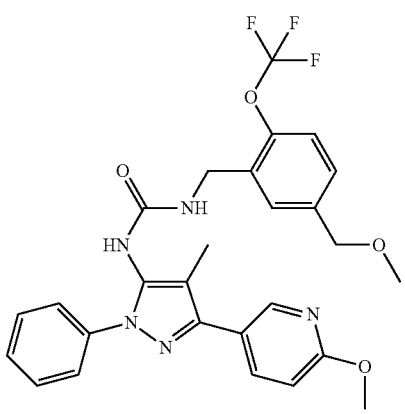 [SMILES: COCc1ccc(OC(F)(F)F)c(CNC(=O)Nc2c(C)c(-c3ccc(OC)nc3)nn2-c2ccccc2)c1]

1-(5-(methoxymethyl)-2-(trifluoromethoxy)benzyl)-3-(3-(6-methoxypyridin-3-yl)-4-methyl-1-phenyl-1H-pyrazol-5-yl)urea Prepared according to the procedure of Example 1, substituting 4-methyl-3-(2-methylpyrimidin-5-yl)-1-phenyl- 1H-pyrazol-5-amine with 3-(6-methoxypyridin-3-yl)-4-methyl-1-phenyl-1H-pyrazol-5-amine and (2-cyclopropyl-5-(methoxymethyl)phenyl)methanamine with (5-(methoxymethyl)-2-(trifluoromethoxy)phenyl)methanamine to give the title compound (43%). MS (APCI) m/z=542.2 (M+H).

Example 54

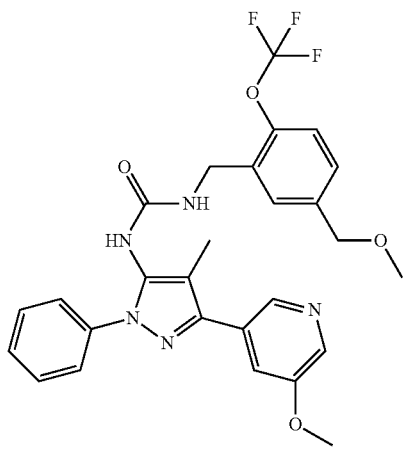 [SMILES: COCc1ccc(OC(F)(F)F)c(CNC(=O)Nc2c(C)c(-c3cncc(OC)c3)nn2-c2ccccc2)c1]

1-(5-(methoxymethyl)-2-(trifluoromethoxy)benzyl)-3-(3-(5-methoxypyridin-3-yl)-4-methyl-1-phenyl-1H-pyrazol-5-yl)urea Prepared according to the procedure of Example 1, substituting 4-methyl-3-(2-methylpyrimidin-5-yl)-1-phenyl-1H-pyrazol-5-amine with 3-(5-methoxypyridin-3-yl)-4-methyl-1-phenyl-1H-pyrazol-5-amine and (2-cyclopropyl-5-(methoxymethyl)phenyl)methanamine with (5-(methoxymethyl)-2-(trifluoromethoxy)phenyl)methanamine to give the title compound (49%). MS (APCI) m/z=542.2 (M+H).

Example 55

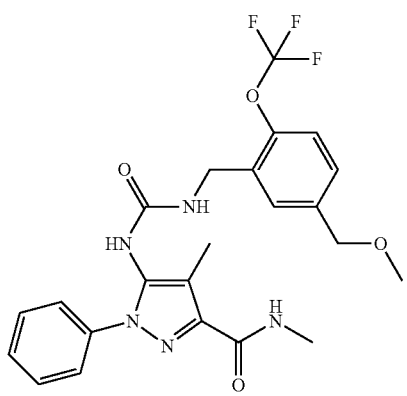 [SMILES: CNC(=O)c1nn(-c2ccccc2)c(NC(=O)NCc2cc(COC)ccc2OC(F)(F)F)c1C]

5-(3-(5-(methoxymethyl)-2-(trifluoromethoxy)benzyl)ureido)-N,4-dimethyl-1-phenyl-1H-pyrazole-3-carboxamide Prepared according to the procedure of Example 1, substituting 4-methyl-3-(2-methylpyrimidin-5-yl)-1-phenyl-1H-pyrazol-5-amine with 5-amino-N,4-dimethyl-1-phenyl-1H-pyrazole-3-carboxamide and (2-cyclopropyl-5-(methoxymethyl)phenyl)methanamine with (5-(methoxymethyl)-2-(trifluoromethoxy)phenyl)methanamine to give the title compound (49%). MS (APCI) m/z=492.2 (M+H).

Example 56

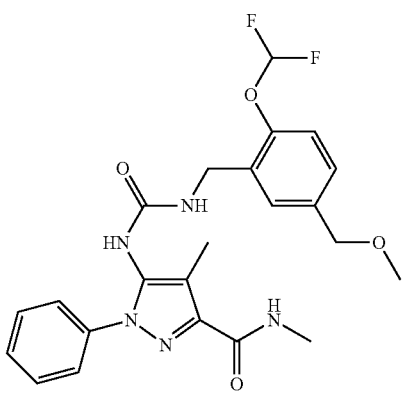 [SMILES: CNC(=O)c1nn(-c2ccccc2)c(NC(=O)NCc2cc(COC)ccc2OC(F)F)c1C]

5-(3-(2-(difluoromethoxy)-5-(methoxymethyl)benzyl)ureido)-N,4-dimethyl-1-phenyl-1H-pyrazole-3-carboxamide Prepared according to the procedure of Example 1, substituting 4-methyl-3-(2-methylpyrimidin-5-yl)-1-phenyl-1H-pyrazol-5-amine with 5-amino-N,4-dimethyl-1-phenyl-1H-pyrazole-3-carboxamide and (2-cyclopropyl-5-(methoxymethyl)phenyl)methanamine with (2-(difluoromethoxy)-5-(methoxymethyl)phenyl)methanamine to give the title compound (39%). MS (APCI) m/z=474.2 (M+H).

Example 57

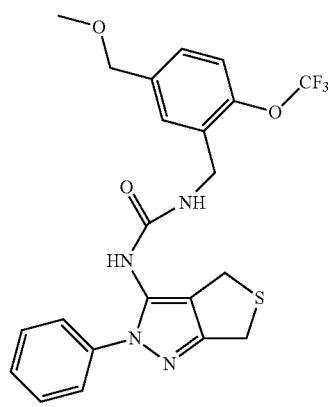 [SMILES: COCc1ccc(OC(F)(F)F)c(CNC(=O)Nc2c3c(nn2-c2ccccc2)CSC3)c1]

1-(5-(methoxymethyl)-2-(trifluoromethoxy)benzyl)-3-(2-phenyl-4,6-dihydro-2H-thieno[3,4-c]pyrazol-3-yl)urea Prepared according to the procedure of Example 2, substituting phenyl (3-ethoxy-4-methyl-1-phenyl-1H-pyrazol- 5-yl)carbamate with phenyl (2-phenyl-4,6-dihydro-2H-thieno[3,4-c]pyrazol-3-yl)carbamate and (2-cyclopropyl-5-(methoxymethyl)phenyl)methanamine with (5-(methoxymethyl)-2-(trifluoromethoxy)phenyl)methanamine to give the title compound (40%). MS (APCI) m/z=477.1 (M−H).

Example 58

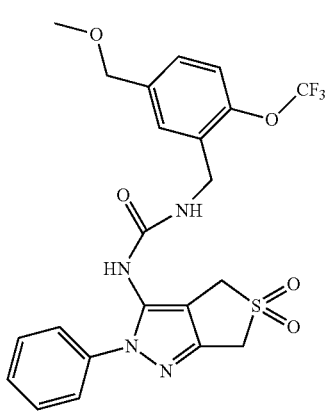 [SMILES: COCc1ccc(OC(F)(F)F)c(CNC(=O)Nc2c3c(nn2-c2ccccc2)CS(=O)(=O)C3)c1]

1-(5,5-dioxido-2-phenyl-4,6-dihydro-2H-thieno[3,4-c]pyrazol-3-yl)-3-(5-(methoxymethyl)-2-(trifluoromethoxy)benzyl)urea Prepared according to the procedure of Example 2, substituting phenyl (3-ethoxy-4-methyl-1-phenyl-1H-pyrazol-5-yl)carbamate with phenyl (5,5-dioxido-2-phenyl-4,6-dihydro-2H-thieno[3,4-c]pyrazol-3-yl)carbamate and (2-cyclopropyl-5-(methoxymethyl)phenyl)methanamine with (5-(methoxymethyl)-2-(trifluoromethoxy)phenyl)methanamine to give the title compound (41%). MS (APCI) m/z=511.1 (M−H).

Example 59

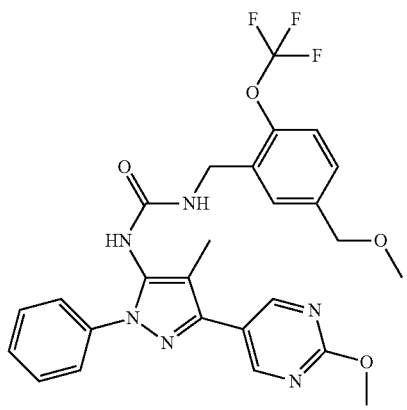 [SMILES: COCc1ccc(OC(F)(F)F)c(CNC(=O)Nc2c(C)c(-c3cnc(OC)nc3)nn2-c2ccccc2)c1]

1-(5-(methoxymethyl)-2-(trifluoromethoxy)benzyl)-3-(3-(2-methoxypyrimidin-5-yl)-4-methyl-1-phenyl-1H-pyrazol-5-yl)urea Prepared according to the procedure of Example 1, substituting 4-methyl-3-(2-methylpyrimidin-5-yl)-1-phenyl-1H-pyrazol-5-amine with 3-(2-methoxypyrimidin-5-yl)-4-methyl-1-phenyl-1H-pyrazol-5-amine and (2-cyclopropyl-5-(methoxymethyl)phenyl)methanamine with (5-(methoxymethyl)-2-(trifluoromethoxy)phenyl)methanamine to give the title compound (21%). MS (APCI) m/z=543.2 (M+H).

Example 60

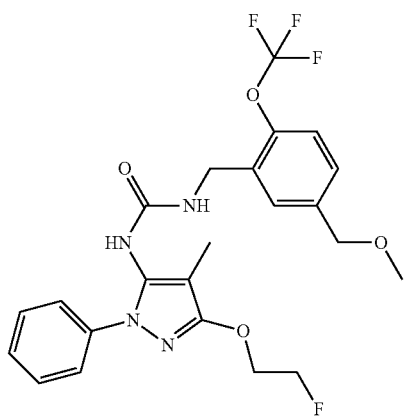 [SMILES: COCc1ccc(OC(F)(F)F)c(CNC(=O)Nc2c(C)c(OCCF)nn2-c2ccccc2)c1]

1-(3-(2-fluoroethoxy)-4-methyl-1-phenyl-1H-pyrazol-5-yl)-3-(5-(methoxymethyl)-2-(trifluoromethoxy)benzyl)urea Prepared according to the procedure of Example 1, substituting 4-methyl-3-(2-methylpyrimidin-5-yl)-1-phenyl-1H-pyrazol-5-amine with 3-(2-fluoroethoxy)-4-methyl-1-phenyl-1H-pyrazol-5-amine and (2-cyclopropyl-5-(methoxymethyl)phenyl)methanamine with (5-(methoxymethyl)-2-(trifluoromethoxy)phenyl)methanamine to give the title compound (20%). MS (APCI) m/z=497.2 (M+H).

Example 61

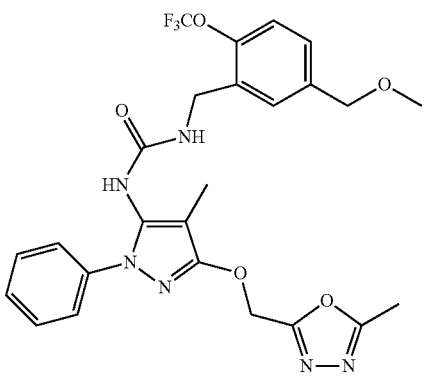 [SMILES: COCc1ccc(OC(F)(F)F)c(CNC(=O)Nc2c(C)c(OCc3nnc(C)o3)nn2-c2ccccc2)c1]

1-(5-(methoxymethyl)-2-(trifluoromethoxy)benzyl)-3-(4-methyl-3-(5-methyl-1,3,4-oxadiazol-2-yl)methoxy)-1-phenyl-1H-pyrazol-5-yl)urea Prepared according to the procedure of Example 1, substituting 4-methyl-3-(2-methylpyrimidin-5-yl)-1-phenyl- 1H-pyrazol-5-amine with 4-methyl-3-((5-methyl-1,3,4-oxadiazol-2-yl)methoxy)-1-phenyl-1H-pyrazol-5-amine and (2-cyclopropyl-5-(methoxymethyl)phenyl)methanamine with (5-(methoxymethyl)-2-(trifluoromethoxy)phenyl)methanamine to give the title compound (38%). MS (APCI) m/z=545.2 (M–H).

Example 62

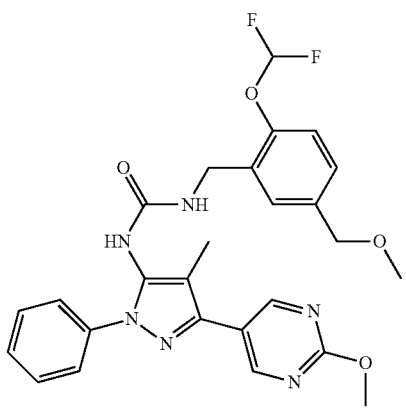 [SMILES: COCc1ccc(OC(F)F)c(CNC(=O)Nc2c(C)c(-c3cnc(OC)nc3)nn2-c2ccccc2)c1]

1-(2-(difluoromethoxy)-5-(methoxymethyl)benzyl)-3-(3-(2-methoxypyrimidin-5-yl)-4-methyl-1-phenyl-1H-pyrazol-5-yl)urea Prepared according to the procedure of Example 1, substituting 4-methyl-3-(2-methylpyrimidin-5-yl)-1-phenyl-1H-pyrazol-5-amine with 3-(2-methoxypyrimidin-5-yl)-4-methyl-1-phenyl-1H-pyrazol-5-amine and (2-cyclopropyl-5-(methoxymethyl)phenyl)methanamine with (2-(difluoromethoxy)-5-(methoxymethyl)phenyl)methanamine to give the title compound (15%). MS (APCI) m/z=523.2 (M–H).

Example 63

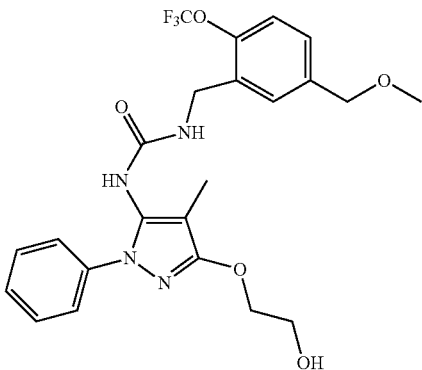 [SMILES: COCc1ccc(OC(F)(F)F)c(CNC(=O)Nc2c(C)c(OCCO)nn2-c2ccccc2)c1]

1-(3-(2-hydroxyethoxy)-4-methyl-1-phenyl-1H-pyrazol-5-yl)-3-(5-(methoxymethyl)-2-(trifluoromethoxy)benzyl)urea Step A: Preparation of 1-(3-(2-((tert-butyldimethylsilyl)oxy)ethoxy)-4-methyl-1-phenyl-1H-pyrazol-5-yl)-3-(5-(methoxymethyl)-2-(trifluoromethoxy)benzyl)urea Prepared according to the procedure of Example 1, substituting 4-methyl-3-(2-methylpyrimidin-5-yl)-1-phenyl-1H-pyrazol-5-amine with 3-(2-((tert-butyldimethyl silyl)oxy)ethoxy)-4-methyl-1-phenyl-1H-pyrazol-5-amine and (2-cyclopropyl-5-(methoxymethyl)phenyl)methanamine with (5-(methoxymethyl)-2-(trifluoromethoxy)phenyl)methanamine to give the title compound (44%).

Step B: Preparation of 1-(3-(2-hydroxyethoxy)-4-methyl-1-phenyl-1H-pyrazol-5-yl)-3-(5-(methoxymethyl)-2-(trifluoromethoxy)benzyl)urea To a round bottom flask containing 1-(3-(2-((tert-butyldimethylsilyl)oxy)ethoxy)-4-methyl-1-phenyl-1H-pyrazol-5-yl)-3-(5-(methoxymethyl)-2-(trifluoromethoxy)benzyl)urea (0.027 g, 0.044 mmol) was added 0.3 mL of AcOH, 0.1 mL of THF, and 0.1 mL of water. This mixture was warmed to 65° C. for 2 hours and then allowed to cool to ambient temperature. The mixture was diluted with EtOAc, washed with 10% aqueous potassium carbonate, dried over sodium sulfate and concentrated under reduced pressure. The crude material was purified by reverse phase HPLC. The fractions containing the product were combined in 10% aqueous potassium carbonate and extracted with EtOAc. The combined extracts were dried over sodium sulfate and concentrated under reduced pressure to provide 15 mgs (68%) of the title compound. MS (APCI) m/z=493.2 (M–H).

Example 64

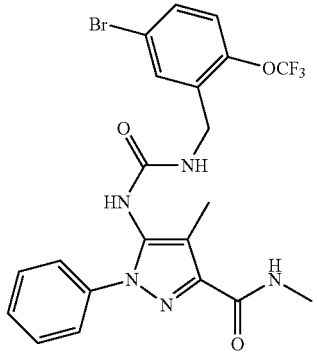 [SMILES: CNC(=O)c1nn(-c2ccccc2)c(NC(=O)NCc2cc(Br)ccc2OC(F)(F)F)c1C]

5-(3-(5-bromo-2-(trifluoromethoxy)benzyl)ureido)-N,4-dimethyl-1-phenyl-1H-pyrazole-3-carboxamide Step A: Preparation of 5-bromo-2-(trifluoromethoxy)benzaldehyde oxime A flask equipped with a nitrogen inlet was charged with 5-bromo-2-(trifluoromethoxy)benzaldehyde (1.00 g, 3.72 mmol), 30 mL of ethanol, and 10 mL of water. To this was added hydroxylamine hydrochloride (0.387 g, 5.58 mmol).

This mixture was stirred at ambient temperature for 3 hours. The mixture was diluted with water and extracted with EtOAc. The combined organic extracts were dried over sodium sulfate and concentrated under reduced pressure to provide 900 mgs of 5-bromo-2-(trifluoromethoxy)benzaldehyde oxime as a white solid.

Step B:
(5-bromo-2-(trifluoromethoxy)phenyl)methanamine

A flask equipped with a nitrogen inlet was charged with 5-bromo-2-(trifluoromethoxy)benzaldehyde oxime (0.500 g, 1.76 mmol) and 20 mL of AcOH. To this was added zinc dust (0.460 g, 7.04 mmol) and the mixture was warmed to 70° C. for 16 hours, then allowed to cool to ambient temperature. The mixture was filtered through GF/F filter paper and the filtrate was concentrated under reduced pressure. The resulting crude material was taken up in EtOAc, washed with 10% aqueous potassium carbonate, dried over sodium sulfate and concentrated under reduced pressure to give 386 mgs of (5-bromo-2-(trifluoromethoxy)phenyl)methanamine as an oil.

Step C: Preparation of 5-(3-(5-bromo-2-(trifluoromethoxy)benzyl)ureido)-N,4-dimethyl-1-phenyl-1H-pyrazole-3-carboxamide Prepared according to the procedure of Example 1, substituting 4-methyl-3-(2-methylpyrimidin-5-yl)-1-phenyl-1H-pyrazol-5-amine with 5-amino-N,4-dimethyl-1-phenyl-1H-pyrazole-3-carboxamide and (2-cyclopropyl-5-(methoxymethyl)phenyl)methanamine with (5-bromo-2-(trifluoromethoxy)phenyl)methanamine to give the title compound (11%). MS (APCI) m/z=524.1 (M+H).

Example 65

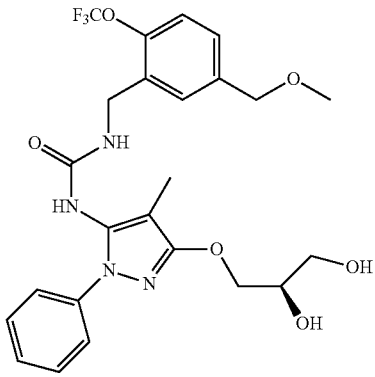 [SMILES: COCc1ccc(OC(F)(F)F)c(CNC(=O)Nc2c(C)c(OC[C@H](O)CO)nn2-c2ccccc2)c1]

(R)-1-(3-(2,3-dihydroxypropoxy)-4-methyl-1-phenyl-1H-pyrazol-5-yl)-3-(5-(methoxymethyl)-2-(trifluoromethoxy)benzyl)urea Step A: Preparation of (S)-1-(3-((2,2-dimethyl-1,3-dioxolan-4-yl)methoxy)-4-methyl-1-phenyl-1H-pyrazol-5-yl)-3-(5-(methoxymethyl)-2-(trifluoromethoxy)benzyl)urea Prepared according to the procedure of Example 1, substituting 4-methyl-3-(2-methylpyrimidin-5-yl)-1-phenyl-1H-pyrazol-5-amine with (S)-3-((2,2-dimethyl-1,3-dioxolan-4-yl)methoxy)-4-methyl-1-phenyl-1H-pyrazol-5-amine and (2-cyclopropyl-5-(methoxymethyl)phenyl)methanamine with (5-(methoxymethyl)-2-(trifluoromethoxy)phenyl)methanamine (54%).

Step B: Preparation of R)-1-(3-(2,3-dihydroxypropoxy)-4-methyl-1-phenyl-1H-pyrazol-5-yl)-3-(5-(methoxymethyl)-2-(trifluoromethoxy)benzyl)urea A round bottom flask was charged with (S)-1-(3-((2,2-dimethyl-1,3-dioxolan-4-yl)methoxy)-4-methyl-1-phenyl-1H-pyrazol-5-yl)-3-(5-(methoxymethyl)-2-(trifluoromethoxy)benzyl)urea (0.025 g, 0.044 mmol), 1 mL of THF and 1 mL of 1N aqueous HCl. This mixture was stirred at ambient temperature for 16 hours. The mixture was then diluted with 10% aqueous potassium carbonate (20 mL), extracted with EtOAc. The combined organic extracts were dried over sodium sulfate and concentrated under reduced pressure. The resulting crude material was purified by reverse phase HPLC. The fractions containing the product were combined in 10% aqueous potassium carbonate and extracted with EtOAc. The combined organic extracts were dried over sodium sulfate and concentrated under reduced pressure to give 11 mgs (47%) of the title compound as a white solid. MS (APCI) m/z=523.2 (M–H).

Example 66

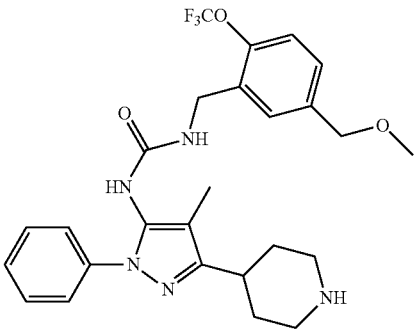 [SMILES: COCc1ccc(OC(F)(F)F)c(CNC(=O)Nc2c(C)c(C3CCNCC3)nn2-c2ccccc2)c1]

1-(5-(methoxymethyl)-2-(trifluoromethoxy)benzyl)-3-(4-methyl-1-phenyl-3-(piperidin-4-yl)-1H-pyrazol-5-yl)urea Step A: Preparation of tert-butyl 4-(5-(3-(5-(methoxymethyl)-2-(trifluoromethoxy)benzyl)ureido)-4-methyl-1-phenyl-1H-pyrazol-3-yl)piperidine-1-carboxylate Prepared according to the procedure of Example 1, substituting 4-methyl-3-(2-methylpyrimidin-5-yl)-1-phenyl-1H-pyrazol-5-amine with 4 tert-butyl 4-(5-amino-4-methyl-1-phenyl-1H-pyrazol-3-yl)piperidine-1-carboxylate and (2-cyclopropyl-5-(methoxymethyl)phenyl)methanamine with (5-(methoxymethyl)-2-(trifluoromethoxy)phenyl) methanamine to give the title compound (58%).

Step B: Preparation of 1-(5-(methoxymethyl)-2-(trifluoromethoxy)benzyl)-3-(4-methyl-1-phenyl-3-(piperidin-4-yl)-1H-pyrazol-5-yl)urea A round bottom flask was charged with tert-butyl 4-(5-(3-(5-(methoxymethyl)-2-(trifluoromethoxy)benzyl)

ureido)-4-methyl-1-phenyl-1H-pyrazol-3-yl)piperidine-1-carboxylate (0.050 g, 0.081 mmol) and 1 mL of TFA. The mixture was stirred at ambient temperature for 2 hours, then concentrated under reduced pressure. The resulting crude material was purified by reverse phase HPLC. The fractions containing the product were combined in 10% aqueous potassium carbonate and extracted with EtOAc. The combined organic extracts were dried over sodium sulfate and concentrated under reduced pressure to give the title compound (55%). MS (APCI) m/z 518.3 (M+H).

Example 67

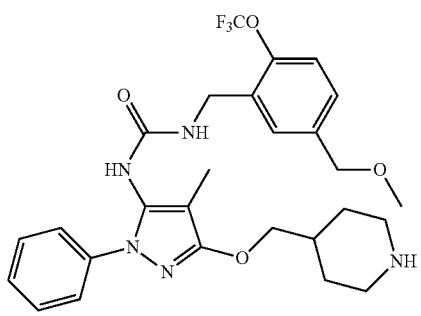 [SMILES: COCc1ccc(OC(F)(F)F)c(CNC(=O)Nc2c(C)c(OCC3CCNCC3)nn2-c2ccccc2)c1]

1-(5-(methoxymethyl)-2-(trifluoromethoxy)benzyl)-3-(4-methyl-1-phenyl-3-(piperidin-4-ylmethoxy)-1H-pyrazol-5-yl)urea Step A: Preparation of tert-butyl 4-(((5-amino-4-methyl-1-phenyl-1H-pyrazol-3-yl)oxy)methyl)piperidine-1-carboxylate A pressure tube containing a stir bar was charged with 5-amino-4-methyl-1-phenyl-1H-pyrazol-3(2H)-one (0.500 g, 2.64 mmol) and 26 mL of DMA. To this was added tert-butyl 4-(((methylsulfonyl)oxy)methyl)piperidine-1-carboxylate (0.775 g, 2.64 mmol) and cesium carbonate (1.72 g, 5.29 mmol). The tube was sealed and heated to 110° C. for 16 hours. The mixture was poured into 200 mL of water and extracted with EtOAc. The combined organic extracts were washed with brine, dried over sodium sulfate and concentrated under reduced pressure. The crude material was passed through an 80 g Redi Sep column, eluting with 1:1 ethyl acetate/hexane, to give 423 mgs of t the title compound (41%).

Step B: Preparation of tert-butyl 4-(((5-(3-(5-(methoxymethyl)-2-(trifluoromethoxy)benzyl)ureido)-4-methyl-1-phenyl-1H-pyrazol-3-yl)oxy)methyl)piperidine-1-carboxylate Prepared according to the procedure of Example 1, substituting 4-methyl-3-(2-methylpyrimidin-5-yl)-1-phenyl-1H-pyrazol-5-amine with tert-butyl 4-(5-amino-4-methyl-1-phenyl-1H-pyrazol-3-yl)piperidine-1-carboxylate and (2-cyclopropyl-5-(methoxymethyl)phenyl)methanamine with (5-(methoxymethyl)-2-(trifluoromethoxy)phenyl)methanamine to give the title compound (36%).

Step C: Preparation of 1-(5-(methoxymethyl)-2-(trifluoromethoxy)benzyl)-3-(4-methyl-1-phenyl-3-(piperidin-4-ylmethoxy)-1H-pyrazol-5-yl)urea Prepared according to the procedure of Example 67, Step B, substituting tert-butyl 4-(5-(3-(5-(methoxymethyl)-2-(tri-fluoromethoxy)benzyl)ureido)-4-methyl-1-phenyl-1H-pyrazol-3-yl)piperidine-1-carboxylate with tert-butyl 4-(((5-amino-4-methyl-1-phenyl-1H-pyrazol-3-yl)oxy)methyl)piperidine-1-carboxylate to give the title compound (59%). MS (APCI) m/z=548.3 (M+H).

Example 68

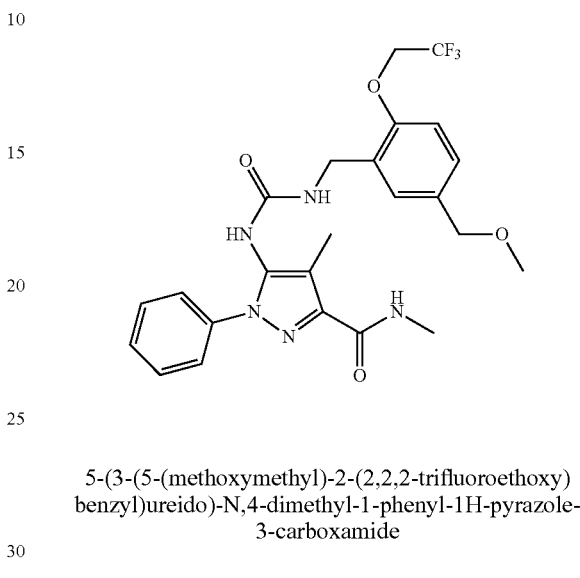

5-(3-(5-(methoxymethyl)-2-(2,2,2-trifluoroethoxy)benzyl)ureido)-N,4-dimethyl-1-phenyl-1H-pyrazole-3-carboxamide Step A: Preparation of 5-bromo-2-(2,2,2-trifluoroethoxy)benzonitrile A round bottom flask was charged with 5-bromo-2-hydroxybenzonitrile (5.00 g, 25.3 mmol), dry DMF (100 mL), cesium carbonate (16.5 g, 50.5 mmol) and 2,2,2-trifluoroethyl 4-methylbenzenesulfonate (7.70 g, 30.3 mmol). This mixture was warmed to 60° C. for 2 hours. Approximately 250 mgs of TBAI were added and the mixture was warmed to 100° C. for 16 hours, then allowed to cool to ambient temperature. The mixture was diluted with water, extracted with EtOAc. The combined organic extracts were washed with brine, dried over sodium sulfate and concentrated under reduced pressure. The crude material was passed through a 120 g Redi Sep column, eluting with 10% ethyl acetate/hexane, and then by preparative TLC (6×1 mm plates, 5% ethyl acetate/hexane, eluted multiple times) to give 5-bromo-2-(2,2,2-trifluoroethoxy)benzonitrile (contaminated with a small amount of the tosylate).

Step B: Preparation of 5-(methoxymethyl)-2-(2,2,2-trifluoroethoxy)benzonitrile

A round bottom flask was charged with 5-bromo-2-(2,2,2-trifluoroethoxy)benzonitrile (940 mgs, 3.36 mmol) and 33 mL of dioxane. To this was added cesium carbonate (5.03 mL, 10.1 mmol, 2M aqueous solution), potassium methoxymethyl trifluoroborate (867 mgs, 5.71 mmol), and 1,1'-Bis(diphenylphosphino)ferrocene-palladium(II)dichloride dichloromethane complex (274 mgs, 0.336 mmol). This mixture was heated to 100° C. for 24 hours, then allowed to cool to ambient temperature. The mixture was diluted with water/EtOAc, and filtered through GF/F filter paper. The combined organic layers were isolated, dried over sodium sulfate, and concentrated under reduced pressure. The crude product was passed through a 120 g Redi Sep column, eluting with 15% ethyl acetate/hexane to give the title compound (44%).

Step C: Preparation of (5-(methoxymethyl)-2-(2,2,2-trifluoroethoxy)phenyl)methanamine A round bottom flask equipped with a reflux condenser was charged with 5-(methoxymethyl)-2-(2,2,2-trifluoroethoxy)benzonitrile (0.355 g, 1.45 mmol) and dry THF (14 mL). LAH (2.90 mL, 2.90 mmol, 1M in THF) was added and the mixture was heated to reflux for 2 hours, then allowed to cool to ambient temperature. The reaction mixture was carefully quenched with 0.11 mL of water, 0.11 mL of 15% aqueous NaOH, and then 0.33 mL of water. The mixture was stirred vigorously for 15 minutes and then diluted with MTBE. The mixture was filtered and the filtrate concentrated under reduced pressure to give the title compound (92%) as an oil.

Step D: Preparation of 5-(3-(5-(methoxymethyl)-2-(2,2,2-trifluoroethoxy)benzyl)ureido)-N,4-dimethyl-1-phenyl-1H-pyrazole-3-carboxamide Prepared according to the procedure of Example 1, substituting 4-methyl-3-(2-methylpyrimidin-5-yl)-1-phenyl-1H-pyrazol-5-amine with 5-amino-N,4-dimethyl-1-phenyl-1H-pyrazole-3-carboxamide and (2-cyclopropyl-5-(methoxymethyl)phenyl)methanamine with (5-(methoxymethyl)-2-(2,2,2-trifluoroethoxy)phenyl)methanamine to give the title compound (11%). MS (APCI) m/z=504.1 (M−H).

Example 69

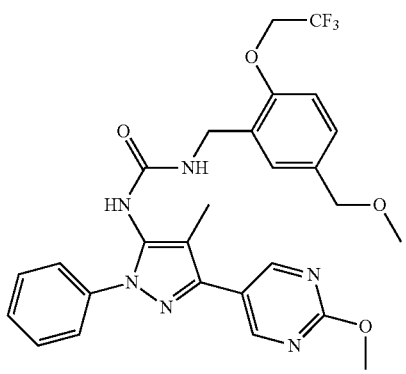 [SMILES: COCc1ccc(OCC(F)(F)F)c(CNC(=O)Nc2c(C)c(-c3cnc(OC)nc3)nn2-c2ccccc2)c1]

1-(5-(methoxymethyl)-2-(2,2,2-trifluoroethoxy)benzyl)-3-(3-(2-methoxypyrimidin-5-yl)-4-methyl-1-phenyl-1H-pyrazol-5-yl)urea Prepared according to the procedure of Example 1, substituting 4-methyl-3-(2-methylpyrimidin-5-yl)-1-phenyl-1H-pyrazol-5-amine with 3-(2-methoxypyrimidin-5-yl)-4-methyl-1-phenyl-1H-pyrazol-5-amine and (2-cyclopropyl-5-(methoxymethyl)phenyl)methanamine with (5-(methoxymethyl)-2-(2,2,2-trifluoroethoxy)phenyl)methanamine to give the title compound (10%). MS (APCI) m/z=557.3 (M+H).

Example 70

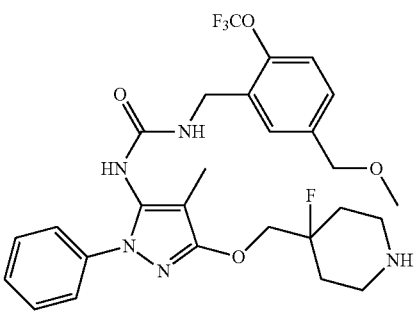 [SMILES: COCc1ccc(OC(F)(F)F)c(CNC(=O)Nc2c(C)c(OCC3(F)CCNCC3)nn2-c2ccccc2)c1]

1-(3-((4-fluoropiperidin-4-yl)methoxy)-4-methyl-1-phenyl-1H-pyrazol-5-yl)-3-(5-(methoxymethyl)-2-(trifluoromethoxy)benzyl)urea Step A: Preparation of tert-butyl 4-fluoro-4-(hydroxymethyl)piperidine-1-carboxylate To a 0° C. solution of 1-tert-butyl 4-ethyl 4-fluoropiperidine-1,4-dicarboxylate (5.0 g, 18.16 mmol) in 90 mL THF was added 1M lithium aluminum hydride in THF (36.32 mL, 36.32 mmol) slowly by syringe. The reaction mixture was stirred at 0° C. for 1 hour and then quenched by the slow addition of 1:1 Na$_2$SO$_4$/10 H$_2$O:Celite. The mixture was then diluted with additional THF, warmed to ambient temperature, and stirred vigorously for 2 hours. The slurry was vacuum filtered through GF/F paper on a Buchner funnel and rinsed with THF. The filtrate was concentrated in vacuo to give the title compound (4.0 g, 94.42% yield) as a thick oil. The crude material was used in the next step without further purification.

Step B: Preparation of tert-Butyl 4-fluoro-4-(((methylsulfonyl)oxy)methyl)piperidine-1-carboxylate To a 0° C. solution of tert-butyl 4-fluoro-4-(hydroxymethyl)piperidine-1-carboxylate (3.50 g, 15.0 mmol) and TEA (5.23 mL, 37.5 mmol) in 90 mL DCM was added neat MsCl (2.09 mL, 27.0 mmol) dropwise by syringe. The mixture was allowed to gradually warm to ambient temperature and stirred for 17 hours. The reaction was cooled to 0° C., and an additional 1.5 equivalents of TEA and 1.1 equivalents of MsCl were added. The reaction mixture was allowed to warm to ambient temperature and then saturated NaHCO$_3$ was added. The mixture was extracted with DCM, and combined extracts were dried (Na$_2$SO$_4$), filtered, and concentrated under reduced pressure. The crude material was purified on an SP1 (Snap 340 g) column. The fractions containing product were concentrated, then concentrated twice from ether to give solids which were dried under vacuum to give the title compound (4.20 g, 89.9% yield) as a white powder.

Step C: Preparation of tert-butyl 4-(((5-amino-4-methyl-1-phenyl-1H-pyrazol-3-yl)oxy)methyl)-4-fluoropiperidine-1-carboxylate Prepared according to the procedure of Example 67, Step A, substituting tert-butyl 4-(((methylsulfonyl)oxy)methyl)

piperidine-1-carboxylate with tert-butyl 4-fluoro-4-((methylsulfonyloxy)methyl)piperidine-1-carboxylate to give the title compound (58%).

Step D: Preparation of tert-butyl 4-fluoro-4-(((5-(3-(5-(methoxymethyl)-2-(trifluoromethoxy)benzyl)ureido)-4-methyl-1-phenyl-1H-pyrazol-3-yl)oxy)methyl)piperidine-1-carboxylate Prepared according to the procedure of Example 1, substituting 4-methyl-3-(2-methylpyrimidin-5-yl)-1-phenyl-1H-pyrazol-5-amine with tert-butyl 4-(((5-amino-4-methyl-1-phenyl-1H-pyrazol-3-yl)oxy)methyl)-4-fluoropiperidine-1-carboxylate and (2-cyclopropyl-5-(methoxymethyl)phenyl)methanamine with (5-(methoxymethyl)-2-(trifluoromethoxy)phenyl)methanamine to give the title compound (33%).

Step E: Preparation of 1-(3-((4-fluoropiperidin-4-yl)methoxy)-4-methyl-1-phenyl-1H-pyrazol-5-yl)-3-(5-(methoxymethyl)-2-(trifluoromethoxy)benzyl)urea Prepared according to the procedure of Example 66, Step B, substituting tert-butyl 4-(5-(3-(5-(methoxymethyl)-2-(trifluoromethoxy)benzyl)ureido)-4-methyl-1-phenyl-1H-pyrazol-3-yl)piperidine-1-carboxylate with tert-butyl 4-fluoro-4-(((5-(3-(5-(methoxymethyl)-2-(trifluoromethoxy)benzyl)ureido)-4-methyl-1-phenyl-1H-pyrazol-3-yl)oxy)methyl)piperidine-1-carboxylate to give the title compound (48%). MS (APCI) m/z=566.3 (M+H).

Example 71

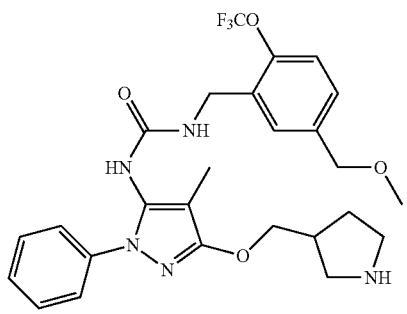 [SMILES: COCc1ccc(OC(F)(F)F)c(CNC(=O)Nc2c(C)c(OCC3CCNC3)nn2-c2ccccc2)c1]

1-(5-methoxymethyl)-2-(trifluoromethoxy)benzyl)-3-(4-methyl-1-phenyl-3-(pyrrolidin-3-ylmethoxy)-1H-pyrazol-5-yl)urea Step A: Preparation of tert-butyl 3-(((5-amino-4-methyl-1-phenyl-1H-pyrazol-3-yl)oxy)methyl)pyrrolidine-1-carboxylate Prepared according to the procedure of Example 67, Step A, substituting tert-butyl 4-(((methylsulfonyl)oxy)methyl)piperidine-1-carboxylate with tert-butyl 3-(((methylsulfonyl)oxy)methyl)pyrrolidine-1-carboxylate to give the title compound (48%).

Step B: Preparation of tert-butyl 3-(((5-(3-(5-(methoxymethyl)-2-(trifluoromethoxy)benzyl)ureido)-4-methyl-1-phenyl-1H-pyrazol-3-yl)oxy)methyl)pyrrolidine-1-carboxylate Prepared according to the procedure of Example 1, substituting 4-methyl-3-(2-methylpyrimidin-5-yl)-1-phenyl-1H-pyrazol-5-amine with tert-butyl 3-(((5-amino-4-methyl-1-phenyl-1H-pyrazol-3-yl)oxy)methyl)pyrrolidine-1-carboxylate and (2-cyclopropyl-5-(methoxymethyl)phenyl)methanamine with (5-(methoxymethyl)-2-(trifluoromethoxy)phenyl)methanamine to give the title compound (56%).

Step C: Preparation of 1-(5-(methoxymethyl)-2-(trifluoromethoxy)benzyl)-3-(4-methyl-1-phenyl-3-(pyrrolidin-3-ylmethoxy)-1H-pyrazol-5-yl)urea Prepared according to the procedure of Example 66, Step B, substituting tert-butyl 4-(5-(3-(5-(methoxymethyl)-2-(trifluoromethoxy)benzyl)ureido)-4-methyl-1-phenyl-1H-pyrazol-3-yl)piperidine-1-carboxylate with tert-butyl 3-(((5-(3-(5-(methoxymethyl)-2-(trifluoromethoxy)benzyl)ureido)-4-methyl-1-phenyl-1H-pyrazol-3-yl)oxy)methyl)pyrrolidine-1-carboxylate to give the title compound (58%). MS (APCI) m/z=534.3 (M+H).

Example 72

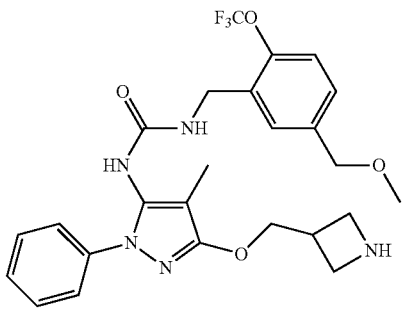 [SMILES: COCc1ccc(OC(F)(F)F)c(CNC(=O)Nc2c(C)c(OCC3CNC3)nn2-c2ccccc2)c1]

1-(3-(azetidin-3-ylmethoxy)-4-methyl-1-phenyl-1H-pyrazol-5-yl)-3-(5-(methoxymethyl)-2-(trifluoromethoxy)benzyl)urea Step A: Preparation of tert-butyl 3-(hydroxymethyl)azetidine-1-carboxylate A round bottom flask equipped with a condenser was charged with dry THF (52 mL) and sodium borohydride (0.587 mgs, 22.99 mmol), followed by addition of 1-(tert-butoxycarbonyl)azetidine-3-carboxylic acid (1.04 g, 5.17 mmol). The mixture was cooled to 0° C., and iodine (1.31 mgs, 5.17 mmol) in 10 mL of THF was added over a 10 minute period to the reaction mixture. The reaction mixture was stirred at 0° C. for 15 minutes, then heated to reflux for 16 hours, during which time the iodine color was discharged. The mixture was then carefully quenched with methanol (20 mL). The reaction mixture was concentrated under reduced pressure and taken up in 200 mL of 20% aqueous KOH, and stirred at ambient temperature for 4 hours. The mixture was extracted with DCM, and the combined organic extracts were dried over sodium sulfate and concentrated under reduced pressure to provide 608 mgs (63%) of the title compound as an oil.

Step B: Preparation of tert-butyl 3-(((methylsulfonyl)oxy)methyl)azetidine-1-carboxylate A round bottom flask containing tert-butyl 3-(hydroxymethyl)azetidine-1-carboxylate (0.605 g, 3.23 mmol) and a stir bar was charged with dry DCM (30 mL) and DIEA (0.844 mL, 4.85 mmol). To this was added MsCl (0.275 mL, 3.55 mmol) and the mixture was stirred at ambient temperature for 2 hours. The mixture was diluted with DCM, washed with 10% aqueous potassium carbonate, dried over sodium sulfate and concentrated to provide a quantitative yield of the title compound as an oil.

Step C: Preparation of tert-butyl 3-(((5-amino-4-methyl-1-phenyl-1H-pyrazol-3-yl)oxy)methyl)azetidine-1-carboxylate Prepared according to the procedure of Example 67, Step A, substituting tert-butyl 4-(((methylsulfonyl)oxy)methyl)piperidine-1-carboxylate with tert-butyl 3-(((methylsulfonyl)oxy)methyl)azetidine-1-carboxylate to give the title compound (44%).

Step D: Preparation of tert-butyl 3-(((5-(3-(5-(methoxymethyl)-2-(trifluoromethoxy)benzyl)ureido)-4-methyl-1-phenyl-1H-pyrazol-3-yl)oxy)methyl)azetidine-1-carboxylate Prepared according to the procedure of Example 1, substituting 4-methyl-3-(2-methylpyrimidin-5-yl)-1-phenyl-1H-pyrazol-5-amine with tert-butyl 3-(((5-amino-4-methyl-1-phenyl-1H-pyrazol-3-yl)oxy)methyl)azetidine-1-carboxylate and (2-cyclopropyl-5-(methoxymethyl)phenyl)methanamine with (5-(methoxymethyl)-2-(trifluoromethoxy)phenyl)methanamine to give the title compound (51%).

Step E: Preparation of 1-(3-(azetidin-3-ylmethoxy)-4-methyl-1-phenyl-1H-pyrazol-5-yl)-3-(5-(methoxymethyl)-2-(trifluoromethoxy)benzyl)urea Prepared according to the procedure of Example 66, Step B, substituting tert-butyl 4-(5-(3-(5-(methoxymethyl)-2-(trifluoromethoxy)benzyl)ureido)-4-methyl-1-phenyl-1H-pyrazol-3-yl)piperidine-1-carboxylate with tert-butyl 3-(((5-(3-(5-(methoxymethyl)-2-(trifluoromethoxy)benzyl)ureido)-4-methyl-1-phenyl-1H-pyrazol-3-yl)oxy)methyl)azetidine-1-carboxylate to give the title compound (45%). MS (APCI) m/z=520.2 (M+H).

Example 73

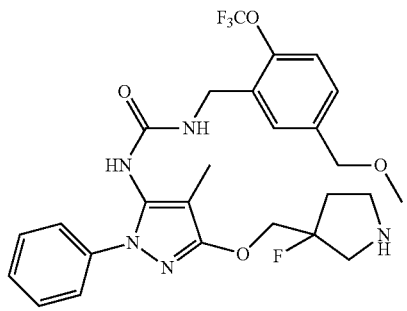 [SMILES: COCc1ccc(OC(F)(F)F)c(CNC(=O)Nc2c(C)c(OCC3(F)CCNC3)nn2-c2ccccc2)c1]

1-(3-((3-fluoropyrrolidin-3-yl)methoxy)-4-methyl-1-phenyl-1H-pyrazol-5-yl)-3-(5-(methoxymethyl)-2-(trifluoromethoxy)benzyl)urea Step A: Preparation of methyl 1-benzyl-3-fluoropyrrolidine-3-carboxylate A flask equipped with a nitrogen inlet was charged with methyl 2-fluoroacrylate (2.00 g, 19.2 mmol) and dry DCM (77 mL). To this was added N-benzyl-1-methoxy-N-((trimethylsilyl)methyl)methanamine (5.47 g, 23.1 mmol) and the mixture was cooled to 0° C. To this was added TFA (0.740 mL, 9.61 mmol) and the mixture was allowed to warm to ambient temperature overnight. The mixture was concentrated under reduced pressure and the crude material was passed through a 120 g Redi Sep column, eluting with 3:1 Hexane/ethyl acetate, to give the title compound (48%).

Step B: Preparation of 1-tert-butyl 3-methyl 3-fluoropyrrolidine-1,3-dicarboxylate A round bottom flask was charged with methyl 1-benzyl-3-fluoropyrrolidine-3-carboxylate (2.20 g, 9.27 mmol) and 45 mL of EtOAc. To this was added BOC anhydride (2.23 g, 10.2 mmol) and Pearlman's catalyst (2 g, 20% Pd(OH)$_2$, Degussa type) and the mixture was hydrogenated under a balloon of hydrogen for 2 hours and then purged with nitrogen. The reaction mixture was filtered under a nitrogen atmosphere through GF/F filter paper, and the filtrate was concentrated under reduced pressure to give the title compound (91%) as an oil.

Step C: Preparation of tert-butyl 3-fluoro-3-(hydroxymethyl)pyrrolidine-1-carboxylate A flask equipped with a nitrogen inlet was charged with 1-tert-butyl 3-methyl 3-fluoropyrrolidine-1,3-dicarboxylate (2.08 g, 8.41 mmol) and dry THF (42 mL). This mixture was cooled to 0° C. and LAH (10.1 mL, 10.1 mmol, 1M in THF) was then added and the mixture was stirred at 0° C. for 2 hours. The mixture was carefully quenched with 0.383 mL of water, 0.383 mL of 15% aqueous NaOH, and 1.15 mL of water. This mixture was vigorously stirred for 30 minutes, diluted with MTBE, and filtered through GF/F paper. The filtrate was concentrated under reduced pressure to provide the title compound (71%) as an oil.

Step D: Preparation of tert-butyl 3-fluoro-3-(((methylsulfonyl)oxy)methyl)pyrrolidine-1-carboxylate A flask equipped with a nitrogen inlet was charged with tert-butyl 3-fluoro-3-(hydroxymethyl)pyrrolidine-1-carboxylate (1.30 g, 5.93 mmol) and dry DCM (60 mL). To this was added DIEA (2.07 mL, 11.9 mmol) and the mixture was cooled to 0° C. MsCl (0.815 g, 7.12 mmol) was added and the mixture was stirred at 0° C. for 2 hours. This mixture was diluted with 100 mL of DCM, washed with 10% aqueous potassium carbonate, dried over sodium sulfate and concentrated under reduced pressure. The resulting crude material was passed through an 80 g Redi Sep column, eluting with 3:1 ethyl acetate/hexane, to provide the title compound as an oil (53%).

Step E: Preparation of tert-butyl 3-(((5-amino-4-methyl-1-phenyl-1H-pyrazol-3-yl)oxy)methyl)-3-fluoropyrrolidine-1-carboxylate Prepared according to the procedure of Example 67, Step A, substituting tert-butyl 4-(((methylsulfonyl)oxy)methyl)

piperidine-1-carboxylate with tert-butyl 3-fluoro-3-(((methylsulfonyl)oxy)methyl)pyrrolidine-1-carboxylate to give the title compound (32%).

Step F: Preparation of tert-butyl 3-fluoro-3-(((5-(3-(5-(methoxymethyl)-2-(trifluoromethoxy)benzyl)ureido)-4-methyl-1-phenyl-1H-pyrazol-3-yl)oxy)methyl)pyrrolidine-1-carboxylate Prepared according to the procedure of Example 1, substituting 4-methyl-3-(2-methylpyrimidin-5-yl)-1-phenyl-1H-pyrazol-5-amine with tert-butyl 3-(((5-amino-4-methyl-1-phenyl-1H-pyrazol-3-yl)oxy)methyl)-3-fluoropyrrolidine-1-carboxylate and (2-cyclopropyl-5-(methoxymethyl)phenyl)methanamine with (5-(methoxymethyl)-2-(trifluoromethoxy)phenyl)methanamine to give the title compound (48%).

Step G: Preparation of 1-(3-((3-fluoropyrrolidin-3-yl)methoxy)-4-methyl-1-phenyl-1H-pyrazol-5-yl)-3-(5-(methoxymethyl)-2-(trifluoromethoxy)benzyl)urea Prepared according to the procedure of Example 66, Step B substituting tert-butyl 4-(5-(3-(5-(methoxymethyl)-2-(trifluoromethoxy)benzyl)ureido)-4-methyl-1-phenyl-1H-pyrazol-3-yl)piperidine-1-carboxylate with tert-butyl 3-fluoro-3-(((5-(3-(5-(methoxymethyl)-2-(trifluoromethoxy)benzyl)ureido)-4-methyl-1-phenyl-1H-pyrazol-3-yl)oxy)methyl)pyrrolidine-1-carboxylate to give the title compound (59%). MS (APCI) m/z=552.2 (M+H).

Example 74

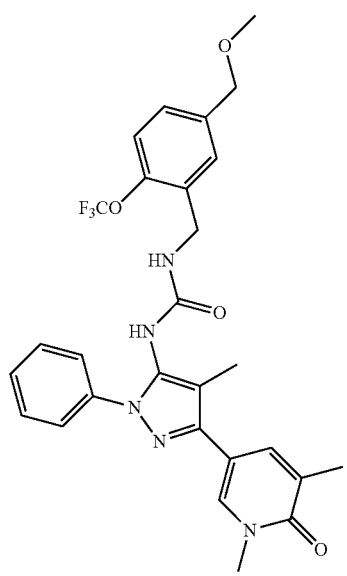 [SMILES: COCc1ccc(OC(F)(F)F)c(CNC(=O)Nc2c(C)c(-c3cc(C)c(=O)n(C)c3)nn2-c2ccccc2)c1]

1-(3-(1,5-dimethyl-6-oxo-1,6-dihydropyridin-3-yl)-4-methyl-1-phenyl-1H-pyrazol-5-yl)-3-(5-(methoxymethyl)-2-(trifluoromethoxy)benzyl)urea Prepared according to the procedure of Example 1, substituting 4-methyl-3-(2-methylpyrimidin-5-yl)-1-phenyl-1H-pyrazol-5-amine with 5-(5-amino-4-methyl-1-phenyl-1H-pyrazol-3-yl)-1,3-dimethylpyridin-2(1H)-one and (2-cyclopropyl-5-(methoxymethyl)phenyl)methanamine with (5-(methoxymethyl)-2-(trifluoromethoxy)phenyl)methanamine to give the title compound (29%). MS (APCI) m/z=554.2 (M−H).

Example 75

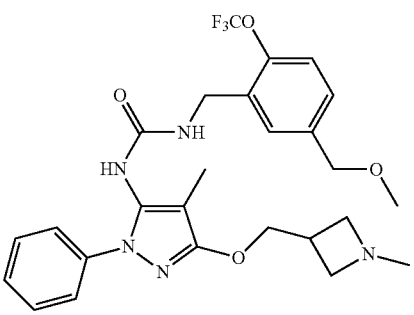 [SMILES: COCc1ccc(OC(F)(F)F)c(CNC(=O)Nc2c(C)c(OCC3CN(C)C3)nn2-c2ccccc2)c1]

1-(5-(methoxymethyl)-2-(trifluoromethoxy)benzyl)-3-(4-methyl-3-((1-methylazetidin-3-yl)methoxy)-1-phenyl-1H-pyrazol-5-yl)urea A round bottom flask containing 1-(3-(azetidin-3-ylmethoxy)-4-methyl-1-phenyl-1H-pyrazol-5-yl)-3-(5-(methoxymethyl)-2-(trifluoromethoxy)benzyl)urea (0.020 g, 0.0385 mmol) was charged with THF (0.5 mL), followed by 37% aqueous formaldehyde (2.87 μL, 0.0385 mmol) and sodium triacetoxyborohydride (0.0112 g, 0.05 mmol). The mixture was stirred at ambient temperature for 16 hours and then concentrated under reduced pressure. The crude material was taken up in 1M aqueous NaOH (5 mL) and stirred at ambient temperature for 1 hour, then extracted with EtOAc. The combined organic extracts were dried over sodium sulfate and concentrated. The crude material was purified by reverse phase chromatography to give the title compound (20%). MS (APCI) m/z=534.2 (M−H).

Example 76

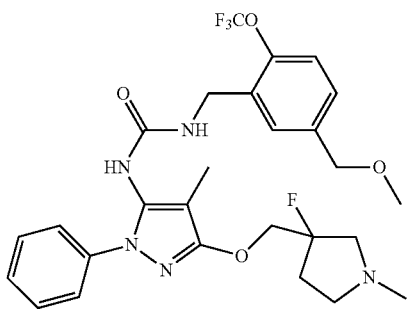 [SMILES: COCc1ccc(OC(F)(F)F)c(CNC(=O)Nc2c(C)c(OCC3(F)CCN(C)C3)nn2-c2ccccc2)c1]

1-(3-((3-fluoro-1-methylpyrrolidin-3-yl)methoxy)-4-methyl-1-phenyl-1H-pyrazol-5-yl)-3-(5-(methoxymethyl)-2-(trifluoromethoxy)benzyl)urea Prepared according to the procedure of Example 75, Step A, substituting 1-(3-(azetidin-3-ylmethoxy)-4-methyl-1- phenyl-1H-pyrazol-5-yl)-3-(5-(methoxymethyl)-2-(trifluoromethoxy)benzyl)urea with 1-(3-((3-fluoropyrrolidin-3-yl)methoxy)-4-methyl-1-phenyl-1H-pyrazol-5-yl)-3-(5-(methoxymethyl)-2-(trifluoromethoxy)benzyl)urea, to give the title compound (16%). MS (APCI) m/z=566.2 (M+H).

Example 77

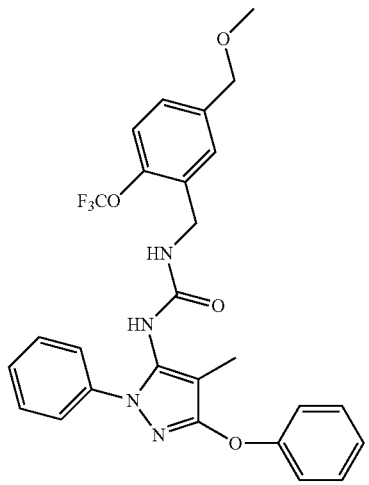 [SMILES: COCc1ccc(OC(F)(F)F)c(CNC(=O)Nc2c(C)c(Oc3ccccc3)nn2-c2ccccc2)c1]

1-(5-(methoxymethyl)-2-(trifluoromethoxy)benzyl)-3-(4-methyl-3-phenoxy-1-phenyl-1H-pyrazol-5-yl)urea Step A: Preparation of 4-methyl-3-phenoxy-1-phenyl-1H-pyrazol-5-amine A round bottom flask containing 5-amino-4-methyl-1-phenyl-1H-pyrazol-3(2H)-one (0.050 g, 0.264 mmol) was charged with 1,2-DCE (2.5 mL), phenyl boronic acid (0.084 g, 0.687 mmol), copper acetate (0.072 g, 0.396 mmol), pyridine (0.064 g, 0.806 mmol), and powdered 4 A molecular sieves (100 mgs). The mixture was stirred at ambient temperature for 16 hours. The mixture was then filtered and the filtrate was concentrated under reduced pressure. The crude material was purified through a 24 g Redi Sep column, eluting with 100% ethyl acetate, to give the title compound (57%).

Step B: Preparation of 1-(5-(methoxymethyl)-2-(trifluoromethoxy)benzyl)-3-(4-methyl-3-phenoxy-1-phenyl-1H-pyrazol-5-yl)urea Prepared according to the procedure of Example 1, substituting 4-methyl-3-(2-methylpyrimidin-5-yl)-1-phenyl-1H-pyrazol-5-amine with 4-methyl-3-phenoxy-1-phenyl-1H-pyrazol-5-amine and (2-cyclopropyl-5-(methoxymethyl)phenyl)methanamine with (5-(methoxymethyl)-2-(trifluoromethoxy)phenyl)methanamine to give the title compound (16%). MS (APCI) m/z=525.2 (M−H).

Example 78

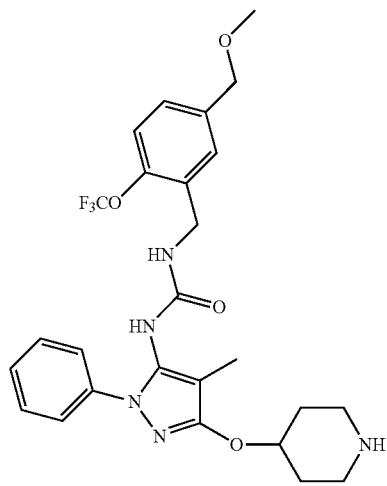 [SMILES: COCc1ccc(OC(F)(F)F)c(CNC(=O)Nc2c(C)c(OC3CCNCC3)nn2-c2ccccc2)c1]

1-(5-(methoxymethyl)-2-(trifluoromethoxy)benzyl)-3-(4-methyl-1-phenyl-3-(piperidin-4-yloxy)-1H-pyrazol-5-yl)urea Step A: Preparation of tert-butyl 4-((5-amino-4-methyl-1-phenyl-1H-pyrazol-3-yl)oxy)piperidine-1-carboxylate Prepared according to the procedure of Example 67, Step A, substituting tert-butyl 4-(((methylsulfonyl)oxy)methyl)piperidine-1-carboxylate with tert-butyl 4-((methylsulfonyl)oxy)piperidine-1-carboxylate to give the title compound (34%).

Step B: Preparation of tert-butyl 4-((5-(3-(5-(methoxymethyl)-2-(trifluoromethoxy)benzyl)ureido)-4-methyl-1-phenyl-1H-pyrazol-3-yl)oxy)piperidine-1-carboxylate Prepared according to the procedure of Example 1, substituting 4-methyl-3-(2-methylpyrimidin-5-yl)-1-phenyl-1H-pyrazol-5-amine with tert-butyl 4-((5-amino-4-methyl-1-phenyl-1H-pyrazol-3-yl)oxy)piperidine-1-carboxylate and (2-cyclopropyl-5-(methoxymethyl)phenyl)methanamine with (5-(methoxymethyl)-2-(trifluoromethoxy)phenyl)methanamine to give the title compound (45%).

Step C: Preparation of 1-(5-(methoxymethyl)-2-(trifluoromethoxy)benzyl)-3-(4-methyl-1-phenyl-3-(piperidin-4-yloxy)-1H-pyrazol-5-yl)urea Prepared according to the procedure of Example 66, Step B, substituting tert-butyl 4-(5-(3-(5-(methoxymethyl)-2-(trifluoromethoxy)benzyl)ureido)-4-methyl-1-phenyl-1H-pyrazol-3-yl)piperidine-1-carboxylate with tert-butyl 4-((5-(3-(5-(methoxymethyl)-2-(trifluoromethoxy)benzyl)ureido)-4-methyl-1-phenyl-1H-pyrazol-3-yl)oxy)piperidine-1-carboxylate to give the title compound (48%). MS (APCI) m/z=534.2 (M+H).

Example 79

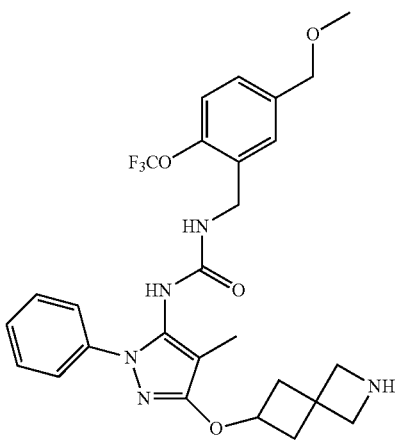 [SMILES: COCc1ccc(OC(F)(F)F)c(CNC(=O)Nc2c(C)c(OC3CC4(CNC4)C3)nn2-c2ccccc2)c1]

1-(3-(2-azaspiro[3.3]heptan-6-yloxy)-4-methyl-1-phenyl-1H-pyrazol-5-yl)-3-(5-(methoxymethyl)-2-(trifluoromethoxy)benzyl)urea Step A: Preparation of tert-butyl 6-((methylsulfonyl)oxy)-2-azaspiro[3.3]heptane-2-carboxylate Prepared according to the procedure of Example 72, Step B, substituting tert-butyl 4-fluoro-4-(hydroxymethyl)piperidine-1-carboxylate with tert-butyl 6-hydroxy-2-azaspiro[3.3]heptane-2-carboxylate to give the title compound (75%).

Step B: Preparation of tert-butyl 6-((5-amino-4-methyl-1-phenyl-1H-pyrazol-3-yl)oxy)-2-azaspiro[3.3]heptane-2-carboxylate Prepared according to the procedure of Example 67, Step A, substituting tert-butyl 4-(((methylsulfonyl)oxy)methyl)piperidine-1-carboxylate with tert-butyl 6-((methylsulfonyl)oxy)-2-azaspiro[3.3]heptane-2-carboxylate to give the title compound (48%).

Step C: Preparation of tert-butyl 6-((5-(3-(5-(methoxymethyl)-2-(trifluoromethoxy)benzyl)ureido)-4-methyl-1-phenyl-1H-pyrazol-3-yl)oxy)-2-azaspiro[3.3]heptane-2-carboxylate Prepared according to the procedure of Example 1, substituting 4-methyl-3-(2-methylpyrimidin-5-yl)-1-phenyl-1H-pyrazol-5-amine with tert-butyl 6-((5-amino-4-methyl-1-phenyl-1H-pyrazol-3-yl)oxy)-2-azaspiro[3.3]heptane-2-carboxylate and (2-cyclopropyl-5-(methoxymethyl)phenyl)methanamine with (5-(methoxymethyl)-2-(trifluoromethoxy)phenyl)methanamine to give the title compound (55%).

Step D: Preparation of 1-(3-(2-azaspiro[3.3]heptan-6-yloxy)-4-methyl-1-phenyl-1H-pyrazol-5-yl)-3-(5-(methoxymethyl)-2-(trifluoromethoxy)benzyl)urea Prepared according to the procedure of Example 66, Step B, substituting tert-butyl 4-(5-(3-(5-(methoxymethyl)-2-(trifluoromethoxy)benzyl)ureido)-4-methyl-1-phenyl-1H-pyrazol-3-yl)piperidine-1-carboxylate with tert-butyl 6-((5-amino-4-methyl-1-phenyl-1H-pyrazol-3-yl)oxy)-2-azaspiro[3.3]heptane-2-carboxylate to give the title compound (59%). MS (APCI) m/z=546.2 (M+H).

Example 80

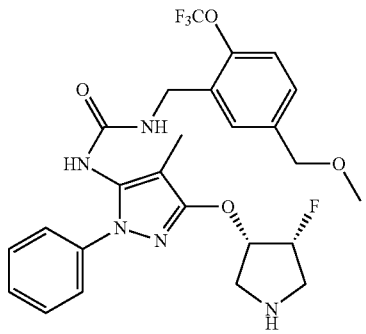 [SMILES: COCc1ccc(OC(F)(F)F)c(CNC(=O)Nc2c(C)c(O[C@H]3CNC[C@H]3F)nn2-c2ccccc2)c1]

1-(3-(((3S,4R)-4-fluoropyrrolidin-3-yl)oxy)-4-methyl-1-phenyl-1H-pyrazol-5-yl)-3-(5-(methoxymethyl)-2-(trifluoromethoxy)benzyl)urea Step A: Preparation of (3R,4R)-tert-butyl 3-fluoro-4-((methylsulfonyl)oxy)pyrrolidine-1-carboxylate Prepared according to the procedure of Example 72, Step B, substituting tert-butyl 4-fluoro-4-(hydroxymethyl)piperidine-1-carboxylate with (3R,4R)-tert-butyl 3-fluoro-4-hydroxypyrrolidine-1-carboxylate to give the title compound (90%).

Step B: Preparation of (3S,4R)-tert-butyl 3-((5-amino-4-methyl-1-phenyl-1H-pyrazol-3-yl)oxy)-4-fluoropyrrolidine-1-carboxylate Prepared according to the procedure of Example 67, Step A, substituting tert-butyl 4-(((methylsulfonyl)oxy)methyl)piperidine-1-carboxylate with (3R,4R)-tert-butyl 3-fluoro-4-((methylsulfonyl)oxy)pyrrolidine-1-carboxylate to give (3S,4R)-tert-butyl 3-((5-amino-4-methyl-1-phenyl-1H-pyrazol-3-yl)oxy)-4-fluoropyrrolidine-1-carboxylate (18%).

Step C: Preparation of (3R,4S)-tert-butyl 3-fluoro-4-((5-(3-(5-(methoxymethyl)-2-(trifluoromethoxy)benzyl)ureido)-4-methyl-1-phenyl-1H-pyrazol-3-yl)oxy)pyrrolidine-1-carboxylate Prepared according to the procedure of Example 1, substituting 4-methyl-3-(2-methylpyrimidin-5-yl)-1-phenyl-1H-pyrazol-5-amine with (3S,4R)-tert-butyl 3-((5-amino-4-methyl-1-phenyl-1H-pyrazol-3-yl)oxy)-4-fluoropyrrolidine-1-carboxylate and (2-cyclopropyl-5-(methoxymethyl)phenyl)methanamine with (5-(methoxymethyl)-2-(trifluoromethoxy)phenyl)methanamine to give the title compound (45%).

Step D: Preparation of 1-(3-(((3S,4R)-4-fluoropyrrolidin-3-yl)oxy)-4-methyl-1-phenyl-1H-pyrazol-5-yl)-3-(5-(methoxymethyl)-2-(trifluoromethoxy)benzyl)urea Prepared according to the procedure of Example 66, Step B, substituting tert-butyl 4-(5-(3-(5-(methoxymethyl)-2-(trifluoromethoxy)benzyl)ureido)-4-methyl-1-phenyl-1H-pyrazol-3-yl)piperidine-1-carboxylate with (3R,4S)-tert-butyl 3-fluoro-4-((5-(3-(5-(methoxymethyl)-2-(trifluoromethoxy)benzyl)ureido)-4-methyl-1-phenyl-1H-pyrazol-3-yl)oxy)pyrrolidine-1-carboxylate to give the title compound. (47%). MS (APCI) m/z=538.2 (M+H).

Example 81

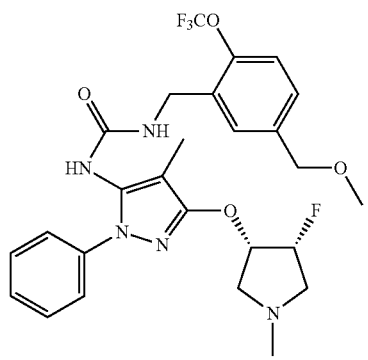 [SMILES: COCc1ccc(OC(F)(F)F)c(CNC(=O)Nc2c(C)c(O[C@H]3CN(C)C[C@H]3F)nn2-c2ccccc2)c1]

1-(3-(((3S,4R)-4-fluoro-1-methylpyrrolidin-3-yl)oxy)-4-methyl-1-phenyl-1H-pyrazol-5-yl)-3-(5-(methoxymethyl)-2-(trifluoromethoxy)benzyl)urea Prepared according to the procedure of Example 75, Step A, substituting 1-(3-(azetidin-3-ylmethoxy)-4-methyl-1-phenyl-1H-pyrazol-5-yl)-3-(5-(methoxymethyl)-2-(trifluoromethoxy)benzyl)urea with 1-(3-(((3S,4R)-4-fluoropyrrolidin-3-yl)oxy)-4-methyl-1-phenyl-1H-pyrazol-5-yl)-3-(5-(methoxymethyl)-2-(trifluoromethoxy)benzyl)urea to give the title compound (14%). MS (APCI) m/z=552.2 (M+H).

Example 82

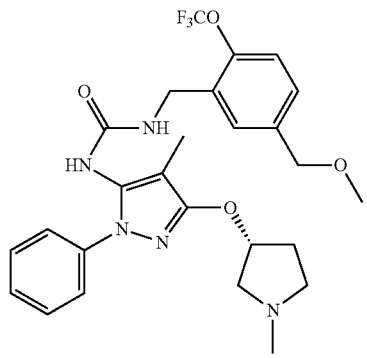 [SMILES: COCc1ccc(OC(F)(F)F)c(CNC(=O)Nc2c(C)c(O[C@@H]3CCN(C)C3)nn2-c2ccccc2)c1]

(R)-1-(5-(methoxymethyl)-2-(trifluoromethoxy)benzyl)-3-(4-methyl-3-((1-methylpyrrolidin-3-yl)oxy)-1-phenyl-1H-pyrazol-5-yl)urea Prepared according to the procedure of Example 75, Step A, substituting 1-(3-(azetidin-3-ylmethoxy)-4-methyl-1-phenyl-1H-pyrazol-5-yl)-3-(5-(methoxymethyl)-2-(trifluoromethoxy)benzyl)urea with (R)-1-(5-(methoxymethyl)-2-(trifluoromethoxy)benzyl)-3-(4-methyl-1-phenyl-3-(pyrrolidin-3-yloxy)-1H-pyrazol-5-yl)urea, to give the title compound (6%). MS (APCI) m/z=534.2 (M+H).

Example 83

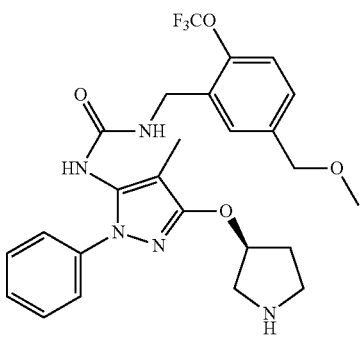 [SMILES: COCc1ccc(OC(F)(F)F)c(CNC(=O)Nc2c(C)c(O[C@H]3CCNC3)nn2-c2ccccc2)c1]

(S)-1-(5-(methoxymethyl)-2-(trifluoromethoxy)benzyl)-3-(4-methyl-1-phenyl-3-(pyrrolidin-3-yloxy)-1H-pyrazol-5-yl)urea Step A: Preparation of (R)-tert-butyl 3-((methylsulfonyl)oxy)pyrrolidine-1-carboxylate Prepared according to the procedure of Example 72, Step B, substituting tert-butyl 4-fluoro-4-(hydroxymethyl)piperidine-1-carboxylate with (R)-tert-butyl 3-hydroxypyrrolidine-1-carboxylate to give (R)-tert-butyl 3-((methylsulfonyl)oxy)pyrrolidine-1-carboxylate (100%).

Step B: Preparation of (S)-tert-butyl 3-((5-amino-4-methyl-1-phenyl-1H-pyrazol-3-yl)oxy)pyrrolidine-1-carboxylate Prepared according to the procedure of Example 67, Step A, substituting tert-butyl 4-(((methylsulfonyl)oxy)methyl)piperidine-1-carboxylate with (R)-tert-butyl 3-((methylsulfonyl)oxy)pyrrolidine-1-carboxylate to give the title compound (40%).

Step C: Preparation of (S)-tert-butyl 3-((5-(3-(5-(methoxymethyl)-2-(trifluoromethoxy)benzyl)ureido)-4-methyl-1-phenyl-1H-pyrazol-3-yl)oxy)pyrrolidine-1-carboxylate Prepared according to the procedure of Example 1, substituting 4-methyl-3-(2-methylpyrimidin-5-yl)-1-phenyl-1H-pyrazol-5-amine with (S)-tert-butyl 3-((5-amino-4-methyl-1-phenyl-1H-pyrazol-3-yl)oxy)pyrrolidine-1-carboxylate and (2-cyclopropyl-5-(methoxymethyl)phenyl)methanamine with (5-(methoxymethyl)-2-(trifluoromethoxy)phenyl)methanamine to give the title compound (33%).

Step D: Preparation of (S)-1-(5-(methoxymethyl)-2-(trifluoromethoxy)benzyl)-3-(4-methyl-1-phenyl-3-(pyrrolidin-3-yloxy)-1H-pyrazol-5-yl)urea Prepared according to the procedure of Example 66, Step B, substituting tert-butyl 4-(5-(3-(5-(methoxymethyl)-2-(trifluoromethoxy)benzyl)ureido)-4-methyl-1-phenyl-1H-pyrazol-3-yl)piperidine-1-carboxylate with (S)-tert-butyl 3-((5-

(3-(5-(methoxymethyl)-2-(trifluoromethoxy)benzyl)ureido)-4-methyl-1-phenyl-1H-pyrazol-3-yl)oxy)pyrrolidine-1-carboxylate to give the title compound (19%). MS (APCI) m/z=520.2 (M+H).

Example 84

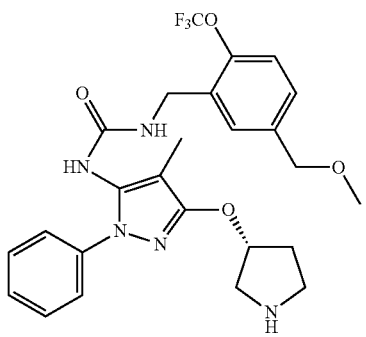 [SMILES: COCc1ccc(OC(F)(F)F)c(CNC(=O)Nc2c(C)c(O[C@@H]3CCNC3)nn2-c2ccccc2)c1]

(R)-1-(5-(methoxymethyl)-2-(trifluoromethoxy)benzyl)-3-(4-methyl-1-phenyl-3-(pyrrolidin-3-yloxy)-1H-pyrazol-5-yl)urea Step A: Preparation of (S)-tert-butyl 3-((methylsulfonyl)oxy)pyrrolidine-1-carboxylate Prepared according to the procedure of Example 72, Step B, substituting tert-butyl 4-fluoro-4-(hydroxymethyl)piperidine-1-carboxylate with (S)-tert-butyl 3-hydroxypyrrolidine-1-carboxylate to give the title compound (100%).

Step B: Preparation of (R)-tert-butyl 3-((5-amino-4-methyl-1-phenyl-1H-pyrazol-3-yl)oxy)pyrrolidine-1-carboxylate Prepared according to the procedure of Example 67, Step A, substituting tert-butyl 4-(((methylsulfonyl)oxy)methyl)piperidine-1-carboxylate with (S)-tert-butyl 3-((methylsulfonyl)oxy)pyrrolidine-1-carboxylate to give the title compound (48%).

Step C: Preparation of (R)-tert-butyl 3-((5-(3-(5-(methoxymethyl)-2-(trifluoromethoxy)benzyl)ureido)-4-methyl-1-phenyl-1H-pyrazol-3-yl)oxy)pyrrolidine-1-carboxylate Prepared according to the procedure of Example 1, substituting 4-methyl-3-(2-methylpyrimidin-5-yl)-1-phenyl-1H-pyrazol-5-amine with (R)-tert-butyl 3-((5-amino-4-methyl-1-phenyl-1H-pyrazol-3-yl)oxy)pyrrolidine-1-carboxylate and (2-cyclopropyl-5-(methoxymethyl)phenyl)methanamine with (5-(methoxymethyl)-2-(trifluoromethoxy)phenyl)methanamine to give the title compound (57%).

Step D: Preparation of (R)-1-(5-(methoxymethyl)-2-(trifluoromethoxy)benzyl)-3-(4-methyl-1-phenyl-3-(pyrrolidin-3-yloxy)-1H-pyrazol-5-yl)urea Prepared according to the procedure of Example 66, Step B, substituting tert-butyl 44543-(5-(methoxymethyl)-2-(trifluoromethoxy)benzyl)ureido)-4-methyl-1-phenyl-1H-pyrazol-3-yl)piperidine-1-carboxylate with (R)-tert-butyl 3-((5-(3-(5-(methoxymethyl)-2-(trifluoromethoxy)benzyl)ureido)-4-methyl-1-phenyl-1H-pyrazol-3-yl)oxy)pyrrolidine-1-carboxylate to give the title compound (35%). MS (APCI) m/z=520.2 (M+H).

Example 85

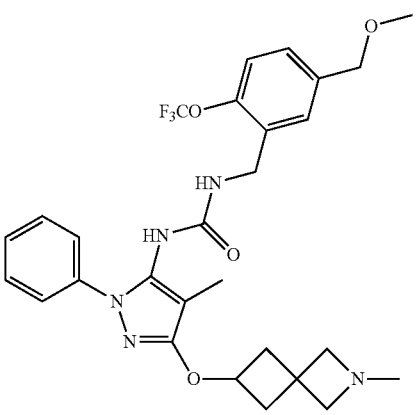 [SMILES: COCc1ccc(OC(F)(F)F)c(CNC(=O)Nc2c(C)c(OC3CC4(C3)CN(C)C4)nn2-c2ccccc2)c1]

1-(5-(methoxymethyl)-2-(trifluoromethoxy)benzyl)-3-(4-methyl-3-((2-methyl-2-azaspiro[3.3]heptan-6-yl)oxy)-1-phenyl-1H-pyrazol-5-yl)urea Prepared according to the procedure of Example 75, Step A, substituting 1-(3-(azetidin-3-ylmethoxy)-4-methyl-1-phenyl-1H-pyrazol-5-yl)-3-(5-(methoxymethyl)-2-(trifluoromethoxy)benzyl)urea with 1-(3-(2-azaspiro[3.3]heptan-6-yloxy)-4-methyl-1-phenyl-1H-pyrazol-5-yl)-3-(5-(methoxymethyl)-2-(trifluoromethoxy)benzyl)urea, to give the title compound (6%). MS (APCI) m/z=560.2 (M+H).

Example 86

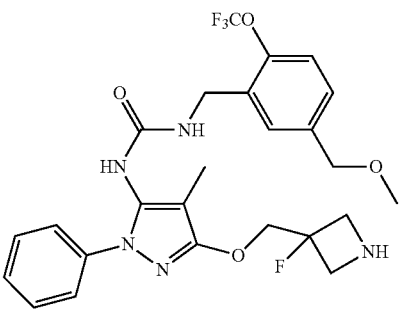 [SMILES: COCc1ccc(OC(F)(F)F)c(CNC(=O)Nc2c(C)c(OCC3(F)CNC3)nn2-c2ccccc2)c1]

1-(3-(((3-fluoroazetidin-3-yl)methoxy)-4-methyl-1-phenyl-1H-pyrazol-5-yl)-3-(5-(methoxymethyl)-2-(trifluoromethoxy)benzyl)urea Step A: Preparation of tert-butyl 3-fluoro-3-(hydroxymethyl)azetidine-1-carboxylate Prepared as outlined in Van Hende, et al., *J. Org. Chem.* 2009, 74, 2250-2253.

Step B: Preparation of tert-butyl 3-fluoro-3-(((methylsulfonyl)oxy)methyl)azetidine-1-carboxylate Prepared according to the procedure of Example 72, Step B, substituting tert-butyl 4-fluoro-4-(hydroxymethyl)piperidine-1-carboxylate with tert-butyl 3-fluoro-3-(hydroxymethyl)azetidine-1-carboxylate to give the title compound (86%).

Step C: Preparation of tert-butyl 3-4(5-amino-4-methyl-1-phenyl-1H-pyrazol-3-yl)oxy)methyl)-3-fluoroazetidine-1-carboxylate Prepared according to the procedure of Example 67, Step A, substituting tert-butyl 4-(((methylsulfonyl)oxy)methyl)piperidine-1-carboxylate with tert-butyl 3-fluoro-3-(((methylsulfonyl)oxy)methyl)azetidine-1-carboxylate to give the title compound (40%).

Step D: Preparation of tert-butyl 3-fluoro-3-(((5-(3-(5-(methoxymethyl)-2-(trifluoromethoxy)benzyl)ureido)-4-methyl-1-phenyl-1H-pyrazol-3-yl)oxy)methyl)azetidine-1-carboxylate Prepared according to the procedure of Example 1, substituting 4-methyl-3-(2-methylpyrimidin-5-yl)-1-phenyl-1H-pyrazol-5-amine with tert-butyl 3-(((5-amino-4-methyl-1-phenyl-1H-pyrazol-3-yl)oxy)methyl)-3-fluoroazetidine-1-carboxylate and (2-cyclopropyl-5-(methoxymethyl)phenyl)methanamine with (5-(methoxymethyl)-2-(trifluoromethoxy)phenyl)methanamine to give the title compound (61%).

Step E: Preparation of 1-(3-((3-fluoroazetidin-3-yl)methoxy)-4-methyl-1-phenyl-1H-pyrazol-5-yl)-3-(5-(methoxymethyl)-2-(trifluoromethoxy)benzyl)urea Prepared according to the procedure of Example 66, Step B, substituting tert-butyl 4-(5-(3-(5-(methoxymethyl)-2-(trifluoromethoxy)benzyl)ureido)-4-methyl-1-phenyl-1H-pyrazol-3-yl)piperidine-1-carboxylate with tert-butyl 3-fluoro-3-(((5-(3-(5-(methoxymethyl)-2-(trifluoromethoxy)benzyl)ureido)-4-methyl-1-phenyl-1H-pyrazol-3-yl)oxy)methyl)azetidine-1-carboxylate to give the title compound (64%). MS (APCI) m/z=538.2 (M+H).

Example 87

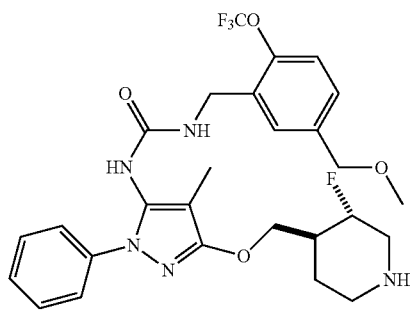

1-(3-(((3S,4S)-3-fluoropiperidin-4-yl)methoxy)-4-methyl-1-phenyl-1H-pyrazol-5-yl)-3-(5-(methoxymethyl)-2-(trifluoromethoxy)benzyl)urea

Step A: Preparation of tert-butyl 3-fluoro-4-oxopiperidine-1-carboxylate

Prepared according to the procedure described in International patent publication WO 2008/124323 A1.

Step B: Preparation of (3S,4S)-tert-butyl 3-fluoro-4-(hydroxymethyl)piperidine-1-carboxylate and (3S,4R)-tert-butyl 3-fluoro-4-(hydroxymethyl)piperidine-1-carboxylate Prepared according to the procedure described in Koudih, R. et al., *European Journal of Medicinal Chemistry*, 2012, 53, p. 408-415.

Step C: Preparation of (3S,4S)-tert-butyl 3-fluoro-4-(((methylsulfonyl)oxy)methyl)piperidine-1-carboxylate Prepared according to the procedure of Example 72, Step B, substituting tert-butyl 4-fluoro-4-(hydroxymethyl)piperidine-1-carboxylate with (3S,4S)-tert-butyl 3-fluoro-4-(hydroxymethyl)piperidine-1-carboxylate to give the title compound (100%).

Step D: Preparation of (3S,4S)-tert-butyl 4-(((5-amino-4-methyl-1-phenyl-1H-pyrazol-3-yl)oxy)methyl)-3-fluoropiperidine-1-carboxylate Prepared according to the procedure of Example 67, Step A, substituting tert-butyl 4-(((methylsulfonyl)oxy)methyl)piperidine-1-carboxylate with (3S,4S)-tert-butyl 3-fluoro-4-(((methylsulfonyl)oxy)methyl)piperidine-1-carboxylate to give the title compound (38%).

Step E: Preparation of (3S,4S)-tert-butyl 3-fluoro-4-(((5-(3-(5-(methoxymethyl)-2-(trifluoromethoxy)benzyl)ureido)-4-methyl-1-phenyl-1H-pyrazol-3-yl)oxy)methyl)piperidine-1-carboxylate Prepared according to the procedure of Example 1, substituting 4-methyl-3-(2-methylpyrimidin-5-yl)-1-phenyl-1H-pyrazol-5-amine with (3S,4S)-tert-butyl 4-(((5-amino-4-methyl-1-phenyl-1H-pyrazol-3-yl)oxy)methyl)-3-fluoropiperidine-1-carboxylate and (2-cyclopropyl-5-(methoxymethyl)phenyl)methanamine with (5-(methoxymethyl)-2-(trifluoromethoxy)phenyl)methanamine to give the title compound (54%).

Step F: Preparation of 1-(3-(((3S,4S)-3-fluoropiperidin-4-yl)methoxy)-4-methyl-1-phenyl-1H-pyrazol-5-yl)-3-(5-(methoxymethyl)-2-(trifluoromethoxy)benzyl)urea Prepared according to the procedure of Example 66, Step B, substituting tert-butyl 4-(5-(3-(5-(methoxymethyl)-2-(trifluoromethoxy)benzyl)ureido)-4-methyl-1-phenyl-1H-pyrazol-3-yl)piperidine-1-carboxylate with (3S,4S)-tert-butyl 3-fluoro-4-(((5-(3-(5-(methoxymethyl)-2-(trifluoromethoxy)benzyl)ureido)-4-methyl-1-phenyl-1H-pyrazol-3-yl)oxy)methyl)piperidine-1-carboxylate to give the title compound (55%). MS (APCI) m/z=566.2 (M+H).

Example 88

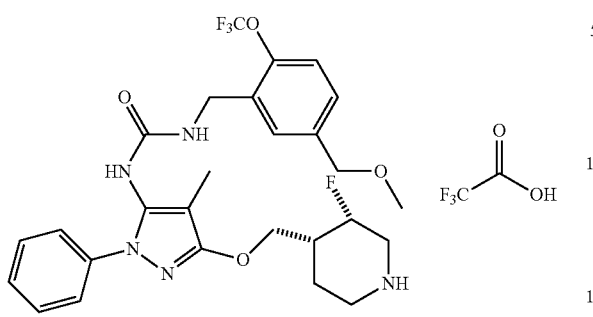

1-(3-(((3S,4R)-3-fluoropiperidin-4-yl)methoxy)-4-methyl-1-phenyl-1H-1-pyrazol-5-yl)-3-(5-(methoxymethyl)-2-(trifluoromethoxy)benzyl)urea 2,2,2-trifluoroacetate Step A: Preparation of (3S,4R)-tert-butyl 3-fluoro-4-(((methylsulfonyl)oxy)methyl)piperidine-1-carboxylate Prepared according to the procedure of Example 72, Step B, substituting tert-butyl 4-fluoro-4-(hydroxymethyl)piperidine-1-carboxylate with (3S,4R)-tert-butyl 3-fluoro-4-(hydroxymethyl)piperidine-1-carboxylate (Example 87, Step B) to give the title compound (89%).

Step B: Preparation of (3S,4R)-tert-butyl 4-(((5-amino-4-methyl-1-phenyl-1H-pyrazol-3-yl)oxy)methyl)-3-fluoropiperidine-1-carboxylate Prepared according to the procedure of Example 67, Step A, substituting tert-butyl 4-(((methylsulfonyl)oxy)methyl)piperidine-1-carboxylate with (3S,4R)-tert-butyl 3-fluoro-4-(((methylsulfonyl)oxy)methyl)piperidine-1-carboxylate to give the title compound (13%).

Step C: Preparation of (3S,4R)-tert-butyl 3-fluoro-4-(((5-(3-(5-(methoxymethyl)-2-(trifluoromethoxy)benzyl)ureido)-4-methyl-1-phenyl-1H-pyrazol-3-yl)oxy)methyl)piperidine-1-carboxylate Prepared according to the procedure of Example 1, substituting 4-methyl-3-(2-methylpyrimidin-5-yl)-1-phenyl-1H-pyrazol-5-amine with (3S,4R)-tert-butyl 4-(((5-amino-4-methyl-1-phenyl-1H-pyrazol-3-yl)oxy)methyl)-3-fluoropiperidine-1-carboxylate and (2-cyclopropyl-5-(methoxymethyl)phenyl)methanamine with (5-(methoxymethyl)-2-(trifluoromethoxy)phenyl)methanamine to give the title compound (46%).

Step D: Preparation of 1-(3-(((3S,4R)-3-fluoropiperidin-4-yl)methoxy)-4-methyl-1-phenyl-1H-pyrazol-5-yl)-3-(5-(methoxymethyl)-2-(trifluoromethoxy)benzyl)urea 2,2,2-trifluoroacetate Prepared according to the procedure of Example 66, Step B, substituting tert-butyl 4-(5-(3-(5-(methoxymethyl)-2-(trifluoromethoxy)benzyl)ureido)-4-methyl-1-phenyl-1H-pyrazol-3-yl)piperidine-1-carboxylate with (3S,4R)-tert-butyl 3-fluoro-4-(((5-(3-(5-(methoxymethyl)-2-(trifluoromethoxy)benzyl)ureido)-4-methyl-1-phenyl-1H-pyrazol-3-yl)oxy)methyl)piperidine-1-carboxylate. The fractions from the reverse phase HPLC purification were concentrated under reduced pressure to give the title compound (67%) as a TFA salt. MS (APCI) m/z=566.3 (M+H).

Example 89

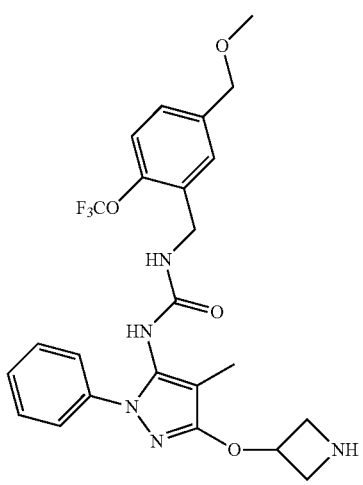 [SMILES: COCc1ccc(OC(F)(F)F)c(CNC(=O)Nc2c(C)c(OC3CNC3)nn2-c2ccccc2)c1]

1-(3-(azetidin-3-yloxy)-4-methyl-1-phenyl-1H-pyrazol-5-yl)-3-(5-(methoxymethyl)-2-(trifluoromethoxy)benzyl)urea Step A: Preparation of tert-butyl 3-((methylsulfonyl)oxy)azetidine-1-carboxylate Prepared according to the procedure of Example 72, Step B, substituting tert-butyl 4-fluoro-4-(hydroxymethyl)piperidine-1-carboxylate with tert-butyl 3-hydroxyazetidine-1-carboxylate to give the title compound (100%).

Step B: Preparation of tert-butyl 3-((5-amino-4-methyl-1-phenyl-1H-pyrazol-3-yl)oxy)azetidine-1-carboxylate Prepared according to the procedure of Example 67, Step A, substituting tert-butyl 4-(((methylsulfonyl)oxy)methyl)piperidine-1-carboxylate with tert-butyl 3-((methylsulfonyl)oxy)azetidine-1-carboxylate to give the title compound (45%).

Step C: Preparation of tert-butyl 3-((5-(3-(5-(methoxymethyl)-2-(trifluoromethoxy)benzyl)ureido)-4-methyl-1-phenyl-1H-pyrazol-3-yl)oxy)azetidine-1-carboxylate Prepared according to the procedure of Example 1, substituting 4-methyl-3-(2-methylpyrimidin-5-yl)-1-phenyl-1H-pyrazol-5-amine with tert-butyl 3-((5-amino-4-methyl-1-phenyl-1H-pyrazol-3-yl)oxy)azetidine-1-carboxylate and (2-cyclopropyl-5-(methoxymethyl)phenyl)methanamine with (5-(methoxymethyl)-2-(trifluoromethoxy)phenyl)methanamine to give the title compound (48%).

Step D: Preparation of 1-(3-(azetidin-3-yloxy)-4-methyl-1-phenyl-1H-pyrazol-5-yl)-3-(5-(methoxymethyl)-2-(trifluoromethoxy)benzyl)urea Prepared according to the procedure of Example 66, Step B, substituting tert-butyl 4-(5-(3-(5-(methoxymethyl)-2-(trifluoromethoxy)benzyl)ureido)-4-methyl-1-phenyl-1H-pyrazol-3-yl)piperidine-1-carboxylate with tert-butyl 3-((5-(3-(5-(methoxymethyl)-2-(trifluoromethoxy)benzyl)ureido)-4-methyl-1-phenyl-1H-pyrazol-3-yl)oxy)azetidine-1-carboxylate to give the title compound (12%). MS (APCI) m/z=506.2 (M+H).

Example 90

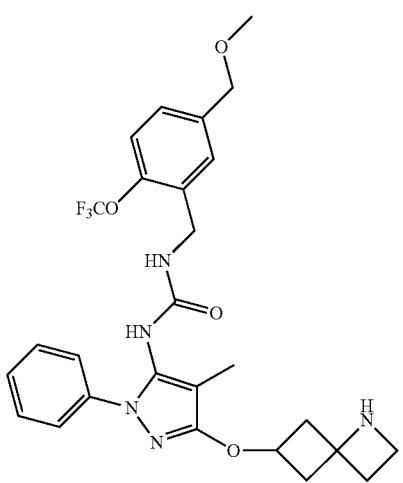 [SMILES: COCc1ccc(OC(F)(F)F)c(CNC(=O)Nc2c(C)c(OC3CC4(CCN4)C3)nn2-c2ccccc2)c1]

1-(3-(1-azaspiro[3.3]heptan-6-yloxy)-4-methyl-1-phenyl-1H-pyrazol-5-yl)-3-(5-(methoxymethyl)-2-(trifluoromethoxy)benzyl)urea Step A: Preparation of tert-butyl 6-((methylsulfonyl)oxy)-1-azaspiro[3.3]heptane-1-carboxylate Prepared according to the procedure of Example 72, Step B, substituting tert-butyl 4-fluoro-4-(hydroxymethyl)piperidine-1-carboxylate with tert-butyl 6-hydroxy-1-azaspiro[3.3]heptane-1-carboxylate to give the title compound (97%).

Step B: Preparation of tert-butyl 6-((5-amino-4-methyl-1-phenyl-1H-1-pyrazol-3-yl)oxy)-1-azaspiro[3.3]heptane-1-carboxylate Prepared according to the procedure of Example 67, Step A, substituting tert-butyl 4-(((methylsulfonyl)oxy)methyl)piperidine-1-carboxylate with tert-butyl 6-((methylsulfonyl)oxy)-1-azaspiro[3.3]heptane-1-carboxylate to give the title compound (11%).

Step C: Preparation of tert-butyl 6-((5-(3-(5-(methoxymethyl)-2-(trifluoromethoxy)benzyl)ureido)-4-methyl-1-phenyl-1H-pyrazol-3-yl)oxy)-1-azaspiro[3.3]heptane-1-carboxylate Prepared according to the procedure of Example 1, substituting 4-methyl-3-(2-methylpyrimidin-5-yl)-1-phenyl-1H-pyrazol-5-amine with tert-butyl 6-((5-amino-4-methyl-1-phenyl-1H-pyrazol-3-yl)oxy)-1-azaspiro[3.3]heptane-1-carboxylate and (2-cyclopropyl-5-(methoxymethyl)phenyl)methanamine with (5-(methoxymethyl)-2-(trifluoromethoxy)phenyl)methanamine to give the title compound.

Step D: Preparation of 1-(3-(1-azaspiro[3.3]heptan-6-yloxy)-4-methyl-1-phenyl-1H-pyrazol-5-yl)-3-(5-(methoxymethyl)-2-(trifluoromethoxy)benzyl)urea Prepared according to the procedure of Example 66, Step B, substituting tert-butyl 4-(5-(3-(5-(methoxymethyl)-2-(trifluoromethoxy)benzyl)ureido)-4-methyl-1-phenyl-1H-pyrazol-3-yl)piperidine-1-carboxylate with tert-butyl 6-((5-(3-(5-(methoxymethyl)-2-(trifluoromethoxy)benzyl)ureido)-4-methyl-1-phenyl-1H-pyrazol-3-yl)oxy)-1-azaspiro[3.3]heptane-1-carboxylate to give the title compound (22%). MS (APCI) m/z=546.2 (M+H).

Example 91

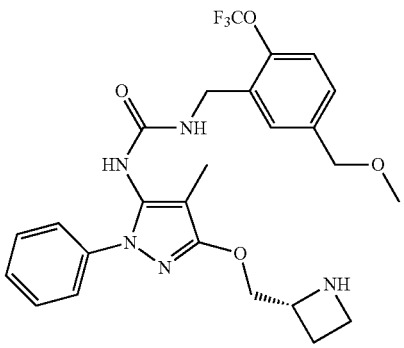 [SMILES: COCc1ccc(OC(F)(F)F)c(CNC(=O)Nc2c(C)c(OC[C@H]3CCN3)nn2-c2ccccc2)c1]

(R)-1-(3-(azetidin-2-ylmethoxy)-4-methyl-1-phenyl-1H-pyrazol-5-yl)-3-(5-(methoxymethyl)-2-(trifluoromethoxy)benzyl)urea Step A: Preparation of (R)-tert-butyl 2-(((methylsulfonyl)oxy)methyl)azetidine-1-carboxylate Prepared according to the procedure of Example 72, Step B, substituting tert-butyl 4-fluoro-4-(hydroxymethyl)piperidine-1-carboxylate with (R)-tert-butyl 2-(hydroxymethyl)azetidine-1-carboxylate to give the title compound (100%).

Step B: Preparation of (R)-tert-butyl 2-(((5-amino-4-methyl-1-phenyl-1H-pyrazol-3-yl)oxy)methyl)azetidine-1-carboxylate Prepared according to the procedure of Example 67, Step A, substituting tert-butyl 4-(((methylsulfonyl)oxy)methyl)piperidine-1-carboxylate with (R)-tert-butyl 2-(((methylsulfonyl)oxy)methyl)azetidine-1-carboxylate to give the title compound (44%).

Step C: Preparation of (R)-tert-butyl 2-(((5-(3-(5-(methoxymethyl)-2-(trifluoromethoxy)benzyl)ureido)-4-methyl-1-phenyl-1H-pyrazol-3-yl)oxy)methyl)azetidine-1-carboxylate Prepared according to the procedure of Example 1, substituting 4-methyl-3-(2-methylpyrimidin-5-yl)-1-phenyl- 1H-pyrazol-5-amine with (R)-tert-butyl 2-(((5-amino-4-methyl-1-phenyl-1H-pyrazol-3-yl)oxy)methyl)azetidine-1-carboxylate and (2-cyclopropyl-5-(methoxymethyl)phenyl)methanamine with (5-(methoxymethyl)-2-(trifluoromethoxy)phenyl)methanamine to give the title compound (62%).

Step D: Preparation of (R)-1-(3-(azetidin-2-ylmethoxy)-4-methyl-1-phenyl-1H-pyrazol-5-yl)-3-(5-(methoxymethyl)-2-(trifluoromethoxy)benzyl)urea Prepared according to the procedure of Example 66, Step B, substituting tert-butyl 4-(5-(3-(5-(methoxymethyl)-2-(trifluoromethoxy)benzyl)ureido)-4-methyl-1-phenyl-1H-pyrazol-3-yl)piperidine-1-carboxylate with (R)-tert-butyl 2-(((5-(3-(5-(methoxymethyl)-2-(trifluoromethoxy)benzyl)ureido)-4-methyl-1-phenyl-1H-pyrazol-3-yl)oxy)methyl)azetidine-1-carboxylate to give the title compound (26%). MS (APCI) m/z=520.2 (M+H).

Example 92

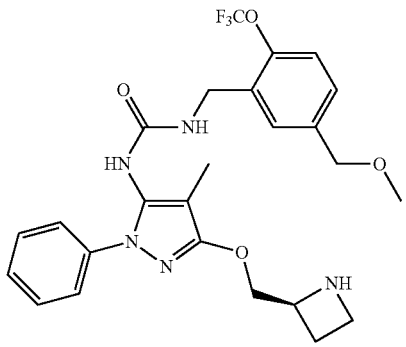 [SMILES: COCc1ccc(OC(F)(F)F)c(CNC(=O)Nc2c(C)c(OC[C@@H]3CCN3)nn2-c2ccccc2)c1]

(S)-1-(3-(azetidin-2-ylmethoxy)-4-methyl-1-phenyl-1H-pyrazol-5-yl)-3-(5-(methoxymethyl)-2-(trifluoromethoxy)benzyl)urea Step A: Preparation of (S)-tert-butyl 2-(((methylsulfonyl)oxy)methyl)azetidine-1-carboxylate Prepared according to the procedure of Example 72, Step B, substituting tert-butyl 4-fluoro-4-(hydroxymethyl)piperidine-1-carboxylate with (S)-tert-butyl 2-(hydroxymethyl)azetidine-1-carboxylate to give the title compound (95%).

Step B: Preparation of (S)-tert-butyl 2-(((5-amino-4-methyl-1-phenyl-1H-pyrazol-3-yl)oxy)methyl)azetidine-1-carboxylate Prepared according to the procedure of Example 67, Step A, substituting tert-butyl 4-(((methylsulfonyl)oxy)methyl)piperidine-1-carboxylate with (S)-tert-butyl 2-(((methylsulfonyl)oxy)methyl)azetidine-1-carboxylate to give the title compound (46%).

Step C: Preparation of (S)-tert-butyl 2-(((5-(3-(5-(methoxymethyl)-2-(trifluoromethoxy)benzyl)ureido)-4-methyl-1-phenyl-1H-pyrazol-3-yl)oxy)methyl)azetidine-1-carboxylate Prepared according to the procedure of Example 1, substituting 4-methyl-3-(2-methylpyrimidin-5-yl)-1-phenyl-1H-pyrazol-5-amine with (S)-tert-butyl 2-(((5-amino-4-methyl-1-phenyl-1H-pyrazol-3-yl)oxy)methyl)azetidine-1-carboxylate and (2-cyclopropyl-5-(methoxymethyl)phenyl)methanamine with (5-(methoxymethyl)-2-(trifluoromethoxy)phenyl)methanamine to give the title compound (64%).

Step D: Preparation of (S)-1-(3-(azetidin-2-ylmethoxy)-4-methyl-1-phenyl-1H-pyrazol-5-yl)-3-(5-(methoxymethyl)-2-(trifluoromethoxy)benzyl)urea Prepared according to the procedure of Example 66, Step B, substituting tert-butyl 4-(5-(3-(5-(methoxymethyl)-2-(trifluoromethoxy)benzyl)ureido)-4-methyl-1-phenyl-1H-pyrazol-3-yl)piperidine-1-carboxylate with (S)-tert-butyl 2445-(3-(5-(methoxymethyl)-2-(trifluoromethoxy)benzyl)ureido)-4-methyl-1-phenyl-1H-pyrazol-3-yl)oxy)methyl)azetidine-1-carboxylate to give the title compound (29%). MS (APCI) m/z=520.2 (M+H).

Example 93

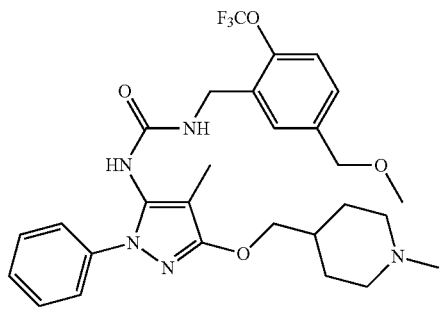 [SMILES: COCc1ccc(OC(F)(F)F)c(CNC(=O)Nc2c(C)c(OCC3CCN(C)CC3)nn2-c2ccccc2)c1]

1-(5-(methoxymethyl)-2-(trifluoromethoxy)benzyl)-3-(4-methyl-3-((1-methylpiperidin-4-yl)methoxy)-1-phenyl-1H-pyrazol-5-yl)urea Prepared according to the procedure of Example 75, Step A, substituting 1-(3-(azetidin-3-ylmethoxy)-4-methyl-1-phenyl-1H-pyrazol-5-yl)-3-(5-(methoxymethyl)-2-(trifluoromethoxy)benzyl)urea with 1-(5-(methoxymethyl)-2-(trifluoromethoxy)benzyl)-3-(4-methyl-1-phenyl-3-(piperidin-4-ylmethoxy)-1H-pyrazol-5-yl)urea (Example 67), to give the title compound (55%). MS (APCI) m/z=562.3 (M+H).

Example 94

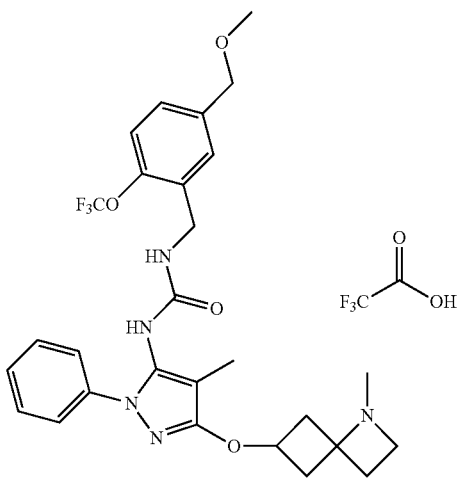 [SMILES: COCc1ccc(OC(F)(F)F)c(CNC(=O)Nc2c(C)c(OC3CC4(CCN4C)C3)nn2-c2ccccc2)c1 ; O=C(O)C(F)(F)F]

1-(5-(methoxymethyl)-2-(trifluoromethoxy)benzyl)-3-(4-methyl-3-((1-methyl-1-azaspiro[3.3]heptan-6-yl)oxy)-1-phenyl-1H-pyrazol-5-yl)urea 2,2,2-trifluoroacetate Prepared according to the procedure of Example 75, Step A, substituting 1-(3-(azetidin-3-ylmethoxy)-4-methyl-1-phenyl-1H-pyrazol-5-yl)-3-(5-(methoxymethyl)-2-(trifluoromethoxy)benzyl)urea with 1-(3-(1-azaspiro[3.3]heptan-6-yloxy)-4-methyl-1-phenyl-1H-pyrazol-5-yl)-3-(5-(methoxymethyl)-2-(trifluoromethoxy)benzyl)urea (Example 89), to give the title compound (39%) as the TFA salt. MS (APCI) m/z=560.2 (M+H).

Example 95

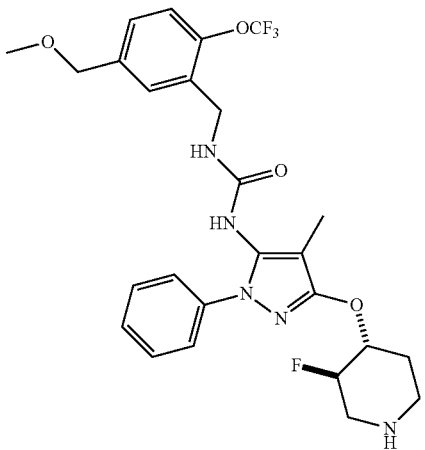

1-(3-(((3R,4R)-3-fluoropiperidin-4-yl)oxy)-4-methyl-1-phenyl-1H-pyrazol-5-yl)-3-(5-(methoxymethyl)-2-(trifluoromethoxy)benzyl)urea Step A: Preparation of (3S,4R)-tert-butyl 3-fluoro-4-hydroxypiperidine-1-carboxylate and (3R,4R)-tert-butyl 3-fluoro-4-hydroxypiperidine-1-carboxylate A round bottom flask was charged with tert-butyl 3-fluoro-4-oxopiperidine-1-carboxylate (3.00 g, 13.8 mmol, Example 86, Step A) and 140 mL of dry methanol. This mixture was cooled to 0° C. and sodium borohydride (1.57 g, 41.4 mmol) was then added in one portion. After 15 minutes at 0° C., the mixture was allowed to warm to ambient temperature and was stirred for 16 hours. The mixture was concentrated under reduced pressure and the resulting crude material was taken up in 50 mL of 1M aqueous NaOH and stirred for 30 minutes. The mixture was extracted with EtOAc, and the combined organic extracts were dried over sodium sulfate, filtered and concentrated under reduced pressure to give the crude product as a mixture of diastereomers. The mixture of diastereomers was passed through an 80 g Redi Sep column, eluting with 5% Ethyl acetate/DCM, to give 0.245 g (9%) of a less polar isomer and 1.14 g (44%) of a more polar isomer. Based on $^1$H NMR, the more polar isomer was consistent with the cis diastereomer.

Step B: Preparation of (3S,4R)-tert-butyl 3-fluoro-4-((methylsulfonyl)oxy)piperidine-1-carboxylate Prepared according to the procedure of Example 72, Step B, substituting tert-butyl 4-fluoro-4-(hydroxymethyl)piperidine-1-carboxylate with (3S,4R)-tert-butyl 3-fluoro-4-hydroxypiperidine-1-carboxylate to give the title compound (97%).

Step C: Preparation of (3S,4S)-tert-butyl 4-((5-amino-4-methyl-1-phenyl-1H-pyrazol-3-yl)oxy)-3-fluoropiperidine-1-carboxylate Prepared according to the procedure of Example 67, Step A, substituting tert-butyl 4-(((methylsulfonyl)oxy)methyl)piperidine-1-carboxylate with (3S,4R)-tert-butyl 3-fluoro-4-((methylsulfonyl)oxy)piperidine-1-carboxylate to give the title compound (25%).

Step D: Preparation of (3S,4S)-tert-butyl 3-fluoro-4-((5-(3-(5-(methoxymethyl)-2-(trifluoromethoxy)benzyl)ureido)-4-methyl-1-phenyl-1H-pyrazol-3-yl)oxy)piperidine-1-carboxylate Prepared according to the procedure of Example 1, substituting 4-methyl-3-(2-methylpyrimidin-5-yl)-1-phenyl-1H-pyrazol-5-amine with (3S,4S)-tert-butyl 4-((5-amino-4-methyl-1-phenyl-1H-pyrazol-3-yl)oxy)-3-fluoropiperidine-1-carboxylate and (2-cyclopropyl-5-(methoxymethyl)phenyl)methanamine with (5-(methoxymethyl)-2-(trifluoromethoxy)phenyl)methanamine to the title compound.

Step E: Preparation of 1-(3-(((3S,4S)-3-fluoropiperidin-4-yl)oxy)-4-methyl-1-phenyl-1H-pyrazol-5-yl)-3-(5-(methoxymethyl)-2-(trifluoromethoxy)benzyl)urea Prepared according to the procedure of Example 66, Step B, substituting tert-butyl 4-(5-(3-(5-(methoxymethyl)-2-(trifluoromethoxy)benzyl)ureido)-4-methyl-1-phenyl-1H-pyrazol-3-yl)piperidine-1-carboxylate with (3S,4S)-tert-butyl 3-fluoro-4-((5-(3-(5-(methoxymethyl)-2-(trifluoromethoxy)benzyl)ureido)-4-methyl-1-phenyl-1H-pyrazol-3-yl)oxy)piperidine-1-carboxylate to give the title compound (47%). MS (APCI) m/z=552.2 (M+H).

Example 96

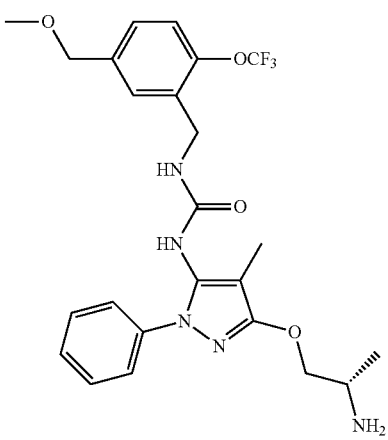 [SMILES: COCc1ccc(OC(F)(F)F)c(CNC(=O)Nc2c(C)c(OC[C@H](C)N)nn2-c2ccccc2)c1]

253

(S)-1-(3-(2-aminopropoxy)-4-methyl-1-phenyl-1H-pyrazol-5-yl)-3-(5-(methoxymethyl)-2-(trifluoromethoxy)benzyl)urea Step A: Preparation of (S)-2-((tert-butoxycarbonyl)amino)propyl methanesulfonate Prepared according to the procedure of Example 72, Step B, substituting tert-butyl 4-fluoro-4-(hydroxymethyl)piperidine-1-carboxylate with (S)-tert-butyl (1-hydroxypropan-2-yl)carbamate to give the title compound (97%).

Step B: Preparation of (S)-tert-butyl (1-((5-amino-4-methyl-1-phenyl-1H-pyrazol-3-yl)oxy)propan-2-yl)carbamate Prepared according to the procedure of Example 67, Step A, substituting tert-butyl 4-(((methylsulfonyl)oxy)methyl)piperidine-1-carboxylate with ((S)-2-((tert-butoxycarbonyl)amino)propyl methanesulfonate to give the title compound (28%).

Step C: Preparation of (S)-tert-butyl (1-((5-(3-(5-(methoxymethyl)-2-(trifluoromethoxy)benzyl)ureido)-4-methyl-1-phenyl-1H-pyrazol-3-yl)oxy)propan-2-yl)carbamate Prepared according to the procedure of Example 1, substituting 4-methyl-3-(2-methylpyrimidin-5-yl)-1-phenyl-1H-pyrazol-5-amine with (S)-tert-butyl (1-((5-amino-4-methyl-1-phenyl-1H-pyrazol-3-yl)oxy)propan-2-yl)carbamate and (2-cyclopropyl-5-(methoxymethyl)phenyl)methanamine with (5-(methoxymethyl)-2-(trifluoromethoxy)phenyl)methanamine to give the title compound (42%).

Step D: Preparation of (S)-1-(3-(2-aminopropoxy)-4-methyl-1-phenyl-1H-pyrazol-5-yl)-3-(5-(methoxymethyl)-2-(trifluoromethoxy)benzyl)urea Prepared according to the procedure of Example 66, Step B, substituting tert-butyl 4-(5-(3-(5-(methoxymethyl)-2-(trifluoromethoxy)benzyl)ureido)-4-methyl-1-phenyl-1H-pyrazol-3-yl)piperidine-1-carboxylate with (S)-tert-butyl (1-((5-(3-(5-(methoxymethyl)-2-(trifluoromethoxy)benzyl)ureido)-4-methyl-1-phenyl-1H-pyrazol-3-yl)oxy)propan-2-yl)carbamate to give the title compound (24%). MS (APCI) m/z=508.2 (M+H).

Example 97

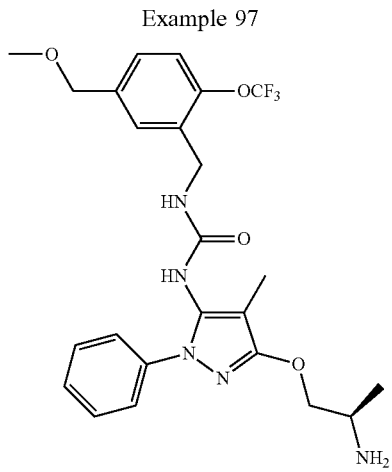

254

(R)-1-(3-(2-aminopropoxy)-4-methyl-1-phenyl-1H-pyrazol-5-yl)-3-(5-(methoxymethyl)-2-(trifluoromethoxy)benzyl)urea Step A: Preparation of (R)-2-((tert-butoxycarbonyl)amino)propyl methanesulfonate Prepared according to the procedure of Example 72, Step B, substituting tert-butyl 4-fluoro-4-(hydroxymethyl)piperidine-1-carboxylate with (R)-tert-butyl (1-hydroxypropan-2-yl)carbamate to give the title compound (97%).

Step B: Preparation of (R)-tert-butyl (1-((5-amino-4-methyl-1-phenyl-1H-pyrazol-3-yl)oxy)propan-2-yl)carbamate Prepared according to the procedure of Example 67, Step A, substituting tert-butyl 4-(((methylsulfonyl)oxy)methyl)piperidine-1-carboxylate with ((R)-2-((tert-butoxycarbonyl)amino)propyl methanesulfonate to give the title compound (28%).

Step C: Preparation of (R)-tert-butyl (1-((5-(3-(5-(methoxymethyl)-2-(trifluoromethoxy)benzyl)ureido)-4-methyl-1-phenyl-1H-pyrazol-3-yl)oxy)propan-2-yl)carbamate Prepared according to the procedure of Example 1, substituting 4-methyl-3-(2-methylpyrimidin-5-yl)-1-phenyl-1H-pyrazol-5-amine with (R)-tert-butyl (1-((5-amino-4-methyl-1-phenyl-1H-pyrazol-3-yl)oxy)propan-2-yl)carbamate and (2-cyclopropyl-5-(methoxymethyl)phenyl)methanamine with (5-(methoxymethyl)-2-(trifluoromethoxy)phenyl)methanamine to give the title compound (42%).

Step D: Preparation of (R)-1-(3-(2-aminopropoxy)-4-methyl-1-phenyl-1H-pyrazol-5-yl)-3-(5-(methoxymethyl)-2-(trifluoromethoxy)benzyl)urea Prepared according to the procedure of Example 66, Step B, substituting tert-butyl 4-(5-(3-(5-(methoxymethyl)-2-(trifluoromethoxy)benzyl)ureido)-4-methyl-1-phenyl-1H-pyrazol-3-yl)piperidine-1-carboxylate with (R)-tert-butyl (1-((5-(3-(5-(methoxymethyl)-2-(trifluoromethoxy)benzyl)ureido)-4-methyl-1-phenyl-1H-pyrazol-3-yl)oxy)propan-2-yl)carbamate to give the title compound (26%). MS (APCI) m/z=508.2 (M+H).

Example 98

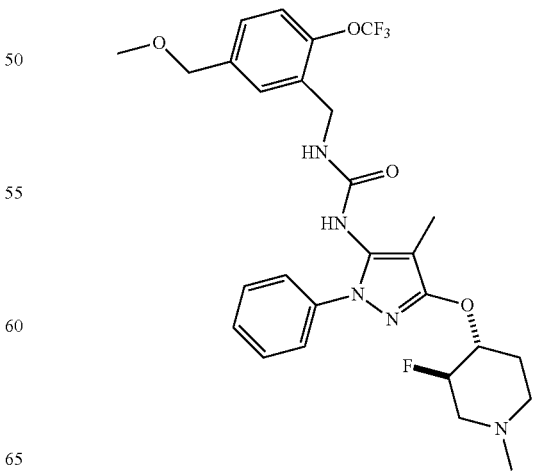

1-(3-(((3R,4R)-3-fluoro-1-methylpiperidin-4-yl)oxy)-4-methyl-1-phenyl-1H-pyrazol-5-yl)-3-(5-(methoxymethyl)-2-(trifluoromethoxy)benzyl)urea Prepared according to the procedure of Example 75, Step A, substituting 1-(3-(azetidin-3-ylmethoxy)-4-methyl-1-phenyl-1H-pyrazol-5-yl)-3-(5-(methoxymethyl)-2-(trifluoromethoxy)benzyl)urea with 1-(3-(((3R,4R)-3-fluoropiperidin-4-yl)oxy)-4-methyl-1-phenyl-1H-pyrazol-5-yl)-3-(5-(methoxymethyl)-2-(trifluoromethoxy)benzyl)urea to give the title compound (39%). MS (APCI) m/z=566.2 (M+H).

Example 99

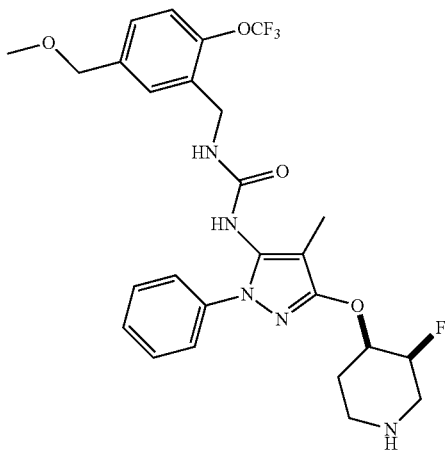

1-(3-(((3S,4R)-3-fluoropiperidin-4-yl)oxy)-4-methyl-1-phenyl-1H-pyrazol-5-yl)-3-(5-(methoxymethyl)-2-(trifluoromethoxy)benzyl)urea Step A: Preparation of (3S,4S)-tert-butyl 3-fluoro-4-((methylsulfonyl)oxy)piperidine-1-carboxylate Prepared according to the procedure of Example 72, Step B, substituting tert-butyl 4-fluoro-4-(hydroxymethyl)piperidine-1-carboxylate with (3S,4S)-tert-butyl 3-fluoro-4-hydroxypiperidine-1-carboxylate (Example 95) to give the title compound (95%).

Step B: Preparation of (3S,4R)-tert-butyl 4-((5-amino-4-methyl-1-phenyl-1H-pyrazol-3-yl)oxy)-3-fluoropiperidine-1-carboxylate Prepared according to the procedure of Example 67, Step A, substituting tert-butyl 4-(((methylsulfonyl)oxy)methyl)piperidine-1-carboxylate with ((R)-2-((tert-butoxycarbonyl)amino)propyl methanesulfonate to give the title compound (26%).

Step C: Preparation of (3S,4R)-tert-butyl 3-fluoro-4-((5-(3-(5-(methoxymethyl)-2-(trifluoromethoxy)benzyl)ureido)-4-methyl-1-phenyl-1H-pyrazol-3-yl)oxy)piperidine-1-carboxylate Prepared according to the procedure of Example 1, substituting 4-methyl-3-(2-methylpyrimidin-5-yl)-1-phenyl-1H-pyrazol-5-amine with (3S,4R)-tert-butyl 4-((5-amino-4-methyl-1-phenyl-1H-pyrazol-3-yl)oxy)-3-fluoropiperidine-1-carboxylate and (2-cyclopropyl-5-(methoxymethyl)phenyl)methanamine with (5-(methoxymethyl)-2-(trifluoromethoxy)phenyl)methanamine to give the title compound (49%).

Step D: Preparation of 1-(3-(((3S,4R)-3-fluoropiperidin-4-yl)oxy)-4-methyl-1-phenyl-1H-pyrazol-5-yl)-3-(5-(methoxymethyl)-2-(trifluoromethoxy)benzyl)urea Prepared according to the procedure of Example 66, Step B, substituting tert-butyl 4-(5-(3-(5-(methoxymethyl)-2-(trifluoromethoxy)benzyl)ureido)-4-methyl-1-phenyl-1H-pyrazol-3-yl)piperidine-1-carboxylate with (3S,4R)-tert-butyl 3-fluoro-4-((5-(3-(5-(methoxymethyl)-2-(trifluoromethoxy)benzyl)ureido)-4-methyl-1-phenyl-1H-pyrazol-3-yl)oxy)piperidine-1-carboxylate to give the title compound (24%). MS (APCI) m/z=552.2 (M+H).

Example 100

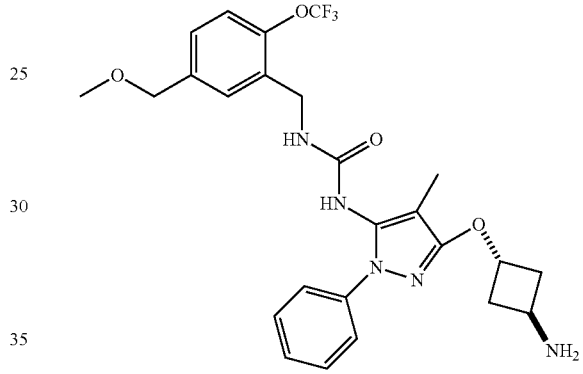

1-(3-((1r,3r)-3-aminocyclobutoxy)-4-methyl-1-phenyl-1H-pyrazol-5-yl)-3-(5-(methoxymethyl)-2-(trifluoromethoxy)benzyl)urea Step A: Preparation of (1s,3s)-3-((tert-butoxycarbonyl)amino)cyclobutyl methanesulfonate Prepared according to the procedure of Example 72, Step B, substituting tert-butyl 4-fluoro-4-(hydroxymethyl)piperidine-1-carboxylate with tert-butyl ((1s,3s)-3-hydroxycyclobutyl)carbamate to give the title compound (92%).

Step B: Preparation of tert-butyl ((1r,3r)-3-((5-amino-4-methyl-1-phenyl-1H-pyrazol-3-yl)oxy)cyclobutyl)carbamate Prepared according to the procedure of Example 67, Step A, substituting tert-butyl 4-(((methylsulfonyl)oxy)methyl)piperidine-1-carboxylate (1s,3s)-3-((tert-butoxycarbonyl)amino)cyclobutyl methanesulfonate to give the title compound (38%).

Step C: Preparation of tert-butyl ((1r,3r)-3-((5-(3-(5-(methoxymethyl)-2-(trifluoromethoxy)benzyl)ureido)-4-methyl-1-phenyl-1H-pyrazol-3-yl)oxy)cyclobutyl)carbamate Prepared according to the procedure of Example 1, substituting 4-methyl-3-(2-methylpyrimidin-5-yl)-1-phenyl- 1H-pyrazol-5-amine with ((1r,3r)-3-((5-amino-4-methyl-1-phenyl-1H-pyrazol-3-yl)oxy)cyclobutyl)carbamate and (2-cyclopropyl-5-(methoxymethyl)phenyl)methanamine with (5-(methoxymethyl)-2-(trifluoromethoxy)phenyl)methanamine to give the title compound (56%).

Step D: Preparation of 1-(3-((1r,3r)-3-aminocyclobutoxy)-4-methyl-1-phenyl-1H-pyrazol-5-yl)-3-(5-(methoxymethyl)-2-(trifluoromethoxy)benzyl)urea Prepared according to the procedure of Example 66, Step B, substituting tert-butyl 4-(5-(3-(5-(methoxymethyl)-2-(trifluoromethoxy)benzyl)ureido)-4-methyl-1-phenyl-1H-pyrazol-3-yl)piperidine-1-carboxylate with tert-butyl ((1r,3r)-3-((5-(3-(5-(methoxymethyl)-2-(trifluoromethoxy)benzyl)ureido)-4-methyl-1-phenyl-1H-pyrazol-3-yl)oxy)cyclobutyl)carbamate to give the title compound (28%). MS (APCI) m/z=520.2 (M+H).

Example 101

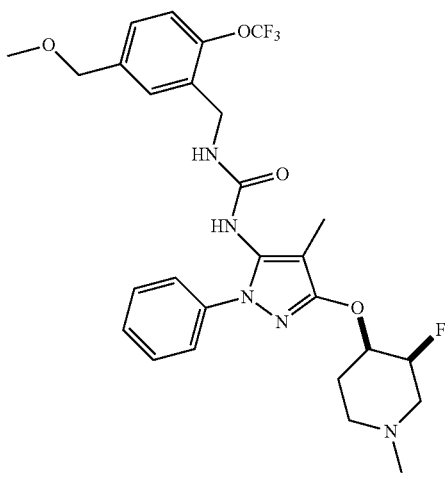

1-(3-(((3S,4R)-3-fluoro-1-methylpiperidin-4-yl)oxy)-4-methyl-1-phenyl-1H-pyrazol-5-yl)-3-(5-(methoxymethyl)-2-(trifluoromethoxy)benzyl)urea Prepared according to the procedure of Example 75, Step A, substituting 1-(3-(azetidin-3-ylmethoxy)-4-methyl-1-phenyl-1H-pyrazol-5-yl)-3-(5-(methoxymethyl)-2-(trifluoromethoxy)benzyl)urea with 1-(3-(((3S,4R)-3-fluoropiperidin-4-yl)oxy)-4-methyl-1-phenyl-1H-pyrazol-5-yl)-3-(5-(methoxymethyl)-2-(trifluoromethoxy)benzyl)urea (Example 99), to give the title compound (46%). MS (APCI) m/z=566.3 (M+H).

Example 102

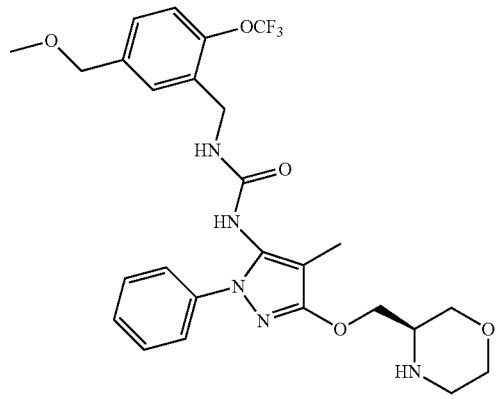 [SMILES: COCc1ccc(OC(F)(F)F)c(CNC(=O)Nc2c(C)c(OC[C@H]3COCCN3)nn2-c2ccccc2)c1]

(R)-1-(5-(methoxymethyl)-2-(trifluoromethoxy)benzyl)-3-(4-methyl-3-(morpholin-3-ylmethoxy)-1-phenyl-1H-pyrazol-5-yl)urea Step A: Preparation of (R)-tert-butyl 3-(((methylsulfonyl)oxy)methyl)morpholine-4-carboxylate Prepared according to the procedure of Example 72, Step B, substituting tert-butyl 4-fluoro-4-(hydroxymethyl)piperidine-1-carboxylate with (S)-tert-butyl 3-(hydroxymethyl)morpholine-4-carboxylate to give the title compound (94%).

Step B: Preparation of (R)-tert-butyl 3-(((5-amino-4-methyl-1-phenyl-1H-pyrazol-3-yl)oxy)methyl)morpholine-4-carboxylate Prepared according to the procedure of Example 67, Step A, substituting tert-butyl 4-(((methylsulfonyl)oxy)methyl)piperidine-1-carboxylate with (R)-tert-butyl 3-(((methylsulfonyl)oxy)methyl)morpholine-4-carboxylate to give the title compound (16%).

Step C: Preparation of (R)-tert-butyl 3-(((5-(3-(5-(methoxymethyl)-2-(trifluoromethoxy)benzyl)ureido)-4-methyl-1-phenyl-1H-pyrazol-3-yl)oxy)methyl)morpholine-4-carboxylate Prepared according to the procedure of Example 1, substituting 4-methyl-3-(2-methylpyrimidin-5-yl)-1-phenyl-1H-pyrazol-5-amine with (R)-tert-butyl 3-(((5-amino-4-methyl-1-phenyl-1H-pyrazol-3-yl)oxy)methyl)morpholine-4-carboxylate and (2-cyclopropyl-5-(methoxymethyl)phenyl)methanamine with (5-(methoxymethyl)-2-(trifluoromethoxy)phenyl)methanamine to give the title compound (20%).

Step D: Preparation of (R)-1-(5-(methoxymethyl)-2-(trifluoromethoxy)benzyl)-3-(4-methyl-3-(morpholin-3-ylmethoxy)-1-phenyl-1H-pyrazol-5-yl)urea Prepared according to the procedure of Example 66, Step B, substituting tert-butyl 4-(5-(3-(5-(methoxymethyl)-2-(trifluoromethoxy)benzyl)ureido)-4-methyl-1-phenyl-1H-pyrazol-3-yl)piperidine-1-carboxylate with (R)-tert-butyl 3-(((5-(3-(5-(methoxymethyl)-2-(trifluoromethoxy)benzyl)ureido)-4-methyl-1-phenyl-1H-pyrazol-3-yl)oxy)methyl)

morpholine-4-carboxylate to give the title compound (10%). MS (APCI) m/z=550.3 (M+H).

Example 103

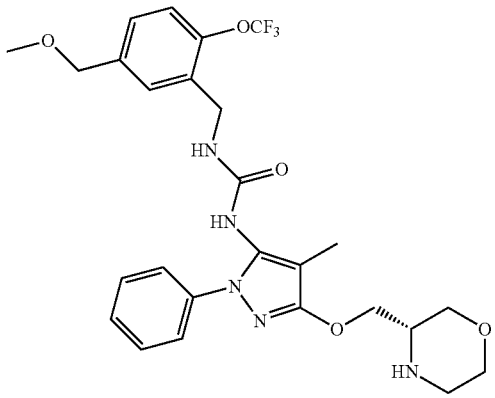 [SMILES: COCc1ccc(OC(F)(F)F)c(CNC(=O)Nc2c(C)c(OC[C@@H]3COCCN3)nn2-c2ccccc2)c1]

(S)-1-(5-(methoxymethyl)-2-(trifluoromethoxy)benzyl)-3-(4-methyl-3-(morpholin-3-ylmethoxy)-1-phenyl-1H-pyrazol-5-yl)urea Step A: Preparation of (S)-tert-butyl 3-(((methylsulfonyl)oxy)methyl)morpholine-4-carboxylate Prepared according to the procedure of Example 72, Step B, substituting tert-butyl 4-fluoro-4-(hydroxymethyl)piperidine-1-carboxylate with (R)-tert-butyl 3-(hydroxymethyl)morpholine-4-carboxylate to give the title compound (94%).

Step B: Preparation of (S)-tert-butyl 3-(((5-amino-4-methyl-1-phenyl-1H-pyrazol-3-yl)oxy)methyl)morpholine-4-carboxylate Prepared according to the procedure of Example 67, Step A, substituting tert-butyl 4-(((methylsulfonyl)oxy)methyl)piperidine-1-carboxylate with (5)-tert-butyl 3-(((methylsulfonyl)oxy)methyl)morpholine-4-carboxylate to give the title compound (19%).

Step C: Preparation of (S)-tert-butyl 3-(((5-(3-(5-(methoxymethyl)-2-(trifluoromethoxy)benzyl)ureido)-4-methyl-1-phenyl-1H-pyrazol-3-yl)oxy)methyl)morpholine-4-carboxylate Prepared according to the procedure of Example 1, substituting 4-methyl-3-(2-methylpyrimidin-5-yl)-1-phenyl-1H-pyrazol-5-amine with (S)-tert-butyl 3-(((5-amino-4-methyl-1-phenyl-1H-pyrazol-3-yl)oxy)methyl)morpholine-4-carboxylate and (2-cyclopropyl-5-(methoxymethyl)phenyl)methanamine with (5-(methoxymethyl)-2-(trifluoromethoxy)phenyl)methanamine to give the title compound (51%).

Step D: Preparation of (S)-1-(5-(methoxymethyl)-2-(trifluoromethoxy)benzyl)-3-(4-methyl-3-(morpholin-3-ylmethoxy)-1-phenyl-1H-pyrazol-5-yl)urea Prepared according to the procedure of Example 66, Step B, substituting tert-butyl 4-(5-(3-(5-(methoxymethyl)-2-(trifluoromethoxy)benzyl)ureido)-4-methyl-1-phenyl-1H-pyrazol-3-yl)piperidine-1-carboxylate with (S)-tert-butyl 3-(((5-(3-(5-(methoxymethyl)-2-(trifluoromethoxy)benzyl)ureido)-4-methyl-1-phenyl-1H-pyrazol-3-yl)oxy)methyl)morpholine-4-carboxylate to give the title compound (39%). MS (APCI) m/z=550.3 (M+H).

Example 104

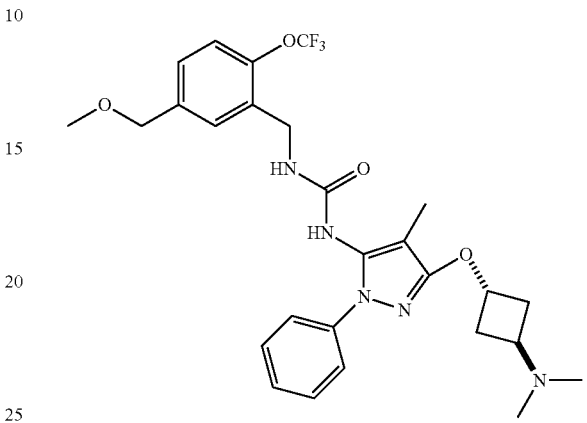

1-(3-((1r,3r)-3-(dimethylamino)cyclobutoxy)-4-methyl-1-phenyl-1H-pyrazol-5-yl)-3-(5-(methoxymethyl)-2-(trifluoromethoxy)benzyl)urea Prepared according to the procedure of Example 75, Step A, substituting 1-(3-(azetidin-3-ylmethoxy)-4-methyl-1-phenyl-1H-pyrazol-5-yl)-3-(5-(methoxymethyl)-2-(trifluoromethoxy)benzyl)urea with 1-(3-((1r,3r)-3-aminocyclobutoxy)-4-methyl-1-phenyl-1H-pyrazol-5-yl)-3-(5-(methoxymethyl)-2-(trifluoromethoxy)benzyl)urea (Example 100) to give the title compound (20%). MS (APCI) m/z=548.3 (M+H).

Example 105

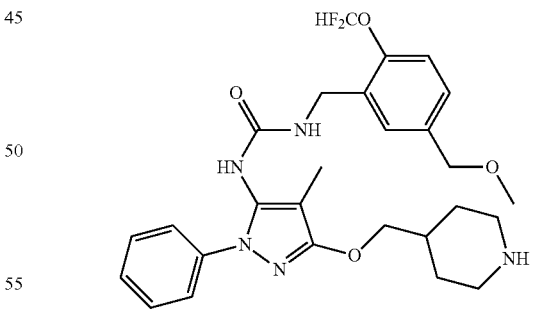

1-(2-(difluoromethoxy)-5-(methoxymethyl)benzyl)-3-(4-methyl-1-phenyl-3-(piperidin-4-ylmethoxy)-1H-pyrazol-5-yl)urea Step A: Preparation of 2-(5-bromo-2-(difluoromethoxy)phenyl)-1,3-dioxolane A round bottom flask equipped with a Dean-Stark trap and condenser was charged with 5-bromo-2-(difluoromethoxy)

benzaldehyde (2.91 g, 11.6 mmol) and 58 mL of toluene. To this was added ethane-1,2-diol (0.72 g, 11.6 mmol) and p-TsOH.H$_2$O (22 mgs, 0.116 mmol). The mixture was heated to reflux and stirred for 6 hours. The mixture was allowed to cool to ambient temperature concentrated under reduced pressure. The resulting crude material was taken up in DCM, washed with 10% aqueous potassium carbonate, dried over sodium sulfate and concentrated under reduced pressure to give the title compound as an oil (92%).

Step B: Preparation of 2-(2-(difluoromethoxy)-5-vinylphenyl)-1,3-dioxolane

A round bottom flask equipped with a condenser was charged with 2-(5-bromo-2-(difluoromethoxy)phenyl)-1,3-dioxolane (2.1 g, 7.12 mmol) and 70 mL of THF. To this was added potassium vinyltrifluoroborate (1.91 g, 14.2 mmol), triphenylphospine (112 mgs, 0.427 mmol), PdCl$_2$ (25 mgs, 0.142 mmol) and aqueous cesium carbonate (10.7 mL, 21.4 mmol, 2M in water). The mixture was heated to reflux for 16 hours then allowed to cool to ambient temperature. The mixture was diluted with water and extracted with EtOAc. The combined organic extracts were dried over sodium sulfate and concentrated under reduced pressure to give the crude product. The crude material was purified by passing it through an 80 g Redi Sep column, eluting with 10% ethyl acetate/hexane, to give the title compound (43%).

Step C: Preparation of 4-(difluoromethoxy)-3-(1,3-dioxolan-2-yl)benzaldehyde

A round bottom flask equipped with a plastic cap was charged with 2-(2-(difluoromethoxy)-5-vinylphenyl)-1,3-dioxolane (0.970 g, 4.00 mmol) and 40 mL of dry DCM. The mixture was cooled to −78° C. and ozone was bubbled through the solution for about 30 minutes until a persistent blue color was observed. The ozone was then purged from the mixture by bubbling nitrogen through the solution for about 5 minutes. PS-triphenylphosine (5.27 g, 12 mmol, 2.28 mmol/g) was then added followed by 25 mL of DCM, and the mixture was allowed to warm to ambient temperature. After stirring for 20 minutes at ambient temperature, the mixture was filtered. The resin was rinsed multiple times with DCM and the filtrate was concentrated under reduced pressure. This material was purified by passing it through a 40 g Redi Sep column, eluting with 35% ethyl acetate/hexane to give the title compound (60%).

Step D: Preparation of (4-(difluoromethoxy)-3-(1,3-dioxolan-2-yl)phenyl)methanol A round bottom flask equipped with a stir and nitrogen inlet was charged with 4-(difluoromethoxy)-3-(1,3-dioxolan-2-yl)benzaldehyde (0.590 g, 2.42 mmol) and 24 mL of methanol. This mixture was cooled to 0° C. and sodium borohydride (0.183 g, 4.83 mmol) was added. The mixture was stirred at 0° C. for 2 hours. The mixture was quenched with saturated ammonium chloride solution (50 mL). Water (50 mL) was added and the mixture was extracted with EtOAc. The combined organic extracts were dried over sodium sulfate and concentrated under reduced pressure to give the title compound (86%).

Step E: Preparation of 2-(2-(difluoromethoxy)-5-(methoxymethyl)phenyl)-1,3-dioxolane A round bottom containing (4-(difluoromethoxy)-3-(1,3-dioxolan-2-yl)phenyl)methanol (0.510 g, 2.07 mmol) was charged with dry THF (21 mL) under a nitrogen atmosphere. This mixture was cooled to 0° C. and sodium hydride (0.166 g, 4.14 mmol, 60% dispersion is mineral oil) was added in one portion and the mixture was stirred at 0° C. for 20 minutes. Methyl iodide (0.882 g, 6.21 mmol) was added and the mixture was allowed to warm to ambient temperature. After 1.5 hours the mixture was carefully quenched with saturated ammonium chloride solution (50 mL). Water (50 mL) was added and the mixture was extracted with EtOAc. The combined organic extracts were dried over sodium sulfate and concentrated under reduced pressure to the title compound (100%).

Step F: Preparation of 2-(difluoromethoxy)-5-(methoxymethyl)benzaldehyde

A round bottom flask was charged with 2-(2-(difluoromethoxy)-5-(methoxymethyl)phenyl)-1,3-dioxolane (0.59 g, 2.27 mmol) and acetone (23 mL). To this was added concentrated HCl (0.189 mL, 2.27 mmol) and the mixture was allowed to stir at ambient temperature for 16 hours. The mixture was diluted with 50 mL of EtOAc, washed with 10% aqueous potassium carbonate solution, dried over sodium sulfate and concentrated under reduced pressure. The resulting crude material was passed through an 80 g Redi Sep column, eluting with 20% ethyl acetate/hexane, to give the title compound (40%).

Step G: Preparation of (E)-2-(difluoromethoxy)-5-(methoxymethyl)benzaldehyde oxime Prepared according to Preparation G, Step B, substituting 5-(methoxymethyl)-2-(trifluoromethoxy)benzaldehyde with 2-(difluoromethoxy)-5-(methoxymethyl)benzaldehyde, to give the title compound (84%).

Step H: Preparation of (2-(difluoromethoxy)-5-(methoxymethyl)phenyl)methanamine

Prepared according to Preparation G, Step C, substituting 5-(methoxymethyl)-2-(trifluoromethoxy)benzaldehyde oxime with (E)-2-(difluoromethoxy)-5-(methoxymethyl) benzaldehyde oxime to give the title compound (84%).

Step I: Preparation of tert-butyl 4-(((5-(3-(2-(difluoromethoxy)-5-(methoxymethyl)benzyl)ureido)-4-methyl-1-phenyl-1H-pyrazol-3-yl)oxy)methyl)piperidine-1-carboxylate Prepared according to the procedure of Example 1, substituting 4-methyl-3-(2-methylpyrimidin-5-yl)-1-phenyl-1H-pyrazol-5-amine with tert-butyl 4-(((5-amino-4-methyl-1-phenyl-1H-pyrazol-3-yl)oxy)methyl)piperidine-1-carboxylate and (2-cyclopropyl-5-(methoxymethyl)phenyl) methanamine with (2-(difluoromethoxy)-5-(methoxymethyl)phenyl)methanamine to give the title compound (53%).

Step J: Preparation of 1-(2-(difluoromethoxy)-5-(methoxymethyl)benzyl)-3-(4-methyl-1-phenyl-3-(piperidin-4-ylmethoxy)-1H-pyrazol-5-yl)urea Prepared according to the procedure of Example 66, Step B, substituting tert-butyl 4-(5-(3-(5-(methoxymethyl)-2-(trifluoromethoxy)benzyl)ureido)-4-methyl-1-phenyl-1H-pyrazol-3-yl)piperidine-1-carboxylate with tert-butyl 4-(((5-(3-(2-(difluoromethoxy)-5-(methoxymethyl)benzyl)ureido)-4- methyl-1-phenyl-1H-pyrazol-3-yl)oxy)methyl)piperidine-1-carboxylate to give the title compound (6%). MS (APCI) m/z=530.3 (M+H).

Example 106

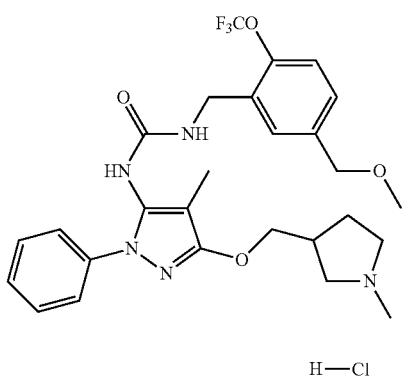 [SMILES: COCc1ccc(OC(F)(F)F)c(CNC(=O)Nc2c(C)c(OCC3CCN(C)C3)nn2-c2ccccc2)c1 ; Cl]

1-(5-(methoxymethyl)-2-(trifluoromethoxy)benzyl)-3-(4-methyl-3-((1-methylpyrrolidin-3-yl)methoxy)-1-phenyl-1H-pyrazol-5-yl)urea hydrochloride Prepared according to the procedure of Example 75, Step A, substituting 1-(3-(azetidin-3-ylmethoxy)-4-methyl-1-phenyl-1H-pyrazol-5-yl)-3-(5-(methoxymethyl)-2-(trifluoromethoxy)benzyl)urea with 1-(5-(methoxymethyl)-2-(trifluoromethoxy)benzyl)-3-(4-methyl-1-phenyl-3-(pyrrolidin-3-ylmethoxy)-1H-pyrazol-5-yl)urea (Example 71). The crude material was then stirred with 5 mL of 6M HCl/IPA for 3 hours and concentrated under reduced pressure to give the title compound (33%). MS (APCI) m/z=548.3 (M+H).

Example 107

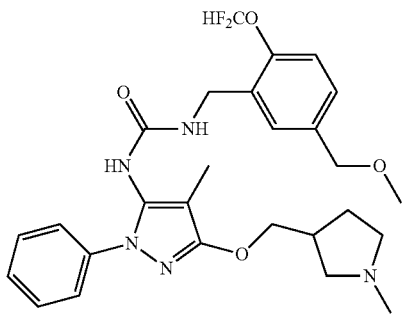

1-(2-(difluoromethoxy)-5-(methoxymethyl)benzyl)-3-(4-methyl-3-((1-methylpyrrolidin-3-yl)methoxy)-1-phenyl-1H-pyrazol-5-yl)urea Step A: Preparation of tert-butyl 3-(((5-(3-(2-(difluoromethoxy)-5-(methoxymethyl)benzyl)ureido)-4-methyl-1-phenyl-1H-pyrazol-3-yl)oxy)methyl)pyrrolidine-1-carboxylate Prepared according to the procedure of Example 1, substituting 4-methyl-3-(2-methylpyrimidin-5-yl)-1-phenyl-1H-pyrazol-5-amine with tert-butyl 3-4(5-amino-4-methyl-1-phenyl-1H-pyrazol-3-yl)oxy)methyl)pyrrolidine-1-carboxylate (Example 71) and (2-cyclopropyl-5-(methoxymethyl)phenyl)methanamine with (2-(difluoromethoxy)-5-(methoxymethyl)phenyl)methanamine to give the title compound (46%).

Step B: Preparation of 1-(2-(difluoromethoxy)-5-(methoxymethyl)benzyl)-3-(4-methyl-1-phenyl-3-(pyrrolidin-3-ylmethoxy)-1H-pyrazol-5-yl)urea Prepared according to the procedure of Example 66, Step B, substituting tert-butyl 4-(5-(3-(5-(methoxymethyl)-2-(trifluoromethoxy)benzyl)ureido)-4-methyl-1-phenyl-1H-pyrazol-3-yl)piperidine-1-carboxylate with tert-butyl 3-(((5-(3-(2-(difluoromethoxy)-5-(methoxymethyl)benzyl)ureido)-4-methyl-1-phenyl-1H-pyrazol-3-yl)oxy)methyl)pyrrolidine-1-carboxylate to give the title compound (9%).

Step C: Preparation of 1-(2-(difluoromethoxy)-5-(methoxymethyl)benzyl)-3-(4-methyl-3-((1-methylpyrrolidin-3-yl)methoxy)-1-phenyl-1H-pyrazol-5-yl)urea Prepared according to the procedure of Example 75, Step A, substituting 1-(3-(azetidin-3-ylmethoxy)-4-methyl-1-phenyl-1H-pyrazol-5-yl)-3-(5-(methoxymethyl)-2-(trifluoromethoxy)benzyl)urea with 1-(2-(difluoromethoxy)-5-(methoxymethyl)benzyl)-3-(4-methyl-1-phenyl-3-(pyrrolidin-3-ylmethoxy)-1H-pyrazol-5-yl)urea to give the title compound (39%). MS (APCI) m/z=530.3 (M+H).

Example 108

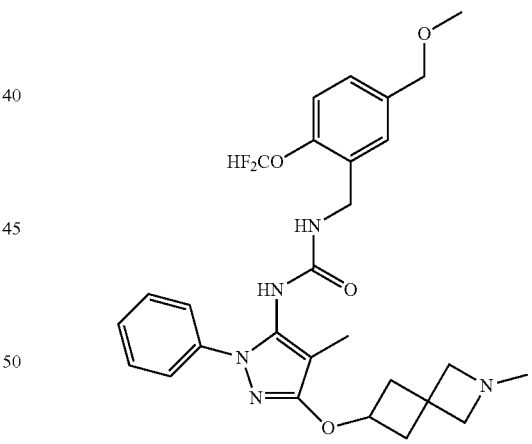

1-(2-(difluoromethoxy)-5-(methoxymethyl)benzyl)-3-(4-methyl-3-((2-methyl-2-azaspiro[3.3]heptan-6-yl)oxy)-1-phenyl-1H-pyrazol-5-yl)urea Step A: Preparation of tert-butyl 6-((5-(3-(2-(difluoromethoxy)-5-(methoxymethyl)benzyl)ureido)-4-methyl-1-phenyl-1H-pyrazol-3-yl)oxy)-2-azaspiro[3.3]heptane-2-carboxylate Prepared according to the procedure of Example 1, substituting 4-methyl-3-(2-methylpyrimidin-5-yl)-1-phenyl-1H-pyrazol-5-amine tert-butyl 6-((5-amino-4-methyl-1-phenyl-1H-pyrazol-3-yl)oxy)-2-azaspiro[3.3]heptane-2-carboxylate (Example 79) and (2-cyclopropyl-5-(methoxymethyl)phenyl)methanamine with (2-(difluoromethoxy)-5-(methoxymethyl)phenyl)methanamine to give the title compound (20%).

Step B: Preparation of 1-(3-(2-azaspiro[3.3]heptan-6-yloxy)-4-methyl-1-phenyl-1H-pyrazol-5-yl)-3-(2-(difluoromethoxy)-5-(methoxymethyl)benzyl)urea Prepared according to the procedure of Example 66, Step B, substituting tert-butyl 4-(5-(3-(5-(methoxymethyl)-2-(trifluoromethoxy)benzyl)ureido)-4-methyl-1-phenyl-1H-pyrazol-3-yl)piperidine-1-carboxylate with tert-butyl 6-((5-(3-(2-(difluoromethoxy)-5-(methoxymethyl)benzyl)ureido)-4-methyl-1-phenyl-1H-pyrazol-3-yl)oxy)-2 azaspiro[3.3]heptane-2-carboxylate to give the title compound (89%).

Step C: Preparation of 1-(2-(difluoromethoxy)-5-(methoxymethyl)benzyl)-3-(4-methyl-3-((2-methyl-2-azaspiro[3.3]heptan-6-yl)oxy)-1-phenyl-1H-pyrazol-5-yl)urea Prepared according to the procedure of Example 75, Step A, substituting 1-(3-(azetidin-3-ylmethoxy)-4-methyl-1-phenyl-1H-pyrazol-5-yl)-3-(5-(methoxymethyl)-2-(trifluoromethoxy)benzyl)urea with tert-butyl 6-((5-(3-(2-(difluoromethoxy)-5-(methoxymethyl)benzyl)ureido)-4-methyl-1-phenyl-1H-pyrazol-3-yl)oxy)-2 azaspiro[3.3]heptane-2-carboxylate to give the title compound (33%). MS (APCI) m/z 542.3 (M+H).

Example 109

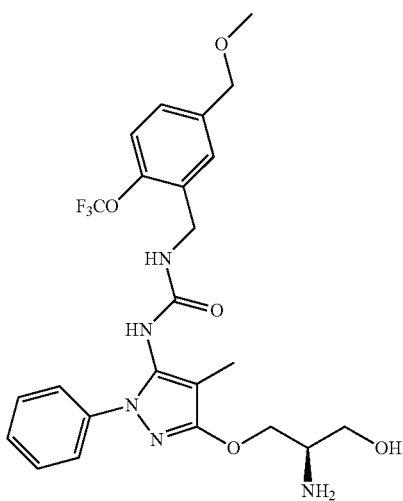 [SMILES: COCc1ccc(OC(F)(F)F)c(CNC(=O)Nc2c(C)c(OC[C@H](N)CO)nn2-c2ccccc2)c1]

(R)-1-(3-(2-amino-3-hydroxypropoxy)-4-methyl-1-phenyl-1H-pyrazol-5-yl)-3-(5-(methoxymethyl)-2-(trifluoromethoxy)benzyl)urea Step A: Preparation of (R)-3-(benzyloxy)-2-((tert-butoxycarbonyl)amino)propyl methanesulfonate Prepared according to the procedure of Example 72, Step B, substituting tert-butyl 4-fluoro-4-(hydroxymethyl)piperidine-1-carboxylate with (S)-tert-butyl (1-(benzyloxy)-3-hydroxypropan-2-yl)carbamate to give the title compound (100%).

Step B: Preparation of (R)-tert-butyl (1-((5-amino-4-methyl-1-phenyl-1H-pyrazol-3-yl)oxy)-3-(benzyloxy)propan-2-yl)carbamate Prepared according to the procedure of Example 67, Step A, substituting tert-butyl 4-(((methylsulfonyl)oxy)methyl)piperidine-1-carboxylate with (R)-3-(benzyloxy)-2-((tert-butoxycarbonyl)amino)propyl methanesulfonate to give the title compound (33%).

Step C: Preparation of (R)-tert-butyl (1-(benzyloxy)-3-((5-(3-(5-(methoxymethyl)-2-(trifluoromethoxy)benzyl)ureido)-4-methyl-1-phenyl-1H-pyrazol-3-yl)oxy)propan-2-yl)carbamate Prepared according to the procedure of Example 1, substituting 4-methyl-3-(2-methylpyrimidin-5-yl)-1-phenyl-1H-pyrazol-5-amine with (R)-tert-butyl (1-((5-amino-4-methyl-1-phenyl-1H-pyrazol-3-yl)oxy)-3-(benzyloxy)propan-2-yl)carbamate and (2-cyclopropyl-5-(methoxymethyl)phenyl)methanamine with (5-(methoxymethyl)-2-(trifluoromethoxy)phenyl)methanamine to give the title compound (61%).

Step D: Preparation of (R)-1-(3-(2-amino-3-(benzyloxy)propoxy)-4-methyl-1-phenyl-1H-pyrazol-5-yl)-3-(5-(methoxymethyl)-2-(trifluoromethoxy)benzyl)urea hydrochloride A round bottom flask was charged with (R)-tert-butyl (1-(benzyloxy)-3-((5-(3-(5-(methoxymethyl)-2-(trifluoromethoxy)benzyl)ureido)-4-methyl-1-phenyl-1H-pyrazol-3-yl)oxy)propan-2-yl)carbamate (0.100 g, 0.140 mmol) and 10 mL of 6M HCl/IPA. This mixture was stirred at ambient temperature for 2 hours, and then concentrated under reduced pressure to give the title compound (100%).

Step E: Preparation of (R)-1-(3-(2-amino-3-hydroxypropoxy)-4-methyl-1-phenyl-1H-pyrazol-5-yl)-3-(5-(methoxymethyl)-2-(trifluoromethoxy)benzyl)urea A round bottom flask was charged with (R)-1-(3-(2-amino-3-(benzyloxy)propoxy)-4-methyl-1-phenyl-1H-pyrazol-5-yl)-3-(5-(methoxymethyl)-2-(trifluoromethoxy)benzyl)urea hydrochloride (0.091 g, 0.140 mmol) and 1.5 mL of MeOH. To this was added 10% Pd/C (90 mgs, 1 weight eq.). This mixture was stirred at ambient temperature under an atmosphere of hydrogen for 16 hours, then filtered through GF/F filter paper. The filtrate was concentrated under reduced pressure and the resulting crude material was purified by reverse phase HPLC. The fractions containing the product were combined in 2M aqueous NaOH and extracted with 25% IPA/DCM. The combined organic extracts were dried over sodium sulfate, filtered and concentrated under reduced pressure to give the title compound (25%). MS (APCI) m/z=524.3 (M+H).

Example 110

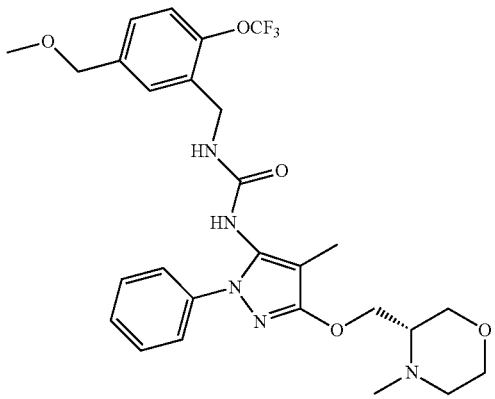 [SMILES: COCc1ccc(OC(F)(F)F)c(CNC(=O)Nc2c(C)c(OC[C@@H]3COCCN3C)nn2-c2ccccc2)c1]

(S)-1-(5-(methoxymethyl)-2-(trifluoromethoxy)benzyl)-3-(4-methyl-3-((4-methylmorpholin-3-yl)methoxy)-1-phenyl-1H-pyrazol-5-yl)urea Prepared according to the procedure of Example 75, Step A, substituting 1-(3-(azetidin-3-ylmethoxy)-4-methyl-1-phenyl-1H-pyrazol-5-yl)-3-(5-(methoxymethyl)-2-(trifluoromethoxy)benzyl)urea with (S)-1-(5-(methoxymethyl)-2-(trifluoromethoxy)benzyl)-3-(4-methyl-3-(morpholin-3-ylmethoxy)-1-phenyl-1H-pyrazol-5-yl)urea to give the title compound (25%). MS (APCI) m/z=564.3 (M+H).

Example 111

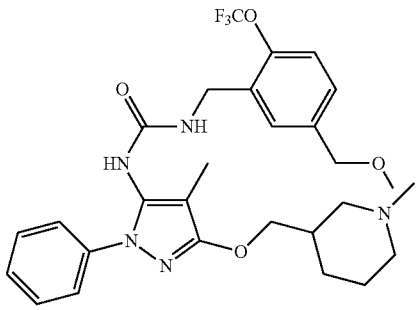 [SMILES: COCc1ccc(OC(F)(F)F)c(CNC(=O)Nc2c(C)c(OCC3CCCN(C)C3)nn2-c2ccccc2)c1]

1-(5-(methoxymethyl)-2-(trifluoromethoxy)benzyl)-3-(4-methyl-3-((1-methylpiperidin-3-yl)methoxy)-1-phenyl-1H-pyrazol-5-yl)urea Step A: Preparation tert-butyl 3-(((5-amino-4-methyl-1-phenyl-1H-pyrazol-3-yl)oxy)methyl)piperidine-1-carboxylate Prepared according to the procedure of Example 67, Step A, substituting tert-butyl 4-(((methylsulfonyl)oxy)methyl) piperidine-1-carboxylate with tert-butyl 3-(((methylsulfonyl)oxy)methyl)piperidine-1-carboxylate to give the title compound (55%).

Step B: Preparation of tert-butyl 3-(((5-(3-(5-(methoxymethyl)-2-(trifluoromethoxy)benzyl)ureido)-4-methyl-1-phenyl-1H-pyrazol-3-yl)oxy)methyl)piperidine-1-carboxylate Prepared according to the procedure of Example 1, substituting 4-methyl-3-(2-methylpyrimidin-5-yl)-1-phenyl-1H-pyrazol-5-amine with tert-butyl 3-(((5-amino-4-methyl-1-phenyl-1H-pyrazol-3-yl)oxy)methyl)piperidine-1-carboxylate and (2-cyclopropyl-5-(methoxymethyl)phenyl) methanamine with (5-(methoxymethyl)-2-(trifluoromethoxy)phenyl)methanamine to give the title compound (57%).

Step C: Preparation of 1-(5-(methoxymethyl)-2-(trifluoromethoxy)benzyl)-3-(4-methyl-1-phenyl-3-(piperidin-3-ylmethoxy)-1H-pyrazol-5-yl)urea Prepared according to the procedure of Example 66, Step B, substituting tert-butyl 4-(5-(3-(5-(methoxymethyl)-2-(trifluoromethoxy)benzyl)ureido)-4-methyl-1-phenyl-1H-pyrazol-3-yl)piperidine-1-carboxylate with tert-butyl 3-(((5-(3-(5-(methoxymethyl)-2-(trifluoromethoxy)benzyl)ureido)-4-methyl-1-phenyl-1H-pyrazol-3-yl)oxy)methyl)piperidine-1-carboxylate to give the title compound (49%).

Step D: Preparation of 1-(5-(methoxymethyl)-2-(trifluoromethoxy)benzyl)-3-(4-methyl-3-(1-methylpiperidin-3-yl)methoxy)-1-phenyl-1H-pyrazol-5-yl) urea Prepared according to the procedure of Example 75, Step A, substituting 1-(3-(azetidin-3-ylmethoxy)-4-methyl-1-phenyl-1H-pyrazol-5-yl)-3-(5-(methoxymethyl)-2-(trifluoromethoxy)benzyl)urea with 1-(5-(methoxymethyl)-2-(trifluoromethoxy)benzyl)-3-(4-methyl-1-phenyl-3-(piperidin-3-ylmethoxy)-1H-pyrazol-5-yl)urea to give the title compound (22%). MS (APCI) m/z=562.3 (M+H).

Example 112

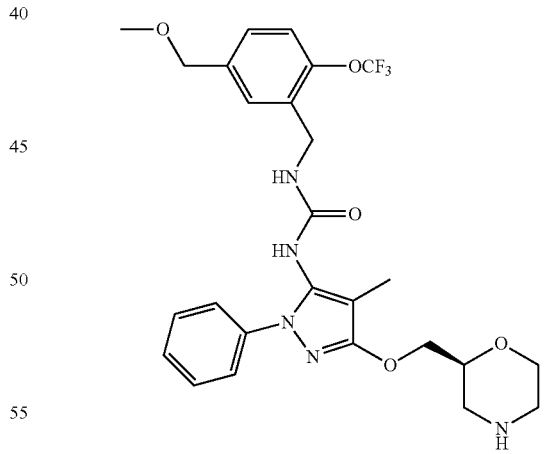

(S)-1-(5-(methoxymethyl)-2-(trifluoromethoxy)benzyl)-3-(4-methyl-3-(morpholin-2-ylmethoxy)-1-phenyl-1H-pyrazol-5-yl)urea Step A: Preparation of (S)-tert-butyl 2-(((methylsulfonyl)oxy)methyl)morpholine-4-carboxylate Prepared according to the procedure of Example 72, Step B, substituting tert-butyl 4-fluoro-4-(hydroxymethyl)piperidine-1-carboxylate with (S)-tert-butyl 2-(hydroxymethyl)morpholine-4-carboxylate to give the title compound (100%).

Step B: Preparation of (S)-tert-butyl 2-(((5-amino-4-methyl-1-phenyl-1H-pyrazol-3-yl)oxy)methyl)morpholine-4-carboxylate Prepared according to the procedure of Example 67, Step A, substituting tert-butyl 4-(((methylsulfonyl)oxy)methyl)piperidine-1-carboxylate with (S)-tert-butyl 2-(((methylsulfonyl)oxy)methyl)morpholine-4-carboxylate to give the title compound (30%).

Step C: Preparation of (S)-tert-butyl 2-(((5-(3-(5-(methoxymethyl)-2-(trifluoromethoxy)benzyl)ureido)-4-methyl-1-phenyl-1H-pyrazol-3-yl)oxy)methyl)morpholine-4-carboxylate Prepared according to the procedure of Example 1, substituting 4-methyl-3-(2-methylpyrimidin-5-yl)-1-phenyl-1H-pyrazol-5-amine with (S)-tert-butyl 2-(((5-amino-4-methyl-1-phenyl-1H-pyrazol-3-yl)oxy)methyl)morpholine-4-carboxylate and (2-cyclopropyl-5-(methoxymethyl)phenyl)methanamine with (5-(methoxymethyl)-2-(trifluoromethoxy)phenyl)methanamine to give the title compound (47%).

Step D: Preparation of (S)-1-(5-(methoxymethyl)-2-(trifluoromethoxy)benzyl)-3-(4-methyl-3-(morpholin-2-ylmethoxy)-1-phenyl-1H-pyrazol-5-yl)urea Prepared according to the procedure of Example 66, Step B, substituting tert-butyl 4-(5-(3-(5-(methoxymethyl)-2-(trifluoromethoxy)benzyl)ureido)-4-methyl-1-phenyl-1H-pyrazol-3-yl)piperidine-1-carboxylate with (S)-tert-butyl 2-(((5-(3-(5-(methoxymethyl)-2-(trifluoromethoxy)benzyl)ureido)-4-methyl-1-phenyl-1H-pyrazol-3-yl)oxy)methyl)morpholine-4-carboxylate to give the title compound (18%). MS (APCI) m/z=550.2 (M+H).

Example 113

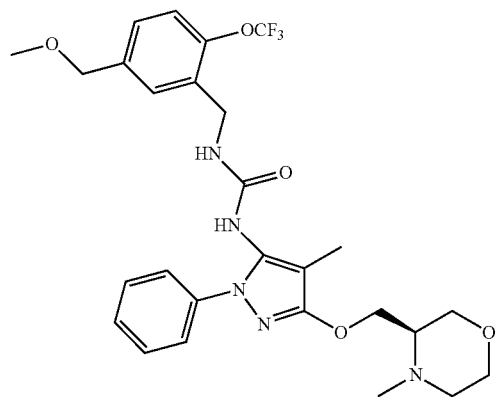 [SMILES: COCc1ccc(OC(F)(F)F)c(CNC(=O)Nc2c(C)c(OC[C@H]3COCCN3C)nn2-c2ccccc2)c1]

(R)-1-(5-(methoxymethyl)-2-(trifluoromethoxy)benzyl)-3-(4-methyl-3-(4-methylmorpholin-3-yl)methoxy)-1-phenyl-1H-pyrazol-5-yl)urea Prepared according to the procedure of Example 75, Step A, substituting 1-(3-(azetidin-3-ylmethoxy)-4-methyl-1-phenyl-1H-pyrazol-5-yl)-3-(5-(methoxymethyl)-2-(trifluoromethoxy)benzyl)urea with (R)-1-(5-(methoxymethyl)-2-(trifluoromethoxy)benzyl)-3-(4-methyl-3-(morpholin-3-ylmethoxy)-1-phenyl-1H-pyrazol-5-yl)urea to give the title compound (15%). MS (APCI) m/z=564.3 (M+H).

Example 114

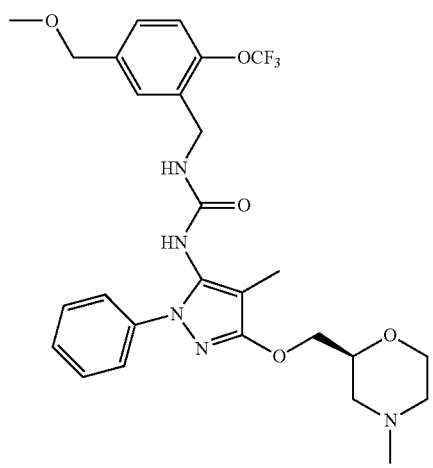 [SMILES: COCc1ccc(OC(F)(F)F)c(CNC(=O)Nc2c(C)c(OC[C@@H]3CN(C)CCO3)nn2-c2ccccc2)c1]

(S)-1-(5-(methoxymethyl)-2-(trifluoromethoxy)benzyl)-3-(4-methyl-3-((4-methylmorpholin-2-yl)methoxy)-1-phenyl-1H-pyrazol-5-yl)urea Prepared according to the procedure of Example 75, Step A, substituting 1-(3-(azetidin-3-ylmethoxy)-4-methyl-1-phenyl-1H-pyrazol-5-yl)-3-(5-(methoxymethyl)-2-(trifluoromethoxy)benzyl)urea with (S)-1-(5-(methoxymethyl)-2-(trifluoromethoxy)benzyl)-3-(4-methyl-3-(morpholin-2-ylmethoxy)-1 phenyl-1H-pyrazol-5-yl)urea to give the title compound (60%). MS (APCI) m/z=564.3 (M+H).

Example 115

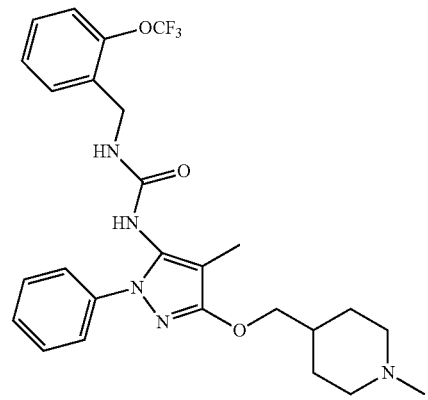 [SMILES: Cc1c(OCC2CCN(C)CC2)nn(-c2ccccc2)c1NC(=O)NCc1ccccc1OC(F)(F)F]

1-(4-methyl-3-((1-methylpiperidin-4-yl)methoxy)-1-phenyl-1H-pyrazol-5-yl)-3-(2-(trifluoromethoxy)benzyl)urea Step A: Preparation of tert-butyl 4-(((4-methyl-1-phenyl-5-(3-(2-(trifluoromethoxy)benzyl)ureido)-1H-pyrazol-3-yl)oxy)methyl)piperidine-1-carboxylate Prepared according to the procedure of Example 1, substituting 4-methyl-3-(2-methylpyrimidin-5-yl)-1-phenyl-1H-pyrazol-5-amine with tert-butyl 4-(((5-amino-4-methyl-1-phenyl-1H-pyrazol-3-yl)oxy)methyl)piperidine-1-carboxylate and (2-cyclopropyl-5-(methoxymethyl)phenyl)methanamine with (2-(trifluoromethoxy)phenyl)methanamine to give the title compound (52%).

Step B: Preparation of 1-(4-methyl-1-phenyl-3-(piperidin-4-ylmethoxy)-1H-pyrazol-5-yl)-3-(2-(trifluoromethoxy)benzyl)urea Prepared according to the procedure of Example 66, Step B, substituting tert-butyl 4-(5-(3-(5-(methoxymethyl)-2-(trifluoromethoxy)benzyl)ureido)-4-methyl-1-phenyl-1H-pyrazol-3-yl)piperidine-1-carboxylate with tert-butyl 4-(((4-methyl-1-phenyl-5-(3-(2-(trifluoromethoxy)benzyl)ureido)-1H-pyrazol-3-yl)oxy)methyl)piperidine-1-carboxylate to give the title compound (45%).

Step C: Preparation of 1-(4-methyl-3-((1-methylpiperidin-4-yl)methoxy)-1-phenyl-1H-pyrazol-5-yl)-3-(2-(trifluoromethoxy)benzyl)urea A microwave reaction vial was charged with the 1-(4-methyl-1-phenyl-3-(piperidin-4-ylmethoxy)-1H-pyrazol-5-yl)-3-(2-(trifluoromethoxy)benzyl)urea (0.059 g, 0.117 mmol) and 1 mL of methanol. To this was added a 37% aqueous solution of formaldehyde (0.0262 mL, 0.352 mmol) and formic acid (0.0221 mL, 0.586 mmol). The tube was sealed and warmed to 70° C. for 3 hours and then concentrated under reduced pressure. The crude material was purified by reverse phase preparative HPLC. The fractions containing the product were combined in 2M aqueous NaOH and extracted with 25% IPA/DCM. The combined organic extracts were dried over sodium sulfate and concentrated under reduced pressure to give the title compound (51%). MS (APCI) m/z=518.3 (M+H).

Example 116

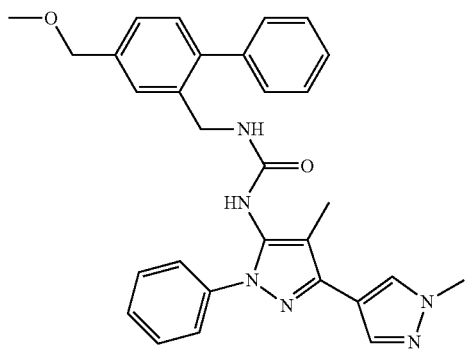

1-(1',4-dimethyl-1-phenyl-1H,1'H-[3,4'-bipyrazol]-5-yl)-3-((4-(methoxymethyl)-[1,1'-biphenyl]-2-yl)methyl)urea Step A: Preparation of 4-(methoxymethyl)[1,1'-biphenyl]-2-carbonitrile A vial was charged with phenylboronic acid (108 mg, 0.885 mmol), cesium carbonate (576 mg, 1.77 mmol), dicyclohexyl(2',6'-dimethoxy-[1,1'-biphenyl]-2-yl)phosphine (18 mg, 0.044 mmol), Pd(OAc)$_2$ (5 mg, 0.02 mmol), and 2-bromo-5-(methoxymethyl)benzonitrile (Preparation L, Step B; 100 mg, 0.442 mmol). 1:1 dioxane/water (2 mL) was added. The mixture was sparged with Ar, and then heated to 90° C. overnight. The mixture was partitioned between EtOAc and saturated aqueous NaHCO$_3$. The organic phase was separated and washed with aqueous with EtOAc. The combined organic phases were washed with brine, dried (MgSO$_4$), filtered, and concentrated. The crude material was purified by preparative TLC (2 mm thickness, R$_f$=0.48) eluting with 25% EtOAc/hexanes to provide the title compound (86 mg; 85%).

Step B: Preparation of (4-(methoxymethyl)-[1,1'-biphenyl]-2-yl)methanamine

A flask was charged with 4-(methoxymethyl)-[1,1'-biphenyl]-2-carbonitrile (86 mg, 0.39 mmol), MeOH (3 mL) and cobalt chloride hexahydrate (183 mg, 0.77 mmol). The mixture was degassed by vacuum purging with N$_2$ three times. The mixture was cooled in an ice bath under N$_2$ and NaBH$_4$ (146 mg, 3.9 mmol) was added. The mixture was stirred for 5 minutes in ice bath and then at ambient temperature for 2 hours. The mixture was quenched with saturated aqueous NH$_4$Cl (2-3 mL), then concentrated under vacuum. The crude material was diluted residue with 2N aqueous NaOH (10 mL) and DCM (10 mL). The biphasic solution was filtered through GF/F paper, rinsing with multiple portions of DCM. The phases were separated, and the aqueous phase was extracted with DCM (2×10 mL). Combined organic phases were dried (MgSO$_4$), filtered, and concentrated to provide the title compound (63 mg; 65%).

Step C: Preparation of 1-(1',4-dimethyl-1-phenyl-1H,1'H-[3,4'-bipyrazol]-5-yl)-3-((4-(methoxymethyl)-[1,1'-biphenyl]-2-yl)methyl)urea A vial was charged with phenyl (1',4-dimethyl-1-phenyl-1H,1'H-[3,4'-bipyrazol]-5-yl)carbamate (Intermediate 5; 49 mg, 0.13 mmol), 1,2-dichloroethane (0.5 mL), (4-(methoxymethyl)-[1,1'-biphenyl]-2-yl)methanamine (30 mg, 0.13 mmol), and N-ethyl-N-isopropylpropan-2-amine (69 μL, 0.40 mmol). The mixture was stirred over the weekend for convenience at ambient temperature. The crude material was purified by preparative TLC (1 mm thickness, R$_f$=0.29) eluting with 7.5% MeOH/DCM to provide the title compound (50 mg; 71%). MS m/z (APCI-pos) M+1=507.2.

Example 117

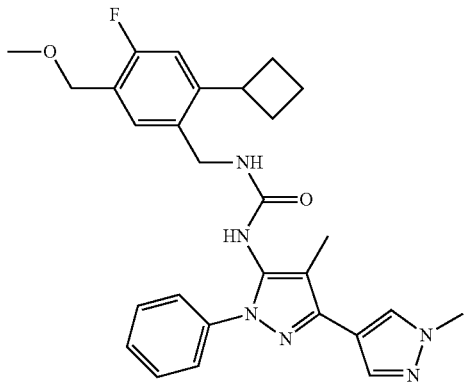

1-(2-cyclobutyl-4-fluoro-5-(methoxymethyl)benzyl)-
3-(1',4-dimethyl-1-phenyl-1H,1'H-[3,4'-bipyrazol]-5-
yl)urea Step A: Preparation of
2-amino-5-bromo-4-fluorobenzonitrile A flask was charged with 2-amino-4-fluorobenzonitrile (10.0 g, 73.5 mmol), DMF (100 mL), and 1-bromopyrrolidine-2,5-dione (13.7 g, 77.1 mmol). The mixture was heated to 100° C. for 2 hours. After cooling to ambient temperature, the mixture was partitioned between EtOAc (200 mL) and water (200 mL). The phases were separated, and the aqueous phase was extracted with EtOAc (100 mL). The combined organic phases were washed with water (100 mL), 10% aqueous sodium thiosulfate (100 mL), and brine (100 mL), dried (MgSO$_4$), filtered and concentrated to provide the title compound (16.1 g; 92%). The material was used in the next step without further purification.

Step B: Preparation of
2,5-dibromo-4-fluorobenzonitrile

To an open round bottomed flask containing a stirred suspension of 2-amino-5-bromo-4-fluorobenzonitrile (10.0 g, 46.5 mmol) in dioxane (20 mL) was added 48% aqueous hydrogen bromide (106 mL, 930 mmol). The mixture was cooled in an ice bath and sodium nitrite (3.53 g, 51.2 mmol) dissolved in water (15 mL) was carefully added dropwise over a 30 minute period, maintaining internal temperature below 3° C., resulting in much gas evolution. The mixture was stirred in an ice bath for 30 minutes, then carefully poured into a stirred mixture of copper(I) bromide (8.67 g, 60.5 mmol) and 48% aqueous HBr (50 mL) that was cooled in an ice bath, with some gas evolution. The mixture was stirred for 15 minutes in the ice bath, then at ambient temperature for 1 hour, and then heated to 50° C. for 1 hour. After cooling to ambient temperature, the mixture was diluted with water and extracted with 10% EtOAc/diethyl ether. The combined organic extracts were washed with 10% aqueous sodium thiosulfate solution (250 mL) and saturated aqueous NH$_4$Cl (250 mL), dried (MgSO$_4$), filtered, and concentrated. The crude product was passed through a Redi-Sep 330 silica gel column eluting with a gradient of hexanes to 10% EtOAc/hexanes. The isolated 10.7 g of an off-white solid was recrystallized twice by dissolving in hot hexanes (50 mL) and allowing solution to cool to ambient temperature, to provide the title compound (6.1 g; 45%).

Step C: Preparation of
2-bromo-4-fluoro-5-formylbenzonitrile

A flask was charged with isopropylmagnesium lithium chloride (18 mL, 24 mmol; 1.3 M in THF). The mixture was cooled to −30 to −40° C. (dry ice/acetonitrile slurry) under N$_2$. 2,5-Dibromo-4-fluorobenzonitrile (6.0 g, 22 mmol) dissolved in THF (30 mL) was added dropwise. The mixture was stirred for 1 hour at −30 to −40° C. N,N-dimethylformamide (5.0 mL, 65 mmol) was added dropwise. The reaction flask was removed from the cold bath and warmed to ambient temperature, and the mixture was stirred for 1 hour, then quenched with saturated aqueous NH$_4$Cl (30 mL) and diluted with EtOAc (30 mL). The phases were separated and the aqueous phase was extracted with EtOAc (30 mL). The combined organic phases were washed with water and brine, dried (MgSO$_4$), filtered, and concentrated. The crude material was passed through a Redi-Sep 330 silica gel column eluting with a gradient of 5%-20% EtOAc/hexanes to provide the title compound (1.3 g; 24%).

Step D: Preparation of
2-bromo-4-fluoro-5-(hydroxymethyl)benzonitrile

A flask was charged with 2-bromo-4-fluoro-5-formylbenzonitrile (1.4 g, 6.1 mmol) and anhydrous MeOH (20 mL). Sodium borohydride (0.47 g, 12 mmol) was added in portions. The mixture was stirred for an hour at ambient temperature and then concentrated under vacuum. Aqueous 1N HCl (20 mL) was added, and the mixture was extracted with EtOAc (3×20 mL). The combined organic phases were washed with brine, dried (MgSO$_4$), filtered, and concentrated to a solid. The crude material was taken up in aqueous 1N HCl (20 mL) and extracted into 10% EtOAc/diethyl ether (30 mL). The aqueous phase was extracted with 10% EtOAc/diethyl ether (20 mL). The combined organic phases were washed with aqueous 1N NaOH (20 mL), dried (MgSO$_4$), filtered, and concentrated to provide the title compound (1.26 g; 82%).

Step E: Preparation of
2-bromo-4-fluoro-5-(methoxymethyl)benzonitrile

A flask was charged with 2-bromo-4-fluoro-5-(hydroxymethyl)benzonitrile (0.96 g, 4.2 mmol), anhydrous acetonitrile (10 mL), iodomethane (0.78 mL, 13 mmol), and Ag$_2$O (1.45 g, 6.26 mmol). The flask was wrapped with Al foil and heated at 60° C. for 5 hours. Due to incomplete reaction, additional Ag$_2$O (500 mg) and iodomethane (250 µL) were added the mixture was heated at 60° C. for 2 hours, then cooled to ambient temperature. The reaction mixture was filtered through GF/F paper rinsing with DCM. The filtrate was concentrated under vacuum, and the crude material was dried under high vacuum to provide the title compound (1.02 g; 80%). The material was used in the next step without further purification.

Step F: Preparation of 2-cyclobutyl-4-fluoro-5-
(methoxymethyl)benzonitrile

A dry flask was charged with 2-bromo-4-fluoro-5-(methoxymethyl)benzonitrile (200 mg, 0.82 mmol), anhydrous THF (2 mL), dicyclohexyl(2',6'-dimethoxy-[1,1'-biphenyl]-2-yl)phosphine (34 mg, 0.082 mmol), and Pd(OAc)$_2$ (9 mg, 0.04 mmol). The mixture was sparged with N$_2$ for 3 minutes, then cooled in an ice bath under N$_2$. Cyclobutylzinc(II) bromide (2.5 mL, 1.2 mmol; 0.5 M in THF) was added over 5 minutes via syringe. The mixture was warmed to ambient temperature and stirred for 2 hours. The mixture was quenched with saturated aqueous NH$_4$Cl and extracted with EtOAc. The organic phase was washed with brine, dried (MgSO$_4$), filtered, and concentrated. The crude material was purified by preparative TLC (2 mm thickness, R$_f$=0.68) eluting with 25% EtOAc/hexanes to provide the title compound (82 mg; 45%).

Step G: Preparation of (2-cyclobutyl-4-fluoro-5-(methoxymethyl)phenyl)methanamine A dry flask equipped with a reflux condenser was charged with 2-cyclobutyl-4-fluoro-5-(methoxymethyl)benzonitrile (82 mg, 0.37 mmol), anhydrous THF (2 mL), and LiAlH$_4$ (374 µL, 0.37 mmol; 1M in THF). The reaction mixture was to reflux with stirring under N$_2$ for 1 hour. After cooling to ambient temperature, the reaction was quenched reaction by addition of water (120 µL), then stirred for 2-3 minutes. NaOH (2N, 120 µL) was added, and the mixture was stirred for 2-3 minutes. Water (400 µL) was added, and the mixture was stirred for 15 minutes at ambient temperature. The mixture was diluted with 2-methoxy-2-methylpropane and filtered, rinsing with 2-methoxy-2-methylpropane. The filtrate was concentrated, using toluene (3×3 mL) to azeotrope water to provide the title compound (80 mg; 48%). The material was used in the next step without further purification.

Step H: Preparation of 1-(2-cyclobutyl-4-fluoro-5-(methoxymethyl)benzyl)-3-(1',4-dimethyl-1-phenyl-1H,1'H-[3,4'-bipyrazol]-5-yl)urea A vial was charged with phenyl (1',4-dimethyl-1-phenyl-1H,1'H-[3,4'-bipyrazol]-5-yl)carbamate (Intermediate 5; 67 mg, 0.18 mmol), 1,2-dichloroethane (0.5 mL), (2-cyclobutyl-4-fluoro-5-(methoxymethyl)phenyl)methanamine (40 mg, 0.18 mmol), and N-ethyl-N-isopropylpropan-2-amine (94 µL, 0.54 mmol). The mixture was stirred overnight at ambient temperature. The crude material was purified by preparative TLC (1 mm thickness, R$_f$=0.39) eluting with 7.5% MeOH/DCM. The resulting product was triturated with diethyl ether, and the resulting white solids were isolated by filtration to provide the title compound (14 mg; 15%). MS m/z (APCI-pos) M+1=503.2.

Example 118

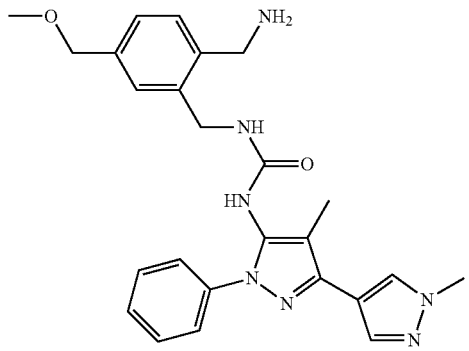

1-(2-(aminomethyl)-5-(methoxymethyl)benzyl)-3-(1',4-dimethyl-1-phenyl-1H,1'H-[3,4'-bipyrazol]-5-yl)urea Step A: Preparation of tert-butyl 2-cyano-4-(methoxymethyl)benzylcarbamate A vial was charged with potassium (((tert-butoxycarbonyl)amino)methyl)trifluoroborate (210 mg, 0.885 mmol; Prepared according to the procedure in Org. Lett., 2012, 14 (12), pp 3138-3141), cesium carbonate (576 mg, 1.77 mmol), dicyclohexyl(2',6'-dimethoxy-[1,1'-biphenyl]-2-yl)phosphine (18 mg, 0.044 mmol), Pd(OAc)$_2$ (5 mg, 0.02 mmol), and 2-bromo-5-(methoxymethyl)benzonitrile (Preparation L, Step B; 100 mg, 0.442 mmol). A 1:1 mixture of dioxane/water (2 mL) was added. The flask was sparged with Ar, and then heated to 90° C. overnight. After cooling to ambient temperature, the mixture was partitioned between EtOAc (2 mL) and saturated aqueous NaHCO$_3$ (2 mL) and the phases were separated phases. The aqueous phase was extracted with EtOAc (1 mL). The combined organic phases were washed with brine (1 mL), dried (MgSO$_4$), filtered, and concentrated. The crude material was purified by preparative TLC (2 mm thickness, R$_f$=0.61) eluting with 1:1 EtOAc/hexanes to provide the title compound (44 mg; 35%).

Step B: Preparation of tert-butyl 2-(aminomethyl)-4-(methoxymethyl)benzylcarbamate A flask was charged with tert-butyl 2-cyano-4-(methoxymethyl)benzylcarbamate (44 mg, 0.16 mmol), MeOH (2 mL) and cobalt chloride hexahydrate (76 mg, 0.32 mmol). The flask was degassed by vacuum purge with N$_2$ three times. The flask was cooled in an ice bath under N$_2$ and NaBH$_4$ (60 mg, 1.6 mmol) was added. The mixture was stirred for 5 minutes in ice bath and then at ambient temperature for 2 hours. The reaction mixture was quenched with saturated aqueous NH$_4$Cl (3 mL), then concentrated under vacuum. The crude material was diluted with aqueous 2N NaOH (10 mL) and DCM (10 mL). The biphasic mixture was filtered through GF/F paper, rinsing the solids with multiple portions of DCM. The phases were separated and the aqueous phase was extracted with DCM (2×10 mL). The combined organic phases were dried (MgSO$_4$), filtered, and concentrated to provide the title compound (29 mg; 62%).

Step C: Preparation of tert-butyl 2-((3-(1',4-dimethyl-1-phenyl-1H,1'H-[3,4'-bipyrazol]-5-yl)ureido)methyl)-4-(methoxymethyl)benzylcarbamate Prepared from tert-butyl 2-(aminomethyl)-4-(methoxymethyl)benzylcarbamate (29 mg, 0.10 mmol) and phenyl (1',4-dimethyl-1-phenyl-1H,1'H-[3,4'-bipyrazol]-5-yl)carbamate (Intermediate 5; 39 mg, 0.10 mmol) according to the procedure described for Example 116, Step C. Yield: 53 mg (89%).

Step D: Preparation of 1-(2-(aminomethyl)-5-(methoxymethyl)benzyl)-3-(1',4-dimethyl-1-phenyl-1H,1'H-[3,4'-bipyrazol]-5-yl)urea A flask was charged with tert-butyl 2-((3-(1',4-dimethyl-1-phenyl-1H,1'H-[3,4'-bipyrazol]-5-yl)ureido)methyl)-4-(methoxymethyl)benzylcarbamate (51 mg, 0.091 mmol), DCM (1 mL) and 2,2,2-trifluoroacetic acid (1 mL). The mixture was stirred at ambient temperature for an hour and then concentrated under vacuum. The mixture was partitioned between DCM (5 mL) and saturated aqueous NaHCO$_3$ (5 mL). The resulting suspension was diluted with EtOH (1 mL) and 2N NaOH (2 mL) was added. The phases were separated and the aqueous phase was extracted with DCM (2×5 mL). The combined organic phases were dried (MgSO$_4$), filtered, and concentrated. The crude material was purified by preparative TLC (0.5 mm thickness, R$_f$=0.15) eluting with 20% MeOH/DCM to provide the title compound (22 mg; 51%). MS m/z (APCI-pos) M+1=460.3.

Example 119

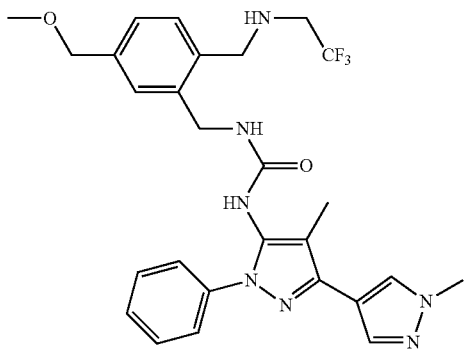

1-(1',4-dimethyl-1-phenyl-1H,1'H-[3,4'-bipyrazol]-5-yl)-3-(5-(methoxymethyl)-2-(((2,2,2-trifluoroethyl)amino)methyl)benzyl)urea Step A: A vial was charged with anhydrous DMF (0.5 mL), 1-(2-(aminomethyl)-5-(methoxymethyl)benzyl)-3-(1',4-dimethyl-1-phenyl-1H,1'H-[3,4'-bipyrazol]-5-yl)urea (Example 118, Step D; 20 mg, 0.044 mmol), triethylamine (12 μL, 0.087 mmol), and 2,2,2-trifluoroethyl trifluoromethanesulfonate (7 μL, 0.05 mmol). The mixture was stirred overnight at ambient temperature. The mixture was partitioned between EtOAc (2 mL) and water (2 mL). The phases were separated and the aqueous phase was extracted with EtOAc (1 mL). The combined organic phases were washed with water (2 mL) and brine (1 mL), dried (MgSO$_4$), filtered, and concentrated. The crude material was purified by preparative TLC (0.5 mm thickness, R$_f$=0.46) eluting with 10% MeOH/DCM to provide the title compound (13 mg; 54%). MS m/z (APCI-pos) M+1=542.3.

Example 120

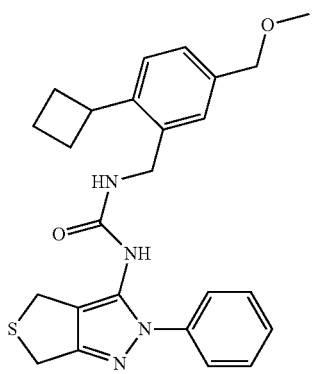 [SMILES: COCc1ccc(C2CCC2)c(CNC(=O)Nc2c3c(nn2-c2ccccc2)CSC3)c1]

1-(2-cyclobutyl-5-(methoxymethyl)benzyl)-3-(2-phenyl-4,6-dihydro-2H-thieno[3,4-c]pyrazol-3-yl)urea A vial was charged with phenyl (2-phenyl-4,6-dihydro-2H-thieno[3,4-c]pyrazol-3-yl)carbamate (Intermediate P130, Step B; 20 mg, 0.059 mmol), 1,2-dichloroethane (0.5 mL), (2-cyclobutyl-5-(methoxymethyl)phenyl)-methanamine (Preparation B; 16 mg, 0.077 mmol), and N-ethyl-N-isopropylpropan-2-amine (31 μL, 0.18 mmol). The mixture was stirred overnight at ambient temperature. The crude material was purified by preparative TLC (0.5 mm thickness, R$_f$=0.66) eluting with 10% MeOH/DCM to provide the title compound (16 mg; 59%). MS m/z (APCI-pos) M+1=449.2.

Example 121

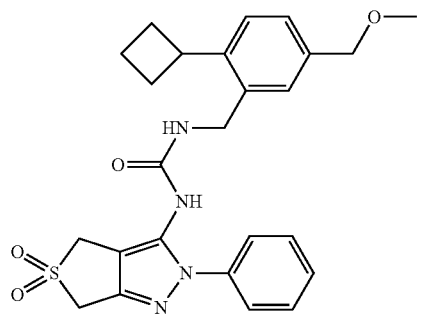 [SMILES: COCc1ccc(C2CCC2)c(CNC(=O)Nc2c3c(nn2-c2ccccc2)CS(=O)(=O)C3)c1]

1-(2-cyclobutyl-5-(methoxymethyl)benzyl)-3-(5,5-dioxido-2-phenyl-4,6-dihydro-2H-thieno[3,4-c]pyrazol-3-yl)urea Prepared from (2-cyclobutyl-5-(methoxymethyl)phenyl)-methanamine (Preparation B; 14 mg, 0.070 mmol) and phenyl (5,5-dioxido-2-phenyl-4,6-dihydro-2H-thieno[3,4-c]pyrazol-3-yl)carbamate (Intermediate P130, Step C; 20 mg, 0.054 mmol) according to the procedure described for Example 120. Yield: 19 mg (69%). MS m/z (APCI-neg) M-1=479.2.

Example 122

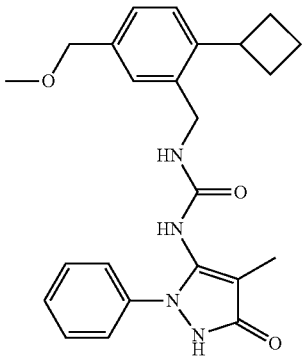 [SMILES: COCc1ccc(C2CCC2)c(CNC(=O)Nc2c(C)c(=O)[nH]n2-c2ccccc2)c1]

1-(2-cyclobutyl-5-(methoxymethyl)benzyl)-3-(4-methyl-5-oxo-2-phenyl-2,5-dihydro-1H-pyrazol-3-yl)urea Step A: Preparation of 5-isocyanato-4-methyl-1-phenyl-1H-pyrazol-3(2H)-one A vial was charged with 5-amino-4-methyl-1-phenyl-1H-pyrazol-3(2H)-one (Intermediate P135, Step A; 50 mg, 0.264 mmol), DMF (0.5 mL), N-ethyl-N-isopropylpropan-2-amine (115 µL, 0.661 mmol), and lastly di(1H-imidazol-1-yl)methanone (94 mg, 0.58 mmol). The mixture was stirred at ambient temperature overnight. The crude reaction mixture was used in the next step without workup or purification.

Step B: Preparation of 1-(2-cyclobutyl-5-(methoxymethyl)benzyl)-3-(4-methyl-5-oxo-2-phenyl-2,5-dihydro-1H-pyrazol-3-yl)urea To one half of the reaction mixture from Example 122, Step A was added (2-cyclobutyl-5-(methoxymethyl)phenyl)-methanamine (Preparation B; 35 mg, 0.17 mmol). The mixture was stirred overnight at ambient temperature. The mixture was partitioned between EtOAc and water. The biphasic mixture was filtered, rinsing multiple times with 30% MeOH/DCM. The phases were separated and the aqueous phase was extracted with EtOAc. The crude material was purified by preparative TLC (0.5 mm thickness) eluting with 10% MeOH/DCM. Fractions containing the product were combined and further purified by preparative reverse phase HPLC (column: YMC ODS-AQ, 250×20 mm). Fractions containing the product were concentrated and azeotroped with $CH_3CN$ (3×5 mL). The resulting solids were dissolved in 20% MeOH/DCM and washed with saturated aqueous $NaHCO_3$ and the aqueous phase was extracted with 20% MeOH/DCM. The combined organic phases were dried ($MgSO_4$), filtered, and concentrated to provide the title compound (2 mg; 3%). MS m/z (APCI-pos) M+1=421.2.

Example 123

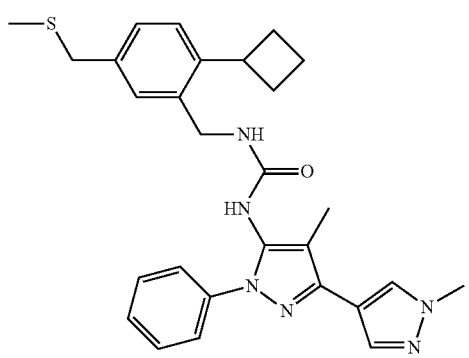

1-(2-cyclobutyl-5-((methylthio)methyl)benzyl)-3-(1',4-dimethyl-1-phenyl-1H,1'H-[3,4'-bipyrazol]-5-yl)urea Step A: Preparation of 2-bromo-5-(bromomethyl)benzonitrile A flask was charged with DCM (5 mL) and 2-bromo-5-(hydroxymethyl)benzonitrile (Preparation L, Step A; 200 mg, 0.943 mmol). The mixture was cooled in an ice bath under $N_2$ and $PBr_3$ (180 µL, 1.9 mmol) was added. The mixture was stirred an ice bath for 1 hour. The mixture was poured onto ice. The phases were separated and the aqueous phase was extracted with DCM (10 mL). The combined organic phases were washed with saturated aqueous $NaHCO_3$ (10 mL), then dried ($MgSO_4$), filtered, and concentrated. The crude material was purified by preparative TLC (1 mm thickness, $R_f$=0.59) eluting with 25% EtOAc/hexanes to provide the title compound (71 mg; 27%).

Step B: Preparation of 2-bromo-5-((methylthio)methyl)benzonitrile

A flask was charged with 2-bromo-5-(bromomethyl)benzonitrile (76 mg, 0.28 mmol), anhydrous DMF (1 mL) and sodium methanethiolate (23 mg, 0.33 mmol). The mixture was stirred at ambient temperature overnight under $N_2$. The mixture was partitioned between EtOAc/water. The phases were separated and the aqueous phase was extracted with EtOAc. The combined organic phases were dried over $MgSO_4$, filtered, and concentrated. The crude material was purified by preparative TLC (1 mm thickness, $R_f$=0.60) eluting with 25% EtOAc/hexanes to provide the title compound (43 mg; 63%).

Step C: Preparation of 2-cyclobutyl-5-((methylthio)methyl)benzonitrile

Prepared from 2-bromo-5-((methylthio)methyl)benzonitrile (43 mg, 0.18 mmol) according to the procedure described in Example 116, Step F. Yield: 20 mg; 51%.

Step D: Preparation of (2-cyclobutyl-5-((methylthio)methyl)phenyl)methanamine

Prepared from 2-cyclobutyl-5-((methylthio)methyl)benzonitrile (20 mg, 0.092 mmol) according to the procedure described in Example 117, Step G. Yield: 20 mg; 69%.

Step E: Preparation of 1-(2-cyclobutyl-5-((methylthio)methyl)benzyl)-3-(1',4-dimethyl-1-phenyl-1H,1'H-[3,4'-bipyrazol]-5-yl)urea Prepared (2-cyclobutyl-5-((methylthio)methyl)phenyl)methanamine (20 mg, 0.088 mmol) and phenyl (1',4-dimethyl-1-phenyl-1H,1'H-[3,4'-bipyrazol]-5-yl)carbamate (Intermediate 5; 30 mg, 0.080 mmol) according to the procedure described for Example 116, Step C. The crude material was purified by preparative reverse phase HPLC (column: YMC ODS-AQ, 250×20 mm). Fractions containing product were concentrated, and the resulting solids were dissolved in 20% MeOH/DCM, washed with saturated aqueous $NaHCO_3$, and extracted aqueous with 20% MeOH/DCM. The combined organic layers were dried ($MgSO_4$), filtered, and concentrated to provide the title compound (9 mg; 21%). MS m/z (APCI-pos) M+1=501.2.

Example 124

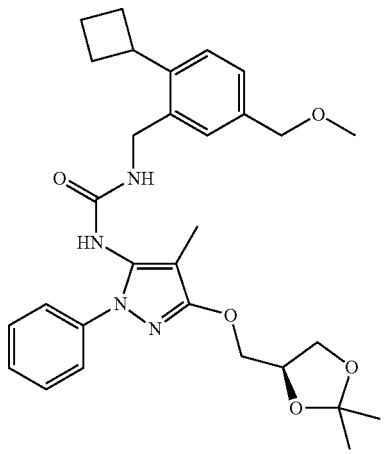 [SMILES: COCc1ccc(C2CCC2)c(CNC(=O)Nc2c(C)c(OC[C@H]3COC(C)(C)O3)nn2-c2ccccc2)c1]

(S)-1-(2-cyclobutyl-5-(methoxymethyl)benzyl)-3-(3-
((2,2-dimethyl-1,3-dioxolan-4-yl)methoxy)-4-
methyl-1-phenyl-1H-pyrazol-5-yl)urea Step A: A flask was charged with (S)-3-((2,2-dimethyl-1,3-dioxolan-4-yl)methoxy)-4-methyl-1-phenyl-1H-pyrazol-5-amine (Intermediate P209; 50 mg, 0.16 mmol) and DCM (0.5 mL), followed by addition of N-ethyl-N-isopropylpropan-2-amine (86 μL, 0.49 mmol) and triphosgene (24 mg, 0.082 mmol). The mixture was stirred for 15 minutes at ambient temperature, and then (2-cyclobutyl-5-(methoxymethyl)phenyl)methanamine (Preparation B; 34 mg, 0.16 mmol) was added, followed by further addition of N-ethyl-N-isopropylpropan-2-amine (86 μL, 0.49 mmol). The mixture was stirred over the weekend at ambient temperature for convenience. The crude material was purified by preparative TLC (1 mm thickness, $R_f$=0.65) eluting with 5% MeOH (containing 7N $NH_3$) in DCM to provide the title compound (33 mg; 37%). MS m/z (APCI-pos) M+1=535.3.

Example 125

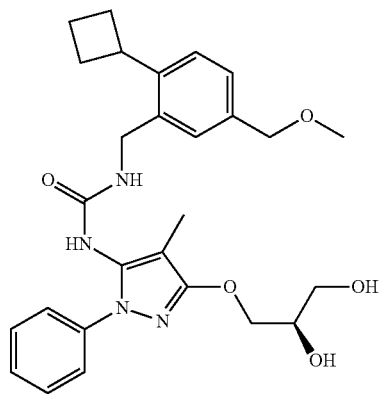 [SMILES: COCc1ccc(C2CCC2)c(CNC(=O)Nc2c(C)c(OC[C@H](O)CO)nn2-c2ccccc2)c1]

(R)-1-(2-cyclobutyl-5-(methoxymethyl)benzyl)-3-(3-
(2,3-dihydroxypropoxy)-4-methyl-1-phenyl-1H-
pyrazol-5-yl)urea Step A: A flask was charged with (S)-1-(2-cyclobutyl-5-(methoxymethyl)benzyl)-3-(3-((2,2-dimethyl-1,3-dioxolan-4-yl)methoxy)-4-methyl-1-phenyl-1H-pyrazol-5-yl)urea (Example 123; 30 mg, 0.056 mmol), THF (2 mL), and 1N aqueous HCl (2 mL). The mixture was stirred at ambient temperature for 3 hours, and then concentrated under vacuum. The mixture was partitioned between EtOAc (10 mL) and saturated aqueous $NaHCO_3$ (10 mL). The phases were separated and the aqueous phase was extracted with EtOAc (2×10 mL). The combined organic phases were washed with brine (10 mL), dried ($MgSO_4$), filtered, and concentrated. The crude material was purified by preparative TLC (0.5 mm thickness), eluting with 10% MeOH/DCM to provide the title compound (18 mg; 62%). MS m/z (APCI-pos) M+1=495.2.

Example 126

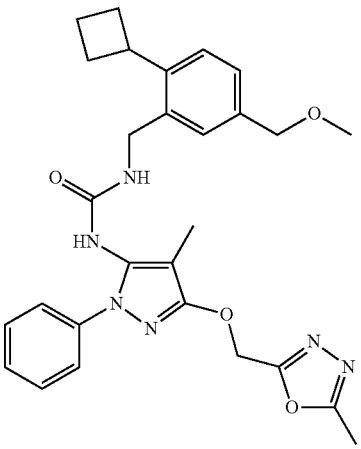 [SMILES: COCc1ccc(C2CCC2)c(CNC(=O)Nc2c(C)c(OCc3nnc(C)o3)nn2-c2ccccc2)c1]

1-(2-cyclobutyl-5-(methoxymethyl)benzyl)-3-(4-
methyl-3-((5-methyl-1,3,4-oxadiazol-2-yl)methoxy)-
1-phenyl-1H-pyrazol-5-yl)urea Prepared from 4-methyl-3-((5-methyl-1,3,4-oxadiazol-2-yl)methoxy)-1-phenyl-1H-pyrazol-5-amine (Intermediate P140; 36 mg, 0.13 mmol) and (2-cyclobutyl-5-(methoxymethyl)phenyl)methanamine (Preparation B; 26 mg, 0.13 mmol) according to the procedure for Example 123. Yield: 29 mg (42%). MS m/z (APCI-pos) M+1=517.2.

Example 127

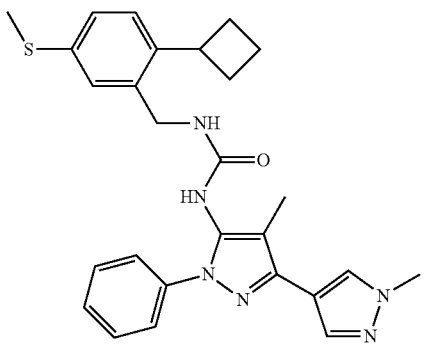

1-(2-cyclobutyl-5-(methylthio)benzyl)-3-(1',4-dimethyl-1-phenyl-1H,1'H-[3,4'-bipyrazol]-5-yl)urea Step A: Preparation of
2-amino-5-thiocyanatobenzonitrile A flask was charged with 2-aminobenzonitrile (4.00 g, 33.9 mmol), MeOH (20 mL) and sodium thiocyanate (3.02 g, 37.2 mmol). The flask was cooled in an ice bath and bromine (1.75 mL, 33.9 mmol) dissolved in MeOH (5 mL) was added dropwise over 20 minutes. During the last few minutes of the addition a thick precipitate formed which stopped stirring. Additional MeOH (10 mL) was added and the remainder of the bromine was added to the thick suspension. The mixture was stirred in ice bath for 30 minutes, then neutralized by pouring into saturated aqueous $NaHCO_3$ (30 mL). The mixture was extracted into EtOAc (2×30 mL). The organic phase was washed with brine (30 mL), dried ($MgSO_4$), filtered, and concentrated. The crude material was triturated with 5% MeOH/DCM (20 mL) with sonication, and the resulting solids were filtered, rinsing with DCM to provide the title compound as an off-white solid. Yield: 3.56 g (54%).

Step B: Preparation of
2-amino-5-(methylthio)benzonitrile

A flask was charged with MeOH (20 mL) and sodium hydroxide (0.85 g, 21 mmol) dissolved in water (3 mL). To this was added 2-amino-5-thiocyanatobenzonitrile (3.56 g, 20.3 mmol). A yellow suspension resulted. The mixture was stirred at ambient temperature for 30 minutes. The flask was cooled in an ice bath and $NaBH_4$ (0.38 g, 10 mmol) was added. The resulting yellow suspension was stirred for 30 minutes in the ice bath. Diethyl sulfate (2.9 mL, 22 mmol) was added dropwise. The mixture was stirred for 15 minutes in the ice bath then for 1 hour at ambient temperature. The mixture was concentrated under vacuum and the resulting solids were partitioned between diethyl ether (40 mL) and water (40 mL). The phases were separated and the aqueous phase was extracted with diethyl ether (20 mL). The combined organic phases were washed with brine (40 mL), dried ($MgSO_4$), filtered, and concentrated. The crude material was purified on a Redi-Sep 220 silica gel column, eluting with a gradient of 10%-30% EtOAc/hexanes to provide 3.38 g of a 60:40 mixture of 2-amino-5-(ethylthio)benzonitrile and 2-amino-5-(methylthio)benzonitrile, respectively. The mixture was used in the next step without purification.

Step C: Preparation of
2-bromo-5-(methylthio)benzonitrile

To an open round bottomed flask containing a stirred suspension of a 60:40 mixture of 2-amino-5-(ethylthio)benzonitrile and 2-amino-5-(methylthio)benzonitrile from Step B (3.38 g, 19.0 mmol) in dioxane (10 mL) was added 48% aqueous hydrogen bromide (43 mL, 379 mmol). The mixture was cooled in an ice bath and sodium nitrite (1.44 g, 20.9 mmol) dissolved in water (5 mL) was added dropwise over a 20 minute period, maintaining internal temperature below 3° C. and monitoring gas evolution. The mixture was stirred in the ice bath for 30 minutes, then carefully poured into a stirred mixture of copper(I) bromide (3.54 g, 24.7 mmol) and 48% aqueous HBr (20 mL) that was cooled in an ice bath. The mixture was stirred for 15 minutes in the ice bath, then at ambient temperature for 1 hour, and then heated to 50° C. for 1 hour. After cooling to ambient temperature, The mixture was diluted with water (75 mL) and extracted with 10% EtOAc in diethyl ether (2×75 mL). The combined organic extracts were washed with 10% aqueous sodium thiosulfate solution (75 mL) and saturated aqueous $NH_4Cl$ (75 mL), dried ($MgSO_4$), filtered, and concentrated. The crude material was purified on a Redi-Sep 330 silica gel column, eluting with a gradient of 5%-10% EtOAc/hexanes. 2-Bromo-5-(ethylthio)benzonitrile (1.8 g) eluted first, followed by 2-bromo-5-(methylthio)benzonitrile (830 mg). Impure 2-bromo-5-(ethylthio)benzonitrile was repurified by Redi-Sep 220 silica gel column eluting with a gradient of 5%-7.5% EtOAc/hexanes to obtain 1.3 g (27% yield) of 2-bromo-5-(ethylthio)benzonitrile. Impure 2-bromo-5-(methylthio)benzonitrile was passed through a Redi-Sep 220 silica gel column eluting with a gradient of 7.5%-10% EtOAc/hexanes to obtain 500 mg (10% yield) of 2-bromo-5-(methylthio)benzonitrile.

Step D: Preparation of
2-cyclobutyl-5-(methylthio)benzonitrile

Prepared from 2-bromo-5-(methylthio)benzonitrile (100 mg, 0.44 mmol) according to the procedure described in Example 117, Step F. Yield: 25 mg (22%).

Step E: Preparation of
(2-cyclobutyl-5-(methylthio)phenyl)methanamine

Prepared from 2-cyclobutyl-5-(methylthio)benzonitrile (25 mg, 0.12 mmol) according to the procedure described in Example 117, Step G. Yield: 26 mg (69%).

Step F: Preparation of 1-(2-cyclobutyl-5-(methylthio)benzyl)-3-(1',4-dimethyl-1-phenyl-1H,1'H-[3,4'-bipyrazol]-5-yl)urea Prepared 2-cyclobutyl-5-(methylthio)phenyl)methanamine (25 mg, 0.12 mmol) and phenyl (1',4-dimethyl-1-phenyl-1H,1'H-[3,4'-bipyrazol]-5-yl)carbamate (Intermediate 5; 38 mg, 0.10 mmol) according to the procedure described for Example 116, Step C. The crude material was purified by preparative reverse phase HPLC (column: YMC ODS-AQ, 250×20 mm). Fractions containing product were concentrated. The resulting solids were dissolved in 20% MeOH/DCM and washed with saturated aqueous $NaHCO_3$. The aqueous layer was extracted with 20% MeOH/DCM (2×), and the combined organic extracts were dried ($MgSO_4$), filtered, and concentrated to provide the title compound (3 mg; 6%). MS m/z (APCI-pos) M+1=487.2.

Example 128

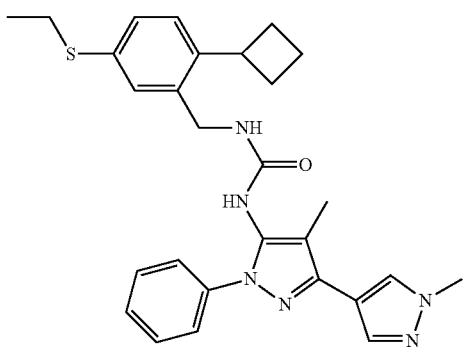 [SMILES: CCSc1ccc(C2CCC2)c(CNC(=O)Nc2c(C)c(-c3cnn(C)c3)nn2-c2ccccc2)c1]

1-(2-cyclobutyl-5-(ethylthio)benzyl)-3-(1',4-dimethyl-1-phenyl-1H,1'H-[3,4'-bipyrazol]-5-yl)urea Step A: Preparation of 2-cyclobutyl-5-(ethylthio)benzonitrile Prepared from 2-bromo-5-(ethylthio)benzonitrile (from Example 127, Step C; 100 mg, 0.41 mmol) according to the procedure described in Example 117, Step F. Yield: 33 mg (26%).

Step B: Preparation of (2-cyclobutyl-5-(ethylthio)phenyl)methanamine

Prepared from 2-cyclobutyl-5-(ethylthio)benzonitrile (33 mg, 0.15 mmol) according to the procedure described in Example 117, Step G. Yield: 35 mg (67%).

Step C: Preparation of 1-(2-cyclobutyl-5-(ethylthio)benzyl)-3-(1',4-dimethyl-1-phenyl-1H,1'H-[3,4'-bipyrazol]-5-yl)urea Prepared 2-cyclobutyl-5-(ethylthio)phenyl)methanamine (34 mg, 0.15 mmol) and phenyl (1',4-dimethyl-1-phenyl-1H,1'H-[3,4'-bipyrazol]-5-yl)carbamate (Intermediate 5; 48 mg, 0.13 mmol) according to the procedure described for Example 116, Step C. The crude material was purified by preparative reverse phase HPLC (column: YMC ODS-AQ, 250×20 mm). Fractions containing product were concentrated. The resulting solids were dissolved in 20% MeOH/DCM and washed with saturated aqueous NaHCO₃. The aqueous phase was extracted with 20% MeOH/DCM (2×), and the combined organic extracts were dried (MgSO₄), filtered, and concentrated to provide the title compound (3 mg; 5%). MS m/z (APCI-pos) M+1=501.2.

Example 129

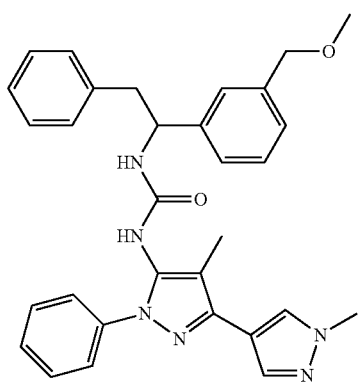 [SMILES: COCc1cccc(C(Cc2ccccc2)NC(=O)Nc2c(C)c(-c3cnn(C)c3)nn2-c2ccccc2)c1]

1-(1',4-dimethyl-1-phenyl-1H,1'H-[3,4'-bipyrazol]-5-yl)-3-(1-(3-(methoxymethyl)phenyl)-2-phenylethyl)urea Step A: Preparation of 1-(3-(methoxymethyl)phenyl)-2-phenylethanone A thick walled glass pressure vessel was charged with 1-(3-bromophenyl)-2-phenylethanone (500 mg, 1.82 mmol), potassium methoxymethyl trifluoroborate (552 mg, 3.63 mmol), PdCl₂(dppf) dichloromethane adduct (148 mg, 0.182 mmol), cesium carbonate (1776 mg, 5.45 mmol) and 1:1 dioxane/water (5 mL). The mixture was sparged with N₂ for several minutes, then heated to 100° C. overnight. After cooling to ambient temperature, the mixture was partitioned between EtOAc (20 mL) and water (20 mL). The phases were separated and the aqueous phase was extracted with EtOAc (10 mL). The combined organic phases were washed with brine (20 mL), dried (MgSO₄), filtered, and concentrated. The crude material was purified on Redi-Sep 80 silica gel column, eluting with a gradient of 5%-20% EtOAc/hexanes, then by preparative TLC (2×2 mm thick plates, R_f=0.49), eluting with 2% MeOH/DCM to provide the title compound (133 mg; 30%).

Step B: Preparation of 1-(3-(methoxymethyl)phenyl)-2-phenylethanone oxime

A flask equipped with a reflux condenser was charged with 1-(3-(methoxymethyl)phenyl)-2-phenylethanone (133 mg, 0.553 mmol), EtOH (2 mL) and hydroxylamine hydrochloride (115 mg, 1.66 mmol). The mixture was heated to reflux for 4 hours. After cooling to ambient temperature, the reaction mixture was partitioned between 1:1 water/saturated NaHCO₃ (20 mL) and EtOAc (20 mL). The phases were separated and the aqueous phase was extracted with EtOAc (20 mL). The combined organic phases were washed with brine (20 mL), dried (MgSO₄), filtered, and concentrated. Recovered 131 mg of the crude desired product which was used in the next step without purification.

Step C: Preparation of 1-(3-(methoxymethyl)phenyl)-2-phenylethanamine

A flask was charged with 1-(3-(methoxymethyl)phenyl)-2-phenylethanone oxime (131 mg, 0.513 mmol), zinc (250 mg, 3.8 mmol) and neat acetic acid (2 mL). The mixture was heated to 70° C. for 3 hours and then concentrated under vacuum. The residue was diluted with 2N aqueous NaOH (5 mL) and EtOAc (5 mL). The solution was filtered mixture through GF/F paper, rinsing multiple times with EtOAc. The phases were separated and the aqueous phase was extracted with EtOAc (10 mL). The combined organic phases were washed with brine (10 mL), dried (MgSO₄), filtered, and concentrated. The crude material was purified by preparative TLC (1 mm thickness, R_f=0.31) eluting with 5% MeOH (containing 7N NH₃) in DCM. Yield: 16 mg (12%).

Step D: Preparation of 1-(1',4-dimethyl-1-phenyl-1H,1'H-[3,4'-bipyrazol]-5-yl)-3-(1-(3-(methoxymethyl)phenyl)-2-phenylethyl)urea Prepared 1-(3-(methoxymethyl)phenyl)-2-phenylethanamine (16 mg, 0.067 mmol) and phenyl (1',4-dimethyl-1-phenyl-1H,1'H-[3,4'-bipyrazol]-5-yl)carbamate (Intermediate 5; 25 mg, 0.067 mmol) according to the procedure described for Example 116, Step C. Yield: 23 mg (63%). MS m/z (APCI-pos) M+1=521.3.

Example 130

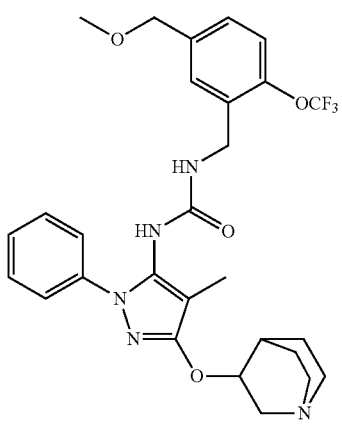 [SMILES: COCc1ccc(OC(F)(F)F)c(CNC(=O)Nc2c(C)c(OC3CN4CCC3CC4)nn2-c2ccccc2)c1]

1-(5-(methoxymethyl)-2-(trifluoromethoxy)benzyl)-3-(4-methyl-1-phenyl-3-(quinuclidin-3-yloxy)-1H-pyrazol-5-yl)urea

Step A: Preparation of quinuclidin-3-yl methanesulfonate

Prepared according to the procedure of Example 72, Step B, substituting tert-butyl 4-fluoro-4-(hydroxymethyl)piperidine-1-carboxylate with quinuclidin-3-ol to give quinuclidin-3-yl methanesulfonate (100%).

Step B: Preparation of 4-methyl-1-phenyl-3-(quinuclidin-3-yloxy)-1H-pyrazol-5-amine Prepared according to the procedure of Example 67, Step A, substituting tert-butyl 4-(((methylsulfonyl)oxy)methyl)piperidine-1-carboxylate with quinuclidin-3-yl methanesulfonate to give 4-methyl-1-phenyl-3-(quinuclidin-3-yloxy)-1H-pyrazol-5-amine (27%).

Step C: Preparation of 1-(5-(methoxymethyl)-2-(trifluoromethoxy)benzyl)-3-(4-methyl-1-phenyl-3-(quinuclidin-3-yloxy)-1H-pyrazol-5-yl)urea Prepared according to the procedure of Example 1, substituting 4-methyl-3-(2-methylpyrimidin-5-yl)-1-phenyl-1H-pyrazol-5-amine with 4-methyl-1-phenyl-3-(quinuclidin-3-yloxy)-1H-pyrazol-5-amine and (2-cyclopropyl-5-(methoxymethyl)phenyl)methanamine with (5-(methoxymethyl)-2-(trifluoromethoxy)phenyl)methanamine to give the title compound (21%). MS (APCI) m/z=560.3 (M+H).

Example 131

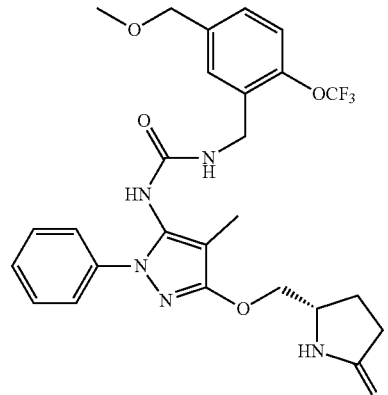

(S)-1-(5-(methoxymethyl)-2-(trifluoromethoxy)benzyl)-3-(4-methyl-3-((5-oxopyrrolidin-2-yl)methoxy)-1-phenyl-1H-pyrazol-5-yl)urea

Step A: Preparation of (S)-(5-oxopyrrolidin-2-yl)methyl methanesulfonate

Prepared according to the procedure of Example 72, Step B, substituting tert-butyl 4-fluoro-4-(hydroxymethyl)piperidine-1-carboxylate with (S)-5-(hydroxymethyl)pyrrolidin-2-one to give (S)-(5-oxopyrrolidin-2-yl)methyl methanesulfonate (25%).

Step B: Preparation of (S)-5-(((5-amino-4-methyl-1-phenyl-1H-pyrazol-3-yl)oxy)methyl)pyrrolidin-2-one Prepared according to the procedure of Example 67, Step A, substituting tert-butyl 4-(((methylsulfonyl)oxy)methyl)piperidine-1-carboxylate with (S)-(5-oxopyrrolidin-2-yl)methyl methanesulfonate to give (S)-5-(((5-amino-4-methyl-1-phenyl-1H-pyrazol-3-yl)oxy)methyl)pyrrolidin-2-one (32%).

Step C: Preparation of (S)-1-(5-(methoxymethyl)-2-(trifluoromethoxy)benzyl)-3-(4-methyl-3-((5-oxopyrrolidin-2-yl)methoxy)-1-phenyl-1H-pyrazol-5-yl)urea Prepared according to the procedure of Example 1, substituting 4-methyl-3-(2-methylpyrimidin-5-yl)-1-phenyl-1H-pyrazol-5-amine with (S)-5-(((5-amino-4-methyl-1-phenyl-1H-pyrazol-3-yl)oxy)methyl)pyrrolidin-2-one and (2-cyclopropyl-5-(methoxymethyl)phenyl)methanamine with (5-(methoxymethyl)-2-(trifluoromethoxy)phenyl)methanamine to give the title compound (25%). MS (APCI) m/z=546.2 (M−H).

Example 132

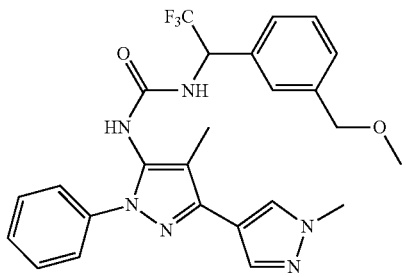 [SMILES: COCc1cccc(C(NC(=O)Nc2c(C)c(-c3cnn(C)c3)nn2-c2ccccc2)C(F)(F)F)c1]

1-(1',4-dimethyl-1-phenyl-1H,1'H-[3,4'-bipyrazol]-5-yl)-3-(2,2,2-trifluoro-1-(3-methoxymethyl)phenyl)ethyl)urea

Step A: Preparation of 2,2,2-trifluoro-1-(3-(methoxymethyl)phenyl)ethanone

A flask equipped with a nitrogen inlet was charged with 1-bromo-3-(methoxymethyl)benzene (1.00 g, 4.974 mmol) and dry THF (50 mL). The mixture was cooled to −78° C. and n-BuLi (2.19 mL, 5.471 mmol, 2.5 M in hexanes) was added by syringe over a 10 minute period, resulting in a light yellow solution. The mixture was stirred at −78° C. for 45 minutes, and 2,2,2-trifluoro-1-(piperidin-1-yl)ethanone (0.991 g, 5.471 mmol) was added by syringe over a 5 minute period. Once addition was complete, the mixture was allowed to warm to ambient temperature, and then quenched with saturated ammonium chloride solution. Water was added and the mixture was extracted with EtOAc. The combined organic extracts were dried over sodium sulfate and concentrated under reduced pressure. The crude material was passed through an 80 g Redi Sep column, eluting with 3:1 Hexane/ethyl acetate, to give 485 mg of an oil (1:1 product/starting material).

Step B: Preparation of 2,2,2-trifluoro-1-(3-(methoxymethyl)phenyl)ethanone oxime A round bottom flask equipped with a condenser was charged with 2,2,2-trifluoro-1-(3-(methoxymethyl)phenyl)ethanone (0.485 g, 2.22 mmol) and 22 mL of ethanol. To this was added hydroxylamine hydrochloride (0.154 g, 2.22 mmol) and the mixture was warmed to 65° C. for 16 hours, then concentrated under reduced pressure. The resulting crude material was taken up in EtOAc, washed with 10% aqueous potassium carbonate, dried over sodium sulfate and concentrated under reduced pressure to give 200 mg of an oil.

Step C: Preparation of 2,2,2-trifluoro-1-(3-(methoxymethyl)phenyl)ethanamine A round bottom flask equipped with a condenser was charged with 2,2,2-trifluoro-1-(3-(methoxymethyl)phenyl)ethanone oxime (0.200 g, 0.858 mmol) and 8 mL of acetic acid. To this was added zinc dust (0.280 g, 4.29 mmol) and the mixture was warmed to 70° C. for 5 hours, then filtered through GF/F filter paper. The filtrate was concentrated under reduced pressure and the resulting crude product was taken up in EtOAc, washed with 10% aqueous potassium carbonate, dried over sodium sulfate and concentrated under reduced pressure to give 138 mg of the title compound as an oil.

Step D: Preparation of 1-(1',4-dimethyl-1-phenyl-1H,1'H-[3,4'-bipyrazol]-5-yl)-3-(2,2,2-trifluoro-1-(3-(methoxymethyl)phenyl)ethyl)urea Prepared according to the procedure of Example 2, substituting phenyl (3-ethoxy-4-methyl-1-phenyl-1H-pyrazol-5-yl)carbamate with phenyl (1',4-dimethyl-1-phenyl-1H,1'H-[3,4'-bipyrazol]-5-yl)carbamate and (2-cyclopropyl-5-(methoxymethyl)phenyl)methanamine with 2,2,2-trifluoro-1-(3-(methoxymethyl)phenyl)ethanamine to give the title compound (12%). MS (APCI) m/z=499.2 (M−H).

What is claimed is:

1. A compound selected from

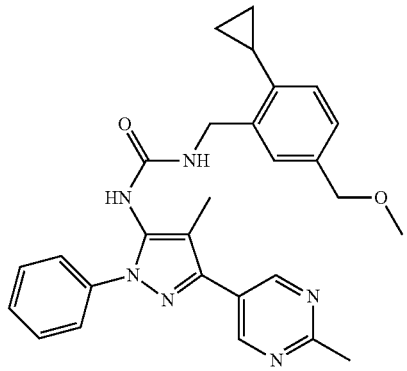

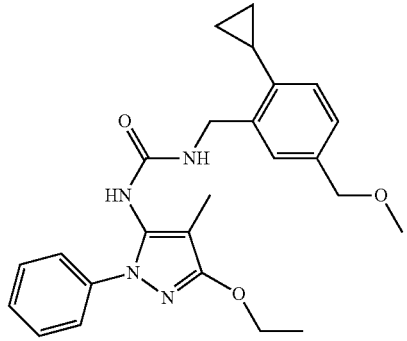

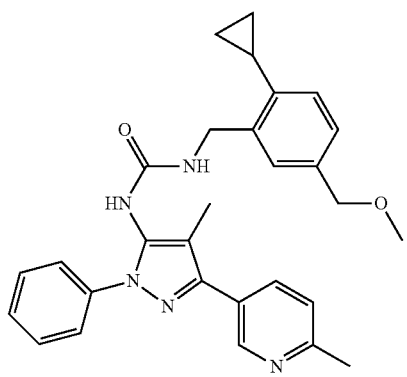

291
-continued
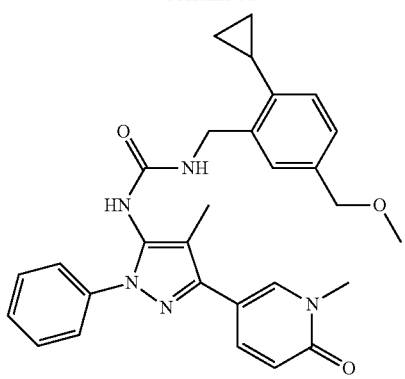
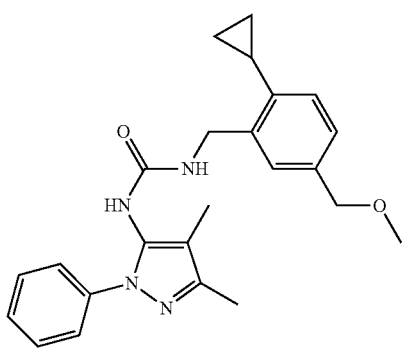
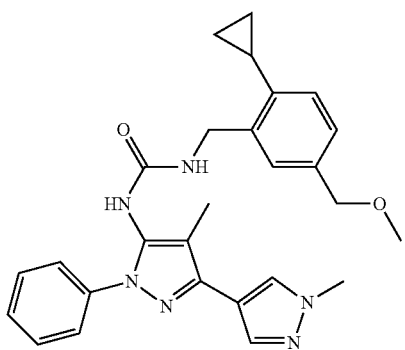
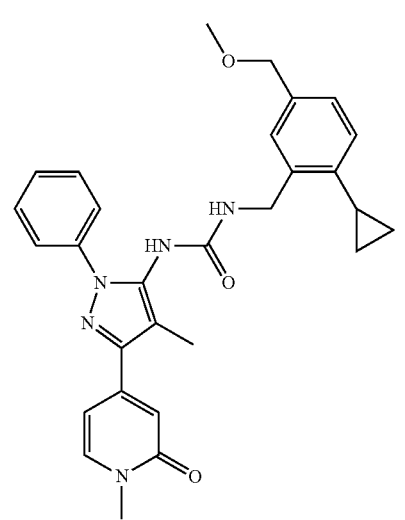
292
-continued
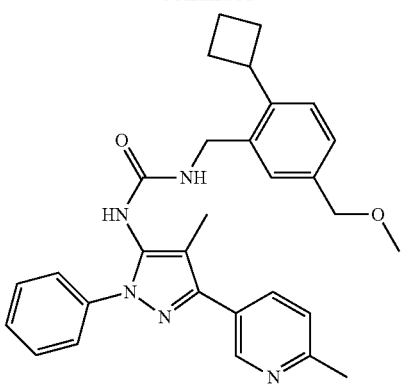
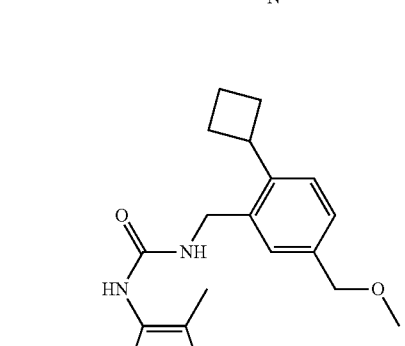
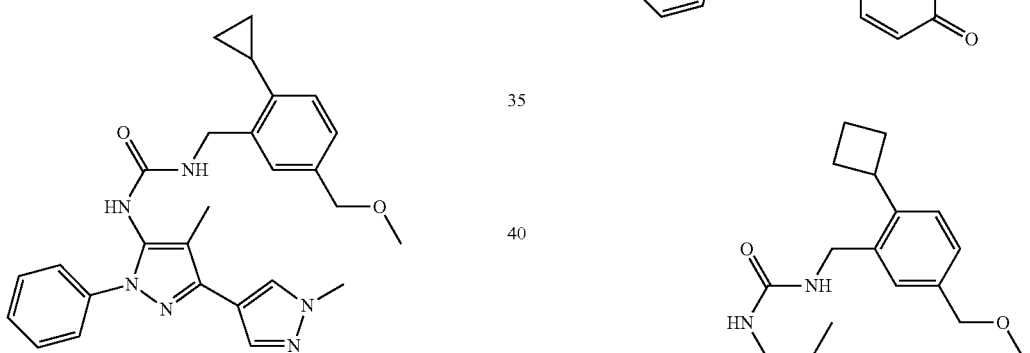

293
-continued
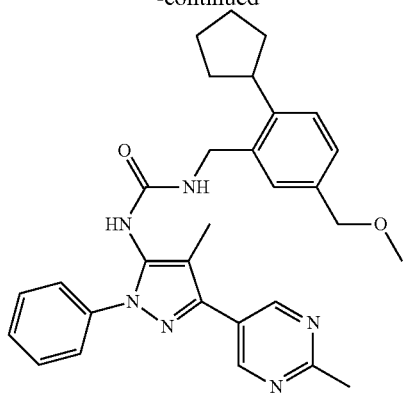
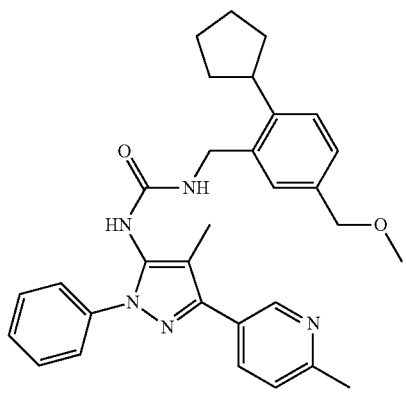
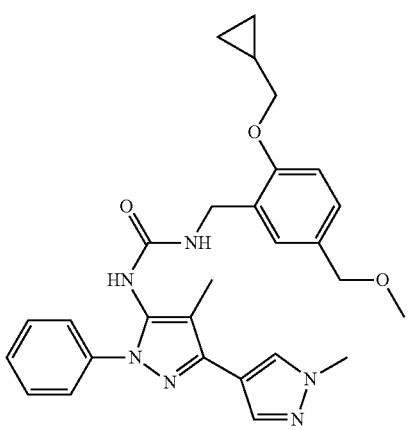
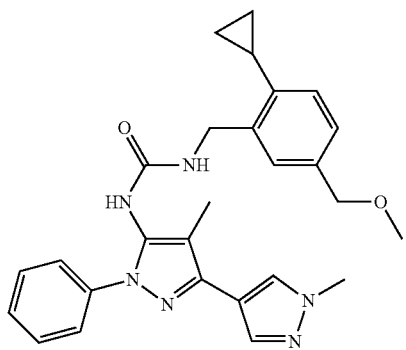
294
-continued
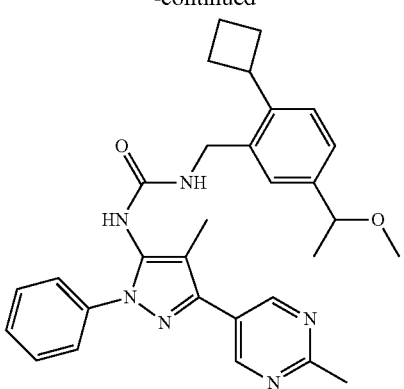
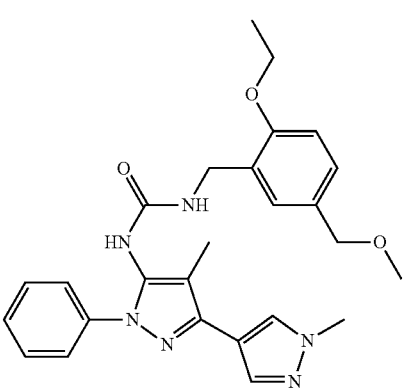
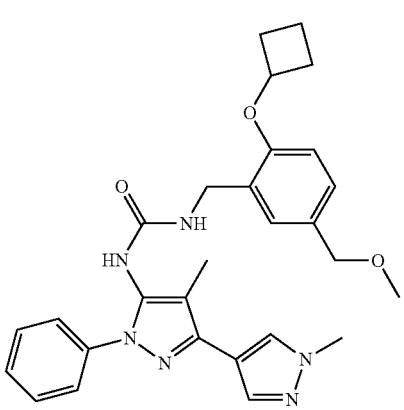
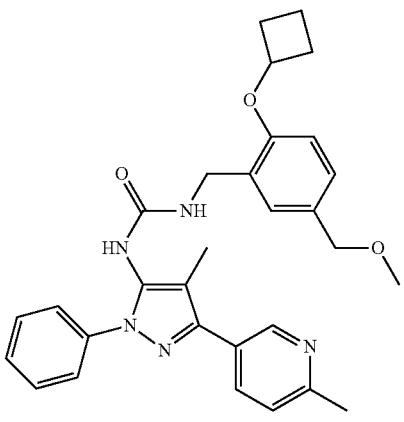

295
-continued
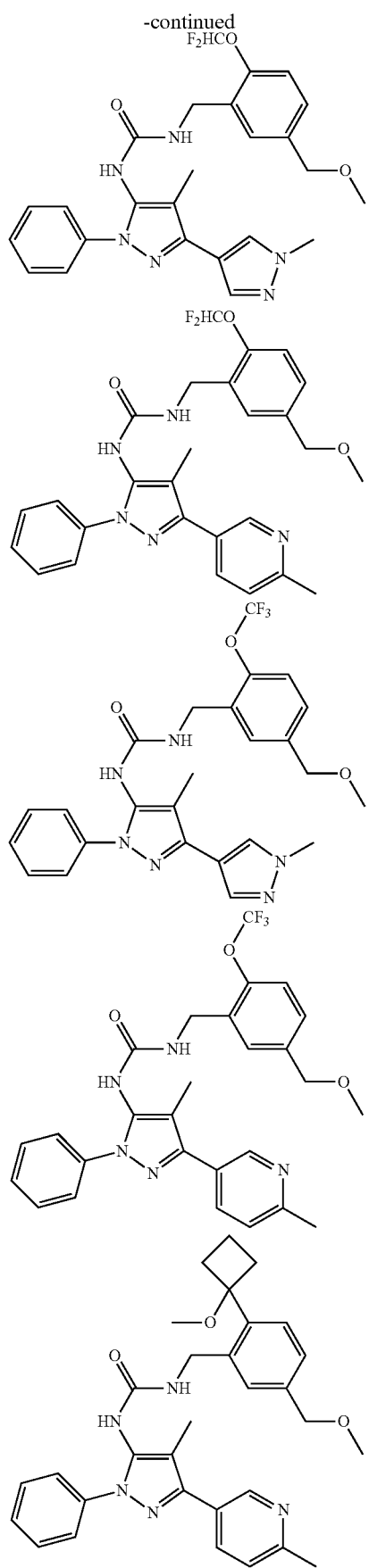
296
-continued
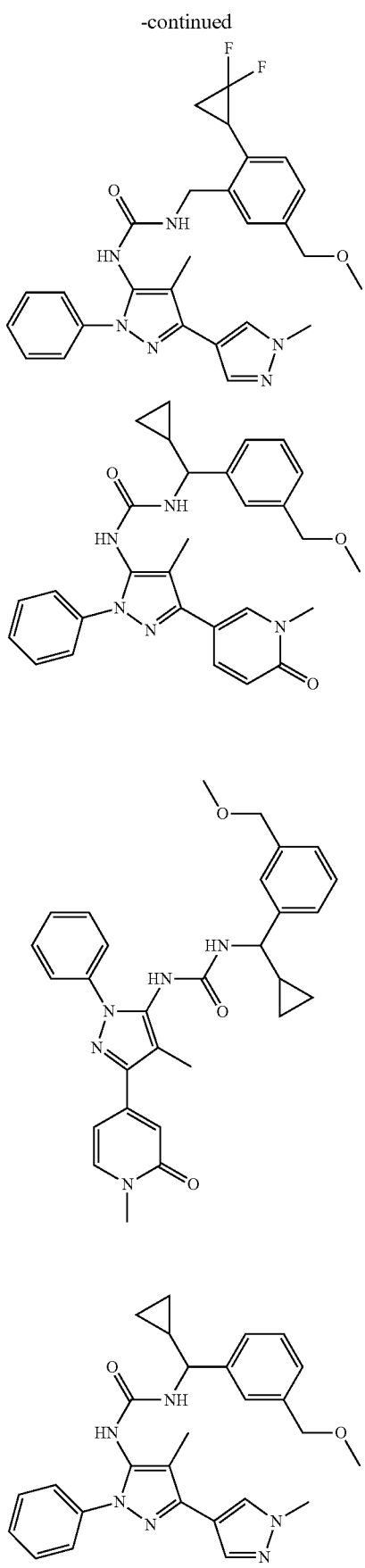

297
-continued
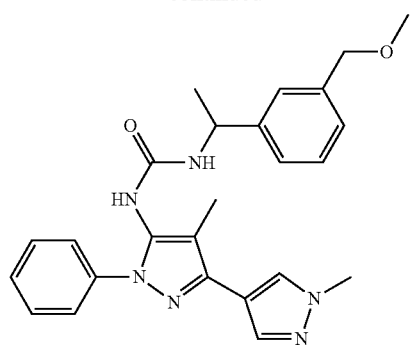
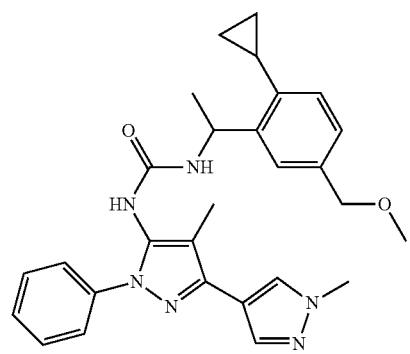
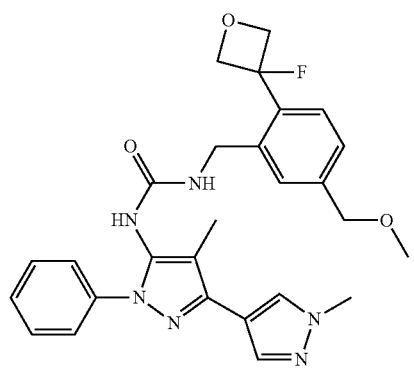
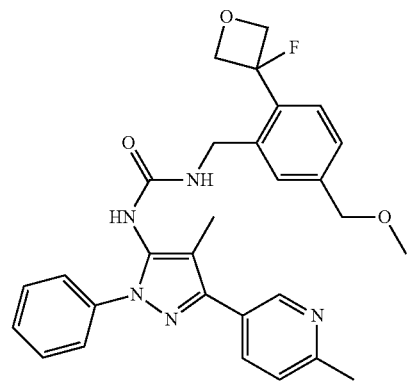
298
-continued
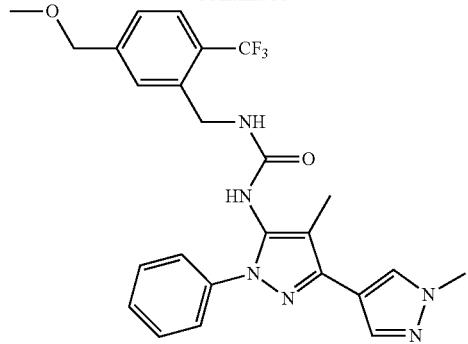
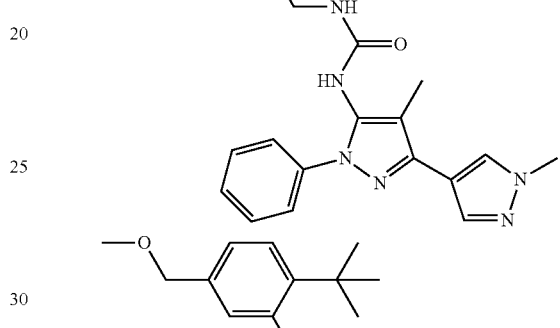
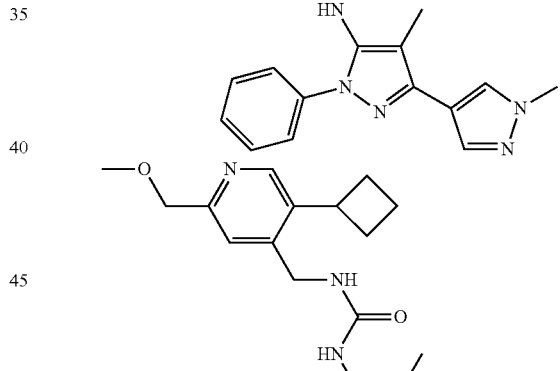
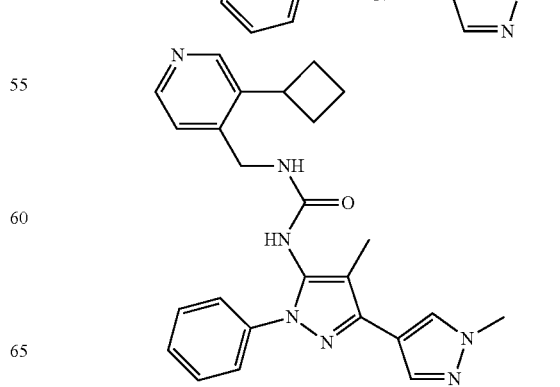

| 299 -continued | 300 -continued |
|---|---|
| 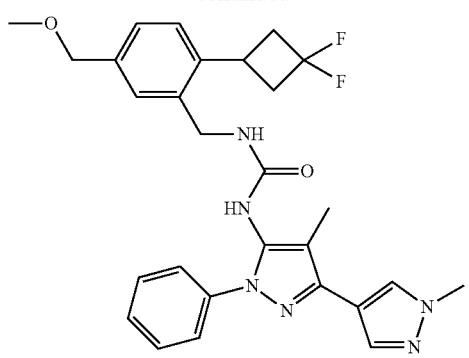 | 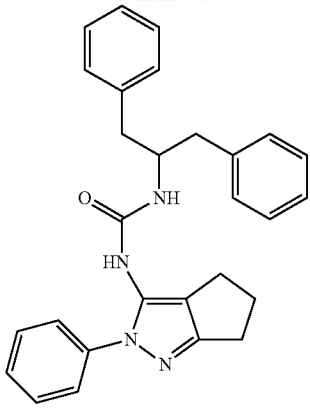 |
| 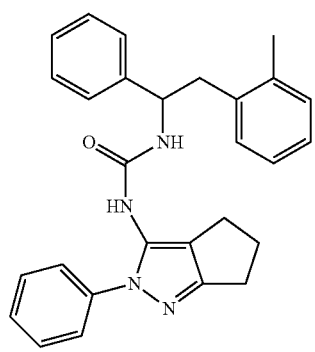 | 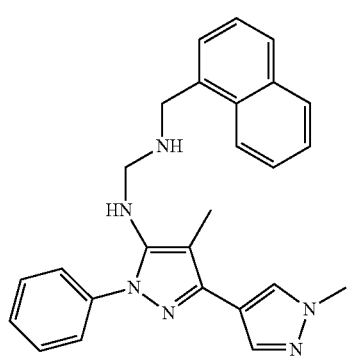 |
| 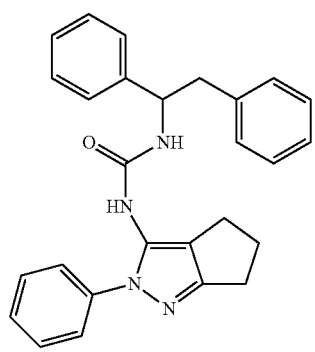 | 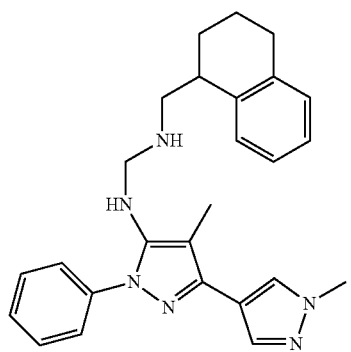 |
| 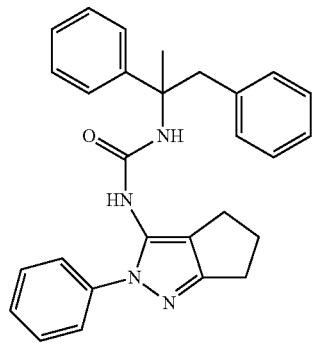 | 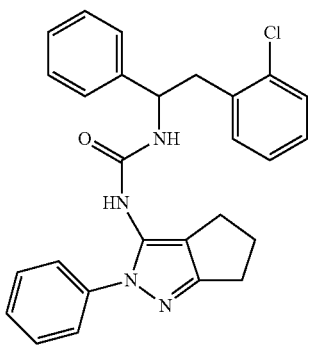 |

301
-continued
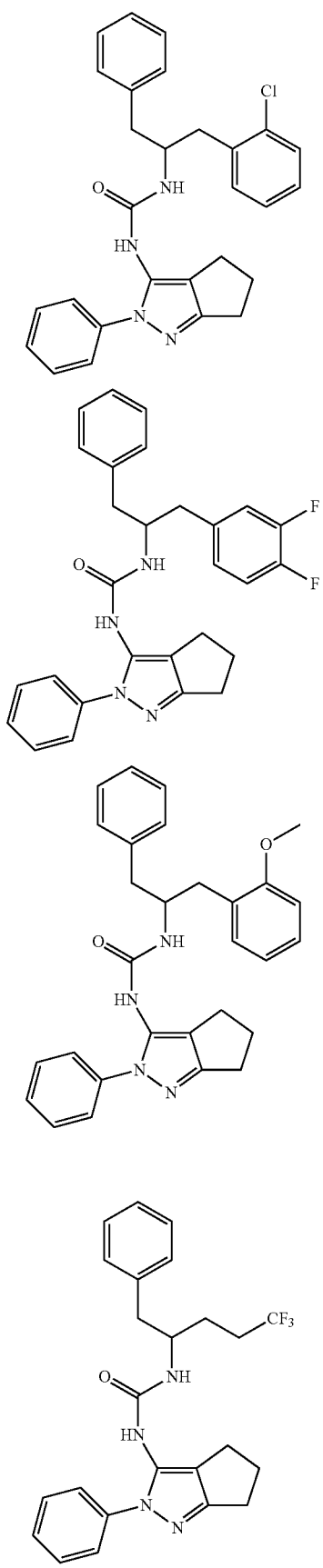
302
-continued
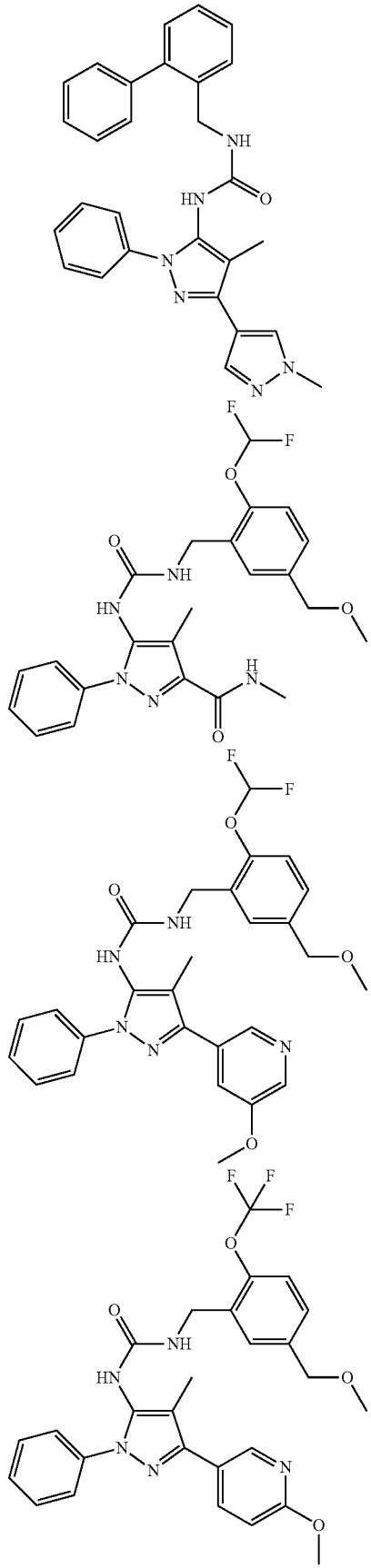

303
-continued
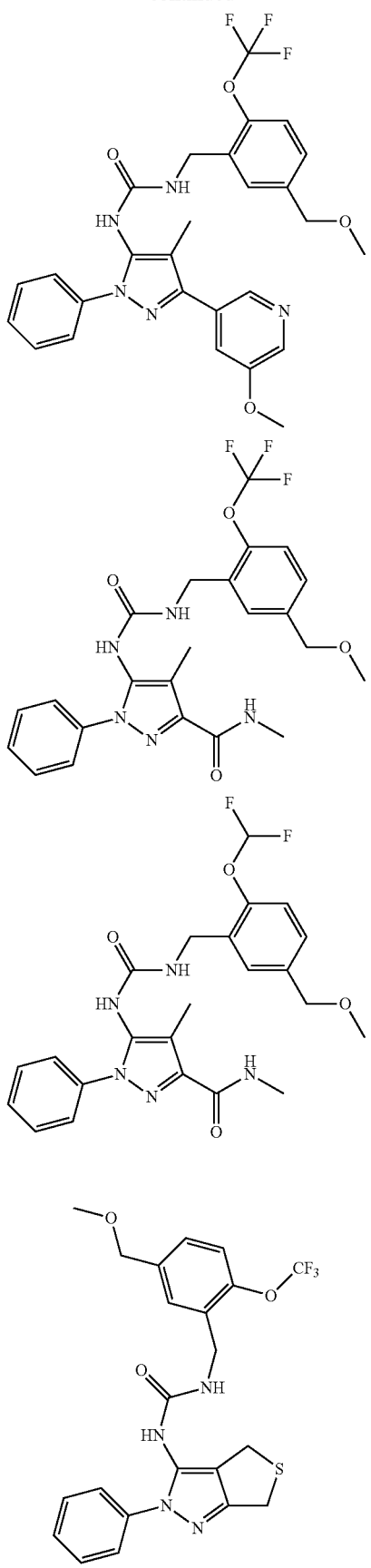
304
-continued
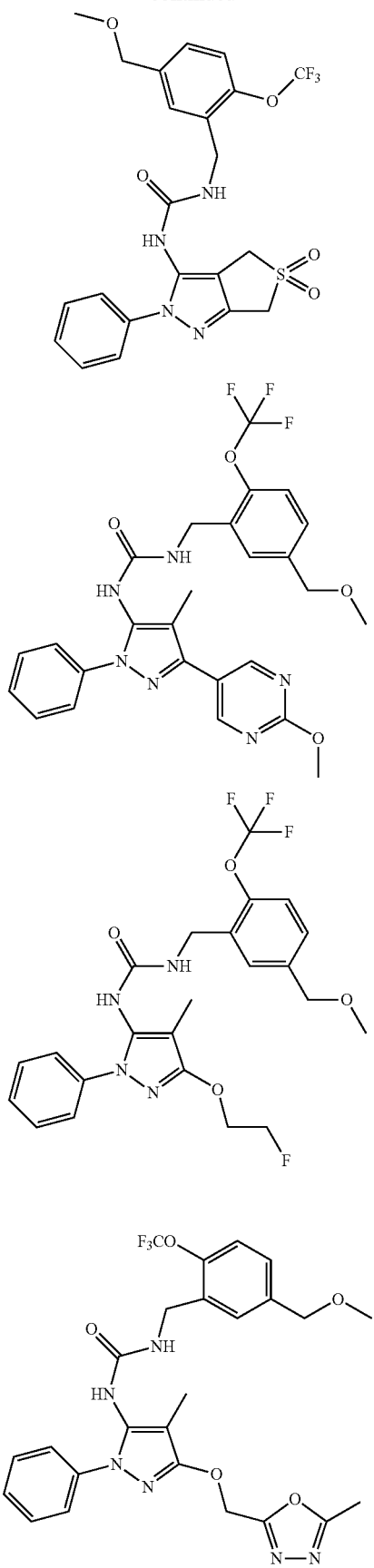

305
-continued
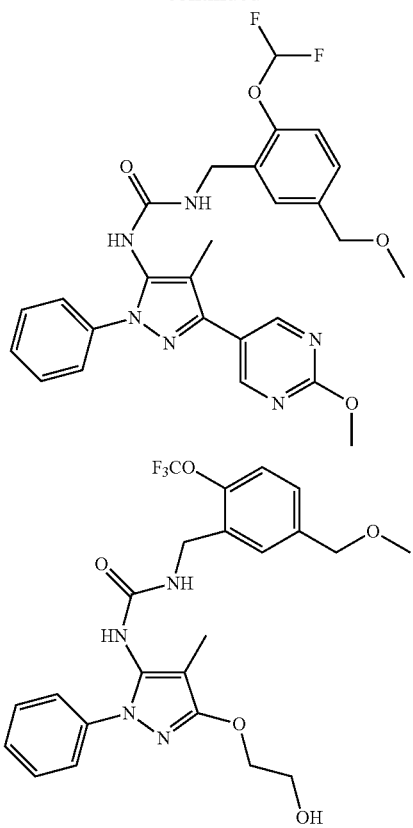
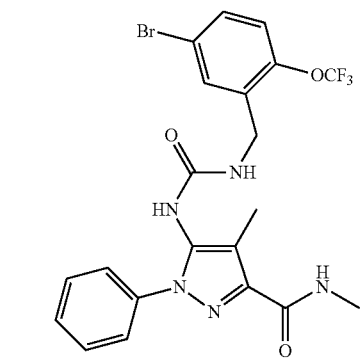
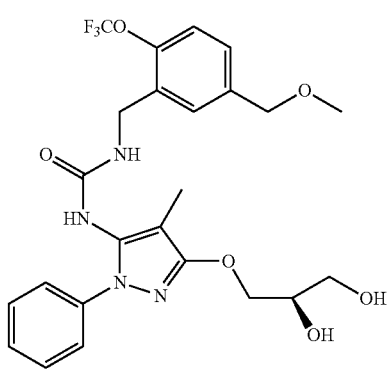
306
-continued
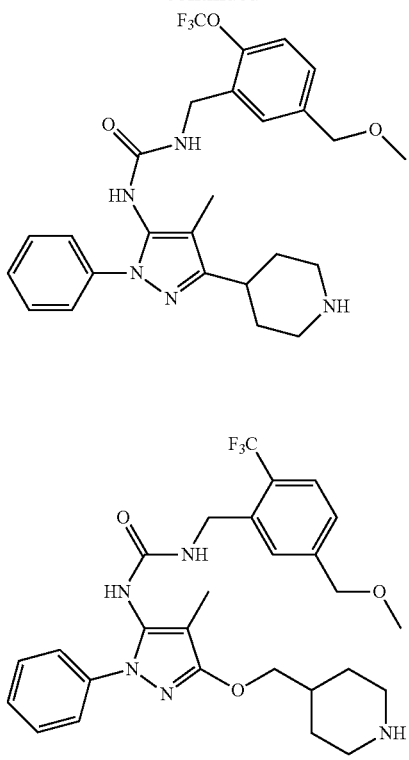
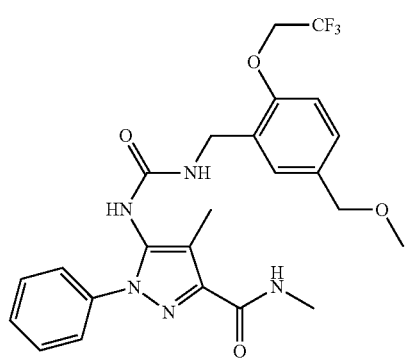
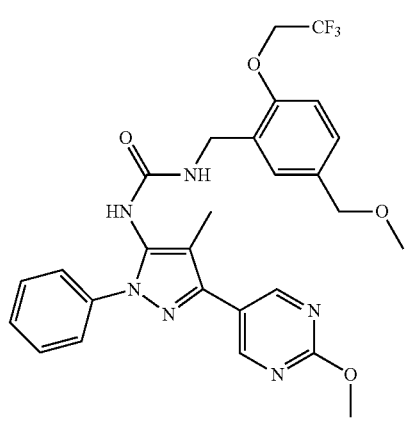

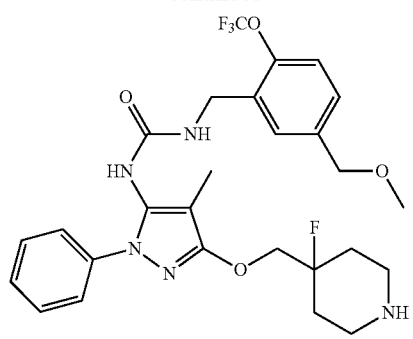
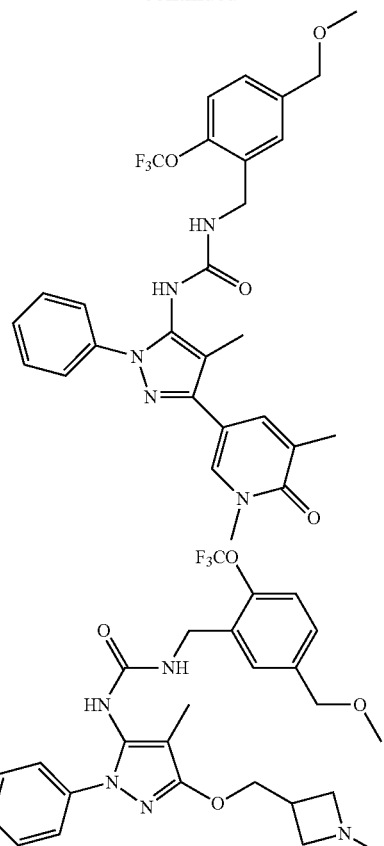
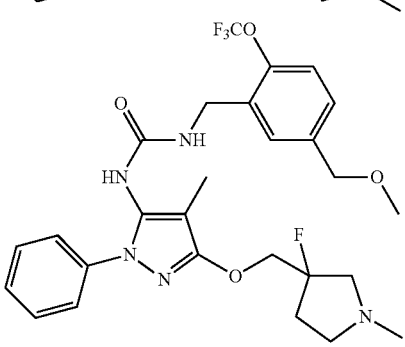
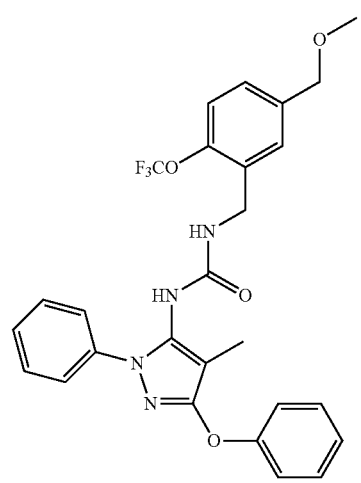

309
-continued
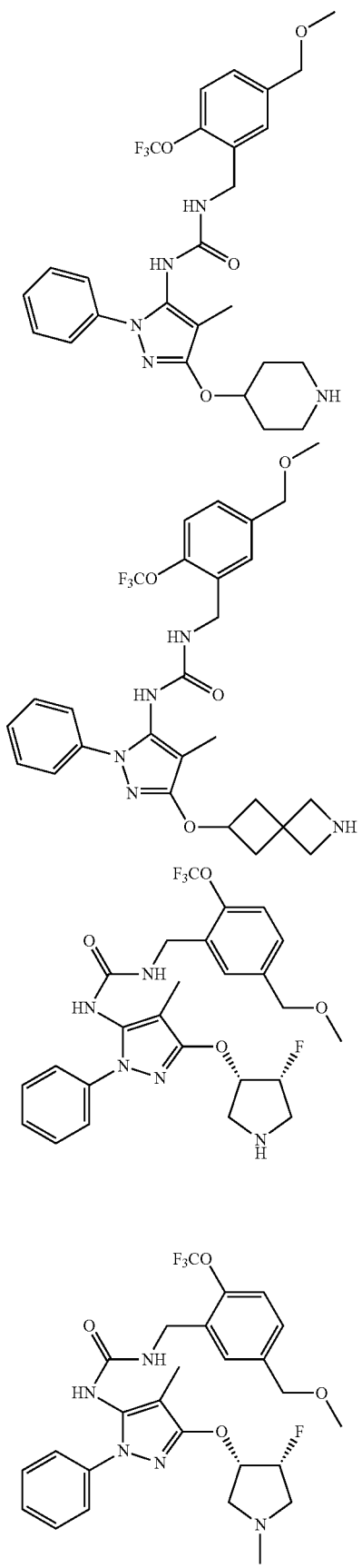
310
-continued
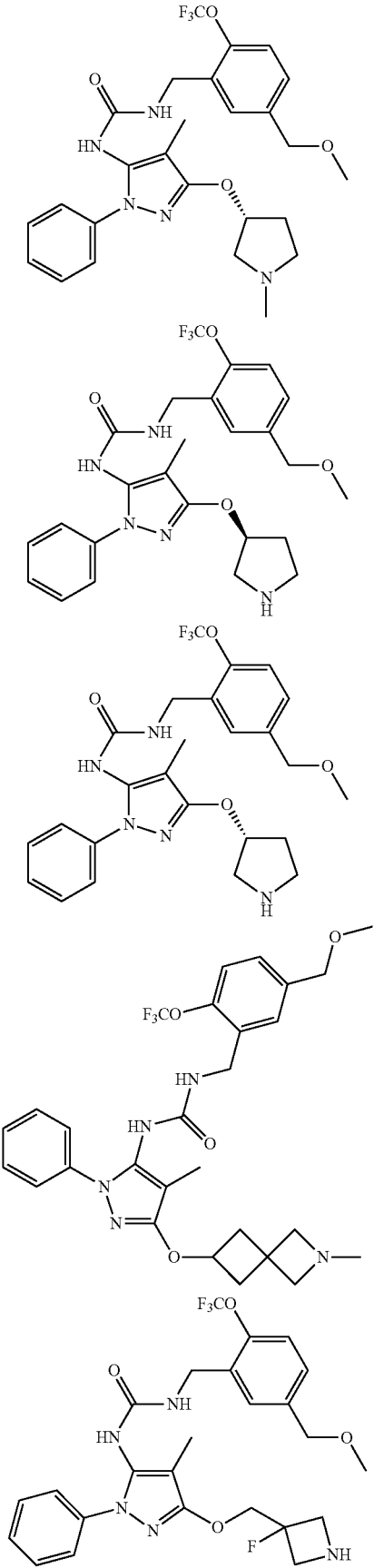

311
-continued
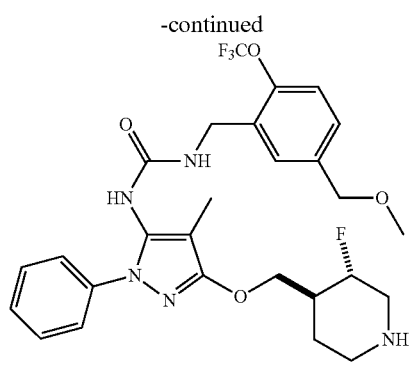
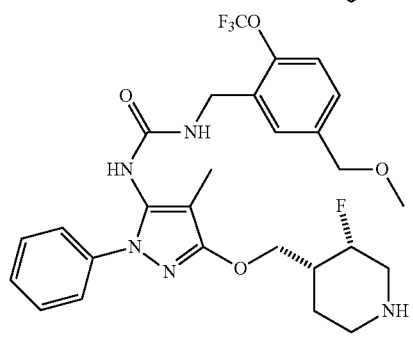
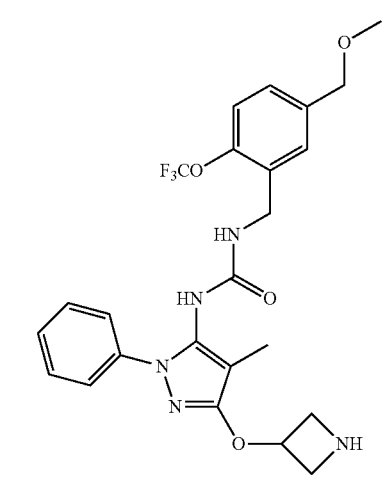
312
-continued
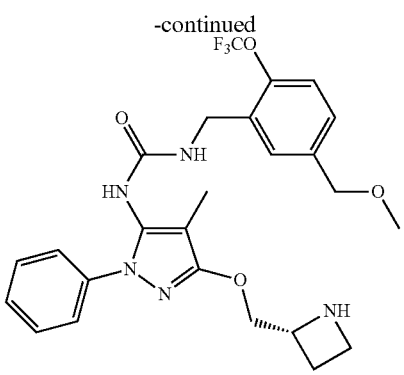
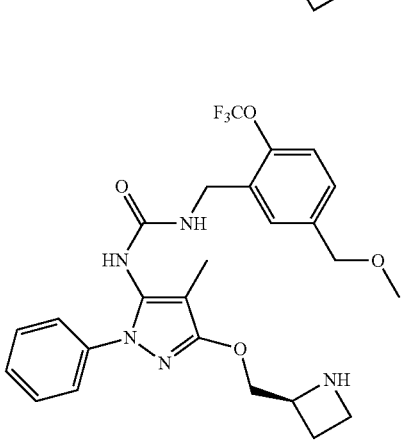
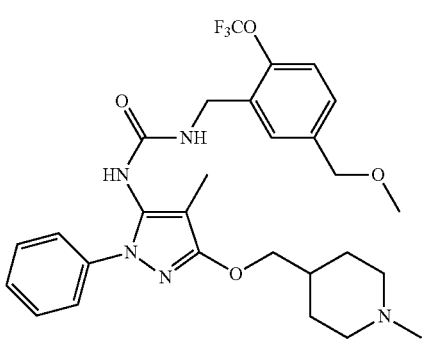
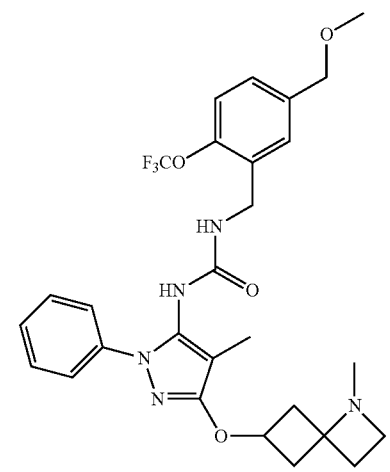

313
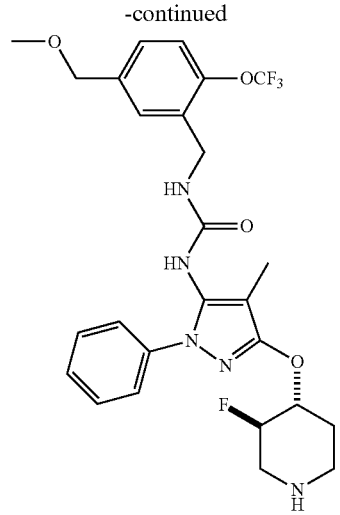
314
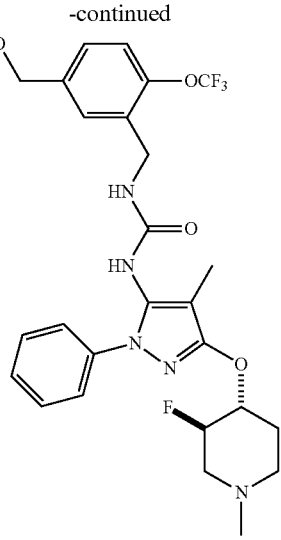
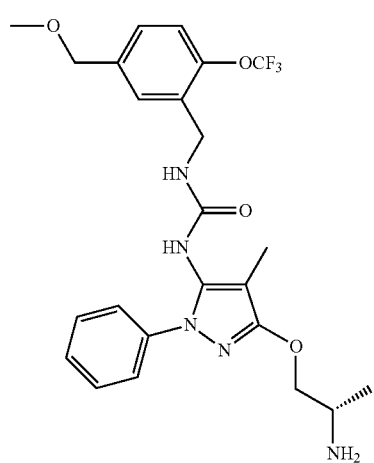
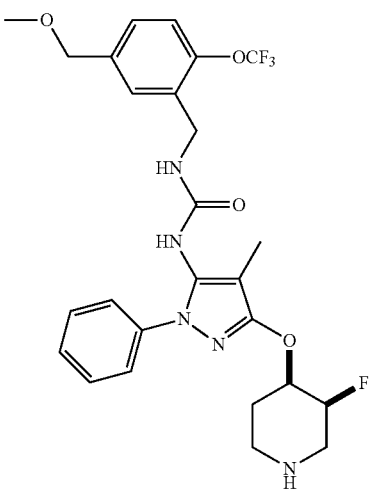
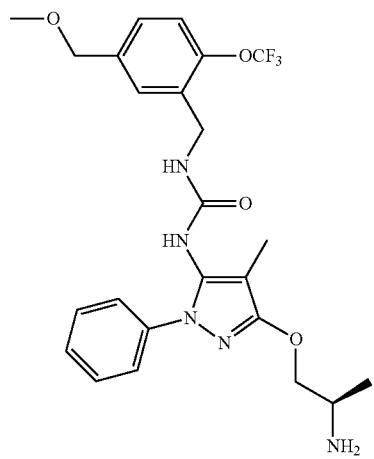
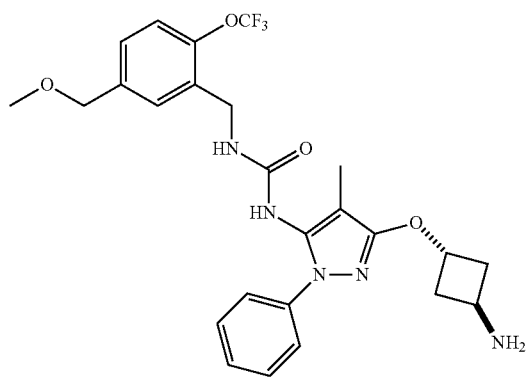

315
-continued
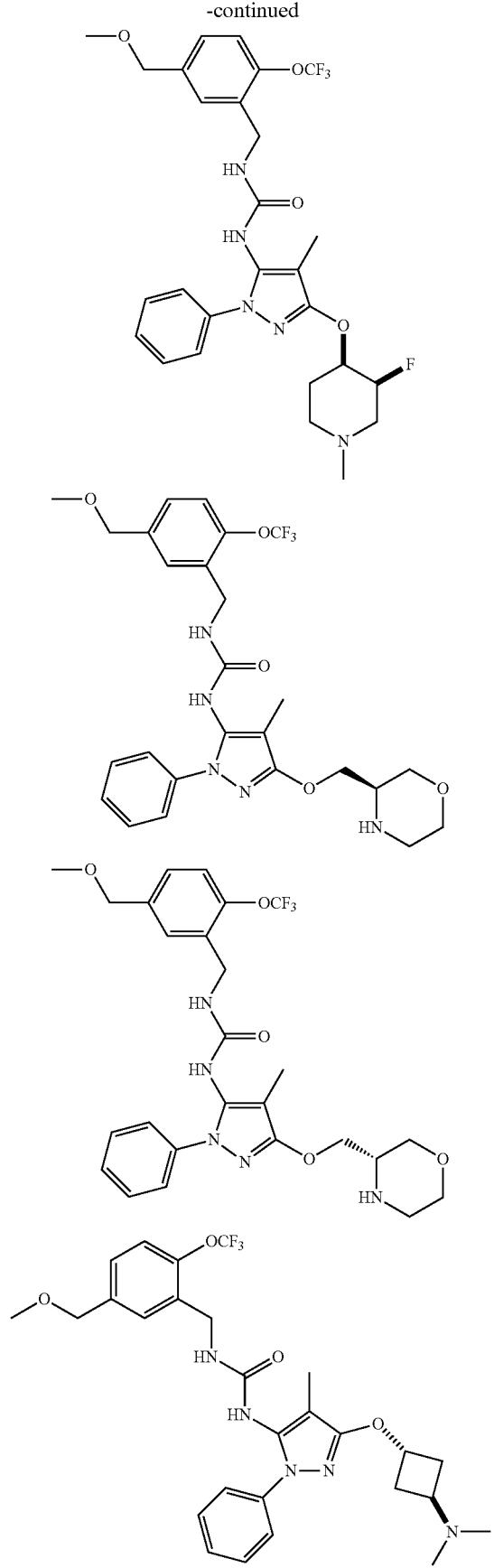
316
-continued
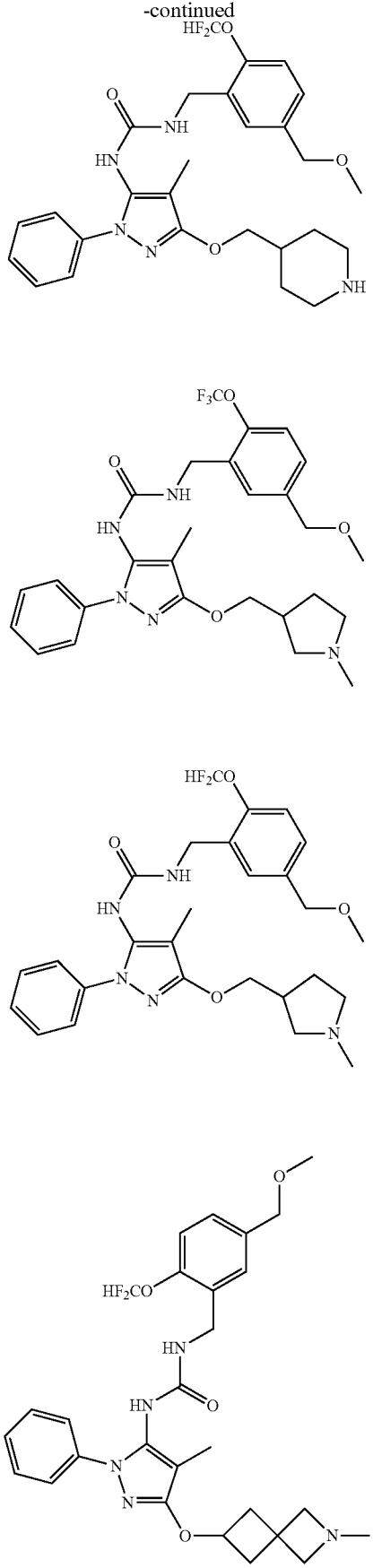

317
-continued
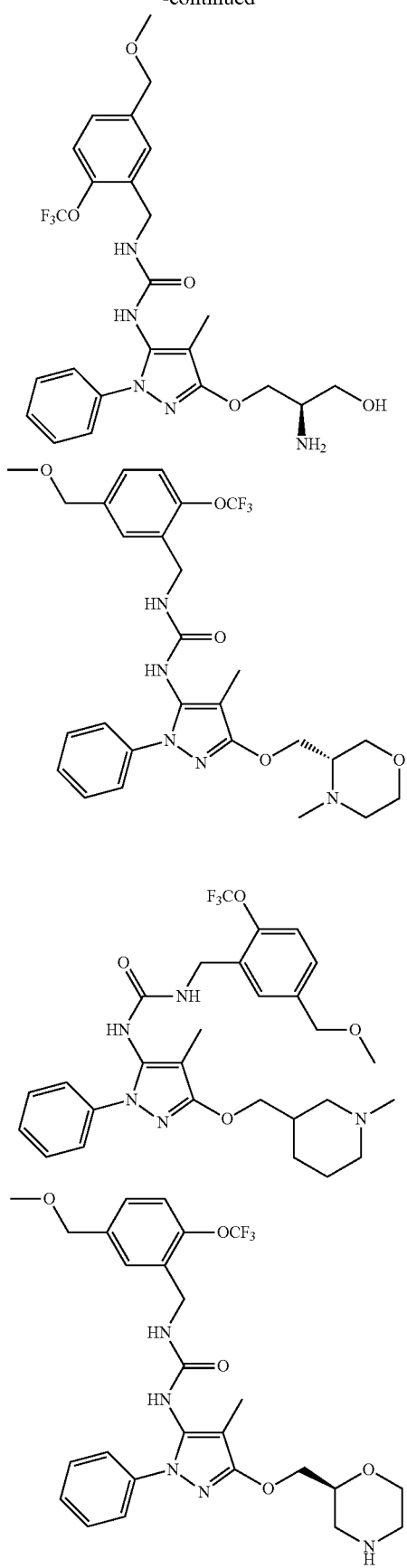
318
-continued
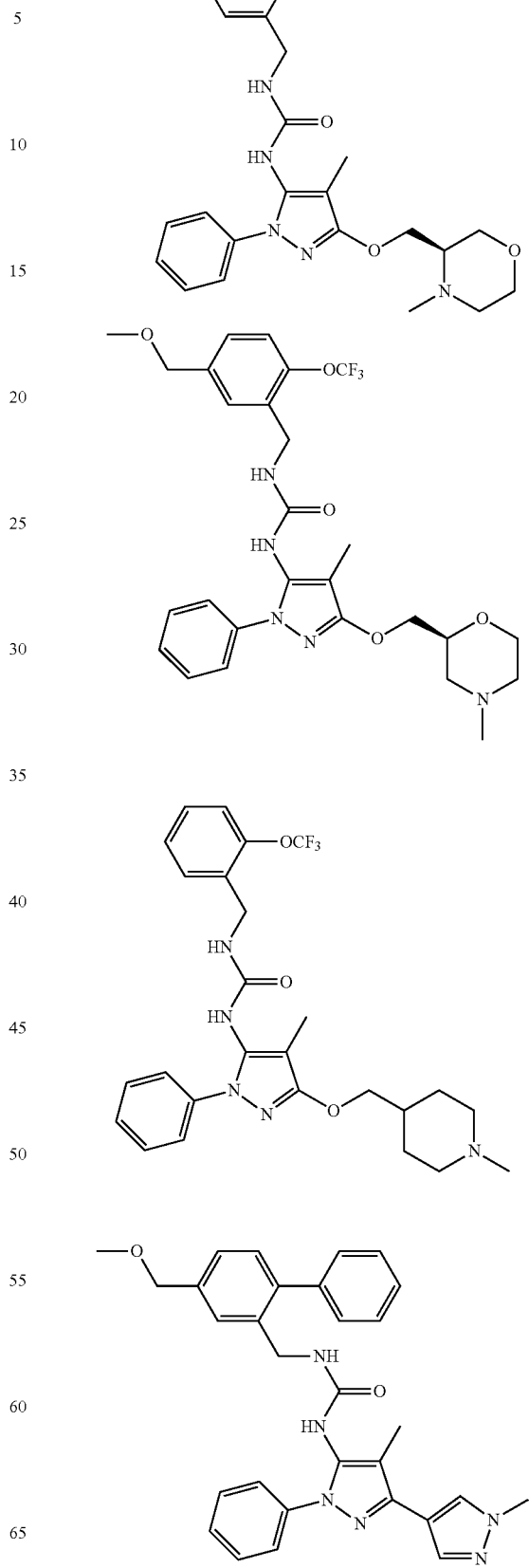

| 319 -continued | 320 -continued |
|---|---|
| 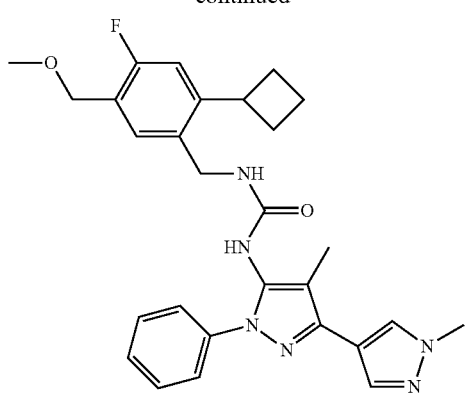 | 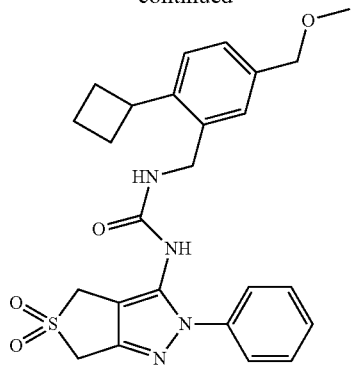 |
| 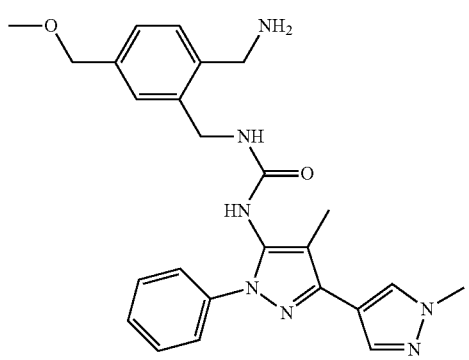 | 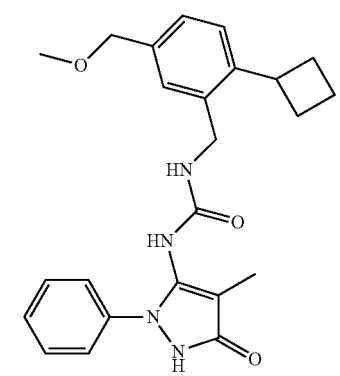 |
| 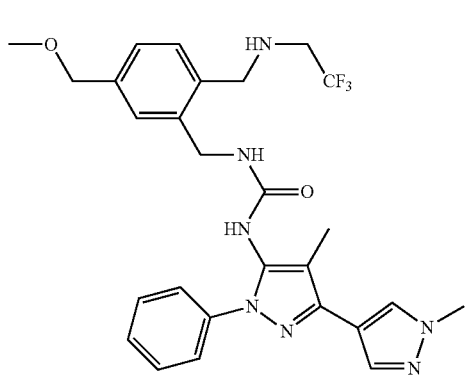 | 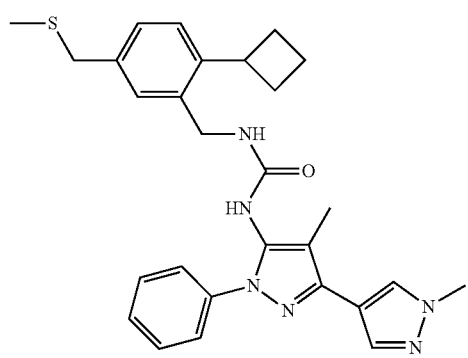 |
| 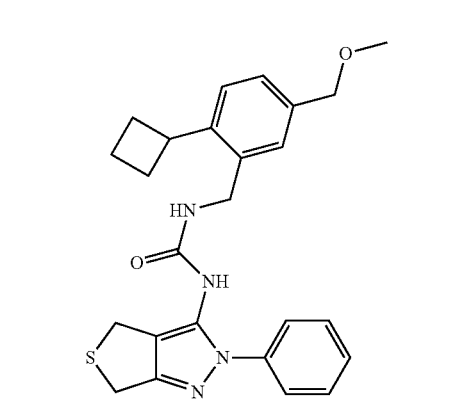 | 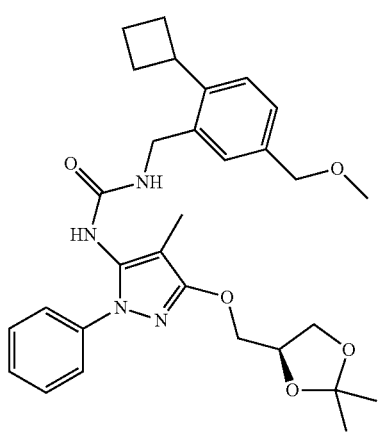 |

321
-continued
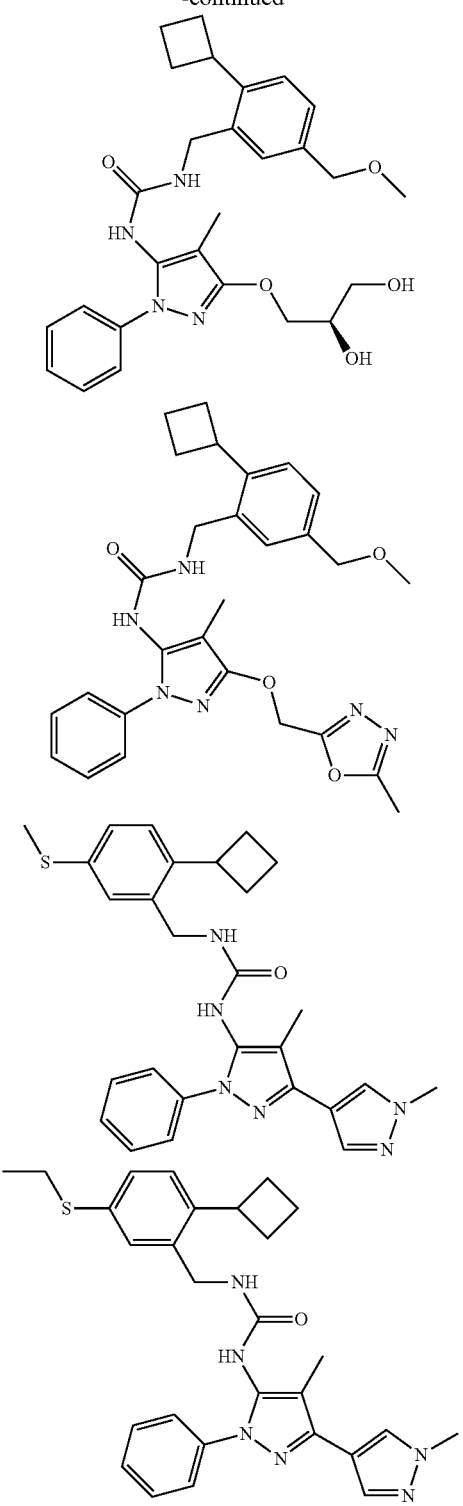
322
-continued
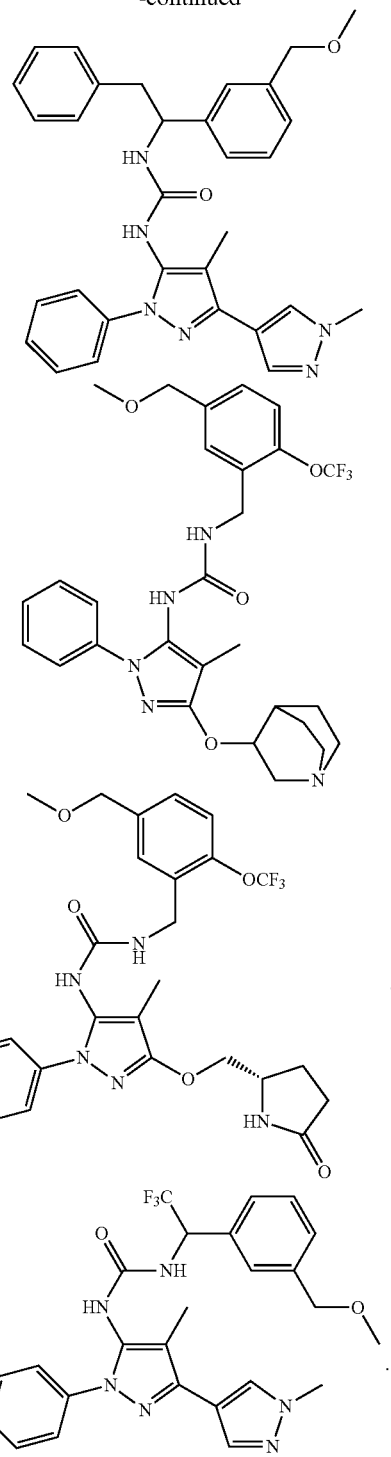
and
* * * * *

UNITED STATES PATENT AND TRADEMARK OFFICE
CERTIFICATE OF CORRECTION

PATENT NO. : 9,969,694 B2
APPLICATION NO. : 14/442576
DATED : May 15, 2018
INVENTOR(S) : James F. Blake et al.

Page 1 of 1

It is certified that error appears in the above-identified patent and that said Letters Patent is hereby corrected as shown below:

In the Claims

Column 293, Lines 54-66, Claim 1, please delete the following compound:

" 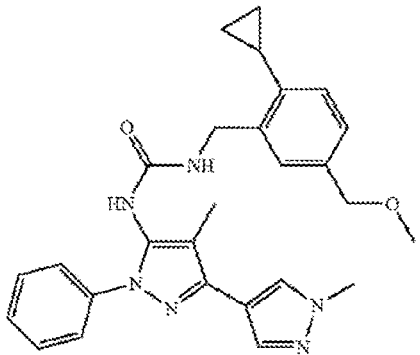 " and insert -- 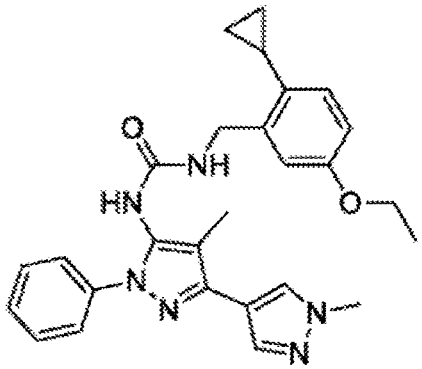 -- therefor.

Signed and Sealed this
Nineteenth Day of June, 2018

Andrei Iancu
*Director of the United States Patent and Trademark Office*